US012807603B2

(12) United States Patent
Lefker et al.

(10) Patent No.: US 12,807,603 B2
(45) Date of Patent: Nov. 24, 2026

(54) SUBSTITUTED MACROCYCLES AS OREXIN-2 RECEPTOR AGONISTS

(71) Applicant: Centessa Pharmaceuticals (UK) Limited, Altrincham (GB)

(72) Inventors: Bruce Lefker, Swampscott, MA (US); Gordon Saxty, Cambridge (GB); Karl Gibson, Sandwich (GB); Mark Pickworth, Cambridge (GB); Matthew Spendiff, Cambridge (GB); Miles Stuart Congreve, Melbourn Royston (GB); Paul Humphries, Santa Clara, CA (US)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 585 days.

(21) Appl. No.: 18/024,236

(22) PCT Filed: Sep. 3, 2021

(86) PCT No.: PCT/US2021/049003
§ 371 (c)(1),
(2) Date: Mar. 1, 2023

(87) PCT Pub. No.: WO2022/051583
PCT Pub. Date: Mar. 10, 2022

(65) Prior Publication Data

US 2023/0331720 A1 Oct. 19, 2023

Related U.S. Application Data

(60) Provisional application No. 63/074,220, filed on Sep. 3, 2020.

(51) Int. Cl.

| | |
|---|---|
| ***A61K 31/407*** | (2006.01) |
| ***A61K 31/4353*** | (2006.01) |
| ***C07D 471/04*** | (2006.01) |
| ***C07D 471/16*** | (2006.01) |
| ***C07D 487/04*** | (2006.01) |
| ***C07D 487/14*** | (2006.01) |
| ***C07D 487/16*** | (2006.01) |
| ***C07D 487/18*** | (2006.01) |
| ***C07D 498/04*** | (2006.01) |
| ***C07D 498/14*** | (2006.01) |
| ***C07D 498/18*** | (2006.01) |

(52) U.S. Cl.
CPC ......... *C07D 471/04* (2013.01); *C07D 487/04* (2013.01); *C07D 487/14* (2013.01); *C07D 487/18* (2013.01); *C07D 498/04* (2013.01); *C07D 498/14* (2013.01); *C07D 498/18* (2013.01)

(58) Field of Classification Search
CPC .............. A61K 31/407; A61K 31/4353; C07D 471/16; C07D 487/16
USPC ..................... 514/294, 411; 546/94; 548/428
See application file for complete search history.

(56) References Cited

U.S. PATENT DOCUMENTS

| | | | |
|---|---|---|---|
| 4,522,811 | A | 6/1985 | Eppstein et al. |
| 5,763,263 | A | 6/1998 | Dehlinger |
| 8,871,794 | B2 | 10/2014 | Yanagisawa |
| 2010/0074863 | A1 | 3/2010 | Or et al. |
| 2017/0226137 | A1 | 8/2017 | Fujimoto et al. |
| 2020/0255403 | A1 | 8/2020 | Bogen et al. |
| 2021/0155636 | A1 | 5/2021 | Pennington et al. |

(Continued)

FOREIGN PATENT DOCUMENTS

| | | | |
|---|---|---|---|
| CN | 101880276 | A | 11/2010 |
| CN | 102471314 | A | 5/2012 |

(Continued)

OTHER PUBLICATIONS

Jordan, V. C. Nature Reviews: Drug Discovery, Feb. 2003, 205. (Year: 2003).*
Dörwald, F. Zaragoza. Side Reactions in Organic Synthesis: A Guide to Successful Synthesis Design, Weinheim: Wiley-VCH Verlag Gmbh & Co. KGaA, 2005, Preface. (Year: 2005).*
Boss, Christoph, et al., Orexin Research: Patent News From 2016. Expert Opinion on Therapeutic Patents 27(10):1123-1133 (2017).

(Continued)

*Primary Examiner* — Douglas M Willis
(74) *Attorney, Agent, or Firm* — WILSON SONSINI GOODRICH & ROSATI

(57) ABSTRACT

The present disclosure relates to compounds of Formula (I'):

(I')

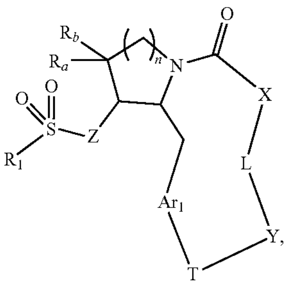

and to their prodrugs, pharmaceutically acceptable salts, pharmaceutical compositions, methods of use, and methods for their preparation. The compounds disclosed herein are useful for modulating orexin-2 receptor activity and may be used in the treatment of disorders in which orexin-2 receptor activity is implicated, such as narcolepsy, a hypersomnia disorder, a neurodegenerative disorder, a symptom of a rare genetic disorder, a mental health disorder, a metabolic syndrome, osteoporosis, cardiac failure, coma, or facilitating emergence from anaesthesia.

20 Claims, No Drawings

(56) References Cited

U.S. PATENT DOCUMENTS

| | | | |
|---|---|---|---|
| 2023/0271973 A1 | 8/2023 | Lefker et al. |
| 2024/0239744 A1 | 7/2024 | Christopher |
| 2024/0360175 A1 | 10/2024 | O'Boyle et al. |
| 2025/0100968 A1 | 3/2025 | Ott et al. |
| 2025/0236629 A1 | 7/2025 | Ott et al. |

FOREIGN PATENT DOCUMENTS

| | | |
|---|---|---|
| CN | 111051295 A | 4/2020 |
| CN | 113395993 A | 9/2021 |
| WO | WO-2008076415 A1 | 6/2008 |
| WO | WO-2008128121 A1 | 10/2008 |
| WO | WO-2009070689 A1 | 6/2009 |
| WO | WO-2011006960 A1 | 1/2011 |
| WO | WO-2011073376 A1 | 6/2011 |
| WO | WO-2012117219 A1 | 9/2012 |
| WO | WO-2012137982 A2 | 10/2012 |
| WO | WO-2013052845 A1 | 4/2013 |
| WO | WO-2013092893 A1 | 6/2013 |
| WO | WO-2015078949 A1 | 6/2015 |
| WO | WO-2016021629 A1 | 2/2016 |
| WO | WO-2016022464 A1 | 2/2016 |
| WO | WO-2017135306 A1 | 8/2017 |
| WO | WO-2017139603 A1 | 8/2017 |
| WO | WO-2018164191 A1 | 9/2018 |
| WO | WO-2018164192 A1 | 9/2018 |
| WO | WO-2019027058 A1 | 2/2019 |
| WO | WO-2019027069 A1 | 2/2019 |
| WO | WO-2020004536 A1 | 1/2020 |
| WO | WO-2020122092 A1 | 6/2020 |
| WO | WO-2020122093 A1 | 6/2020 |
| WO | WO-2020158958 A1 | 8/2020 |
| WO | WO-2020167706 A1 | 8/2020 |
| WO | WO-2021048821 A1 | 3/2021 |
| WO | WO-2021048822 A1 | 3/2021 |
| WO | WO-2021065893 A1 | 4/2021 |
| WO | WO-2021107023 A1 | 6/2021 |
| WO | WO-2021108628 A1 | 6/2021 |
| WO | WO-2022051583 A1 | 3/2022 |
| WO | WO-2022051596 A1 | 3/2022 |
| WO | WO-2022140316 A1 | 6/2022 |
| WO | WO-2022207935 A1 | 10/2022 |
| WO | WO-2023017180 A1 | 2/2023 |
| WO | WO-2023167865 A1 | 9/2023 |
| WO | WO-2023167925 A1 | 9/2023 |
| WO | WO-2024152973 A1 | 7/2024 |

OTHER PUBLICATIONS

Database STN, CAS, File Registry, RN 1422063-50-0, "Methanesulfonamide, N-[(2R,3S)-2-(phenylmethyl)-3-pyrrolidinyl]- , rei- ," (CA Index Name) Supplier WuXi AppTec Corporate Limited American Chemical Society CAS; Entered STN: 3 Printed Pages (Feb. 28, 2013).

PCT/EP2022/058817 International Search Report and Written Opinion dated Aug. 3, 2022.

PCT/US2021/049003 International Search Report and Written Opinion dated Nov. 11, 2021.

PCT/US2021/049021 International Search Report and Written Opinion dated Nov. 11, 2021.

PCT/US2023/014139 International Search Report and Written Opinion dated May 30, 2023.

PCT/US2023/014275 International Search Report and Written Opinion dated Jun. 15, 2023.

U.S. Appl. No. 18/024,216 Notice of Allowance dated Jul. 22, 2025.

Chemical Abstracts Service. CAS Registry: 70693-62-8, PubChem SID: 117687804. ABBLIS Chemicals: pp. 1-5. STN Entry Date Apr. 12, 2011. Retrieved Nov. 7, 2024. Retrieved from: https://pubchem.ncbi.nlm.nih.gov/substance/117687804.

Li, Kangnan. et al. Diastereoselective and Enantiospecific Synthesis of 1,3-Diamines via 2-Azaallyl Anion Benzylic Ring-Opening of Aziridines. Organic Letters 19(16):4239-4242 (2017).

Tanaka, Kouichi. et al. Reductive Amination of Ketonic Compounds Catalyzed by Cp*Ir(III) Complexes Bearing a Picolinamidato Ligand. The Journal of Organic Chemistry 84(17):10962-10977 (2019).

Baykal, S. et al. Decreased serum orexin A levels in drug-naive children with attention deficit and hyperactivity disorder. Neurol Sci. Mar. 2019;40(3):593-602. doi: 10.1007/s10072-018-3692-8. Epub Jan. 7, 2019.

Black, S.W. et al. Challenges in the development of therapeutics for narcolepsy. Prog. Neurobiol., 2017; 152:89-113.

Calva, C.B. et al. Intranasal administration of orexin peptides: Mechanisms and therapeutic potential for age-related cognitive dysfunction. Brain Res. Mar. 15, 2020;1731:145921. doi: 10.1016/j.brainres.2018.08.024. Epub Aug. 24, 2018; 9 pages.

Cheong, R.Y. et al. The Role of Hypothalamic Pathology for Non-Motor Features of Huntington's Disease. J Huntingtons Dis. 2019;8(4):375-391. doi: 10.3233/JHD-190372.

De Lecea, L. et al. The hypocretins: hypothalamus-specific peptides with neuroexcitatory activity. Proc Natl Acad Sci USA. Jan. 1998;95:322-7.

Funato, H. et al. Enhanced orexin receptor-2 signaling prevents diet-induced obesity and improves leptin sensitivity. Cell Metab. Jan. 7, 2009;9(1):64-76. doi: 10.1016/j.cmet.2008.10.010.

Hara, J. et al. Genetic ablation of orexin neurons in mice results in narcolepsy, hypophagia, and obesity. Neuron. May 2001;30(2):345-54. doi: 10.1016/s0896-6273(01)00293-8.

Hasegawa, E. et al. Orexin neurons suppress narcolepsy via 2 distinct efferent pathways. J Clin Invest. Feb. 2014;124(2):604-16. doi: 10.1172/JCI71017. Epub Jan. 2, 2014.

Irukayama-Tomobe, Y. et al. Nonpeptide orexin type-2 receptor agonist ameliorates narcolepsy-cataplexy symptoms in mouse models. PNAS, May 30, 2017;114(22):5731-6.

Kelz, M.B. et al. An essential role for orexins in emergence from general anesthesia. Proc Natl Acad Sci U S A. Jan. 29, 2008;105(4):1309-14. doi: 10.1073/pnas.0707146105. Epub Jan. 14, 2008.

Liu, M.F. et al. Orexin-A Exerts Neuroprotective Effects via OX1R in Parkinson's Disease. Front Neurosci. Nov. 15, 2018;12:835. doi: 10.3389/fnins.2018.00835; 18 pages.

Mahoney, C.E, et al. The neurobiological basis of narcolepsy. Nat Rev Neurosci. Feb. 2019;20(2):83-93. doi: 10.1038/s41583-018-0097-x.

Mieda, M. et al. Orexin peptides prevent cataplexy and improve wakefulness in an orexin neuron-ablated model of narcolepsy in mice. PNAS, Mar. 30, 2004;101:4649-54.

Mignot, E. et al. Sleeping with the hypothalamus: emerging therapeutic targets for sleep disorders. Nat Neurosci. Nov. 2002;5 Suppl: 1071-5. doi: 10.1038/nn944.

Mignot, E. Narcolepsy: genetics, immunology, and pathophysiology. In: Kryger M, Roth T, Dement WC, eds. Principles and Practice of Sleep Medicine. 6th ed. Philadelphia, PA: Elsevier; 2017; Chapter 89, pp. 855-872.e7.

Mochizuki, T. et al. Orexin receptor 2 expression in the posterior hypothalamus rescues sleepiness in narcoleptic mice. Proc Natl Acad Sci U S A. Mar. 15, 2011;108(11):4471-6. doi: 10.1073/pnas.1012456108. Epub Feb. 28, 2011.

Modi, H.R., et al. Intranasal post-cardiac arrest treatment with orexin-A facilitates arousal from coma and ameliorates neuroinflammation. PLoS One. Sep. 28, 2017;12(9):e0182707. doi: 10.1371/journal.pone.0182707; 20 pages.

Nishino, S. et al. Hypocretin (orexin) deficiency in human narcolepsy. Lancet. Jan. 1, 2000;355(9197):39-40. doi: 10.1016/S0140-6736(99)05582-8.

Pallais, J.P. et al. Orexin/hypocretinin in multiple sclerosis and experimental autoimmune encephalomyelitis. Neural Regen Res. Jun. 2020; 5(6):1039-1040. doi: 10.4103/1673-5374.270310.

Patel, V.H. et al. Functional cardiac orexin receptors: role of orexin-B/orexin 2 receptor in myocardial protection. Clin Sci (Lond). Dec. 13, 2018;132(24):2547-2564. doi: 10.1042/CS20180150.

(56) References Cited

OTHER PUBLICATIONS

Peyron, R. et al. Functional imaging of brain responses to pain. A review and meta-analysis (2000). Neurophysiol Clin. Oct. 2000;30(5):263-88. doi: 10.1016/s0987-7053(00)00227-6.
Sakurai, T. et al. Orexins and orexin receptors: a family of hypothalamic neuropeptides and G protein-coupled receptors that regulate feeding behavior. Cell, Feb. 20, 1998;92:573-585.
Tabuchi, S. et al. Conditional ablation of orexin/hypocretin neurons: a new mouse model for the study of narcolepsy and orexin system function. J. Neurosci., May 7, 2014;34(19):6495-6509.
Thannickal, T.C. et al. Reduced number of hypocretin neurons in human narcolepsy. Neuron. Sep. 2000;27(3):469-74. doi: 10.1016/s0896-6273(00)00058-1.
Thomasy, H.E. et al. Hypocretin Mediates Sleep and Wake Disturbances in a Mouse Model of Traumatic Brain Injury. J Neurotrauma. Mar. 1, 2019;36(5):802-814. doi: 10.1089/neu.2018.5810. Epub Oct. 3, 2018.
Um, Y.H. and Lim, H.K . . . Orexin and Alzheimer's Disease: A New Perspective. Psychiatry Investig. Jul. 2020; 17(7):621-626. doi: 10.30773/pi.2020.0136. Epub Jun. 11, 2020.
Wei, W, et al. Orexin regulates bone remodeling via a dominant positive central action and a subordinate negative peripheral action. Cell Metab. Jun. 3, 2014;19(6):927-40. doi: 10.1016/j.cmet.2014.03.016. Epub May 1, 2014.
Yukitake, H. et al. TAK-925, an orexin 2 receptor-selective agonist, shows robust wake-promoting effects in mice. Pharmacol Biochem Behav, 2019;187:172794, 10 pages.
Disabato, Damon J. et al. Neuroinflammation: the devil is in the details. Journal of Neurochemistry 139:136-153 (2016).
Meanwell, Nicholas A. Synopsis of some recent tactical application of bioisosteres in drug design. Journal of Medicinal Chemistry 54(8):2529-2591 (2011).
Zugazagoitia, Jon. et al. Current challenges in cancer treatment. Clinical Therapeutics 38(7):1551-1566 (2016).

* cited by examiner

SUBSTITUTED MACROCYCLES AS OREXIN-2 RECEPTOR AGONISTS

CROSS-REFERENCE TO RELATED APPLICATIONS

This application is a U.S. National Phase Application, filed under U.S.C. § 371(c), of International Application No. PCT/US2021/049003, filed Sep. 3, 2021, which claims priority to and benefit of U.S. Provisional Application No. 63/074,220, filed Sep. 3, 2020, both of which are incorporated herein by reference in their entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

The present disclosure relates to small molecule, potent agonists of the orexin-2 receptor (OX2R), designed for the treatment of narcolepsy and other disorders associated with orexin insufficiency and/or excessive sleepiness. Narcolepsy afflicts 1 in 2000 individuals worldwide. Onset may occur during adolescence for a lifelong duration and debilitating impact on quality of life. Narcolepsy Type 1 (NT1) is caused by the loss of neurons in the brain which produce orexin neuropeptides. There is no known cure, and currently approved treatments are symptomatic. Thus, development of pharmacotherapeutics to restore lost orexin signaling is critically important for treatment of the root cause of NT1.

In narcolepsy Type 1 (NT1), the sole population of neurons that produce orexin A and B (also known as hypocretin-1 and 2) peptides are destroyed by an immune mechanism which causes arousal state boundary dysfunction. Mouse models of narcolepsy type 1 recapitulate the loss of orexin neurons and the two cardinal symptoms observed in NT1 patients, specifically excessive daytime sleepiness and cataplexy. Common symptoms of narcolepsy type 1 and type 2 may include excessive daytime sleepiness, disturbed nighttime sleep, and inappropriately timed rapid-eye-movement (REM) sleep, as well as sleep paralysis and hypnopompic/hypnogogic hallucinations. Cataplexy is the intrusion of sudden, reversible loss of muscle tone (the atonia of REM sleep) into wakefulness in response to emotional stimuli and is pathognomonic of NT1.

The two predominant symptoms of narcolepsy type 1, excessive daytime sleepiness and cataplexy, can be reduced by re-activation of orexin neurotransmission at OX2R in mouse models. Reversal of cataplexy-like events and sleep/wake fragmentation has been achieved by genetic, focal restoration of OX2R signaling in the dorsal raphe nucleus of the pons and the tuberomammillary nucleus of the hypothalamus, respectively, in mice that otherwise lack orexin receptors in those regions. Intracerebroventricular (ICV) administration of orexin A (OXA) has been shown to increase time spent awake and decreases cataplexy-like behavior in orexin-neuron ablated mice. Selective OX2R agonist, YNT-185 administered intraperitoneally or ICV, modestly increases wakefulness in wild type (WT) and orexin ligand-deficient mice, and decrease sleep-onset REM periods and cataplexy-like events in an NT1 mouse model. Subcutaneous administration of the selective OX2R agonist TAK-925 modestly increased wakefulness in WT mice, but not in OX2R-knockout mice. Brain penetrant and stable OX2R agonists that are bioavailable after alternative routes of administration (including but not limited to oral, intranasal, transmucosal, and transdermal) and that bind with high affinity for potent excitation of arousal-state regulating neurons will provide an improvement to current therapeutics for patients with NT1. In fact, initial clinical studies reported with TAK-925 showed both substantial levels of increased wakefulness and trends for decreasing cataplexy in individuals with NT1. Activation of the OX1R is implicated in regulation of mood and reward behaviors, and may also contribute to arousal.

Orexin receptor agonists may also be useful in other indications marked by some degree of orexin neurodegeneration and excessive daytime sleepiness, such as Parkinson's disease, Alzheimer's disease, Huntington's disease, multiple sclerosis, and traumatic brain injury. Because stimulation of OX2R promotes wakefulness in orexin-intact animals, orexin receptor agonists may treat excessive daytime sleepiness in patients with normal levels of orexin, including narcolepsy type 2, idiopathic hypersomnia, or sleep apnea. Similarly, orexin receptor agonists may confer wake-promoting benefits in disorders of recurrent hypersomnia, such as Klein-Levin syndrome, or inappropriately timed sleep (i.e., circadian rhythm sleep disorders), such as delayed- or advanced-sleep phase disorder, shift work disorder, and jet lag disorder. The abnormal daytime sleepiness, sleep onset REM periods, and cataplexy-like symptoms of rare genetic disorders (e.g., ADCA-DN, Coffin-Lowry syndrome, Moebius syndrome, Norrie disease, Niemann-Pick disease type C, and Prader-Willi syndrome) could be alleviated with orexin receptor agonists. Other indications in which orexin receptor agonists have been suggested to confer benefits include attention deficit hyperactivity disorder, age-related cognitive dysfunction, metabolic syndrome and obesity, osteoporosis, cardiac failure, coma, and emergence from anesthesia.

The disclosure arises from a need to provide further compounds for the modulation of orexin receptor activity in the brain, including activation of the orexin-2 receptor, with improved therapeutic potential. In particular, compounds with improved physicochemical, pharmacological and pharmaceutical properties to existing compounds are desirable.

BRIEF SUMMARY OF THE INVENTION

In some aspects, the present disclosure provides a compound of Formula (I'):

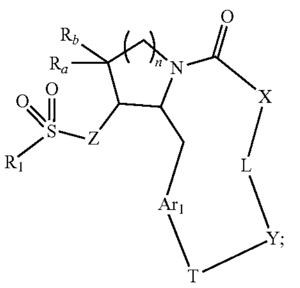

(I')

or a pharmaceutically acceptable salt thereof, wherein:

X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy; L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$—$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6;

Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

n is an integer ranging from 0 to 3;

$R_a$ and $R_b$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_S$; or $R_a$ and $R_b$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_S$;

each $R_S$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

Z is —O— or —$NR_Z$—; wherein $R_Z$ is H or $C_1$-$C_6$ alkyl;

$R_1$ is —OH, —$NH_2$, —NH($C_1$-$C_6$ alkyl), —N($C_1$-$C_6$ alkyl)$_2$, —SH, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A1}$;

each $R_{A1}$ independently is $Ar_2$, halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is absent or $Ar_2$;

each $Ar_2$ independently is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

In some aspects, the present disclosure provides a compound obtainable by, or obtained by, a method for preparing a compound as described herein (e.g., a method comprising one or more steps described in Schemes 1-5).

In some aspects, the present disclosure provides a pharmaceutical composition comprising a compound of the present disclosure, or a pharmaceutically acceptable salt thereof, and a pharmaceutically acceptable diluent or carrier.

In some aspects, the present disclosure provides an intermediate as described herein, being suitable for use in a method for preparing a compound as described herein (e.g., the intermediate is selected from the intermediates described in Examples 1-37).

In some aspects, the present disclosure provides a method of modulating orexin-2 receptor activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in modulating orexin-2 receptor activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for modulating orexin-2 receptor activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTION OF THE SEVERAL VIEWS OF THE DRAWING

Not Applicable

DETAILED DESCRIPTION OF THE INVENTION

The present disclosure relates to macrocyclic ([1,1'-biphenyl]-3-ylmethyl)-substituted heterocycle derivatives, prodrugs, and pharmaceutically acceptable salts thereof, which may modulate orexin-2 receptor activity and are accordingly useful in methods of treatment of the human or animal body. The present disclosure also relates to processes for the preparation of these compounds, to pharmaceutical compositions comprising them and to their use in the treatment of disorders in which the orexin-2 receptor is implicated, such as narcolepsy, a neurodegenerative disorder, a symptom of a rare genetic disorder, a mental health disorder, a metabolic syndrome, osteoporosis, cardiac failure, coma, or emergence from anesthesia.

DEFINITIONS

Unless otherwise stated, the following terms used in the specification and claims have the following meanings set out below.

Without wishing to be limited by this statement, it is understood that, while various options for variables are described herein, the disclosure intends to encompass operable embodiments having combinations of the options. The disclosure may be interpreted as excluding the non-operable embodiments caused by certain combinations of the options. For example, while various options for variables X, L, and Y are described herein, the disclosure may be interpreted as excluding structures for non-operable compound caused by certain combinations of variables X, L, and Y (e.g., when each of X, L, and Y is —O—).

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

It is understood that when a variable has two attachments to the rest of the formula of the compound, the two attachments could be at the same atom or different atoms of the variable. For example, when a variable (e.g., variable X) is cycloalkyl or heterocycloalkyl, and has two attachments to the rest of the formula of the compound, the two attachments could be at the same atom or different atoms of the cycloalkyl or heterocycloalkyl.

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidised (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, isothiazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl). In some embodiments, the heteroaryl is thiophenyl or benzothiophenyl. In some embodiments, the heteroaryl is thiophenyl. In some embodiments, the heteroaryl benzothiophenyl.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O—.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; Greene, T. W., Wuts, P. G. M., *Protective Groups in Organic Synthesis,* $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for organic Synthesis,* John Wiley and Sons (1994); and L. Paquette, ed., *Encyclopedia of Reagents for organic Synthesis,* John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* $3^{rd}$ edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models.

As used herein, the term "subject" includes human and non-human animals, as well as cell lines, cell cultures, tissues, and organs. In some embodiments, the subject is a mammal. The mammal can be e.g., a human or appropriate non-human mammal, such as primate, mouse, rat, dog, cat, cow, horse, goat, camel, sheep or a pig. The subject can also be a bird or fowl. In some embodiments, the subject is a human.

As used herein, the term "subject in need thereof" refers to a subject having a disease or having an increased risk of developing the disease. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology,* John Wiley & Sons, N.Y.; Enna et al., *Current Protocols in Pharmacology*, John Wiley & Sons, N.Y.; Fingl et al., The Pharmacological Basis of Therapeutics (1975), *Remington's Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, the term "therapeutically effective amount", refers to an amount of a pharmaceutical agent to treat or ameliorate an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), cyclodextrins and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, capsules or sachets. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, orange flavoring.

For administration by inhalation, the compounds are delivered in the form of an aerosol spray from pressured container or dispenser, which contains a suitable propellant, e.g., a gas such as carbon dioxide, or a nebuliser.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, powders or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral organic acid salts of basic residues such as amines, alkali organic salts of acidic residues such as carboxylic acids, and the like. The pharmaceutically acceptable salts include the conventional non-toxic salts or the quaternary ammonium salts of the parent compound formed, for example, from non-toxic inorganic organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in *Remington: the Science and Practice of Pharmacy,* $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

COMPOUNDS OF THE PRESENT DISCLOSURE

In some aspects, the present disclosure provides a compound of Formula (I'):

(I')

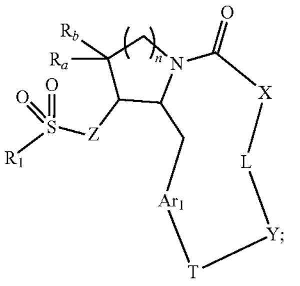

or a pharmaceutically acceptable salt thereof, wherein:

X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6;

Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

n is an integer ranging from 0 to 3;

$R_a$ and $R_b$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_S$; or $R_a$ and $R_b$, together with the atom to which they attach, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_S$;

each $R_S$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

Z is —O— or —$NR_Z$—; wherein $R_Z$ is H or $C_1$-$C_6$ alkyl;

$R_1$ is —OH, —$NH_2$, —NH($C_1$-$C_6$ alkyl), —N($C_1$-$C_6$ alkyl)$_2$, —SH, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A1}$;

each $R_{A1}$ independently is $Ar_2$, halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is absent or $Ar_2$;

each $Ar_2$ independently is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

In some aspects, the present disclosure provides a compound of Formula (I):

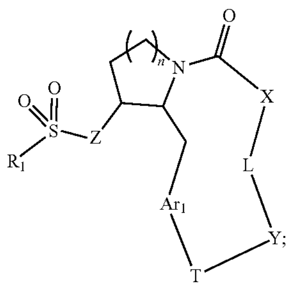

(I)

or a pharmaceutically acceptable salt thereof, wherein:

X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6;

Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

n is an integer ranging from 0 to 3;

Z is —O— or —$NR_Z$—; wherein $R_Z$ is H or $C_1$-$C_6$ alkyl;

$R_1$ is —OH, —$NH_2$, —NH($C_1$-$C_6$ alkyl), —N($C_1$-$C_6$ alkyl)$_2$, —SH, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A1}$;

each $R_{A1}$ independently is $Ar_2$, halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is absent or $Ar_2$;

each $Ar_2$ independently is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

In some aspects, the present disclosure provides a compound of Formula (I) or a pharmaceutically acceptable salt thereof, wherein:

X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6;

Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

n is an integer ranging from 0 to 3;

Z is —O— or —$NR_Z$—; wherein $R_Z$ is H or $C_1$-$C_6$ alkyl;

$R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more $R_{1S}$;

each $R_{1S}$ independently is halogen, —CN, —OH, or $C_1$-$C_6$ alkoxy;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A1}$;

each $R_{A1}$ independently is $Ar_2$, halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is absent or $Ar_2$;

each $Ar_2$ independently is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

In some aspects, the present disclosure provides a compound of Formula (I) or a pharmaceutically acceptable salt thereof, wherein:

X is —O—, —NH—, —N($C_1$-$C_6$ alkyl)-, or $C_1$-$C_6$ alkyl;

L is absent or $C_1$-$C_6$ alkyl;

Y is —O— or $C_1$-$C_6$ alkyl;

n is an integer ranging from 0 to 3;

Z is —$NR_Z$—; wherein $R_Z$ is H or $C_1$-$C_6$ alkyl;

$R_1$ is $C_1$-$C_6$ alkyl;

$Ar_1$ is $C_6$-$C_{10}$ aryl optionally substituted with one or more $Ar_2$;

T is absent or $Ar_2$; and each $Ar_2$ independently is $C_6$-$C_{10}$ aryl.

In some aspects, the present disclosure provides a compound of Formula (I) or a pharmaceutically acceptable salt thereof, wherein:

X is —O—, —NH—, —N($C_1$-$C_6$ alkyl)-, or $C_1$-$C_6$ alkyl;

L is absent or $C_1$-$C_6$ alkyl;

Y is —O— or $C_1$-$C_6$ alkyl;

n is an integer ranging from 0 to 3;

Z is —$NR_Z$—; wherein $R_Z$ is H or $C_1$-$C_6$ alkyl;

$R_1$ is $C_1$-$C_6$ alkyl;

$Ar_1$ is $C_6$-$C_{10}$ aryl;

T is $C_6$-$C_{10}$ aryl.

In some aspects, the present disclosure provides a compound of Formula (I) or a pharmaceutically acceptable salt thereof, wherein:

X is —O—, —NH—, —N($C_1$-$C_6$ alkyl)-, or $C_1$-$C_6$ alkyl;

L is absent or $C_1$-$C_6$ alkyl;

Y is —O— or $C_1$-$C_6$ alkyl;

n is an integer ranging from 0 to 3;

Z is —$NR_Z$—; wherein $R_Z$ is H or $C_1$-$C_6$ alkyl;

$R_1$ is $C_1$-$C_6$ alkyl;

$Ar_1$ is $C_6$-$C_{10}$ aryl optionally substituted with one or more $C_6$-$C_{10}$ aryl; and T is absent.

In some aspects, the present disclosure provides a compound of Formula (I) or a pharmaceutically acceptable salt thereof, wherein:

X is —O—, —NH—, —N($C_1$-$C_6$ alkyl)-, or $C_1$-$C_6$ alkyl;

L is absent or $C_1$-$C_6$ alkyl;

Y is —O— or $C_1$-$C_6$ alkyl;

n is 2;

Z is —$NR_Z$—; wherein $R_Z$ is H or $C_1$-$C_6$ alkyl;

$R_1$ is —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more $R_{1S}$ and $C_1$-$C_6$ alkyl is substituted with one or more $R_{1S}$;

each $R_{1S}$ independently is halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$Ar_1$ is $C_6$-$C_{10}$ aryl optionally substituted with one or more $R_{A1}$;

each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is $Ar_2$;

$Ar_2$ is $C_6$-$C_{10}$ aryl optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

It is understood that, for a compound of the present disclosure, variables X, L, nl, Y, n, $R_a$, $R_b$, Z, $R_Z$, $R_1$, $R_{1S}$, $Ar_1$, $R_{A1}$, T, $Ar_2$, and $R_{A2}$ can each be, where applicable, selected from the groups described herein, and any group described herein for any of variables X, L, nl, Y, n, $R_a$, $R_b$, Z, $R_Z$, $R_1$, $R_{1S}$, $Ar_1$, $R_{A1}$, T, $Ar_2$, and $R_{A2}$ can be combined, where applicable, with any group described herein for one or more of the remainder of variables X, L, nl, Y, n, $R_a$, $R_b$, Z, $R_Z$, $R_1$, $R_{1S}$, $Ar_1$, $R_{A1}$, T, $Ar_2$, and $R_{A2}$.

Variable X

In some embodiments, X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is —O—.

In some embodiments, X is —NH— or —N($C_1$-$C_6$ alkyl)-, wherein the —N($C_1$-$C_6$ alkyl)- is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is —NH—.

In some embodiments, X is —N($C_1$-$C_6$ alkyl)- optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is —N($C_1$-$C_6$ alkyl)- optionally substituted with one or more halogen or —OH.

In some embodiments, X is —N($C_1$-$C_6$ alkyl)- optionally substituted with one or more F or —OH.

In some embodiments, X is —N($C_1$-$C_6$ alkyl)-.

In some embodiments, X is —N($CH_3$)—.

In some embodiments, X is —N($C_1$-$C_6$ alkyl)- substituted with one or more halogen or —OH.

In some embodiments, X is —N($C_1$-$C_6$ alkyl)- substituted with one or more F or —OH.

In some embodiments, X is —N($C_1$-$C_6$ alkyl)- substituted with at least one F and at least one —OH.

In some embodiments, X is —N($C_1$-$C_6$ alkyl)- substituted with one to three F and one —OH.

In some embodiments, X is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_1$-$C_6$ alkyl (e.g., methyl, ethyl, or propyl) optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_1$-$C_6$ alkyl (e.g., methyl, ethyl, or propyl) optionally substituted with one or more halogen, —CN, —OH, —$NH_2$, —NH($C_1$-$C_6$ alkyl), or —N($C_1$-$C_6$ alkyl)$_2$.

In some embodiments, X is $C_1$-$C_6$ alkyl (e.g., methyl, ethyl, or propyl) optionally substituted with one or more halogen (e.g., F).

In some embodiments, X is $C_1$-$C_6$ alkyl (e.g., methyl, ethyl, or propyl) optionally substituted with one or more $C_1$-$C_6$ haloalkyl.

In some embodiments, X is $C_1$-$C_6$ alkyl (e.g., methyl, ethyl, or propyl) optionally substituted with one or more $C_1$-$C_6$ alkoxy.

In some embodiments, X is $C_1$-$C_6$ alkyl (e.g., methyl, ethyl, or propyl).

In some embodiments, X is $C_1$-$C_6$ alkyl (e.g., methyl, ethyl, or propyl) substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_1$-$C_6$ alkyl (e.g., methyl, ethyl, or propyl) substituted with one or more halogen, —CN, —OH, —$NH_2$, —NH($C_1$-$C_6$ alkyl), or —N($C_1$-$C_6$ alkyl)$_2$.

In some embodiments, X is $C_1$-$C_6$ alkyl (e.g., methyl, ethyl, or propyl) substituted with one or more halogen (e.g., F).

In some embodiments, X is $C_1$-$C_6$ alkyl (e.g., methyl, ethyl, or propyl) substituted with one or more $C_1$-$C_6$ haloalkyl.

In some embodiments, X is $C_1$-$C_6$ alkyl (e.g., methyl, ethyl, or propyl) substituted with one or more $C_1$-$C_6$ alkoxy.

In some embodiments, X is $C_3$-$C_8$ cycloalkyl, $C_6$-$C_{10}$ aryl, 3- to 8-membered heterocycloalkyl, or 5- to 10-membered heteroaryl, wherein the $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_3$-$C_8$ cycloalkyl (e.g., cyclopropyl, cyclobutyl, cyclopentyl, or cyclohexyl) optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_3$-$C_8$ cycloalkyl (e.g., cyclopropyl, cyclobutyl, cyclopentyl, or cyclohexyl).

In some embodiments, X is $C_3$-$C_8$ cycloalkyl (e.g., cyclopropyl, cyclobutyl, cyclopentyl, or cyclohexyl)substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_6$-$C_{10}$ aryl optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_6$-$C_{10}$ aryl.

In some embodiments, X is $C_6$-$C_{10}$ aryl substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is 3- to 8-membered heterocycloalkyl (e.g., azetidinyl, pyrrolidinyl, or piperidinyl) optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is 3- to 8-membered heterocycloalkyl (e.g., acetidinyl, pyrrolidinyl, or piperidinyl).

In some embodiments, X is 3- to 8-membered heterocycloalkyl (e.g., acetidinyl, pyrrolidinyl, or piperidinyl) substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is acetidinyl (e.g., 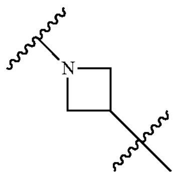 or 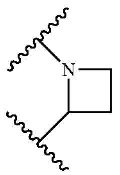)

optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is acetidinyl (e.g., 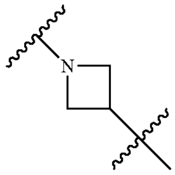 or 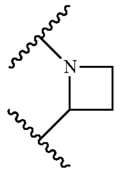).

In some embodiments, X is acetidinyl (e.g., 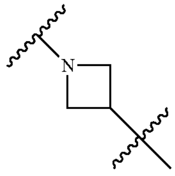 or 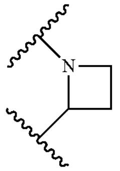)

substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is 5- to 10-membered heteroaryl optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is 5- to 10-membered heteroaryl.

In some embodiments, X is 5- to 10-membered heteroaryl substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Variable L and nl

In some embodiments, L is absent.

In some embodiments, L is —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$.

In some embodiments, L is —O—.

In some embodiments, L is —NH— or —N($C_1$-$C_6$ alkyl)-, wherein the —N($C_1$-$C_6$ alkyl)- is optionally substituted with one or more halogen, —CN, —OH, —$NH_2$, —NH($C_1$-$C_6$ alkyl), or —N($C_1$-$C_6$ alkyl)$_2$.

In some embodiments, L is —NH—.

In some embodiments, L is —N($C_1$-$C_6$ alkyl)- optionally substituted with one or more halogen, —CN, —OH, —$NH_2$, —NH($C_1$-$C_6$ alkyl), or —N($C_1$-$C_6$ alkyl)$_2$.

In some embodiments, L is —N($C_1$-$C_6$ alkyl)-.

In some embodiments, L is —N($C_1$-$C_6$ alkyl)- substituted with one or more halogen, —CN, —OH, —$NH_2$, —NH($C_1$-$C_6$ alkyl), or —N($C_1$-$C_6$ alkyl)$_2$.

In some embodiments, L is $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$.

In some embodiments, L is $C_1$-$C_6$ alkyl or $C_2$-$C_6$ alkenyl, wherein the $C_1$-$C_6$ alkyl or $C_2$-$C_6$ alkenyl is optionally substituted with one or more halogen, —CN, —OH, —$NH_2$, —NH($C_1$-$C_6$ alkyl), or —N($C_1$-$C_6$ alkyl)$_2$.

In some embodiments, L is $C_1$-$C_6$ alkyl (e.g., methyl, ethyl, or propyl) optionally substituted with one or more halogen, —CN, —OH, —$NH_2$, —NH($C_1$-$C_6$ alkyl), or —N($C_1$-$C_6$ alkyl)$_2$.

In some embodiments, L is $C_1$-$C_6$ alkyl (e.g., methyl, ethyl, or propyl).

In some embodiments, L is $C_1$-$C_6$ alkyl (e.g., methyl, ethyl, or propyl) substituted with one or more halogen, —CN, —OH, —$NH_2$, —NH($C_1$-$C_6$ alkyl), or —N($C_1$-$C_6$ alkyl)$_2$.

In some embodiments, L is $C_2$-$C_6$ alkenyl optionally substituted with one or more halogen, —CN, —OH, —$NH_2$, —NH($C_1$-$C_6$ alkyl), or —N($C_1$-$C_6$ alkyl)$_2$.

In some embodiments, L is $C_2$-$C_6$ alkenyl.

In some embodiments, L is $C_2$-$C_6$ alkenyl substituted with one or more halogen, —CN, —OH, —$NH_2$, —NH($C_1$-$C_6$ alkyl), or —N($C_1$-$C_6$ alkyl)$_2$.

In some embodiments, L is —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_1$-$C_6$ alkyl)-O)$_{nl}$— or —(O—($C_1$-$C_6$ alkyl))$_{nl}$-, wherein the —(($C_1$-$C_6$ alkyl)-O)$_{nl}$— or —(O—($C_1$-$C_6$ alkyl))$_{nl}$- is optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_1$-$C_6$ alkyl)-O)$_{nl}$— optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_1$-$C_6$ alkyl)-O)$_{nl}$—.

In some embodiments, L is —(($C_1$-$C_6$ alkyl)-O)$_{nl}$— substituted with one or more halogen, —CN, —OH, —$NH_2$, —NH($C_1$-$C_6$ alkyl), or —N($C_1$-$C_6$ alkyl)$_2$.

In some embodiments, L is —(O—($C_1$-$C_6$ alkyl))$_{nl}$- optionally substituted with one or more halogen, —CN, —OH, —$NH_2$, —NH($C_1$-$C_6$ alkyl), or —N($C_1$-$C_6$ alkyl)$_2$.

In some embodiments, L is —(O—($C_1$-$C_6$ alkyl))$_{nl}$-.

In some embodiments, L is —(O—($C_1$-$C_6$ alkyl))$_{nl}$- substituted with one or more halogen, —CN, —OH, —$NH_2$, —NH($C_1$-$C_6$ alkyl), or —N($C_1$-$C_6$ alkyl)$_2$.

In some embodiments, L is —(($C_2$-$C_6$ alkenyl)-O)$_{nl}$— or —(O—($C_2$-$C_6$ alkenyl))$_{nl}$-, wherein the —(($C_2$-$C_6$ alkenyl)-O)$_{nl}$— or —(O—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_2$-$C_6$ alkenyl)-O)$_{nl}$— optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_2$-$C_6$ alkenyl)-O)$_{nl}$—.

In some embodiments, L is —(($C_2$-$C_6$ alkenyl)-O)$_{nl}$— substituted with one or more halogen, —CN, —OH, —$NH_2$, —NH($C_1$-$C_6$ alkyl), or —N($C_1$-$C_6$ alkyl)$_2$.

In some embodiments, L is —(O—($C_2$-$C_6$ alkenyl))$_{nl}$- optionally substituted with one or more halogen, —CN, —OH, —$NH_2$, —NH($C_1$-$C_6$ alkyl), or —N($C_1$-$C_6$ alkyl)$_2$.

In some embodiments, L is —(O—($C_2$-$C_6$ alkenyl))$_{nl}$-.

In some embodiments, L is —(O—($C_2$-$C_6$ alkenyl))$_{nl}$- substituted with one or more halogen, —CN, —OH, —$NH_2$, —NH($C_1$-$C_6$ alkyl), or —N($C_1$-$C_6$ alkyl)$_2$.

In some embodiments, L is —(($C_1$-$C_6$ alkyl)-NH)$_{nl}$— or —(NH—($C_1$-$C_6$ alkyl))$_{nl}$-, wherein the —(($C_1$-$C_6$ alkyl)-NH)$_{nl}$— or —(NH—($C_1$-$C_6$ alkyl))$_{nl}$- is optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_1$-$C_6$ alkyl)-NH)$_{nl}$— optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_1$-$C_6$ alkyl)-NH)$_{nl}$—.

In some embodiments, L is —(($C_1$-$C_6$ alkyl)-NH)$_{nl}$— substituted with one or more halogen, —CN, —OH, —$NH_2$, —NH($C_1$-$C_6$ alkyl), or —N($C_1$-$C_6$ alkyl)$_2$.

In some embodiments, L is —(NH—($C_1$-$C_6$ alkyl))$_{nl}$- optionally substituted with one or more halogen, —CN, —OH, —$NH_2$, —NH($C_1$-$C_6$ alkyl), or —N($C_1$-$C_6$ alkyl)$_2$.

In some embodiments, L is —(NH—($C_1$-$C_6$ alkyl))$_{nl}$-.

In some embodiments, L is —(NH—($C_1$-$C_6$ alkyl))$_{nl}$- substituted with one or more halogen, —CN, —OH, —$NH_2$, —NH($C_1$-$C_6$ alkyl), or —N($C_1$-$C_6$ alkyl)$_2$.

In some embodiments, L is —(($C_2$-$C_6$ alkenyl)-NH)$_{nl}$— or —(NH—($C_2$-$C_6$ alkenyl))$_{nl}$-, wherein the —(($C_2$-$C_6$ alkenyl)-NH)$_{nl}$— or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_2$-$C_6$ alkenyl)-NH)$_{nl}$— optionally substituted with one or more halogen, —CN, —OH, —$NH_2$, —NH($C_1$-$C_6$ alkyl), or —N($C_1$-$C_6$ alkyl)$_2$.

In some embodiments, L is —(($C_2$-$C_6$ alkenyl)-NH)$_{nl}$—.

In some embodiments, L is —(($C_2$-$C_6$ alkenyl)-NH)$_{nl}$— substituted with one or more halogen, —CN, —OH, —$NH_2$, —NH($C_1$-$C_6$ alkyl), or —N($C_1$-$C_6$ alkyl)$_2$.

In some embodiments, L is —(NH—($C_2$-$C_6$ alkenyl))$_{nl}$- optionally substituted with one or more halogen, —CN, —OH, —$NH_2$, —NH($C_1$-$C_6$ alkyl), or —N($C_1$-$C_6$ alkyl)$_2$.

In some embodiments, L is —(NH—($C_2$-$C_6$ alkenyl))$_{nl}$-.

In some embodiments, L is —(NH—($C_2$-$C_6$ alkenyl))$_{nl}$- substituted with one or more halogen, —CN, —OH, —$NH_2$, —NH($C_1$-$C_6$ alkyl), or —N($C_1$-$C_6$ alkyl)$_2$.

In some embodiments, nl is an integer ranging from 1 to 6.

In some embodiments, nl is 6.

In some embodiments, nl is an integer ranging from 1 to 5.

In some embodiments, nl is 5.

In some embodiments, nl is an integer ranging from 1 to 4.

In some embodiments, nl is 4.

In some embodiments, nl is an integer ranging from 1 to 3.

In some embodiments, nl is 1. In some embodiments, nl is 2. In some embodiments, nl is 3.

Variable Y

In some embodiments, Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, Y is —O—.

In some embodiments, Y is —NH— or —N($C_1$-$C_6$ alkyl)-, wherein the —N($C_1$-$C_6$ alkyl)- is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, Y is —NH—.

In some embodiments, —N($C_1$-$C_6$ alkyl)- optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, —N($C_1$-$C_6$ alkyl)-.

In some embodiments, —N($C_1$-$C_6$ alkyl)- substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, Y is $C_1$-$C_6$ alkyl or $C_2$-$C_6$ alkenyl, wherein the $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, Y is $C_1$-$C_6$ alkyl (e.g., methyl, ethyl, or propyl) optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, Y is $C_1$-$C_6$ alkyl (e.g., methyl, ethyl, or propyl).

In some embodiments, Y is $C_1$-$C_6$ alkyl (e.g., methyl, ethyl, or propyl) substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, Y is $C_2$-$C_6$ alkenyl optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, Y is $C_2$-$C_6$ alkenyl.

In some embodiments, Y is $C_2$-$C_6$ alkenyl substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiments of Variables X L, And Y

In some embodiments, at most one of X and L is —O—, —NH—, or optionally substituted —N($C_1$-$C_6$ alkyl)-.

In some embodiments, at most one of L and Y is —O—, —NH—, or optionally substituted —N($C_1$-$C_6$ alkyl)-.

In some embodiments, at most one of X and Y is —O—, —NH—, or optionally substituted —N($C_1$-$C_6$ alkyl)-.

In some embodiments, at most two of X, L, and Y are —O—, —NH—, or optionally substituted —N($C_1$-$C_6$ alkyl)-.

In some embodiments, at most one of X, L, and Y is —O—, —NH—, or optionally substituted —N($C_1$-$C_6$ alkyl)-.

In some embodiments, when X is —O—, —NH—, or optionally substituted —N($C_1$-$C_6$ alkyl)-, and Y is —O—, —NH—, or optionally substituted —N($C_1$-$C_6$ alkyl)-, then L is not absent, —O—, —NH—, or optionally substituted —N($C_1$-$C_6$ alkyl)-.

In some embodiments, X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6; and Y is $C_1$-$C_6$ alkyl or $C_2$-$C_6$ alkenyl, wherein the $C_1$-$C_6$ alkyl or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$—$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6; and Y is $C_1$-$C_6$ alkyl or $C_2$-$C_6$ alkenyl, wherein the $C_1$-$C_6$ alkyl or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6; and Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

In some embodiments, X is —O—, —NH—, —N($C_1$-$C_6$ alkyl)-, or $C_1$-$C_6$ alkyl; L is absent or $C_1$-$C_6$ alkyl; and Y is —O— or $C_1$-$C_6$ alkyl.

In some embodiments, X is —O—, —NH—, or —N($C_1$-$C_6$ alkyl)-; L is $C_1$-$C_6$ alkyl; and Y is —O—.

In some embodiments, X is $C_1$-$C_6$ alkyl; L is absent; and Y is $C_1$-$C_6$ alkyl.

Variable n

In some embodiments, n is an integer ranging from 0 to 3.

In some embodiments, n is 0. In some embodiments, n is 1. In some embodiments, n is 2.

In some embodiments, n is 3.

Variables $R_a$, $R_b$, and $R_S$

In some embodiments, $R_a$ and $R_b$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_S$; or $R_a$ and $R_b$, together with the atom to which they attach, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_S$.

In some embodiments, one of $R_a$ and $R_b$ is H, and one of $R_a$ and $R_b$ is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_S$; or $R_a$ and $R_b$, together with the atom to which they attach, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_S$.

In some embodiments, $R_a$ is H, and $R_b$ is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_S$; or $R_a$ and $R_b$, together with the atom to which they attach, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_S$.

In some embodiments, $R_a$ and $R_b$ each independently are H or halogen; or $R_a$ and $R_b$, together with the atom to which they attach, form $C_3$-$C_7$ cycloalkyl optionally substituted with one or more $R_S$.

In some embodiments, $R_a$ and $R_b$ each independently are H or halogen; or $R_a$ and $R_b$, together with the atom to which they attach, form $C_3$-$C_7$ cycloalkyl.

In some embodiments, $R_a$ and $R_b$ each independently are H or halogen; or $R_a$ and $R_b$, together with the atom to which they attach, form cyclopropyl optionally substituted with one or more $R_S$.

In some embodiments, $R_a$ and $R_b$ each independently are H or halogen; or $R_a$ and $R_b$, together with the atom to which they attach, form cyclopropyl.

In some embodiments, $R_a$ and $R_b$ each independently are H or halogen.

In some embodiments, at least one of $R_a$ and $R_b$ is H.

In some embodiments, one of $R_a$ and $R_b$ is H.

In some embodiments, $R_a$ and $R_b$ each are H.

In some embodiments, $R_a$ and $R_b$ each independently are halogen.

In some embodiments, $R_a$ and $R_b$ each independently are F or Cl.

In some embodiments, at least one of $R_a$ and $R_b$ is halogen.

In some embodiments, at least one of $R_a$ and $R_b$ is F or Cl.

In some embodiments, one of $R_a$ and $R_b$ is H, and one of $R_a$ and $R_b$ is halogen (e.g., F or Cl).

In some embodiments, $R_a$ is H, and $R_b$ is halogen (e.g., F or Cl).

In some embodiments, at least one of $R_a$ and $R_b$ is —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_S$.

In some embodiments, at least one of $R_a$ and $R_b$ is —CN.

In some embodiments, at least one of $R_a$ and $R_b$ is —OH or —O($C_1$-$C_6$ alkyl), wherein the —O($C_1$-$C_6$ alkyl) is optionally substituted with one or more $R_S$.

In some embodiments, at least one of $R_a$ and $R_b$ is —$NH_2$, —NH($C_1$-$C_6$ alkyl), or —N($C_1$-$C_6$ alkyl)$_2$, wherein the —NH($C_1$-$C_6$ alkyl) or —N($C_1$-$C_6$ alkyl)$_2$ is optionally substituted with one or more $R_S$.

In some embodiments, at least one of $R_a$ and $R_b$ is $C_1$-$C_6$ alkyl, $C_2$-$C_6$ alkenyl, or $C_2$-$C_6$, wherein the $C_1$-$C_6$ alkyl, $C_2$-$C_6$ alkenyl, or $C_2$-$C_6$ alkynyl is optionally substituted with one or more $R_S$.

In some embodiments, $R_a$ and $R_b$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_S$.

In some embodiments, $R_a$ and $R_b$, together with the atom they attach to, form $C_3$-$C_7$ cycloalkyl or 3- to 7-membered heterocycloalkyl.

In some embodiments, $R_a$ and $R_b$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is substituted with one or more $R_S$.

In some embodiments, $R_a$ and $R_b$, together with the atom they attach to, form $C_3$-$C_7$ cycloalkyl optionally substituted with one or more $R_S$.

In some embodiments, $R_a$ and $R_b$, together with the atom they attach to, form $C_3$-$C_7$ cycloalkyl.

In some embodiments, $R_a$ and $R_b$, together with the atom they attach to, form $C_3$-$C_7$ cycloalkyl substituted with one or more $R_S$.

In some embodiments, $R_a$ and $R_b$, together with the atom they attach to, form cyclopropyl optionally substituted with one or more $R_S$.

In some embodiments, $R_a$ and $R_b$, together with the atom they attach to, form cyclopropyl.

In some embodiments, $R_a$ and $R_b$, together with the atom they attach to, form cyclopropyl substituted with one or more $R_S$.

In some embodiments, $R_a$ and $R_b$, together with the atom they attach to, form 3- to 7-membered heterocycloalkyl optionally substituted with one or more $R_S$.

In some embodiments, $R_a$ and $R_b$, together with the atom they attach to, form 3- to 7-membered heterocycloalkyl.

In some embodiments, $R_a$ and $R_b$, together with the atom they attach to, form 3- to 7-membered heterocycloalkyl substituted with one or more $R_S$.

In some embodiments, at least one $R_S$ is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl.

In some embodiments, at least one $R_S$ is halogen or —CN

In some embodiments, at least one $R_S$ is —OH or —O($C_1$-$C_6$ alkyl).

In some embodiments, at least one $R_S$ is —$NH_2$, —NH ($C_1$-$C_6$ alkyl), or —N($C_1$-$C_6$ alkyl)$_2$.

In some embodiments, at least one $R_S$ is $C_1$-$C_6$ alkyl, $C_2$-$C_6$ alkenyl, $C_2$-$C_6$ alkynyl, or $C_1$-$C_6$ haloalkyl.

Variables Z and $R_Z$

In some embodiments, Z is —O— or —$NR_Z$—; wherein $R_Z$ is H or $C_1$-$C_6$ alkyl;

In some embodiments, Z is —O—. In some embodiments, Z is —$NR_Z$—. In some embodiments, Z is —NH—. In some embodiments, Z is —N($C_1$-$C_6$ alkyl)-. In some embodiments, $R_Z$ is H. In some embodiments, $R_Z$ is $C_1$-$C_6$ alkyl (e.g., methyl, ethyl, or propyl).

Variable $R_1$ and $R_{1S}$

In some embodiments, $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more $R_{1S}$.

In some embodiments, $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more halogen, —CN, —OH, or $C_1$-$C_6$ alkoxy.

In some embodiments, $R_1$ is —OH.

In some embodiments, $R_1$ is —$NH_2$, —NH($C_1$-$C_6$ alkyl), or —N($C_1$-$C_6$ alkyl)$_2$, wherein the —NH($C_1$-$C_6$ alkyl), or —N($C_1$-$C_6$ alkyl)$_2$ is optionally substituted with one or more $R_{1S}$.

In some embodiments, $R_1$ is —$NH_2$.

In some embodiments, $R_1$ is —NH($C_1$-$C_6$ alkyl) optionally substituted with one or more $R_{1S}$.

In some embodiments, $R_1$ is —N($C_1$-$C_6$ alkyl)$_2$ optionally substituted with one or more $R_{1S}$.

In some embodiments, $R_1$ is —SH, —S($C_1$-$C_6$ alkyl), or —S($C_6$-$C_{10}$ aryl), wherein the —S($C_1$-$C_6$ alkyl) or —S($C_6$-$C_{10}$ aryl) is optionally substituted with one or more $R_{1S}$.

In some embodiments, $R_1$ is —SH.

In some embodiments, $R_1$ —S($C_1$-$C_6$ alkyl) or —S($C_6$-$C_{10}$ aryl), wherein the —S($C_1$-$C_6$ alkyl) or —S($C_6$-$C_{10}$ aryl) is optionally substituted with one or more $R_{1S}$.

In some embodiments, $R_1$ —S($C_1$-$C_6$ alkyl) optionally substituted with one or more $R_{1S}$.

In some embodiments, $R_1$ —S($C_1$-$C_6$ alkyl).

In some embodiments, $R_1$ —S($C_1$-$C_6$ alkyl) substituted with one or more $R_{1S}$.

In some embodiments, $R_1$ is —S($C_6$-$C_{10}$ aryl) optionally substituted with one or more $R_{1S}$.

In some embodiments, $R_1$ is —S($C_6$-$C_{10}$ aryl).

In some embodiments, $R_1$ is —S($C_6$-$C_{10}$ aryl) substituted with one or more $R_{1S}$.

In some embodiments, $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, or 3- to 7-membered heterocycloalkyl, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, or 3- to 7-membered heterocycloalkyl is optionally substituted with one or more $R_{1S}$.

In some embodiments, $R_1$ is $C_1$-$C_6$ alkyl (e.g., methyl, ethyl, or propyl) optionally substituted with one or more $R_{1S}$.

In some embodiments, $R_1$ is $C_1$-$C_6$ alkyl (e.g., methyl, ethyl, or propyl).

In some embodiments, $R_1$ is methyl.

In some embodiments, $R_1$ is ethyl.

In some embodiments, $R_1$ is propyl.

In some embodiments, $R_1$ is $C_1$-$C_6$ alkyl (e.g., methyl, ethyl, or propyl) substituted with one or more $R_{1S}$.

In some embodiments, $R_1$ is methyl substituted with one or more $R_{1S}$.

In some embodiments, $R_1$ is ethyl substituted with one or more $R_{1S}$.

In some embodiments, $R_1$ is propyl substituted with one or more $R_{1S}$.

In some embodiments, $R_1$ is $C_2$-$C_6$ alkenyl optionally substituted with one or more $R_{1S}$.

In some embodiments, $R_1$ is $C_2$-$C_6$ alkynyl optionally substituted with one or more $R_{1S}$.

In some embodiments, $R_1$ is $C_1$-$C_6$ haloalkyl optionally substituted with one or more $R_{1S}$.

In some embodiments, $R_1$ is $C_1$-$C_6$ alkoxy optionally substituted with one or more $R_{1S}$.

In some embodiments, $R_1$ is $C_6$-$C_{10}$ aryl optionally substituted with one or more $R_{1S}$.

In some embodiments, $R_1$ is 5- to 10-membered heteroaryl optionally substituted with one or more $R_{1S}$.

In some embodiments, $R_1$ is $C_3$-$C_7$ cycloalkyl optionally substituted with one or more $R_{1S}$.

In some embodiments, $R_1$ is $C_3$-$C_7$ cycloalkyl optionally substituted with one or more $R_{1S}$.

In some embodiments, $R_1$ is cyclopropyl optionally substituted with one or more $R_{1S}$.

In some embodiments, $R_1$ is cyclopropyl optionally substituted with one or more halogen.

In some embodiments, $R_1$ is cyclopropyl optionally substituted with one or more F.

In some embodiments, $R_1$ is 3- to 7-membered heterocycloalkyl optionally substituted with one or more $R_{1S}$.

In some embodiments, $R_1$ is —O—($C_6$-$C_{10}$ aryl), —O-(5- to 10-membered heteroaryl), —O—($C_3$-$C_{10}$ cycloalkyl), or —O-(3- to 7-membered heterocycloalkyl), wherein the —O—($C_6$-$C_{10}$ aryl), —O-(5- to 10-membered heteroaryl), —O—($C_3$-$C_{10}$ cycloalkyl), or —O-(3- to 7-membered heterocycloalkyl) is optionally substituted with one or more $R_{1S}$.

In some embodiments, $R_1$ is —O—($C_6$-$C_{10}$ aryl) optionally substituted with one or more $R_{1S}$.

In some embodiments, $R_1$ is —O-(5- to 10-membered heteroaryl) optionally substituted with one or more $R_{1S}$.

In some embodiments, $R_1$ is —O—($C_3$-$C_{10}$ cycloalkyl) optionally substituted with one or more $R_{1S}$.

In some embodiments, $R_1$ is —O-(3- to 7-membered heterocycloalkyl) optionally substituted with one or more $R_{1S}$.

In some embodiments, $R_1$ is —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$.

In some embodiments, $R_1$ is —NH—($C_6$-$C_{10}$ aryl) optionally substituted with one or more $R_{1S}$.

In some embodiments, $R_1$ is —NH-(5- to 10-membered heteroaryl) optionally substituted with one or more $R_{1S}$.

In some embodiments, $R_1$ is —NH—($C_3$-$C_{10}$ cycloalkyl) optionally substituted with one or more $R_{1S}$.

In some embodiments, $R_1$ is —NH-(3- to 7-membered heterocycloalkyl) optionally substituted with one or more $R_{1S}$.

In some embodiments, at least one $R_{1S}$ is halogen (e.g., F), —CN, —OH, or $C_1$-$C_6$ alkoxy.

In some embodiments, at least one $R_{1S}$ is oxo.

In some embodiments, at least one $R_{1S}$ is halogen (e.g., F, Cl, or Br).

In some embodiments, at least one $R_{1S}$ is F. In some embodiments, at least one $R_{1S}$ is Cl.

In some embodiments, at least one $R_{1S}$ is Br.

In some embodiments, at least one $R_{1S}$ is —CN. In some embodiments, at least one $R_{1S}$ is —OH.

In some embodiments, at least one $R_{1S}$ is —$NH_2$, —NH($C_1$-$C_6$ alkyl), or —N($C_1$-$C_6$ alkyl)$_2$.

In some embodiments, at least one $R_{1S}$ is —S($C_1$-$C_6$ alkyl). In some embodiments, at least one $R_{1S}$ is —$SO_2$($C_1$-$C_6$ alkyl).

In some embodiments, at least one $R_{1S}$ is $C_1$-$C_6$ alkyl, $C_2$-$C_6$ alkenyl, $C_2$-$C_6$ alkynyl, or $C_1$-$C_6$ alkoxy.

In some embodiments, at least one $R_{1S}$ is $C_1$-$C_6$ alkyl. In some embodiments, at least one $R_{1S}$ is $C_2$-$C_6$ alkenyl. In some embodiments, at least one $R_{1S}$ is $C_2$-$C_6$ alkynyl.

In some embodiments, at least one $R_{1S}$ is $C_1$-$C_6$ alkoxy.

In some embodiments, at least one $R_{1S}$ is $C_3$-$C_7$ cycloalkyl or 3- to 7-membered heterocycloalkyl.

In some embodiments, at least one $R_{1S}$ is $C_3$-$C_7$ cycloalkyl.

In some embodiments, at least one $R_{1S}$ is 3- to 7-membered heterocycloalkyl.

Variables $Ar_1$ and $R_{A1}$

In some embodiments, $Ar_1$ is $C_6$-$C_{10}$ aryl optionally substituted with one or more $R_{A1}$.

In some embodiments, $Ar_1$ is $C_6$-$C_{10}$ aryl.

In some embodiments, $Ar_1$ is $C_6$-$C_{10}$ aryl substituted with one or more $R_{A1}$.

In some embodiments, $Ar_1$ is phenyl optionally substituted with one or more $R_{A1}$.

In some embodiments, $Ar_1$ is

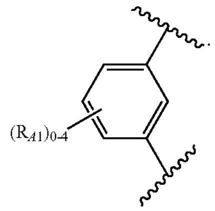

In some embodiments, $Ar_1$ is

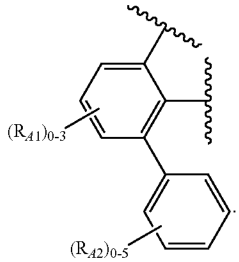

In some embodiments, $Ar_1$ is phenyl.

In some embodiments, $Ar_1$ is phenyl substituted with one or more $R_{A1}$.

In some embodiments, $Ar_1$ is 5- to 10-membered heteroaryl optionally substituted with one or more $R_{A1}$.

In some embodiments, $Ar_1$ is 5- to 10-membered heteroaryl.

In some embodiments, $Ar_1$ is 5- to 10-membered heteroaryl substituted with one or more $R_{A1}$.

In some embodiments, $Ar_1$ is pyridyl or thiazolyl optionally substituted with one or more $R_{A1}$.

In some embodiments, $Ar_1$ is pyridyl or thiazolyl.

In some embodiments, $Ar_1$ is pyridyl or thiazolyl substituted with one or more $R_{A1}$.

In some embodiments, $Ar_1$ is pyridyl optionally substituted with one or more $R_{A1}$.

In some embodiments, $Ar_1$ is

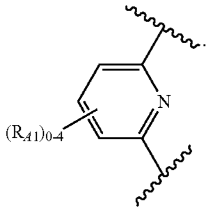

In some embodiments, $Ar_1$ is pyridyl.

In some embodiments, $Ar_1$ is pyridyl substituted with one or more $R_{A1}$.

In some embodiments, $Ar_1$ is thiazolyl optionally substituted with one or more $R_{A1}$.

In some embodiments, $Ar_1$ is thiazolyl.

In some embodiments, $Ar_1$ is thiazolyl substituted with one or more $R_{A1}$.

In some embodiments, at least one $R_{A1}$ is $Ar_2$.

In some embodiments, one $R_{A1}$ is $Ar_2$.

In some embodiments, at least one $R_{A1}$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$.

In some embodiments, at least one $R_{A1}$ is $C_6$-$C_{10}$ aryl optionally substituted with one or more $R_{A2}$.

In some embodiments, at least one $R_{A1}$ is $C_6$-$C_{10}$ aryl.

In some embodiments, at least one $R_{A1}$ is $C_6$-$C_{10}$ aryl substituted with one or more $R_{A2}$.

In some embodiments, at least one $R_{A1}$ is phenyl optionally substituted with one or more $R_{A2}$.

In some embodiments, at least one $R_{A1}$ is phenyl.

In some embodiments, at least one $R_{A1}$ is phenyl substituted with one or more $R_{A2}$.

In some embodiments, at least one $R_{A1}$ is 5- to 10-membered heteroaryl optionally substituted with one or more $R_{A2}$.

In some embodiments, at least one $R_{A1}$ is 5- to 10-membered heteroaryl.

In some embodiments, at least one $R_{A1}$ is 5- to 10-membered heteroaryl substituted with one or more $R_{A2}$.

In some embodiments, at least one $R_{A1}$ is pyridyl or thiazolyl optionally substituted with one or more $R_{A2}$.

In some embodiments, at least one $R_{A1}$ is pyridyl or thiazolyl.

In some embodiments, at least one $R_{A1}$ is pyridyl or thiazolyl substituted with one or more $R_{A2}$.

In some embodiments, at least one $R_{A1}$ is pyridyl optionally substituted with one or more $R_{A2}$.

In some embodiments, at least one $R_{A1}$ is pyridyl.

In some embodiments, at least one $R_{A1}$ is pyridyl substituted with one or more $R_{A2}$.

In some embodiments, at least one $R_{A1}$ is thiazolyl optionally substituted with one or more $R_{A2}$.

In some embodiments, at least one $R_{A1}$ is thiazolyl.

In some embodiments, at least one $R_{A1}$ is thiazolyl substituted with one or more $R_{A2}$.

In some embodiments, at least one $R_{A1}$ is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

In some embodiments, at least one $R_{A1}$ is halogen (e.g., F, Cl, or Br).

In some embodiments, at least one $R_{A1}$ is F. In some embodiments, at least one $R_{A1}$ is Cl.

In some embodiments, at least one $R_{A1}$ is Br.

In some embodiments, at least one $R_{A1}$ is —CN. In some embodiments, at least one $R_{A1}$ is —OH.

In some embodiments, at least one $R_{A1}$ is —$NH_2$, —NH ($C_1$-$C_6$ alkyl), or —N($C_1$-$C_6$ alkyl)$_2$.

In some embodiments, at least one $R_{A1}$ is $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

In some embodiments, at least one $R_{A1}$ is $C_1$-$C_6$ alkyl.

In some embodiments, at least one $R_{A1}$ is $C_1$-$C_6$ haloalkyl (e.g., —$CH_2F$, —$CHF_2$, or —$CF_3$).

In some embodiments, at least one $R_{A1}$ is $C_1$-$C_6$ alkoxy.

In some embodiments, at least one $R_{A1}$ is $C_1$-$C_6$ haloalkoxy (e.g., —$OCH_2F$, —$OCHF_2$, or —$OCF_3$).

In some embodiments, at least one $R_{A1}$ is $C_2$-$C_6$ alkenyl. In some embodiments, at least one $R_{A1}$ is $C_2$-$C_6$ alkynyl.

Variable T

In some embodiments, T is absent.

In some embodiments, T is $Ar_2$.

In some embodiments, T is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$.

In some embodiments, T is $C_6$-$C_{10}$ aryl optionally substituted with one or more $R_{A2}$.

In some embodiments, T is

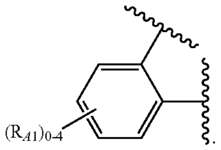

In some embodiments, T is $C_6$-$C_{10}$ aryl.

In some embodiments, T is $C_6$-$C_{10}$ aryl substituted with one or more $R_{A2}$.

In some embodiments, T is phenyl optionally substituted with one or more $R_{A2}$.

In some embodiments, T is phenyl.

In some embodiments, T is phenyl substituted with one or more $R_{A2}$.

In some embodiments, T is 5- to 10-membered heteroaryl optionally substituted with one or more $R_{A2}$.

In some embodiments, T is 5- to 10-membered heteroaryl.

In some embodiments, T is 5- to 10-membered heteroaryl substituted with one or more $R_{A2}$.

In some embodiments, T is pyridyl or thiazolyl optionally substituted with one or more $R_{A2}$.

In some embodiments, T is pyridyl or thiazolyl.

In some embodiments, T is pyridyl or thiazolyl substituted with one or more $R_{A2}$.

In some embodiments, T is pyridyl optionally substituted with one or more $R_{A2}$.

In some embodiments, T is pyridyl.

In some embodiments, T is pyridyl substituted with one or more $R_{A2}$.

In some embodiments, T is thiazolyl optionally substituted with one or more $R_{A2}$.

In some embodiments, T is thiazolyl.

In some embodiments, T is thiazolyl substituted with one or more $R_{A2}$.

Exemplary Embodiments of Variables $Ar_1$, $R_{A1}$, and T

In some embodiments, at least one $R_{A1}$ is $Ar_2$, and T is absent.

In some embodiments, at least one $R_{A1}$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$, and T is absent.

In some embodiments, at least one $R_{A1}$ is $C_6$-$C_{10}$ aryl optionally substituted with one or more $R_{A2}$, and T is absent.

In some embodiments, at least one $R_{A1}$ is phenyl optionally substituted with one or more $R_{A2}$, and T is absent.

In some embodiments, at least one $R_{A1}$ is 5- to 10-membered heteroaryl optionally substituted with one or more $R_{A2}$, and T is absent.

In some embodiments, at least one $R_{A1}$ is pyridyl or thiazolyl optionally substituted with one or more $R_{A2}$, and T is absent.

In some embodiments, $Ar_1$ is

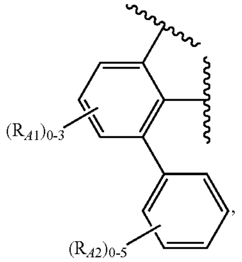

and T is absent.

In some embodiments, each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is $Ar_2$.

In some embodiments, $Ar_1$ is $C_6$-$C_{10}$ aryl optionally substituted with one or more $R_{A1}$, and T is $Ar_2$.

In some embodiments, $Ar_1$ is 5- to 10-membered heteroaryl optionally substituted with one or more $R_{A1}$, and T is $Ar_2$.

In some embodiments, $Ar_1$ is

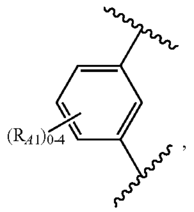

and T is $Ar_2$.

In some embodiments, $Ar_1$ is

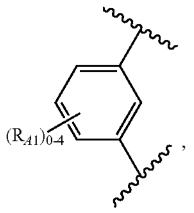

and T is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$.

In some embodiments, $Ar_1$ is

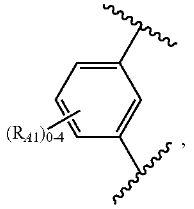

and T is $C_6$-$C_{10}$ aryl optionally substituted with one or more $R_{A2}$.

In some embodiments, $Ar_1$ is

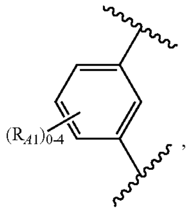

and T is phenyl optionally substituted with one or more $R_{A2}$.

In some embodiments, $Ar_1$ is

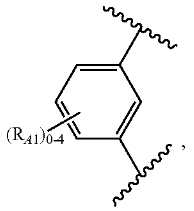

and T is

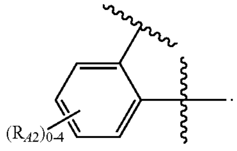

In some embodiments, $Ar_1$ is

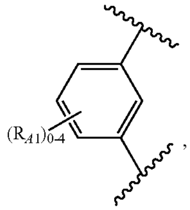
, and T is 5- to 10-membered heteroaryl optionally substituted with one or more $R_{A2}$.

In some embodiments, $Ar_1$ is

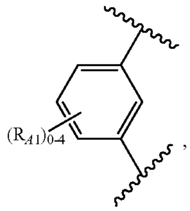
, and T is pyridyl or thiazolyl optionally substituted with one or more $R_{A2}$.

In some embodiments, $Ar_1$ is

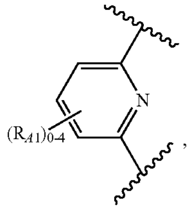
, and T is $Ar_2$.

In some embodiments, each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is $Ar_2$.

In some embodiments, each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$.

In some embodiments, each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is $C_6$-$C_{10}$ aryl optionally substituted with one or more $R_{A2}$.

In some embodiments, each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is phenyl optionally substituted with one or more $R_{A2}$.

In some embodiments, each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is

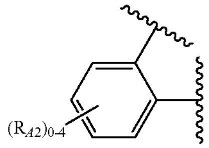
.

In some embodiments, each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is 5- to 10-membered heteroaryl optionally substituted with one or more $R_{A2}$.

In some embodiments, each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is pyridyl or thiazolyl optionally substituted with one or more $R_{A2}$.

Variables $Ar_2$ and $R_{A2}$

In some embodiments, at least one $Ar_2$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$.

In some embodiments, at least one $Ar_2$ is $C_6$-$C_{10}$ aryl optionally substituted with one or more $R_{A2}$.

In some embodiments, at least one $Ar_2$ is $C_6$-$C_{10}$ aryl.

In some embodiments, at least one $Ar_2$ is $C_6$-$C_{10}$ aryl substituted with one or more $R_{A2}$.

In some embodiments, at least one $Ar_2$ is phenyl optionally substituted with one or more $R_{A2}$.

In some embodiments, at least one $Ar_2$ is phenyl.

In some embodiments, at least one $Ar_2$ is phenyl substituted with one or more $R_{A2}$.

In some embodiments, at least one $Ar_2$ is 5- to 10-membered heteroaryl optionally substituted with one or more $R_{A2}$.

In some embodiments, at least one $Ar_2$ is 5- to 10-membered heteroaryl.

In some embodiments, at least one $Ar_2$ is 5- to 10-membered heteroaryl substituted with one or more $R_{A2}$.

In some embodiments, at least one $Ar_2$ is pyridyl or thiazolyl optionally substituted with one or more $R_{A2}$.

In some embodiments, at least one $Ar_2$ is pyridyl or thiazolyl.

In some embodiments, at least one $Ar_2$ is pyridyl or thiazolyl substituted with one or more $R_{A2}$.

In some embodiments, at least one $Ar_2$ is pyridyl optionally substituted with one or more $R_{A2}$.

In some embodiments, at least one $Ar_2$ is pyridyl.

In some embodiments, at least one $Ar_2$ is pyridyl substituted with one or more $R_{A2}$.

In some embodiments, at least one $Ar_2$ is thiazolyl optionally substituted with one or more $R_{A2}$.

In some embodiments, at least one $Ar_2$ is thiazolyl.

In some embodiments, at least one $Ar_2$ is thiazolyl substituted with one or more $R_{A2}$.

In some embodiments, at least one $R_{A2}$ is halogen (e.g., F, Cl, or Br).

In some embodiments, at least one $R_{A2}$ is F. In some embodiments, at least one $R_{A2}$ is Cl.

In some embodiments, at least one $R_{A2}$ is Br.

In some embodiments, at least one $R_{A2}$ is —CN. In some embodiments, at least one $R_{A2}$ is —OH.

In some embodiments, at least one $R_{A2}$ is —$NH_2$, —NH($C_1$-$C_6$ alkyl), or —N($C_1$-$C_6$ alkyl)$_2$.

In some embodiments, at least one $R_{A2}$ is $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

In some embodiments, at least one $R_{A2}$ is $C_1$-$C_6$ alkyl.

In some embodiments, at least one $R_{A2}$ is $C_1$-$C_6$ alkoxy.

In some embodiments, at least one $R_{A2}$ is $C_1$-$C_6$ haloalkyl (e.g., —$CH_2F$, —$CHF_2$, or —$CF_3$).

In some embodiments, at least one $R_{A2}$ is $C_2$-$C_6$ alkenyl. In some embodiments, at least one $R_{A2}$ is $C_2$-$C_6$ alkynyl.

EXEMPLARY EMBODIMENTS OF THE COMPOUNDS

In some embodiments, the compound is of Formula (I'-a) or (I'-b):

(I'-a)

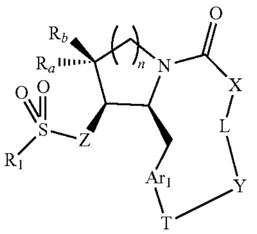

or (I'-b)

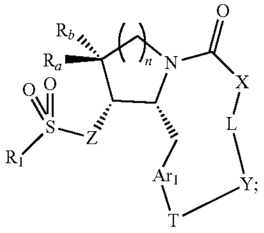

or a pharmaceutically acceptable salt thereof.

In some embodiments, the compound is of Formula (IA'), (IA'-a), or (IA'-b):

(IA')

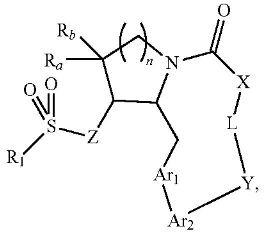

(IA'-a)

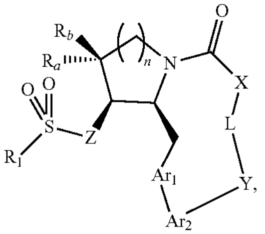

or

-continued (IA'-b)

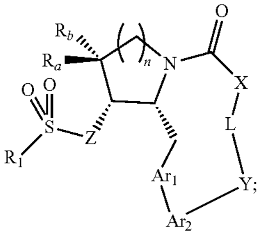

or a pharmaceutically acceptable salt thereof.

In some embodiments, the compound is of Formula (IB'), (IB'-a), or (IB'-b):

(IB')

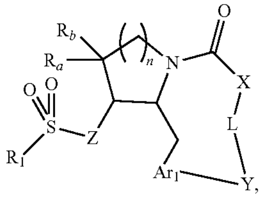

(IB'-a)

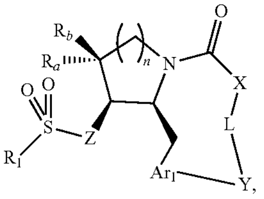

or (IB'-b)

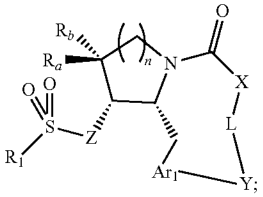

or a pharmaceutically acceptable salt thereof.

In some embodiments, the compound is of Formula (II'), (II'-a), or (II'-b):

(II')

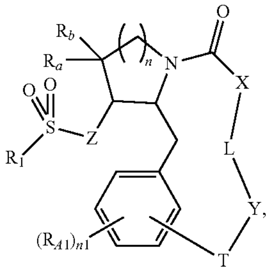

-continued (II'-a)

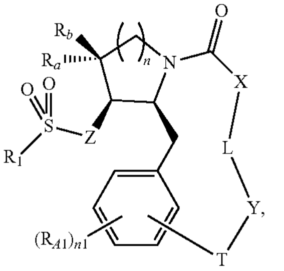

or (II'-b)

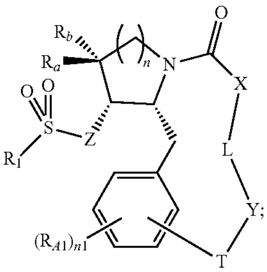

or a pharmaceutically acceptable salt thereof, wherein:

n1 is an integer ranging from 0 to 4.

In some embodiments, the compound is of Formula (IIA'), (IIA'-a), or (IIA'-b):

(IIA')

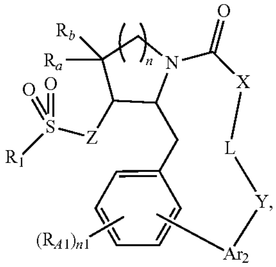

(IIA'-a)

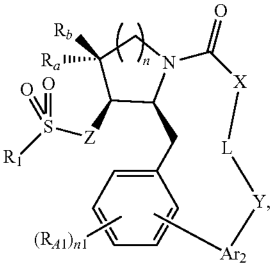

(IIA'-b)

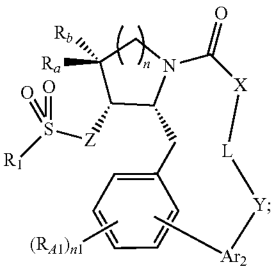

or a pharmaceutically acceptable salt thereof.

In some embodiments, the compound is of Formula (IIB'), (IIB'-a), or (IIB'-b):

(IIB')

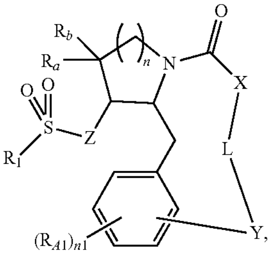

(IIB'-a)

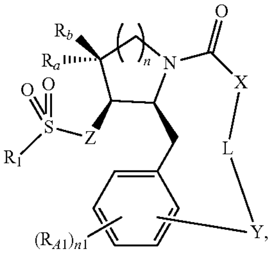

or (IIB'-b)

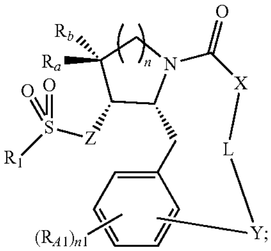

or a pharmaceutically acceptable salt thereof.

In some embodiments, the compound is of Formula (IIIA'), (IIIA'-a), or (IIIA'-b):

(IIIA')

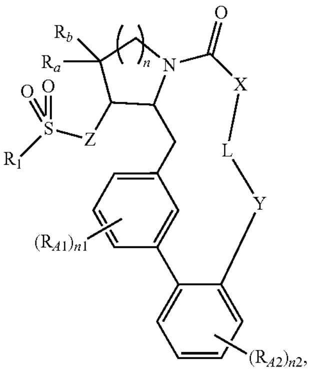

-continued (IIIA'-a)

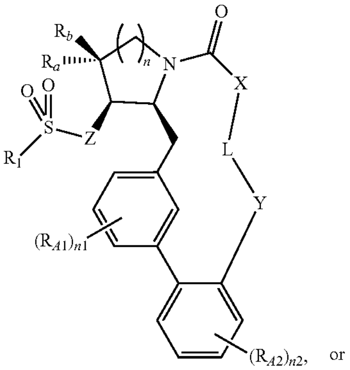

or (IIIA'-b)

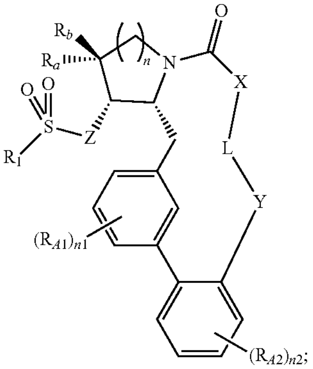

or a pharmaceutically acceptable salt thereof, wherein:

n1 is an integer ranging from 0 to 4; and n2 is an integer ranging from 0 to 4.

In some embodiments, the compound is of Formula (IIIB'), (IIIB'-a), or (IIIB'-b):

(IIIB')

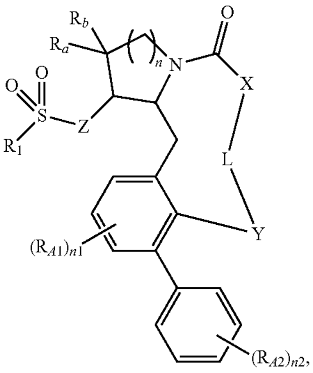

-continued (IIIB'-a)

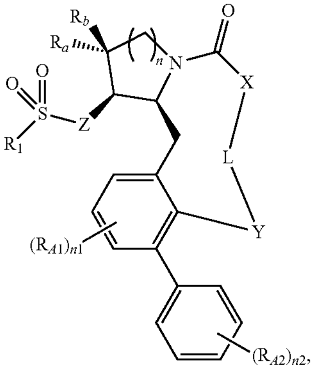

or (IIIB'-b)

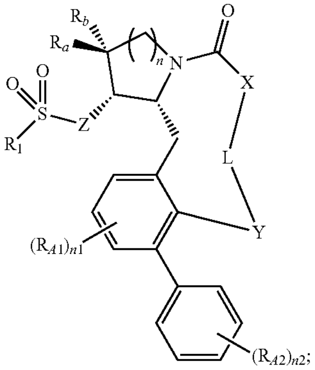

or a pharmaceutically acceptable salt thereof, wherein:

n1 is an integer ranging from 0 to 3; and n2 is an integer ranging from 0 to 5.

In some embodiments, the compound is of Formula (IVA'), (IVA'-a), or (IVA'-b):

(IVA')

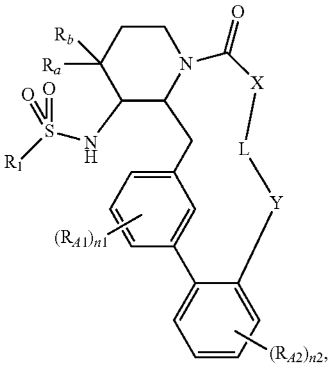

-continued (IVA′-a)

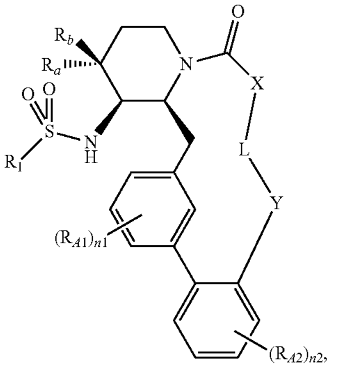

or (IVA′-b)

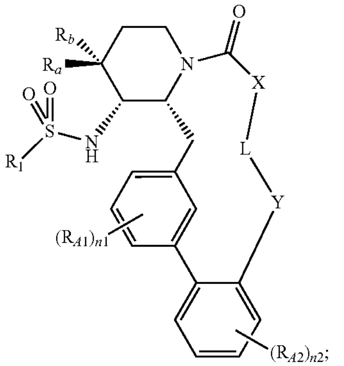

or a pharmaceutically acceptable salt thereof, wherein:

n1 is an integer ranging from 0 to 4; and n2 is an integer ranging from 0 to 4.

In some embodiments, the compound is of Formula (VA'), (VA'-a), or (VA'-b):

(VA′)

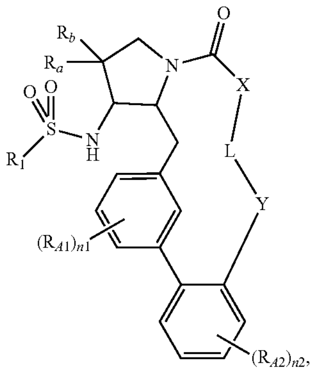

-continued (VA′-a)

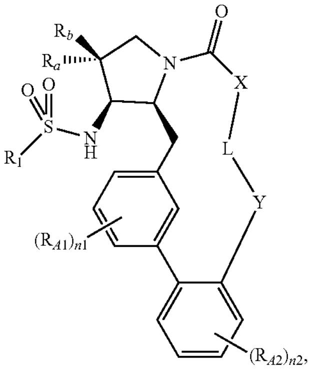

or (VA′-b)

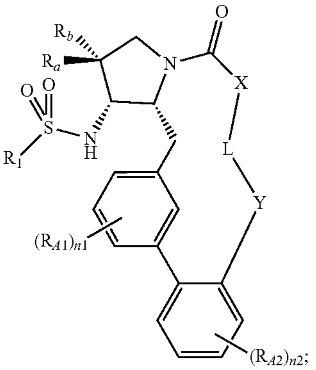

or a pharmaceutically acceptable salt thereof, wherein:

n1 is an integer ranging from 0 to 4; and n2 is an integer ranging from 0 to 4.

In some embodiments, the compound is of Formula (I-a) or (I-b):

(I-a)

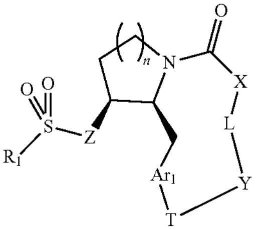

or (I-b)

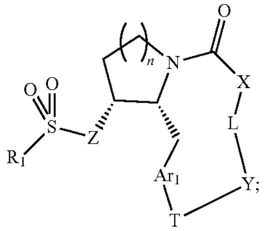

or a pharmaceutically acceptable salt thereof.

In some embodiments, the compound is of Formula (IA), (IA-a), or (IA-b):

(IA)

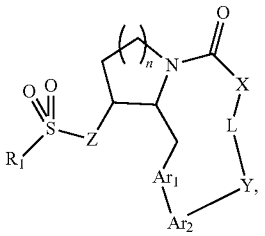

(IA-a)

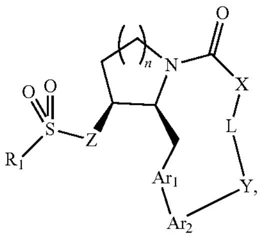

or (IA-b)

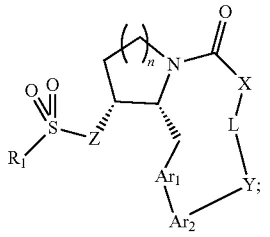

or a pharmaceutically acceptable salt thereof.

In some embodiments, the compound is of Formula (IB), (IB-a), or (IB-b):

(IB)

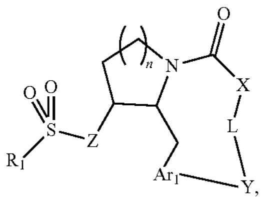

(IB-a)

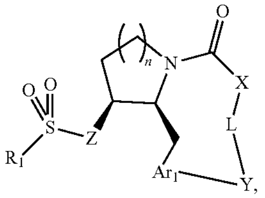

or (IB-b)

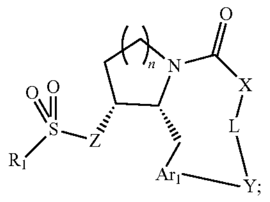

or a pharmaceutically acceptable salt thereof.

In some embodiments, the compound is of Formula (II), (II-a), or (II-b):

(II)

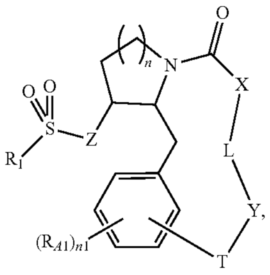

(II-a)

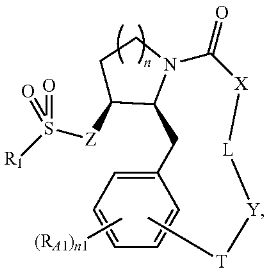

or (II-b)

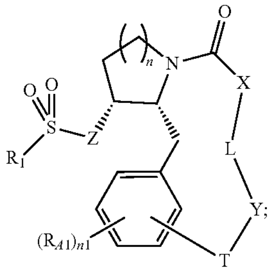

or a pharmaceutically acceptable salt thereof, wherein:

n1 is an integer ranging from 0 to 4.

In some embodiments, the compound is of Formula (IIA), (IIA-a), or (IIA-b):

(IIA)

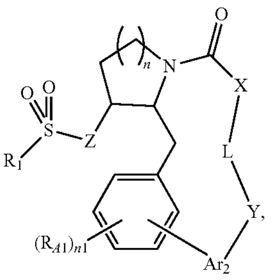

-continued (IIA-a)

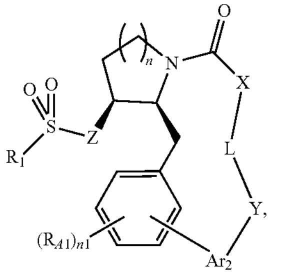

or (IIA-b)

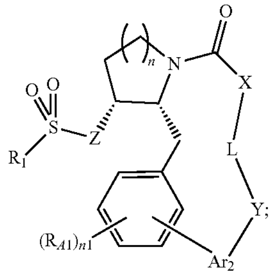

or a pharmaceutically acceptable salt thereof.

In some embodiments, the compound is of Formula (IIB), (IIB-a), or (IIB-b):

(IIB)

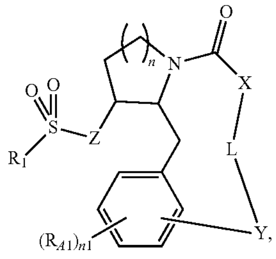

(IIB-a)

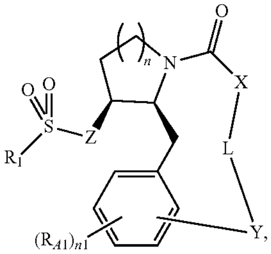

or (IIB-b)

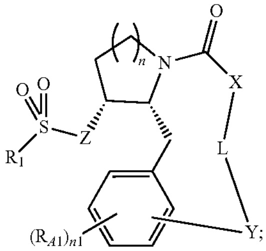

or a pharmaceutically acceptable salt thereof.

In some embodiments, the compound is of Formula (IIIA), (IIIA-a), or (IIIA-b):

(IIIA)

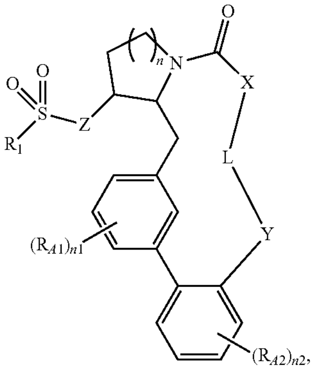

(IIIA-a)

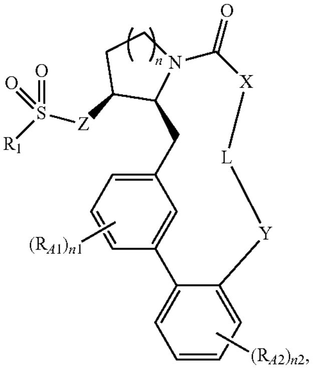

or (IIIA-b)

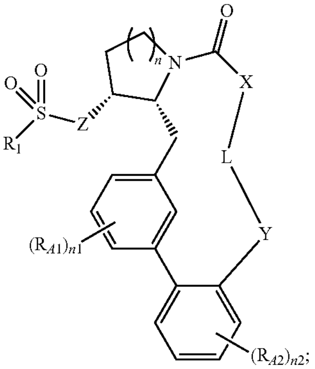

or a pharmaceutically acceptable salt thereof, wherein:

n1 is an integer ranging from 0 to 4; and n2 is an integer ranging from 0 to 4.

In some embodiments, the compound is of Formula (IIIB), (IIIB-a), or (IIIB-b):

(IIIB)

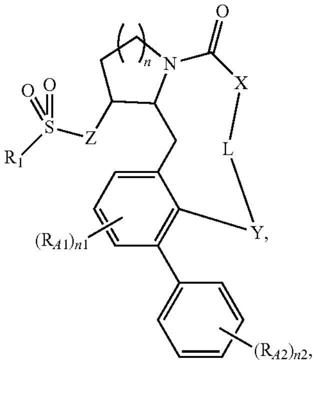

(IIIB-a)

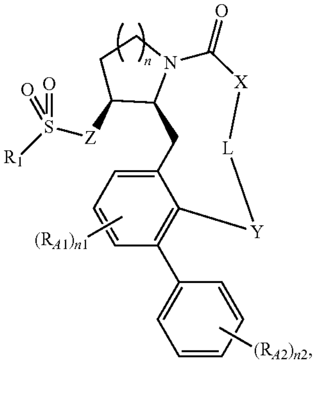

or (IIIB-b)

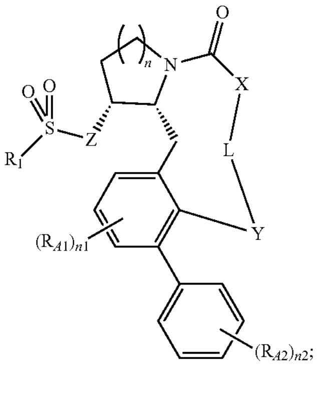

or a pharmaceutically acceptable salt thereof, wherein:

n1 is an integer ranging from 0 to 3; and n2 is an integer ranging from 0 to 5.

In some embodiments, the compound is of Formula (IVA), (IVA-a), or (IVA-b):

(IVA)

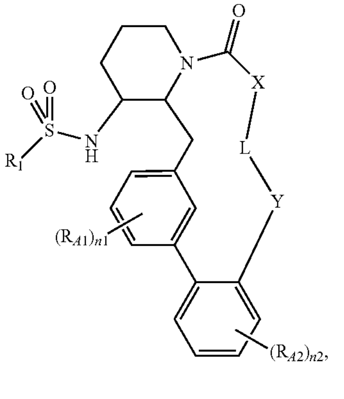

(IVA-a)

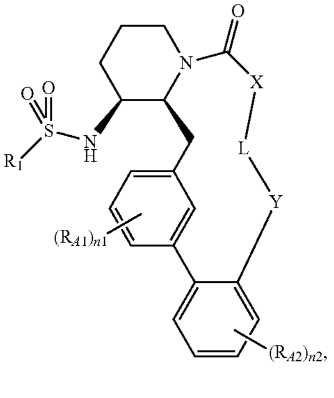

or (IVA-b)

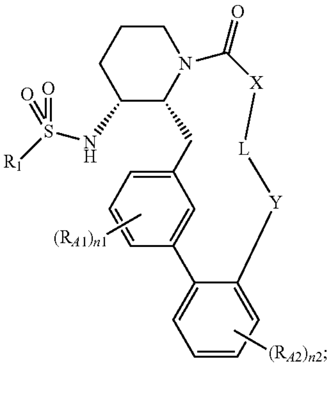

or a pharmaceutically acceptable salt thereof, wherein:

n1 is an integer ranging from 0 to 4; and n2 is an integer ranging from 0 to 4.

In some embodiments, the compound is of Formula (VA), (VA-a), or (VA-b):

(VA)

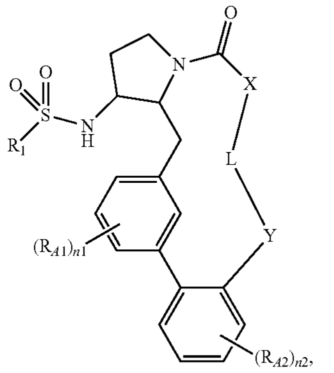

(VA-a)

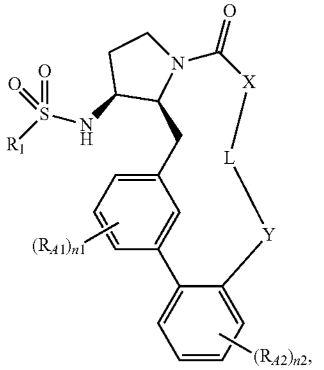

or (VA-b)

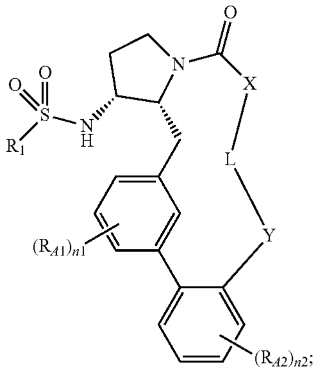

or a pharmaceutically acceptable salt thereof, wherein:

n1 is an integer ranging from 0 to 4; and n2 is an integer ranging from 0 to 4.

In some embodiments, the compound is of a Formula described herein or a pharmaceutically acceptable salt thereof, wherein:

$R_1$ is —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more $R_{1S}$ and $C_1$-$C_6$ alkyl is substituted with one or more $R_{1S}$;

each $R_{1S}$ is independently halogen or $C_1$-$C_6$ alkyl;

each $R_{A1}$ is independently halogen;

each $R_{A2}$ is independently halogen;

n1 is an integer ranging from 0 to 4; and n2 is an integer ranging from 0 to 4.

In some embodiments, the compound is selected from the compounds described in Table A1 and pharmaceutically acceptable salts thereof.

In some embodiments, the compound is selected from Compound Nos. A1-6, A1-6, A1-10, A1-15, A1-42, A1-58, A1-59, A1-60, A1-61, A1-63 to A1-102, and pharmaceutically acceptable salts thereof.

In some embodiments, the compound is selected from the compounds described in Table A2 and pharmaceutically acceptable salts thereof.

In some embodiments, the compound is selected from the compounds described in Table B1 and pharmaceutically acceptable salts thereof.

In some embodiments, the compound is selected from the compounds described in Table B2 and pharmaceutically acceptable salts thereof.

TABLE A1

| Compound No. | Structure |
|---|---|
| A1-1 | 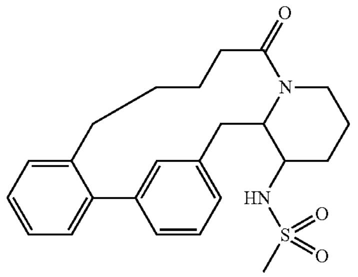 [SMILES: CS(=O)(=O)NC1CCCN2C(=O)CCCCc3ccccc3-c3cccc(c3)CC12] |
| A1-2 | 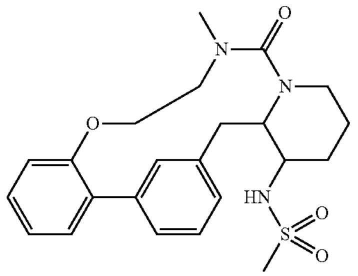 [SMILES: CN1CCOc2ccccc2-c2cccc(c2)CC2C(NS(C)(=O)=O)CCCN2C1=O] |
| A1-3 | 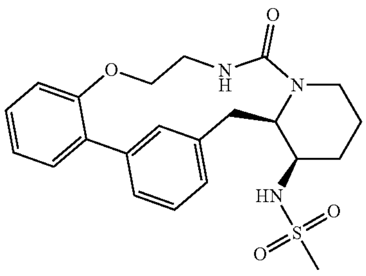 [SMILES: CS(=O)(=O)N[C@@H]1CCCN2C(=O)NCCOc3ccccc3-c3cccc(c3)C[C@H]12] |

TABLE A1-continued
| Compound No. | Structure |
|---|---|
| A1-4 | 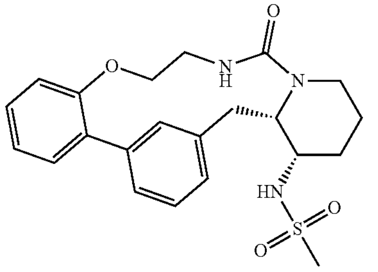 |
| A1-5 | 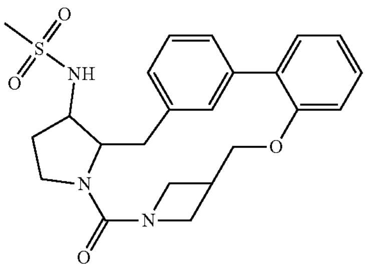 [SMILES: CS(=O)(=O)NC1CCN2C(=O)N3CC(COc4ccccc4-c4cccc(c4)CC12)C3] |
| A1-6 | 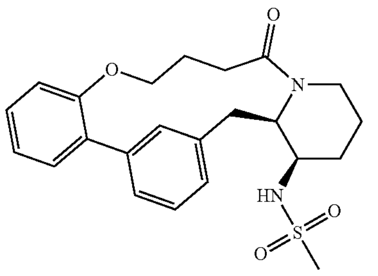 [SMILES: CS(=O)(=O)N[C@@H]1CCCN2C(=O)CCCOc3ccccc3-c3cccc(c3)C[C@H]12] |
| A1-7 | 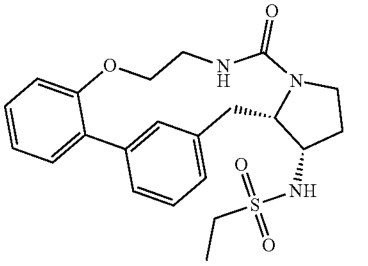 [SMILES: CCS(=O)(=O)N[C@H]1CCN2C(=O)NCCOc3ccccc3-c3cccc(c3)C[C@@H]12] |
| A1-8 | 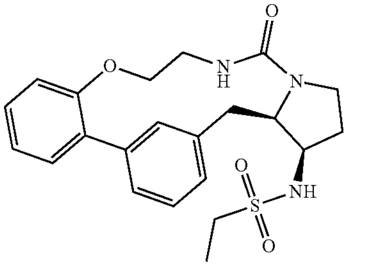 [SMILES: CCS(=O)(=O)N[C@@H]1CCN2C(=O)NCCOc3ccccc3-c3cccc(c3)C[C@H]12] |
TABLE A1-continued
| Compound No. | Structure |
|---|---|
| A1-9 | 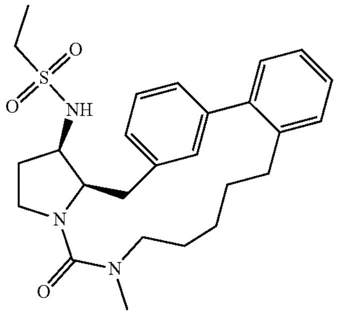 [SMILES: CCS(=O)(=O)N[C@@H]1CCN2C(=O)N(C)CCCCCc3ccccc3-c3cccc(c3)C[C@H]12] |
| A1-10 | 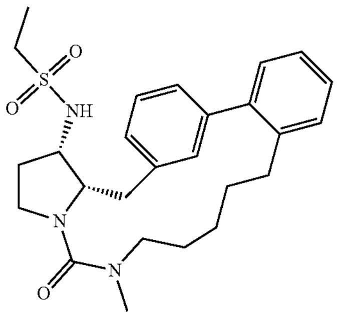 [SMILES: CCS(=O)(=O)N[C@H]1CCN2C(=O)N(C)CCCCCc3ccccc3-c3cccc(c3)C[C@@H]12] |
| A1-11 | 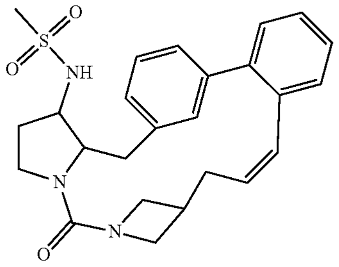 [SMILES: CS(=O)(=O)NC1CCN2C(=O)N3CC(C/C=C\c4ccccc4-c4cccc(c4)CC12)C3] |
| A1-12 | 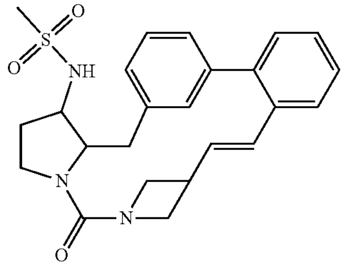 [SMILES: CS(=O)(=O)NC1CCN2C(=O)N3CC(/C=C/c4ccccc4-c4cccc(c4)CC12)C3] |
| A1-13 | 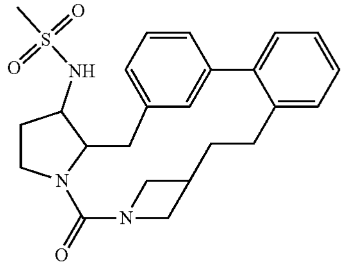 [SMILES: CS(=O)(=O)NC1CCN2C(=O)N3CC(CCc4ccccc4-c4cccc(c4)CC12)C3] |

TABLE A1-continued
| Compound No. | Structure |
|---|---|
| A1-14 | 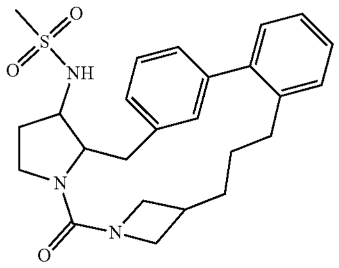 [SMILES: CS(=O)(=O)NC1CCN2C(=O)N3CC(CCCc4ccccc4-c4cccc(c4)CC12)C3] |
| A1-15 | 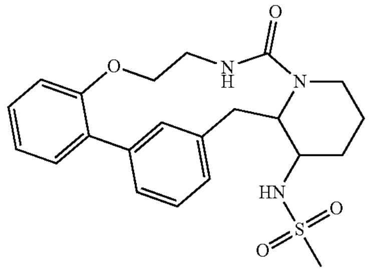 [SMILES: CS(=O)(=O)NC1CCCN2C(=O)NCCOc3ccccc3-c3cccc(c3)CC12] |
| A1-16 | 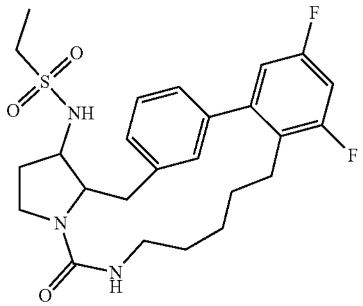 [SMILES: CCS(=O)(=O)NC1CCN2C(=O)NCCCCCc3c(F)cc(F)cc3-c3cccc(c3)CC12] |
| A1-17 | 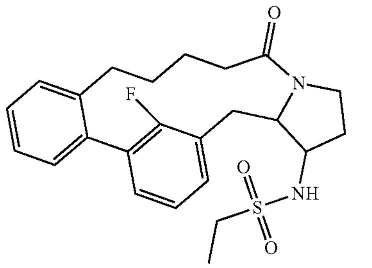 [SMILES: CCS(=O)(=O)NC1CCN2C(=O)CCCCc3ccccc3-c3cccc(c3F)CC12] |
| A1-18 | 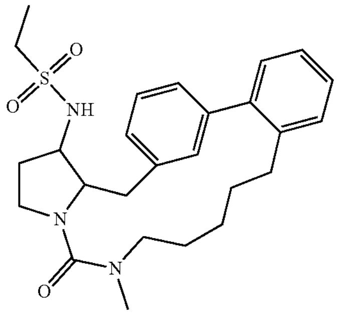 [SMILES: CCS(=O)(=O)NC1CCN2C(=O)N(C)CCCCCc3ccccc3-c3cccc(c3)CC12] |
| A1-19 | 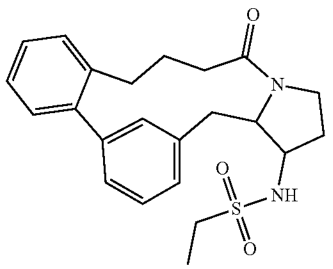 [SMILES: CCS(=O)(=O)NC1CCN2C(=O)CCCc3ccccc3-c3cccc(c3)CC12] |
| A1-20 | 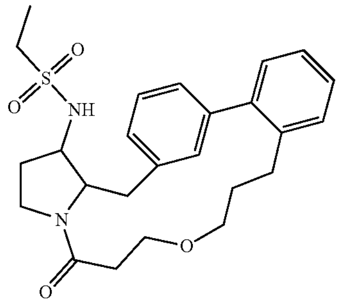 [SMILES: CCS(=O)(=O)NC1CCN2C(=O)CCOCCCc3ccccc3-c3cccc(c3)CC12] |
| A1-21 | 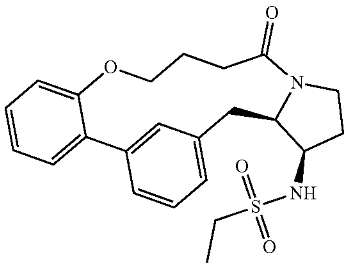 [SMILES: CCS(=O)(=O)N[C@@H]1CCN2C(=O)CCCOc3ccccc3-c3cccc(c3)C[C@H]12] |
| A1-22 | 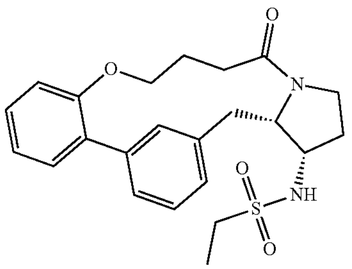 [SMILES: CCS(=O)(=O)N[C@H]1CCN2C(=O)CCCOc3ccccc3-c3cccc(c3)C[C@@H]12] |
| A1-23 | 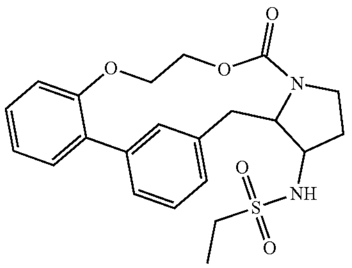 [SMILES: CCS(=O)(=O)NC1CCN2C(=O)OCCOc3ccccc3-c3cccc(c3)CC12] |

TABLE A1-continued
| Compound No. | Structure |
| --- | --- |
| A1-24 | 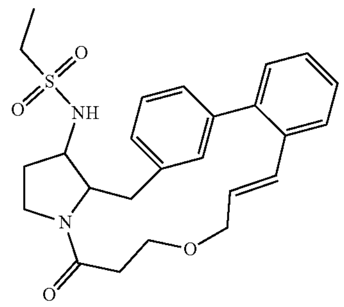 [SMILES: CCS(=O)(=O)NC1CCN2C(=O)CCOC/C=C/c3ccccc3-c3cccc(c3)CC12] |
| A1-25 | 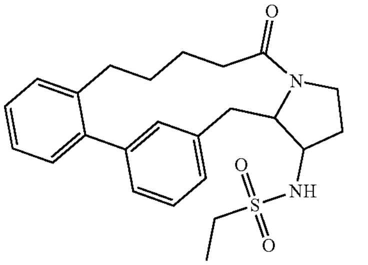 [SMILES: CCS(=O)(=O)NC1CCN2C(=O)CCCCc3ccccc3-c3cccc(c3)CC12] |
| A1-26 | 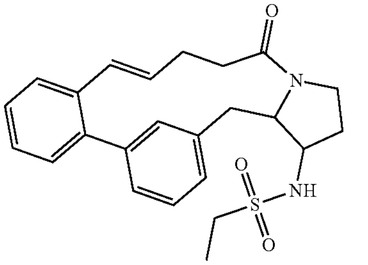 [SMILES: CCS(=O)(=O)NC1CCN2C(=O)CC/C=C/c3ccccc3-c3cccc(c3)CC12] |
| A1-27 | 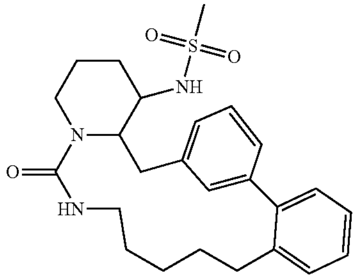 [SMILES: CS(=O)(=O)NC1CCCN2C(=O)NCCCCCc3ccccc3-c3cccc(c3)CC12] |
| A1-28 | 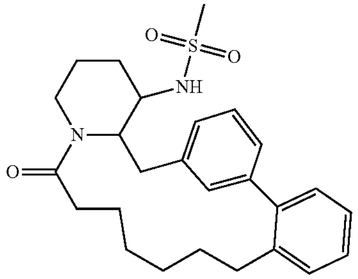 [SMILES: CS(=O)(=O)NC1CCCN2C(=O)CCCCCCc3ccccc3-c3cccc(c3)CC12] |
TABLE A1-continued
| Compound No. | Structure |
| --- | --- |
| A1-29 | 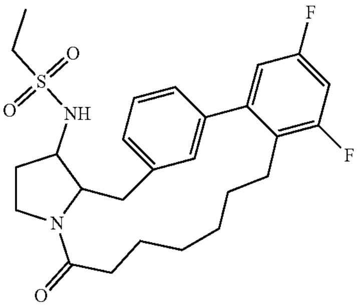 [SMILES: CCS(=O)(=O)NC1CCN2C(=O)CCCCCCc3c(F)cc(F)cc3-c3cccc(c3)CC12] |
| A1-30 | 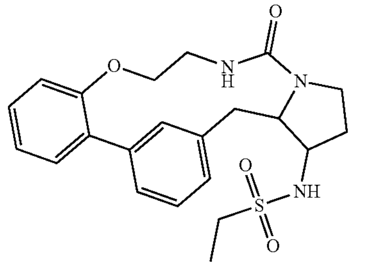 [SMILES: CCS(=O)(=O)NC1CCN2C(=O)NCCOc3ccccc3-c3cccc(c3)CC12] |
| A1-31 | 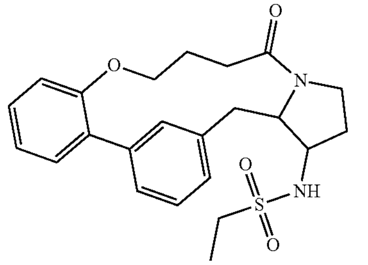 [SMILES: CCS(=O)(=O)NC1CCN2C(=O)CCCOc3ccccc3-c3cccc(c3)CC12] |
| A1-32 | 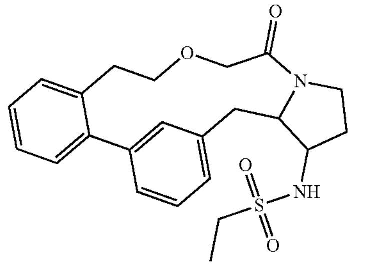 [SMILES: CCS(=O)(=O)NC1CCN2C(=O)COCCc3ccccc3-c3cccc(c3)CC12] |
| A1-33 | 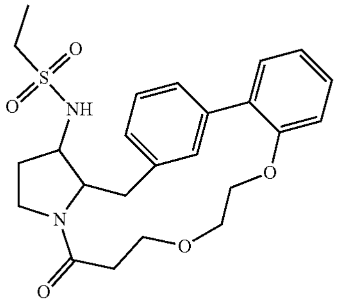 [SMILES: CCS(=O)(=O)NC1CCN2C(=O)CCOCCOc3ccccc3-c3cccc(c3)CC12] |

TABLE A1-continued
| Compound No. | Structure |
| --- | --- |
| A1-34 | 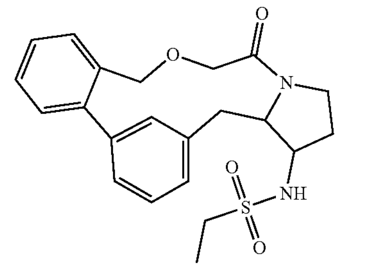 [SMILES: CCS(=O)(=O)NC1CCN2C(=O)COCc3ccccc3-c3cccc(c3)CC12] |
| A1-35 | 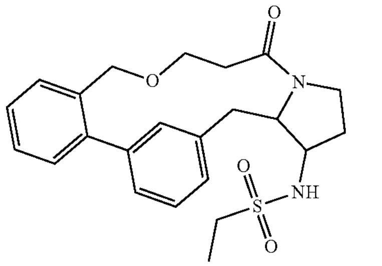 [SMILES: CCS(=O)(=O)NC1CCN2C(=O)CCOCc3ccccc3-c3cccc(c3)CC12] |
| A1-36 | 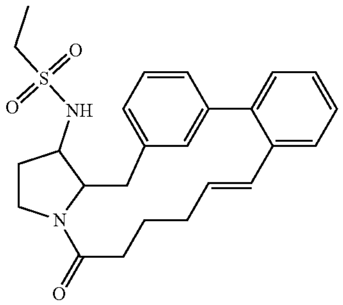 [SMILES: CCS(=O)(=O)NC1CCN2C(=O)CCC/C=C/c3ccccc3-c3cccc(c3)CC12] |
| A1-37 | 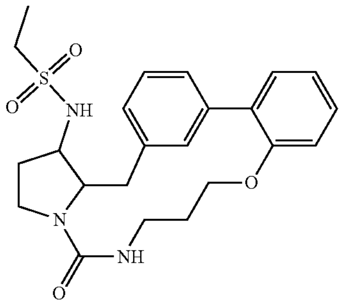 [SMILES: CCS(=O)(=O)NC1CCN2C(=O)NCCCOc3ccccc3-c3cccc(c3)CC12] |
| A1-38 | 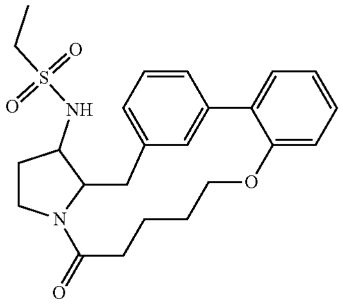 [SMILES: CCS(=O)(=O)NC1CCN2C(=O)CCCCOc3ccccc3-c3cccc(c3)CC12] |
TABLE A1-continued
| Compound No. | Structure |
| --- | --- |
| A1-39 | 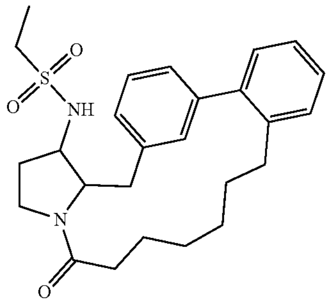 [SMILES: CCS(=O)(=O)NC1CCN2C(=O)CCCCCCc3ccccc3-c3cccc(c3)CC12] |
| A1-40 | 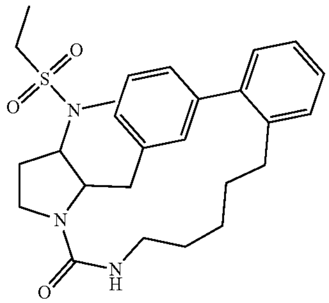 [SMILES: CCS(=O)(=O)N(C)C1CCN2C(=O)NCCCCCc3ccccc3-c3cccc(c3)CC12] |
| A1-41 | 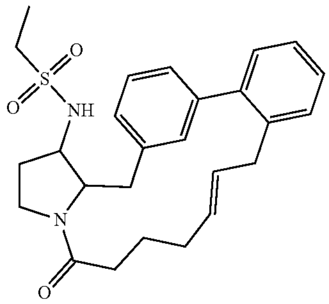 [SMILES: CCS(=O)(=O)NC1CCN2C(=O)CCC/C=C/Cc3ccccc3-c3cccc(c3)CC12] |
| A1-42 | 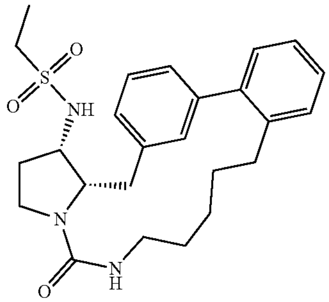 [SMILES: CCS(=O)(=O)N[C@H]1CCN2C(=O)NCCCCCc3ccccc3-c3cccc(c3)C[C@@H]12] |
| A1-43 | 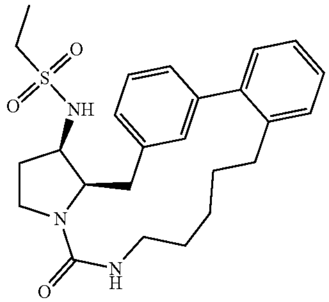 [SMILES: CCS(=O)(=O)N[C@@H]1CCN2C(=O)NCCCCCc3ccccc3-c3cccc(c3)C[C@H]12] |

TABLE A1-continued
| Compound No. | Structure |
|---|---|
| A1-44 | 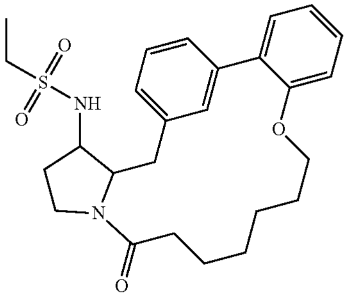 [SMILES: CCS(=O)(=O)NC1CCN2C(=O)CCCCCCOc3ccccc3-c3cccc(c3)CC12] |
| A1-45 | 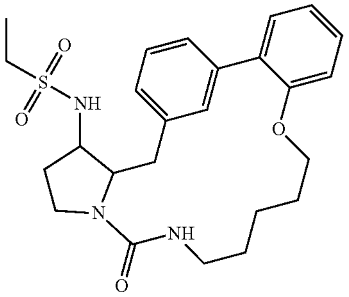 [SMILES: CCS(=O)(=O)NC1CCN2C(=O)NCCCCCOc3ccccc3-c3cccc(c3)CC12] |
| A1-46 | 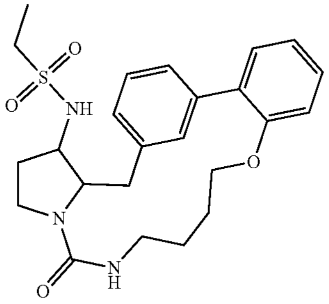 [SMILES: CCS(=O)(=O)NC1CCN2C(=O)NCCCCOc3ccccc3-c3cccc(c3)CC12] |
| A1-47 | 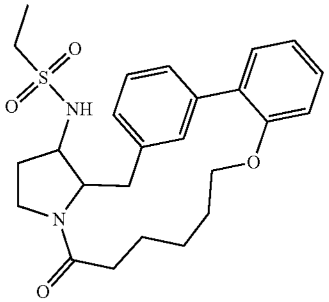 [SMILES: CCS(=O)(=O)NC1CCN2C(=O)CCCCCOc3ccccc3-c3cccc(c3)CC12] |
| A1-48 | 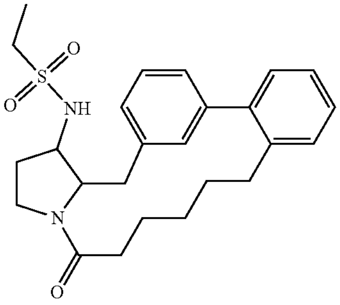 [SMILES: CCS(=O)(=O)NC1CCN2C(=O)CCCCCc3ccccc3-c3cccc(c3)CC12] |
TABLE A1-continued
| Compound No. | Structure |
|---|---|
| A1-49 | 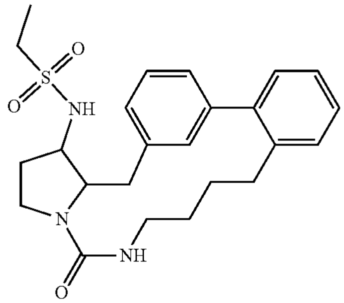 [SMILES: CCS(=O)(=O)NC1CCN2C(=O)NCCCCc3ccccc3-c3cccc(c3)CC12] |
| A1-50 | 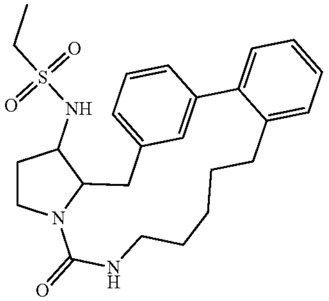 [SMILES: CCS(=O)(=O)NC1CCN2C(=O)NCCCCCc3ccccc3-c3cccc(c3)CC12] |
| A1-51 | 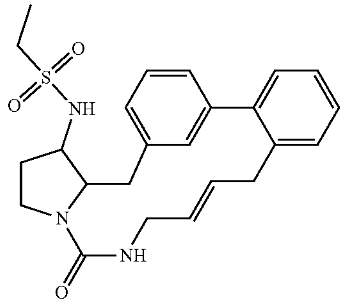 [SMILES: CCS(=O)(=O)NC1CCN2C(=O)NC/C=C/Cc3ccccc3-c3cccc(c3)CC12] |
| A1-52 | 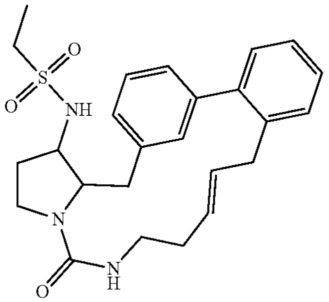 [SMILES: CCS(=O)(=O)NC1CCN2C(=O)NCC/C=C/Cc3ccccc3-c3cccc(c3)CC12] |
| A1-53 | 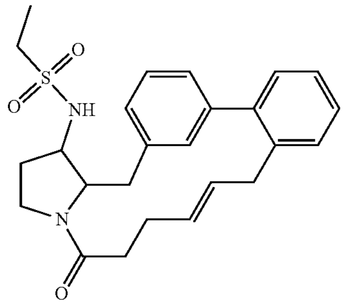 [SMILES: CCS(=O)(=O)NC1CCN2C(=O)CC/C=C/Cc3ccccc3-c3cccc(c3)CC12] |

TABLE A1-continued
| Compound No. | Structure |
|---|---|
| A1-54 | 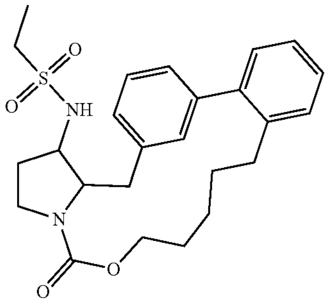 [SMILES: CCS(=O)(=O)NC1CCN2C(=O)OCCCCCc3ccccc3-c3cccc(c3)CC12] |
| A1-55 | 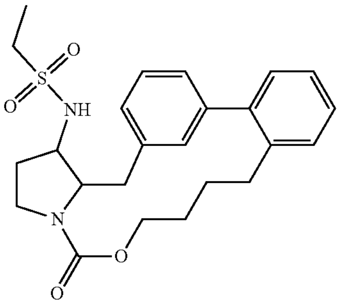 [SMILES: CCS(=O)(=O)NC1CCN2C(=O)OCCCCc3ccccc3-c3cccc(c3)CC12] |
| A1-56 | 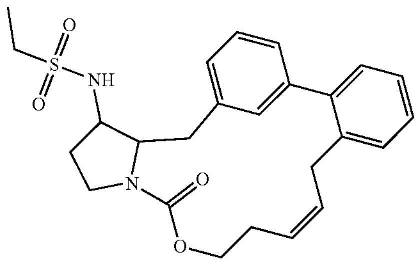 [SMILES: CCS(=O)(=O)NC1CCN2C(=O)OCC/C=C\Cc3ccccc3-c3cccc(c3)CC12] |
| A1-57 | 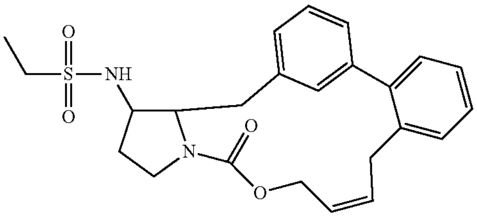 [SMILES: CCS(=O)(=O)NC1CCN2C(=O)OC/C=C\Cc3ccccc3-c3cccc(c3)CC12] |
| A1-58 | 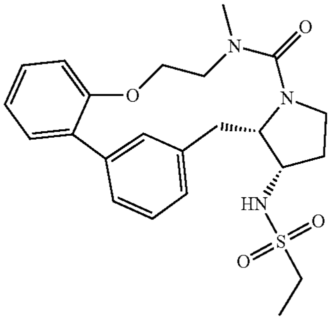 [SMILES: CCS(=O)(=O)N[C@H]1CCN2C(=O)N(C)CCOc3ccccc3-c3cccc(c3)C[C@@H]12] |
TABLE A1-continued
| Compound No. | Structure |
|---|---|
| A1-59 | 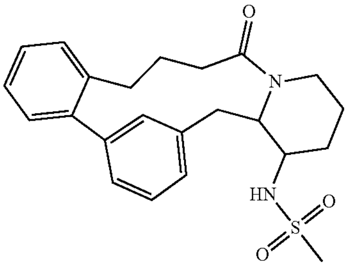 [SMILES: CS(=O)(=O)NC1CCCN2C(=O)CCCc3ccccc3-c3cccc(c3)CC12] |
| A1-60 | 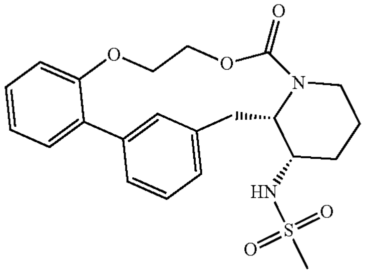 [SMILES: CS(=O)(=O)N[C@H]1CCCN2C(=O)OCCOc3ccccc3-c3cccc(c3)C[C@@H]12] |
| A1-61 | 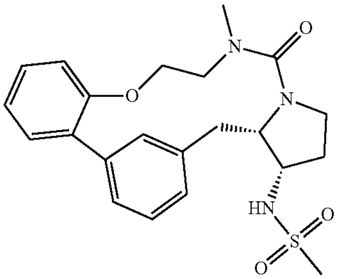 [SMILES: CN1CCOc2ccccc2-c2cccc(c2)C[C@H]2[C@@H](NS(C)(=O)=O)CCN2C1=O] |
| A1-62 | 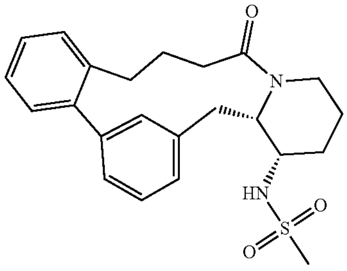 [SMILES: CS(=O)(=O)N[C@H]1CCCN2C(=O)CCCc3ccccc3-c3cccc(c3)C[C@@H]12] |
| A1-63 | 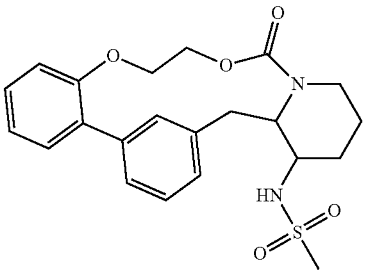 [SMILES: CS(=O)(=O)NC1CCCN2C(=O)OCCOc3ccccc3-c3cccc(c3)CC12] |

TABLE A1-continued
| Compound No. | Structure |
|---|---|
| A1-64 | 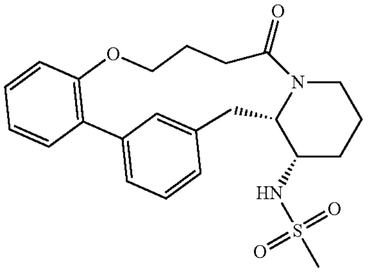 [SMILES: CS(=O)(=O)N[C@H]1CCCN2C(=O)CCCOc3ccccc3-c3cccc(c3)C[C@@H]12] |
| A1-65 | 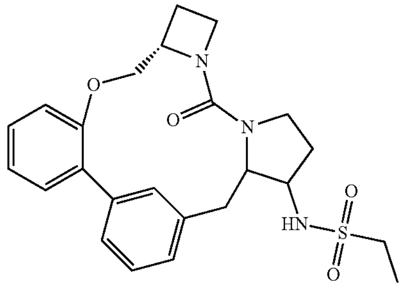 [SMILES: CCS(=O)(=O)NC1CCN2C(=O)N3CC[C@H]3COc3ccccc3-c3cccc(c3)CC12] |
| A1-66 | 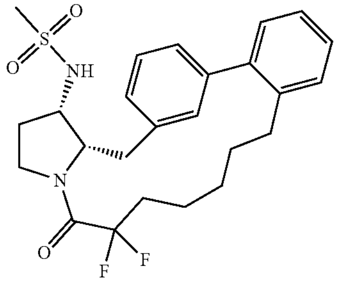 [SMILES: CS(=O)(=O)N[C@H]1CCN2C(=O)C(F)(F)CCCCCc3ccccc3-c3cccc(c3)C[C@@H]12] |
| A1-67 | 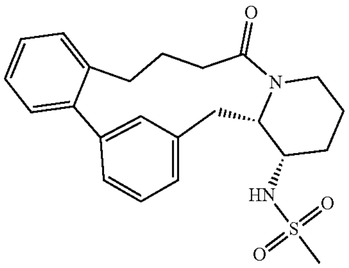 [SMILES: CS(=O)(=O)N[C@H]1CCCN2C(=O)CCCc3ccccc3-c3cccc(c3)C[C@@H]12] |
| A1-68 | 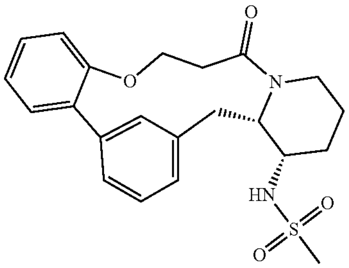 [SMILES: CS(=O)(=O)N[C@H]1CCCN2C(=O)CCOc3ccccc3-c3cccc(c3)C[C@@H]12] |
TABLE A1-continued
| Compound No. | Structure |
|---|---|
| A1-69 | 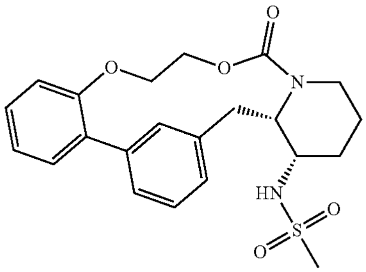 [SMILES: CS(=O)(=O)N[C@H]1CCCN2C(=O)OCCOc3ccccc3-c3cccc(c3)C[C@@H]12] |
| A1-70 | 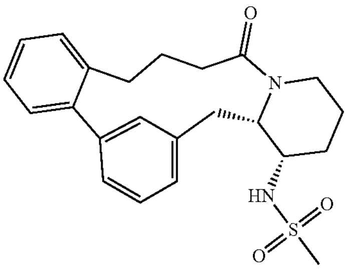 [SMILES: CS(=O)(=O)N[C@H]1CCCN2C(=O)CCCc3ccccc3-c3cccc(c3)C[C@@H]12] |
| A1-71 | 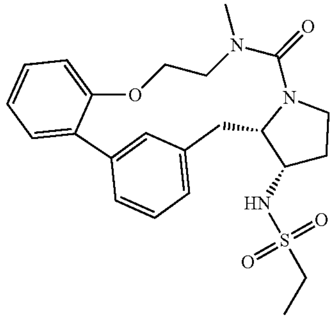 [SMILES: CCS(=O)(=O)N[C@H]1CCN2C(=O)N(C)CCOc3ccccc3-c3cccc(c3)C[C@@H]12] |
| A1-72 | 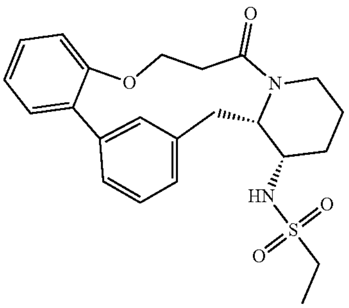 [SMILES: CCS(=O)(=O)N[C@H]1CCCN2C(=O)CCOc3ccccc3-c3cccc(c3)C[C@@H]12] |
| A1-73 | 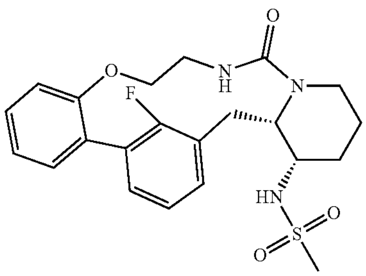 [SMILES: CS(=O)(=O)N[C@H]1CCCN2C(=O)NCCOc3ccccc3-c3cccc(c3F)C[C@@H]12] |

TABLE A1-continued
| Compound No. | Structure |
|---|---|
| A1-74 | 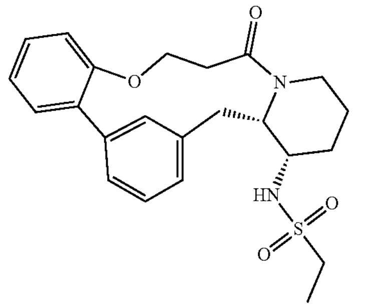 [SMILES: CCS(=O)(=O)N[C@H]1CCCN2C(=O)CCOc3ccccc3-c3cccc(c3)C[C@@H]12] |
| A1-75 | 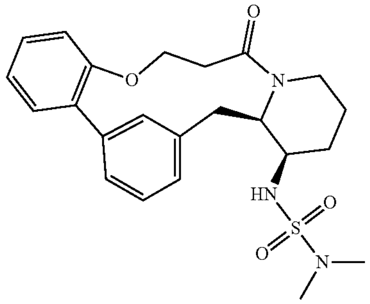 [SMILES: CN(C)S(=O)(=O)N[C@@H]1CCCN2C(=O)CCOc3ccccc3-c3cccc(c3)C[C@H]12] |
| A1-76 | 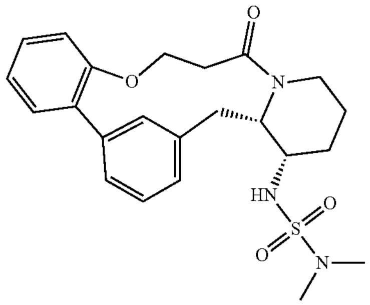 [SMILES: CN(C)S(=O)(=O)N[C@H]1CCCN2C(=O)CCOc3ccccc3-c3cccc(c3)C[C@@H]12] |
| A1-77 | 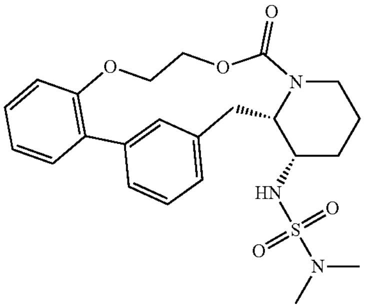 [SMILES: CN(C)S(=O)(=O)N[C@H]1CCCN2C(=O)OCCOc3ccccc3-c3cccc(c3)C[C@@H]12] |
| A1-78 | 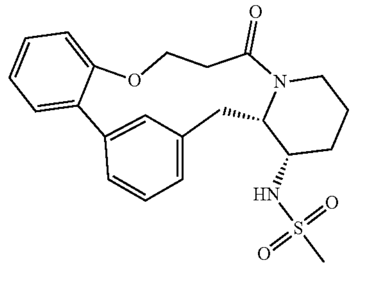 [SMILES: CS(=O)(=O)N[C@H]1CCCN2C(=O)CCOc3ccccc3-c3cccc(c3)C[C@@H]12] |
TABLE A1-continued
| Compound No. | Structure |
|---|---|
| A1-79 | 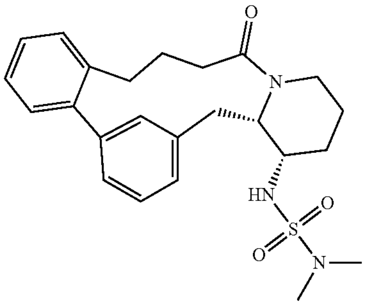 [SMILES: CN(C)S(=O)(=O)N[C@H]1CCCN2C(=O)CCCc3ccccc3-c3cccc(c3)C[C@@H]12] |
| A1-80 | 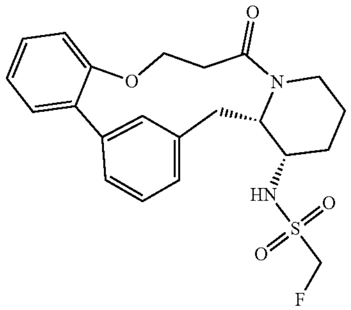 [SMILES: O=C1CCOc2ccccc2-c2cccc(c2)C[C@H]2[C@@H](NS(=O)(=O)CF)CCCN12] |
| A1-81 | 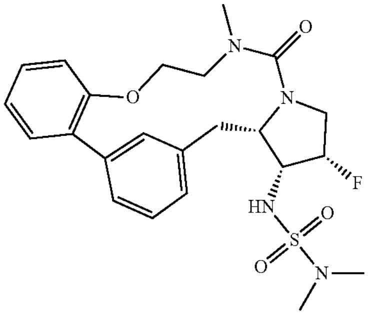 [SMILES: CN1CCOc2ccccc2-c2cccc(c2)C[C@H]2[C@@H](NS(=O)(=O)N(C)C)[C@@H](F)CN2C1=O] |
| A1-82 | 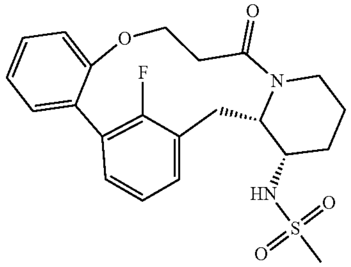 [SMILES: CS(=O)(=O)N[C@H]1CCCN2C(=O)CCOc3ccccc3-c3cccc(c3F)C[C@@H]12] |
| A1-83 | 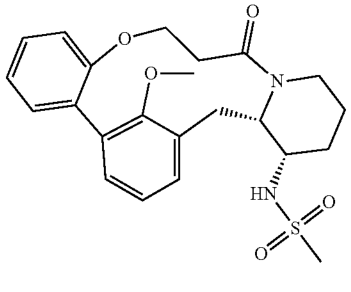 [SMILES: COc1c2cccc1-c1ccccc1OCCC(=O)N1CCC[C@H](NS(C)(=O)=O)[C@@H]1C2] |

TABLE A1-continued
| Compound No. | Structure |
|---|---|
| A1-84 | 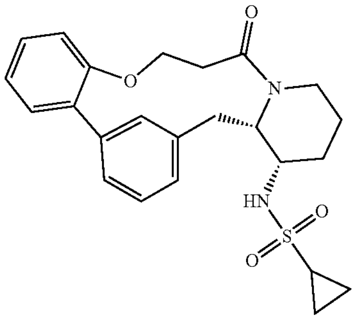 [SMILES: O=C1CCOc2ccccc2-c2cccc(c2)C[C@H]2[C@@H](NS(=O)(=O)C3CC3)CCCN12] |
| A1-85 | 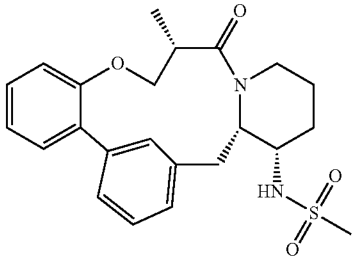 [SMILES: C[C@H]1COc2ccccc2-c2cccc(c2)C[C@H]2[C@@H](NS(C)(=O)=O)CCCN2C1=O] |
| A1-86 | 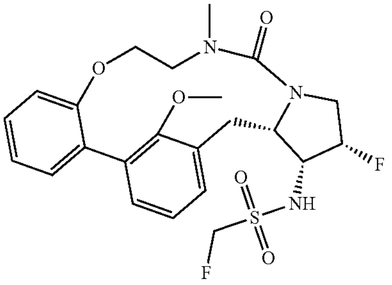 [SMILES: COc1c2cccc1-c1ccccc1OCCN(C)C(=O)N1C[C@H](F)[C@H](NS(=O)(=O)CF)[C@@H]1C2] |
| A1-87 | 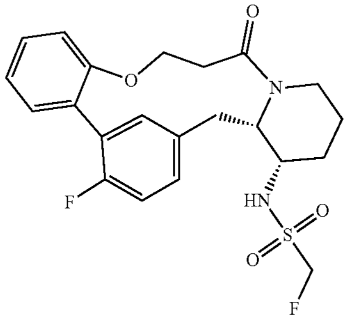 [SMILES: O=C1CCOc2ccccc2-c2cc(ccc2F)C[C@H]2[C@@H](NS(=O)(=O)CF)CCCN12] |
| A1-88 | 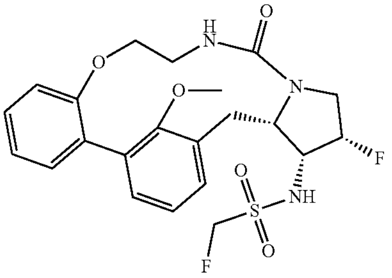 [SMILES: COc1c2cccc1-c1ccccc1OCCNC(=O)N1C[C@H](F)[C@H](NS(=O)(=O)CF)[C@@H]1C2] |
TABLE A1-continued
| Compound No. | Structure |
|---|---|
| A1-89 | 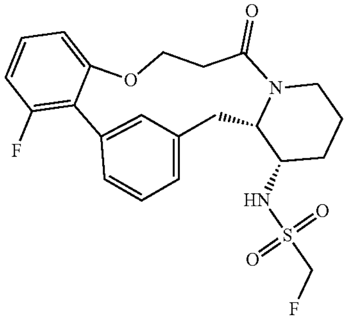 [SMILES: O=C1CCOc2cccc(F)c2-c2cccc(c2)C[C@H]2[C@@H](NS(=O)(=O)CF)CCCN12] |
| A1-90 | 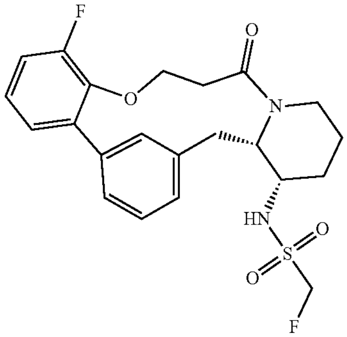 [SMILES: O=C1CCOc2c(F)cccc2-c2cccc(c2)C[C@H]2[C@@H](NS(=O)(=O)CF)CCCN12] |
| A1-91 | 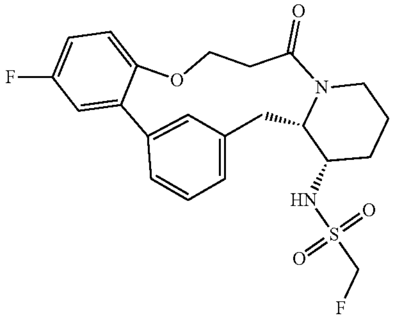 [SMILES: O=C1CCOc2ccc(F)cc2-c2cccc(c2)C[C@H]2[C@@H](NS(=O)(=O)CF)CCCN12] |
| A1-92 | 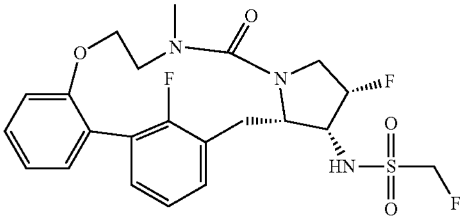 [SMILES: CN1CCOc2ccccc2-c2cccc(c2F)C[C@H]2[C@@H](NS(=O)(=O)CF)[C@@H](F)CN2C1=O] |
| A1-93 | 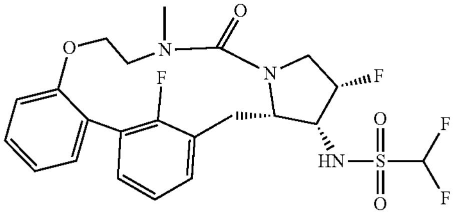 [SMILES: CN1CCOc2ccccc2-c2cccc(c2F)C[C@H]2[C@@H](NS(=O)(=O)C(F)F)[C@@H](F)CN2C1=O] |

TABLE A1-continued
| Compound No. | Structure |
|---|---|
| A1-94 | 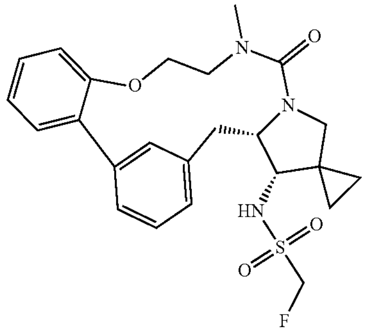 [SMILES: CN1CCOc2ccccc2-c2cccc(c2)C[C@H]2[C@@H](NS(=O)(=O)CF)C3(CC3)CN2C1=O] |
| A1-95 | 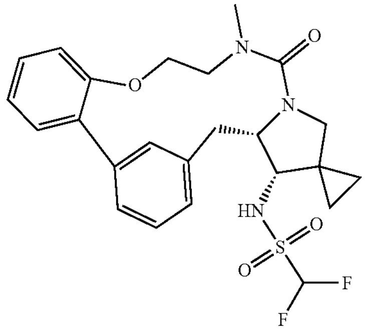 [SMILES: CN1CCOc2ccccc2-c2cccc(c2)C[C@H]2[C@@H](NS(=O)(=O)C(F)F)C3(CC3)CN2C1=O] |
| A1-96 | 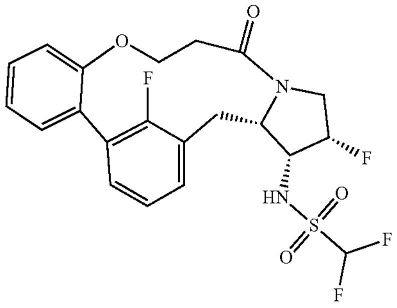 [SMILES: O=C1CCOc2ccccc2-c2cccc(c2F)C[C@H]2[C@@H](NS(=O)(=O)C(F)F)[C@@H](F)CN12] |
| A1-97 | 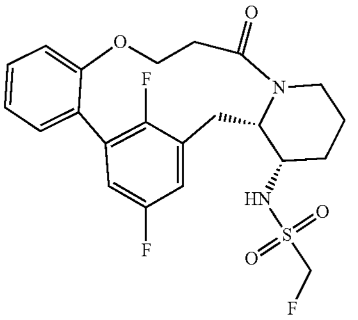 [SMILES: O=C1CCOc2ccccc2-c2cc(F)cc(c2F)C[C@H]2[C@@H](NS(=O)(=O)CF)CCCN12] |
| A1-98 | 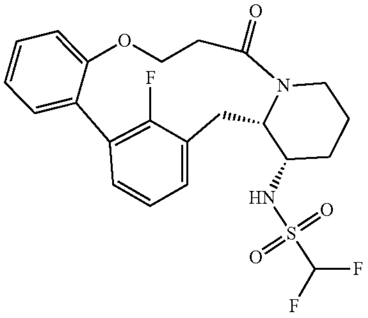 [SMILES: O=C1CCOc2ccccc2-c2cccc(c2F)C[C@H]2[C@@H](NS(=O)(=O)C(F)F)CCCN12] |
| A1-99 | 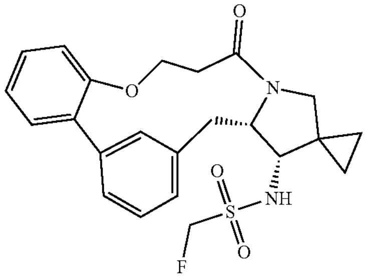 [SMILES: O=C1CCOc2ccccc2-c2cccc(c2)C[C@H]2[C@@H](NS(=O)(=O)CF)C3(CC3)CN12] |
| A1-100 | 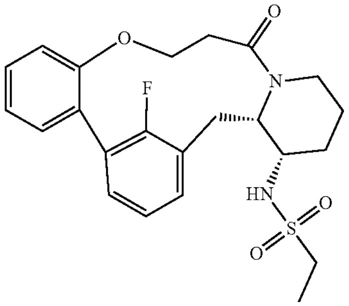 [SMILES: CCS(=O)(=O)N[C@H]1CCCN2C(=O)CCOc3ccccc3-c3cccc(c3F)C[C@@H]12] |
| A1-101 | 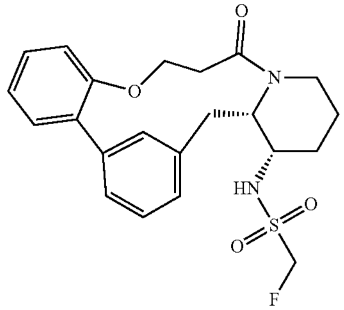 [SMILES: O=C1CCOc2ccccc2-c2cccc(c2)C[C@H]2[C@@H](NS(=O)(=O)CF)CCCN12] |
| A1-102 | 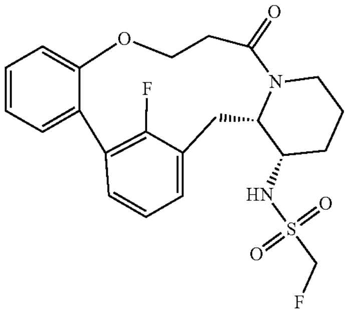 [SMILES: O=C1CCOc2ccccc2-c2cccc(c2F)C[C@H]2[C@@H](NS(=O)(=O)CF)CCCN12] |

TABLE A2
| Compound No. | Structure |
|---|---|
| A2-1 | 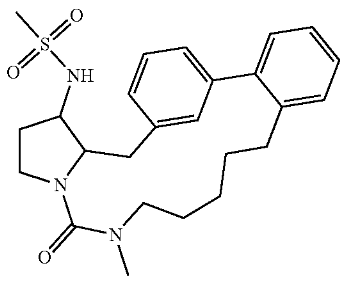 [SMILES: CN1CCCCCc2ccccc2-c2cccc(c2)CC2C(NS(C)(=O)=O)CCN2C1=O] |
| A2-2 | 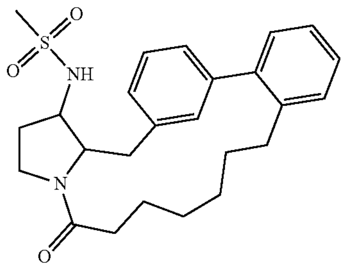 [SMILES: CS(=O)(=O)NC1CCN2C(=O)CCCCCCc3ccccc3-c3cccc(c3)CC12] |
| A2-3 | 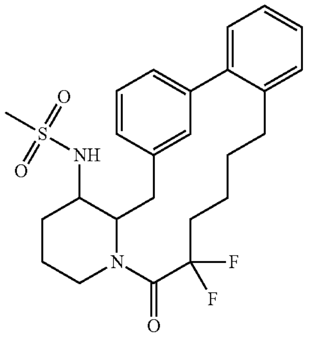 [SMILES: CS(=O)(=O)NC1CCCN2C(=O)C(F)(F)CCCCc3ccccc3-c3cccc(c3)CC12] |
| A2-4 | 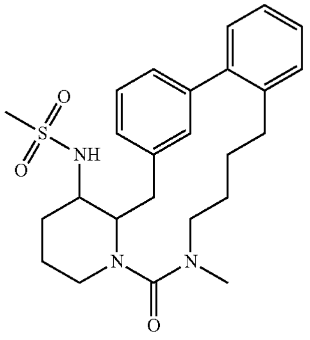 [SMILES: CN1CCCCc2ccccc2-c2cccc(c2)CC2C(NS(C)(=O)=O)CCCN2C1=O] |
| A2-5 | 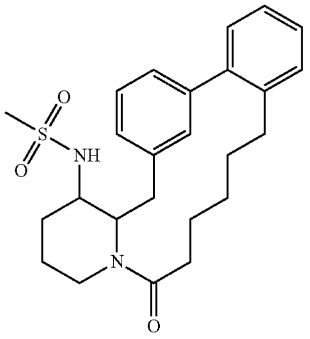 [SMILES: CS(=O)(=O)NC1CCCN2C(=O)CCCCCc3ccccc3-c3cccc(c3)CC12] |
TABLE A2-continued
| Compound No. | Structure |
|---|---|
| A2-6 | 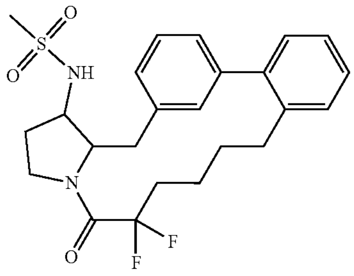 |
| A2-7 | 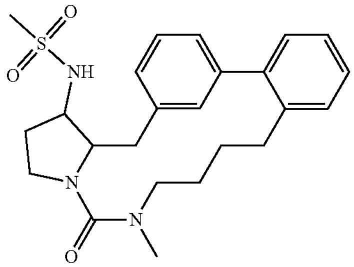 [SMILES: CN1CCCCc2ccccc2-c2cccc(c2)CC2C(NS(C)(=O)=O)CCN2C1=O] |
| A2-8 | 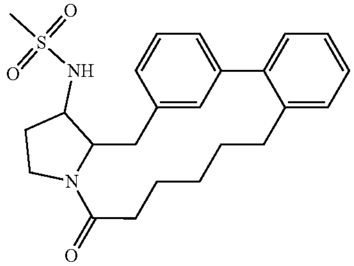 |
| A2-9 | 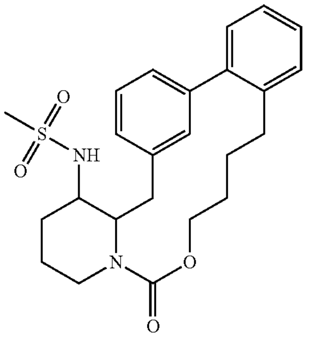 [SMILES: CS(=O)(=O)NC1CCCN2C(=O)OCCCCc3ccccc3-c3cccc(c3)CC12] |
| A2-10 | 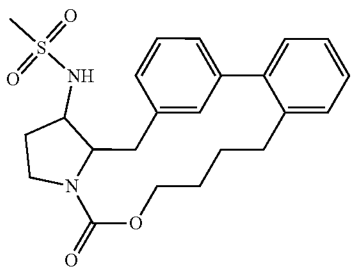 [SMILES: CS(=O)(=O)NC1CCN2C(=O)OCCCCc3ccccc3-c3cccc(c3)CC12] |

TABLE A2-continued
| Compound No. | Structure |
|---|---|
| A2-11 | 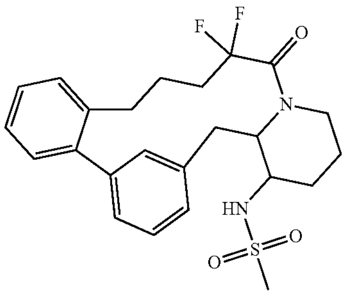 [SMILES: CS(=O)(=O)NC1CCCN2C(=O)C(F)(F)CCCc3ccccc3-c3cccc(c3)CC12] |
| A2-12 | 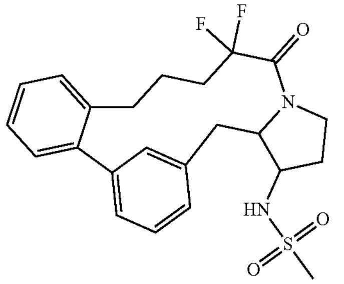 [SMILES: CS(=O)(=O)NC1CCN2C(=O)C(F)(F)CCCc3ccccc3-c3cccc(c3)CC12] |
| A2-13 | 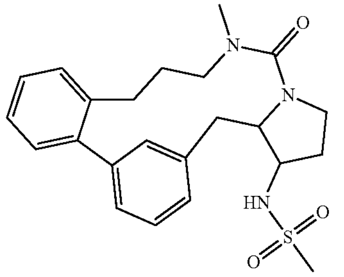 [SMILES: CN1CCCc2ccccc2-c2cccc(c2)CC2C(NS(C)(=O)=O)CCN2C1=O] |
| A2-14 | 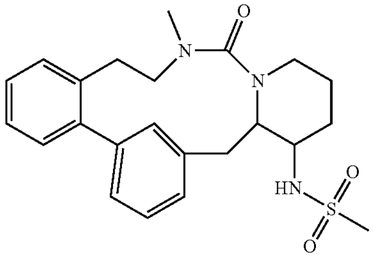 [SMILES: CN1CCc2ccccc2-c2cccc(c2)CC2C(NS(C)(=O)=O)CCCN2C1=O] |
| A2-15 | 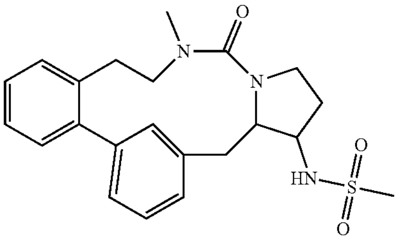 [SMILES: CN1CCc2ccccc2-c2cccc(c2)CC2C(NS(C)(=O)=O)CCN2C1=O] |
TABLE A2-continued
| Compound No. | Structure |
|---|---|
| A2-16 | 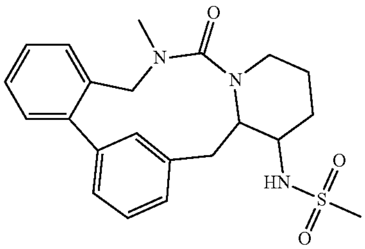 [SMILES: CN1Cc2ccccc2-c2cccc(c2)CC2C(NS(C)(=O)=O)CCCN2C1=O] |
| A2-17 | 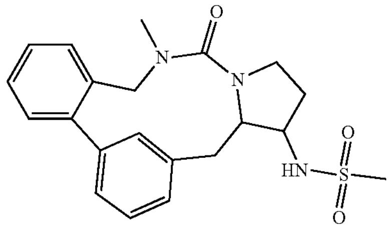 [SMILES: CN1Cc2ccccc2-c2cccc(c2)CC2C(NS(C)(=O)=O)CCN2C1=O] |
| A2-18 | 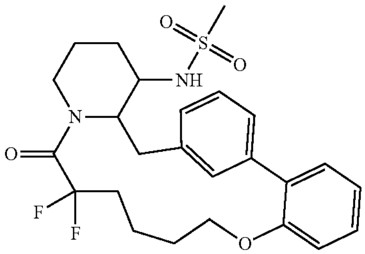 [SMILES: CS(=O)(=O)NC1CCCN2C(=O)C(F)(F)CCCCOc3ccccc3-c3cccc(c3)CC12] |
| A2-19 | 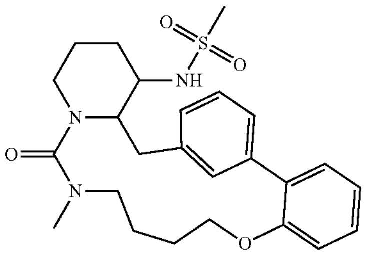 [SMILES: CN1CCCCOc2ccccc2-c2cccc(c2)CC2C(NS(C)(=O)=O)CCCN2C1=O] |
| A2-20 | 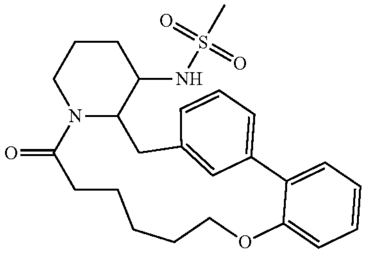 [SMILES: CS(=O)(=O)NC1CCCN2C(=O)CCCCCOc3ccccc3-c3cccc(c3)CC12] |
| A2-21 | 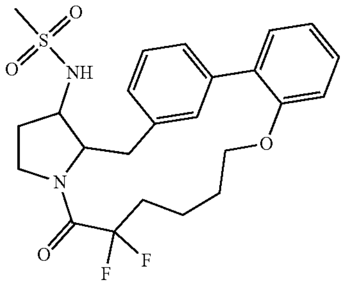 [SMILES: CS(=O)(=O)NC1CCN2C(=O)C(F)(F)CCCCOc3ccccc3-c3cccc(c3)CC12] |

TABLE A2-continued
| Compound No. | Structure |
|---|---|
| A2-22 | 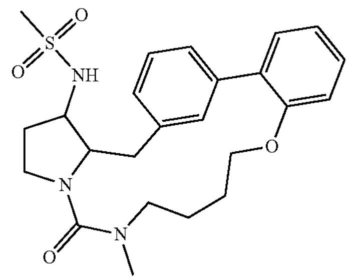 [SMILES: CN1CCCCOc2ccccc2-c2cccc(c2)CC2C(NS(C)(=O)=O)CCN2C1=O] |
| A2-23 | 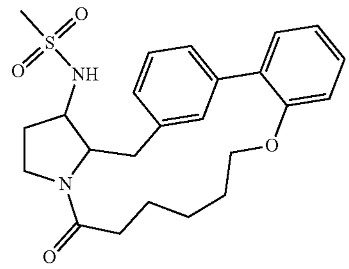 [SMILES: CS(=O)(=O)NC1CCN2C(=O)CCCCCOc3ccccc3-c3cccc(c3)CC12] |
| A2-24 | 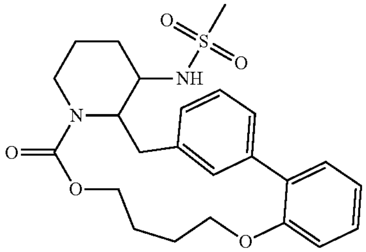 [SMILES: CS(=O)(=O)NC1CCCN2C(=O)OCCCCOc3ccccc3-c3cccc(c3)CC12] |
| A2-25 | 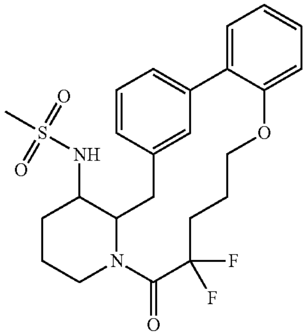 [SMILES: CS(=O)(=O)NC1CCCN2C(=O)C(F)(F)CCCOc3ccccc3-c3cccc(c3)CC12] |
| A2-26 | 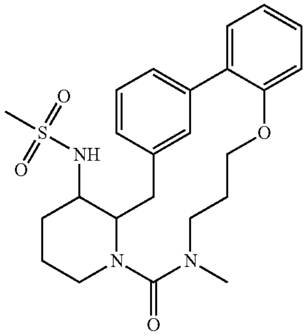 [SMILES: CN1CCCOc2ccccc2-c2cccc(c2)CC2C(NS(C)(=O)=O)CCCN2C1=O] |
| A2-27 | 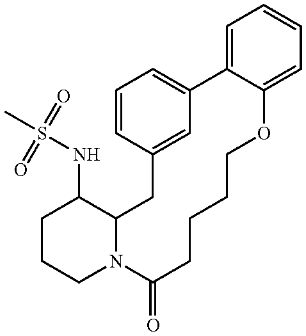 [SMILES: CS(=O)(=O)NC1CCCN2C(=O)CCCCOc3ccccc3-c3cccc(c3)CC12] |
| A2-28 | 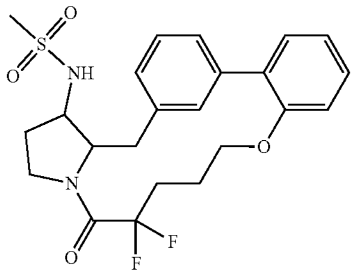 [SMILES: CS(=O)(=O)NC1CCN2C(=O)C(F)(F)CCCOc3ccccc3-c3cccc(c3)CC12] |
| A2-29 | 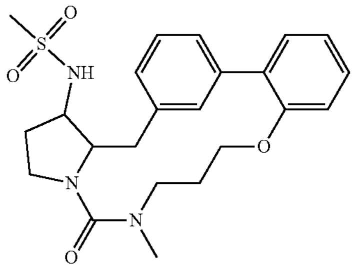 |
| A2-30 | 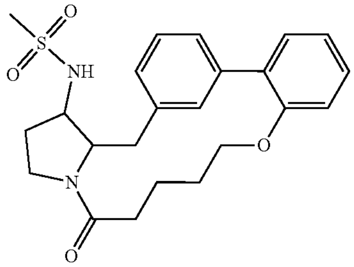 [SMILES: CS(=O)(=O)NC1CCN2C(=O)CCCCOc3ccccc3-c3cccc(c3)CC12] |
| A2-31 | 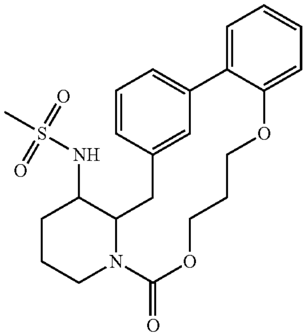 [SMILES: CS(=O)(=O)NC1CCCN2C(=O)OCCCOc3ccccc3-c3cccc(c3)CC12] |

TABLE A2-continued
| Compound No. | Structure |
| --- | --- |
| A2-32 | 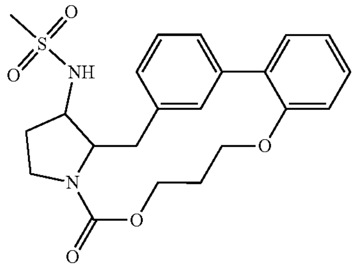 |
| A2-33 | 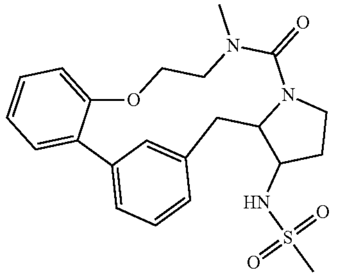 [SMILES: CN1CCOc2ccccc2-c2cccc(c2)CC2C(NS(C)(=O)=O)CCN2C1=O] |
| A2-34 | 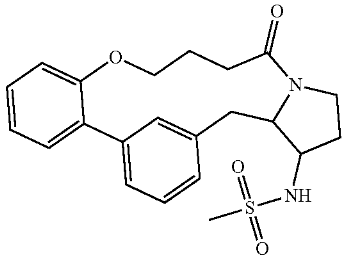 [SMILES: CS(=O)(=O)NC1CCN2C(=O)CCCOc3ccccc3-c3cccc(c3)CC12] |
| A2-35 | 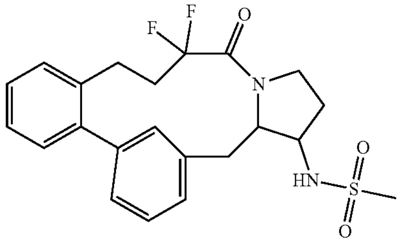 [SMILES: CS(=O)(=O)NC1CCN2C(=O)C(F)(F)CCc3ccccc3-c3cccc(c3)CC12] |
| A2-36 | 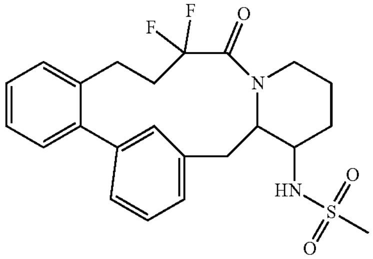 [SMILES: CS(=O)(=O)NC1CCCN2C(=O)C(F)(F)CCc3ccccc3-c3cccc(c3)CC12] |
TABLE A2-continued
| Compound No. | Structure |
| --- | --- |
| A2-37 | 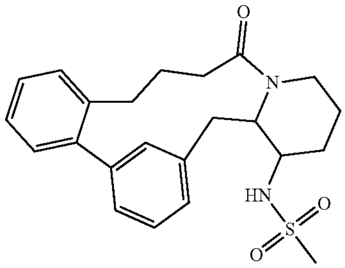 [SMILES: CS(=O)(=O)NC1CCCN2C(=O)CCCc3ccccc3-c3cccc(c3)CC12] |
| A2-38 | 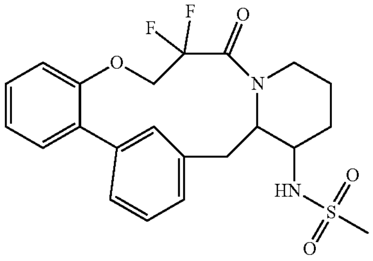 |
| A2-39 | 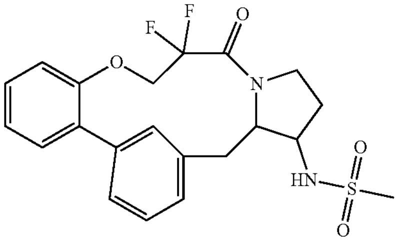 |
| A2-40 | 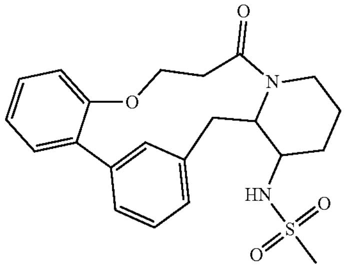 [SMILES: CS(=O)(=O)NC1CCCN2C(=O)CCOc3ccccc3-c3cccc(c3)CC12] |
| A2-41 | 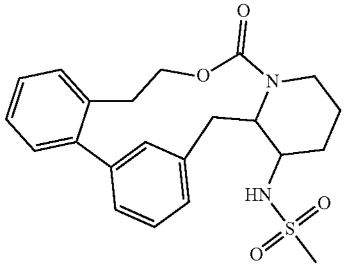 [SMILES: CS(=O)(=O)NC1CCCN2C(=O)OCCc3ccccc3-c3cccc(c3)CC12] |
| A2-42 | 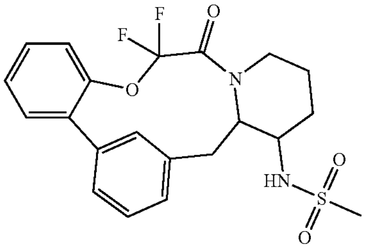 [SMILES: CS(=O)(=O)NC1CCCN2C(=O)C(F)(F)Oc3ccccc3-c3cccc(c3)CC12] |

TABLE A2-continued
| Compound No. | Structure |
|---|---|
| A2-43 | 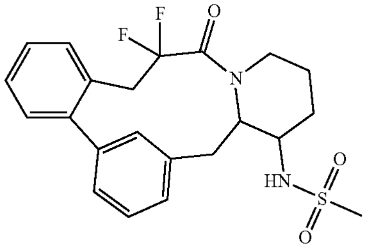 [SMILES: CS(=O)(=O)NC1CCCN2C(=O)C(F)(F)Cc3ccccc3-c3cccc(c3)CC12] |
| A2-44 | 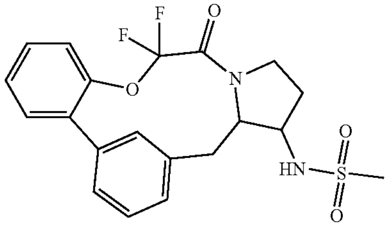 |
| A2-45 | 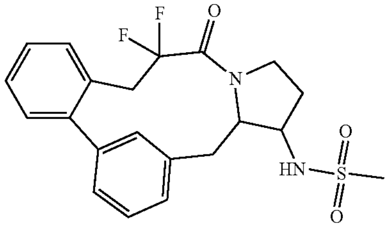 [SMILES: CS(=O)(=O)NC1CCN2C(=O)C(F)(F)Oc3ccccc3-c3cccc(c3)CC12] |
| A2-46 | 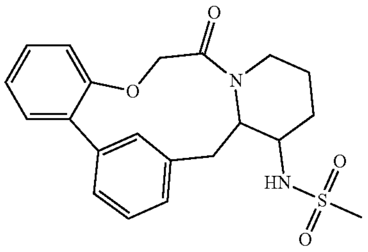 [SMILES: CS(=O)(=O)NC1CCCN2C(=O)COc3ccccc3-c3cccc(c3)CC12] |
| A2-47 | 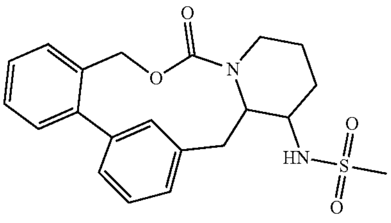 [SMILES: CS(=O)(=O)NC1CCCN2C(=O)OCc3ccccc3-c3cccc(c3)CC12] |
| A2-48 | 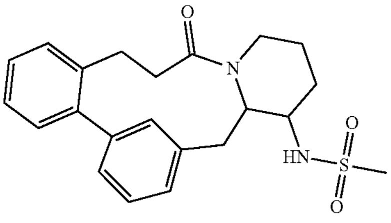 [SMILES: CS(=O)(=O)NC1CCCN2C(=O)CCc3ccccc3-c3cccc(c3)CC12] |
TABLE A2-continued
| Compound No. | Structure |
|---|---|
| A2-49 | 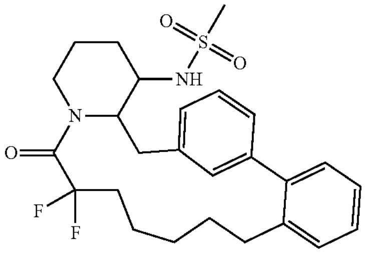 [SMILES: CS(=O)(=O)NC1CCCN2C(=O)C(F)(F)CCCCCc3ccccc3-c3cccc(c3)CC12] |
| A2-50 | 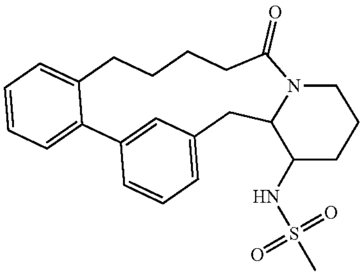 [SMILES: CS(=O)(=O)NC1CCCN2C(=O)CCCCc3ccccc3-c3cccc(c3)CC12] |
| A2-51 | 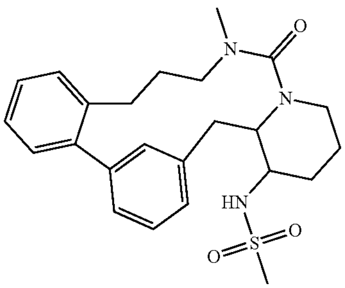 [SMILES: CN1CCCc2ccccc2-c2cccc(c2)CC2C(NS(C)(=O)=O)CCCN2C1=O] |
| A2-52 | 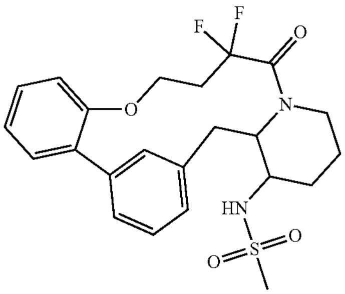 [SMILES: CS(=O)(=O)NC1CCCN2C(=O)C(F)(F)CCOc3ccccc3-c3cccc(c3)CC12] |
| A2-53 | 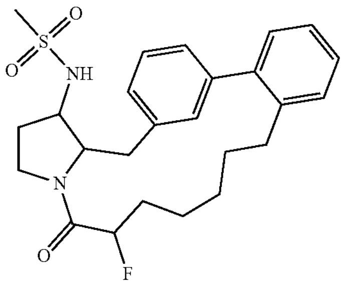 [SMILES: CS(=O)(=O)NC1CCN2C(=O)C(F)CCCCCc3ccccc3-c3cccc(c3)CC12] |

TABLE A2-continued
| Compound No. | Structure |
| --- | --- |
| A2-54 | 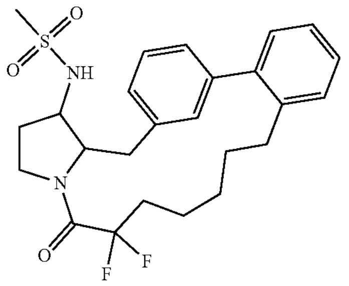 [SMILES: CS(=O)(=O)NC1CCN2C(=O)C(F)(F)CCCCCc3ccccc3-c3cccc(c3)CC12] |
| A2-55 | 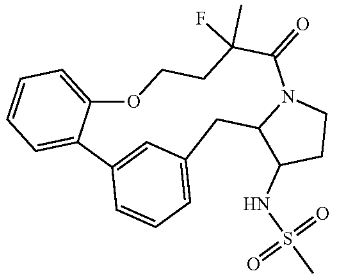 [SMILES: CC1(F)CCOc2ccccc2-c2cccc(c2)CC2C(NS(C)(=O)=O)CCN2C1=O] |
| A2-56 | 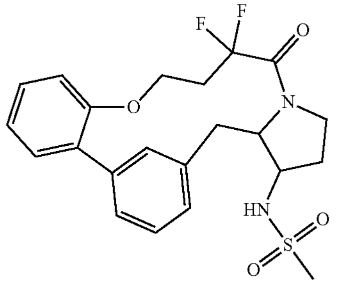 [SMILES: CS(=O)(=O)NC1CCN2C(=O)C(F)(F)CCOc3ccccc3-c3cccc(c3)CC12] |
| A2-57 | 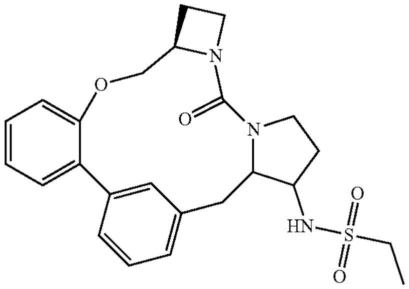 [SMILES: CCS(=O)(=O)NC1CCN2C(=O)N3CC[C@@H]3COc3ccccc3-c3cccc(c3)CC12] |
| A2-58 | 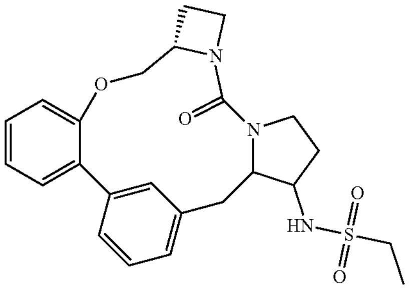 [SMILES: CCS(=O)(=O)NC1CCN2C(=O)N3CC[C@H]3COc3ccccc3-c3cccc(c3)CC12] |
TABLE A2-continued
| Compound No. | Structure |
| --- | --- |
| A2-59 | 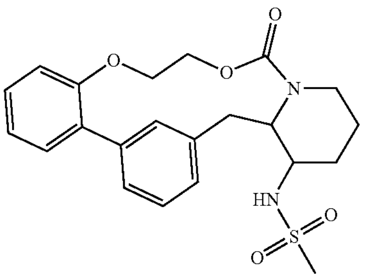 [SMILES: CS(=O)(=O)NC1CCCN2C(=O)OCCOc3ccccc3-c3cccc(c3)CC12] |
| A2-60 | 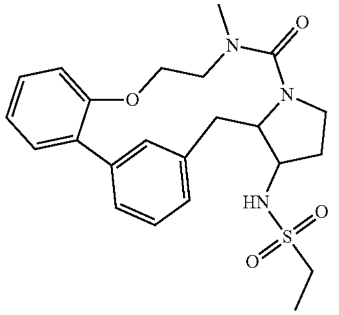 [SMILES: CCS(=O)(=O)NC1CCN2C(=O)N(C)CCOc3ccccc3-c3cccc(c3)CC12] |
| A2-61 | 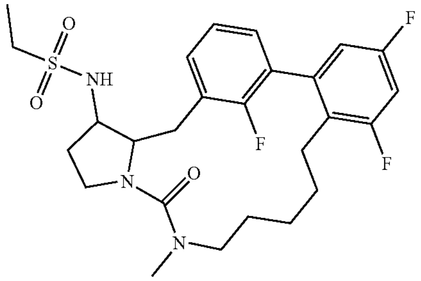 [SMILES: CCS(=O)(=O)NC1CCN2C(=O)N(C)CCCCCc3c(F)cc(F)cc3-c3cccc(c3F)CC12] |
| A2-62 | 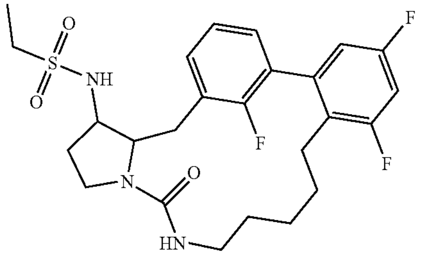 [SMILES: CCS(=O)(=O)NC1CCN2C(=O)NCCCCCc3c(F)cc(F)cc3-c3cccc(c3F)CC12] |
| A2-63 | 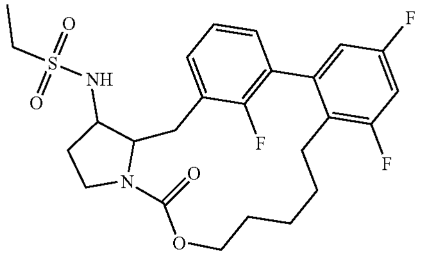 [SMILES: CCS(=O)(=O)NC1CCN2C(=O)OCCCCCc3c(F)cc(F)cc3-c3cccc(c3F)CC12] |

TABLE A2-continued
| Compound No. | Structure |
|---|---|
| A2-64 | 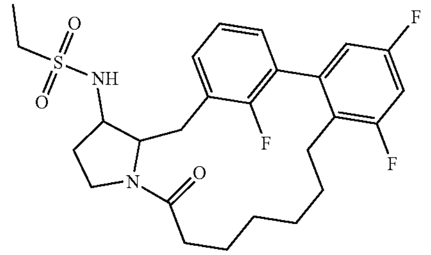 [SMILES: CCS(=O)(=O)NC1CCN2C(=O)CCCCCCc3c(F)cc(F)cc3-c3cccc(c3F)CC12] |
| A2-65 | 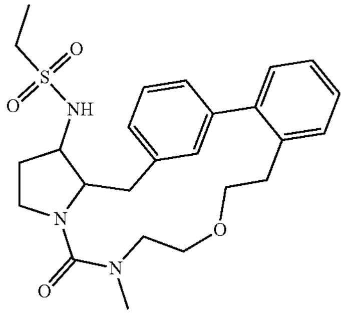 [SMILES: CCS(=O)(=O)NC1CCN2C(=O)N(C)CCOCCc3ccccc3-c3cccc(c3)CC12] |
| A2-66 | 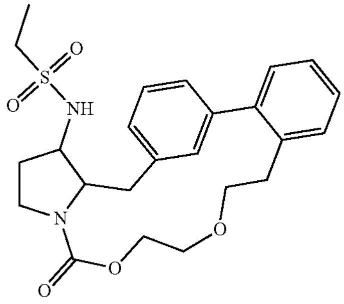 [SMILES: CCS(=O)(=O)NC1CCN2C(=O)OCCOCCc3ccccc3-c3cccc(c3)CC12] |
| A2-67 | 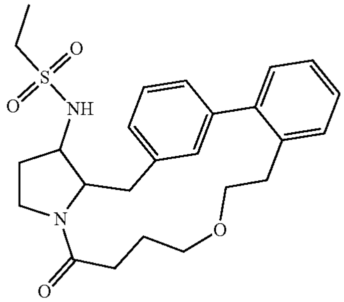 [SMILES: CCS(=O)(=O)NC1CCN2C(=O)CCCOCCc3ccccc3-c3cccc(c3)CC12] |
| A2-68 | 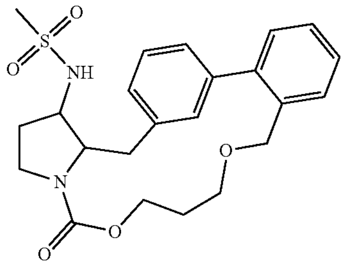 [SMILES: CS(=O)(=O)NC1CCN2C(=O)OCCCOCc3ccccc3-c3cccc(c3)CC12] |
TABLE A2-continued
| Compound No. | Structure |
|---|---|
| A2-69 | 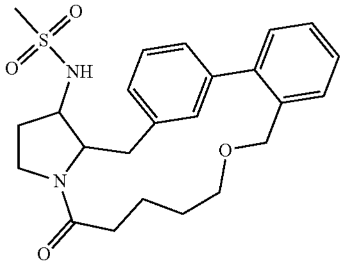 [SMILES: CS(=O)(=O)NC1CCN2C(=O)CCCCOCc3ccccc3-c3cccc(c3)CC12] |
| A2-70 | 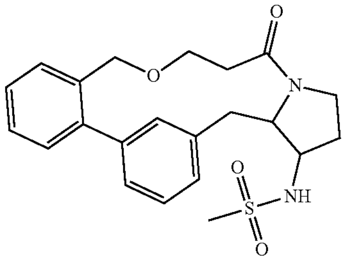 [SMILES: CS(=O)(=O)NC1CCN2C(=O)CCOCc3ccccc3-c3cccc(c3)CC12] |
| A2-71 | 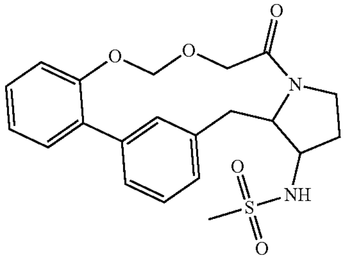 [SMILES: CS(=O)(=O)NC1CCN2C(=O)COCOc3ccccc3-c3cccc(c3)CC12] |
| A2-72 | 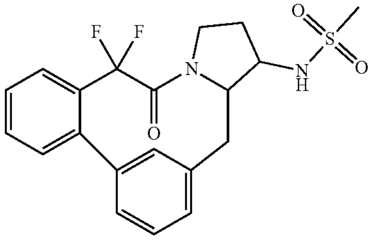 [SMILES: CS(=O)(=O)NC1CCN2C(=O)C(F)(F)c3ccccc3-c3cccc(c3)CC12] |
| A2-73 | 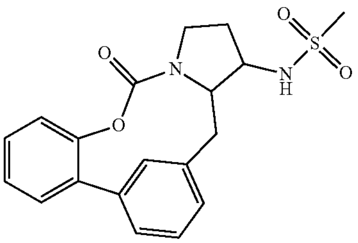 [SMILES: CS(=O)(=O)NC1CCN2C(=O)Oc3ccccc3-c3cccc(c3)CC12] |
| A2-74 | 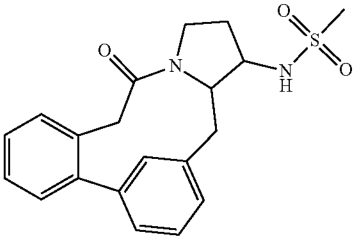 [SMILES: CS(=O)(=O)NC1CCN2C(=O)Cc3ccccc3-c3cccc(c3)CC12] |

TABLE A2-continued
| Compound No. | Structure |
| --- | --- |
| A2-75 | 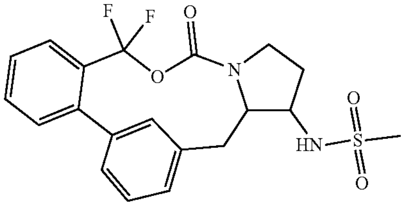 [SMILES: CS(=O)(=O)NC1CCN2C(=O)OC(F)(F)c3ccccc3-c3cccc(c3)CC12] |
| A2-76 | 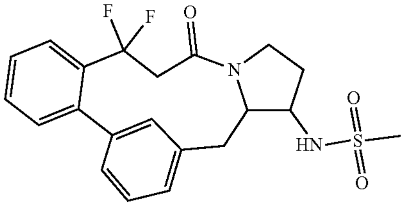 |
| A2-77 | 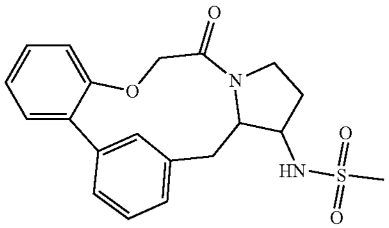 [SMILES: CS(=O)(=O)NC1CCN2C(=O)COc3ccccc3-c3cccc(c3)CC12] |
| A2-78 | 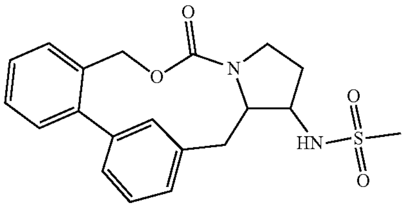 [SMILES: CS(=O)(=O)NC1CCN2C(=O)OCc3ccccc3-c3cccc(c3)CC12] |
| A2-79 | 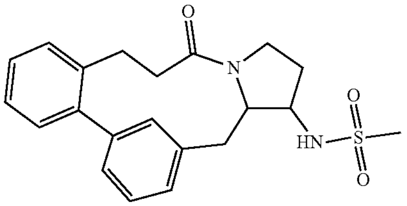 [SMILES: CS(=O)(=O)NC1CCN2C(=O)CCc3ccccc3-c3cccc(c3)CC12] |
| A2-80 | 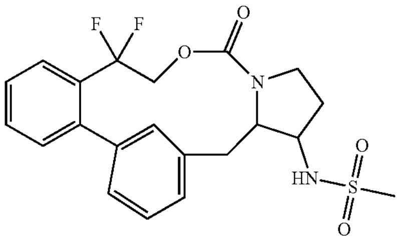 [SMILES: CS(=O)(=O)NC1CCN2C(=O)OCC(F)(F)c3ccccc3-c3cccc(c3)CC12] |
| A2-81 | 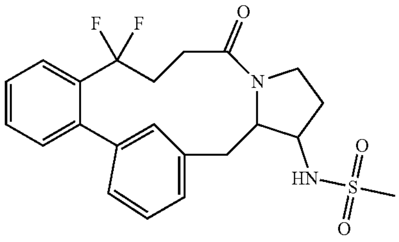 [SMILES: CS(=O)(=O)NC1CCN2C(=O)CCC(F)(F)c3ccccc3-c3cccc(c3)CC12] |
TABLE A2-continued
| Compound No. | Structure |
| --- | --- |
| A2-82 | 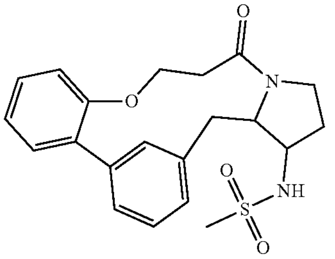 [SMILES: CS(=O)(=O)NC1CCN2C(=O)CCOc3ccccc3-c3cccc(c3)CC12] |
| A2-83 | 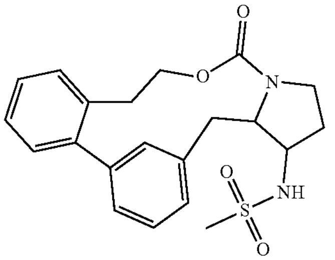 [SMILES: CS(=O)(=O)NC1CCN2C(=O)OCCc3ccccc3-c3cccc(c3)CC12] |
| A2-84 | 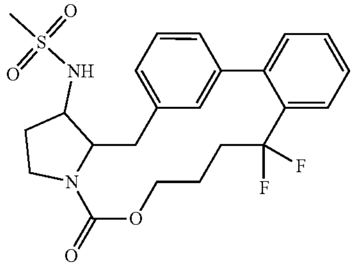 [SMILES: CS(=O)(=O)NC1CCN2C(=O)OCCCC(F)(F)c3ccccc3-c3cccc(c3)CC12] |
| A2-85 | 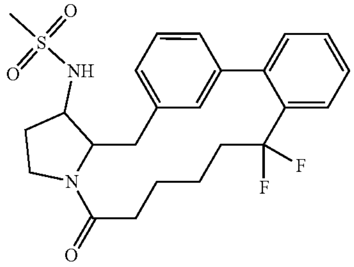 [SMILES: CS(=O)(=O)NC1CCN2C(=O)CCCCC(F)(F)c3ccccc3-c3cccc(c3)CC12] |
| A2-86 | 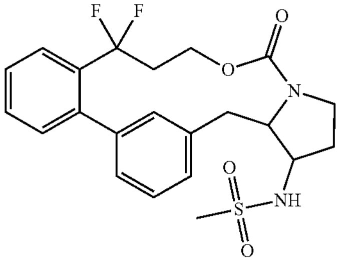 [SMILES: CS(=O)(=O)NC1CCN2C(=O)OCCC(F)(F)c3ccccc3-c3cccc(c3)CC12] |

TABLE A2-continued
| Compound No. | Structure |
|---|---|
| A2-87 | 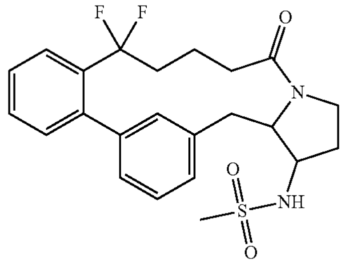 [SMILES: CS(=O)(=O)NC1CCN2C(=O)CCCC(F)(F)c3ccccc3-c3cccc(c3)CC12] |
| A2-88 | 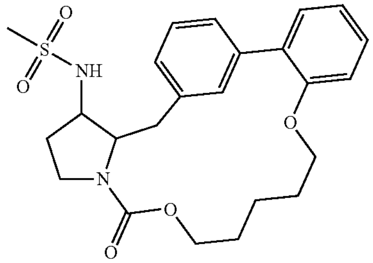 [SMILES: CS(=O)(=O)NC1CCN2C(=O)OCCCCCOc3ccccc3-c3cccc(c3)CC12] |
| A2-89 | 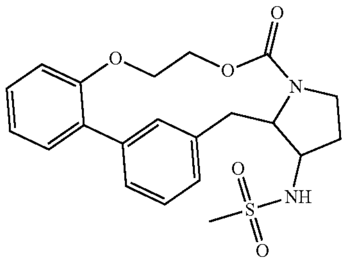 [SMILES: CS(=O)(=O)NC1CCN2C(=O)OCCOc3ccccc3-c3cccc(c3)CC12] |
| A2-90 | 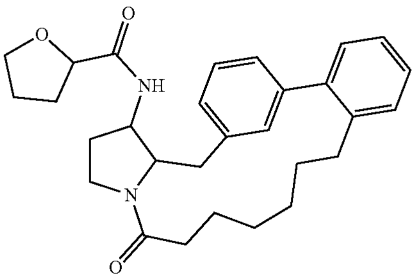 [SMILES: O=C(NC1CCN2C(=O)CCCCCCc3ccccc3-c3cccc(c3)CC12)C1CCCO1] |
| A2-91 | 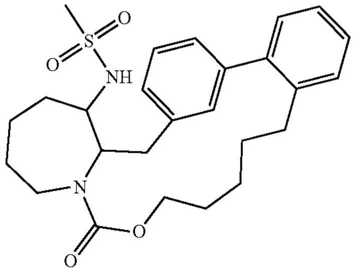 [SMILES: CS(=O)(=O)NC1CCCCN2C(=O)OCCCCCc3ccccc3-c3cccc(c3)CC12] |
TABLE A2-continued
| Compound No. | Structure |
|---|---|
| A2-92 | 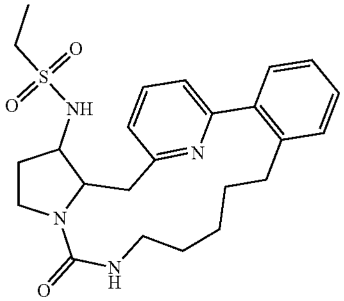 [SMILES: CCS(=O)(=O)NC1CCN2C(=O)NCCCCCc3ccccc3-c3cccc(n3)CC12] |
| A2-93 | 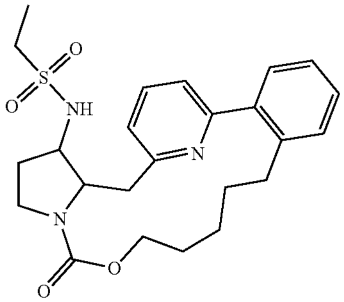 |
| A2-94 | 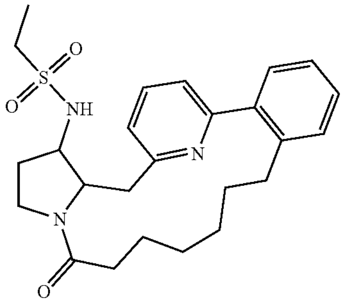 [SMILES: CCS(=O)(=O)NC1CCN2C(=O)CCCCCCc3ccccc3-c3cccc(n3)CC12] |
| A2-95 | 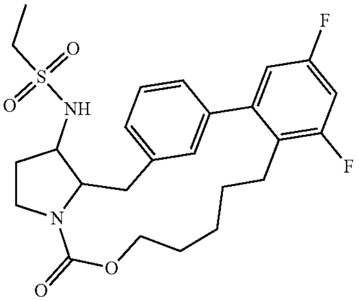 [SMILES: CCS(=O)(=O)NC1CCN2C(=O)OCCCCCc3c(F)cc(F)cc3-c3cccc(c3)CC12] |
| A2-96 | 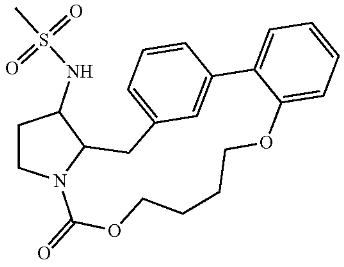 [SMILES: CS(=O)(=O)NC1CCN2C(=O)OCCCCOc3ccccc3-c3cccc(c3)CC12] |

TABLE A2-continued
| Compound No. | Structure |
|---|---|
| A2-97 | 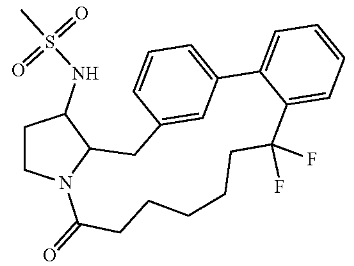 [SMILES: CS(=O)(=O)NC1CCN2C(=O)CCCCCC(F)(F)c3ccccc3-c3cccc(c3)CC12] |
| A2-98 | 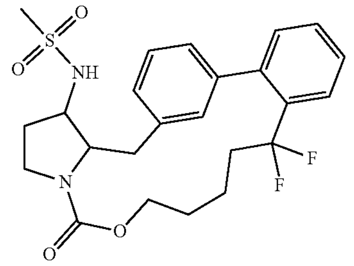 [SMILES: CS(=O)(=O)NC1CCN2C(=O)OCCCCC(F)(F)c3ccccc3-c3cccc(c3)CC12] |
| A2-99 | 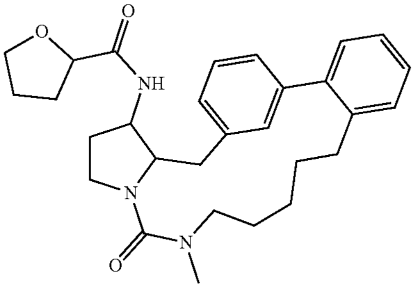 [SMILES: CN1CCCCCc2ccccc2-c2cccc(c2)CC2C(NC(=O)C3CCCO3)CCN2C1=O] |
| A2-100 | 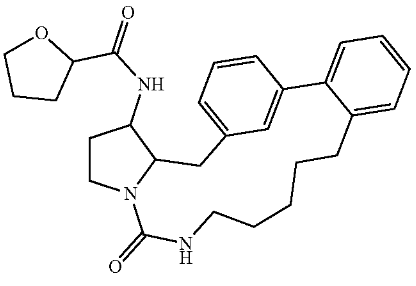 [SMILES: O=C(NC1CCN2C(=O)NCCCCCc3ccccc3-c3cccc(c3)CC12)C1CCCO1] |
| A2-101 | 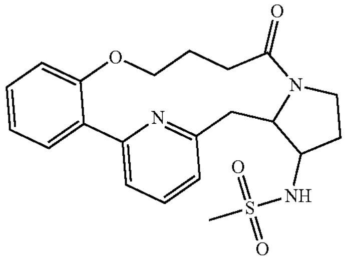 [SMILES: CS(=O)(=O)NC1CCN2C(=O)CCCOc3ccccc3-c3cccc(n3)CC12] |
TABLE A2-continued
| Compound No. | Structure |
|---|---|
| A2-102 | 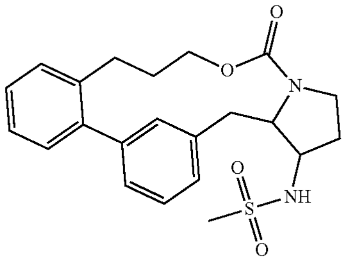 [SMILES: CS(=O)(=O)NC1CCN2C(=O)OCCCc3ccccc3-c3cccc(c3)CC12] |
| A2-103 | 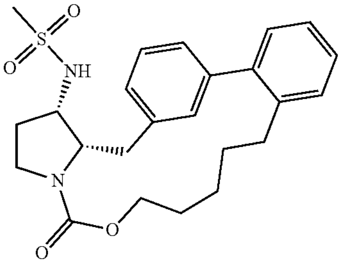 [SMILES: CS(=O)(=O)N[C@H]1CCN2C(=O)OCCCCCc3ccccc3-c3cccc(c3)C[C@@H]12] |
| A2-104 | 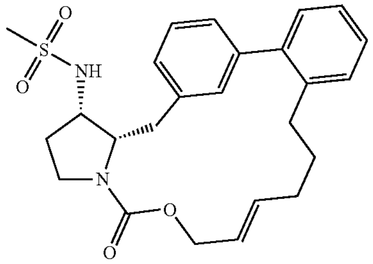 [SMILES: CS(=O)(=O)N[C@H]1CCN2C(=O)OC/C=C/CCCc3ccccc3-c3cccc(c3)C[C@@H]12] |
| A2-105 | 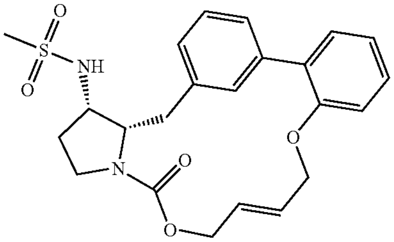 [SMILES: CS(=O)(=O)N[C@H]1CCN2C(=O)OC/C=C/COc3ccccc3-c3cccc(c3)C[C@@H]12] |
| A2-106 | 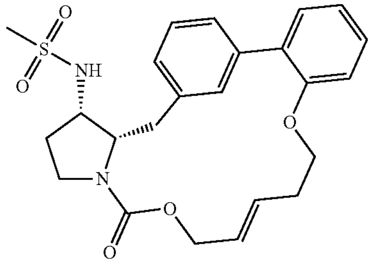 [SMILES: CS(=O)(=O)N[C@H]1CCN2C(=O)OC/C=C/CCOc3ccccc3-c3cccc(c3)C[C@@H]12] |
| A2-107 | 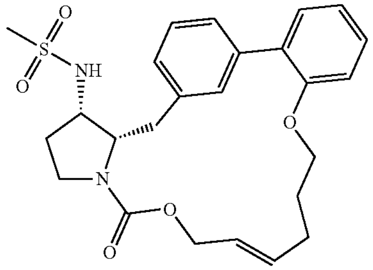 [SMILES: CS(=O)(=O)N[C@H]1CCN2C(=O)OC/C=C/CCCOc3ccccc3-c3cccc(c3)C[C@@H]12] |

TABLE A2-continued
| Compound No. | Structure |
|---|---|
| A2-108 | 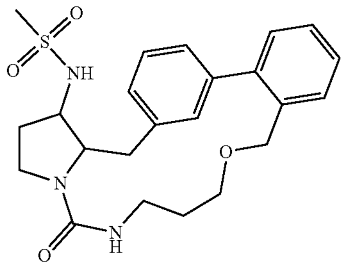 [SMILES: CS(=O)(=O)NC1CCN2C(=O)NCCCOCc3ccccc3-c3cccc(c3)CC12] |
| A2-109 | 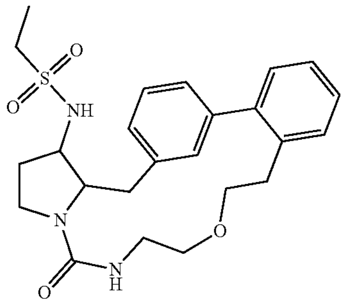 [SMILES: CCS(=O)(=O)NC1CCN2C(=O)NCCOCCc3ccccc3-c3cccc(c3)CC12] |
| A2-110 | 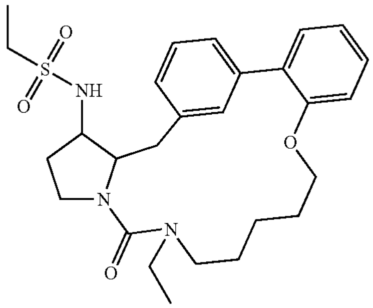 [SMILES: CCN1CCCCCOc2ccccc2-c2cccc(c2)CC2C(NS(=O)(=O)CC)CCN2C1=O] |
| A2-111 | 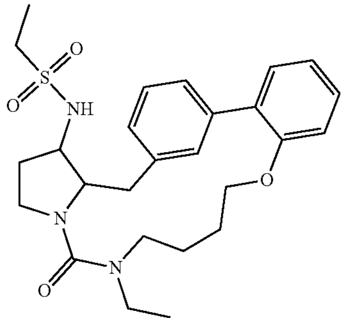 [SMILES: CCN1CCCCOc2ccccc2-c2cccc(c2)CC2C(NS(=O)(=O)CC)CCN2C1=O] |
| A2-112 | 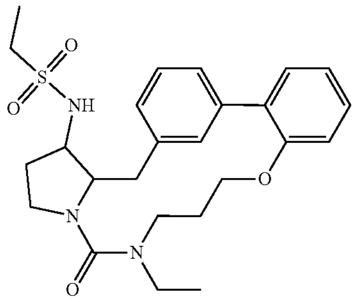 [SMILES: CCN1CCCOc2ccccc2-c2cccc(c2)CC2C(NS(=O)(=O)CC)CCN2C1=O] |
TABLE A2-continued
| Compound No. | Structure |
|---|---|
| A2-113 | 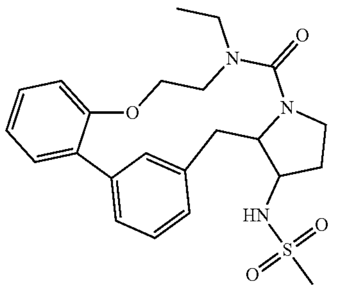 [SMILES: CCN1CCOc2ccccc2-c2cccc(c2)CC2C(NS(C)(=O)=O)CCN2C1=O] |
| A2-114 | 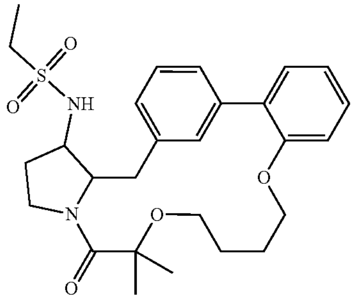 [SMILES: CCS(=O)(=O)NC1CCN2C(=O)C(C)(C)OCCCCOc3ccccc3-c3cccc(c3)CC12] |
| A2-115 | 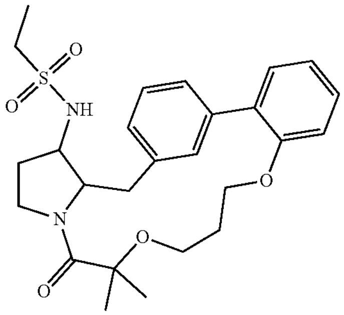 [SMILES: CCS(=O)(=O)NC1CCN2C(=O)C(C)(C)OCCCOc3ccccc3-c3cccc(c3)CC12] |
| A2-116 | 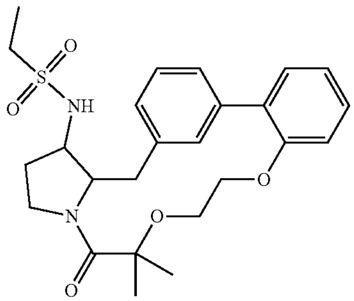 [SMILES: CCS(=O)(=O)NC1CCN2C(=O)C(C)(C)OCCOc3ccccc3-c3cccc(c3)CC12] |
| A2-117 | 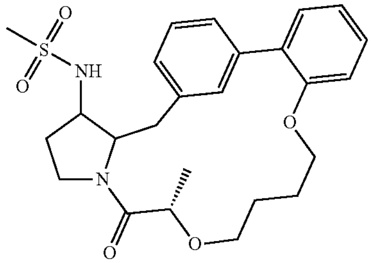 [SMILES: C[C@@H]1OCCCCOc2ccccc2-c2cccc(c2)CC2C(NS(C)(=O)=O)CCN2C1=O] |

TABLE A2-continued
| Compound No. | Structure |
|---|---|
| A2-118 | 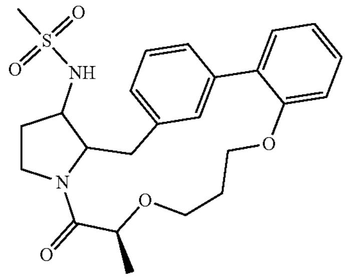 [SMILES: C[C@@H]1OCCCOc2ccccc2-c2cccc(c2)CC2C(NS(C)(=O)=O)CCN2C1=O] |
| A2-119 | 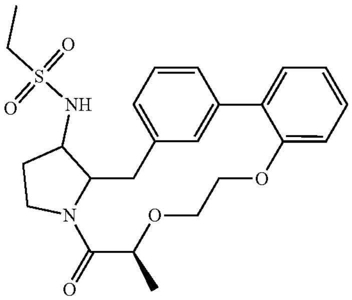 [SMILES: CCS(=O)(=O)NC1CCN2C(=O)[C@H](C)OCCOc3ccccc3-c3cccc(c3)CC12] |
| A2-120 | 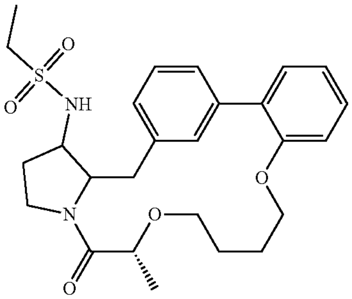 [SMILES: CCS(=O)(=O)NC1CCN2C(=O)[C@@H](C)OCCCCOc3ccccc3-c3cccc(c3)CC12] |
| A2-121 | 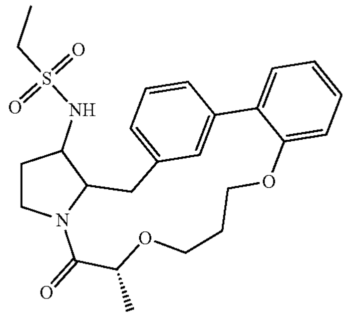 [SMILES: CCS(=O)(=O)NC1CCN2C(=O)[C@@H](C)OCCCOc3ccccc3-c3cccc(c3)CC12] |
| A2-122 | 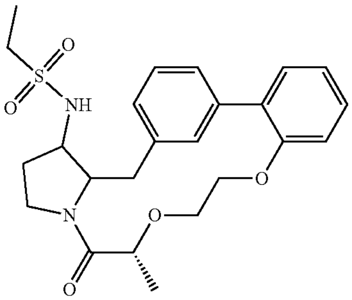 [SMILES: CCS(=O)(=O)NC1CCN2C(=O)[C@@H](C)OCCOc3ccccc3-c3cccc(c3)CC12] |
TABLE A2-continued
| Compound No. | Structure |
|---|---|
| A2-123 | 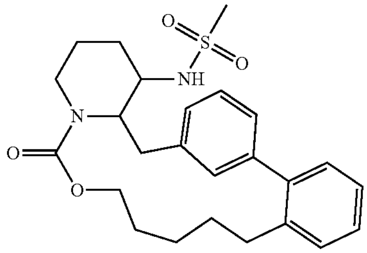 [SMILES: CS(=O)(=O)NC1CCCN2C(=O)OCCCCCc3ccccc3-c3cccc(c3)CC12] |
| A2-124 | 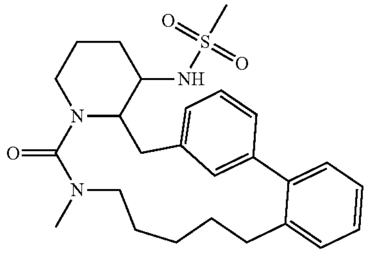 [SMILES: CN1CCCCCc2ccccc2-c2cccc(c2)CC2C(NS(C)(=O)=O)CCCN2C1=O] |
| A2-127 | 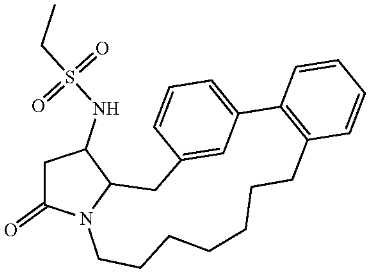 [SMILES: CCS(=O)(=O)NC1CC(=O)N2CCCCCCCc3ccccc3-c3cccc(c3)CC12] |
| A2-128 | 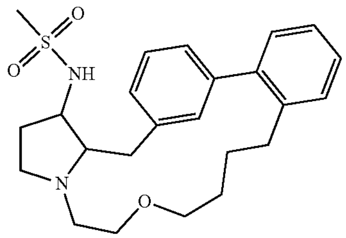 [SMILES: CS(=O)(=O)NC1CCN2CCOCCCCc3ccccc3-c3cccc(c3)CC12] |
| A2-129 | 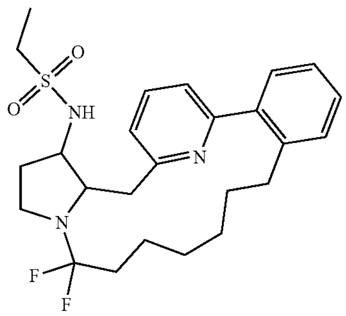 [SMILES: CCS(=O)(=O)NC1CCN2C1Cc1cccc(n1)-c1ccccc1CCCCCCC2(F)F] |

TABLE A2-continued
| Compound No. | Structure |
| --- | --- |
| A2-130 | 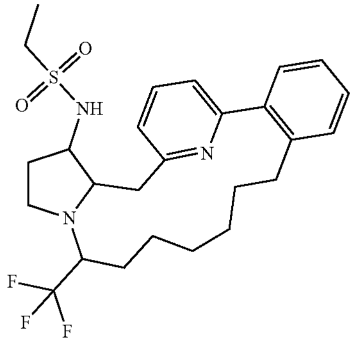 [SMILES: CCS(=O)(=O)NC1CCN2C1Cc1cccc(n1)-c1ccccc1CCCCCCC2C(F)(F)F] |
| A2-131 | 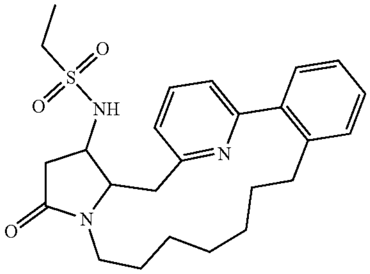 |
| A2-132 | 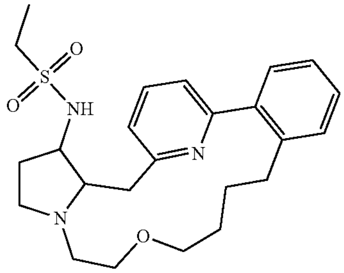 [SMILES: CCS(=O)(=O)NC1CCN2CCOCCCCc3ccccc3-c3cccc(n3)CC12] |
| A2-133 | 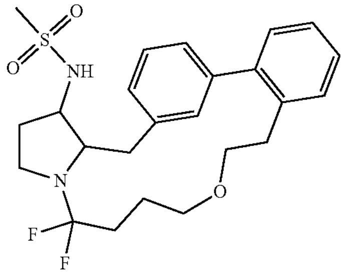 [SMILES: CS(=O)(=O)NC1CCN2C1Cc1cccc(c1)-c1ccccc1CCOCCCC2(F)F] |
| A2-134 | 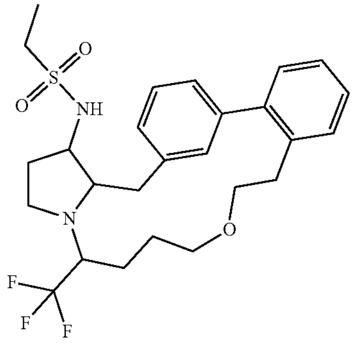 [SMILES: CCS(=O)(=O)NC1CCN2C1Cc1cccc(c1)-c1ccccc1CCOCCCC2C(F)(F)F] |
TABLE A2-continued
| Compound No. | Structure |
| --- | --- |
| A2-135 | 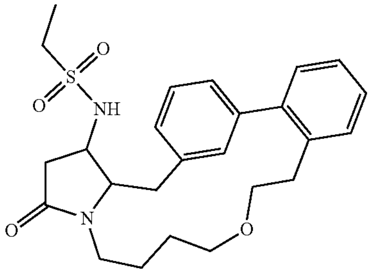 |
| A2-136 | 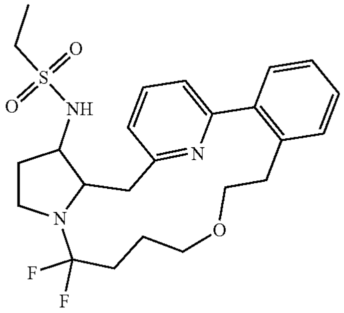 [SMILES: CCS(=O)(=O)NC1CCN2C1Cc1cccc(n1)-c1ccccc1CCOCCCC2(F)F] |
| A2-137 | 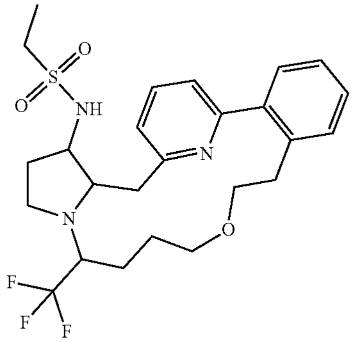 [SMILES: CCS(=O)(=O)NC1CCN2C1Cc1cccc(n1)-c1ccccc1CCOCCCC2C(F)(F)F] |
| A2-138 | 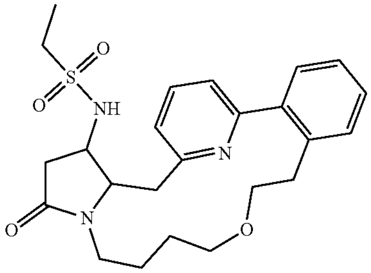 [SMILES: CCS(=O)(=O)NC1CC(=O)N2CCCCOCCc3ccccc3-c3cccc(n3)CC12] |
| A2-139 | 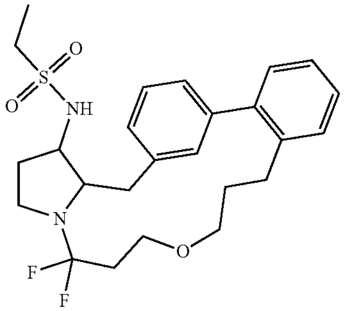 [SMILES: CCS(=O)(=O)NC1CCN2C1Cc1cccc(c1)-c1ccccc1CCCOCCC2(F)F] |

TABLE A2-continued
| Compound No. | Structure |
|---|---|
| A2-140 | 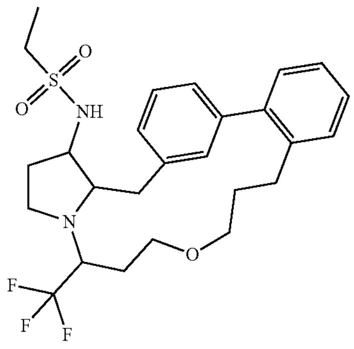 [SMILES: CCS(=O)(=O)NC1CCN2C1Cc1cccc(c1)-c1ccccc1CCCOCCC2C(F)(F)F] |
| A2-141 | 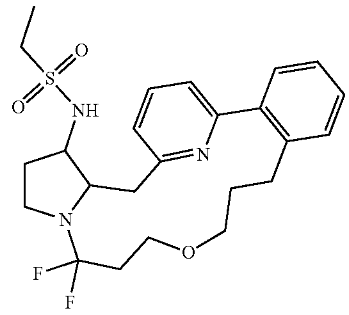 [SMILES: CCS(=O)(=O)NC1CCN2C1Cc1cccc(n1)-c1ccccc1CCCOCCC2(F)F] |
| A2-142 | 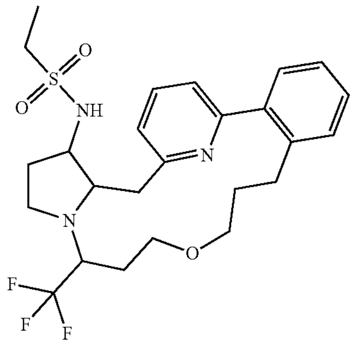 [SMILES: CCS(=O)(=O)NC1CCN2C1Cc1cccc(n1)-c1ccccc1CCCOCCC2C(F)(F)F] |
| A2-143 | 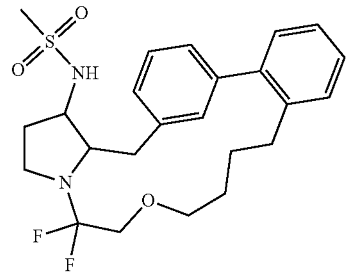 [SMILES: CS(=O)(=O)NC1CCN2C1Cc1cccc(c1)-c1ccccc1CCCCOCC2(F)F] |
| A2-144 | 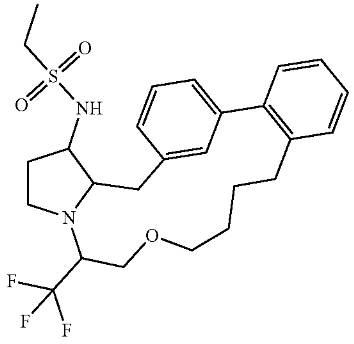 [SMILES: CCS(=O)(=O)NC1CCN2C1Cc1cccc(c1)-c1ccccc1CCCCOCC2C(F)(F)F] |
| A2-145 | 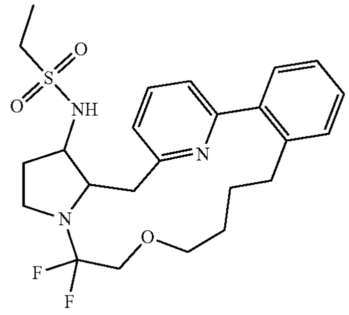 [SMILES: CCS(=O)(=O)NC1CCN2C1Cc1cccc(n1)-c1ccccc1CCCCOCC2(F)F] |
| A2-146 | 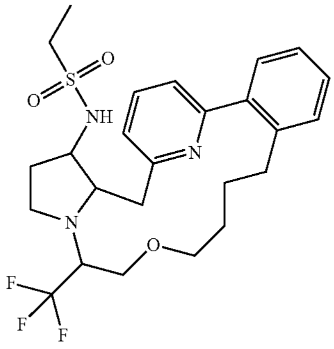 [SMILES: CCS(=O)(=O)NC1CCN2C1Cc1cccc(n1)-c1ccccc1CCCCOCC2C(F)(F)F] |
TABLE B1
| Compound No. | Structure |
|---|---|
| B1-1 | 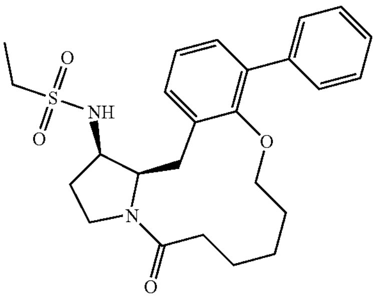 [SMILES: CCS(=O)(=O)N[C@@H]1CCN2C(=O)CCCCCOc3c(cccc3-c3ccccc3)C[C@H]12] |

TABLE B1-continued
| Compound No. | Structure |
|---|---|
| B1-2 | 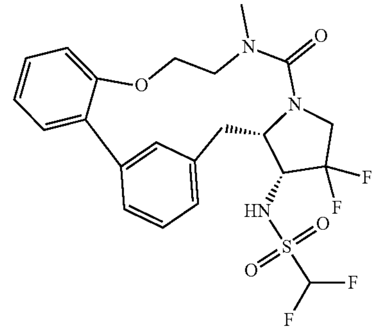 [SMILES: CN1CCOc2ccccc2-c2cccc(c2)C[C@H]2[C@@H](NS(=O)(=O)C(F)F)C(F)(F)CN2C1=O] |
| B1-3 | 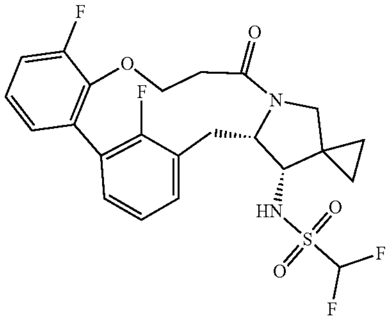 [SMILES: O=C1CCOc2c(F)cccc2-c2cccc(c2F)C[C@H]2[C@@H](NS(=O)(=O)C(F)F)C3(CC3)CN12] |
| B1-4 | 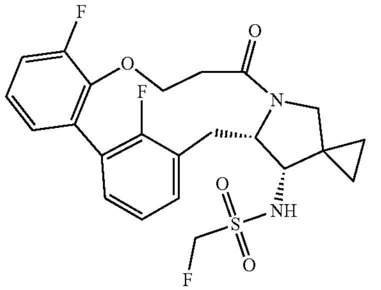 [SMILES: O=C1CCOc2c(F)cccc2-c2cccc(c2F)C[C@H]2[C@@H](NS(=O)(=O)CF)C3(CC3)CN12] |
| B1-5 | 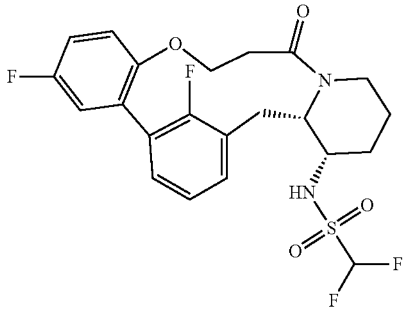 [SMILES: O=C1CCOc2ccc(F)cc2-c2cccc(c2F)C[C@H]2[C@@H](NS(=O)(=O)C(F)F)CCCN12] |
| B1-6 | 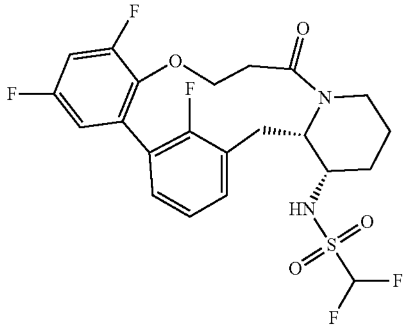 [SMILES: O=C1CCOc2c(F)cc(F)cc2-c2cccc(c2F)C[C@H]2[C@@H](NS(=O)(=O)C(F)F)CCCN12] |
TABLE B1-continued
| Compound No. | Structure |
|---|---|
| B1-7 | 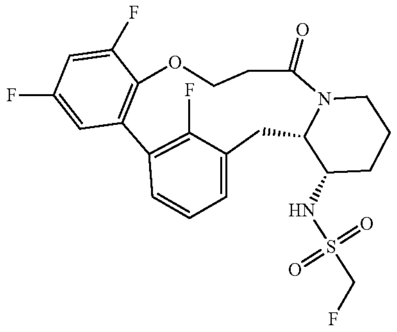 [SMILES: O=C1CCOc2c(F)cc(F)cc2-c2cccc(c2F)C[C@H]2[C@@H](NS(=O)(=O)CF)CCCN12] |
| B1-8 | 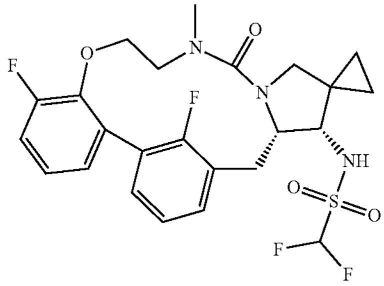 [SMILES: CN1CCOc2c(F)cccc2-c2cccc(c2F)C[C@H]2[C@@H](NS(=O)(=O)C(F)F)C3(CC3)CN2C1=O] |
| B1-9 | 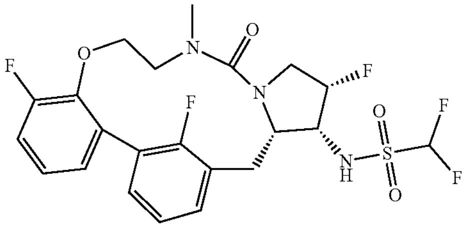 [SMILES: CN1CCOc2c(F)cccc2-c2cccc(c2F)C[C@H]2[C@@H](NS(=O)(=O)C(F)F)[C@@H](F)CN2C1=O] |
| B1-10 | 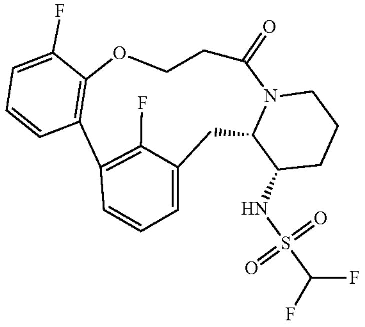 [SMILES: O=C1CCOc2c(F)cccc2-c2cccc(c2F)C[C@H]2[C@@H](NS(=O)(=O)C(F)F)CCCN12] |
| B1-11 | 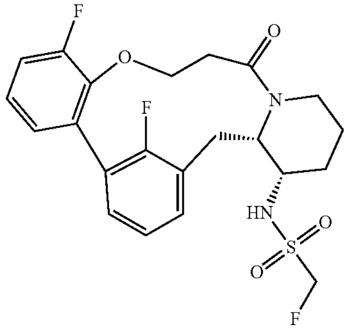 [SMILES: O=C1CCOc2c(F)cccc2-c2cccc(c2F)C[C@H]2[C@@H](NS(=O)(=O)CF)CCCN12] |

TABLE B1-continued
| Compound No. | Structure |
|---|---|
| B1-12 | 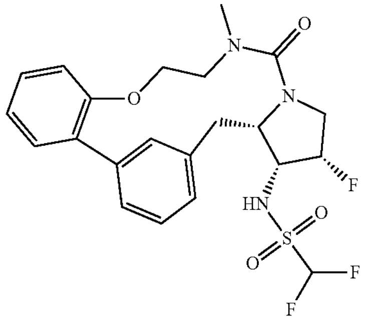 [SMILES: CN1CCOc2ccccc2-c2cccc(c2)C[C@H]2[C@@H](NS(=O)(=O)C(F)F)[C@@H](F)CN2C1=O] |
| B1-13 | 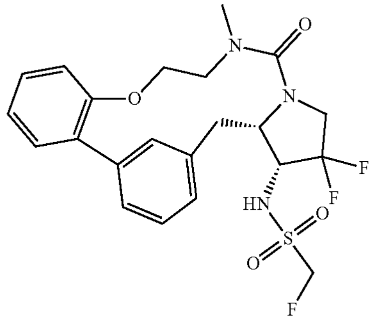 [SMILES: CN1CCOc2ccccc2-c2cccc(c2)C[C@H]2[C@@H](NS(=O)(=O)CF)C(F)(F)CN2C1=O] |
| B1-14 | 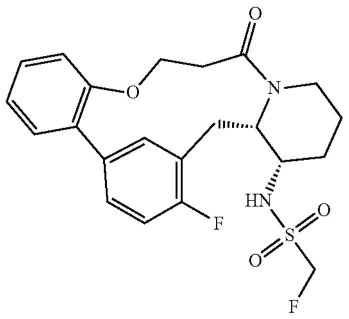 [SMILES: O=C1CCOc2ccccc2-c2ccc(F)c(c2)C[C@H]2[C@@H](NS(=O)(=O)CF)CCCN12] |
| B1-15 | 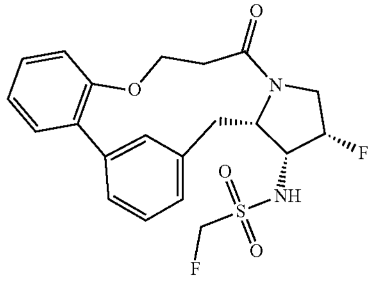 [SMILES: O=C1CCOc2ccccc2-c2cccc(c2)C[C@H]2[C@@H](NS(=O)(=O)CF)[C@@H](F)CN12] |
| B1-16 | 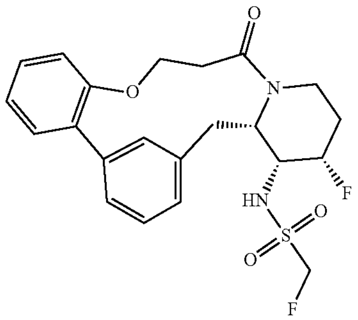 [SMILES: O=C1CCOc2ccccc2-c2cccc(c2)C[C@H]2[C@@H](NS(=O)(=O)CF)[C@@H](F)CCN12] |
TABLE B1-continued
| Compound No. | Structure |
|---|---|
| B1-17 | 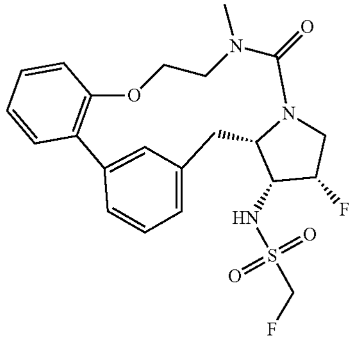 [SMILES: CN1CCOc2ccccc2-c2cccc(c2)C[C@H]2[C@@H](NS(=O)(=O)CF)[C@@H](F)CN2C1=O] |
TABLE B2
| Compound No. | Structure |
|---|---|
| B2-1 | 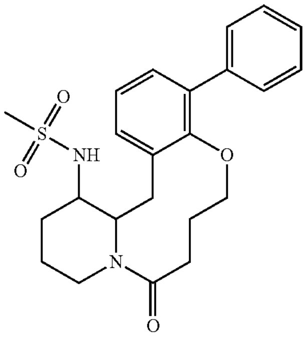 |
| B2-2 | 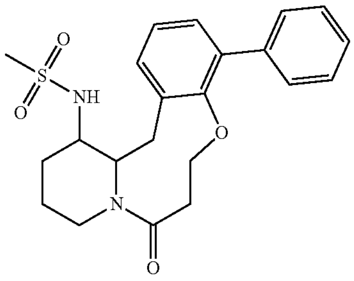 [SMILES: CS(=O)(=O)NC1CCCN2C(=O)CCOc3c(cccc3-c3ccccc3)CC12] |
| B2-3 | 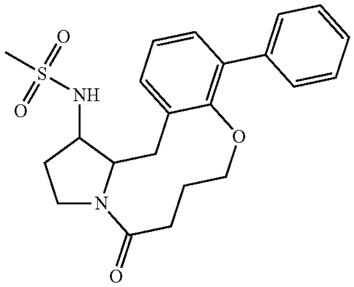 [SMILES: CS(=O)(=O)NC1CCN2C(=O)CCCOc3c(cccc3-c3ccccc3)CC12] |

TABLE B2-continued
| Compound No. | Structure |
|---|---|
| B2-4 | 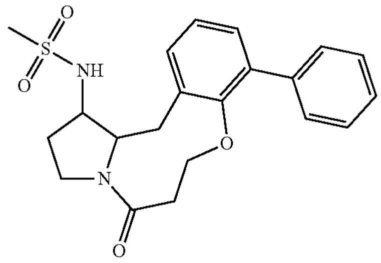 [SMILES: CS(=O)(=O)NC1CCN2C(=O)CCOc3c(cccc3-c3ccccc3)CC12] |
| B2-5 | 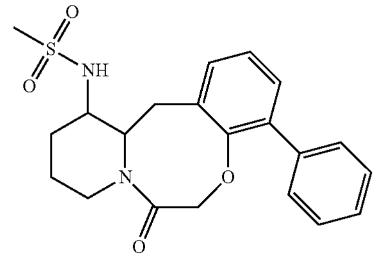 [SMILES: CS(=O)(=O)NC1CCCN2C(=O)COc3c(cccc3-c3ccccc3)CC12] |
| B2-6 | 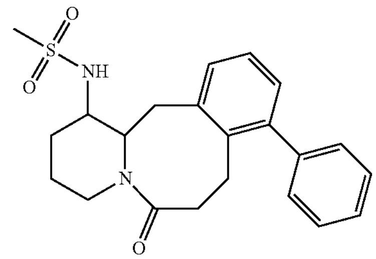 [SMILES: CS(=O)(=O)NC1CCCN2C(=O)CCc3c(cccc3-c3ccccc3)CC12] |
| B2-7 | 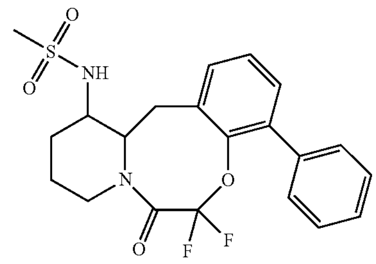 [SMILES: CS(=O)(=O)NC1CCCN2C(=O)C(F)(F)Oc3c(cccc3-c3ccccc3)CC12] |
| B2-8 | 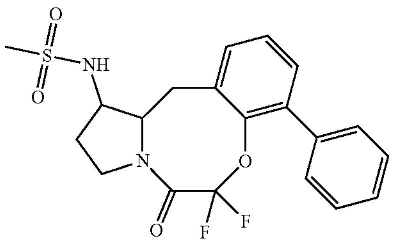 [SMILES: CS(=O)(=O)NC1CCN2C(=O)C(F)(F)Oc3c(cccc3-c3ccccc3)CC12] |
| B2-9 | 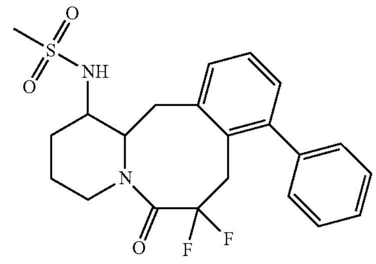 [SMILES: CS(=O)(=O)NC1CCCN2C(=O)C(F)(F)Cc3c(cccc3-c3ccccc3)CC12] |
TABLE B2-continued
| Compound No. | Structure |
|---|---|
| B2-10 | 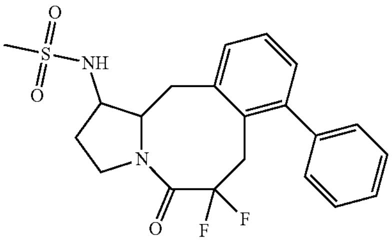 [SMILES: CS(=O)(=O)NC1CCN2C(=O)C(F)(F)Cc3c(cccc3-c3ccccc3)CC12] |
| B2-11 | 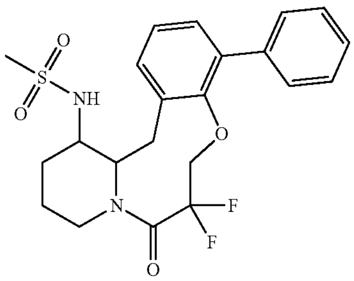 [SMILES: CS(=O)(=O)NC1CCCN2C(=O)C(F)(F)COc3c(cccc3-c3ccccc3)CC12] |
| B2-12 | 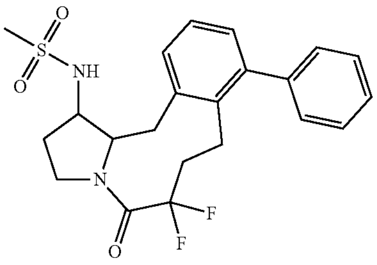 [SMILES: CS(=O)(=O)NC1CCN2C(=O)C(F)(F)CCc3c(cccc3-c3ccccc3)CC12] |
| B2-13 | 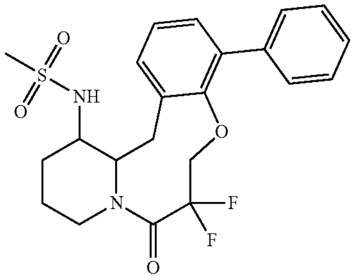 [SMILES: CS(=O)(=O)NC1CCCN2C(=O)C(F)(F)COc3c(cccc3-c3ccccc3)CC12] |
| B2-14 | 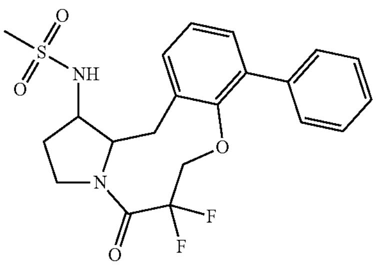 [SMILES: CS(=O)(=O)NC1CCN2C(=O)C(F)(F)COc3c(cccc3-c3ccccc3)CC12] |

TABLE B2-continued
| Compound No. | Structure |
|---|---|
| B2-15 | 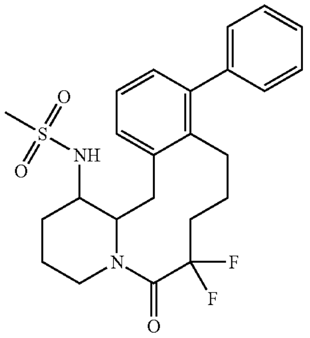 |
| B2-16 | 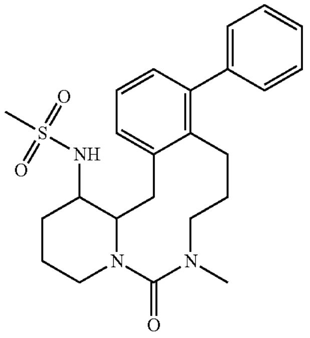 |
| B2-17 | 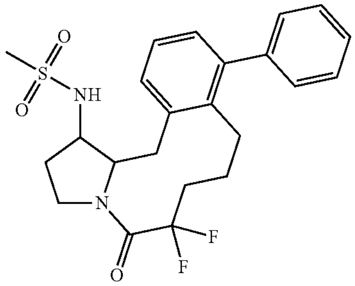 [SMILES: CS(=O)(=O)NC1CCN2C(=O)C(F)(F)CCCc3c(cccc3-c3ccccc3)CC12] |
| B2-18 | 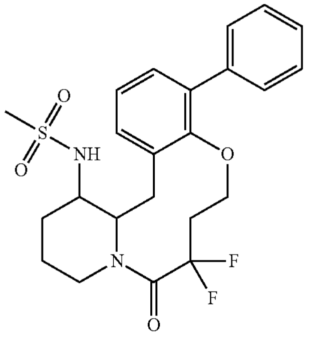 [SMILES: CS(=O)(=O)NC1CCCN2C(=O)C(F)(F)CCOc3c(cccc3-c3ccccc3)CC12] |
TABLE B2-continued
| Compound No. | Structure |
|---|---|
| B2-19 | 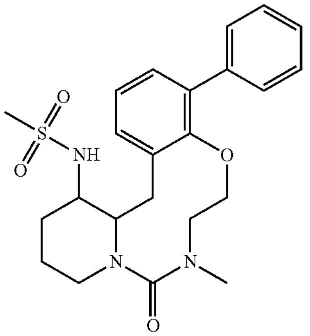 [SMILES: CN1CCOc2c(cccc2-c2ccccc2)CC2C(NS(C)(=O)=O)CCCN2C1=O] |
| B2-20 | 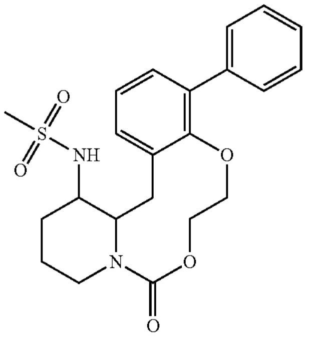 [SMILES: CS(=O)(=O)NC1CCCN2C(=O)OCCOc3c(cccc3-c3ccccc3)CC12] |
| B2-21 | 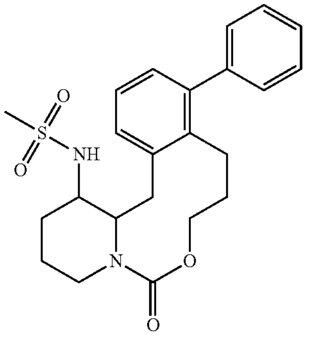 [SMILES: CS(=O)(=O)NC1CCCN2C(=O)OCCCc3c(cccc3-c3ccccc3)CC12] |
| B2-22 | 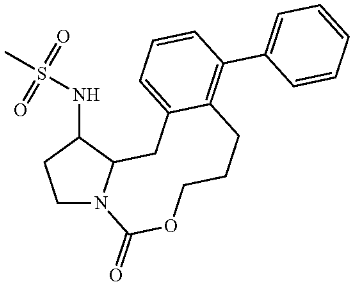 [SMILES: CS(=O)(=O)NC1CCN2C(=O)OCCCc3c(cccc3-c3ccccc3)CC12] |
| B2-23 | 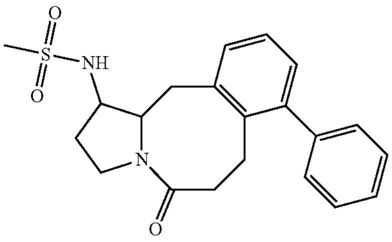 [SMILES: CS(=O)(=O)NC1CCN2C(=O)CCc3c(cccc3-c3ccccc3)CC12] |

TABLE B2-continued
| Compound No. | Structure |
|---|---|
| B2-24 | 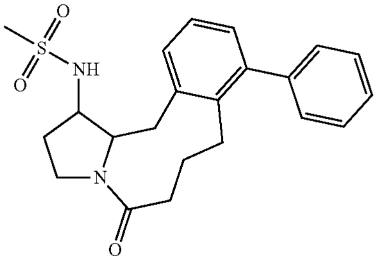 [SMILES: CS(=O)(=O)NC1CCN2C(=O)CCCc3c(cccc3-c3ccccc3)CC12] |
| B2-25 | 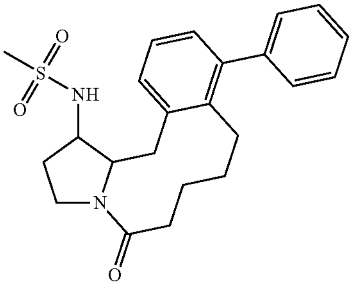 [SMILES: CS(=O)(=O)NC1CCN2C(=O)CCCCc3c(cccc3-c3ccccc3)CC12] |
| B2-26 | 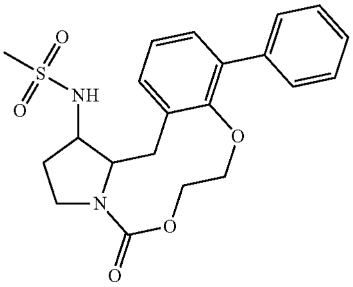 [SMILES: CS(=O)(=O)NC1CCN2C(=O)OCCOc3c(cccc3-c3ccccc3)CC12] |
| B2-27 | 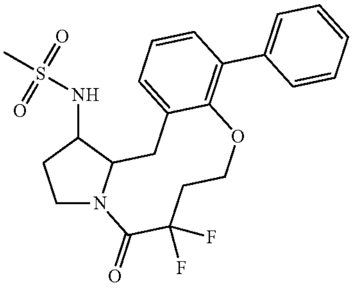 [SMILES: CS(=O)(=O)NC1CCN2C(=O)C(F)(F)CCOc3c(cccc3-c3ccccc3)CC12] |
| B2-28 | 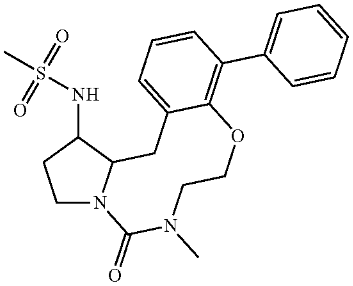 [SMILES: CN1CCOc2c(cccc2-c2ccccc2)CC2C(NS(C)(=O)=O)CCN2C1=O] |
TABLE B2-continued
| Compound No. | Structure |
|---|---|
| B2-29 | 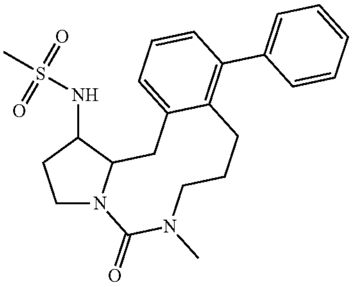 [SMILES: CN1CCCc2c(cccc2-c2ccccc2)CC2C(NS(C)(=O)=O)CCN2C1=O] |
| B2-30 | 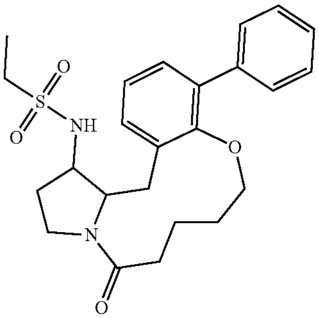 [SMILES: CCS(=O)(=O)NC1CCN2C(=O)CCCCOc3c(cccc3-c3ccccc3)CC12] |
| B2-31 | 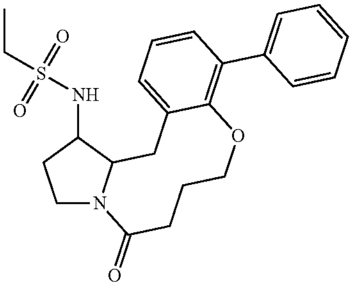 [SMILES: CCS(=O)(=O)NC1CCN2C(=O)CCCOc3c(cccc3-c3ccccc3)CC12] |
| B2-32 | 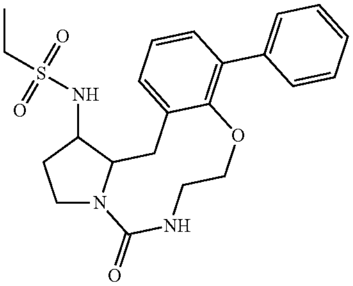 [SMILES: CCS(=O)(=O)NC1CCN2C(=O)NCCOc3c(cccc3-c3ccccc3)CC12] |
| B2-33 | 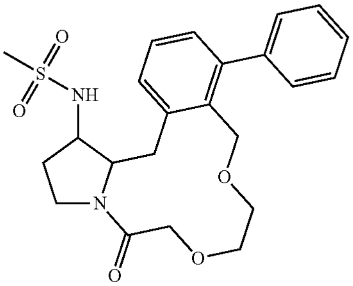 [SMILES: CS(=O)(=O)NC1CCN2C(=O)COCCOCc3c(cccc3-c3ccccc3)CC12] |

TABLE B2-continued

| Compound No. | Structure |
| --- | --- |
| B2-34 | 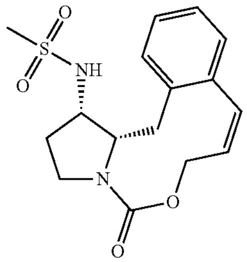 [SMILES: CS(=O)(=O)N[C@H]1CCN2C(=O)OC/C=C\c3ccccc3C[C@@H]12] |
| B2-35 | 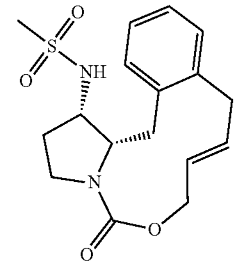 [SMILES: CS(=O)(=O)N[C@H]1CCN2C(=O)OC/C=C/Cc3ccccc3C[C@@H]12] |
| B2-36 | 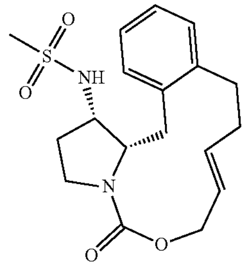 [SMILES: CS(=O)(=O)N[C@H]1CCN2C(=O)OC/C=C/CCc3ccccc3C[C@@H]12] |
| B2-37 | 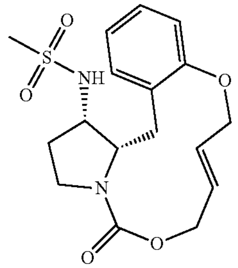 [SMILES: CS(=O)(=O)N[C@H]1CCN2C(=O)OC/C=C/COc3ccccc3C[C@@H]12] |
| B2-38 | 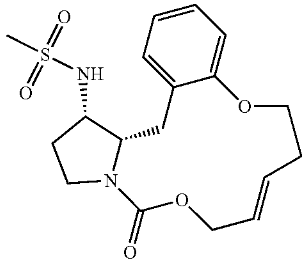 [SMILES: CS(=O)(=O)N[C@H]1CCN2C(=O)OC/C=C/CCOc3ccccc3C[C@@H]12] |

TABLE B2-continued

| Compound No. | Structure |
| --- | --- |
| B2-39 | 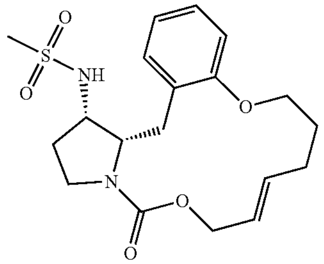 [SMILES: CS(=O)(=O)N[C@H]1CCN2C(=O)OC/C=C/CCCOc3ccccc3C[C@@H]12] |

In some embodiments, the compound is a pharmaceutically acceptable salt of any one of the compounds described in Tables A1, A2, B1, and B2.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Tables A1, A2, B1, and B2 and prodrugs and pharmaceutically acceptable salts thereof.

In some embodiments, the compound is an isotopic derivative of any one of the compounds described in Tables A1, A2, B1, and B2 and pharmaceutically acceptable salts thereof.

In some embodiments, the compound is an isotopic derivative of any one of prodrugs of the compounds described in Tables A1, A2, B1, and B2 and pharmaceutically acceptable salts thereof.

In some embodiments, the compound is an isotopic derivative of any one of the compounds described in Tables A1, A2, B1, and B2.

It is understood that the isotopic derivative can be prepared using any of a variety of art-recognised techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I) is isotopically enriched with regard to, or labelled with, one or more isotopes as compared to the corresponding compound of Formula (I). In some embodiments, the isotopic derivative is enriched with regard to, or labelled with, one or more atoms selected from $^{2}H$, $^{13}C$, $^{14}C$, $^{15}N$, $^{18}O$, $^{29}Si$, $^{31}P$, and $^{34}S$. In some embodiments, the isotopic derivative is a deuterium labeled compound (i.e., being enriched with $^{2}H$ with regard to one or more atoms thereof). In some embodiments, the compound is a $^{18}F$ labeled compound. In some embodiments, the compound is a $^{123}I$ labeled compound, a $^{124}I$ labeled compound, a $^{125}I$ labeled compound, a $^{129}I$ labeled compound, a $^{131}I$ labeled compound, a $^{135}I$ labeled compound, or any combination thereof. In some embodiments, the compound is a 33S labeled compound, a $^{34}S$ labeled compound, a 35S labeled compound, a $^{36}S$ labeled compound, or any combination thereof.

It is understood that the $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$ labeled compound, can be prepared using any of a variety of art-recognised techniques. For example, the deuterium labeled compound can generally be prepared by carrying out the procedures disclosed in the Schemes and/or in the Examples described herein, by substituting a $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled reagent for a non-isotope labeled reagent.

A compound of the invention or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{32}S$, $^{34}S$, $^{35}S$, and $^{36}S$ atom(s) is within the scope of the invention. Further, substitution with isotope (e.g., $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

The various functional groups and substituents making up the compounds of the Formula (I) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure which is sufficiently basic, for example, an acid-addition salt with, for example, an inorganic organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

It will be understood that while compounds disclosed herein may be presented in one particular configuration. Such particular configuration is not to be construed as limiting the disclosure to one or another isomer, tautomer, regioisomer or stereoisomer, nor does it exclude mixtures of isomers, tautomers, regioisomers or stereoisomers. In some embodiments, the presentation of a compound herein in a particular configuration intends to encompass, and to refer to, each of the available isomers, tautomers, regioisomers, and stereoisomers of the compound, or any mixture thereof, while the presentation further intends to refer to the specific configuration of the compound. For example, when a compound is presented with a moiety of

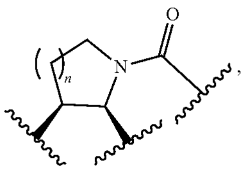
, the presentation may intend to encompass, and to refer to, the compound with the moiety of

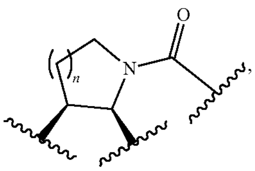
,

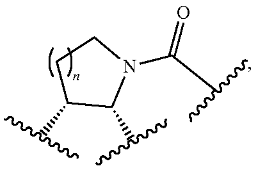
,

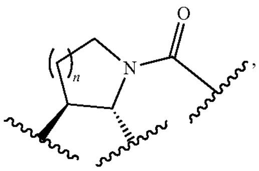
, or

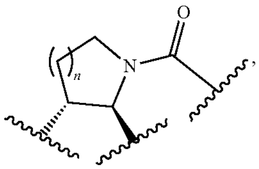
, or any mixture thereof. Further, the presentation may intend to refer to the compound with the particular configuration of the moiety of

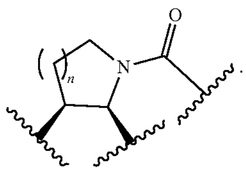
.

It will be understood that while compounds disclosed herein may be presented without specified configuration (e.g., without specified stereochemistry). Such presentation intends to encompass all available isomers, tautomers, regioisomers, and stereoisomers of the compound. In some embodiments, the presentation of a compound herein without specified configuration intends to refer to each of the available isomers, tautomers, regioisomers, and stereoisomers of the compound, or any mixture thereof. For example, when a compound is presented with a moiety of

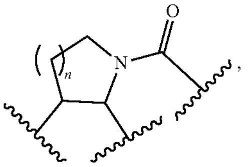

the presentation may intend to encompass, and to refer to, the compound with the moiety of

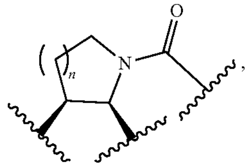, 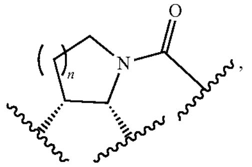,

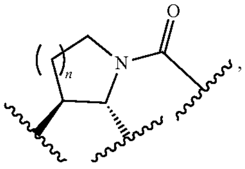, or 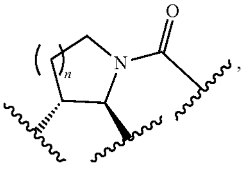, or any mixture thereof. Further, the presentation may intend to refer to the compound with a mixture of cis-isomers of the moiety, e.g., a mixture of the moieties of

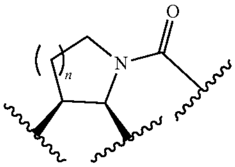 and 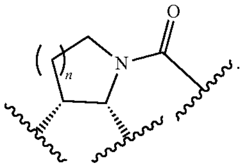.

For another example, when a compound is presented with a moiety of

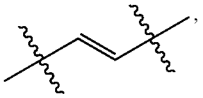, the presentation may intend to refer to the compound with the moiety

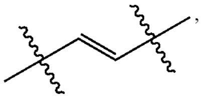 [SMILES: */C=C/*], 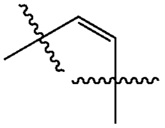, or a mixture thereof.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral centre" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterised by the absolute configuration of its asymmetric centre and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centres (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVoie, *Chem. Rev.* 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I) include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

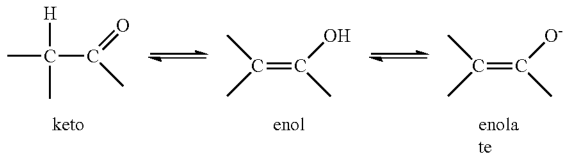

Compounds of any one of the Formulae disclosed herein containing an amine function may also form N-oxides. A reference herein to a compound of Formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl,morpholinomethyl,piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

METHODS OF SYNTHESIS

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesised by any one of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof; and/or (iv) forming a prodrug thereof.

The resultant compounds of Formula (I) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100 °C and 300 °C, depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

General routes for the preparation of a compound of the application are described in Schemes 1-5 herein.

Scheme 1

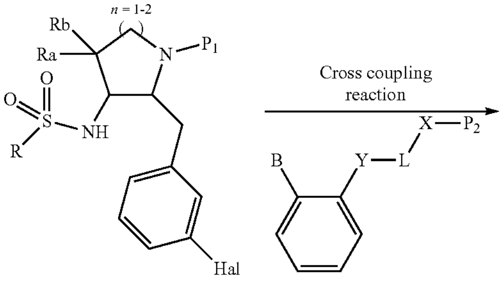

(I) (II)

-continued

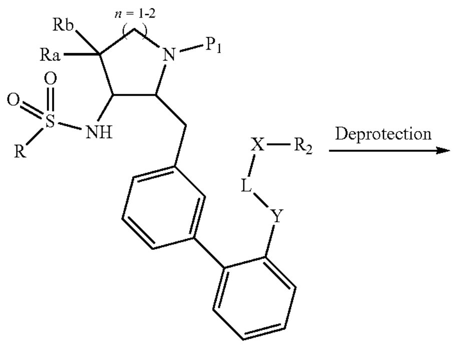

(III)

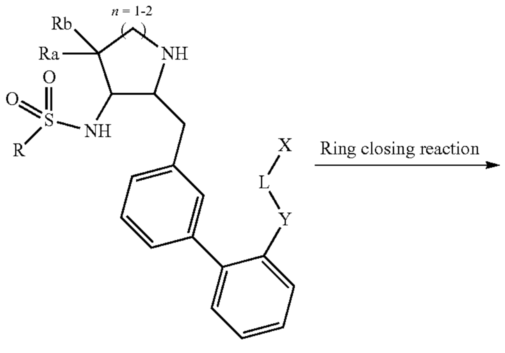

(IV)

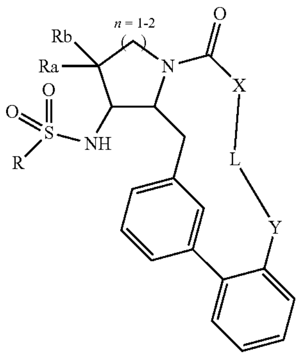

(V)

Compound V can be prepared from Compound I according to the method shown in Scheme 1. Compound I can be produced according to the previously reported route in WO2019/027058 from commercially available materials or according to a method analogous thereto. As used herein, Hal is a halogen atom.

Examples of the protecting group represented by $P_1$ for an amino group include carbamate-type protecting groups such as tert-butyl carbamate and the like. Compound II when Y is oxygen may be commercially available or can be prepared by alkylation or Mitsunobu reaction from commercially available materials. B represents boronic acid, or boronic ester and the like.

Examples of the protecting group represented by $P_2$ when X is nitrogen include phthalamide-type protecting groups and the like. Examples of the protecting group represented by $P_2$ when X is carbon or oxygen include carboxyl protecting groups such as methyl, ethyl ester and the like.

Compound III can be produced by subjecting Compound I and Compound II to palladium mediated cross-coupling Suzuki type reaction. When the coupling reaction is carried out, examples of the metal catalyst to be used include palladium compounds such as palladium (II) acetate, tetrakis (triphenylphosphine)palladium(O), dichlorobis(triphenylphosphine)-palladium (II), tris(dibenzylideneacetone) dipalladium(O), 1,1'-bis(diphenylphosphino)-ferrocene palladium(II) chloride, (2-Dicyclohexylphosphino-2',4',6'-triisopropyl-1,1'-biphenyl)[2-(2'-amino-1,1'-biphenyl)] palladium(II) methanesulfonate and the like. In addition, a base can be added to the reaction system, and examples thereof include inorganic bases and the like.

Compound IV can be produced by removing protecting groups represented by $P_1$ and $P_2$ according to a method known per se, for example, by employing a method using acid, base, or a nucleophile such hydrazine, and the like, a reduction method, and the like.

Compound V can be produced by subjecting compound IV to a ring closing reaction. When ring closing is carried out by amidation reaction, urea or carbamate formation, examples of the reagent to be used include activated carboxylic acids such as acid anhydrides, activated esters, activated carbamates and the like. Examples of the activating agent of the carboxylic acid include carbodiimide condensing agents such as N-(3-Dimethylaminopropyl)-N'-ethylcarbodiimide hydrochloride (EDCI) and the like; carbonate condensing agents such as 1,1-carbonyldiimidazole (CDI), triphosgene and the like; O-(7-azabenzotriazol-1-yl)-N,N,N', N'-tetramethyluronium hexafluorophosphorate (HATU); combinations thereof and the like. In addition, a base may be added to the reaction system. Examples of the base include inorganic bases, organic bases and the like. When a carbodiimide condensing agent is used, an additive such as 1-hydroxybenzotriazole (HOBt), dimethylaminopyridine (DMAP) and the like may be further added to the reaction system.

Scheme 2

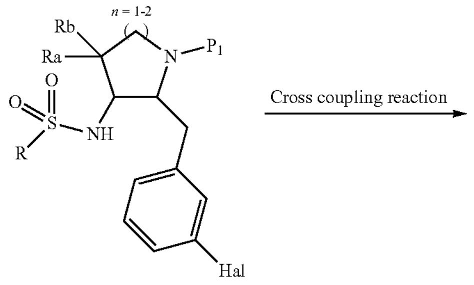

(I)

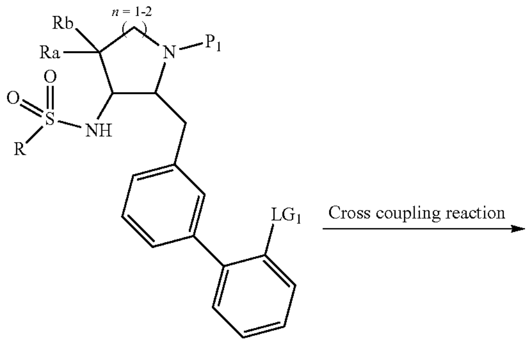

(VI)

-continued

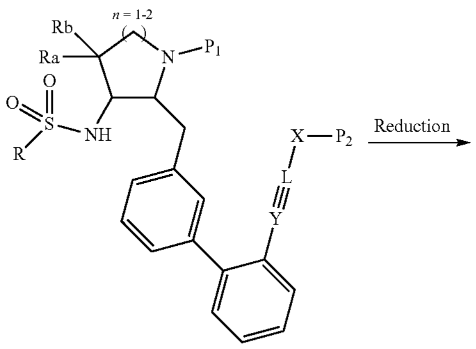

(VII)

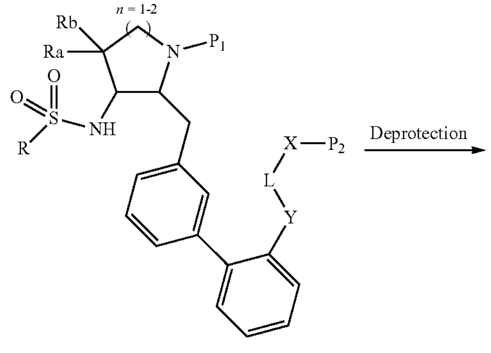

(VIII)

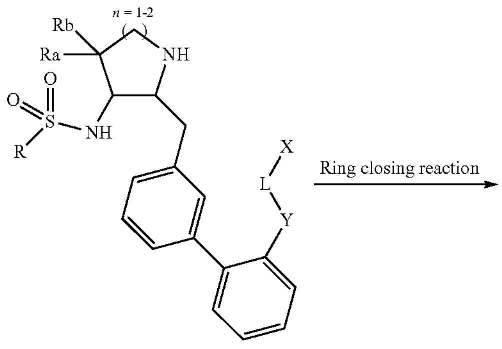

(IV)

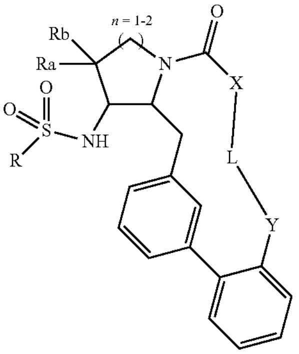

(V)

Alternatively, Compound V can be produced from Compound I according to the method shown in Reaction Scheme 2. Compound VI can be produced by subjecting a combination of Compound I, arylboronic acid or aryl boronic ester and the like to palladium mediated cross-coupling Suzuki type reaction. When coupling reaction is carried out in each step, examples of the metal catalyst to be used include palladium compounds such as palladium(II) acetate, tetrakis (triphenylphosphine)palladium(O), dichlorobis(triphenylphosphine)palladium (II), tris(dibenzylideneacetone)dipalladium(O), 1,1'-bis(diphenylphosphino)ferrocene palladium(II) chloride, (2-Dicyclohexylphosphino-2',4',6'-triisopropyl-1,1'-biphenyl)[2-(2'-amino-1,1'-biphenyl)]palladium(II) methanesulfonate and the like. In addition, a base can be added to the reaction system, and examples thereof include inorganic bases and the like. Examples of the "leaving group" represented by $LG_1$ include halogen atoms, optionally halogenated $C_{1-6}$ alkylsulfonyloxy groups (e.g., methanesulfonyloxy, ethanesulfonyloxy, trifluoromethanesulfonyloxy) and the like.

Compound VII when Y is carbon can be produced by subjecting Compound VI and an appropriate acetylene, available commercially or according to a known method, to Sonogashira type cross-coupling reaction using a metal catalyst. Examples of the metal catalyst to be used include palladium compounds such as palladium(II) acetate, tetrakis (triphenylphosphine)palladium(O), dichlorobis(triphenylphosphine)palladium (II), Bis(acetonitrile)dichloropalladium(II) and the like. A phosphine ligand can also be added to the reaction system such as 2-Dicyclohexylphosphino-2',4',6'triisopropylbiphenyl (XPhos), 2-Dicyclohexylphosphino-2',6'-dimethoxybiphenyl (SPhos) and the like. In addition, a base can be added to the reaction system, and examples thereof include inorganic bases and the like.

Compound VIII can be produced by reduction of Compound VII. When carbon-carbon double bond or triple bond is reduced, a method using a catalyst such as palladium-carbon, Lindlar's catalyst and the like may be employed in conjunction with hydrogen gas.

Compound VIII when Y is oxygen and $LG_1$ represents hydroxy can be prepared directly from Compound VI by Mitsunobu reaction from commercially available materials. When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

Compound IV can be produced by removing protecting groups represented by $P_1$ and $P_2$ according to a method known per se, for example, by employing a method using acid, base, hydrazine, and the like, a reduction method, and the like.

Compound V can be produced by the ring closing reaction as shown in reaction scheme 1.

Compound V can also be prepared through ring-closing metathesis reaction approaches as outlined in Schemes 3-5.

Scheme 3

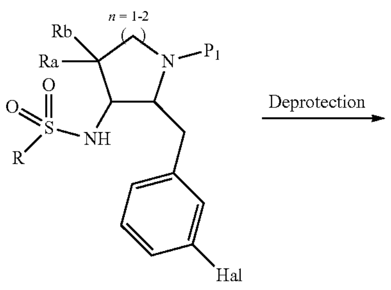

(I)

-continued

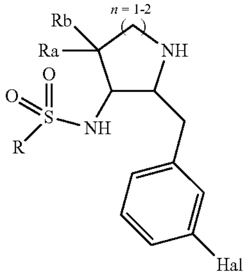

(IX)

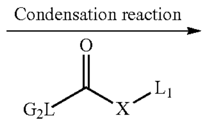

(X)

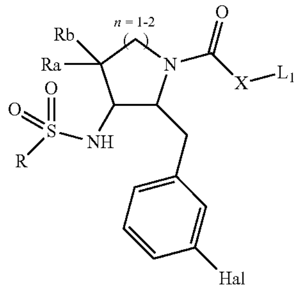

(XI)

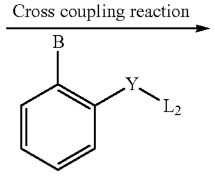

(XII)

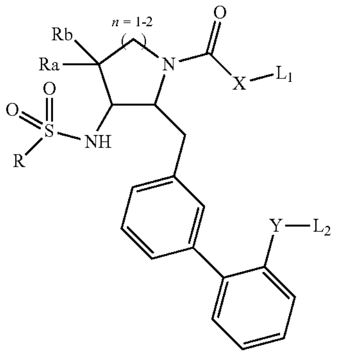

(XIII)

Compound IX can be produced by removing protecting groups from Compound (I) represented by $P_1$ according to an appropriate known method, for example, by using acid, base, hydrazine, and the like, or a reduction method, and the like.

Compound XI can be produced by subjecting Compound IX and Compound X to a condensation reaction. Where $LG_2$ is an appropriate leaving group. When condensation reaction is carried out examples of the reagent to be used include activated carboxylic acids such as acid anhydrides, activated esters, activated carbonates, activated carbamates, isocyanates and the like.

Examples of the activating agent of the carboxylic acid include carbodiimide condensing agents such as N-(3-Dimethylaminopropyl)-N'-ethylcarbodiimide hydrochloride (EDCI); carbonate condensing agents such as 1,1-carbonyldiimidazole (CDI), triphosgene and the like; O-(7-azabenzotriazol-1-yl)-N,N,N', N'-tetramethyluronium hexafluorophosphorate (HATU); combinations thereof and the like. In addition, a base may be added to the reaction system.

Examples of the base include inorganic bases, organic bases and the like. When a carbodiimide condensing agent is used, an additive such as 1-hydroxybenzotriazole (HOBt) or dimethylaminopyridine (DMAP) may be further added to the reaction system. Compound X may be commercially available or produced from commercially available materials according to a method known per se or a method analogous thereto. $L_1$ represents $C_{1-5}$ allyl, allyloxy and the like. Examples of leaving group represented by $LG_2$ include halogen atoms, optionally halogenated $C_{1-6}$ alkylsulfonyloxy groups (e.g., methanesulfonyloxy, ethanesulfonyloxy, trifluoromethane-sulfonyloxy), p-nitrophenol and the like.

Compound XII may be commercially available or produced from commercially available materials according to a method known per se or a method analogous thereto. B represents boronic acid, ester and the like. $L_1$ represents $C_{1-3}$ allyl and the like.

Compound XIII can produced by subjecting a combination of Compound XI and Compound XII to the aforementioned palladium mediated cross-coupling Suzuki type as shown in Scheme 1.

Scheme 4

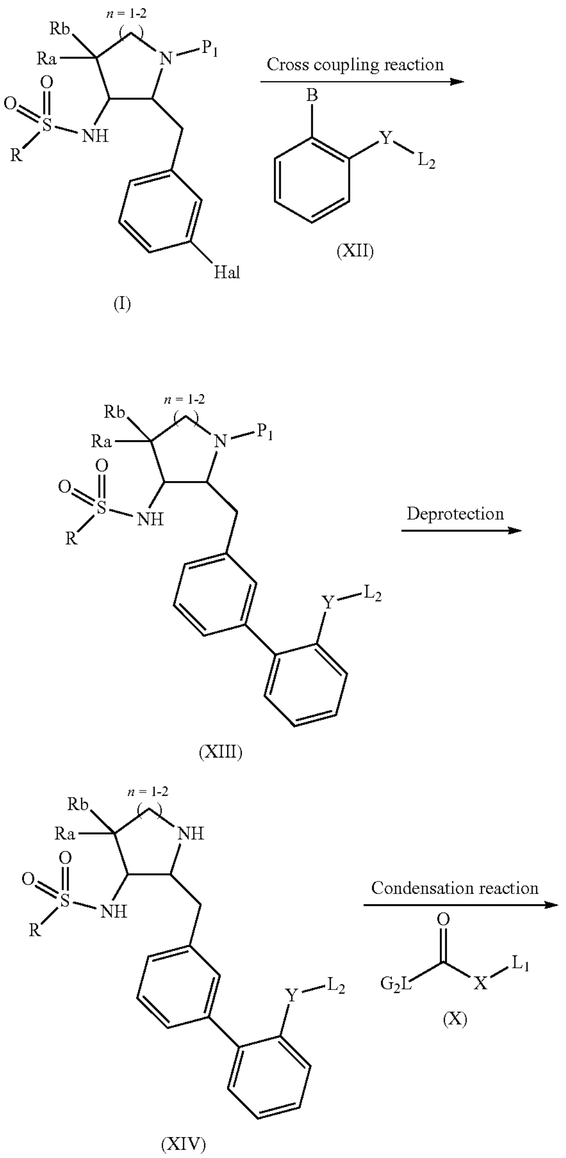

(I) (XII) (XIII) (XIV) (X)

-continued

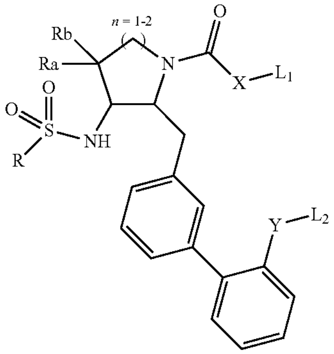

(XIII)

Compound XIII can be produced by subjecting a combination of compound I and Compound XII to the aforementioned palladium mediated cross-coupling Suzuki type as shown in Scheme 1.

Compound XIV can be produced by removing protecting groups represented by $P_1$ according to a known method, for example, by employing an acid, base, hydrazine, and the like, or a reduction method, and the like.

Compound XIII can be produced by subjecting Compound XIV and Compound X to a condensation reaction as aforementioned in Scheme 3.

Scheme 5

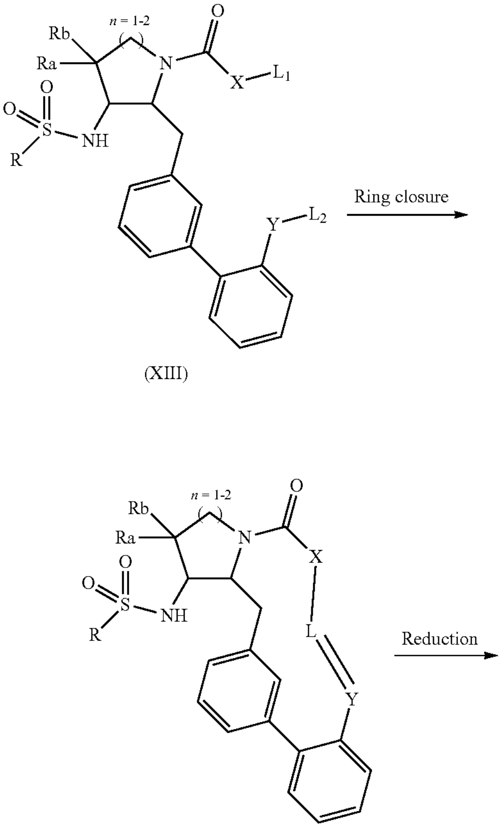

(XIII) (XIV)

-continued

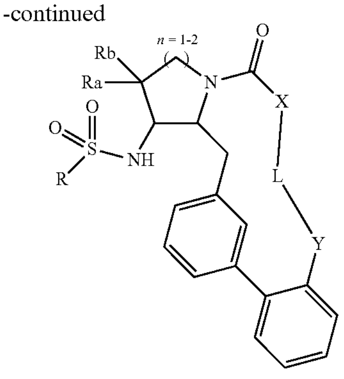

(V)

Compound XIV can be produced by subjecting Compound XIII to ring closing reaction. When ring closing is carried out by ring closing metathesis reaction, examples of the catalyst to be used include Ruthenium compounds such as Grubbs I, Grubbs II, Hoveyda Grubbs and the like.

Compound V can be produced by reduction of Compound XIV. When carbon-carbon double bond is reduced, a method using a catalyst such as palladium-carbon, Lindlar's catalyst and the like may be employed with hydrogen gas.

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Despite orexin cell loss and decreased orexin peptides in cerebrospinal fluid in NT1, orexin receptors on post synaptic neurons remain intact as suitable targets for pharmacotherapeutic intervention. The orexin peptides A and B (OXA and OXB) may be cleaved from a single precursor molecule (prepro-orexin) that is produced exclusively in the lateral hypothalamus. Both orexin peptides bind with similar high affinity to OX2R, but the orexin-1 receptor (OX1R) may be preferentially bound by OXA. Postsynaptic excitation of these G-protein coupled orexin receptors may stimulate the release of monoaminergic and cholinergic neurotransmitters that promote wakefulness and inhibitory neurotransmitters that suppress REM sleep atonia.

In some embodiments, the biological assay is described in the Examples herein.

In some embodiments, the biological assay is an assay mearing the agonist activity of the compound toward cells expressing human orexin type 2 or human orexin type 1 receptor.

In some embodiments, the assay involves preparing Chinese hamster ovary (CHO) cells expressing human orexin type 2 receptor (hOX2R) or human orexin type 1 receptor (hOX1R).

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Tables A1, A2, B1, and B2.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilise the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and F-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

An effective amount of a compound of the present disclosure for use in therapy is an amount sufficient to treat an inflammasome related condition referred to herein, slow its progression and/or reduce the symptoms associated with the condition.

The size of the dose for therapeutic or prophylactic purposes of a compound of Formula (I) will naturally vary according to the nature and severity of the conditions, the age and sex of the animal or patient and the route of administration, according to well-known principles of medicine.

Methods of Use

In some aspects, the present disclosure provides a method of modulating orexin-2 receptor activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some embodiments, the disease or disorder is associated with an implicated orexin receptor activity. In some embodiments, the disease or disorder is a disease or disorder in which orexin receptor activity is implicated.

In some embodiments, the disease or disorder is associated with an implicated orexin-2 receptor activity. In some embodiments, the disease or disorder is a disease or disorder in which orexin-2 receptor activity is implicated.

In some embodiments, the disease or disorder is narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia.

In some aspects, the present disclosure provides a method of treating or preventing narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing narcolepsy in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a hypersomnia disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a neurodegenerative disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a symptom of a rare genetic disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a mental health disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a metabolic syndrome in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing osteoporosis in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing cardiac failure in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing coma in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating narcolepsy in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a hypersomnia disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a neurodegenerative disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a symptom of a rare genetic disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a mental health disorder in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a metabolic syndrome in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating osteoporosis in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating cardiac failure in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating coma in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a complication in emergence from anesthesia in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in modulating orexin receptor activity (e.g., in vitro or in vivo).

In some aspects, the present disclosure provides a compound of the present disclosure or a pharmaceutically acceptable salt thereof for use in modulating orexin-2 receptor activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides a compound of the present disclosure or a pharmaceutically acceptable salt thereof for use in treating or preventing narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides a compound of the present disclosure or a pharmaceutically acceptable salt thereof for use in treating or preventing narcolepsy in a subject in need thereof.

In some aspects, the present disclosure provides a compound of the present disclosure or a pharmaceutically acceptable salt thereof for use in treating or preventing a hypersomnia disorder in a subject in need thereof.

In some aspects, the present disclosure provides a compound of the present disclosure or a pharmaceutically acceptable salt thereof for use in treating or preventing a neurodegenerative disorder in a subject in need thereof.

In some aspects, the present disclosure provides a compound of the present disclosure or a pharmaceutically acceptable salt thereof for use in treating or preventing a symptom of a rare genetic disorder in a subject in need thereof.

In some aspects, the present disclosure provides a compound of the present disclosure or a pharmaceutically acceptable salt thereof for use in treating or preventing a mental health disorder in a subject in need thereof.

In some aspects, the present disclosure provides a compound of the present disclosure or a pharmaceutically acceptable salt thereof for use in treating or preventing a metabolic syndrome in a subject in need thereof.

In some aspects, the present disclosure provides a compound of the present disclosure or a pharmaceutically acceptable salt thereof for use in treating or preventing osteoporosis in a subject in need thereof.

In some aspects, the present disclosure provides a compound of the present disclosure or a pharmaceutically acceptable salt thereof for use in treating or preventing cardiac failure in a subject in need thereof.

In some aspects, the present disclosure provides a compound of the present disclosure or a pharmaceutically acceptable salt thereof for use in treating or preventing coma in a subject in need thereof.

In some aspects, the present disclosure provides a compound of the present disclosure or a pharmaceutically acceptable salt thereof for use in treating or preventing a complication in emergence from anesthesia in a subject in need thereof.

In some aspects, the present disclosure provides a compound of the present disclosure or a pharmaceutically acceptable salt thereof for use in treating narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides a compound of the present disclosure or a pharmaceutically acceptable salt thereof for use in treating narcolepsy in a subject in need thereof.

In some aspects, the present disclosure provides a compound of the present disclosure or a pharmaceutically acceptable salt thereof for use in treating a hypersomnia disorder in a subject in need thereof.

In some aspects, the present disclosure provides a compound of the present disclosure or a pharmaceutically acceptable salt thereof for use in treating a neurodegenerative disorder in a subject in need thereof.

In some aspects, the present disclosure provides a compound of the present disclosure or a pharmaceutically acceptable salt thereof for use in treating a symptom of a rare genetic disorder in a subject in need thereof.

In some aspects, the present disclosure provides a compound of the present disclosure or a pharmaceutically acceptable salt thereof for use in treating a mental health disorder in a subject in need thereof.

In some aspects, the present disclosure provides a compound of the present disclosure or a pharmaceutically acceptable salt thereof for use in treating a metabolic syndrome in a subject in need thereof.

In some aspects, the present disclosure provides a compound of the present disclosure or a pharmaceutically acceptable salt thereof for use in treating osteoporosis in a subject in need thereof.

In some aspects, the present disclosure provides a compound of the present disclosure or a pharmaceutically acceptable salt thereof for use in treating cardiac failure in a subject in need thereof.

In some aspects, the present disclosure provides a compound of the present disclosure or a pharmaceutically acceptable salt thereof for use in treating coma in a subject in need thereof.

In some aspects, the present disclosure provides a compound of the present disclosure or a pharmaceutically acceptable salt thereof for use in treating a complication in emergence from anesthesia in a subject in need thereof.

In some aspects, the present disclosure provides use of a compound of the present disclosure or a pharmaceutically acceptable salt thereof in the manufacture of a medicament for modulating orexin activity (e.g., in vitro or in vivo).

In some aspects, the present disclosure provides use of a compound of the present disclosure or a pharmaceutically acceptable salt thereof in the manufacture of a medicament for modulating orexin-2 activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides use of a compound of the present disclosure or a pharmaceutically acceptable salt thereof in the manufacture of a medicament for treating or preventing narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides use of a compound of the present disclosure or a pharmaceutically acceptable salt thereof in the manufacture of a medicament for treating or preventing narcolepsy in a subject in need thereof.

In some aspects, the present disclosure provides use of a compound of the present disclosure or a pharmaceutically acceptable salt thereof in the manufacture of a medicament for treating or preventing a hypersomnia disorder in a subject in need thereof.

In some aspects, the present disclosure provides use of a compound of the present disclosure or a pharmaceutically acceptable salt thereof in the manufacture of a medicament for treating or preventing a neurodegenerative disorder in a subject in need thereof.

In some aspects, the present disclosure provides use of a compound of the present disclosure or a pharmaceutically acceptable salt thereof in the manufacture of a medicament for treating or preventing a symptom of a rare genetic disorder in a subject in need thereof.

In some aspects, the present disclosure provides use of a compound of the present disclosure or a pharmaceutically acceptable salt thereof in the manufacture of a medicament for treating or preventing a mental health disorder in a subject in need thereof.

In some aspects, the present disclosure provides use of a compound of the present disclosure or a pharmaceutically acceptable salt thereof in the manufacture of a medicament for treating or preventing a metabolic syndrome in a subject in need thereof.

In some aspects, the present disclosure provides use of a compound of the present disclosure or a pharmaceutically acceptable salt thereof in the manufacture of a medicament for treating or preventing osteoporosis in a subject in need thereof.

In some aspects, the present disclosure provides use of a compound of the present disclosure or a pharmaceutically acceptable salt thereof in the manufacture of a medicament for treating or preventing cardiac failure in a subject in need thereof.

In some aspects, the present disclosure provides use of a compound of the present disclosure or a pharmaceutically acceptable salt thereof in the manufacture of a medicament for treating or preventing coma in a subject in need thereof.

In some aspects, the present disclosure provides use of a compound of the present disclosure or a pharmaceutically acceptable salt thereof in the manufacture of a medicament for treating or preventing a complication in emergence from anesthesia in a subject in need thereof.

In some aspects, the present disclosure provides use of a compound of the present disclosure or a pharmaceutically acceptable salt thereof in the manufacture of a medicament for treating narcolepsy, a hypersomnia disorder, a neurodegenerative disorder, a symptom of a rare genetic disorder, a mental health disorder, a metabolic syndrome, osteoporosis, cardiac failure, coma, or a complication in emergence from anesthesia in a subject in need thereof.

In some aspects, the present disclosure provides use of a compound of the present disclosure or a pharmaceutically acceptable salt thereof in the manufacture of a medicament for treating narcolepsy in a subject in need thereof.

In some aspects, the present disclosure provides use of a compound of the present disclosure or a pharmaceutically acceptable salt thereof in the manufacture of a medicament for treating a hypersomnia disorder in a subject in need thereof.

In some aspects, the present disclosure provides use of a compound of the present disclosure or a pharmaceutically acceptable salt thereof in the manufacture of a medicament for treating a neurodegenerative disorder in a subject in need thereof.

In some aspects, the present disclosure provides use of a compound of the present disclosure or a pharmaceutically acceptable salt thereof in the manufacture of a medicament for treating a symptom of a rare genetic disorder in a subject in need thereof.

In some aspects, the present disclosure provides use of a compound of the present disclosure or a pharmaceutically acceptable salt thereof in the manufacture of a medicament for treating a mental health disorder in a subject in need thereof.

In some aspects, the present disclosure provides use of a compound of the present disclosure or a pharmaceutically acceptable salt thereof in the manufacture of a medicament for treating a metabolic syndrome in a subject in need thereof.

In some aspects, the present disclosure provides use of a compound of the present disclosure or a pharmaceutically acceptable salt thereof in the manufacture of a medicament for treating osteoporosis in a subject in need thereof.

In some aspects, the present disclosure provides use of a compound of the present disclosure or a pharmaceutically acceptable salt thereof in the manufacture of a medicament for treating cardiac failure in a subject in need thereof.

In some aspects, the present disclosure provides use of a compound of the present disclosure or a pharmaceutically acceptable salt thereof in the manufacture of a medicament for treating coma in a subject in need thereof.

In some aspects, the present disclosure provides use of a compound of the present disclosure or a pharmaceutically acceptable salt thereof in the manufacture of a medicament for treating a complication in emergence from anesthesia in a subject in need thereof.

The present disclosure provides compounds that function as modulators of orexin receptor activity.

In some embodiments, the compounds of the present disclosure are agonists of the orexin receptor.

The present disclosure provides compounds that function as modulators of orexin-2 receptor activity.

In some embodiments, the compounds of the present disclosure are agonists of the orexin-2 receptor.

In some embodiments, the modulation of the orexin receptor is activation of the orexin receptor.

Effectiveness of compounds of the disclosure can be determined by industry-accepted assays/disease models according to standard practices of elucidating the same as described in the art and are found in the current general knowledge.

The present disclosure also provides a method of treating a disease or disorder in which orexin receptor activity is implicated in a patient in need of such treatment, said method comprising administering to said patient a therapeutically effective amount of a compound, or a pharmaceutically acceptable salt thereof, or a pharmaceutical composition as defined herein.

The present disclosure also provides a method of treating a disease or disorder in which orexin-2 receptor activity is implicated in a patient in need of such treatment, said method comprising administering to said patient a therapeutically effective amount of a compound, or a pharmaceutically acceptable salt thereof, or a pharmaceutical composition as defined herein.

In some embodiments, the present disclosure also provides a method for treating a disease or disorder by decreasing excessive sleepiness and/or excessive daytime sleepiness.

In some embodiments, the present disclosure also provides a method for treating a disease or disorder by decreasing excessive sleepiness.

In some embodiments, the present disclosure also provides a method for treating a disease or disorder by decreasing excessive daytime sleepiness.

In some embodiments, the disease or disorder is associated with excessive sleepiness and/or excessive daytime sleepiness.

In some embodiments, the disease or disorder is a primary hypersomnia disorder, neurodegenerative disorder, a symptom of a hypersomnia/neurodegenerative disorder, a symptom of a rare genetic disorder, a mental health disorder, a metabolic syndrome, osteoporosis, cardiac failure, coma, or emergence from anesthesia.

In some embodiments, the disease or disorder is a primary hypersomnia disorder, neurodegenerative disorder, a symptom of a hypersomnia/neurodegenerative disorder, a symptom of a rare genetic disorder, a mental health disorder, a metabolic syndrome, osteoporosis, cardiac failure, coma, or a complication in emergence from anesthesia.

In some embodiments, the excessive daytime sleepiness is associated with a neurodegenerative disorder.

In some embodiments, the neurodegenerative disorder associated with excessive daytime sleepiness is Parkinson's disease, Alzheimer's disease, Huntington's disease, or multiple sclerosis.

In some embodiments, the disease or disorder is a recurrence of hypersomnia.

In some embodiments, the recurrence of hypersomnia is narcolepsy type 1, narcolepsy type 2, or idiopathic hypersomnia.

In some embodiments, the disease or disorder is sleep apnea, traumatic brain injury, age-related cognitive dysfunction, or excessive daytime sleepiness.

In some embodiments, excessive daytime sleepingess is associated with sleep apnea, traumatic brain injury, or age-related cognitive dysfunction.

In some embodiments, the disorder is narcolepsy. In some embodiments, the narcolepsy is narcolepsy type 1. In some embodiments, the narcolepsy is narcolepsy type 2.

In some embodiments, the hypersomnia is a symptom of narcolepsy.

In some embodiments, the disease or disorder is a symptom of narcolepsy.

In some embodiments, the symptom of narcolepsy is excessive daytime sleepiness, cataplexy, sleep paralysis, hypnopompic and hynogogic hallucinations, disturbed nighttime sleep, or inappropriately timed rapid-eye-movement (REM) sleep.

In some embodiments, the symptom of narcolepsy is excessive daytime sleepiness.

In some embodiments, the symptom of narcolepsy is cataplexy. In some embodiments, cataplexy is pathognomonic of narcolepsy (e.g., narcolepsy type 1)

In some embodiments, the symptom of narcolepsy is sleep paralysis.

In some embodiments, the symptom of narcolepsy is hypnopompic and hynogogic hallucinations.

In some embodiments, the symptom of narcolepsy is disturbed nighttime sleep.

In some embodiments, the symptom of narcolepsy is inappropriately timed rapid-eye-movement (REM) sleep.

In some embodiments, the neurodegenerative disorder is characterized by cataplexy.

In some embodiments, the neurodegenerative disorder is characterized by excessive daytime sleepiness.

In some embodiments, the neurodegenerative disorder is Parkinson's disease.

In some embodiments, the neurodegenerative disorder is Alzheimer's disease.

In some embodiments, the neurodegenerative disorder is Huntington's disease.

In some embodiments, the neurodegenerative disorder is multiple sclerosis.

In some embodiments, the neurodegenerative disorder is a traumatic brain injury.

In some embodiments, the neurodegenerative disorder is sleep apnea.

In some embodiments, the neurodegenerative disorder is age-related cognitive dysfunction.

In some embodiments, the neurodegenerative disorder is a disorder of recurrent hypersomnia.

In some embodiments, a disorder of recurrent hypersomnia is Klein-Levin syndrome, inappropriately timed sleep, (e.g., delayed- or advanced-sleep phase disorder), shift work disorder, or jet lag disorder.

In some embodiments, the disease or disorder is a symptom of a rare genetic disorder.

In some embodiments, the symptom of a rare genetic disorder is abnormal daytime sleepiness.

In some embodiments, the symptom of a rare genetic disorder is excessive daytime sleepiness.

In some embodiments, the symptom of a rare genetic disorder is sleep onset REM periods.

In some embodiments, the symptom of a rare genetic disorder is characterized by cataplexy-like symptoms.

In some embodiments, the rare genetic disorder is ADCA-DN, Coffin-Lowry syndrome, Moebius syndrome, Norrie disease, Niemann-Pick disease type C, or Prader-Willi syndrome.

In some embodiments, the disease or disorder is a mental health disorder.

In some embodiments, the mental health disorder is attention deficit hyperactivity disorder.

In some embodiments, the mental health disorder is attention deficit disorder.

In some embodiments, the disease or disorder is a metabolic syndrome.

In some embodiments, the metabolic syndrome is obesity.

In some embodiments, the disease or disorder is osteoporosis.

In some embodiments, the disease or disorder is cardiac failure.

In some embodiments, the disease or disorder is a coma.

In some embodiments, the disease or disorder is emergence from anesthesia.

In some embodiments, the disease or disorder is a complication in emergence from anesthesia.

In some embodiments, the disease or disorder is narcolepsy, a hypersomnia disorder, a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or a complication in emergence from anesthesia.

In some embodiments, the disease or disorder is narcolepsy, idiopathic hypersomnia, or sleep apnea.

Routes of Administration

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which orexin activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I) and pharmaceutically acceptable salts thereof are also useful as pharmacological tools in the development and standardisation of in vitro and in vivo test systems for the evaluation of the effects of modulators of orexin-2 receptor activity in laboratory animals such as dogs, rabbits, monkeys, mini-pigs, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray or powder); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXEMPLARY EMBODIMENTS

Exemplary Embodiment No. 1. A compound of Formula (I'):

(I')

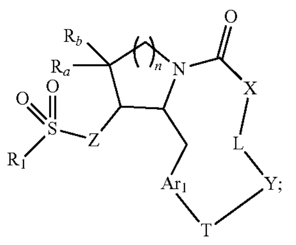

or a pharmaceutically acceptable salt thereof, wherein:

X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$—$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6;

Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

n is an integer ranging from 0 to 3;

$R_a$ and $R_b$ each independently are H, halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R_S$; or $R_a$ and $R_b$, together with the atom they attach to, form $C_3$-$C_7$ cycloalkyl or 3- to 7-membered heterocycloalkyl, wherein the $C_3$-$C_7$ cycloalkyl or 3- to 7-membered heterocycloalkyl is optionally substituted with one or more $R_S$;

each $R_S$ independently is halogen, —CN, —OH, —O($C_1$-$C_6$ alkyl), —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, or $C_1$-$C_6$ haloalkyl;

Z is —O— or —$NR_Z$—; wherein $R_Z$ is H or $C_1$-$C_6$ alkyl;

$R_1$ is —OH, —$NH_2$, —NH($C_1$-$C_6$ alkyl), —N($C_1$-$C_6$ alkyl)$_2$, —SH, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A1}$;

each $R_{A1}$ independently is $Ar_2$, halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is absent or $Ar_2$;

each $Ar_2$ independently is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

Exemplary Embodiment No. 2. A compound of Formula (I):

(I)

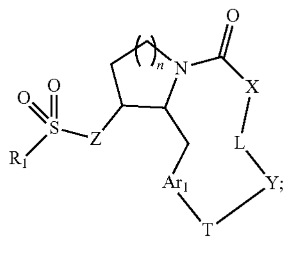

or a pharmaceutically acceptable salt thereof, wherein:

X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6;

Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

n is an integer ranging from 0 to 3;

Z is —O— or —$NR_Z$—; wherein $R_Z$ is H or $C_1$-$C_6$ alkyl;

$R_1$ is —OH, —$NH_2$, —NH($C_1$-$C_6$ alkyl), —N($C_1$-$C_6$ alkyl)$_2$, —SH, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, —S($C_1$-$C_6$ alkyl), —S($C_6$-$C_{10}$ aryl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, 3- to 7-membered heterocycloalkyl, —O—($C_6$-$C_{10}$ aryl), —O-(5- to 10-membered heteroaryl), —O—($C_3$-$C_{10}$ cycloalkyl), —O-(3- to 7-membered heterocycloalkyl), —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$;

each $R_{1S}$ independently is oxo, halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A1}$;

each $R_{A1}$ independently is $Ar_2$, halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is absent or $Ar_2$;

each $Ar_2$ independently is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

Exemplary Embodiment No. 3. The compound of any one of the preceding Exemplary Embodiments, wherein:

X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6;

Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

n is an integer ranging from 0 to 3;

Z is —O— or —$NR_Z$—; wherein $R_Z$ is H or $C_1$-$C_6$ alkyl;

$R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more $R_{1S}$;

each $R_{1S}$ independently is halogen, —CN, —OH, or $C_1$-$C_6$ alkoxy;

$Ar_1$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A1}$;

each $R_{A1}$ independently is $Ar_2$, halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is absent or $Ar_2$;

each $Ar_2$ independently is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

Exemplary Embodiment No. 4. The compound of any one of the preceding Exemplary Embodiments, wherein:

X is —O—, —NH—, —N($C_1$-$C_6$ alkyl)-, or $C_1$-$C_6$ alkyl;

L is absent or $C_1$-$C_6$ alkyl;

Y is —O— or $C_1$-$C_6$ alkyl;

n is an integer ranging from 0 to 3;

Z is —$NR_Z$—; wherein $R_Z$ is H or $C_1$-$C_6$ alkyl;

$R_1$ is $C_1$-$C_6$ alkyl;

$Ar_1$ is $C_6$-$C_{10}$ aryl optionally substituted with one or more $Ar_2$;

T is absent or $Ar_2$; and each $Ar_2$ independently is $C_6$-$C_{10}$ aryl.

Exemplary Embodiment No. 5. The compound of any one of the preceding Exemplary Embodiments, wherein:

X is —O—, —NH—, —N($C_1$-$C_6$ alkyl)-, or $C_1$-$C_6$ alkyl;

L is absent or $C_1$-$C_6$ alkyl;

Y is —O— or $C_1$-$C_6$ alkyl;

n is an integer ranging from 0 to 3;

Z is —$NR_Z$—; wherein $R_Z$ is H or $C_1$-$C_6$ alkyl;

$R_1$ is $C_1$-$C_6$ alkyl;

$Ar_1$ is $C_6$-$C_{10}$ aryl;

T is $C_6$-$C_{10}$ aryl.

Exemplary Embodiment No. 6. The compound of any one of the preceding Exemplary Embodiments, wherein:

X is —O—, —NH—, —N($C_1$-$C_6$ alkyl)-, or $C_1$-$C_6$ alkyl;

L is absent or $C_1$-$C_6$ alkyl;

Y is —O— or $C_1$-$C_6$ alkyl;

n is an integer ranging from 0 to 3;

Z is —$NR_Z$—; wherein $R_Z$ is H or $C_1$-$C_6$ alkyl;

$R_1$ is $C_1$-$C_6$ alkyl;

$Ar_1$ is $C_6$-$C_{10}$ aryl optionally substituted with one or more $C_6$-$C_{10}$ aryl; and T is absent.

Exemplary Embodiment No. 7. The compound of Exemplary Embodiment 1, wherein:

X is —O—, —NH—, —N($C_1$-$C_6$ alkyl)-, or $C_1$-$C_6$ alkyl;

L is absent or $C_1$-$C_6$ alkyl;

Y is —O— or $C_1$-$C_6$ alkyl;

n is 2;

Z is —$NR_Z$—; wherein $R_Z$ is H or $C_1$-$C_6$ alkyl;

$R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl) is substituted with one or more $R_{1S}$;

each $R_{1S}$ independently is halogen, —CN, —OH, —$NH_2$, —NH($C_1$-$C_6$ alkyl), —N($C_1$-$C_6$ alkyl)$_2$, —S($C_1$-$C_6$ alkyl), —$SO_2$($C_1$-$C_6$ alkyl), $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, or 3- to 7-membered heterocycloalkyl;

$Ar_1$ is $C_6$-$C_{10}$ aryl optionally substituted with one or more $R_{A1}$;

each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl;

T is $Ar_2$;

$Ar_2$ is $C_6$-$C_{10}$ aryl optionally substituted with one or more $R_{A2}$; and each $R_{A2}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

Exemplary Embodiment No. 8. The compound of any one of the preceding Exemplary Embodiments, wherein X is —O—.

Exemplary Embodiment No. 9. The compound of any one of the preceding Exemplary Embodiments, wherein X is —NH— or —N($C_1$-$C_6$ alkyl)-, wherein the —N($C_1$-$C_6$ alkyl)- is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 10. The compound of any one of the preceding Exemplary Embodiments, wherein X is —NH—.

Exemplary Embodiment No. 11. The compound of any one of the preceding Exemplary Embodiments, wherein X is —N($C_1$-$C_6$ alkyl)-.

Exemplary Embodiment No. 12. The compound of any one of the preceding Exemplary Embodiments, wherein X is —N($CH_3$)—.

Exemplary Embodiment No. 13. The compound of any one of the preceding Exemplary Embodiments, wherein X is —N($C_1$-$C_6$ alkyl)- substituted with one or more halogen or —OH.

Exemplary Embodiment No. 14. The compound of any one of the preceding Exemplary Embodiments, wherein X is —N($C_1$-$C_6$ alkyl)- substituted with one to three F and one —OH.

Exemplary Embodiment No. 15. The compound of any one of the preceding Exemplary Embodiments, wherein X is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 16. The compound of any one of the preceding Exemplary Embodiments, wherein X is $C_1$-$C_6$ alkyl optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 17. The compound of any one of the preceding Exemplary Embodiments, wherein X is 3- to 8-membered heterocycloalkyl optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 18. The compound of any one of the preceding Exemplary Embodiments, wherein X is azetidinyl optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 19. The compound of any one of the preceding Exemplary Embodiments, wherein X is

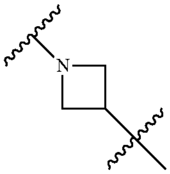

or

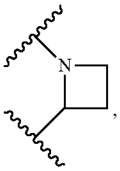

, wherein the

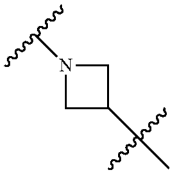

or

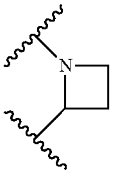

is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 20. The compound of any one of the preceding Exemplary Embodiments, wherein X is acetidinyl.

Exemplary Embodiment No. 21. The compound of any one of the preceding Exemplary Embodiments, wherein X is

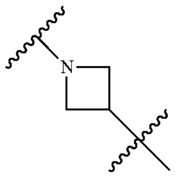
or
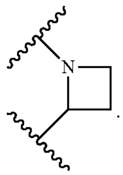
.

Exemplary Embodiment No. 22. The compound of any one of the preceding Exemplary Embodiments, wherein L is absent.

Exemplary Embodiment No. 23. The compound of any one of the preceding Exemplary Embodiments, wherein L is —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$.

Exemplary Embodiment No. 24. The compound of any one of the preceding Exemplary Embodiments, wherein L is —O—.

Exemplary Embodiment No. 25. The compound of any one of the preceding Exemplary Embodiments, wherein L is —NH— or —N($C_1$-$C_6$ alkyl)-, wherein the —N($C_1$-$C_6$ alkyl)- is optionally substituted with one or more halogen, —CN, —OH, —$NH_2$, —NH($C_1$-$C_6$ alkyl), or —N($C_1$-$C_6$ alkyl)$_2$.

Exemplary Embodiment No. 26. The compound of any one of the preceding Exemplary Embodiments, wherein L is $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$—, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, -(($C_2$—$C_6$ alkenyl)-NH)$_{nl}$—, or —(NH—($C_2$-$C_6$ alkenyl))$_{nl}$-, wherein the $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$.

Exemplary Embodiment No. 27. The compound of any one of the preceding Exemplary Embodiments, wherein L is $C_1$-$C_6$ alkyl or $C_2$-$C_6$ alkenyl, wherein the $C_1$-$C_6$ alkyl or $C_2$-$C_6$ alkenyl is optionally substituted with one or more halogen, —CN, —OH, —$NH_2$, —NH($C_1$-$C_6$ alkyl), or —N($C_1$-$C_6$ alkyl)$_2$.

Exemplary Embodiment No. 28. The compound of any one of the preceding Exemplary Embodiments, wherein L is —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$.

Exemplary Embodiment No. 29. The compound of any one of the preceding Exemplary Embodiments, wherein L is —(($C_1$-$C_6$ alkyl)-O)$_{nl}$— or —(O—($C_1$-$C_6$ alkyl))$_{nl}$-, wherein the —(($C_1$-$C_6$ alkyl)-O)$_{nl}$— or —(O—($C_1$-$C_6$ alkyl))$_{nl}$- is optionally substituted with one or more halogen, —CN, —OH, —$NH_2$, —NH($C_1$-$C_6$ alkyl), or —N($C_1$-$C_6$ alkyl)$_2$.

Exemplary Embodiment No. 30. The compound of any one of the preceding Exemplary Embodiments, wherein L is —(($C_1$-$C_6$ alkyl)-NH)$_{nl}$— or —(NH—($C_1$-$C_6$ alkyl))$_{nl}$-, wherein the —(($C_1$-$C_6$ alkyl)-NH)$_{nl}$— or —(NH—($C_1$-$C_6$ alkyl))$_{nl}$- is optionally substituted with one or more halogen, —CN, —OH, —$NH_2$, —NH($C_1$-$C_6$ alkyl), or —N($C_1$-$C_6$ alkyl)$_2$.

Exemplary Embodiment No. 31. The compound of any one of the preceding Exemplary Embodiments, wherein nl is an integer ranging from 1 to 3.

Exemplary Embodiment No. 32. The compound of any one of the preceding Exemplary Embodiments, wherein nl is 1.

Exemplary Embodiment No. 33. The compound of any one of the preceding Exemplary Embodiments, wherein nl is 2.

Exemplary Embodiment No. 34. The compound of any one of the preceding Exemplary Embodiments, wherein nl is 3.

Exemplary Embodiment No. 35. The compound of any one of the preceding Exemplary Embodiments, wherein Y is —O—.

Exemplary Embodiment No. 36. The compound of any one of the preceding Exemplary Embodiments, wherein Y is —NH— or —N($C_1$-$C_6$ alkyl)-, wherein the —N($C_1$-$C_6$ alkyl)- is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 37. The compound of any one of the preceding Exemplary Embodiments, wherein Y is —NH—.

Exemplary Embodiment No. 38. The compound of any one of the preceding Exemplary Embodiments, wherein —N($C_1$-$C_6$ alkyl)- optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 39. The compound of any one of the preceding Exemplary Embodiments, wherein Y is $C_1$-$C_6$ alkyl or $C_2$-$C_6$ alkenyl, wherein the $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 40. The compound of any one of the preceding Exemplary Embodiments, wherein Y is $C_1$-$C_6$ alkyl optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 41. The compound of any one of the preceding Exemplary Embodiments, wherein Y is $C_2$-$C_6$ alkenyl optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 42. The compound of any one of the preceding Exemplary Embodiments, wherein at most one of X and L is —O—, —NH—, or optionally substituted —N($C_1$-$C_6$ alkyl)-.

Exemplary Embodiment No. 43. The compound of any one of the preceding Exemplary Embodiments, wherein at most one of L and Y is —O—, —NH—, or optionally substituted —N($C_1$-$C_6$ alkyl)-.

Exemplary Embodiment No. 44. The compound of any one of the preceding Exemplary Embodiments, wherein at most one of X and Y is —O—, —NH—, or optionally substituted —N($C_1$-$C_6$ alkyl)-.

Exemplary Embodiment No. 45. The compound of any one of the preceding Exemplary Embodiments, wherein at most two of X, L, and Y are —O—, —NH—, or optionally substituted —N($C_1$-$C_6$ alkyl)-.

Exemplary Embodiment No. 46. The compound of any one of the preceding Exemplary Embodiments, wherein at most one of X, L, and Y is —O—, —NH—, or optionally substituted —N($C_1$-$C_6$ alkyl)-.

Exemplary Embodiment No. 47. The compound of any one of the preceding Exemplary Embodiments, wherein when X is —O—, —NH—, or optionally substituted —N($C_1$-$C_6$ alkyl)-, and Y is —O—, —NH—, or optionally substituted —N($C_1$-$C_6$ alkyl)-, then L is not absent, —O—, —NH—, or optionally substituted —N($C_1$-$C_6$ alkyl)-.

Exemplary Embodiment No. 48. The compound of any one of the preceding Exemplary Embodiments, wherein: X is —O—, —NH—, —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the —N($C_1$-$C_6$ alkyl)-, $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6; and Y is $C_1$-$C_6$ alkyl or $C_2$-$C_6$ alkenyl, wherein the $C_1$-$C_6$ alkyl or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 49. The compound of any one of the preceding Exemplary Embodiments, wherein:

X is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, —O—, —NH—, —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the —N($C_1$-$C_6$ alkyl)-, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6; and Y is $C_1$-$C_6$ alkyl or $C_2$-$C_6$ alkenyl, wherein the $C_1$-$C_6$ alkyl or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 50. The compound of any one of the preceding Exemplary Embodiments, wherein:

X is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy;

L is absent, $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$-, wherein the $C_1$-$C_6$ alkyl, $C_2$-$C_6$ alkenyl, —(($C_1$-$C_6$ alkyl)-O)$_{nl}$—, —(O—($C_1$-$C_6$ alkyl))$_{nl}$-, —(($C_2$-$C_6$ alkenyl)-O)$_{nl}$—, —(O—($C_2$-$C_6$ alkenyl))$_{nl}$-, —(($C_1$-$C_6$ alkyl)-NH)$_{nl}$—, —(NH—($C_1$-$C_6$ alkyl))$_{nl}$-, —(($C_2$-$C_6$ alkenyl)-NH)$_{nl}$—, or —(NH—($C_2$-$C_6$ alkenyl))$_{nl}$- is optionally substituted with one or more halogen, —CN, —OH, —$NH_2$, —NH($C_1$-$C_6$ alkyl), or —N($C_1$-$C_6$ alkyl)$_2$; and nl is an integer ranging from 1 to 6; and Y is —O—, —NH—, —N($C_1$-$C_6$ alkyl)-, $C_1$-$C_6$ alkyl, or $C_2$-$C_6$ alkenyl, wherein the —N($C_1$-$C_6$ alkyl)-, $C_1$-$C_6$ alkyl, or $C_2$-$C_6$ alkenyl is optionally substituted with one or more halogen, —CN, —OH, —$NH_2$, —NH($C_1$-$C_6$ alkyl), —N($C_1$-$C_6$ alkyl)$_2$, $C_1$-$C_6$ haloalkyl, or $C_1$-$C_6$ alkoxy.

Exemplary Embodiment No. 51. The compound of any one of the preceding Exemplary Embodiments, X is —O—, —NH—, —N($C_1$-$C_6$ alkyl)-, or $C_1$-$C_6$ alkyl; L is absent or $C_1$-$C_6$ alkyl; and Y is —O— or $C_1$-$C_6$ alkyl.

Exemplary Embodiment No. 52. The compound of any one of the preceding Exemplary Embodiments, X is —O—, —NH—, or —N($C_1$-$C_6$ alkyl)-; L is $C_1$-$C_6$ alkyl; and Y is —O—.

Exemplary Embodiment No. 53. The compound of any one of the preceding Exemplary Embodiments, X is $C_1$-$C_6$ alkyl; L is absent; and Y is $C_1$-$C_6$ alkyl.

Exemplary Embodiment No. 54. The compound of any one of the preceding Exemplary Embodiments, wherein n is 1.

Exemplary Embodiment No. 55. The compound of any one of the preceding Exemplary Embodiments, wherein n is 2.

Exemplary Embodiment No. 56. The compound of any one of the preceding Exemplary Embodiments, wherein $R_a$ and $R_b$ each independently are H or halogen; or $R_a$ and $R_b$, together with the atom they attach to, form $C_3$-$C_7$ cycloalkyl optionally substituted with one or more $R_S$.

Exemplary Embodiment No. 57. The compound of any one of the preceding Exemplary Embodiments, wherein one of $R_a$ and $R_b$ is H, and one of $R_a$ and $R_b$ is halogen.

Exemplary Embodiment No. 58. The compound of any one of the preceding Exemplary Embodiments, wherein $R_a$ and $R_b$, together with the atom they attach to, form cyclopropyl.

Exemplary Embodiment No. 59. The compound of any one of the preceding Exemplary Embodiments, wherein Z is —O—.

Exemplary Embodiment No. 60. The compound of any one of the preceding Exemplary Embodiments, wherein Z is —$NR_Z$—.

Exemplary Embodiment No. 61. The compound of any one of the preceding Exemplary Embodiments, wherein Z is —NH—.

Exemplary Embodiment No. 62. The compound of any one of the preceding Exemplary Embodiments, wherein $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more $R_{1S}$.

Exemplary Embodiment No. 63. The compound of any one of the preceding Exemplary Embodiments, wherein $R_1$ is —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —$NH_2$, —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more halogen, —CN, —OH, or $C_1$-$C_6$ alkoxy.

Exemplary Embodiment No. 64. The compound of any one of the preceding Exemplary Embodiments, wherein $R_1$ is —OH.

Exemplary Embodiment No. 65. The compound of any one of the preceding Exemplary Embodiments, wherein $R_1$ is —$NH_2$, —NH($C_1$-$C_6$ alkyl), or —N($C_1$-$C_6$ alkyl)$_2$, wherein the —NH($C_1$-$C_6$ alkyl), or —N($C_1$-$C_6$ alkyl)$_2$ is optionally substituted with one or more $R_{1S}$.

Exemplary Embodiment No. 66. The compound of any one of the preceding Exemplary Embodiments, wherein $R_1$ is —SH, —S($C_1$-$C_6$ alkyl), or —S($C_6$-$C_{10}$ aryl), wherein the —S($C_1$-$C_6$ alkyl) or —S($C_6$-$C_{10}$ aryl) is optionally substituted with one or more $R_{1S}$.

Exemplary Embodiment No. 67. The compound of any one of the preceding Exemplary Embodiments, wherein $R_1$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, or 3- to 7-membered heterocycloalkyl, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_6$-$C_{10}$ aryl, 5- to 10-membered heteroaryl, $C_3$-$C_7$ cycloalkyl, or 3- to 7-membered heterocycloalkyl is optionally substituted with one or more $R_{1S}$.

Exemplary Embodiment No. 68. The compound of any one of the preceding Exemplary Embodiments, wherein $R_1$ is $C_1$-$C_6$ alkyl optionally substituted with one or more $R_{1S}$.

Exemplary Embodiment No. 69. The compound of any one of the preceding Exemplary Embodiments, wherein $R_1$ is $C_1$-$C_6$ alkyl.

Exemplary Embodiment No. 70. The compound of any one of the preceding Exemplary Embodiments, wherein $R_1$ is methyl.

Exemplary Embodiment No. 71. The compound of any one of the preceding Exemplary Embodiments, wherein $R_1$ is ethyl.

Exemplary Embodiment No. 72. The compound of any one of the preceding Exemplary Embodiments, wherein $R_1$ is $C_3$-$C_7$ cycloalkyl optionally substituted with one or more $R_{1S}$.

Exemplary Embodiment No. 73. The compound of any one of the preceding Exemplary Embodiments, wherein $R_1$ is cyclopropyl optionally substituted with one or more $R_{1S}$.

Exemplary Embodiment No. 74. The compound of any one of the preceding Exemplary Embodiments, wherein $R_1$ is cyclopropyl optionally substituted with one or more F.

Exemplary Embodiment No. 75. The compound of any one of the preceding Exemplary Embodiments, wherein $R_1$ is —O—($C_6$-$C_{10}$ aryl), —O-(5- to 10-membered heteroaryl), —O—($C_3$-$C_{10}$ cycloalkyl), or —O-(3- to 7-membered heterocycloalkyl), wherein the —O—($C_6$-$C_{10}$ aryl), —O-(5- to 10-membered heteroaryl), —O—($C_3$-$C_{10}$ cycloalkyl), or —O-(3- to 7-membered heterocycloalkyl) is optionally substituted with one or more $R_{1S}$.

Exemplary Embodiment No. 76. The compound of any one of the preceding Exemplary Embodiments, wherein $R_1$ is —NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl), wherein the NH—($C_6$-$C_{10}$ aryl), —NH-(5- to 10-membered heteroaryl), —NH—($C_3$-$C_{10}$ cycloalkyl), or —NH-(3- to 7-membered heterocycloalkyl) is optionally substituted with one or more $R_{1S}$.

Exemplary Embodiment No. 77. The compound of any one of the preceding Exemplary Embodiments, wherein at least one $R_{1S}$ is halogen, —CN, —OH, or $C_1$-$C_6$ alkoxy.

Exemplary Embodiment No. 78. The compound of any one of the preceding Exemplary Embodiments, wherein at least one $R_{1S}$ is halogen.

Exemplary Embodiment No. 79. The compound of any one of the preceding Exemplary Embodiments, wherein at least one $R_{1S}$ is $C_1$-$C_6$ alkyl, $C_2$-$C_6$ alkenyl, $C_2$-$C_6$ alkynyl, or $C_1$-$C_6$ alkoxy.

Exemplary Embodiment No. 80. The compound of any one of the preceding Exemplary Embodiments, wherein at least one $R_{1S}$ is $C_3$-$C_7$ cycloalkyl or 3- to 7-membered heterocycloalkyl.

Exemplary Embodiment No. 81. The compound of any one of the preceding Exemplary Embodiments, wherein $Ar_1$ is $C_6$-$C_{10}$ aryl optionally substituted with one or more $R_{A1}$.

Exemplary Embodiment No. 82. The compound of any one of the preceding Exemplary Embodiments, wherein $Ar_1$ is phenyl optionally substituted with one or more $R_{A1}$.

Exemplary Embodiment No. 83. The compound of any one of the preceding Exemplary

Embodiments, wherein $Ar_1$ is

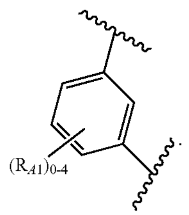

Exemplary Embodiment No. 84. The compound of any one of the preceding Exemplary Embodiments, wherein $Ar_1$ is

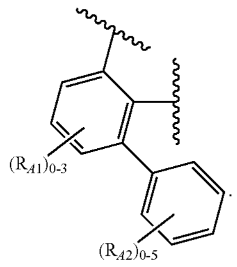

Exemplary Embodiment No. 85. The compound of any one of the preceding Exemplary Embodiments, wherein $Ar_1$ is 5- to 10-membered heteroaryl optionally substituted with one or more $R_{A1}$.

Exemplary Embodiment No. 86. The compound of any one of the preceding Exemplary Embodiments, wherein $Ar_1$ is pyridyl or thiazolyl optionally substituted with one or more $R_{A1}$.

Exemplary Embodiment No. 87. The compound of any one of the preceding Exemplary Embodiments, wherein $Ar_1$ is pyridyl optionally substituted with one or more $R_{A1}$.

Exemplary Embodiment No. 88. The compound of any one of the preceding Exemplary Embodiments, wherein $Ar_1$ is

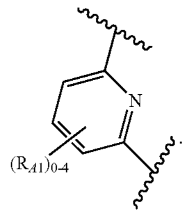

Exemplary Embodiment No. 89. The compound of any one of the preceding Exemplary Embodiments, wherein at least one $R_{A1}$ is $Ar_2$.

Exemplary Embodiment No. 90. The compound of any one of the preceding Exemplary Embodiments, wherein at least one $R_{A1}$ is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$.

Exemplary Embodiment No. 91. The compound of any one of the preceding Exemplary Embodiments, wherein at least one $R_{A1}$ is $C_6$-$C_{10}$ aryl optionally substituted with one or more $R_{A2}$.

Exemplary Embodiment No. 92. The compound of any one of the preceding Exemplary Embodiments, wherein at least one $R_{A1}$ is phenyl optionally substituted with one or more $R_{A2}$.

Exemplary Embodiment No. 93. The compound of any one of the preceding Exemplary Embodiments, wherein at least one $R_{A1}$ is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

Exemplary Embodiment No. 94. The compound of any one of the preceding Exemplary Embodiments, wherein at least one $R_{A1}$ is halogen.

Exemplary Embodiment No. 95. The compound of any one of the preceding Exemplary Embodiments, wherein at least one $R_{A1}$ is F.

Exemplary Embodiment No. 96. The compound of any one of the preceding Exemplary Embodiments, wherein T is absent.

Exemplary Embodiment No. 97. The compound of any one of the preceding Exemplary Embodiments, wherein T is $Ar_2$.

Exemplary Embodiment No. 98. The compound of any one of the preceding Exemplary Embodiments, wherein T is $C_6$-$C_{10}$ aryl or 5- to 10-membered heteroaryl, wherein the $C_6$-$C_{10}$ aryl or 5- to 10-membered heteroaryl is optionally substituted with one or more $R_{A2}$.

Exemplary Embodiment No. 99. The compound of any one of the preceding Exemplary Embodiments, wherein T is $C_6$-$C_{10}$ aryl optionally substituted with one or more $R_{A2}$.

Exemplary Embodiment No. 100. The compound of any one of the preceding Exemplary Embodiments, wherein T is phenyl optionally substituted with one or more $R_{A2}$.

Exemplary Embodiment No. 101. The compound of any one of the preceding Exemplary Embodiments, wherein T is

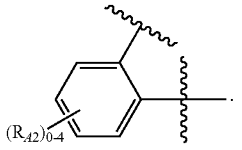

Exemplary Embodiment No. 102. The compound of any one of the preceding Exemplary Embodiments, wherein T is 5- to 10-membered heteroaryl optionally substituted with one or more $R_{A2}$.

Exemplary Embodiment No. 103. The compound of any one of the preceding Exemplary Embodiments, wherein at least one $R_{A1}$ is $Ar_2$, and T is absent.

Exemplary Embodiment No. 104. The compound of any one of the preceding Exemplary Embodiments, wherein $Ar_1$ is

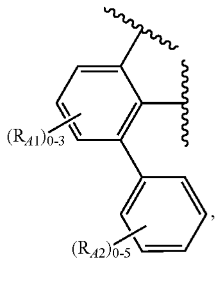

and T is absent.

Exemplary Embodiment No. 105. The compound of any one of the preceding Exemplary Embodiments, wherein each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is $Ar_2$.

Exemplary Embodiment No. 106. The compound of any one of the preceding Exemplary Embodiments, wherein $Ar_1$ is

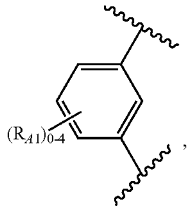

, and T is $Ar_2$.

Exemplary Embodiment No. 107. The compound of any one of the preceding Exemplary Embodiments, wherein $Ar_1$ is

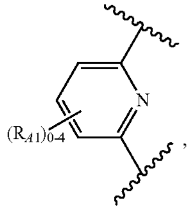

, and T is $Ar_2$.

Exemplary Embodiment No. 108. The compound of any one of the preceding Exemplary Embodiments, wherein each $R_{A1}$ independently is halogen, —CN, —OH, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl; and T is $Ar_2$.

Exemplary Embodiment No. 109. The compound of any one of the preceding Exemplary Embodiments, wherein at least one $Ar_2$ is $C_6$-$C_{10}$ aryl optionally substituted with one or more $R_{A2}$.

Exemplary Embodiment No. 110. The compound of any one of the preceding Exemplary Embodiments, wherein at least one $Ar_2$ is phenyl optionally substituted with one or more $R_{A2}$.

Exemplary Embodiment No. 111. The compound of any one of the preceding Exemplary Embodiments, wherein at least one $Ar_2$ is 5- to 10-membered heteroaryl optionally substituted with one or more $R_{A2}$.

Exemplary Embodiment No. 112. The compound of any one of the preceding Exemplary Embodiments, wherein at least one $R_{A2}$ is halogen.

Exemplary Embodiment No. 113. The compound of any one of the preceding Exemplary Embodiments, wherein at least one $R_{A2}$ is F.

Exemplary Embodiment No. 114. The compound of any one of the preceding Exemplary Embodiments, wherein at least one $R_{A2}$ is $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, or $C_2$-$C_6$ alkynyl.

Exemplary Embodiment No. 115. The compound of any one of the preceding Exemplary Embodiments, wherein the compound is of Formula (I'-a), (I'-b), (IA'), (IA'-a), (IA'-b), (IB'), (IB'-a), (IB'-b), (II'), (II'-a), (II'-b), (IIA'), (IIA'-a), (IIA'-b), (IIB'), (IIB'-a), (IIB'-b), (IIIA'), (IIIA'-a), (IIIA'-b), (IIIB'), (IIIB'-a), or (IIIB'-b), (IVA'), (IVA'-a), (IVA'-b), (VA'), (VA'-a), or (VA'-b), or a pharmaceutically acceptable salt thereof, wherein: n1 is an integer ranging from 0 to 4; and n2 is an integer ranging from 0 to 4.

Exemplary Embodiment No. 116. The compound of any one of the preceding Exemplary Embodiments, wherein the compound is of Formula (I-a), (I-b), (IA), (IA-a), (IA-b), (IB), (IB-a), (IB-b), (II), (II-a), (II-b), (IIA), (IIA-a), (IIA-b), (IIB), (IIB-a), (IIB-b), (IIIA), (IIIA-a), (IIIA-b), (IIIB), (IIIB-a), or (IIIB-b), (IVA), (IVA-a), (IVA-b), (VA), (VA-a), or (VA-b), or a pharmaceutically acceptable salt thereof, wherein: n1 is an integer ranging from 0 to 4; and n2 is an integer ranging from 0 to 4.

Exemplary Embodiment No. 117. The compound of any one of the preceding Exemplary Embodiments, wherein:

$R_1$ is —NH($C_1$-$C_6$ alkyl), —N($C_1$-$C_6$ alkyl)$_2$, $C_1$-$C_6$ alkyl, 5- to 10-membered heteroaryl, 3- to 7-membered heterocycloalkyl, —NH—($C_3$-$C_{10}$ cycloalkyl), or —NH-(3- to 7-membered heterocycloalkyl), wherein the —NH($C_1$-$C_6$ alkyl), —N($C_1$-$C_6$ alkyl)$_2$, 5- to 10-membered heteroaryl, 3- to 7-membered heterocycloalkyl, —NH—($C_3$-$C_{10}$ cycloalkyl), or —NH-(3- to 7-membered heterocycloalkyl) is optionally substituted with one or more $R_{1S}$ and $C_1$-$C_6$ alkyl is substituted with one or more $R_{1S}$;

each $R_{1S}$ is independently halogen or $C_1$-$C_6$ alkyl;

each $R_{A1}$ is independently halogen;

each $R_{A2}$ is independently halogen n1 is an integer ranging from 0 to 4; and n2 is an integer ranging from 0 to 4.

Exemplary Embodiment No. 118. The compound of any one of the preceding Exemplary Embodiments, wherein the compound is selected from the compounds described in Table A1 and pharmaceutically acceptable salts thereof.

Exemplary Embodiment No. 119. The compound of any one of the preceding Exemplary Embodiments, wherein the compound is selected from Compound Nos. A1-6, A1-6, A1-10, A1-15, A1-42, A1-58, A1-59, A1-60, A1-61, A1-63 to A1-102, and pharmaceutically acceptable salts thereof.

Exemplary Embodiment No. 120. The compound of any one of the preceding Exemplary Embodiments, wherein the compound is selected from the compounds described in Table A2 and pharmaceutically acceptable salts thereof.

Exemplary Embodiment No. 121. The compound of any one of the preceding Exemplary Embodiments, wherein the compound is selected from the compounds described in Table B1 and pharmaceutically acceptable salts thereof.

Exemplary Embodiment No. 122. The compound of any one of the preceding Exemplary Embodiments, wherein the compound is selected from the compounds described in Table B2 and pharmaceutically acceptable salts thereof.

Exemplary Embodiment No. 123. A compound obtainable by, or obtained by, a method described herein; optionally, the method comprises one or more steps described in Schemes 1-5.

Exemplary Embodiment No. 124. A pharmaceutical composition comprising the compound of any one of the preceding Exemplary Embodiments or a pharmaceutically acceptable salt thereof, and a pharmaceutically acceptable diluent or carrier.

Exemplary Embodiment No. 125. The pharmaceutical composition of any one of the preceding Exemplary Embodiments, wherein the compound is selected from the compounds described in Tables A1, A2, B1, and B2.

Exemplary Embodiment No. 126. A method of modulating orexin-2 receptor activity, comprising contacting a cell with an effective amount of the compound of any one of the preceding Exemplary Embodiments; optionally the activity is in vitro or in vivo.

Exemplary Embodiment No. 127. A method of treating or preventing a disease or disorder in a subject in need thereof, comprising administering to the subject a therapeutically effective amount of the compound or pharmaceutical composition of any one of the preceding Exemplary Embodiments.

Exemplary Embodiment No. 128. The compound or pharmaceutical composition of any one of the preceding Exemplary Embodiments for use in modulating orexin-2 receptor activity; optionally, the activity is in vitro or in vivo.

Exemplary Embodiment No. 129. The compound or pharmaceutical composition of any one of the preceding Exemplary Embodiments for use in treating or preventing a disease or disorder.

Exemplary Embodiment No. 130. Use of the compound of any one of the preceding Exemplary Embodiments in the manufacture of a medicament for modulating orexin-2 receptor activity; optionally, the activity is in vitro or in vivo.

Exemplary Embodiment No. 131. Use of the compound of any one of the preceding Exemplary Embodiments in the manufacture of a medicament for treating or preventing a disease or disorder.

Exemplary Embodiment No. 132. The method, compound, pharmaceutical composition, or use of any one of the preceding Exemplary Embodiments, wherein the disease or disorder is associated with an implicated orexin-2 receptor.

Exemplary Embodiment No. 133. The method, compound, pharmaceutical composition, or use of any one of the preceding Exemplary Embodiments, wherein the disease or disorder is a neurodegenerative disorder, a neurological disorder, a symptom of a rare genetic disorder, a psychiatric disorder, a mental health disorder, a circadian rhythm disorder, a metabolic syndrome, osteoporosis, cardiac failure, coma, or a complication in emergence from anesthesia.

Exemplary Embodiment No. 134. The method, compound, pharmaceutical composition, or use of any one of the preceding Exemplary Embodiments, wherein the disease or disorder is narcolepsy, idiopathic hypersomnia, sleep apnea, or insomnia.

EXAMPLES

Abbreviations

ACN Acetonitrile
AIBN Azobisisobutyronitrile
BOC tert-butyl carbamate
BOP (benzotriazol-1-yloxy)tris(dimethylamino)phosphonium
hexafluorophosphate
BTC bis(trichloromethyl) carbonate
CDI carbonyl diimidazole
DAD diode array detector
DCM Dichloromethane
DIEA/DIPEA N,N-diisopropylethylamine
DMF N,N-dimethylformamide
DMSO Dimethylsulfoxide
EA ethyl acetate
EDCI 1-ethyl-3-(3-dimethylaminopropyl) carbodiimide
ELSD evaporative light scattering detector
ES/ESI electrospray ionisation
HATU 1-[Bis(dimethylamino)methylene]-1H-1,2,3-triazolo[4,5-b]pyridinium 3-oxid hexafluorophosphate
HOAT 1-hydroxy-7-azabenzotriazole
HOBT hydroxy benzotriazole
HPLC high-performance liquid chromatography
IPA Isopropylalcohol
LC liquid chromatography
LiHMDS lithium hexamethyl disilazide
MS mass spectrometry NMR nuclear magnetic resonance
Py Pyridine
RT retention time
SFC supercritical fluid chromatography
TBAI tetrabutyl ammonium iodide
TEA Triethylamine
TFA trifluoroacetic acid
TFAA trifluoroacetic anhydride
THF Tetrahydrofuran
TLC thin layer chromatography
TMS tetramethyl silane
UV Ultraviolet NMRs NMR spectra were recorded on Bruker Avance III HD UltraShield 400 MHz with a 5 mm PABBO probe, Bruker DPX 300 MHz equipped with a 5 mm BBI probe, Bruker AV 400 MHz equipped with a 5 mm PABBO probe, Bruker DRX 500 MHz equipped with a 5 mm PABBI probe and Bruker Avance III 600 spectrometer equipped with a 5 mm RT BBI probe. The samples were recorded at 25 °C using DMSO-$d_6$, $CDCl_3$ or MeOH-$d_4$ as a solvent and TMS as the internal standard.

LCMS Conditions

Condition A. General UPLC method parameters: gradient mobile phase of 0.1% formic acid in $H_2O$ and $CH_3CN$ or 0.05% $NH_3$ in $H_2O$ and $CH_3CN$. Column: Acquity BEH 2.1×50 mm, 1.7 μm and Acquity BEH 2.1×100 mm, 1.7 μm. PDA detector settings: wavelength: 210-400 nm, resolution: 1.2 nm, sampling rate: 1.0 points/sec, filter response: 1. MS detector settings: MS scan: centroid, ionization mode: ES+ and ES−, mass range: 100-1250, scan time: 0.225 s, capillary: 1.30 kV (ES+) and 0.80 kV (ES−), cone: 15 V, extractor: 3.00 V, RF Lens: 0.2 V, source temp.: 120 °C, desolvation temp.: 600 °C, LM 1 resolution: 0.02, HM 1 resolution: 0.11.

Condition B. LC/MS Agilent Technologies 1260 Infinity LC with Chemstation software, Aqueous (A2): Water (2.5 L) with 2.5 mL of 28% Ammonia in water solution Organic (B2): Acetonitrile (2.5 L) with 125 mL Water and 2.5 mL of 28% Ammonia in water solution, System runs at a flow rate of 1.5 mL/min, Injection volume of 0.5 μL, Phenomenex Gemini-NX, 5 μm, C18, 30×2 mm. Column oven temp of 40 °C. Diode Array Detector with UV detection from 190 to 400 nm and Agilent Mass Spectrometer 6120 Single Quadrupole with API-ES source. Gradients written in the following format: [Time (min)/% A2: % B2], Short Run: [0.00/95:5], [2.0/5:95], [2.5/5:95], [2.6/95:5], [3.0/95:5].

Condition C. LC/MS Agilent Technologies 1260 Infinity LC with Chemstation software, Aqueous (A2): Water (2.5 L) with 2.5 mL of 28% Ammonia in water solution Organic (B2): Acetonitrile (2.5 L) with 125 mL Water and 2.5 mL of 28% Ammonia in water solution, System runs at a flow rate of 1.5 mL/min, Injection volume of 0.5 μL, Phenomenex Gemini-NX, 5 μm, C18, 30×2 mm. Column oven temp of 40 °C. Diode Array Detector with UV detection from 190 to 400 nm and Agilent Mass Spectrometer 6120 Single Quadrupole with API-ES source. Gradients written in the following format: [Time (min)/% A2: % B2], Long Run: [0.00/98:2], [0.1/98:2], [8.4/5:95], [10.0/5:95], [10.1/98:2], [12.0/98:2].

Condition D. Hewlett Packard 1100 series with Masslynx software, Aqueous (C): Water (2.5 L) with 2.5 mL of 28% Ammonia in water solution Organic (D): Acetonitrile (2.5 L) with 125 mL Water and 2.5 mL of 28% Ammonia in water solution, System runs at a flow rate of 1.5 mL/min, Injection volume of 1 μL, Phenomenex Gemini-NX, 5 μm, C18, 30×2 mm. Column oven temp of 45 °C. Hewlett Packard G1315A Diode Array Detector with UV detection from 230 to 400 nm and Waters micromass ZQ mass spectrometer. Gradients written in the following format: [Time (min)/% C: % D], Short Run: [0.00/98:2], [0.1/98:2], [2.5/5:95], [3.5/5:95].

Condition E. Hewlett Packard 1100 series with Masslynx software, Aqueous (C): Water (2.5 L) with 2.5 mL of 28% Ammonia in water solution Organic (D): Acetonitrile (2.5 L) with 125 mL Water and 2.5 mL of 28% Ammonia in water solution, System runs at a flow rate of 1.5 mL/min, Injection volume of 1 μL, Phenomenex Gemini-NX, 5 μm, C18, 30×2 mm. Column oven temp of 45 °C. Hewlett Packard G1315A Diode Array Detector with UV detection from 230 to 400 nm and Waters micromass ZQ mass spectrometer. Gradients written in the following format: [Time (min)/% C: % D], Long Run: [0.00/98:2], [0.1/98:2], [8.4/5:95], [10.0/5:95]. Condition F.

LC Parameter

| | |
|---|---|
| Instrument: | AQUITY with PDA detector and QDA Performance |
| Column: | C18, 50*2.1 mm, 1.6 μm |
| Mobile Phase: | (A) 0.1% Formic acid inMilli Q water (pH = 2.70) |
| | (B) 0.1% Formic acid in water:Acetonitrile (10:90) |
| Column Temperature: | 35° C. |
| Auto Sampler Temperature: | 5° C. |
| Run Time: | 4 min |

Gradient

| TIME (Minute) | (%)A | (%)B | Flow (ml/min) |
|---|---|---|---|
| 0.00 | 97 | 03 | 0.8 |
| 0.20 | 97 | 03 | 0.8 |
| 2.70 | 02 | 98 | 0.8 |
| 3.00 | 00 | 100 | 1.0 |
| 3.50 | 00 | 100 | 1.0 |
| 3.51 | 97 | 03 | 0.8 |
| 4.00 | 97 | 03 | 0.8 |

Mass Parameter

Probe: ESI capillary
Source Temperature: 120 °C
Probe Temperature: 600 °C
Capillary Voltage: 0.8 KV (+Ve and −Ve)
Cone Voltage: 10 & 30 V
Mode of Ionization: +Ve and −Ve Condition G. LC/MS (The gradient was 5% B in 0.40 min and 5-95% B at 0.40-3.00 min, hold on 95% B for 1.00 min, and then 95-5% B in 0.01 min, the flow rate was 1.0 mL/min. Mobile phase A was 0.04% trifluoroacetic acid in water, mobile phase B was 0.02% trifluoroacetic acid in acetonitrile. The column used for chromatography was a Luna C18 50*2.0 mm column (5 μm particles). Detection methods are diode array (DAD) and evaporative light scattering (ELSD) detection as well as positive electrospray ionization. MS range was 100-1000.

Condition H. LC/MS (The gradient was 5% B in 0.40 min and 5-95% B at 0.40-3.40 min, hold on 95% B for 0.45 min, and then 95-5% B in 0.01 min, the flow rate was 0.8 mL/min. Mobile phase A was $H_2O$+10 mM $NH_4HCO_3$, mobile phase B was acetonitrile. The column used for chromatography was a Xbridge-C18 2.1*50 mm column (5 μm particles). Detection methods are diode array (DAD) and evaporative light scattering (ELSD) detection as well as positive electrospray ionization. MS range was 100-1000.

Condition I. 5-95 AB_2 min: LC/MS (The column used for chromatography was a Kinetex 5 m EVO C18 100A. Detection methods are diode array (DAD). MS mode was positive electrospray ionization. MS range was 100-1000. Mobile phase A was 0.04% trifluoroacetic acid in water, and mobile phase B was 0.02% trifluoroacetic acid in HPLC grade acetonitrile. The gradient was 5-95% B in 1.50 min 0.5% B in 0.01 min, 5-95% B (0.01-0.70 min) 95% B for 0.46 min. 95-5% B (1.61-1.50 min) with a hold at 5% B for 0.11 min. The flow rate was 1.5 mL/min.

Condition J. LC/MS (The gradient was 5-95% B in 0.7 min, 95-95% B in 0.45 min, 95-5% B in 0.01 min, and then held at 0% B for 0.44 min (1.5 mL/min flow rate). Mobile phase A was 0.0375% trifluoroacetic in water, mobile phase B was 0.018% trifluoroacetic acid in acetonitrile. The column used for the chromatography is a Chromolith Flash RP-18e25-2 mm column. Detection methods are diode array (DAD) and evaporative light scattering (ELSD) detection as well as positive electrospray ionization (MS).

Synthesis of Intermediate 1

Step 1: tert-butyl 2-(3-bromobenzyl)-3-oxopyrrolidine-1-carboxylate

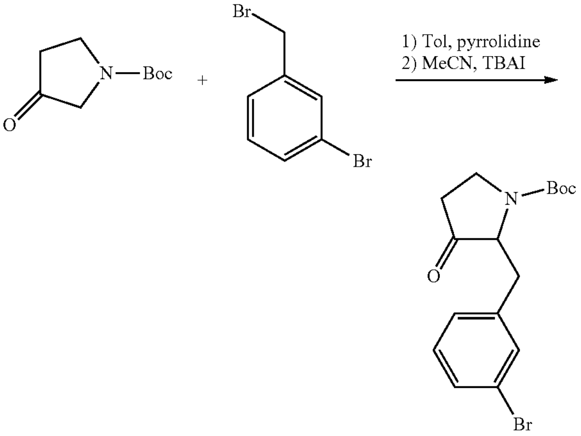

2-methyl-2-((3-oxopyrrolidine-1-carbonyl)oxy)propan-1-ylium (50.00 g, 270 mmol) was dissolved in toluene (500 mL) at room temperature. Pyrrolidine (33.25 mL, 405 mmol) was added at room temperature and reaction mixture stirred at 120 °C for 5 h using Dean-Stark apparatus. Reaction mixture was concentrated in vacuo to get red sticky residue. Residue was re-dissolved in acetonitrile (500 mL). 1-bromo-3-(bromomethyl)benzene (66.9 g, 270 mmol) and tetrabutylammonium iodide (19.94 g, 54 mmol) were added at room temperature and reaction mixture was allowed to stir at 80 °C for 2 h. The reaction mixture was diluted with water (1000 mL) and extracted with dichloromethane (250 mL). The aqueous layer was further extracted with dichloromethane (3×250 mL). Organic layers were combined and dried ($Na_2SO_4$). Solvent was removed in vacuo to afford crude compound which was purified by normal phase gradient column chromatography (Normal phase, Silica), product eluted at 0% to 2% EtOAc in Hexane to afford the title compound (24.00 g, 26% yield) as a yellow gum. LCMS (method F) m/z 298 (ES+, M-$^t$Bu) at 2.43 min.

Step 2: tert-butyl 3-amino-2-(3-bromobenzyl)pyrrolidine-1-carboxylate_cis racemic

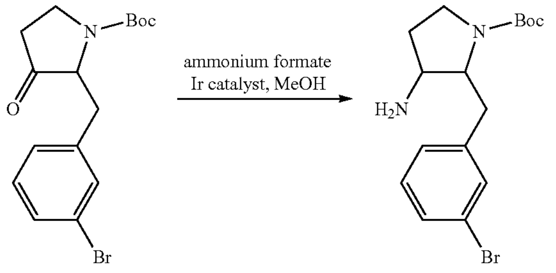 [SMILES: CC(C)(C)OC(=O)N1CCC(=O)C1Cc1cccc(Br)c1 ; "ammonium formateIr catalyst, MeOH" ; CC(C)(C)OC(=O)N1CCC(N)C1Cc1cccc(Br)c1]

Tert-butyl 2-(3-bromobenzyl)-3-oxopyrrolidine-1-carboxylate (20.00 g, 56.67 mmol) was dissolved in methanol (100 mL). Ammonium formate (28.58 g, 453 mmol) and chloro[N-[4(dimethylamino)phenyl]-2-pyridinecarboxamidato](pentamethylcyclopentadienyl) iridium(III) (0.68 g, 1.13 mmol) were added at room temperature. The reaction mixture was stirred at 80 °C for 2 h. The reaction mixture was diluted with water (500 mL) and extracted with EtOAc (250 mL). The aqueous layer was further extracted with EtOAc (3×150 mL). The organic layers were combined and dried ($Na_2SO_4$) and the solvent was removed in vacuo. Crude product was purified by reverse phase gradient flash column chromatography (reverse phase, C18 silica), product eluted at 0% to 30% acetonitrile in water with 0.1% formic acid and 5 mmol ammonium acetate as a modifier to afford a yellow solid. The solid was dissolved in saturated aqueous $NaHCO_3$ solution (500 mL) and extracted with dichloromethane (3×250 mL). The organic layers were combined and dried ($Na_2SO_4$). Solvent was evaporated in vacuo to afford the title compound (6.50 g, 26% yield) as an orange gum. LCMS (method F) m/z 299 (ES+, M-Bu) at 1.38 min Step 3: tert-butyl 2-(3-bromobenzyl)-3-(methylsulfonamido)pyrrolidine-1-carboxylate_cis racemic (Intermediate 1)

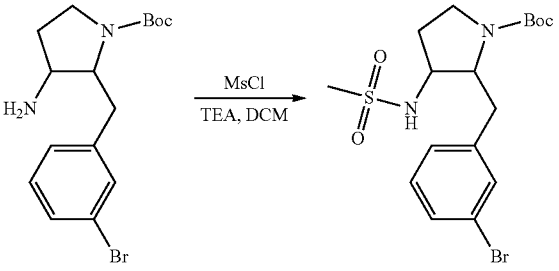 [SMILES: "MsCl" ; CC(C)(C)OC(=O)N1CCC(N)C1Cc1cccc(Br)c1 ; CC(C)(C)OC(=O)N1CCC(NS(C)(=O)=O)C1Cc1cccc(Br)c1]

To a solution of tert-butyl 3-amino-2-(3-bromobenzyl) pyrrolidine-1-carboxylate_cis racemic (2.00 g, 5.63 mmol) in dichloromethane (25 mL), methanesulfonyl chloride (0.654 mL, 8.44 mmol) and N,N-diisopropylethylamine (2.45 mL, 14.1 mmol) were added at 0 °C and the mixture was stirred at r.t. overnight. The reaction mixture was washed with sat. $NaHCO_3$ and brine, dried over MgSO4, and evaporated. The residue was purified on InterChim PuriFlash 520 plus purification system (25 g Si column, 15 m, eluents 0-100% ethylacetate/cyclohexane) to afford the title compound (1.02 g). LCMS (method A) (ESI−): 431.04 [1:1, M−H]

Synthesis of Intermediate 2 tert-butyl 2-(3-bromobenzyl)-3-(ethylsulfonamido) pyrrolidine-1-carboxylate_cis racemic (intermediate 2)

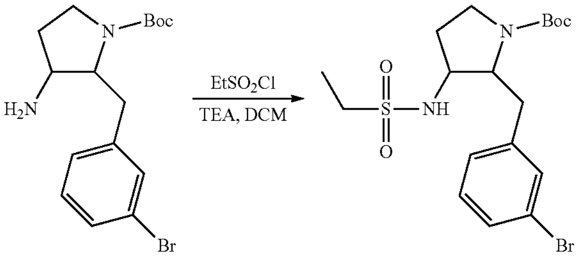 [SMILES: "EtSO2Cl" ; CC(C)(C)OC(=O)N1CCC(N)C1Cc1cccc(Br)c1 ; CCS(=O)(=O)NC1CCN(C(=O)OC(C)(C)C)C1Cc1cccc(Br)c1]

To a cooled (<5 °C) solution of tert-butyl 3-amino-2-(3-bromobenzyl)pyrrolidine-1-carboxylate_cis racemic (5.7 g, 16 mmol) and $Et_3N$ (4.52 mL, 32 mmol) in dichloromethane (80 mL) was added ethanesulfonyl chloride (2.09 mL, 24.07 mmol) and the reaction stirred at RT for 1 h. The crude reaction was diluted with dichloromethane (50 mL), washed with 10% citric acid (50 mL), brine (50 mL), the organic layer separated, dried over $MgSO_4$, filtered and concentrated in vacuo to afford the title compound (6.85 g, 15.31 mmol) as a light brown waxy solid. LCMS (method D) m/z 447 (ES+, M+H) at 2.22 min Synthesis of Intermediate 3

Step 1: tert-butyl 2-(3-bromobenzyl)-3-oxopiperidine-1-carboxylate

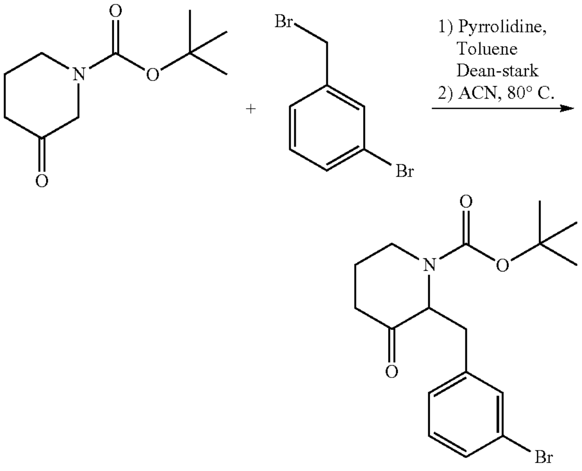

tert-butyl 3-oxopiperidine-1-carboxylate (50.00 g, 251 mmol) was dissolved in toluene (500 mL) at room temperature. Pyrrolidine (51.5 mL, 628 mmol) was added at 0 °C and the reaction mixture was allowed to stir at 120 °C for 5 h. The reaction mixture was concentrated in vacuo to get orange sticky residue. The residue was re-dissolved in acetonitrile (500 mL). 1-bromo-3-(bromomethyl)benzene (37.36 g, 151 mmol) and tetrabutylammonium iodide (18.54 g, 50 mmol) were added at 0 °C and reaction mixture was allowed to stir at 80 °C for 3 h. The reaction mixture was concentrated under vacuo to afford crude compound which was purified by normal phase gradient column chromatography (normal phase, silica), the product eluted at 0% to 8% EtOAc in Hexane to afford the title compound (35.50 g, 38% yield) as a yellow sticky solid. LCMS (method F) m/z 268 (ES+, M-Boc) at 2.497 min Step 2: tert-butyl 3-amino-2-(3-bromobenzyl)piperidine-1-carboxylate_cis racemic

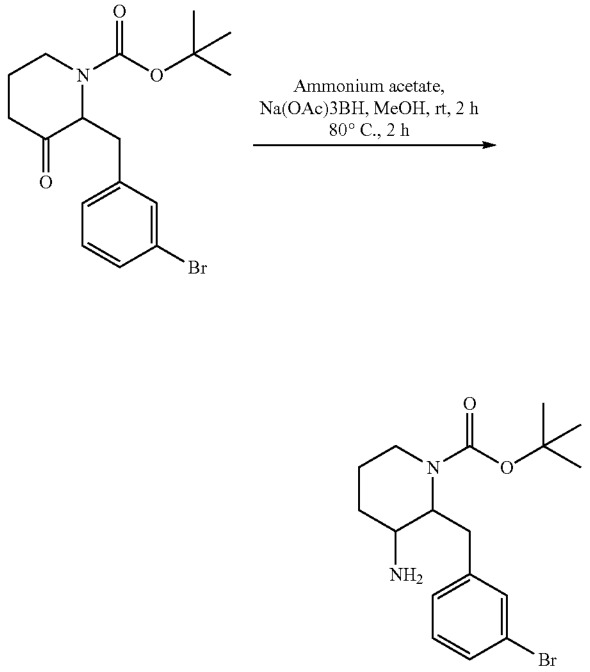

tert-butyl 2-(3-bromobenzyl)-3-oxopiperidine-1-carboxylate (33.3 g, 91 mmol) was dissolved in methanol (600 mL). Ammonium acetate (209.6 g, 2722 mmol) was added at room temperature and the reaction mixture was stirred at room temperature for 5 h. Then, Sodium triacetoxyborohydride (38.45 g, 181 mmol) was added at 0 °C and the reaction mixture stirred at 80 °C for 2 h. The reaction mixture was concentrated under vacuo. The reaction mixture was then diluted with saturated aqueous $NaHCO_3$ solution (600 mL) and extracted with EtOAc (300 mL). The aqueous layer was further extracted with EtOAc (3×100 mL). The organic layers were combined and dried ($Na_2SO_4$). Crude product was purified by normal phase gradient column chromatography (normal phase, Silica gel), product eluted at 0% to 10% MeOH in dichloromethane to afford the title compound (16.6 g, 50% yield) as yellow sticky solid. LCMS (method F) m/z 313 (ES+, M-$^t$Bu), at 1.59 min Step 3: tert-butyl 2-(3-bromobenzyl)-3-(methylsulfonamido)piperidine-1-carboxylate_cis racemic (Intermediate 3)

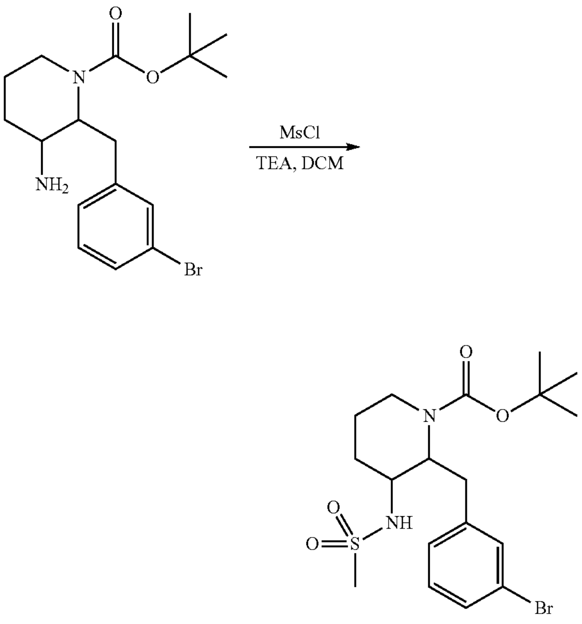

To a solution of tert-butyl 3-amino-2-(3-bromobenzyl)piperidine-1-carboxylate_cis racemic (12.9 g, 35 mmol) and $Et_3N$ (9.74 mL, 70 mmol) in dichloromethane (175 mL) cooled to <5 °C was added methanesulfonyl chloride (3.24 mL, 42 mmol) and the reaction stirred at room temperature for 1 h. The reaction was washed with sat. $NaHCO_3$, washed with brine, the organic layer separated, dried over $MgSO_4$, filtered and concentrated in vacuo to afford the title compound (15 g, 95% yield) as a yellow solid. LCMS (method B) m/z 347 (ES+, M-Boc) at 1.46 min Synthesis of Intermediate 4 tert-butyl 2-((2'-hydroxy-[1,1'-biphenyl]-3-yl)methyl)-3-(methylsulfonamido)-piperidine-1-carboxylate_cis racemic (Intermediate 4)

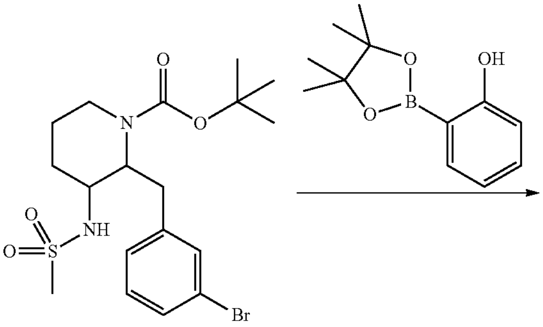

-continued

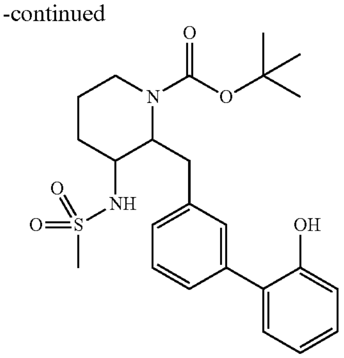

To a solution of tert-butyl 2-(3-bromobenzyl)-3-(methylsulfonamido)piperidine-1-carboxylate_cis racemic (Intermediate 3) (2.0 g, 4.47 mmol), 2-hydroxybenzeneboronic acid, pinacol ester (1.08 g, 4.92 mmol) and XPhos-Pd-G3 (189 mg, 0.22 mmol) in THF (45 mL) was added tripotassium phosphate 1M solution (18 mL, 18 mmol) and the reaction heated at 70 °C for 1 h. The reaction was washed with sat. $NaHCO_3$ and brine, the organic layer separated, dried over $MgSO_4$, filtered and concentrated in vacuo. The resulting oil was purified by flash column chromatography on Biotage Isolera 50 g silica cartridge eluting with 0%-100% Ethyl acetate/isohexane to afford the title compound (2.4 g, 93% yield) as a light brown gum. LCMS (method B) m/z 461 (ES+, M+H) at 1.41 min.

Synthesis of Intermediate 5 tert-butyl 3-(methylsulfonamido)-2-((2'-(((trifluoromethyl)sulfonyl)oxy)-[1,1'-biphenyl]-3-yl)methyl) piperidine-1-carboxylate_cis racemic (Intermediate 5)

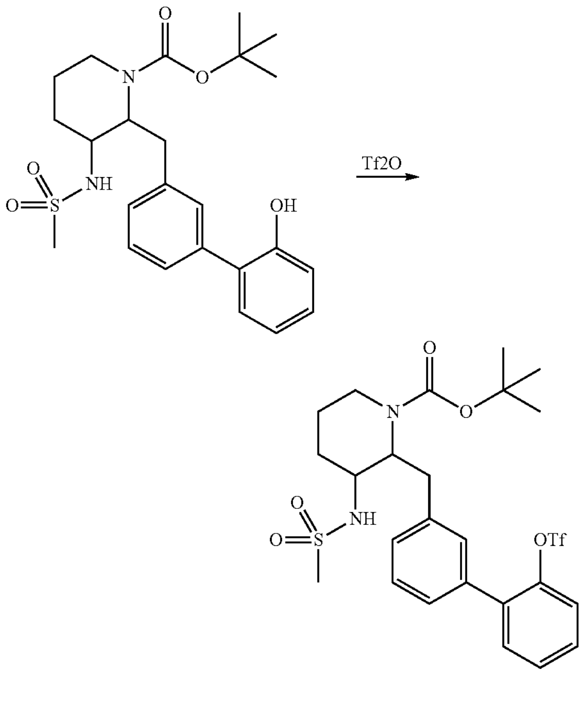

To a solution of tert-butyl 2-((2'-hydroxy-[1,1'-biphenyl]-3-yl)methyl)-3-(methylsulfonamido)piperidine-1-carboxylate_cis racemic (1.0 g, 2.17 mmol) in dichloromethane (43 mL) at 0 °C was added $Et_3N$ (920 μL, 6.5 mmol) and trifluoromethanesulfonic anhydride (560 μL, 3.3 mmol) and the reaction stirred at room temperature for 1 h. The reaction was concentrated in vacuo to afford the title compound (1.28 g, 99% yield) as a brown gum which was taken on crude. LCMS (method B) m/z 593 (ES+, M+H) at 1.80 min Example 1. Synthesis of Compound No. A1-13

Step 1: N-(2-(3-bromobenzyl)pyrrolidin-3-yl)methanesulfonamide_cis racemic (Intermediate 6)

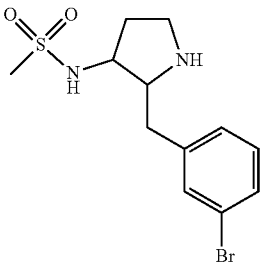 [SMILES: CS(=O)(=O)NC1CCNC1Cc1cccc(Br)c1]

A solution of tert-butyl 2-(3-bromobenzyl)-3-(methylsulfonamido)pyrrolidine-1-carboxylate_cis racemic (Intermediate 1) (130 mg, 0.30 mmol) in 4 M HCl/dioxane (1.12 mL, 4.50 mmol) was stirred at room temperature for 30 min. The solvent was evaporated and the residue dissolved in dichloromethane (15 mL)/water (8 mL), pH was adjusted to ~10 with 1 M NaOH and product extracted with dichloromethane (3×10 mL). Organic layers were combined, dried over $Na_2SO_4$, and evaporated to afford 100 mg of the title compound. LC-MS (method A) (ESI+): 333 [M+H].

Step 2: N-(2-(3-bromobenzyl)-1-(3-vinylazetidine-1-carbonyl)pyrrolidin-3-yl)methanesulfonamide_cis racemic

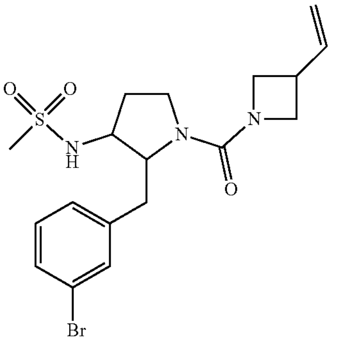 [SMILES: C=CC1CN(C(=O)N2CCC(NS(C)(=O)=O)C2Cc2cccc(Br)c2)C1]

To a solution of triphosgene (33 mg, 0.111 mmol) in dichloromethane (2.0 mL) at 0 °C, a mixture of 3-vinylazetidine×TFA (59 mg, 0.30 mmol) and N,N-diisopropylethylamine (116 mg, 0.90 mmol) in 1.0 mL dichloromethane was added dropwise. After 20 min, a second mixture containing N-(2-(3-bromobenzyl)pyrrolidin-3-yl)methanesulfonamide_cis racemic, Intermediate 6 (100 mg, 0.30 mmol) and N,N-diisopropylethylamine (116 mg, 0.90 mmol) in dichloromethane (2.0 mL) was added in one portion. The reaction mixture was stirred at room temperature for 17 h. The reaction mixture was washed with sat. aq. $NaHCO_3$ (25 mL), the organic layer was dried over $Na_2SO_4$, and evaporated to afford 140 mg of the title compound. LC-MS (method A) (ESI+): 442 [M+H].

Step 3: N-(2-((2'-vinyl-[1,1'-biphenyl]-3-yl)methyl)-1-(3-vinylazetidine-1-carbonyl)pyrrolidin-3-yl)methanesulfonamide_cis racemic

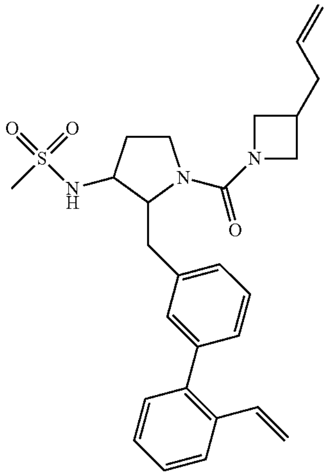 [SMILES: C=CCC1CN(C(=O)N2CCC(NS(C)(=O)=O)C2Cc2cccc(-c3ccccc3C=C)c2)C1]

To a solution of N-(2-(3-bromobenzyl)-1-(3-vinylazetidine-1-carbonyl)pyrrolidin-3-yl)methanesulfonamide_cis racemic (133 mg, 0.30 mmol) in THF/water (2:1, 6 ml), (2-vinylphenyl)boronic acid (49 mg, 0.33 mmol), XPhos G3 (25 mg, 0.03 mmol) and $K_3PO_4$ (191 mg, 0.9 mmol) were added and reaction mixture was heated at 80 °C for 1 h. Reaction mixture was diluted with water (20 mL), extracted with ethyl acetate (100 mL), dried over $Na_2SO_4$, and evaporated. The residue was purified using Interchim PuriFlash (4 g column, 15 μm, 15 mL/min, 0-100% dichloromethane/MeOH/$NH_{3=90/9/1.5}$ in dichloromethane) to afford 50 mg of the title compound. LC-MS (method A) (ESI+): 466 [M+H].

Step 4: N-(5-oxo-4(2,1)-pyrrolidina-6(1,3)-azetidina-1(1,2),2(1,3)-dibenzenacyclo-octaphan-7-en-$4^3$-yl)methanesulfonamide_cis racemic

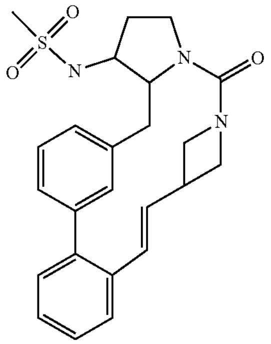 [SMILES: CS(=O)(=O)NC1CCN2C(=O)N3CC(/C=C/c4ccccc4-c4cccc(c4)CC12)C3]

To a solution of N-(2-((2'-vinyl-[1,1'-biphenyl]-3-yl)methyl)-1-(3-vinylazetidine-1-carbonyl)pyrrolidin-3-yl)methanesulfonamide_cis racemic (50.0 mg, 0.11 mmol) in dichloromethane (50 ml), Grubbs catalyst 2nd generation (18 mg, 0.022 mmol) was added and reaction mixture was stirred at 40 °C for 1 h. The solvent was evaporated and the residue was purified using Interchim PuriFlash (4 g column, 15 μm, 15 mL/min, 0-100% dichloromethane/MeOH/$NH_{3=90/9/1.5}$ in dichloromethane) to afford 45 mg of the title compound. LC-MS (method A) (ESI+): 438 [M+H].

Step 5: N-(5-oxo-4-(2,1)-pyrrolidina-6-(1,3)-azetidina-1-(1,2),2-(1,3)-dibenzena-cyclooctaphane-$4^3$-yl)methanesulfonamide_cis racemic (Compound No. A1-13)

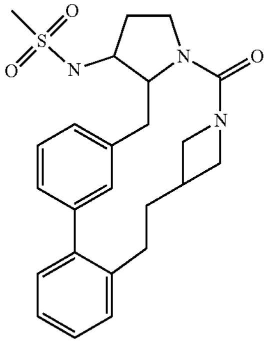 [SMILES: CS(=O)(=O)NC1CCN2C(=O)N3CC(CCc4ccccc4-c4cccc(c4)CC12)C3]

To suspension of N-(5-oxo-4(2,1)-pyrrolidina-6-(1,3)-azetidina-1-(1,2),2-(1,3)-dibenzenacyclooctaphan-7-en-$4^3$-yl)methanesulfonamide_cis racemic (45.0 mg, 0.10 mmol) in MeOH (15 mL), ammonium formate (45 mg, 0.72 mmol) and Pd/C (10.0%, 55 mg, 0.051 mmol) were added. Reaction mixture was heated in a microwave reactor at 70 °C for 10 min. The reaction mixture was filtrated and solvent evaporated. The residue was purified using Interchim PuriFlash (4 g column, 15 μm 10 mL/min, 0-100% dichloromethane/MeOH/$NH_{3=90/5/0.5}$ in dichloromethane) to afford 12 mg of the title compound. $^1H$ NMR (500 MHz, $CDCl_3$-d) δ ppm: 7.36-7.44 (m), 7.29-7.33 (m), 7.20-7.26 (m), 7.11 (d), 7.04 (br s), 4.62-4.88 (m), 3.99 (dq), 3.90 (t), 3.63 (d), 3.27-3.38 (m), 3.13-3.24 (m), 3.08 (s), 3.06 (d), 2.79-2.92 (m), 2.59-2.76 (m), 2.31-2.47 (m), 2.01 (dd), 1.89-1.96 (m), 1.44 (q), 1.26 (br s). LCMS (method A): m/z 440 $(M+H)^+$ (ES+)

Example 2. Synthesis of Compound No. A1-14

Step 1: N-(1-(3-allylazetidine-1-carbonyl)-2-(3-bromobenzyl)pyrrolidin-3-yl)methanesulfonamide_cis racemic

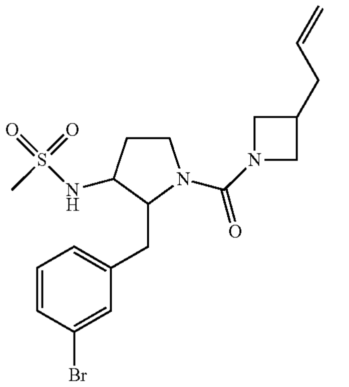 [SMILES: C=CCC1CN(C(=O)N2CCC(NS(C)(=O)=O)C2Cc2cccc(Br)c2)C1]

To a solution of triphosgene (25.0 mg, 0.084 mmol) in dichloromethane (2.0 mL) at 0 °C, a mixture of 3-allylazetidine TFA salt (48 mg, 0.228 mmol) and N,N-diisopropylethylamine (88 mg, 0.684 mmol) in 1.0 mL dichloromethane was added dropwise. After 20 min, a second mixture containing N-(2-(3-bromobenzyl)pyrrolidin-3-yl)methanesulfonamide_cis racemic, Intermediate 6 (76.0 mg, 0.228 mmol) and N,N-diisopropylethylamine (88 mg, 0.684 mmol) in dichloromethane (2.0 mL) was added in one portion. The reaction mixture was stirred at rt for 4 h. Reaction mixture was washed with sat. aq. $NaHCO_3$ (25 mL), organic layer was dried over $Na_2SO_4$, and evaporated to afford 100 mg of the title compound. LC-MS (method A) (ESI+): 456 [M+H].

Step 2: N-(1-(3-allylazetidine-1-carbonyl)-2-((2'-vinyl-[1,1'-biphenyl]-3-yl)methyl)pyrrolidin-3-yl) methanesulfonamide_cis racemic

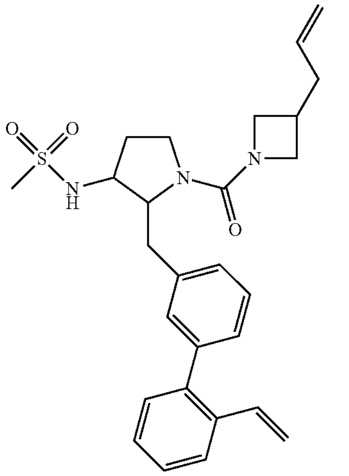 [SMILES: C=CCC1CN(C(=O)N2CCC(NS(C)(=O)=O)C2Cc2cccc(-c3ccccc3C=C)c2)C1]

To a solution of N-(1-(3-allylazetidine-1-carbonyl)-2-(3-bromobenzyl)pyrrolidin-3-yl)methanesulfonamide_cis racemic (100 mg, 0.22 mmol) in THF/water (2:1, 6.0 mL), (2-vinylphenyl)boronic acid (36 mg, 0.24 mmol), XPhos G3 (19 mg, 0.022 mmol) and $K_3PO_4$ (93 mg, 0.44 mmol) were added and reaction mixture was heated at 80 °C for 3 h. The reaction mixture was diluted with water (20 mL), extracted with ethyl acetate (100 mL), dried over $Na_2SO_4$, and evaporated. The residue was purified using Interchim PuriFlash (12 g column, 15 μm, 0-100% dichloromethane/MeOH/$NH_{3=90/9/1.5}$ in dichloromethane) to afford 70 mg of the title compound. LC-MS (method A) (ESI+): 480 [M+H].

Step 3: N-(5-oxo-4(2,1)-pyrrolidina-6(1,3)-azetidina-1(1,2),2(1,3)-dibenzenacyclo-nonaphan-8-en-4[3]-yl)methanesulfonamide_cis racemic

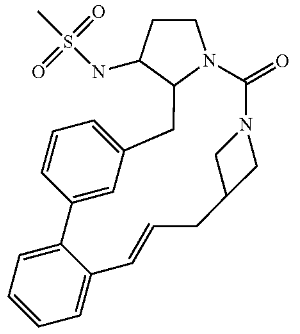 [SMILES: CS(=O)(=O)NC1CCN2C(=O)N3CC(C/C=C/c4ccccc4-c4cccc(c4)CC12)C3]

To a solution of N-(1-(3-allylazetidine-1-carbonyl)-2-((2'-vinyl-[1,1'-biphenyl]-3-yl)methyl)pyrrolidin-3-yl)methanesulfonamide_cis racemic (70.0 mg, 0.146 mmol) in dichloromethane (50 mL), Grubbs catalyst 2nd generation (25 mg, 0.029 mmol) was added and reaction mixture was stirred at 40 °C for 1 h. The solvent was evaporated. The residue was purified using Interchim PuriFlash (4 g column, 15 μm, 0-100% dichloromethane/MeOH/$NH_{3=90/5/0.5}$ in dichloromethane) to afford 28 mg of the title compound. LC-MS (method A) (ESI+): 452 [M+H].

Step 4: N-(5-oxo-4(2,1)-pyrrolidina-6(1,3)-azetidina-1(1,2),2(1,3)-dibenzenacyclo-nonaphane-4[3]-yl)methanesulfonamide_cis racemic (Compound No. A1-14)

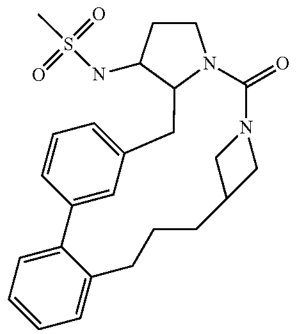 [SMILES: CS(=O)(=O)NC1CCN2C(=O)N3CC(CCCc4ccccc4-c4cccc(c4)CC12)C3]

To suspension of N-(5-oxo-4(2,1)-pyrrolidina-6(1,3)-azetidina-1(1,2),2(1,3)-dibenzenacyclononaphan-8-en-43-yl) methanesulfonamide_cis racemic (18.0 mg, 0.040 mmol) in MeOH (10 mL), ammonium formate (18 mg, 0.28 mmol) and Pd/C (10.0%, 21 mg, 0.02 mmol) were added. The reaction mixture was heated in a microwave reactor at 70 °C for 10 min. Reaction mixture was filtrated and solvent evaporated. The residue was purified using Interchim PuriFlash (4 g column, 15 μm, 0-100% dichloromethane/MeOH/$NH_{3=90/5/0.5}$ in dichloromethane) to afford 9 mg of the title compound. $^1$H NMR (500 MHz, $CDCl_3$-d) δ ppm 7.32-7.39 (m, 1H), 7.21-7.31 (m, 6H), 7.17 (br d, 1H), 7.01 (br s, 1H), 4.74 (br s, 1H), 4.67 (br d, 1H), 3.82-3.97 (m, 2H), 3.64 (br s, 1H), 3.52-3.61 (m, 1H), 3.23-3.37 (m, 3H), 3.07 (s, 3H), 3.03 (br dd, 1H), 2.94 (br s, 1H), 2.32-2.52 (m, 4H), 1.96 (q, 1H), 1.31-1.46 (m, 2H), 0.99-1.14 (m, 2H). LCMS (method A): m/z 454 $(M+H)^+$ (ES+).

Example 3. Synthesis of Compound No. A1-18

Step 1: N-(2-(3-bromobenzyl)pyrrolidin-3-yl)ethanesulfonamide_cis racemic

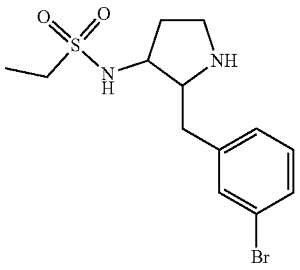 [SMILES: CCS(=O)(=O)NC1CCNC1Cc1cccc(Br)c1]

A solution of tert-butyl 2-(3-bromobenzyl)-3-(ethylsulfonamido)pyrrolidine-1-carboxylate_cis racemic, Intermediate 2 (2.52 g, 5.63 mmol) in 4M HCl/dioxane (14.1 mL, 56.3 mmol) was stirred at room temperature for 30 min. Solvent was evaporated, residue dissolved in dissolved in water (40 mL) and extracted with ethyl acetate (25 mL). The pH of the water fraction was adjusted to ~10 and product extracted with dichloromethane (3×75 mL). Organic layers were combined, dried over $Na_2SO_4$, and evaporated to afford 1.35 g of the title compound. LC-MS (method A) (ESI+): 346 [M+H].

Step 2: N-(2-((2'-vinyl-[1,1'-biphenyl]-3-yl)methyl)pyrrolidin-3-yl)ethane-sulfonamide cis racemic

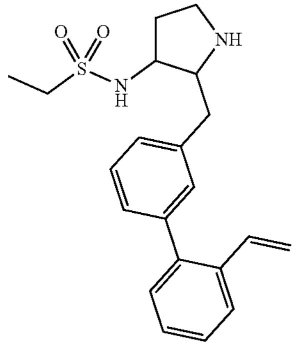 [SMILES: C=Cc1ccccc1-c1cccc(CC2NCCC2NS(=O)(=O)CC)c1]

To a solution of N-(2-(3-bromobenzyl)pyrrolidin-3-yl)ethanesulfonamide_cis racemic (500 mg, 1.44 mmol) in THF/water (2:1, 9.0 mL), (2-vinylphenyl)boronic acid (213 mg, 1.44 mmol), XPhos G3 (122 mg, 0.144 mmol) and $K_3PO_4$ (611 mg, 2.88 mmol) were added and reaction mixture was heated at 80 °C for 3 h. Reaction mixture was diluted with water (20 mL), extracted with ethyl acetate (100 mL), dried over $Na_2SO_4$, and evaporated. The residue was purified using Interchim PuriFlash (12 g column, 15 μm, 0-100% dichloromethane/MeOH/$NH_{3=90/9/1.5}$ in dichloromethane) to afford 356 mg of the title compound. LC-MS (method A) (ESI+): 371 [M+H].

Step 3: 3-(ethylsulfonamido)-N-methyl-N-(pent-4-en-1-yl)-2-((2'-vinyl-[1,1'-biphenyl]-3-yl)methyl)pyrrolidine-1-carboxamide_cis racemic

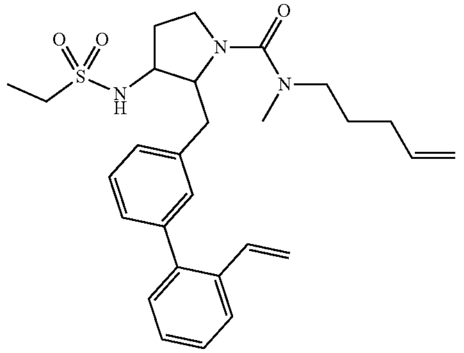 [SMILES: C=CCCCN(C)C(=O)N1CCC(NS(=O)(=O)CC)C1Cc1cccc(-c2ccccc2C=C)c1]

To a solution of triphosgene (105 mg, 0.356 mmol) in dichloromethane (5.0 mL) at 0 °C, a mixture of N-(2-((2'-vinyl-[1,1'-biphenyl]-3-yl)methyl)pyrrolidin-3-yl)ethanesulfonamide_cis racemic (356 mg, 0.961 mmol) and N,N-diisopropylethylamine (137 mg, 1.06 mmol) in 2.0 mL dichloromethane was added dropwise. After 20 min, a second mixture containing N-methylpent-4-en-1-amine×HCl (130 mg, 0.961 mmol) and N,N-diisopropylethylamine (137 mg, 1.06 mmol) in dichloromethane (5.0 mL) was added in one portion. The reaction mixture was stirred at room temperature for 17 h. The reaction mixture was washed with sat. aq. $NaHCO_3$ (25 mL), organic layer was dried over $Na_2SO_4$, and evaporated. The residue was purified using Interchim PuriFlash (4 g column, 15 μm, 0-50% dichloromethane/MeOH/$NH_{3=90/9/0.5}$ in dichloromethane) to afford 84 mg of the title compound. LC-MS (method A) (ESI+): 496 [M+H].

Step 4: N-(6-methyl-5-oxo-6-aza-4(2,1)-pyrrolidina-1(1,2),2(1,3)-dibenzena-cycloundecaphan-10-en-43-yl)ethanesulfonamide_cis racemic

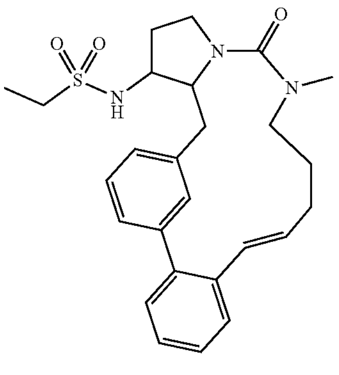 [SMILES: CCS(=O)(=O)NC1CCN2C(=O)N(C)CCC/C=C/c3ccccc3-c3cccc(c3)CC12]

To a solution of 3-(ethylsulfonamido)-N-methyl-N-(pent-4-en-1-yl)-2-((2'-vinyl-[1,1'-biphenyl]-3-yl)methyl)pyrrolidine-1-carboxamide_cis racemic (84.0 mg, 0.169 mmol) in dichloromethane (40 mL), Grubbs catalyst 2nd generation (28.8 mg, 0.034 mmol) was added and reaction mixture was stirred at 40 °C for 2 h. The solvent was evaporated and the residue was purified using Interchim PuriFlash (4 g column, 15 μm, 0-100% dichloromethane/MeOH/$NH_3$=90/9/1.5 in dichloromethane) to afford 47 mg of the title compound. LC-MS (method A) (ESI+): 468 [M+H].

Step 5: N-(6-methyl-5-oxo-6-aza-4(2,1)-pyrrolidina-1(1,2),2(1,3)-dibenzenacyclo-undecaphane-43-yl) ethanesulfonamide_cis racemic (Compound No. A1-18)

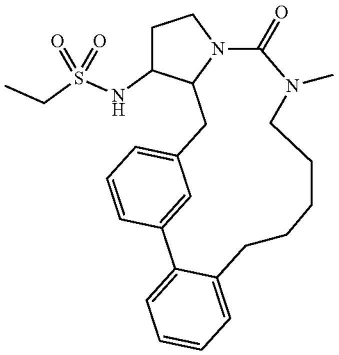 [SMILES: CCS(=O)(=O)NC1CCN2C(=O)N(C)CCCCCc3ccccc3-c3cccc(c3)CC12]

To suspension of N-(6-methyl-5-oxo-6-aza-4(2,1)-pyrrolidina-1(1,2),2(1,3)-dibenzenacycloundecaphan-10-en-43-yl)ethanesulfonamide_cis racemic (46.0 mg, 0.098 mmol) in MeOH (15 mL), ammonium formate (43 mg, 0.69 mmol) and Pd/C (10.0%, 52 mg, 0.049 mmol) were added. The reaction mixture was heated in a microwave reactor at 70 °C for 10 min. The reaction mixture was filtrated and solvent evaporated. The residue was purified using Interchim PuriFlash (4 g column, 15 μm, 0-30% dichloromethane/MeOH/$NH_{3=90/5/0.5}$ in dichloromethane) to afford 31 mg of the title compound. $^1$H NMR (500 MHz, $CDCl_3$-d) δ ppm 7.27-7.35 (m, 4H), 7.23 (td, 1H), 7.17-7.20 (m, 1H), 7.13 (d, 1H), 7.02 (s, 1H), 4.90-4.96 (m, 1H), 4.38 (br d, 1H), 3.92-3.99 (m, 1H), 3.50 (td, 1H), 3.03-3.24 (m, 5H), 2.75-2.87 (m, 2H), 2.55-2.61 (m, 4H), 2.37-2.48 (m, 2H), 1.85-1.96 (m, 1H), 1.38-1.53 (m, 4H), 1.26 (s, 1H), 1.04-1.19 (m, 1H), 0.82-0.94 (m, 2H), 0.65-0.74 (m, 1H). LCMS (method A): m/z 470 $(M+H)^+$ (ES+).

Example 4. Synthesis of Compound No. A1-10

N-(($4^2$S,$4^3$S)-6-methyl-5-oxo-6-aza-4(2,1)-pyrrolidina-1(1,2),2(1,3)-dibenzena-cycloundecaphane-$4^3$-yl)ethanesulfonamide (Compound No. A1-10)

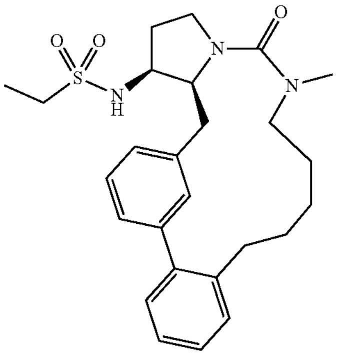 [SMILES: CCS(=O)(=O)N[C@H]1CCN2C(=O)N(C)CCCCCc3ccccc3-c3cccc(c3)C[C@@H]12]

N-(6-methyl-5-oxo-6-aza-4(2,1)-pyrrolidina-1(1,2),2(1,3)-dibenzenacyclo-undecaphane-43-yl)ethanesulfonamide_cis racemic (Example 3) resolved on the Sepiatec SFC Prep100 system using a Lux A1 column and isocratic conditions of $CO_2$:(IPA+0.2% $NH_3$) 70:30 to afford the title compound having the shorter retention time. LCMS (method C): m/z 470 $(M+H)^+$ (ES+) at 4.36 min.

Example 5. Synthesis of Compound No. A1-19

Step 1: methyl 4-(2-bromophenyl)butanoate

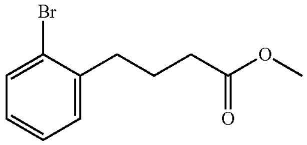

To a solution of AIBN (45 mg, 0.273 mmol) in DCE (10 mL), 1-bromo-2-vinyl-benzene (685 μL, 5.46 mmol), methyl 2-sulfanylacetate (733 μL, 8.19 mmol) and triethyl phosphite (1.12 mL, 6.56 mmol) were added. The tube was degassed with nitrogen for the whole time. The mixture was stirred at 80 °C overnight. The mixture was diluted with water and extracted twice with dichloromethane. The combined organic extracts were washed with brine, dried over $MgSO_4$, and evaporated. Crude was purified on Biotage purification system (40 g column, 15 μm, eluent: 0-50% of 6% EtOAC/cyhex) to afford 755 mg of the title compound. LC-MS (method A) (ESI+): 257 [M+H].

Step 2: methyl 4-(2-(4,4,5,5-tetramethyl-1,3,2-dioxaborolan-2-yl)phenyl)-butanoate

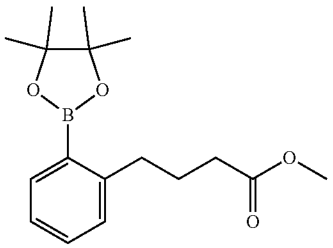

To a solution of methyl 4-(2-bromophenyl)butanoate (700 mg, 534 μL, 2.18 mmol), and bis(pinacolato)diboron (1.66 g, 6.54 mmol) in 1,4-dioxane (20 mL) potassium acetate (1.28 g, 13.06 mmol) was added. The reaction mixture was degassed with nitrogen for 10 min then $Pd(dppf)Cl_2$ (638 mg, 0.872 mmol) was added. The reaction was stirred at 80 °C overnight. The reaction was cooled to room temperature and filtered through a pad of celite and evaporated. The residue was dissolved in EtOAc (30 mL) and washed twice with brine (2×30 mL). The organic layer was dried over anhydrous $MgSO_4$ and evaporated. The crude product was purified on Biotage purification system (40 g column, 15 μm and pre-column, eluents: 0-50%, 5% MeOH/DCM) to afford 310 mg of the title compound. LC-MS (method A) (ESI+): 305 [M+H].

Step 3: tert-butyl 3-(ethylsulfonamido)-2-((2'-(4-methoxy-4-oxobutyl)-[1,1'-biphenyl]-3-yl)methyl)pyrrolidine-1-carboxylate_cis racemic

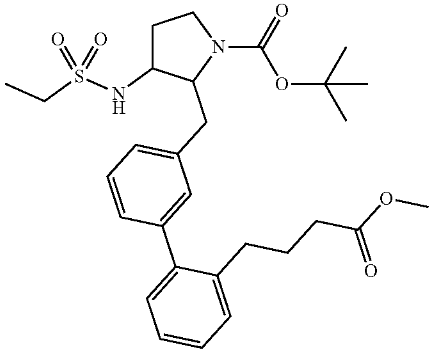 [SMILES: CCS(=O)(=O)NC1CCN(C(=O)OC(C)(C)C)C1Cc1cccc(-c2ccccc2CCCC(=O)OC)c1]

To a solution of tert-butyl 2-(3-bromobenzyl)-3-(ethylsulfonamido)pyrrolidine-1-carboxylate_cis racemic, Intermediate 2 (453 mg, 1.012 mmol) in THF (15 mL), methyl 4-[2-(4,4,5,5-tetramethyl-1,3,2-dioxaborolan-2-yl)phenyl]butanoate (310 mg, 1.02 mmol), $K_3PO_4$ (634 mg, 2.99 mmol), dissolved in water (5.0 mL) and Pd XPhos G3 (169 mg, 0.199 mmol) were added. The reaction mixture was sealed and stirred at 70 °C overnight. The reaction was cooled to room temperature and filtered through a pad of celite. The filtrate was evaporated and then dissolved in EtOAc (50 mL) and extracted with water (2×30 mL). The layers were separated and the organic layer was dried over $MgSO_4$ and evaporated. The crude product was purified on Biotage purification system (40 g column, 15 μm, eluents: 0-100%, 5% MeOH in dichloromethane) to afford 683 mg of the title compound. LC-MS (method A) (ESI−): 543 [M−H].

Step 4: methyl 4-(3'-((3-(ethylsulfonamido)pyrrolidin-2-yl)methyl)-[1,1'-biphenyl]-2-yl)butanoate hydrochloride_cis racemic

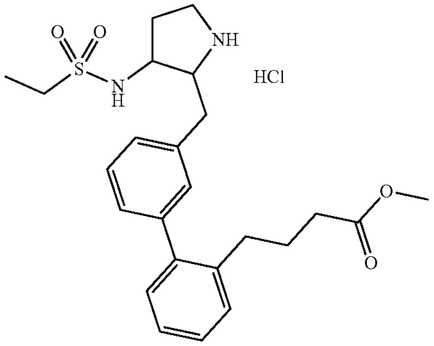 [SMILES: CCS(=O)(=O)NC1CCNC1Cc1cccc(-c2ccccc2CCCC(=O)OC)c1 ; Cl]

Tert-butyl 3-(ethylsulfonamido)-2-((2'-(4-methoxy-4-oxobutyl)-[1,1'-biphenyl]-3-yl)methyl)pyrrolidine-1-carboxylate_cis racemic (683 mg, 1.2 mmol) was dissolved in 4 M HCl in 1,4-dioxane (5 mL) and mixture was stirred at room temperature for 1 h. The solvent was evaporated to afford 630 mg of the title compound. LC-MS (method A) (ESI+): 445 [M+H].

Step 5: 4-(3'-((3-(ethylsulfonamido)pyrrolidin-2-yl)methyl)-[1,1'-biphenyl]-2-yl)butanoic acid_cis racemic

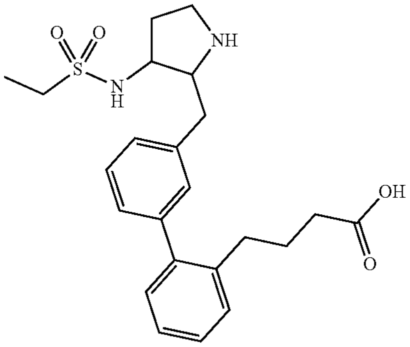 [SMILES: CCS(=O)(=O)NC1CCNC1Cc1cccc(-c2ccccc2CCCC(=O)O)c1]

Methyl 4-(3'-((3-(ethylsulfonamido)pyrrolidin-2-yl)methyl)-[1,1'-biphenyl]-2-yl)-butanoate hydrochloride_cis racemic (630 mg, 1.4 mmol) was dissolved in THF (5.0 mL). $LiOH·H_2O$ (595 mg, 14 mmol) was dissolved in water (1.0 mL) and added to the reaction mixture which was stirred at 40 °C overnight. The solvent was evaporated. The residue was diluted with water (10 mL) and neutralized with 2 M HCl to pH 7 before extracting with EtOAc. Layers were separated and organic layer was dried over anhydrous $MgSO_4$ and evaporated to dryness to afford 290 mg of the title compound. LC-MS (method A) (ESI+): 431 [M+H].

Step 6: N-(5-oxo-4(2,1)-pyrrolidina-1(1,2),2(1,3)-dibenzenacyclooctaphane-$4^3$-yl)ethanesulfonamide-_cis racemic (Compound No. A1-19)

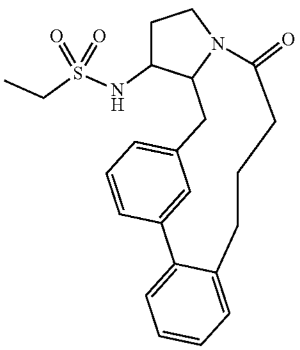 [SMILES: CCS(=O)(=O)NC1CCN2C(=O)CCCc3ccccc3-c3cccc(c3)CC12]

To a solution of N,N-diisopropylethylamine (230 μL, 1.3 mmol) and HATU (384 mg, 1.0 mmol) in DMF (60 mL), a solution of N,N-diisopropylethylamine (120 μL, 0.67 mmol) and 4-(3'-((3-(ethylsulfonamido)pyrrolidin-2-yl)methyl)-[1,1'-biphenyl]-2-yl)butanoic acid_cis racemic (290 mg, 0.67 mmol) in DMF (40 mL) was added dropwise over 30 min and stirred at room temperature for 2 h. The solvent was evaporated and the residue was dissolved in EtOAc, washed with $NaHCO_3$, brine and 5% solution of LiCl. The layers were separated and the organic layer was dried over $MgSO_4$ and evaporated. Crude was purified on Biotage purification system (12 g column, 15 μm, eluents: 0-50% of 5% MeOH/dichloromethane) to afford 53 mg of the title compound. $^1H$ NMR (400 MHz, $CDCl_3$): δ ppm 7.53 (d, 1H) 7.09-7.35 (m, 5H) 6.96 (d, 1H) 6.88 (s, 1H) 4.31-4.47 (m, 1H) 3.73 (br dd, 1H) 3.58-3.67 (m, 1H) 3.44-3.55 (m, 1H) 3.01-3.18 (m, 2H) 2.82 (dd, 1H) 2.24-2.35 (m, 3H) 2.14-2.23 (m, 1H) 1.89-2.12 (m, 2H) 1.72 (br d, 2H) 1.24 (t, 5H). LCMS (method A): m/z 413 $(M+H)^+$ (ES+).

Example 6. Synthesis of Compound No. A1-20

Step 1: tert-butyl 3-(ethylsulfonamido)-2-((2'-vinyl-[1,1'-biphenyl]-3-yl)methyl)-pyrrolidine-1-carboxylate_cis racemic

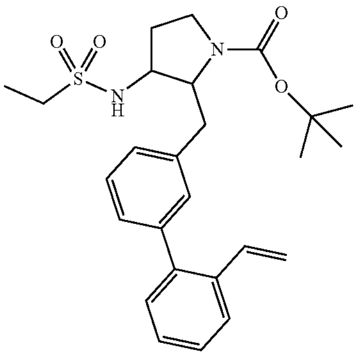 [SMILES: C=Cc1ccccc1-c1cccc(CC2C(NS(=O)(=O)CC)CCN2C(=O)OC(C)(C)C)c1]

To a solution of tert-butyl 2-(3-bromobenzyl)-3-(ethylsulfonamido)pyrrolidine-1-carboxylate_cis racemic, Intermediate 2 (966 mg, 2.16 mmol) in THF/water (10/5 mL), (2-vinylphenyl)boronic acid (335 mg, 2.27 mmol), XPhos G3 (183 mg, 0.216 mmol), and $K_3PO_4$ (917 mg, 4.32 mmol) were added and reaction mixture was heated and stirred at 70 °C for 2 h, then at room temperature overnight. The reaction mixture was diluted with ethyl acetate (150 mL), extracted with water (2×50 mL), dried over $Na_2SO_4$, and evaporated till dry to afford 1.5 g of crude product. The crude product was dry loaded and purified by chromatography on Interchim 520+(25 g column, eluents 0-7% dichloromethane-MeOH) to afford 238 mg of the title compound. LC-MS (method A) (ESI−): 469 [M−H]

Step 2: N-(2-((2'-vinyl-[1,1'-biphenyl]-3-yl)methyl)pyrrolidin-3-yl)ethane-sulfonamide hydrochloride-_cis racemic (Intermediate 7)

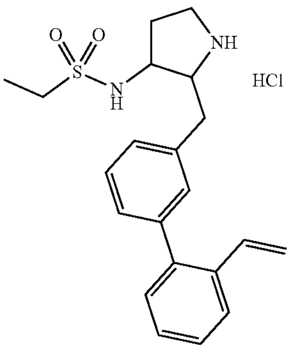 [SMILES: C=Cc1ccccc1-c1cccc(CC2NCCC2NS(=O)(=O)CC)c1 ; Cl]

Solution of tert-butyl 3-(ethylsulfonamido)-2-((2'-vinyl-[1,1'-biphenyl]-3-yl)methyl)-pyrrolidine-1-carboxylate_cis racemic (236 mg, 0.501 mmol) in 4M HCl/dioxane (1.25 mL, 5.01 mmol) was stirred at room temperature for 60 min. The solvent was evaporated to obtain 273 mg of title compound. LC-MS (method A) (ESI+): 371 [M+H]

Step 3: N-(1-(3-(allyloxy)propanoyl)-2-((2'-vinyl-[1,1'-biphenyl]-3-yl)methyl)-pyrrolidin-3-yl)ethanesulfonamide_cis racemic

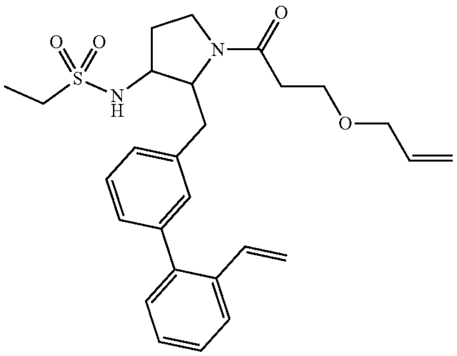 [SMILES: C=CCOCCC(=O)N1CCC(NS(=O)(=O)CC)C1Cc1cccc(-c2ccccc2C=C)c1]

To a solution of HATU (108 mg, 0.29 mmol) in DMF (1.8 mL), N,N-diisopropylethylamine (0.12 mL, 0.71 mmol) and 3-allyloxypropanoic acid (32 mg, 0.25 mmol) were added and the mixture stirred at room temperature for 10 min. A solution of N-(2-((2'-vinyl-[1,1'-biphenyl]-3-yl)methyl)pyrrolidin-3-yl)ethanesulfonamide hydrochloride_cis racemic, Intermediate 7 (88 mg, 0.24 mmol) in DMF (2.0 mL) was added dropwise and the reaction stirred at room temperature for 1 h. The reaction was evaporated and the crude product was purified by Interchim 520+(12 g column eluents 0-50% cyclohexane:EtOAc) to afford 68 mg of title compound. LC-MS (method A) (ESI+): 483 [M+H]

Step 4: N-(5-oxo-8-oxa-4(2,1)-pyrrolidina-1(1,2),2(1,3)-dibenzenacyclo-undecaphan-10-en-$4^3$-yl)ethanesulfonamide_cis racemic

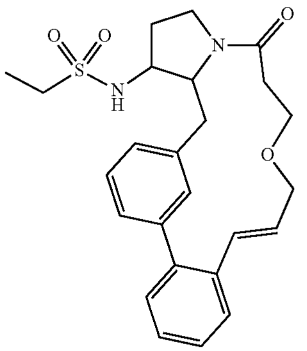 [SMILES: CCS(=O)(=O)NC1CCN2C(=O)CCOC/C=C/c3ccccc3-c3cccc(c3)CC12]

To a solution of N-(1-(3-(allyloxy)propanoyl)-2-((2'-vinyl-[1,1'-biphenyl]-3-yl)methyl)pyrrolidin-3-yl)ethanesulfonamide_cis racemic (68 mg, 0.141 mmol) in dichloromethane (15 ml), Grubbs catalyst II (25 mg, 0.028 mmol) was added and reaction mixture was stirred at 40 °C for 2 h. The solvent was evaporated and the crude product was purified by Interchim 520+(12 g column, eluents 0-100% dichloromethane/50% acetonitrile in dichloromethane) and repurified by Interchim 520+(4 g column, eluents 0-5% dichloromethane-MeOH) to afford 4.5 mg of title compound. LC-MS (method A) (ESI+): 455 [M+H]

Step 5: N-(5-oxo-8-oxa-4(2,1)-pyrrolidina-1(1,2),2(1,3)-dibenzenacyclo-undecaphane-$4^3$-yl)ethanesulfonamide_cis racemic (Compound No. A1-20)

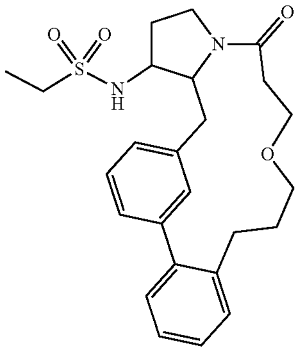 [SMILES: CCS(=O)(=O)NC1CCN2C(=O)CCOCCCc3ccccc3-c3cccc(c3)CC12]

Hydrogenation of N-(5-oxo-8-oxa-4-(2,1)-pyrrolidina-1-(1,2),2-(1,3)-dibenzenacyclo-undecaphan-10-en-43-yl) ethanesulfonamide_cis racemic (130 mg, 0.229 mmol) was performed in EtOH (25 mL) in presence of Pd/C (10% wt, 48.7 mg, 0.046 mmol) at 2.5 bar pressure for 5 h. The mixture was filtered, washed with methanol and evaporated. The crude product was purified on Biotage purification system (12 g column, 15 µm and pre-column, eluents: 0-30% of 20% acetonitrile in dichloromethane) to afford to afford 7.71 mg of the title compound. 1H NMR (500 MHz, $CDCl_3$): δ ppm 7.34-7.42 (m, 3H) 7.12-7.25 (m, 4H) 7.03-7.11 (m, 1H) 4.70 (br s, 1H) 4.35 (br d, 1H) 3.94 (br d, 1H) 3.78 (br d, 1H) 3.30-3.58 (m, 5H) 3.02-3.28 (m, 5H) 2.74 (br d, 2H) 2.47 (br d, 1H) 2.34 (br s, 1H) 2.02 (br dd, 2H) 1.81-1.97 (m, 1H) 1.43 (br d, 3H). LCMS (method A): m/z 457 $(M+H)^+$ (ES+)

Example 7. Synthesis of Compound No. A1-26

Step 1: methyl pent-4-ynoate

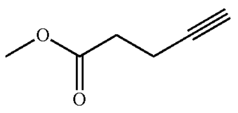

To a solution of pent-4-ynoic acid (3 g, 30.6 mmol) in dichloromethane (20 mL) and MeOH (4 mL), p-TsOH (263 mg, 1.53 mmol) was added. The reaction mixture was stirred at 50 °C overnight. The solvents were evaporated and residue was dissolved in dichloromethane and washed with sat. $NaHCO_3$ and extracted. The organic layer was dried over $MgSO_4$ and evaporated to afford 3.62 g of the title compound.

Step 2: methyl 5-(2-bromophenyl)pent-4-ynoate

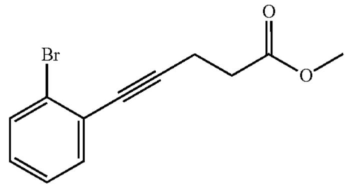

To a solution of 1-bromo-2-iodo-benzene (2.77 mL, 21.6 mmol), $Pd(PPh_3)_2Cl_2$ (682 mg, 0.972 mmol), CuI (370 mg, 1.94 mmol) in TEA (15 mL) was added methyl pent-4-ynoate (3.62 g, 32.3 mmol). The mixture was stirred at 50 °C overnight. The mixture was dissolved in EtOAc and filtered through a pad of celite. The filtrate was washed with 1 M HCl and then with brine. The organic layer was dried over $MgSO_4$ and evaporated. The crude was purified on Biotage purification system (40 g column, 15 µm, eluents: 0-100%, 30% EtOAc/cyclohexane) to afford 3.62 g of the title compound. LC-MS (method A) (ESI+): 267 [M+H].

Step 3: methyl 5-(2-(4,4,5,5-tetramethyl-1,3,2-dioxaborolan-2-yl)phenyl)pent-4-ynoate

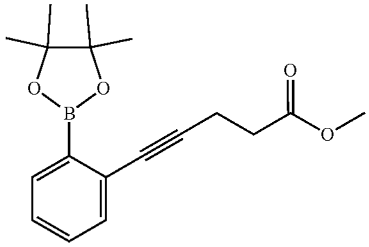

To a solution of methyl 5-(2-bromophenyl)pent-4-ynoate (1.5 g, 1.14 mL, 5.62 mmol), bis(pinacolato)diboron (1.78 g, 7.02 mmol) in 1,4-dioxane (18 mL), potassium acetate (1.79 g, 18.3 mmol) was added. The reaction mixture was degassed with nitrogen for 10 min when Pd(dppf)$Cl_2$ (822 mg, 1.12 mmol) was added. The reaction was stirred at 80 °C overnight before cooling to room temperature and filtering through a pad of celite and evaporating. The residue was dissolved in EtOAC (40 mL) and washed twice with brine (2×20 mL). The organic layer was dried over anhydrous $MgSO_4$ and evaporated. The crude product was purified on Biotage purification system (40 g column, 15 μm and pre-column, eluents: 0-100%, 30% EtOAc/cyclohexane) to afford 1.29 g of the title compound. LC-MS (method A) (ESI+): 315 [M+H].

Step 4: tert-butyl 3-(ethylsulfonamido)-2-((2'-(5-methoxy-5-oxopent-1-yn-1-yl)-[1,1'-biphenyl]-3-yl) methyl)pyrrolidine-1-carboxylate_cis racemic

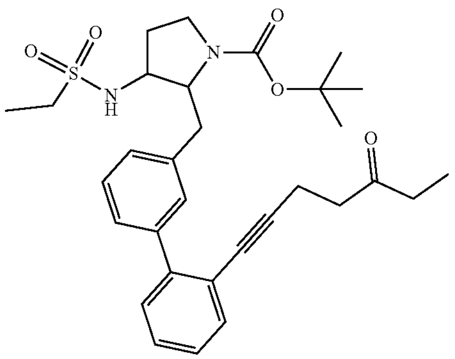 [SMILES: CCC(=O)CCC#Cc1ccccc1-c1cccc(CC2C(NS(=O)(=O)CC)CCN2C(=O)OC(C)(C)C)c1]

To a solution of tert-butyl 2-(3-bromobenzyl)-3-(ethylsulfonamido)pyrrolidine-1-carboxylate_cis racemic, Intermediate 2 (500 mg, 1.12 mmol) in THF (15 mL), methyl 5-[2-(4,4,5,5-tetramethyl-1,3,2-dioxaborolan-2-yl)phenyl] pent-4-ynoate (527 mg, 1.68 mmol), $K_3PO_4$ (712 mg, 3.35 mmol), dissolved in water (5 mL) and Pd XPhos G3 (189 mg, 0.224 mmol) were added. The reaction mixture was sealed and stirred at 70 °C for 3 h before cooling to room temperature, filtering through a pad of celite and evaporating. The residue was dissolved in EtOAc (50 mL) and extracted with water (2×30 mL). The organic layer was dried over $MgSO_4$ and evaporated. The crude was purified on Biotage purification system (25 g column, 15 μm, eluents: 0-100%, 5% MeOH in dichloromethane) to afford 640 mg of the title compound. LC-MS (method A) (ESI−): 553 [M−H].

Step 5: tert-butyl 3-(ethylsulfonamido)-2-((2'-(5-methoxy-5-oxopent-1-en-1-yl)-[1,1'-biphenyl]-3-yl) methyl)pyrrolidine-1-carboxylate_cis racemic

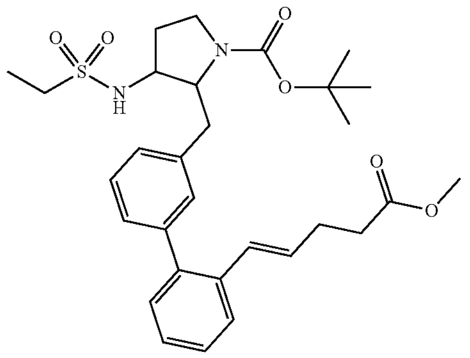 [SMILES: CCS(=O)(=O)NC1CCN(C(=O)OC(C)(C)C)C1Cc1cccc(-c2ccccc2/C=C/CCC(=O)OC)c1]

Hydrogenation of tert-butyl 3-(ethylsulfonamido)-2-((2'-(5-methoxy-5-oxopent-1-yn-1-yl)-[1,1'-biphenyl]-3-yl) methyl)pyrrolidine-1-carboxylate_cis racemic (640 mg, 1.10 mmol) was performed in EtOH (25 mL) in presence of Pd/C (10% wt, 233 mg, 0.219 mmol) at 4 bar pressure overnight. The reaction mixture was filtered, washed with EtOAc and evaporated. The crude product was purified on Biotage purification system (12 g column, 15 μm, eluents: 0-50% of 5% MeOH/dichloromethane) to afford 424 mg of the title compound. LC-MS (method A) (ESI−): 555 [M−H].

Step 6: methyl 5-(3'-((3-(ethylsulfonamido)pyrrolidin-2-yl)methyl)-[1,1'-biphenyl]-2-yl)pent-4-enoate hydrochloride_cis racemic

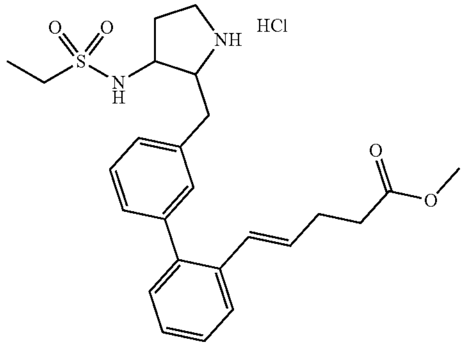 [SMILES: CCS(=O)(=O)NC1CCNC1Cc1cccc(-c2ccccc2/C=C/CCC(=O)OC)c1 ; Cl]

Tert-butyl 3-(ethylsulfonamido)-2-((2'-(5-methoxy-5-oxopent-1-yn-1-yl)-[1,1'-biphenyl]-3-yl)methyl)pyrrolidine-1-carboxylate_cis racemic (424 mg, 0.61 mmol) was dissolved in 4 M HCl in 1,4-dioxane (3 mL) and the mixture was stirred at room temperature for 1 h. Solvent was evaporated to afford 410 mg of the title compound. LC-MS (method A) (ESI−): 455 [M−H].

Step 7: 5-(3'-((3-(ethylsulfonamido)pyrrolidin-2-yl) methyl)-[1,1'-biphenyl]-2-yl)pent-4-enoic acid_cis racemic

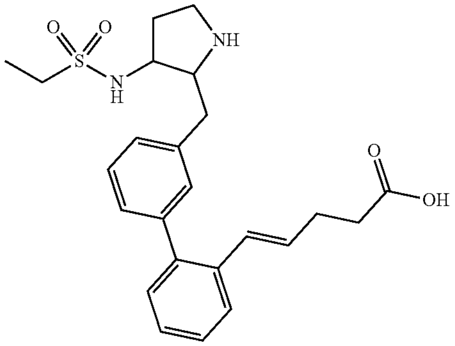 [SMILES: CCS(=O)(=O)NC1CCNC1Cc1cccc(-c2ccccc2/C=C/CCC(=O)O)c1]

Methyl 5-(3'-((3-(ethylsulfonamido)pyrrolidin-2-yl) methyl)-[1,1'-biphenyl]-2-yl)pent-4-enoate hydrochloride_ cis racemic (410 mg, 0.89 mmol) was dissolved in tetrahydrofuran (5 mL). LiOH·$H_2O$ (375 mg, 8.9 mmol) was dissolved in water (1.0 mL) and added to the reaction mixture which was stirred at room temperature for 2 h. The solvent was removed in vacuo and the residue diluted with water (10 mL) then neutralized with 2 M HCl to pH 7. After extraction with EtOAc, the layers were separated and the organic layer dried over anhydrous $MgSO_4$ and evaporated to afford 315 mg of the title compound. LC-MS (method A) (ESI−): 441 [M−H].

Step 8: (E/Z)—N-(5-oxo-4(2,1)-pyrrolidina-1(1,2),2 (1,3)-dibenzenacyclononaphan-8-en-4$^3$-yl)ethane-sulfonamide_cis racemic (Compound No. A1-26)

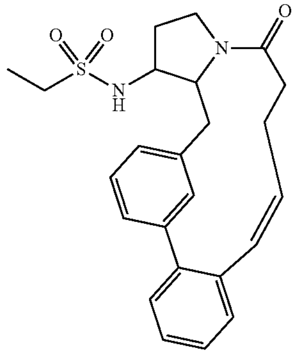 [SMILES: CCS(=O)(=O)NC1CCN2C(=O)CC/C=C\c3ccccc3-c3cccc(c3)CC12]

To a solution of N,N-diisopropylethylamine (0.250 mL, 1.4 mmol) and HATU (404 mg, 1.1 mmol) in DMF (60 mL), a solution of N,N-diisopropylethylamine (0.120 mL, 0.71 mmol) and 5-(3'-((3-(ethylsulfonamido)pyrrolidin-2-yl) methyl)-[1,1'-biphenyl]-2-yl)pent-4-enoic acid_cis racemic (315 mg, 0.71 mmol) in DMF (40 mL) was added dropwise over 30 min and stirred at room temperature for 4 h. The solvent was evaporated and residue was dissolved in EtOAc and washed with $NaHCO_3$, then with brine. The organic layer was dried over $MgSO_4$ and evaporated. The crude product was purified on Biotage purification system (4 g column, 15 μm, eluents: 0-50% of 20% acetonitrile/dichloromethane) to afford 30 mg of the title compound (E/Z alkene mixture). $^1$H NMR (500 MHz, $CDCl_3$): δ ppm 7.42-7.49 (m, 1H) 7.28-7.41 (m, 5H) 7.20 (br d, 1H) 7.14 (s, 1H) 6.24-6.36 (m, 1H) 6.11-6.23 (m, 1H) 4.68 (br d, 1H) 4.51 (br d, 1H) 3.95-4.08 (m, 1H) 3.43 (br d, 1H) 3.09-3.34 (m, 4) 2.98 (br dd, 1H) 2.84 (br dd, 1H) 2.57-2.70 (m, 1H) 2.17-2.40 (m, 3H) 1.76 (br t, 1H) 1.39-1.53 (m, 3H). LCMS (method A): m/z 425 $(M+H)^+$ (ES+)

Example 8. Synthesis of Compound No. A1-53

Step 1: 2-(2-allylphenyl)-4,4,5,5-tetramethyl-1,3,2-dioxaborolane

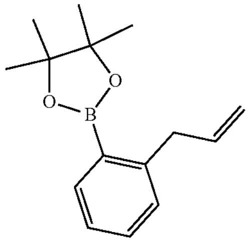 [SMILES: C=CCc1ccccc1B1OC(C)(C)C(C)(C)O1]

A solution of 1-allyl-2-bromo-benzene (500 mg, 2.54 mmol), bis(pinacolato)diboron (709 mg, 2.79 mmol), potassium acetate (822 mg, 8.37 mmol) and Pd(dppf)$Cl_2$ (186 mg, 0.254 mmol) in 1,4-dioxane (10 mL) was stirred at 80 °C for 3 h. The reaction mixture was filtered through a pad of celite, and the celite was washed with ethyl acetate. The combined filtrates were evaporated. The residue was dissolved in EtOAc (100 mL) and washed twice with water and brine (20 mL each). the organic layer was dried over anhydrous $Na_2SO_4$ and evaporated under reduced pressure. The crude product was dryloaded and purified on InterChim PuriFlash 520+(80 g column, eluents cyclohexane/EtOAc 0-10%) to afford 245 mg of the title compound.

Step 2: tert-butyl 2-((2'-allyl-[1,1'-biphenyl]-3-yl) methyl)-3-(ethylsulfonamido)-pyrrolidine-1-carboxylate_cis racemic

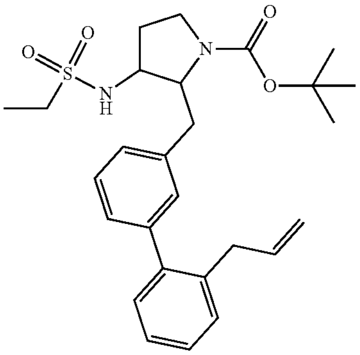 [SMILES: C=CCc1ccccc1-c1cccc(CC2C(NS(=O)(=O)CC)CCN2C(=O)OC(C)(C)C)c1]

To a solution of tert-butyl 2-(3-bromobenzyl)-3-(ethylsulfonamido)pyrrolidine-1-carboxylate_cis racemic, Intermediate 2 (910 mg, 2 mmol) in THF/water (10/5 mL), 2-(2-allylphenyl)-4,4,5,5-tetramethyl-1,3,2-dioxaborolane (521 mg, 2.14 mmol), XPhos Pd-G3 (172 mg, 0.203 mmol), and $K_3PO_4$ (864 mg, 4.07 mmol) were added and reaction mixture was heated and stirred at 70 °C for 3 h, then at room temperature overnight. The reaction was diluted with ethyl acetate (100 mL), washed with water (2×30 mL), dried over $Na_2SO_4$, and evaporated to afford crude product. The crude product was dryloaded and purified by chromatography on Interchim 520+(40 g column, eluents dichloromethane-MeOH 0-7%) to afford 1.08 g of the title compound. LC-MS (method A) (ESI−): 483 [M−H]

Step 3: N-(2-((2'-allyl-[1,1'-biphenyl]-3-yl)methyl)pyrrolidin-3-yl)ethane-sulfonamide_cis racemic (Intermediate 8)

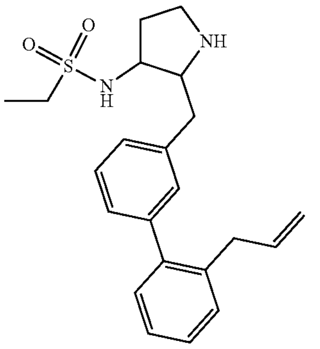 [SMILES: C=CCc1ccccc1-c1cccc(CC2NCCC2NS(=O)(=O)CC)c1]

A solution of tert-butyl 2-((2'-allyl-[1,1'-biphenyl]-3-yl)methyl)-3-(ethylsulfonamido)-pyrrolidine-1-carboxylate-_cis racemic (1.08 g, 1.87 mmol) in 4 M HCl/dioxane (4.68 mL, 18.7 mmol) was stirred at room temperature for 30 min. The solvent was evaporated, the residue dissolved in $NaHCO_3$ (20 ml) and extracted with dichloromethane (3×20 mL) and with 1 mL of isopropanol. The organic layer was dried over $Na_2SO_4$ and evaporated to afford 780 mg of the title compound. LC-MS (method A) (ESI+): 385 [M+H]

Step 4: N-(2-((2'-allyl-[1,1'-biphenyl]-3-yl)methyl)-1-(pent-4-enoyl)pyrrolidin-3-yl)ethanesulfonamide-_cis racemic

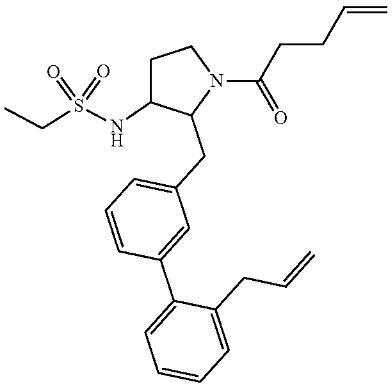 [SMILES: C=CCCC(=O)N1CCC(NS(=O)(=O)CC)C1Cc1cccc(-c2ccccc2CC=C)c1]

To a solution of N-(2-((2'-allyl-[1,1'-biphenyl]-3-yl)methyl)pyrrolidin-3-yl)ethanesulfonamide_cis racemic, Intermediate 8 (100 mg, 0.260 mmol) and pent-4-enoic acid (31 mg, 0.312 mmol) in DMF (2.0 mL), EDCI HCl (62 mg, 0.325 mmol), 1-hydroxybenzotriazole hydrate (50 mg, 0.325 mmol), and N,N-diisopropylethylamine (0.136 mL, 0.78 mmol) were added and reaction mixture was stirred at room temperature for 2 h. The solvent was evaporated and the residue purified by chromatography on Interchim 520+(4 g column, eluents 0-5% MeOH/dichloromethane) to afford 116 mg of the title compound. LC-MS (method A) (ESI+): 467 [M+H].

Step 5: (E/Z)—N-(5-oxo-4(2,1)-pyrrolidina-1(1,2),2(1,3)-dibenzenacyclodecaphan-8-en-4$^3$-yl)ethane-sulfonamide_cis racemic (Compound No. A1-53)

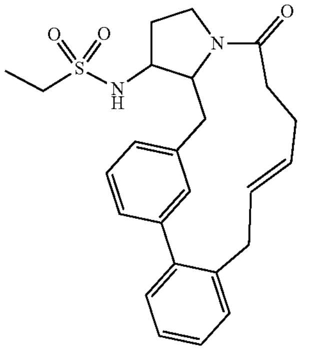 [SMILES: CCS(=O)(=O)NC1CCN2C(=O)CC/C=C/Cc3ccccc3-c3cccc(c3)CC12]

To a solution of N-(2-((2'-allyl-[1,1'-biphenyl]-3-yl)methyl)-1-(pent-4-enoyl)-pyrrolidin-3-yl)ethanesulfonamide_cis racemic (116 mg, 0.249 mmol) in dichloromethane (30 mL), Grubbs II (42 mg, 0.049 mmol) was added and reaction mixture was stirred at 40 °C for 2 h. Solvent was evaporated and the residue purified by chromatography on Interchim 520+(4 g column, eluents 0-5% MeOH/dichloromethane) to afford 35 mg of the title compound (E/Z alkene mixture). $^1$H NMR (500 MHz, $CDCl_3$). δ/ppm: 7.59 (s), 7.38 (t,), 7.29-7.35 (m), 7.22-7.26 (m), 7.18-7.21 (m), 7.13-7.17 (m), 6.86 (s), 5.81 (d), 5.14-5.21 (m), 4.86-4.93 (m), 4.67-4.72 (m), 4.58 (d), 4.54 (t), 4.35 (d), 4.27-4.32 (m), 3.88-3.96 (m), 3.75-3.81 (m), 3.38-3.55 (m), 3.24-3.30 (m), 3.08-3.18 (m), 2.60-2.72 (m), 2.41-2.53 (m), 2.26-2.37 (m), 2.16-2.22 (m), 2.05-2.10 (m), 1.95-2.00 (m), 1.84-1.92 (m), 1.65-1.70 (m), 1.44 (t), 1.42 (t), 1.25-1.28 (m), 1.09-1.19 (m). 1H NMR shows a mixture of double bond isomers (approx. ratio of 2:1). LCMS (method A): m/z 439 $(M+H)^+$ (ES+)

Example 9. Synthesis of Compound No. A1-48

Step 1: N-(5-oxo-4(2,1)-pyrrolidina-1(1,2),2(1,3)-dibenzenacyclodecaphane-4$^3$-yl)ethanesulfonamide-_cis racemic (Compound No. A1-48)

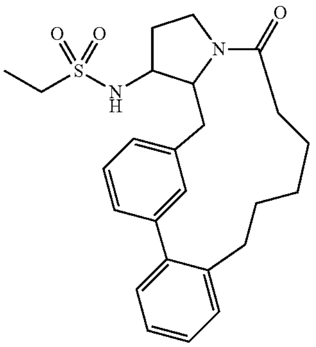 [SMILES: CCS(=O)(=O)NC1CCN2C(=O)CCCCCc3ccccc3-c3cccc(c3)CC12]

To a solution of (E/Z)—N-(5-oxo-4(2,1)-pyrrolidina-1(1,2),2(1,3)-dibenzenacyclo-decaphan-8-en-43-yl)ethanesulfonamide_cis racemic (21.0 mg, 0.048 mmol) in ethanol (30 mL), Pd/C (10.0%, 10 mg, 0.010 mmol) was added and reaction mixture was hydrogenated for 2 h (2 barr). The catalyst was filtered off, the solvent was evaporated, and the residue purified on Biotage purification system (4 g column, 15 μm, eluents: 0-2.5% of MeOH/dichloromethane) to afford 11 mg of the title compound. $^1$H NMR (600 MHz, $CDCl_3$). δ/ppm: 7.11-7.27 (m, 7H), 6.89 (d, 1H), 4.74 (d, 1H), 4.27-4.31 (m, 1H), 3.82-3.89 (m, 1H), 3.70-3.76 (m, 1H), 3.39 (t, 1H), 3.12 (dd, 1H), 3.06 (q, 2H), 2.55-2.61 (m, 1H), 2.36-2.44 (m, 2H), 2.27-2.34 (m, 1H), 1.89-1.97 (m, 1H), 1.51-1.55 (m, 1H), 1.39-1.47 (m, 1H), 1.35 (t, 3H), 1.26-1.36 (m, 2H), 1.17-1.22 (m, 1H), 1.04-1.11 (m, 1H), 0.90-0.96 (m, 1H), 0.55-0.62 (m, 1H). LCMS (method A): m/z 441 $(M+H)^+$ (ES+)

Examples 10 and 11. Synthesis of Compound Nos. A1-41 and A1-36

Step 1: N-(2-((2'-allyl-[1,1'-biphenyl]-3-yl)methyl)-1-(hex-5-enoyl)pyrrolidin-3-yl)ethanesulfonamide-_cis racemic

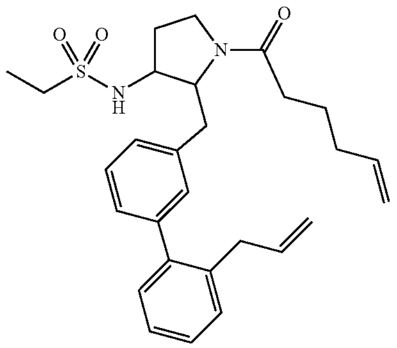 [SMILES: C=CCCCC(=O)N1CCC(NS(=O)(=O)CC)C1Cc1cccc(-c2ccccc2CC=C)c1]

To a solution of hex-5-enoic acid (81 μL, 0.718 mmol), EDCI HCl (143 mg, 0.748 mg), HOBt (101 mg, 0.748 mmol) and N,N-diisopropylethylamine (313 μL, 1.79 mmol) in dry DMF (2.0 mL), after 15 min N-(2-((2'-allyl-[1,1'-biphenyl]-3-yl)methyl)pyrrolidin-3-yl)ethanesulfonamide_cis racemic, Intermediate 8 (230 mg, 0.598 mmol) was added. Reaction mixture was stirred at room temperature for 2 h. Solvent was evaporated and crude was purified on Biotage purification system (4 g column, 15 μm, eluents 0-100%, 5% MeOH in dichloromethane) to afford 190 mg of the title compound. LC-MS (method A) (ESI+): 481 [M+H].

Step 2: (E/Z)—N-(5-oxo-4(2,1)-pyrrolidina-1(1,2),2(1,3)-dibenzenacyclo-undecaphan-9-en-4$^3$-yl)ethanesulfonamide_cis racemic (Example 10; Compound No. A1-41) and (E/Z)—N-(5-oxo-4(2,1)-pyrrolidina-1(1,2),2(1,3)-dibenzenacyclodecaphan-9-en-4$^3$-yl)ethanesulfonamide (Example 11; Compound No. A1-36)

Ex10

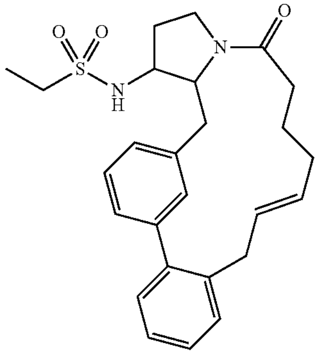

Ex11

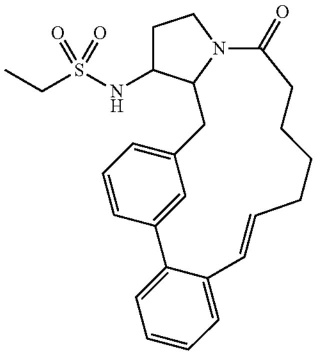

To a solution of N-(2-((2'-allyl-[1,1'-biphenyl]-3-yl)methyl)-1-(hex-5-enoyl)-pyrrolidin-3-yl)ethanesulfonamide_cis racemic (190 mg, 0.395 mmol) in dichloromethane (60 mL), Grubbs catalyst 2$^{nd}$ generation (67 mg, 0.079 mmol) was added. Reaction was stirred at 40 °C for 1 h. The solvent was evaporated and the crude product was purified on Biotage purification system (12 g column, 15 μm, eluents: 0-50% of 5% MeOH/dichloromethane) to afford 85 mg of product that was separated by preparative HPLC to afford 8 mg of the title compound (Compound No. A1-41, E/Z alkene mixture) and 8.5 mg of the title compound (Compound No. A1-36, E/Z alkene mixture).

Compound No. A1-41. $^1$H NMR (500 MHz, $CDCl_3$): δ/ppm: 7.38 (br d, 1H) 7.17-7.31 (m, 6H) 6.97 (br d, 1H) 5.07-5.22 (m, 1H) 4.86 (br d, 2H) 4.08-4.27 (m, 1H) 3.67-3.98 (m, 3H) 3.48 (t, 2H) 3.33 (br d, 1H) 3.09-3.21 (m, 2H) 2.97-3.07 (m, 2H) 2.39-2.52 (m, 1H) 2.27-2.38 (m, 1H) 2.05-2.17 (m, 1H) 1.89-2.04 (m, 1H) 1.65 (br s, 2H) 1.30-1.37 (m, 3H) 0.99-1.14 (m, 1H). LCMS (method A): m/z 453 $(M+H)^+$ (ES+).

Compound No. A1-36. $^1$H NMR (500 MHz, $CDCl_3$): δ/ppm: 7.21-7.36 (m, 6H) 7.13 (s, 1H) 7.04 (br d, 1H) 5.34-5.44 (m, 1H) 4.83 (br d, 1H) 4.26-4.38 (m, 1H) 3.86-3.97 (m, 1H) 3.79 (dt, 1H) 3.45 (br t, 1H) 3.07-3.18 (m, 3H) 2.24-2.46 (m, 4H) 1.73-2.03 (m, 4H) 1.30-1.45 (m, 5H). LCMS (method A): m/z 439 $(M+H)^+$ (ES+).

Example 12. Synthesis of Compound No. A1-39

Step 3: N-(5-oxo-4(2,1)-pyrrolidina-1(1,2),2(1,3)-dibenzenacycloundecaphane-4[3]-yl)ethanesulfonamide_cis racemic (Compound No. A1-39)

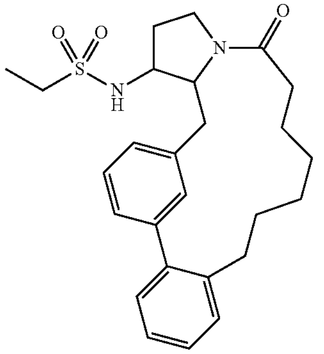 [SMILES: CCS(=O)(=O)NC1CCN2C(=O)CCCCCCc3ccccc3-c3cccc(c3)CC12]

Hydrogenation of (E/Z)—N-(5-oxo-4(2,1)-pyrrolidina-1-(1,2),2-(1,3)-dibenzenacyclo-undecaphan-9-en-43-yl)ethanesulfonamide_cis racemic (85 mg, 0.131 mmol) was performed in EtOH (15 mL) in presence of Pd/C (10% wt, 28 mg, 0.026 mmol) at 2 bar pressure for 2 h. The reaction mixture was filtered, washed with methanol, evaporated and the crude product was purified on Biotage purification system (4 g column, 15 μm, eluents: 0-50% of 5% MeOH/dichloromethane) to afford 15 mg of the title compound. $^1H$ NMR (300 MHz, $CDCl_3$): δ/ppm: 7.28 (br d, 3H) 7.12-7.24 (m, 5H) 7.03 (br d, 1H) 4.47 (d, 1H) 4.21-4.38 (m, 1H) 3.67-4.04 (m, 1H) 3.37-3.55 (m, 1H) 3.03-3.24 (m, 2H) 2.65-2.80 (m, 1H) 2.26-2.62 (m, 4H) 1.80-2.02 (m, 1H) 1.60-1.77 (m, 1H) 1.40 (t, 3H) 1.07-1.30 (m, 6H) 0.93-1.06 (m, 3H). LCMS (method A): m/z 455 $(M+H)^+$ (ES+)

Example 13. Synthesis of Compound No. A1-56

Step 1: but-3-en-1-yl 2-((2'-allyl-[1,1'-biphenyl]-3-yl)methyl)-3-(ethylsulfon-amido)pyrrolidine-1-carboxylate_cis racemic

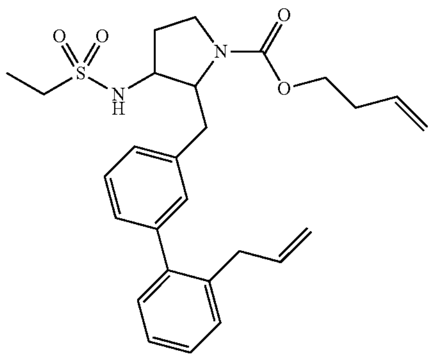 [SMILES: C=CCCOC(=O)N1CCC(NS(=O)(=O)CC)C1Cc1cccc(-c2ccccc2CC=C)c1]

To a solution of N-(2-((2'-allyl-[1,1'-biphenyl]-3-yl)methyl)pyrrolidin-3-yl)ethanesulfonamide_cis racemic, Intermediate 8 (100 mg, 0.208 mmol) in DMF (2.0 mL), DIPEA (109 μL, 0.624 mmol) and but-3-enyl p-tolyl carbonate (52 mg, 0.25 mmol) were added and reaction mixture was stirred on shaker at 100 °C for 1 h. The solvent was evaporated and the crude mixture was purified on Biotage purification system (4 g column, 15 μm and pre-column, eluents: 0-50% 5% MeOH in dichloromethane) to afford 120 mg of the title compound. LC-MS (method A) (ESI+): 483 [M+H].

Step 2: (E/Z)—N-(5-oxo-6-oxa-4(2,1)-pyrrolidina-1(1,2),2(1,3)-dibenzenacyclo-undecaphan-9-en-4[3]-yl)ethanesulfonamide_cis racemic (Compound No. A1-56)

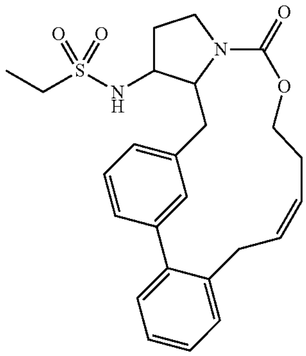 [SMILES: CCS(=O)(=O)NC1CCN2C(=O)OCC/C=C\Cc3ccccc3-c3cccc(c3)CC12]

To a solution of but-3-en-1-yl 2-((2'-allyl-[1,1'-biphenyl]-3-yl)methyl)-3-(ethylsulfonamido)pyrrolidine-1-carboxylate_cis racemic (120 mg, 0.224 mmol) in dichloromethane (5.0 mL), Grubbs catalyst $2^{nd}$ generation (38 mg, 0.0448 mmol) was added. The reaction was stirred at 40 °C for 2 h. The solvent was evaporated and the crude product was purified by chromatography on Interchim puriflash 430 (4 g column, 15 μm and pre-column, eluents 0-100% cyclohexane/EtOAc=1:1) to afford 38 mg of the title compound (E/Z alkene mixture). $^1H$ NMR (500 MHz, $CDCl_3$): δ/ppm: 7.66 (br. s, 1H) 7.28-7.40 (m, 6H) 7.24 (d, 2H) 7.14 (d, 1H) 5.70 (d, 1H) 5.15-5.27 (m, 1H) 4.29-4.48 (m, 3H) 4.25 (br. s, 1H) 3.99 (d, 2H) 3.51 (t, 1H) 3.21-3.46 (m, 3H) 2.87-2.98 (m, 1H) 2.75-2.87 (m, 1H) 2.62-2.73 (m, 1H) 2.47-2.62 (m, 1H) 2.36 (br. s, 3H) 1.99 (t, 1H) 1.07 (t, 3H). LCMS (method A): m/z 455 $(M+H)^+$ (ES+)

Example 14. Synthesis of Compound No. A1-54

Step 1: N-(5-oxo-6-oxa-4(2,1)-pyrrolidina-1(1,2),2(1,3)-dibenzenacyclo-undecaphane-4[3]-yl)ethanesulfonamide_cis racemic (Compound No. A1-54)

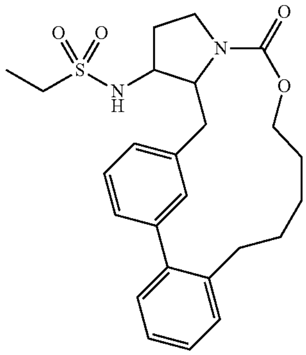 [SMILES: CCS(=O)(=O)NC1CCN2C(=O)OCCCCCc3ccccc3-c3cccc(c3)CC12]

Hydrogenation of (E/Z)—N-(5-oxo-6-oxa-4(2,1)-pyrrolidina-1-(1,2),2-(1,3)-dibenzena-cycloundecaphan-9-en-43-yl)ethanesulfonamide_cis racemic (25 mg, 0.052 mmol) was performed in EtOH (15 mL) in presence of Pd/C (10% wt, 11 mg, 0.010 mmol) at 2 bar pressure for 1.5 h. The mixture was filtered, washed with methanol and evaporated. The crude was purified on Biotage purification system (4 g column, 15 μm, eluents: 0-100% of 5% MeOH/dichloromethane) to afford 22 mg of the title compound. $^1$H NMR (500 MHz, $CDCl_3$): δ/ppm: 7.33 (br d, 1H), 7.25-7.30 (m, 5H), 7.11 (br s, 1H), 4.48 (d, 1H), 4.34 (br s, 1H), 3.90-4.07 (m, 2H), 3.82 (br s, 1H) 3.21-3.70 (m, 3H), 2.90-3.20 (m, 3H), 2.48-2.87 (m, 2H), 2.32-2.41 (m, 1H), 1.97 (quin, 1H), 1.39-1.55 (m, 3H), 1.24-1.38 (m, 4H), 1.19 (br s, 2H). LCMS (method A): m/z 457 $(M+H)^+$ (ES+)

Example 15. Synthesis of Compound No. A1-51

Step 1: N-allyl-2-((2'-allyl-[1,1'-biphenyl]-3-yl)methyl)-3-(ethylsulfonamido)-pyrrolidine-1-carboxamide_cis racemic

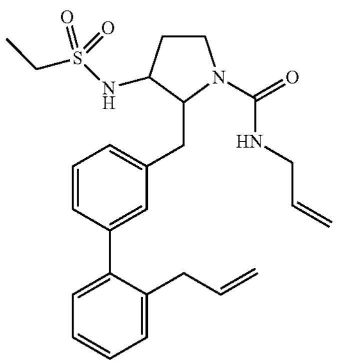 [SMILES: C=CCNC(=O)N1CCC(NS(=O)(=O)CC)C1Cc1cccc(-c2ccccc2CC=C)c1]

N-(2-((2'-allyl-[1,1'-biphenyl]-3-yl)methyl)pyrrolidin-3-yl)ethanesulfonamide_cis racemic, Intermediate 8 (100 mg, 0.260 mmol) was dissolved in dry dichloromethane (2.5 mL), and TEA (217 μL, 1.56 mmol) was added. The solution was cooled in an ice bath and allyl isocyanate (108 mg, 1.30 mmol) was diluted in dichloromethane (0.5 mL) and added dropwise to the solution. The reaction was brought up to room temperature and stirred for 2 h. TEA (76.1 μL, 0.546 mmol) and allyl isocyanate (43.2 mg, 0.26 mmol) were added and the reaction mixture was stirred at room temperature overnight. The reaction was dry loaded and purified on Interchim 520+(12 g column eluents dichloromethane: MeOH 0-10%) to afford 60 mg of the title compound. LC-MS (method A) (ESI+): 468 [M+H]

Step 2: (E/Z)—N-(5-oxo-6-aza-4(2,1)-pyrrolidina-1(1,2),2(1,3)-dibenzenacyclo-decaphan-8-en-4$^3$-yl)ethanesulfonamide_cis racemic (Compound No. A1-51)

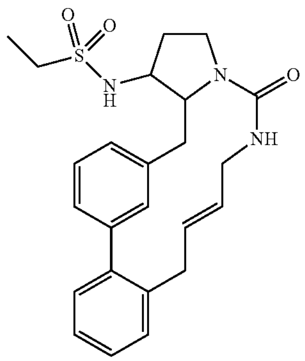 [SMILES: CCS(=O)(=O)NC1CCN2C(=O)NC/C=C/Cc3ccccc3-c3cccc(c3)CC12]

tert-Butyl 2-((2'-(2-(1,3-dioxoisoindolin-2-yl)ethoxy)-[1,1'-biphenyl]-3-yl)methyl)-3-(ethylsulfonamido)pyrrolidine-1-carboxylate_cis racemic (60 mg, 0.128 mmol) was dissolved in dichloromethane (14 mL) and Grubbs cat II. (22 mg, 0.026 mmol) was added. The reaction was heated and stirred at 40 °C for 2 h, dry loaded and purified on Interchim 520+(12 g column eluents cyclohexane-EtOAc:diethylamine (10:0.2) 0-100%.) Fractions were combined and triturated with diethyl ether and evaporated until dry to afford 55 mg of the title compound (E/Z alkene mixture). $^1$H NMR (600 MHz, $CDCl_3$) δ/ppm: 7.33-7.28 (m, 1H), 7.28-7.19 (m, 3H), 7.18-7.10 (m, 3H), 7.10-6.96 (m, 1H), 5.18-5.06 (m, 1H), 4.63 (d, 1H), 4.62-4.53 (m, 1H), 4.01-3.92 (m, 1H), 3.88-3.72 (m, 3H), 3.65-3.54 (m, 1H), 3.44-3.35 (m, 2H), 3.19-3.11 (m, 2H), 3.10-3.01 (m, 2H), 2.80-2.68 (m, 1H), 2.33-2.19 (m, 2H), 1.97-1.82 (m, 1H), 1.35 (t, 3H). LCMS (method A): m/z 440 $(M+H)^+$ (ES+)

Example 16. Synthesis of Compound No. A1-49

Step 1: N-(5-oxo-6-aza-4(2,1)-pyrrolidina-1(1,2),2(1,3)-dibenzenacyclodecaphane-4$^3$-yl)ethanesulfonamide_cis racemic (Compound No. A1-49)

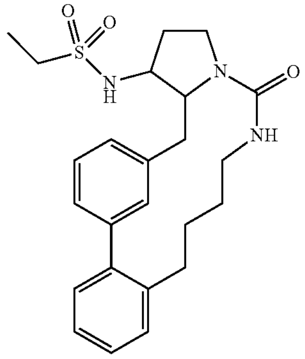 [SMILES: CCS(=O)(=O)NC1CCN2C(=O)NCCCCc3ccccc3-c3cccc(c3)CC12]

(E/Z)—N-(5-oxo-6-aza-4(2,1)-pyrrolidina-1(1,2),2(1,3)-dibenzenacyclodecaphan-8-en-4$^3$-yl)ethanesulfonamide_cis racemic (35 mg, 0.080 mmol) was dissolved in ethanol (40 mL) and Pd/C (17 mg, 0.016 mmol) was added and hydrogenated under 2 bar of $H_2$ and shaken for 2 h. The reaction was filtered and the filtrate evaporated until dry to obtain crude product. The crude product was dry loaded and purified on Interchim 520+(4 g column, eluents cyclohexane-EtOAc:diethylamine (10:0.2) 50-100%) to afford 15 mg of the title compound. $^1H$ NMR (500 MHz, $CDCl_3$) δ/ppm: 7.37 (t, 1H), 7.31-7.27 (m, 1H), 7.25-7.20 (m, 4H), 7.20-7.16 (m, 2H), 4.66 (d, 1H), 4.05-3.96 (m, 1H), 3.93-3.83 (m, 1H), 3.78-3.68 (m, 1H), 3.42 (t, 1H), 3.31-3.21 (m, 2H), 3.13 (q, J=14.89, 7.56 Hz, 2H), 3.18-3.01 (m, 1H), 2.76-2.49 (m, 2H), 2.44-2.33 (m, 3H), 2.01-1.88 (m, 1H), 1.43 (t, 3H) 1.39-1.30 (m, 2H), 1.27-1.15 (m, 1H), 1.15-1.05 (m, 1H). LCMS (method A): m/z 442 $(M+H)^+$ (ES+)

Example 17. Synthesis of Compound No. A1-52

Step 1: 4-nitrophenyl but-3-en-1-ylcarbamate

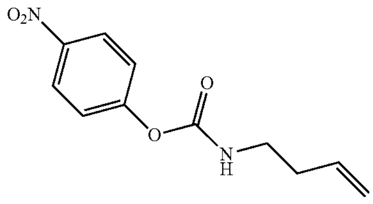 [SMILES: C=CCCNC(=O)Oc1ccc([N+](=O)[O-])cc1]

To a solution of but-3-en-1-amine (0.129 mL, 0.140 mmol) in THF (5 mL), 4-nitrophenyl chloroformate (235 mg, 1.17 mmol) and Pyridine (0.184 mL, 2.33 mmol) were added. The mixture was stirred at room temperature for 1.5 h, diluted with ethyl acetate (50 mL), washed with sat $NH_4Cl$ (3x30 mL) and brine (30 mL), dried over $Na_2SO_4$, and evaporated. The crude product was purified by chromatography on SPE 5 g column, eluents petrol Ether:EtOAc 0-10%. Then repurified on Interchim 520+(12 g column eluents cyclohexane:EtOAc 0-10%) to afford 88 mg of the title compound. LC-MS (method A) (ESI+): 237 [M+H]

Step 2: 2-((2'-allyl-[1,1'-biphenyl]-3-yl)methyl)-N-(but-3-en-1-yl)-3-(ethylsulfon-amido)pyrrolidine-1-carboxamide_cis racemic

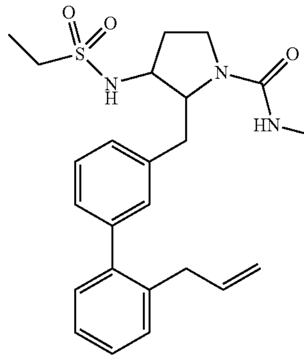

To a solution of N-(2-((2'-allyl-[1,1'-biphenyl]-3-yl) methyl)pyrrolidin-3-yl)-ethanesulfonamide_cis racemic, Intermediate 8 (75 mg, 0.198 mmol) in DMF (2 mL), N,N-diisopropylethylamine (0.103 mL, 0.593 mmol) and 4-nitrophenyl but-3-en-1-ylcarbamate (53 mg, 0.224 mmol) were added and reaction mixture was shaken at 100 °C for 1 h. The reaction was diluted with water (30 mL), extracted with ethyl acetate (150 mL), dried over $Na_2SO_4$, and evaporated to afford 316 mg of crude product. The crude product was purified on Interchim 520+(12 g column eluents dichloromethane:MeOH 0-10%) to afford 72 mg of the title compound. LC-MS (method A) (ESI+): 482 [M+H]

Step 3: (E/Z)—N-(5-oxo-6-aza-4(2,1)-pyrrolidina-1 (1,2),2(1,3)-dibenzenacyclo-undecaphan-9-en-43-yl) ethanesulfonamide_cis racemic (Compound No. A1-52)

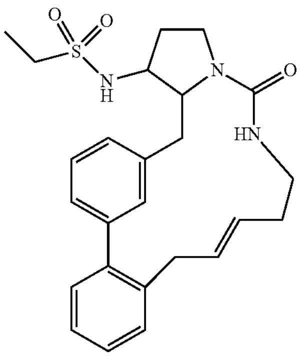 [SMILES: CCS(=O)(=O)NC1CCN2C(=O)NCC/C=C/Cc3ccccc3-c3cccc(c3)CC12]

2-((2'-allyl-[1,1'-biphenyl]-3-yl)methyl)-N-(but-3-en-1-yl)-3-(ethylsulfonamido)-pyrrolidine-1-carboxamide_cis racemic (70 mg, 0.145 mmol) was dissolved in dichloromethane (16 mL) and Grubbs catalyst second gen. (25 mg, 0.029 mmol) was added. The reaction mixture was heated and stirred at 40 °C for 1.5 h. The mixture was dry loaded and purified on Interchim 520+(12 g column eluents cyclohexane-EtOAc:diethylamine (10:0.2) 0-100%). Fractions were combined and evaporated, triturated with diethyl ether and then evaporated till dry to afford 47 mg of the title compound (E/Z alkene mixture). $^1H$ NMR (600 MHz, $CDCl_3$) δ/ppm: 7.31-7.28 (m, 1H), 7.27-7.24 (m, 1H), 7.24-7.20 (m, 2H), 7.17-7.12 (m, 3H), 7.10-7.07 (m, 1H), 5.26-5.17 (m, 1H), 4.78-4.71 (m, 1H), 4.58 (d, 1H), 3.95-3.86 (m, 1H), 3.83-3.75 (m, 1H), 3.74-3.67 (m, 1H), 3.57-3.44 (m, 2H), 3.37 (q, 1H), 3.27 (t, 1H), 3.12 (dd, 1H), 3.01 (q, 2H), 2.96-2.88 (m, 1H), 2.85-2.78 (m, 1H), 2.38-2.32 (m, 1H), 2.23-2.15 (m, 1H), 2.13-2-05 (m, 1H), 1.86-1.74 (m, 2H), 1.32 (t, 3H). LCMS (method A): m/z 454 $(M+H)^+$ (ES+)

Example 18. Synthesis of Compound No. A1-50

N-(5-oxo-6-aza-4(2,1)-pyrrolidina-1(1,2),2(1,3)-dibenzenacyclo-undecaphane-43-yl)ethanesulfonamide_cis racemic (Compound No. A1-50)

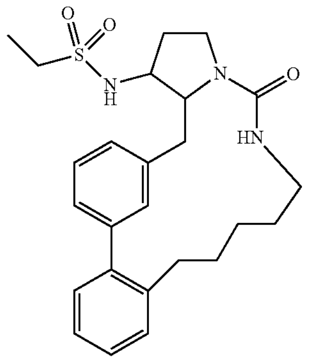 [SMILES: CCS(=O)(=O)NC1CCN2C(=O)NCCCCCc3ccccc3-c3cccc(c3)CC12]

(E/Z)—N-(5-oxo-6-aza-4(2,1)-pyrrolidina-1(1,2),2(1,3)-dibenzenacycloundecaphan-9-en-43-yl)ethanesulfonamide_cis racemic (19 mg, 0.042 mmol) was dissolved in ethanol (20 mL) and Pd/C(9 mg, 0.085 mmol) was added and the reaction put under 2 bar of $H_2$ and shaken for 2.5 h. The reaction was filtered and the filtrate was evaporated until dry to obtain crude product which was dry loaded and purified on Interchim 520+(4 g column eluents cyclohexane-EtOAc: diethylamine (10:0.2) 50-100%) to afford 7 mg of the title compound. $^1$H NMR (500 MHz, $CDCl_3$) δ/ppm: 7.40-7.33 (m, 1H), 7.31-7.21 (m, 2H), 7.26-7.21 (m, 3H), 7.21-7.17 (m, 3H), 4.74 (d, 1H), 4.15-4.05 (m, 1H), 3.72 (q, 1H), 3.83 (t, 1H), 3.43-3.29 (m, 1H), 3.23 (d, 1H), 3.14 (q, 2H), 3.12-3.05 (m, 1H), 3.01-2.91 (m, 1H), 2.83-2.69 (m, 2H), 2.39 (t, 1H), 2.34-2.25 (m, 1H), 2.01-1.90 (m, 1H), 1.50-1.39 (m, 5H), 1.10-1.05 (m, 1H), 1.00-0.93 (m, 3H). LCMS (method A): m/z 456 $(M+H)^+$ (ES+)

Example 19 and 20. Synthesis of Compound Nos. A1-43 and A1-42

N-(5-oxo-6-aza-4(2,1)-pyrrolidina-1(1,2),2(1,3)-dibenzenacycloundecaphane-43-yl)ethanesulfonamide_cis racemic (Example 18) resolved on the Sepiatec SFC Prep100 system using a Lux A1 column and isocratic conditions of $CO_2$:(EtOH+0.2% $NH_3$) 65:35.

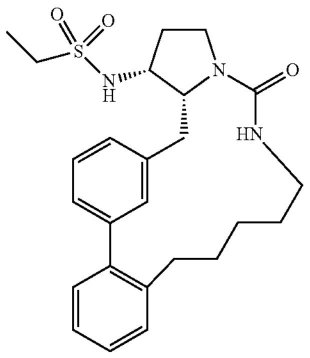 [SMILES: CCS(=O)(=O)N[C@@H]1CCN2C(=O)NCCCCCc3ccccc3-c3cccc(c3)C[C@H]12]

N-(($4^2$R,$4^3$R)-5-oxo-6-aza-4(2,1)-pyrrolidina-1(1,2),2(1,3)-dibenzenacycloundecaphane-$4^3$-yl)ethanesulfonamide (Example 19; Compound No. A1-43)

Isomer 1: 99% ee retention time=2.02 mins. LCMS (method E): m/z 456 $(M+H)^+$ (ES+) at 4.26 min.

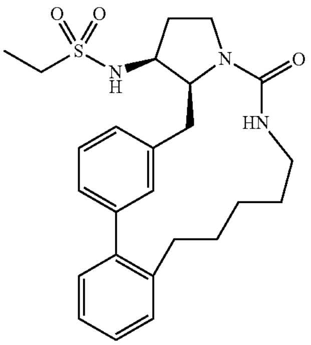 [SMILES: CCS(=O)(=O)N[C@H]1CCN2C(=O)NCCCCCc3ccccc3-c3cccc(c3)C[C@@H]12]

N-(($4^2$S,$4^3$S)-5-oxo-6-aza-4(2,1)-pyrrolidina-1(1,2),2(1,3)-dibenzenacycloundecaphane-$4^3$-yl)ethanesulfonamide (Example 20; Compound No. A1-42)

Isomer 2: 99% ee retention time=2.16 mins. LCMS (method E): m/z 456 $(M+H)^+$ (ES+) at 4.26 min.

Example 21. Synthesis of Compound No. A1-30

Step 1: 2-(2-(2-(4,4,5,5-tetramethyl-1,3,2-dioxaborolan-2-yl)phenoxy)ethyl)-isoindoline-1,3-dione

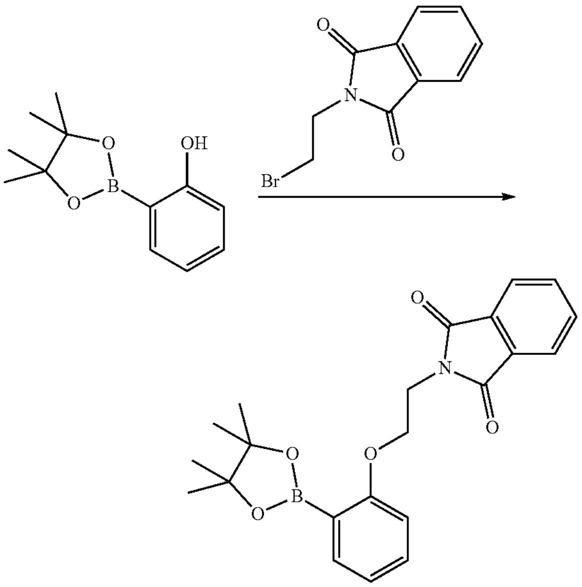

To a solution of 2-(2-bromoethyl)isoindoline-1,3-dione (1.34 g, 5 mmol) and 2-hydroxy-benzeneboronic acid, pinacol ester (1.0 g, 4.54 mmol) in DMF (30 mL) was added potassium carbonate (1.26 g, 9.09 mmol) and the reaction heated at 80 °C for 18 h. The reaction was diluted with EtOAc (50 mL), washed with water (50 mL), sat. brine (25 mL), the organic layer separated and concentrated in vacuo. The residue was purified by flash column chromatography eluting with 0-50% EtOAc/isohexane to afford the title compound (178 mg 10% yield) as a white solid. LCMS (method B) m/z 394 (ES+, M+H) at 1.73 min Step 2: tert-butyl 2-((2'-(2-(1,3-dioxoisoindolin-2-yl)ethoxy)-[1,1'-biphenyl]-3-yl)methyl)-3-(ethylsulfonamido)pyrrolidine-1-carboxylate_cis racemic

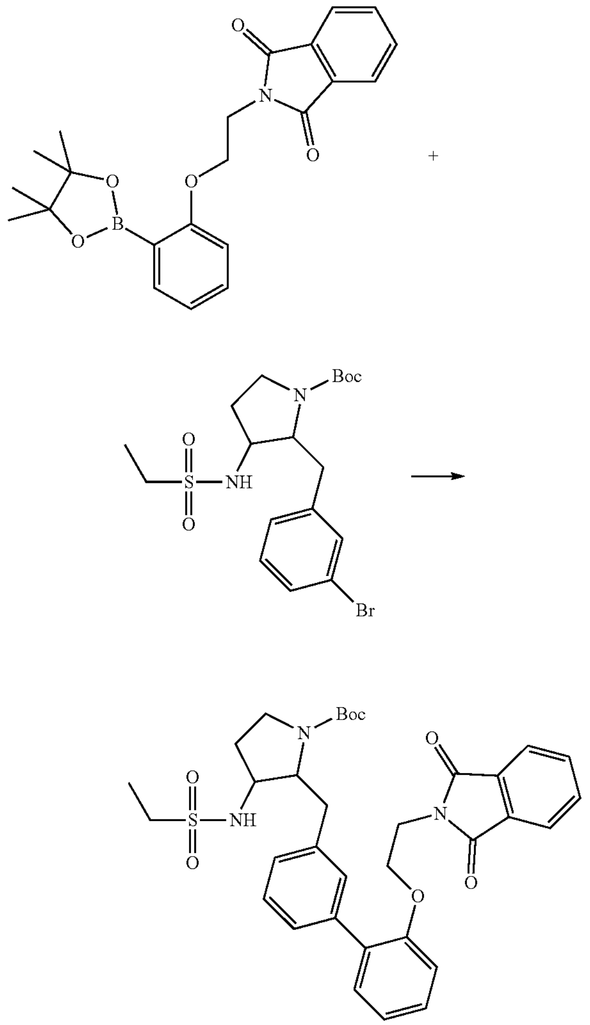

To a solution of tert-butyl 2-(3-bromobenzyl)-3-(ethylsulfonamido)pyrrolidine-1-carboxylate_cis racemic (Intermediate 2) (200 mg, 0.45 mmol) and 2-[2-[2-(4,4,5,5-tetramethyl-1,3,2-dioxaborolan-2-yl)phenoxy]ethyl] isoindoline-1,3-dione (176 mg, 0.45 mmol) in THF (9 mL) was added XPhos-Pd-G3 (19 mg, 0.02 mmol) and tripotassium phosphate 1 M solution (1.8 mL, 1.8 mmol). The reaction was heated at 70 °C for 2 h. The reaction was extracted into EtOAc (50 mL), washed with water (25 mL), sat. brine (25 mL), the organic layer separated and concentrated in vacuo. The resulting residue was purified by flash column chromatography eluting with 0%-100% EtOAc in iso-hexane to afford the title compound (170 mg, 60% yield) as a yellow gum. LCMS (method B) m/z 634 (ES+, M+H) at 1.69 min Step 3: tert-butyl 2-((2'-(2-aminoethoxy)-[1,1'-biphenyl]-3-yl)methyl)-3-(ethylsulfonamido)pyrrolidine-1-carboxylate_cis racemic

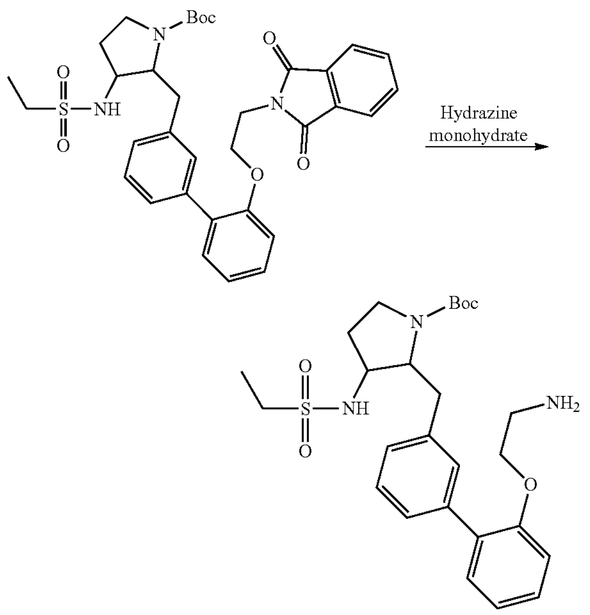

To a solution of tert-butyl 2-((2'-(2-(1,3-dioxoisoindolin-2-yl)ethoxy)-[1,1'-biphenyl]-3-yl)methyl)-3-(ethylsulfonamido)pyrrolidine-1-carboxylate_cis racemic (170 mg, 0.27 mmol) in ethanol (5 mL) and was added Hydrazine hydrate (131 μL, 2.68 mmol) and the mixture stirred at room temperature for 2 h. The reaction was partitioned between EtOAc (25 mL) and sat. brine (25 mL), the organic layer separated, dried over $MgSO_4$, filtered and concentrated in vacuo. The resulting residue was purified by flash column chromatography eluting with 0-20% MeOH+10% 7M $NH_3$ in MeOH/dichloromethane to afford the title compound (57 mg, 49% yield) as a colourless gum. LCMS (method B) m/z 504 (ES+, M+H) at 1.43 min Step 4: N-(2-((2'-(2-aminoethoxy)-[1,1'-biphenyl]-3-yl)methyl)pyrrolidin-3-yl)ethanesulfonamide dihydrochloride_cis racemic

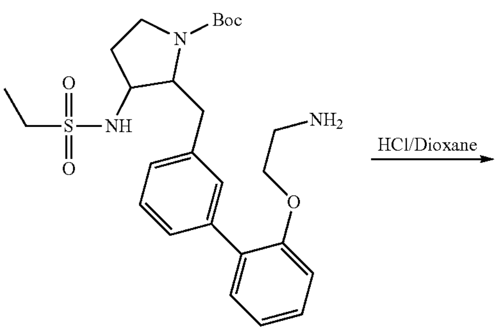

-continued

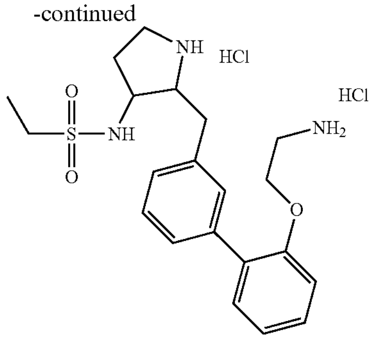

To a solution of tert-butyl 2-((2'-(2-aminoethoxy)-[1,1'-biphenyl]-3-yl)methyl)-3-(ethylsulfonamido)pyrrolidine-1-carboxylate_cis racemic (57 mg, 0.11 mmol) in 1,4-dioxane (2.0 mL) and was added 4 M HCl in dioxane (0.28 mL, 1.13 mmol) and the mixture stirred at room temperature for 2 h. The reaction was concentrated in vacuo to afford the title compound (54 mg, 100% yield) as a light brown gum. LCMS (method B) m/z 404 (ES+, M+H) at 1.89 min Step 5: N-(5-oxo-9-oxa-6-aza-4(2,1)-pyrrolidina-1(1,2),2(1,3)-dibenzenacyclo-nonaphane-4$^3$-yl)ethanesulfonamide_cis racemic (Compound No. A1-30)

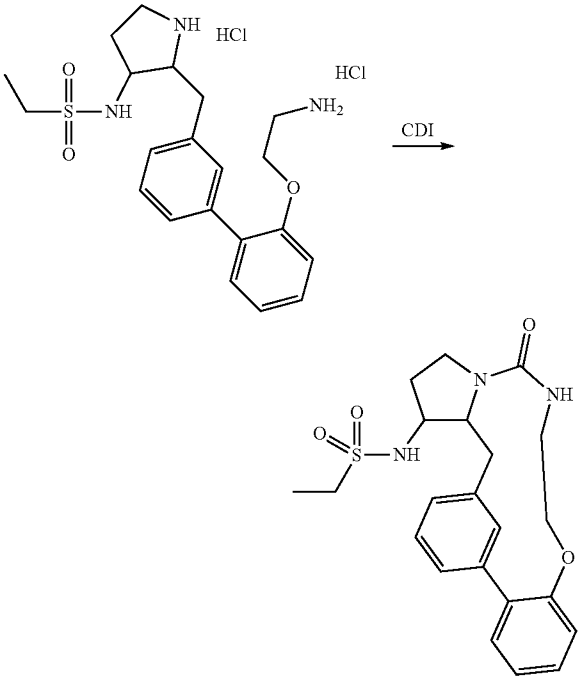

To a solution of N-(2-((2'-(2-aminoethoxy)-[1,1'-biphenyl]-3-yl)methyl)pyrrolidin-3-yl)ethanesulfonamide dihydrochloride_cis racemic (54 mg, 0.11 mmol) and N,N-diisopropylethylamine (0.08 mL, 0.45 mmol) in DMF (11 mL) was added CDI (22 mg, 0.14 mmol) and the mixture was stirred at room temperature for 2 h and then heated at 70 °C for 1 h. The reaction was diluted with EtOAc (25 mL), washed with 10% citric acid (10 mL), sat. brine (10 mL), the organic layer separated and concentrated in vacuo. The resulting residue was purified by reverse phase flash column chromatography eluting with 10% to 100% MeOH in $H_2O$+0.2% $NH_4OH$ to afford the title compound (6.4 mg, 13% yield) as an off-white solid. $^1$H NMR (400 MHz, DMSO-$d_6$) δ 7.56 (s, 1H), 7.35-7.16 (m, 4H), 7.16-6.95 (m, 4H), 5.83 (d, 1H), 4.33-4.21 (m, 1H), 3.94 (d, 1H), 3.84-3.64 (m, 3H), 3.25 (d, 1H), 3.12 (dt, 3H), 2.98 (d, 1H), 2.81 (dd, 1H), 2.47-2.36 (m, 1H), 2.20 (dt, 1H), 2.00 (t, 1H), 1.26 (t, 3H). LCMS (method E): m/z 430 $(M+H)^+$ (ES+) at 3.22 min.

Example 22. Synthesis of Compound No. A1-7

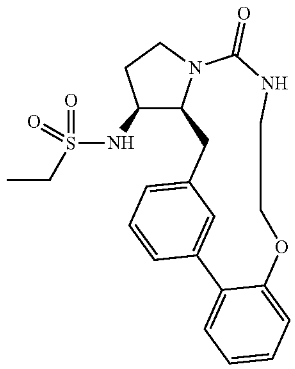 [SMILES: CCS(=O)(=O)N[C@H]1CCN2C(=O)NCCCOc3ccccc3-c3cccc(c3)C[C@@H]12]

N-(5-oxo-9-oxa-6-aza-4(2,1)-pyrrolidina-1(1,2),2(1,3)-dibenzenacyclononaphane-4$^3$-yl)ethanesulfonamide_cis racemic (example 22) was resolved on the Sepiatec SFC Prep100 system using a Lux A1 column and isocratic conditions of $CO_2$:MeOH+0.2% $NH_3$ 60:40 to afford N-((4$^2$S,4$^3$S)-5-oxo-9-oxa-6-aza-4(2,1)-pyrrolidina-1-(1,2),2-(1,3)-dibenzenacyclo-nonaphane-4$^3$-yl)ethanesulfonamide having the longer retention time. LCMS (method E): m/z 430 $(M+H)^+$ (ES+) at 2.91 min.

Example 23. Synthesis of Compound No. A1-31

Step 1: methyl 4-(2-(4,4,5,5-tetramethyl-1,3,2-dioxaborolan-2-yl)phenoxy)-butanoate (Intermediate 9)

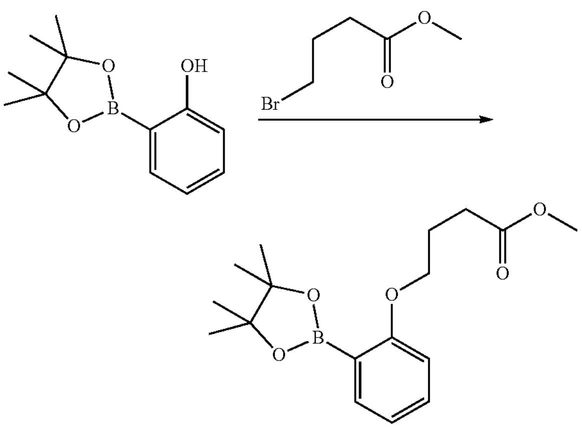

To methyl-4-bromobutanoate (857 μL, 6.82 mmol) and 2-hydroxybenzeneboronic acid, pinacol ester (1.0 g, 4.54 mmol) in DMF (30 mL) was added potassium carbonate (1.26 g, 9.09 mmol) and the reaction heated at 80 °C for 18 h. The reaction was diluted with EtOAc (50 mL), washed with water (50 mL), sat. brine (25 mL), the organic layer separated and concentrated in vacuo. The residue was purified by flash column chromatography eluting with 0-50% EtOAc/isohexane to afford the title compound (811 mg, 55% yield) as a colourless oil. LCMS (method B) m/z 321 (ES+, M+H) at 1.55 min Step 2: tert-butyl 3-(ethylsulfonamido)-2-((2'-(4-methoxy-4-oxobutoxy)-[1,1'-biphenyl]-3-yl)methyl) pyrrolidine-1-carboxylate_cis racemic

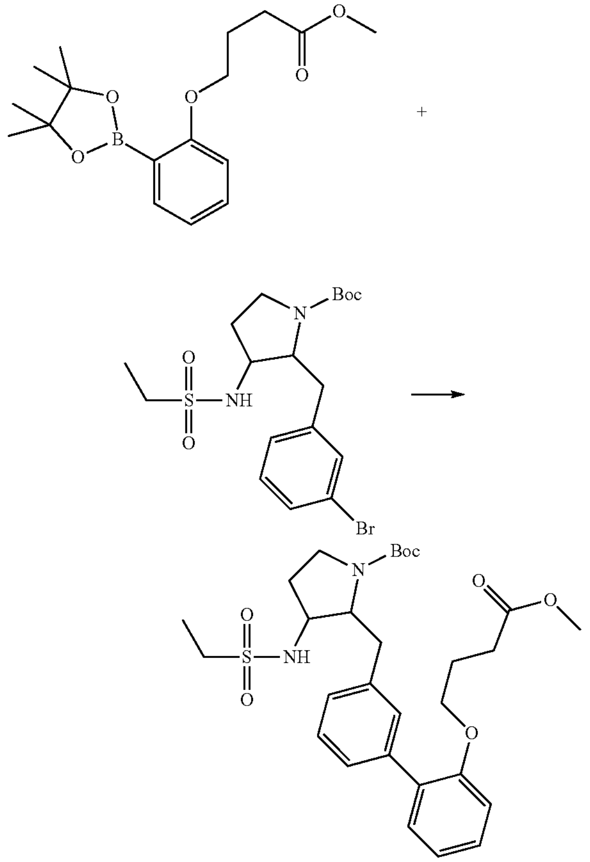

To a solution of tert-butyl 2-(3-bromobenzyl)-3-(ethylsulfonamido)pyrrolidine-1-carboxylate_cis racemic (Intermediate 2) (200 mg, 0.45 mmol) and methyl 4-[2-(4,4,5,5-tetramethyl-1,3,2-dioxaborolan-2-yl)phenoxy]butanoate, Intermediate 9 (172 mg, 0.54 mmol) in THF (9 mL) was added XPhos-Pd-G3 (19 mg, 0.02 mmol) and tripotassium phosphate 1 M solution (1.79 mL, 1.79 mmol). The reaction was heated at 70 °C for 2 h. The reaction was extracted into EtOAc (50 mL), washed with water (25 mL), sat. brine (25 mL), the organic layer separated and concentrated in vacuo. The resulting residue was purified by flash column chromatography eluting with 0%-100% EtOAc in iso-hexane. The fractions were combined and the solvent removed in vacuo to afford the title compound (230 mg, 92% yield) as a yellow gum. LCMS (method B) m/z 461 (ES+, M-Boc) at 1.69 min Step 3: 4-((3'-((1-(tert-butoxycarbonyl)-3-(ethylsulfonamido)pyrrolidin-2-yl)methyl)-[1,1'-biphenyl]-2-yl)oxy)butanoic acid_cis racemic

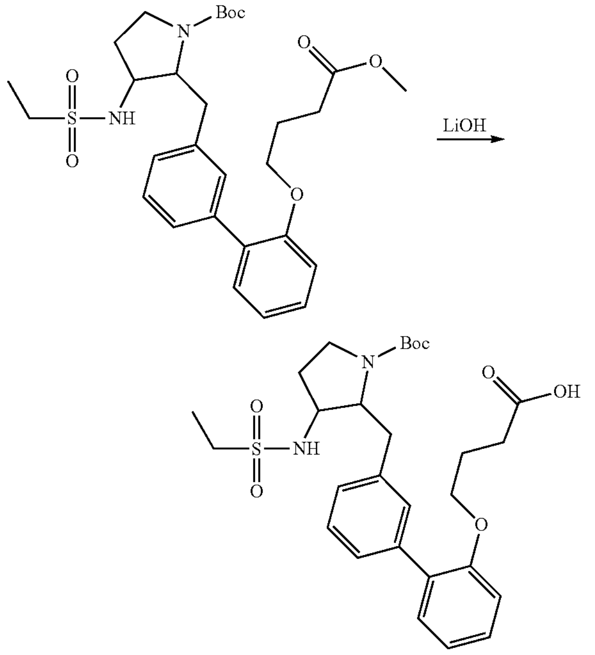

To a solution of tert-butyl 3-(ethylsulfonamido)-2-((2'-(4-methoxy-4-oxobutoxy)-[1,1'-biphenyl]-3-yl)methyl)pyrrolidine-1-carboxylate_cis racemic (230 mg, 0.41 mmol) in THF (9 mL) and water (3 mL) was added lithium hydroxide monohydrate (52 mg, 1.23 mmol) and the mixture was stirred at room temperature for 2 h. The reaction was acidified with 1 M HCl (10 mL), extracted into EtOAc (25 mL), the organic layer separated, dried over $MgSO_4$, filtered and the solvent removed in vacuo to afford the title compound (210 mg, 93% yield) as a colourless gum. LCMS (method B) m/z 447 (ES+, M-Boc) at 0.86 min Step 4: 4-((3'-((3-(ethylsulfonamido)pyrrolidin-2-yl) methyl)-[1,1'-biphenyl]-2-yl)oxy)butanoic acid hydrochloride_cis racemic

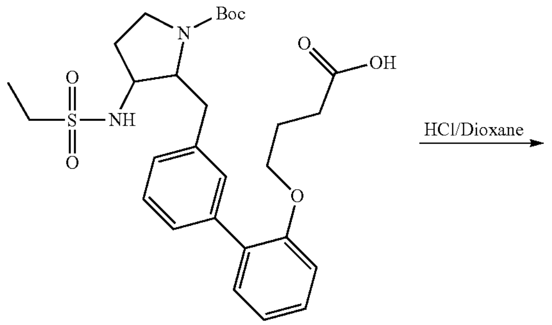

-continued

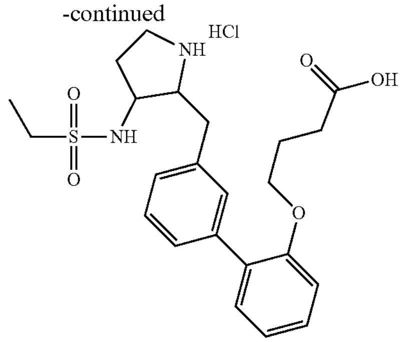

To a solution of 4-((3'-((1-(tert-butoxycarbonyl)-3-(ethylsulfonamido)pyrrolidin-2-yl)methyl)-[1,1'-biphenyl]-2-yl)oxy)butanoic acid_cis racemic (210 mg, 0.38 mmol) in 1,4-dioxane (4 mL) and was added 4 M HCl in dioxane (0.96 mL, 3.84 mmol) and the mixture stirred at room temperature for 2 h. The reaction was concentrated in vacuo to afford the title compound (185 mg, 99% yield) as a light brown gum. LCMS (method D) m/z 447 (ES+, M+H) at 1.35 min Step 5: N-(5-oxo-9-oxa-4(2,1)-pyrrolidina-1(1,2),2(1,3)-dibenzenacyclo-nonaphane-$4^3$-yl)ethanesulfonamide_cis racemic (Compound No. A1-31)

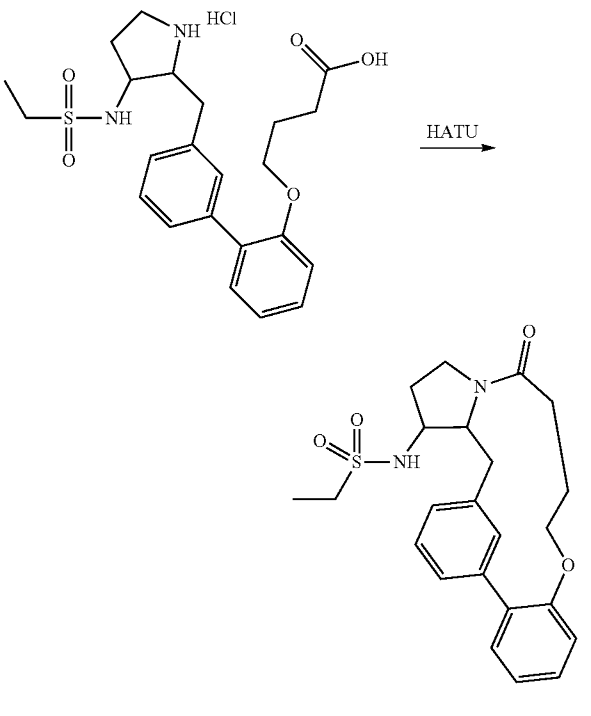

To a solution of 4-((3'-((3-(ethylsulfonamido)pyrrolidin-2-yl)methyl)-[1,1'-biphenyl]-2-yl)oxy)butanoic acid hydrochloride_cis racemic (185 mg, 0.38 mmol) and N,N-diisopropylethylamine (0.27 mL, 1.53 mmol) in DMF (38 mL) was added HATU (219 mg, 0.57 mmol) and the mixture was stirred at room temperature for 2 h. The reaction was concentrated in vacuo, extracted into EtOAc (50 mL), washed with sat. brine (25 mL), the organic layer separated and concentrated in vacuo. The residue was purified by reverse phase flash column chromatography eluting with 10% to 100% MeOH in $H_2O$+0.2% $NH_4OH$ to afford the title compound (81 mg, 49% yield) as a beige solid. $^1H$ NMR (400 MHz, DMSO-$d_6$) δ 7.59 (d, 1H), 7.41-7.10 (m, 5H), 7.08-7.04 (m, 1H), 7.04-6.95 (m, 2H), 4.40 (td, 1H), 3.94-3.86 (m, 1H), 3.74 (dd, 2H), 3.58 (d, 1H), 3.44 (d, 1H), 3.19-3.08 (m, 2H), 2.83 (dd, 1H), 2.45-2.01 (m, 6H), 1.68 (dd, 1H), 1.26 (td, 3H). LCMS (method E): m/z 429 $(M+H)^+$ (ES+) at 3.69 min.

Example 24. Synthesis of Compound No. A1-22

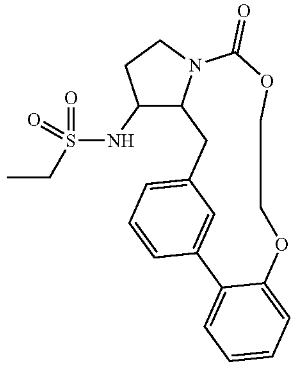 [SMILES: CCS(=O)(=O)NC1CCN2C(=O)OCCCOc3ccccc3-c3cccc(c3)CC12]

N-(5-oxo-9-oxa-4(2,1)-pyrrolidina-1(1,2),2(1,3)-dibenzenacyclononaphane-$4^3$-yl)-ethanesulfonamide_cis racemic (example 24) resolved on the Sepiatec SFC Prep100 system using a Lux A1 column and isocratic conditions of $CO_2$: IPA+0.2% $NH_3$ 60:40 to afford N-(($4^2$S,$4^3$S)-5-oxo-9-oxa-4(2,1)-pyrrolidina-1-(1,2),2-(1,3)-dibenzenacyclononaphane-$4^3$-yl)ethanesulfonamide having the shorter retention time. $^1H$ NMR (400 MHz, DMSO-$d_6$) δ 7.55 (s, 1H), 7.36-7.26 (m, 2H), 7.25-6.96 (m, 6H), 4.96-4.83 (m, 1H), 4.08 (dd, 2H), 3.93 (d, 1H), 3.87-3.80 (m, 2H), 3.45 (td, 2H), 3.15-3.06 (m, 2H), 2.83 (dd, 1H), 2.43 (d, 1H), 2.21-2.13 (m, 1H), 2.01 (q, 1H), 1.24 (dt, 3H). LCMS (method E): m/z 431 $(M+H)^+$ (ES+) at 3.74 min Example 25. Synthesis of Compound No. A1-22

Step 1: methyl 2-(2-(4,4,5,5-tetramethyl-1,3,2-dioxaborolan-2-yl)phenoxy)acetate

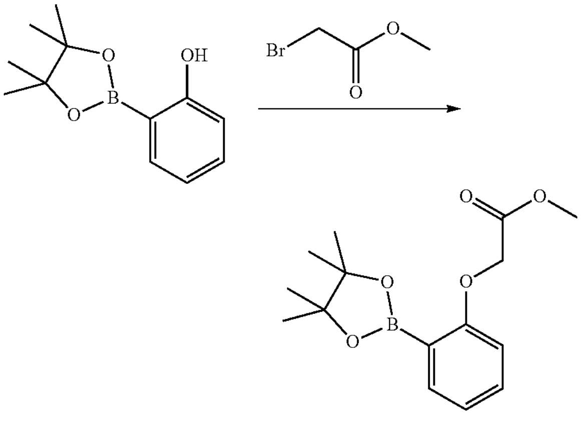

To methyl bromoacetate (645 μL, 6.82 mmol) and 2-hydroxybenzeneboronic acid, pinacol ester (1.0 g, 4.54 mmol) in DMF (30 mL) was added potassium carbonate (1.26 g, 9.09 mmol) and the reaction heated at 50 °C for 18 h. The reaction was diluted with EtOAc (50 mL), washed with water (50 mL), sat. brine (25 mL), the organic layer separated and concentrated in vacuo. The residue was purified by flash column chromatography eluting with 0-50% EtOAc/isohexane to afford the title compound (960 mg, 72% yield) as a colourless oil. LCMS (method B) m/z 293 (ES+, M+H) at 0.92 min.

Step 2: tert-butyl 3-(ethylsulfonamido)-2-((2'-(2-methoxy-2-oxoethoxy)-[1,1'-biphenyl]-3-yl)methyl) pyrrolidine-1-carboxylate_cis racemic

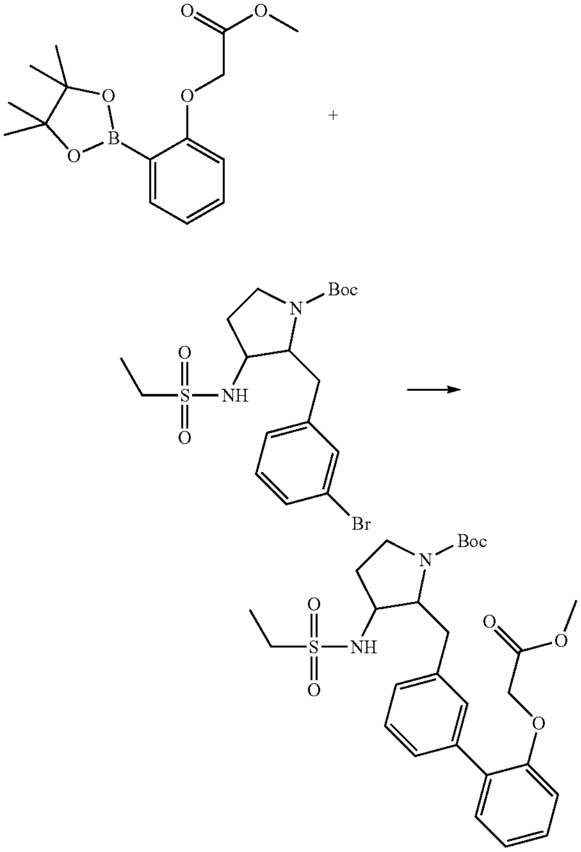

To a solution of tert-butyl 2-(3-bromobenzyl)-3-(ethylsulfonamido)pyrrolidine-1-carboxylate_cis racemic (Intermediate 2) (500 mg, 1.12 mmol) and methyl 2-(2-(4,4,5,5-tetramethyl-1,3,2-dioxaborolan-2-yl)phenoxy)acetate (359 mg, 1.23 mmol) in THF (11 mL) was added XPhos-Pd-G3 (47 mg, 0.06 mmol) and tripotassium phosphate 1 M solution (4.47 mL, 4.47 mmol). The reaction was heated at 70 °C for 2 h. The reaction was extracted into EtOAc (50 mL), washed with water (25 mL), sat. brine (25 mL), the organic layer separated and concentrated in vacuo. The resulting residue was purified by flash column chromatography eluting with 0%-100% EtOAc in iso-hexane to afford the title compound (480 mg, 60% yield) as a brown gum. LCMS (method B) m/z 533 (ES+, M+H) at 1.58 min Step 3: tert-butyl 3-(ethylsulfonamido)-2-((2'-(2-hydroxyethoxy)-[1,1'-biphenyl]-3-yl)methyl)pyrrolidine-1-carboxylate_cis racemic

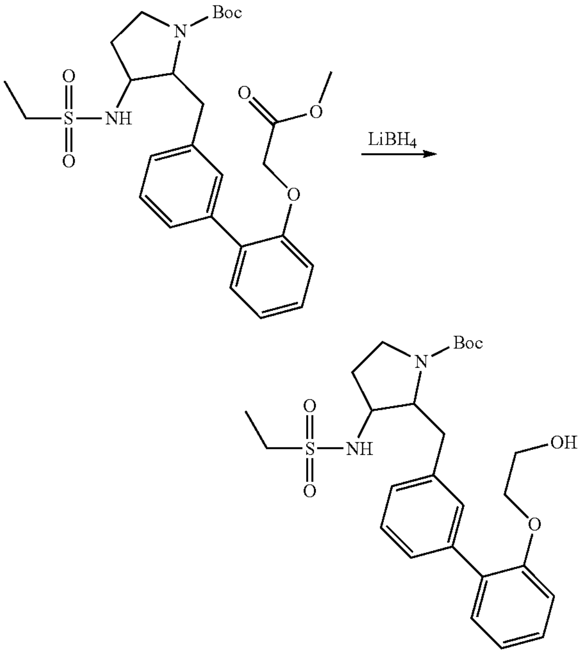

To a solution of tert-butyl 3-(ethylsulfonamido)-2-((2'-(2-methoxy-2-oxoethoxy)-[1,1'-biphenyl]-3-yl)methyl)pyrrolidine-1-carboxylate_cis racemic (480 mg, 0.68 mmol) and in THF (13 mL) was added lithium borohydride, 2 M in THF (676 μL, 1.35 mmol). The reaction was stirred at room temperature for 18 h. The reaction was extracted into EtOAc (50 mL), washed with 1 M HCl (25 mL), sat. brine (25 mL), the organic layer separated, dried over $MgSO_4$, filtered and concentrated in vacuo to afford the title compound (302 mg, 88% yield) as a pale yellow oil. LCMS (method D) m/z 405 (ES+, M-Boc) at 2.15 min Step 4: N-(2-((2'-(2-hydroxyethoxy)-[1,1'-biphenyl]-3-yl)methyl)pyrrolidin-3-yl)-ethanesulfonamide hydrochloride_cis racemic

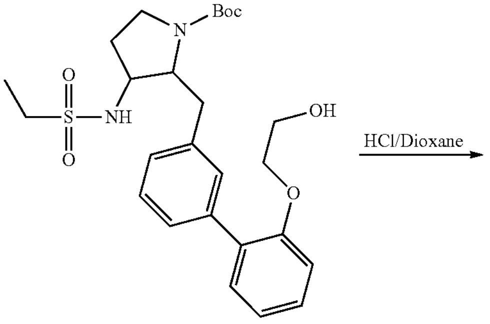

-continued

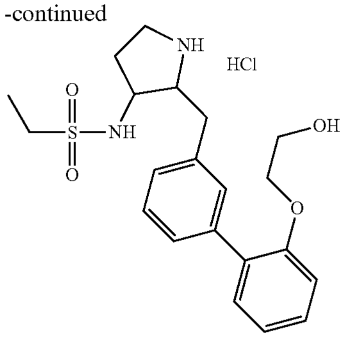

To a solution of tert-butyl 3-(ethylsulfonamido)-2-((2'-(2-hydroxyethoxy)-[1,1'-biphenyl]-3-yl)methyl)pyrrolidine-1-carboxylate_cis racemic (302 mg, 0.60 mmol) in 1,4-dioxane (6.0 mL) was added 4 M HCl in dioxane (10 eq) and the reaction stirred at room temperature for 36 h. The reaction was concentrated in vacuo to afford the title compound (220 mg, 83% yield) as a white foam. LCMS (method D) m/z 405 (ES+, M+H) at 1.87 min Step 5: N-(5-oxo-6,9-dioxa-4(2,1)-pyrrolidina-1(1,2),2(1,3)-dibenzenacyclo-nonaphane-$4^3$-yl)ethanesulfonamide_cis racemic (Compound No. A1-22)

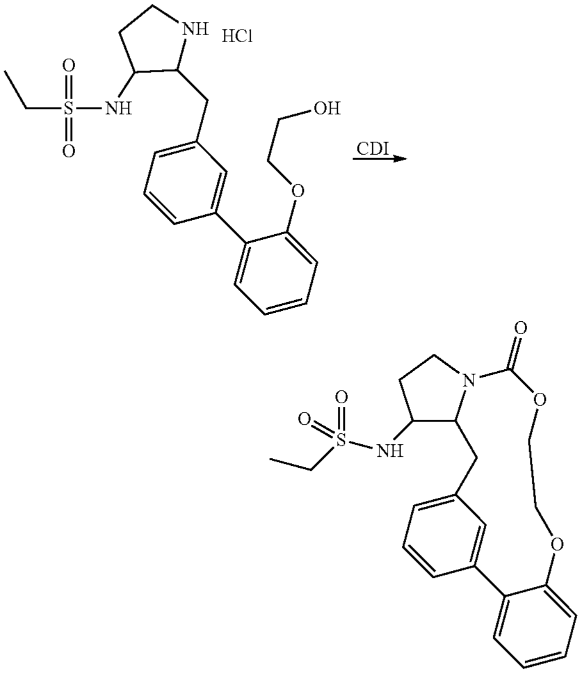

To a solution of N-(2-((2'-(2-hydroxyethoxy)-[1,1'-biphenyl]-3-yl)methyl)pyrrolidin-3-yl)ethanesulfonamide hydrochloride_cis racemic (220 mg, 0.50 mmol) in DMF (50 mL) and DIPEA (216 μL, 1.25 mmol) was added CDI (89 mg, 0.55 mmol) and the mixture was stirred at room temperature for 2 h and then heated at 80 °C for 2. The reaction was concentrated in vacuo, the product extracted with EtOAc (25 mL), washed with 10% citric acid (10 mL), sat. brine (10 mL), the organic layer separated and concentrated in vacuo. The resulting residue was purified by reverse phase flash column chromatography eluting with 10% to 100% MeOH in $H_2O$+0.2% $NH_4OH$. The residue was further purified by reverse phase prep HPLC to afford the title compound (49 mg, 22% yield) as a white solid. $^1H$ NMR (400 MHz, DMSO-$d_6$) δ 7.55 (s, 1H), 7.36-7.26 (m, 2H), 7.25-6.96 (m, 6H), 4.96-4.83 (m, 1H), 4.08 (dd, 2H), 3.93 (d, 1H), 3.87-3.80 (m, 2H), 3.45 (td, 2H), 3.15-3.06 (m, 2H), 2.83 (dd, 1H), 2.43 (d, 1H), 2.21-2.13 (m, 1H), 2.01 (q, 1H), 1.24 (dt, 3H). LCMS (method E): m/z 431 $(M+H)^+$ (ES+) at 3.74 min Example 26. Synthesis of Compound No. A1-23

Step 1: 2-(5-(2-(4,4,5,5-tetramethyl-1,3,2-dioxaborolan-2-yl)phenoxy)pentyl)-isoindoline-1,3-dione

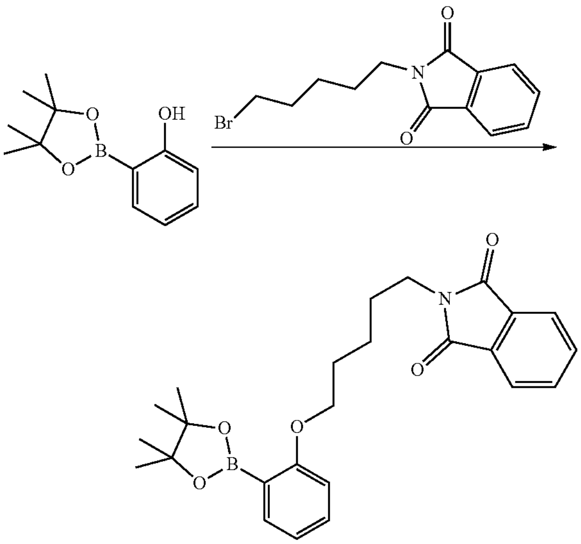

To a solution of 2-(5-bromopentyl)isoindoline-1,3-dione (740 mg, 2.5 mmol) and 2-hydroxybenzeneboronic acid, pinacol ester (500 mg, 2.27 mmol) in DMF (15 mL) was added potassium carbonate (628 mg, 4.54 mmol) and the reaction heated at 80 °C for 18 h. The reaction was diluted with EtOAc (50 mL), washed with water (50 mL), sat. brine (25 mL), the organic layer separated and concentrated in vacuo. The residue was purified by flash column chromatography eluting with 0-50% EtOAc/isohexane to afford the title compound (660 mg, 58% yield) as a colourless oil. LCMS (method B) m/z 436 (ES+, M+H) at 1.39 min Step 2: tert-butyl 2-((2'-((5-(1,3-dioxoisoindolin-2-yl)pentyl)oxy)-[1,1'-biphenyl]-3-yl)methyl)-3-(ethylsulfonamido)pyrrolidine-1-carboxylate_cis racemic

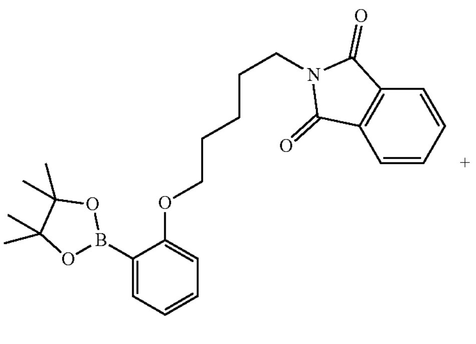

-continued

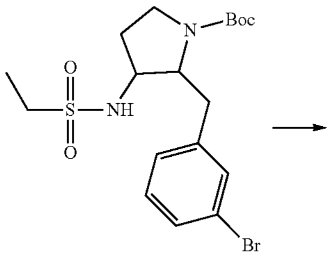

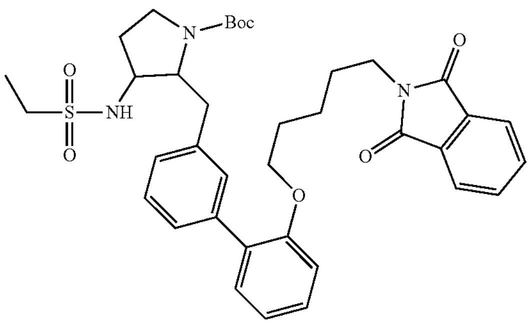

To a solution of tert-butyl 2-(3-bromobenzyl)-3-(ethylsulfonamido)pyrrolidine-1-carboxylate_cis racemic (Intermediate 2) (300 mg, 0.67 mmol) and 2-[5-[2-(4,4,5,5-tetramethyl-1,3,2-dioxaborolan-2-yl)phenoxy]pentyl]isoindoline-1,3-dione (350 mg, 0.80 mmol) in THF (9 mL) was added XPhos-Pd-G3 (28 mg, 0.03 mmol) and tripotassium phosphate 1 M solution (2.68 mL, 2.68 mmol). The reaction was heated at 70 °C for 2 h. The reaction was extracted into EtOAc (50 mL), washed with water (25 mL), sat. brine (25 mL), the organic layer separated and concentrated in vacuo. The resulting residue was purified by flash column chromatography eluting with 0%-100% EtOAc in iso-hexane to afford the title compound (376 mg, 83% yield) as a yellow gum. LCMS (method B) m/z 576 (ES+, M-100) at 1.85 min Step 3: tert-butyl 2-((2'-((5-aminopentyl)oxy)-[1,1'-biphenyl]-3-yl)methyl)-3-(ethylsulfonamido)pyrrolidine-1-carboxylate_cis racemic

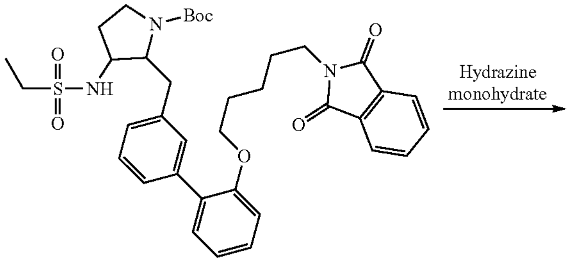

-continued

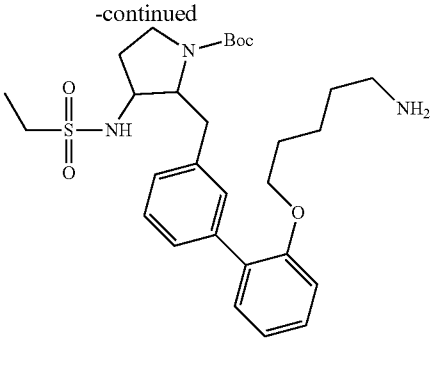

To a solution of tert-butyl 2-((2'-((5-(1,3-dioxoisoindolin-2-yl)pentyl)oxy)-[1,1'-biphenyl]-3-yl)methyl)-3-(ethylsulfonamido)pyrrolidine-1-carboxylate_cis racemic (376 mg, 0.56 mmol) in ethanol (5 mL) was added hydrazine hydrate (271 μL, 5.56 mmol) and the mixture stirred at room temperature for 2 h. The reaction was partitioned between EtOAc (25 mL) and sat. brine (25 mL), the organic layer separated, dried over $MgSO_4$, filtered and concentrated in vacuo. The resulting residue was purified by flash column chromatography eluting with 0%-20% MeOH+10% 7 N $NH_3$/MeOH in DCM to afford the title compound (111 mg, 36% yield) as a colourless gum. LCMS (method B) m/z 546 (ES+, M+H) at 1.96 min Step 4: N-(2-((2'-((5-aminopentyl)oxy)-[1,1'-biphenyl]-3-yl)methyl)pyrrolidin-3-yl)ethanesulfonamide dihydrochloride_cis racemic

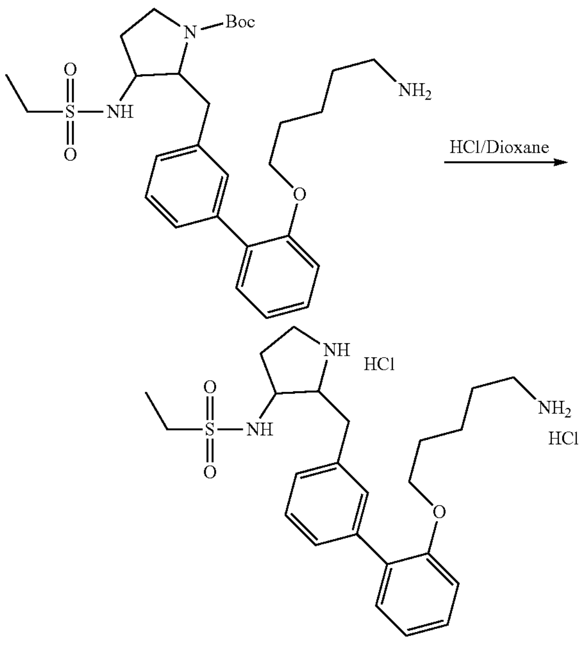

To a solution of tert-butyl 2-((2'-((5-aminopentyl)oxy)-[1,1'-biphenyl]-3-yl)methyl)-3-(ethylsulfonamido)pyrrolidine-1-carboxylate_cis racemic (111 mg, 0.20 mmol) in 1,4-dioxane (4.0 mL) and was added 4 M HCl in dioxane (0.51 mL, 2.03 mmol) and the mixture stirred at room temperature for 2 hrs. The reaction was concentrated in vacuo to afford the title compound (160 mg, 98% yield) as a light brown gum. LCMS (method B) m/z 446 (ES+, M+H) at 1.72 min Step 5: N-(5-oxo-12-oxa-6-aza-4(2,1)-pyrrolidina-1(1,2),2(1,3)-dibenzenacyclo-dodecaphane-43-yl) ethanesulfonamide_cis racemic (Compound No. A1-23)

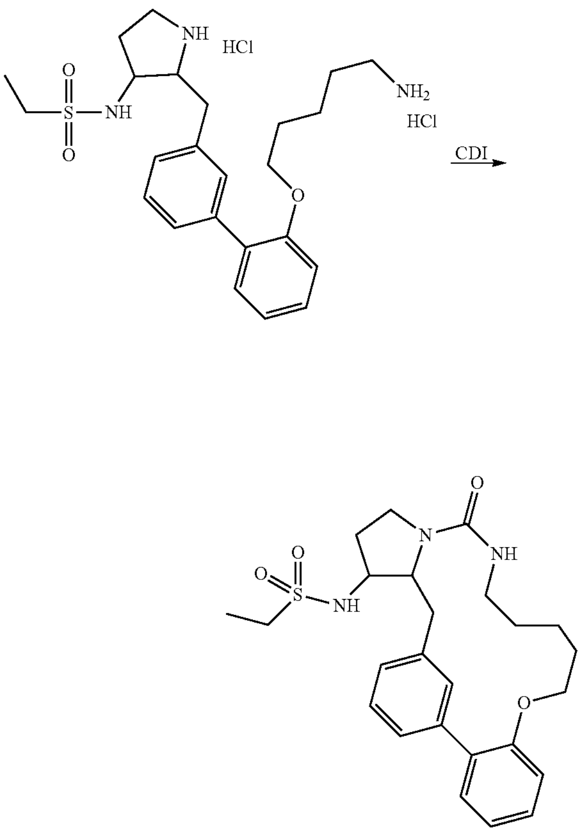

To a solution N-(2-((2'-((5-aminopentyl)oxy)-[1,1'-biphenyl]-3-yl)methyl)pyrrolidin-3-yl)ethanesulfonamide dihydrochloride_cis racemic of (105 mg, 0.20 mmol) in THF (16 mL) and DMF (4.0 mL) was added DIPEA (0.14 mL, 0.81 mmol) followed by CDI (39 mg, 0.24 mmol) and the mixture was stirred at room temperature for 2 h. The reaction was then heated at 70 °C for 1 h. The reaction was diluted with EtOAc (25 mL), washed with 10% citric acid (10 mL), sat. brine (10 mL), the organic layer separated and concentrated in vacuo. The resulting oil was purified by reverse phase flash column chromatography (gradient 10% to 100% MeOH in $H_2O$+0.2% $NH_4OH$) to afford the title compound (37 mg, 38% yield) as an off-white solid. $^1H$ NMR (400 MHz, DMSO-$d_6$) δ 7.46 (s, 1H), 7.35-7.25 (m, 5H), 7.21 (dt, 1H), 7.11-7.06 (m, 1H), 7.01 (td, 1H), 5.19 (t, 1H), 4.18-4.09 (m, 1H), 4.02 (dq, 2H), 3.77 (s, 1H), 3.24-3.12 (m, 2H), 3.07-2.87 (m, 4H), 2.58 (td, 2H), 2.06-1.96 (m, 1H), 1.76 (t, 1H), 1.68-1.55 (m, 2H), 1.24 (t, 2H), 1.18 (t, 3H), 1.11 (d, 2H). LCMS (method E): m/z 472 $(M+H)^+$ (ES+) at 4.21 min Example 27. Synthesis of Compound No. A1-16

Step 1: tert-butyl 2-((3',5'-difluoro-2'-hydroxy-[1,1'-biphenyl]-3-yl)methyl)-3-(ethylsulfonamido)pyrrolidine-1-carboxylate_cis racemic

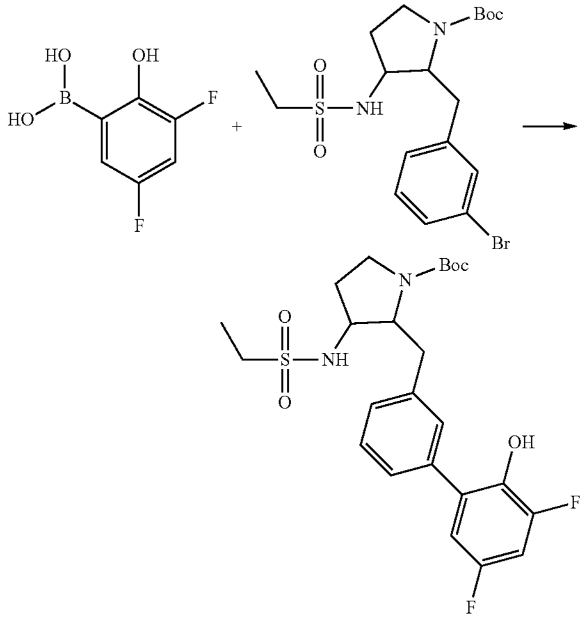

To a solution of 2-(3-bromobenzyl)-3-(ethylsulfonamido) pyrrolidine-1-carboxylate_cis racemic (Intermediate 2) (537 mg, 1.2 mmol) and tripotassium phosphate 1 M solution (4.8 mL, 4.8 mmol) in THF (12 mL) was added 3,5-difluoro-2-hydroxyphenylboronic acid (209 mg, 1.2 mmol) and XPhos-Pd-G3 (51 mg, 0.06 mmol). The reaction was heated at 70 °C for 2 h, extracted into EtOAc (50 mL), washed with water (25 mL), sat. brine (25 mL), the organic layer separated and concentrated in vacuo. The resulting residue was purified by flash column chromatography eluting with 0%-100% EtOAc in iso-hexane to afford the title compound (565 mg, 95% yield) as an off white solid. LCMS (method D) m/z 497 (ES+, M+H) at 2.15 min Step 2: tert-butyl 2-((3',5'-difluoro-2'-(((trifluoromethyl)sulfonyl)oxy)-[1,1'-biphenyl]-3-yl)methyl)-3-(ethylsulfonamido)pyrrolidine-1-carboxylate_cis racemic (Intermediate 10)

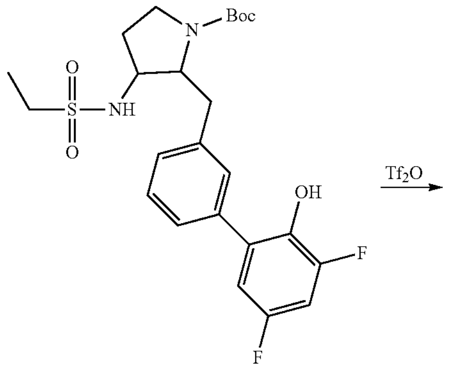

-continued

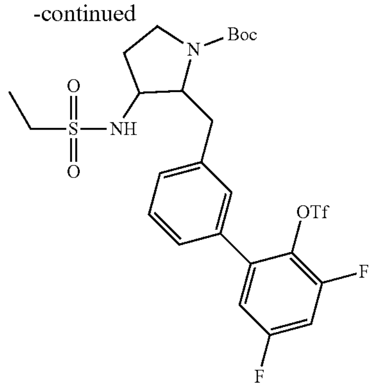

To a suspension of tert-butyl 2-((3',5'-difluoro-2'-hydroxy-[1,1'-biphenyl]-3-yl)methyl)-3-(ethylsulfonamido) pyrrolidine-1-carboxylate_cis racemic (565 mg, 1.14 mmol) in dichloromethane (12 mL) at 0 °C was added $Et_3N$ (0.48 mL, 3.41 mmol) and trifluoromethanesulfonic anhydride (0.23 mL, 1.37 mmol) and the reaction stirred at room temperature for 1 h, washed with water (10 mL), the aqueous layer extracted with dichloromethane (3×10 mL) the organics separated and concentrated in vacuo. to afford the title compound as a brown oil. LCMS (method D) m/z 629 (ES+, M+H) at 1.69 min Step 3: tert-butyl 2-((2'-(5-(1,3-dioxoisoindolin-2-yl)pent-1-yn-1-yl)-3',5'-difluoro-[1,1'-biphenyl]-3-yl) methyl)-3-(ethylsulfonamido)pyrrolidine-1-carboxylate_cis racemic

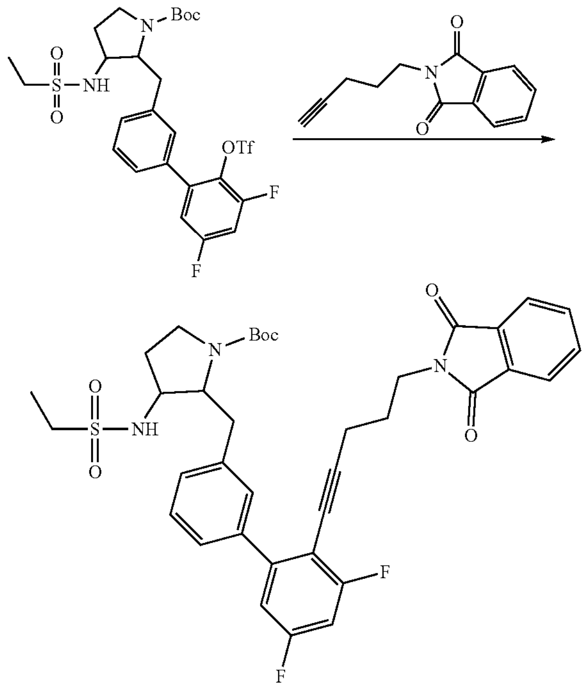

A mixture of bis(acetonitrile)dichloropalladium(II) (7 mg, 0.03 mmol), 2-Dicyclohexylphosphino-2',4',6'triisopropylbiphenyl (42 mg, 0.08 mmol), cesium carbonate (552 mg, 1.69 mmol) and tert-butyl 2-((3',5'-difluoro-2'-(((trifluoromethyl)sulfonyl)oxy)-[1,1'-biphenyl]-3-yl)methyl)-3-(ethylsulfonamido)pyrrolidine-1-carboxylate_cis racemic, Intermediate 10 (355 mg, 0.56 mmol) in MeCN (7.0 mL) was stirred at room temperature for 30 min. To the reaction was then added N-(4-Pentynyl)phthalimide (0.05 mL, 1.13 mmol) and the reaction heated at 70 °C for 18 h. The reaction was partitioned between dichloromethane (20 mL) and water (20 mL), the organics were separated, dried (frit) and concentrated to give a residue which was purified by flash column chromatography [gradient 0% to 100% Ethyl Acetate in Iso-hexane] to afford the title compound (190 mg, 48% yield) as a brown foam. LCMS (method D) m/z 629 (ES+, M+H) at 1.69 min Step 4: tert-butyl 2-((2'-(5-(1,3-dioxoisoindolin-2-yl)pentyl)-3',5'-difluoro-[1,1'-biphenyl]-3-yl) methyl)-3-(ethylsulfonamido)pyrrolidine-1-carboxylate_cis racemic

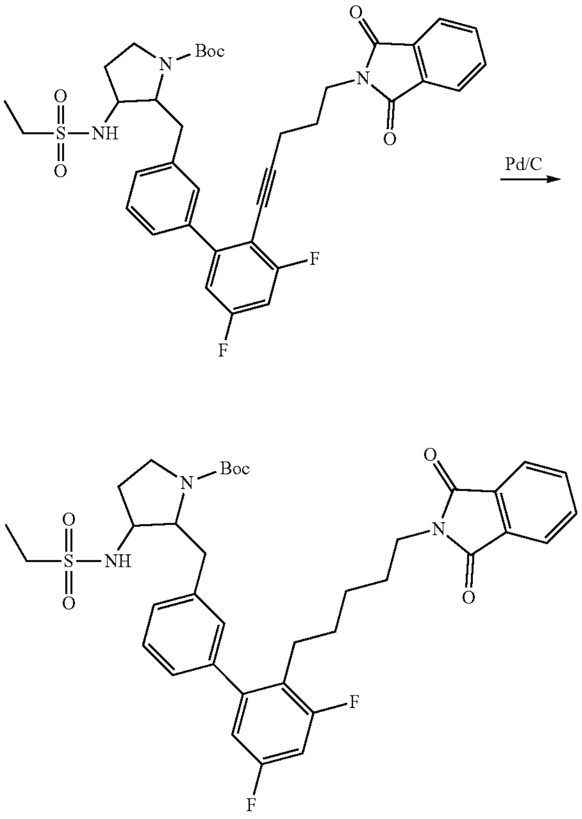

To a solution of tert-butyl 2-((2'-(5-(1,3-dioxoisoindolin-2-yl)pent-1-yn-1-yl)-3',5'-difluoro-[1,1'-biphenyl]-3-yl) methyl)-3-(ethylsulfonamido)pyrrolidine-1-carboxylate_cis racemic (190 mg, 0.27 mmol) in ethanol (14 mL) was added 10% palladium on carbon (DRY) (58 mg, 0.05 mmol) and the reaction stirred under 1 atm $H_2$ for 36 h. The crude reaction was filtered through a pad of celite washing with EtOAc (250 mL) and the filtrate was concentrated in vacuo to afford the title compound (150 mg, 78% yield) as a colourless oil. LCMS (method B) m/z 596 (ES+, M-100) at 1.95 min Step 5: tert-butyl 2-((2'-(5-aminopentyl)-3',5'-difluoro-[1,1'-biphenyl]-3-yl)methyl)-3-(ethylsulfonamido)pyrrolidine-1-carboxylate_cis racemic

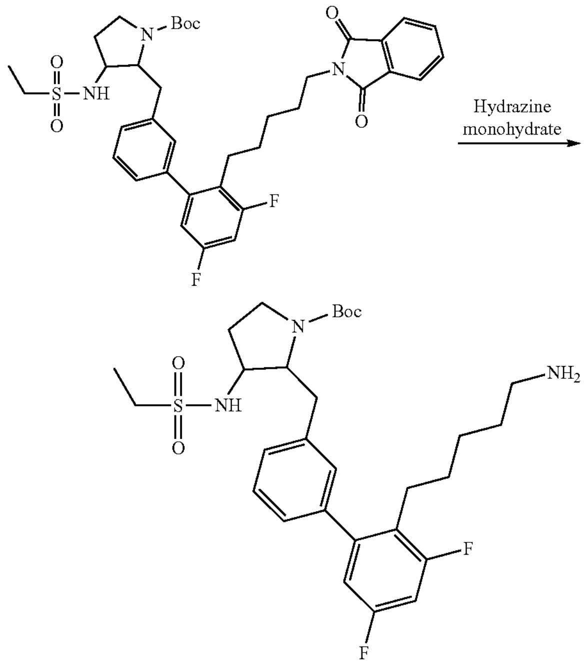

To a solution of tert-butyl 2-((2'-(5-(1,3-dioxoisoindolin-2-yl)pentyl)-3',5'-difluoro-[1,1'-biphenyl]-3-yl)methyl)-3-(ethylsulfonamido)pyrrolidine-1-carboxylate_cis racemic (150 mg, 0.22 mmol) in ethanol (2 mL) and was added hydrazine hydrate (105 μL, 2.16 mmol) and the mixture stirred at room temperature for 18 h. The reaction was partitioned between EtOAc (25 mL) and sat. brine (25 mL), the organic layer separated, dried over $MgSO_4$, filtered and concentrated in vacuo to afford the title compound (122 mg, 100% yield) as a yellow gum. LCMS (method B) m/z 566 (ES+, M+H) at 2.20 min Step 6: N-(2-((2'-(5-aminopentyl)-3',5'-difluoro-[1,1'-biphenyl]-3-yl)methyl)-pyrrolidin-3-yl)ethanesulfonamide dihydrochloride_cis racemic

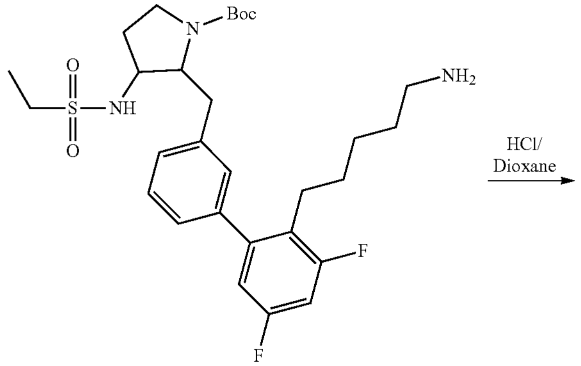

-continued

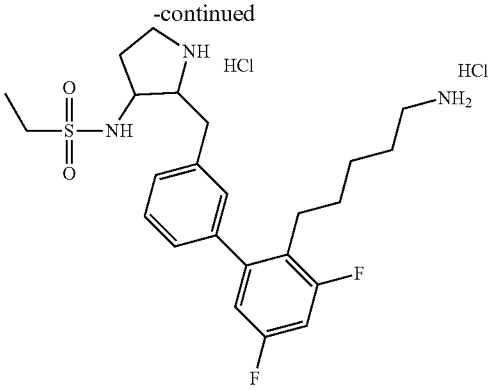

To a solution of 4 M HCl in dioxane (0.5 mL, 2.12 mmol) in 1,4-Dioxane (4 mL) was added tert-butyl 2-((2'-(5-aminopentyl)-3',5'-difluoro-[1,1'-biphenyl]-3-yl)methyl)-3-(ethylsulfonamido)pyrrolidine-1-carboxylate_cis racemic (120 mg, 0.21 mmol) and the mixture stirred at room temperature for 1 h. The reaction was concentrated in vacuo to afford the title compound (106 mg, 99% yield) as a brown solid. LCMS (method B) m/z 466 (ES+, M+H) at 2.13 min Step 7: N-($1^3$,$1^5$-difluoro-5-oxo-6-aza-4(2,1)-pyrrolidina-1-(1,2),2-(1,3)-dibenzena-cycloundecaphane-$4^3$-yl)ethanesulfonamide_cis racemic (Compound No. A1-16)

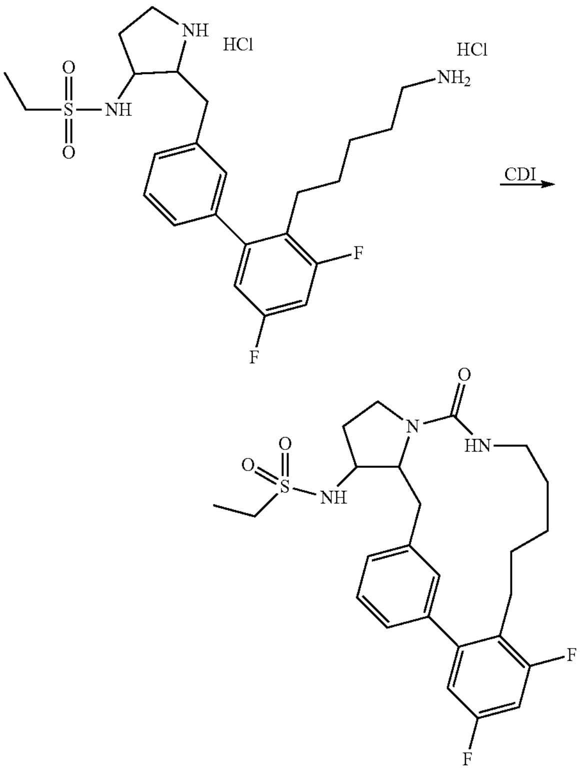

To a solution of N-(2-((2'-(5-aminopentyl)-3',5'-difluoro-[1,1'-biphenyl]-3-yl)methyl)pyrrolidin-3-yl)ethanesulfonamide dihydrochloride_cis racemic (106 mg, 0.21 mmol) and CDI (38 mg, 0.23 mmol) in DMF (4 mL) was added DIPEA (0.07 mL, 0.42 mmol) and the mixture was stirred at room temperature for 1 h. The reaction was partitioned between dichloromethane (10 mL) and water (20 mL), the organics were separated, dried (frit) and concentrated to give a residue which was purified by prep HPLC using a gradient of 40-70% to afford the title compound (11 mg, 11% yield) as a white solid. $^1$H NMR (400 MHz, $CDCl_3$) 7.36-7.28 (1H, m), 7.26-7.20 (2H, m), 7.13-7.08 (1H, m), 6.76-6.65 (2H, m), 4.59 (1H, d), 4.05 (1H, ddd), 3.87-3.75 (1H, m), 3.69-3.59 (1H, m), 3.32 (1H, ddd), 3.26-3.12 (2H, m), 3.12-3.02 (3H, m), 2.84-2.62 (2H, m), 2.38-2.18 (2H, m), 1.96-1.82 (1H, m), 1.54-1.23 (6H, m), 1.00-0.74 (2H, m). LCMS (method E): m/z 492 $(M+H)^+$ (ES+) at 4.48 min.

Example 28. Synthesis of Compound No. A1-29

Step 1: methyl hept-6-ynoate (Intermediate 11)

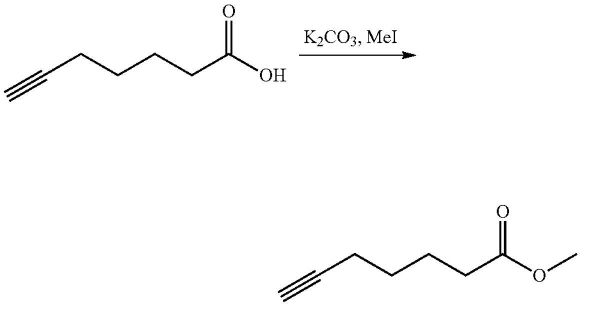

To a mixture of 6-heptynoic acid (1.0 g, 7.93 mmol) and $K_2CO_3$ (1.64 g, 11.9 mmol) in DMF (20 mL) was added iodomethane (691 μL, 11.1 mmol) and the reaction stirred at room temperature for 72 h. The reaction was extracted into EtOAc (50 mL), washed with water (2×50 mL), sat. brine (50 mL), the organic layer separated and dried over $MgSO_4$. The solvent was removed in vacuo to afford the title compound (903 mg, 81% yield) as a colourless oil. $^1$H NMR (400 MHz, Chloroform-d) δ 3.67 (s, 3H), 2.34 (t, 2H), 2.22 (td, 2H), 1.95 (t, 1H), 1.81-1.70 (m, 2H), 1.62-1.56 (m, 2H).

Step 2: tert-butyl 2-((3',5'-difluoro-2'-(7-methoxy-7-oxohept-1-yn-1-yl)-[1,1'-biphenyl]-3-yl)methyl)-3-(ethylsulfonamido)pyrrolidine-1-carboxylate_cis racemic

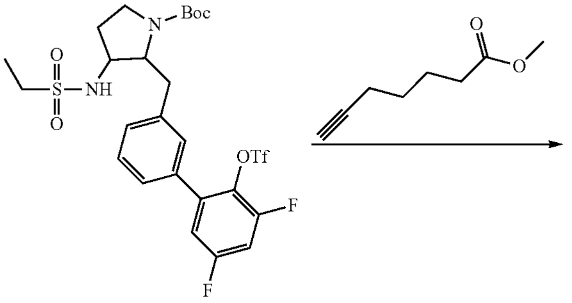

-continued

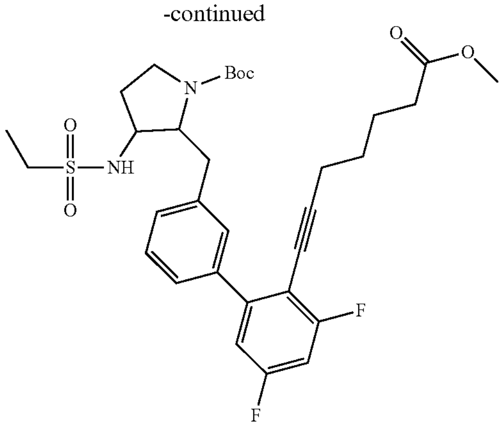

A solution of bis(acetonitrile)dichloropalladium(II) (6 mg, 0.02 mmol), 2-dicyclohexylphosphino-2',4',6'triisopropylbiphenyl (35 mg, 0.07 mmol), cesium carbonate (472 mg, 1.45 mmol) and tert-butyl 2-((3',5'-difluoro-2'-(((trifluoromethyl)sulfonyl)oxy)-[1,1'-biphenyl]-3-yl)methyl)-3(ethylsulfonamido)pyrrolidine-1-carboxylate_cis racemic, Intermediate 10 (303 mg, 0.48 mmol) in MeCN (5.0 mL) was stirred at room temperature for 30 min. To the reaction was then added methyl hept-6-ynoate, Intermediate 11 (88 mg, 0.63 mmol) and the reaction heated at 70 °C for 18 h. Further methyl hept-6-ynoate, Intermediate 11 (88 mg, 0.63 mmol) was added and the reaction heated at 70 °C for another 18 h. The reaction was partitioned between dichloromethane (20 mL) and water (20 mL), the organics were separated, dried (frit) and concentrated to give a residue which was purified by flash column chromatography [gradient 0% to 100% Ethyl Acetate in Iso-hexane] to afford the title compound (230 mg, 77% yield) as a brown foam. LCMS (method D) m/z 519 (ES+, M-Boc) at 2.65 min

Step 3: tert-butyl 2-((3',5'-difluoro-2'-(7-methoxy-7-oxoheptyl)-[1,1'-biphenyl]-3-yl)methyl)-3-(ethylsulfonamido)pyrrolidine-1-carboxylate_cis racemic

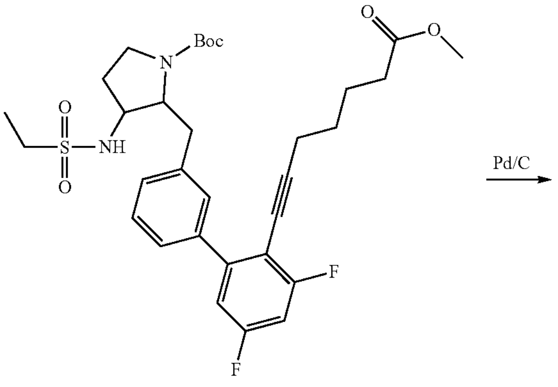

-continued

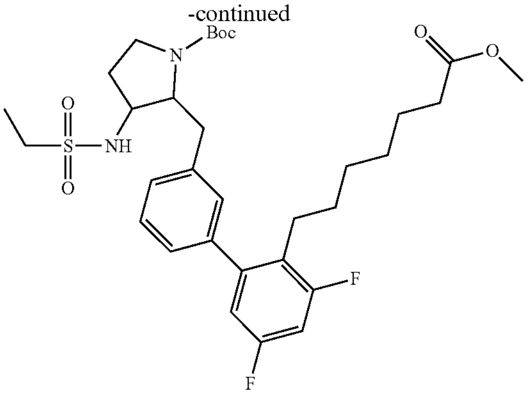

To a solution of tert-butyl 2-((3',5'-difluoro-2'-(7-methoxy-7-oxoheptyl)-[1,1'-biphenyl]-3-yl)methyl)-3-(ethylsulfonamido)pyrrolidine-1-carboxylate_cis racemic (230 mg, 0.37 mmol) in ethanol (18 mL) was added 10% Pd/C (DRY) (79 mg, 0.07 mmol) and the reaction stirred under 1 atm $H_2$ for 40 h. The crude reaction was filtered through a pad of celite washing with EtOAc (25 mL) and the filtrate was concentrated in vacuo to afford the title compound (218 mg, 94% yield) as a yellow oil. LCMS (method D) m/z 523 (ES+, M-Boc) at 2.78 min Step 4: 7-(3'-((1-(tert-butoxycarbonyl)-3-(ethylsulfonamido)pyrrolidin-2-yl)-methyl)-3,5-difluoro-[1,1'-biphenyl]-2-yl)heptanoic acid_cis racemic

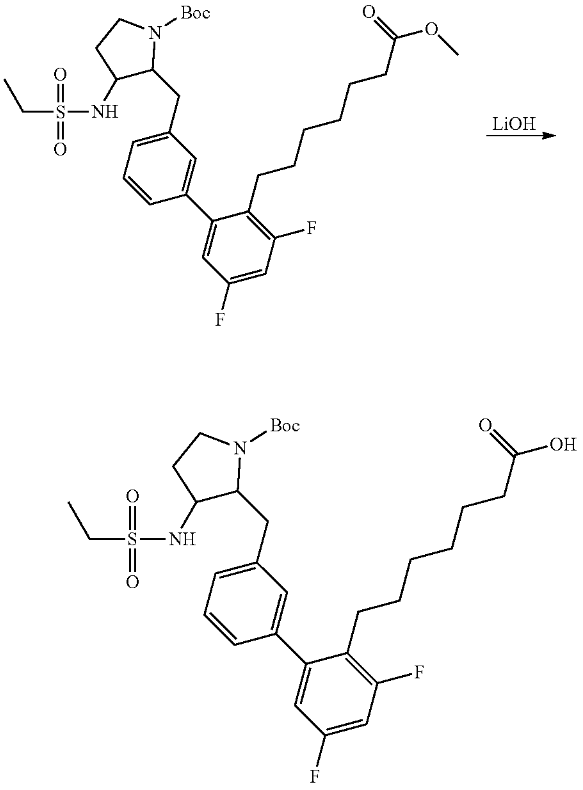

To a solution of tert-butyl 2-((3',5'-difluoro-2'-(7-methoxy-7-oxoheptyl)-[1,1'-biphenyl]-3-yl)methyl)-3-(ethylsulfonamido)pyrrolidine-1-carboxylate_cis racemic (218 mg, 0.35 mmol) in THF (3 mL) and water (1 mL) was added lithium hydroxide monohydrate (44 mg, 1.05 mmol) and the mixture was stirred at room temperature for 18 h. The reaction was acidified with 1 M HCl (10 mL), extracted into EtOAc (25 mL), the organic layer separated, dried over $MgSO_4$, filtered and the solvent removed in vacuo to afford the title compound (210 mg, 98% yield) as a colourless gum. LCMS (method D) m/z 509 (ES+, M-Boc) at 1.69 min Step 5: 7-(3'-((3-(ethylsulfonamido)pyrrolidin-2-yl)methyl)-3,5-difluoro-[1,1'-biphenyl]-2-yl)heptanoic acid hydrochloride_cis racemic

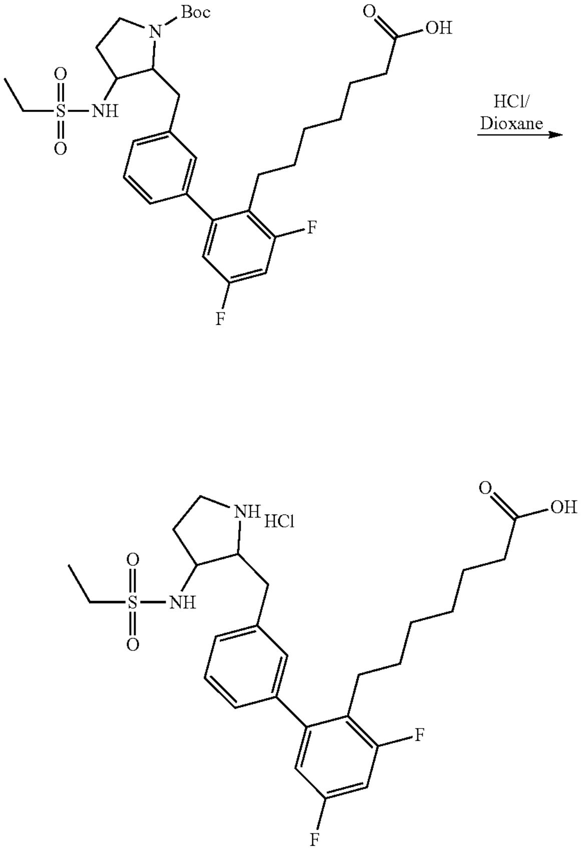

To a solution of 4 M HCl in dioxane (0.88 mL, 3.5 mmol) in 1,4-dioxane (3.0 mL) was added 7-(3'-((1-(tert-butoxycarbonyl)-3-(ethylsulfonamido)pyrrolidin-2-yl)methyl)-3,5-difluoro-[1,1'-biphenyl]-2-yl)heptanoic acid_cis racemic (213 mg, 0.35 mmol) and the mixture stirred at room temperature for 18 h. The reaction was concentrated in vacuo to afford the title compound (190 mg, 99% yield) as a white solid. LCMS (method D) m/z 509 (ES+, M+H) at 1.60 min Step 6: N-($1^3$,$1^5$-difluoro-5-oxo-4(2,1)-pyrrolidina-1(1,2),2(1,3)-dibenzenacyclo-undecaphane-$4^3$-yl)ethanesulfonamide_cis racemic (Compound No. A1-29)

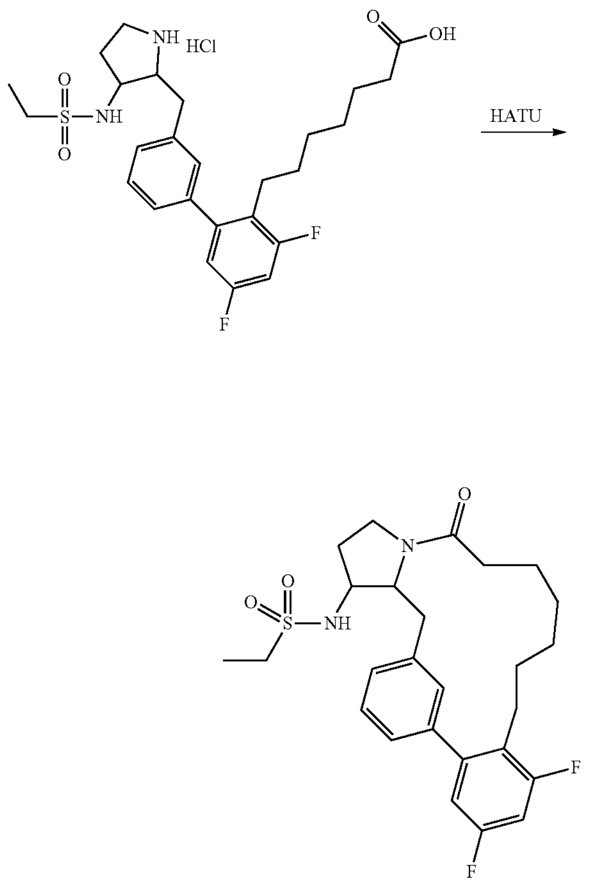

To a solution of 7-(3'-((3-(ethylsulfonamido)pyrrolidin-2-yl)methyl)-3,5-difluoro-[1,1'-biphenyl]-2-yl)heptanoic acid hydrochloride_cis racemic (190 mg, 0.35 mmol) and DIPEA (0.24 mL, 1.39 mmol) in dichloromethane (30 mL) was added HATU (199 mg, 0.52 mmol) and the mixture was stirred at room temperature for 18 h. The reaction was partitioned between dichloromethane (10 mL) and water (20 mL), the organics were separated, dried (frit) and concentrated to give a residue was purified by prep HPLC (50-80% organic in aqueous) to afford the title compound (15 mg, 8% yield) as an off-white solid. $^1H$ NMR (400 MHz, $CDCl_3$) 7.39-7.20 (1H, m), 7.17-7.11 (2H, m), 7.09-6.96 (1H, m), 6.77-6.59 (2H, m), 4.78-4.66 (1H, m), 4.25 (1H, ddd,), 3.91-3.79 (1H, m), 3.79-3.68 (1H, m), 3.51-3.33 (2H, m), 3.22-2.99 (3H, m), 2.76-2.47 (2H, m), 2.46-2.22 (2H, m), 2.16-1.96 (2H, m), 1.96-1.79 (1H, m), 1.73-1.40 (4H, m), 1.40-1.31 (3H, m), 1.26-1.03 (1H, m), 1.02-0.55 (1H, m). LCMS (method E): m/z 491 $(M+H)^+$ (ES+) at 4.78 min.

Example 29. Synthesis of Compound No. A1-1

Step 1: tert-butyl 2-((2'-(5-methoxy-5-oxopent-1-yn-1-yl)-[1,1'-biphenyl]-3-yl)-methyl)-3-(methylsulfonamido)piperidine-1-carboxylate_cis racemic

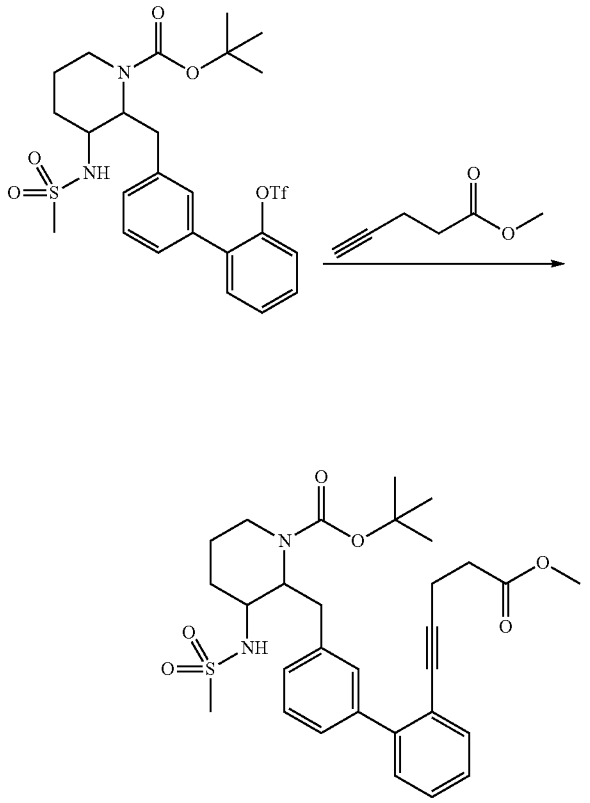

To a solution of bis(acetonitrile)dichloropalladium(II) (28 mg, 0.11 mmol), 2-dicyclohexylphosphino-2',4',6'triisopropylbiphenyl (160 mg, 0.33 mmol), cesium carbonate (2.12 g, 6.51 mmol) and tert-butyl 3-(methylsulfonamido)-2-((2'-(((trifluoromethyl)-sulfonyl)oxy)-[1,1'-biphenyl]-3-yl)methyl)piperidine-1-carboxylate_cis racemic, Intermediate 5 (1.29 g, 2.17 mmol) in MeCN (32 mL) was added methyl pent-4-ynoate (487 mg, 4.34 mmol) and the reaction heated at 70 °C for 18 h. The reaction mixture was diluted with EtOAc (50 mL), washed with water (25 mL), sat. brine (25 mL), the organic layer separated, dried over $MgSO_4$, filtered and concentrated in vacuo. The residue was purified by flash column chromatography on Biotage Isolera 25g silica cartridge eluting with 0%-100% Ethyl acetate/isohexane to afford the title compound (1.04 g, 86% yield) as a brown gum. LCMS (method B) m/z 572 (ES+, M+18) at 1.70 min Step 2: tert-butyl 2-((2'-(5-methoxy-5-oxopentyl)-[1,1'-biphenyl]-3-yl)methyl)-3-(methylsulfonamido) piperidine-1-carboxylate_cis racemic

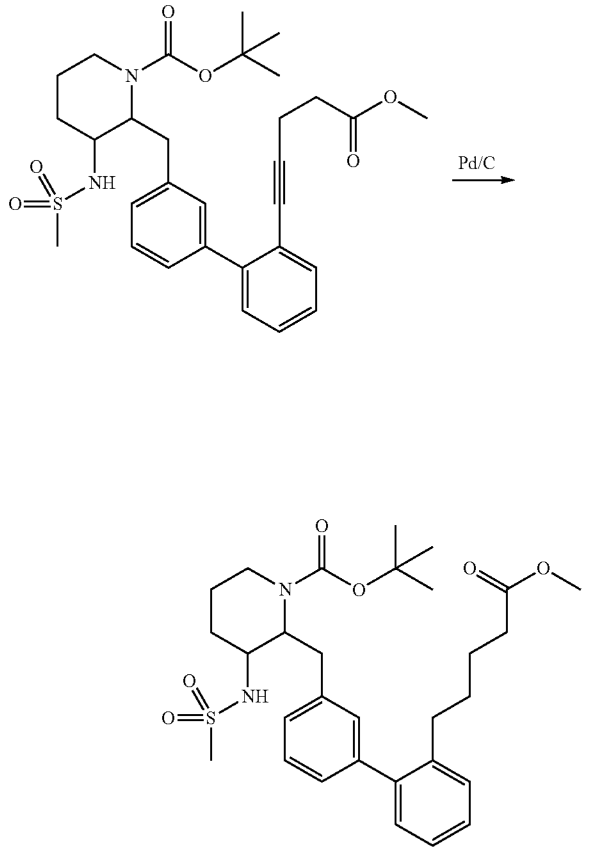

To a 20 mL microwave vial was added tert-butyl 2-((2'-(5-methoxy-5-oxopent-1-yn-1-yl)-[1,1'-biphenyl]-3-yl) methyl)-3-(methylsulfonamido)piperidine-1-carboxylate-_cis racemic (1.04 g, 1.87 mmol) in methanol (19 mL). To this was added ammonium formate (828 mg, 13.12 mmol) and 10% Pd/C (DRY) (399 mg, 0.37 mmol) and the reaction heated at 60 °C for 1 h under microwave irradiation. To the reaction was added further 10% Pd/C (DRY) (399 mg, 0.37 mmol) and ammonium formate (828 mg, 13.12 mmol) and the reaction heated at 80 °C for 2 h. The reaction was filtered through a pad of celite, washing with EtOAc (2×25 mL). The solvent was removed in vacuo and the resulting oil purified by flash column chromatography on Biotage Isolera 25 g silica cartridge eluting with 0%-100% Ethyl acetate/isohexane to afford the title compound (663 mg, 63% yield) as a colourless oil. LCMS (method B) m/z 576 (ES+, M+18) at 1.80 min Step 3: 5-(3'-((1-(tert-butoxycarbonyl)-3-(methylsulfonamido)piperidin-2-yl)-methyl)-[1,1'-biphenyl]-2-yl)pentanoic acid_cis racemic

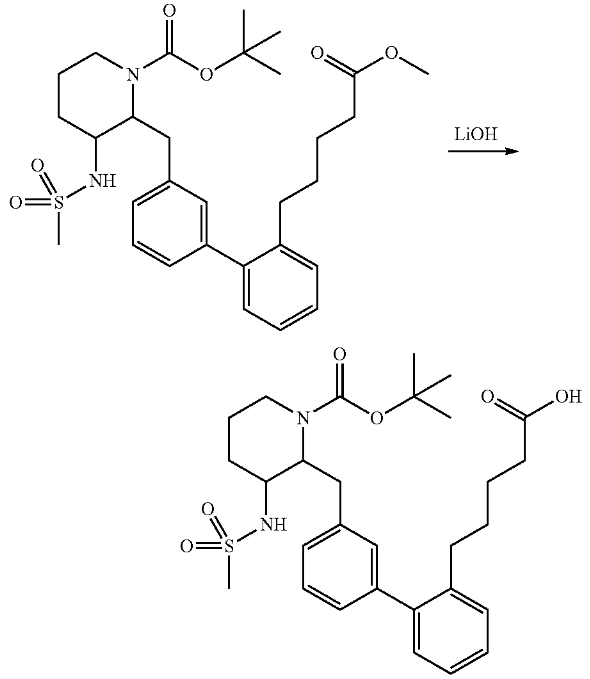

To a solution of tert-butyl 2-((2'-(5-methoxy-5-oxopentyl)-[1,1'-biphenyl]-3-yl)methyl)-3-(methylsulfonamido)piperidine-1-carboxylate_cis racemic (663 mg, 1.19 mmol) in THF (9 mL) and water (3 mL) was added lithium hydroxide monohydrate (149 mg, 3.56 mmol) and the mixture was stirred at room temperature for 18 h. The reaction was acidified with 1 M HCl, extracted into EtOAc (25 mL), the organic layer separated, dried over $MgSO_4$, filtered and the solvent removed in vacuo to afford the title compound (532 mg, 82% yield) as a yellow gum. LCMS (method B) m/z 445 (ES+, M-Boc) at 0.88 min Step 4: 5-(3'-((3-(methylsulfonamido)piperidin-2-yl) methyl)-[1,1'-biphenyl]-2-yl)-pentanoic acid hydrochloride_cis racemic

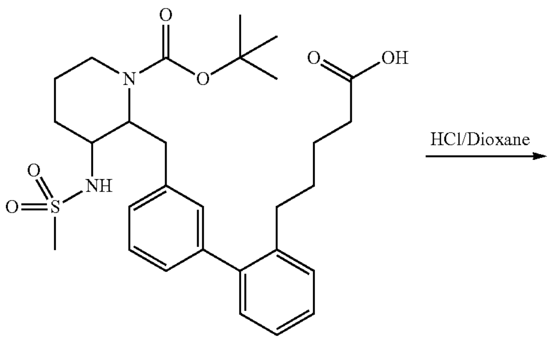

-continued

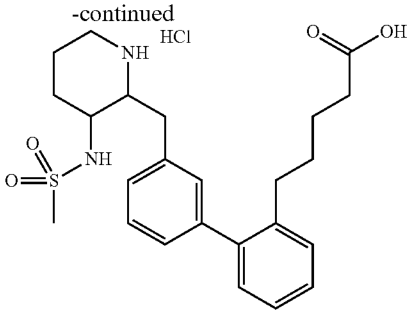

To a solution of 5-(3'-((1-(tert-butoxycarbonyl)-3-(methylsulfonamido)piperidin-2-yl)methyl)-[1,1'-biphenyl]-2-yl) pentanoic acid_cis racemic (532 mg, 0.98 mmol) in 1,4-dioxane (10 mL) was added 4 M HCl in dioxane (2.5 mL, 9.8 mmol) and the reaction stirred at room temperature for 18 h. The reaction was concentrated in vacuo to afford the title compound (469 mg, 99% yield) as a yellow foam. LCMS (method B) m/z 445 (ES+, M+H) at 0.77 min Step 5: N-(5-oxo-4(2,1)-piperidina-1(1,2),2(1,3)-dibenzenacyclononaphane-$4^3$-yl)-methanesulfonamide_cis racemic (Compound No. A1-1)

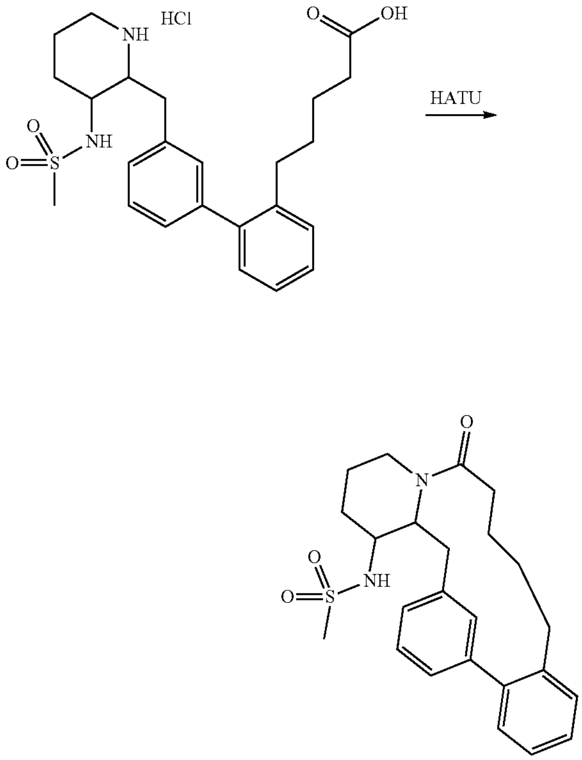

To a solution of 5-(3'-((3-(methylsulfonamido)piperidin-2-yl)methyl)-[1,1'-biphenyl]-2-yl)pentanoic acid hydrochloride_cis racemic (469 mg, 0.97 mmol) and DIPEA (0.67 mL, 3.9 mmol) in DMF (98 mL) was added HATU (557 mg, 1.46 mmol) and the mixture was stirred at room temperature for 2 h. The reaction was concentrated in vacuo, extracted into EtOAc (50 mL), washed with sat. brine (25 mL), the organic layer separated and concentrated in vacuo. The residue was purified by reverse phase flash column chromatography, 30 g Biotage® SNAP KP-C18-HS, eluting with 10% to 100% MeOH in $H_2O$+0.2% $NH_4OH$ to afford the title compound (113 mg, 27% yield) as a beige solid. $^1H$ NMR (400 MHz, DMSO-$d_6$) δ 7.40 (dd, 1H), 7.32 (t, 1H), 7.28-7.09 (m, 5H), 7.09-6.98 (m, 2H), 5.02 (dt, 1H), 3.73 (d, 1H), 3.32 (s, 2H), 3.00 (d, 3H), 2.96-2.69 (m, 3H), 2.69-2.59 (m, 1H), 2.41-2.26 (m, 1H), 1.93-1.61 (m, 4H), 1.42 (t, 2H), 1.27-0.82 (m, 3H). LCMS (method C): m/z 427 $(M+H)^+$ (ES+) at 3.88 min.

Example 30. Synthesis of Compound No. A1-2

Step 1: tert-butyl 2-((2'-(2-((tert-butoxycarbonyl)(methyl)amino)ethoxy)-[1,1'-biphenyl]-3-yl)methyl)-3-(methylsulfonamido)piperidine-1-carboxylate_cis racemic

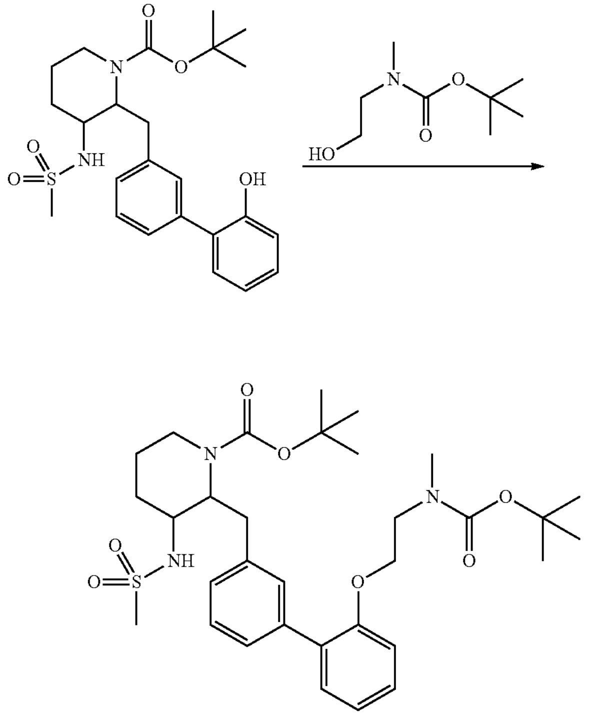

To a solution of tert-butyl 2-((2'-hydroxy-[1,1'-biphenyl]-3-yl)methyl)-3-(methyl-sulfonamido)piperidine-1-carboxylate_cis racemic (500 mg, 1.09 mmol) in THF (22 mL) at 0 °C was added triphenylphosphine (427 mg, 1.63 mmol) and diisopropyl azodicarboxylate (320 μL, 1.63 mmol) and the reaction stirred at room temperature for 1 h. The reaction was diluted with dichloromethane, washed with water, sat. brine, the organic layer separated, dried over $MgSO_4$, filtered and the solvent removed in vacuo. The resulting oil was purified by flash column chromatography on Biotage Isolera 10 g silica cartridge eluting with 0%-100% Ethyl acetate/isohexane. The solvent was removed in vacuo and the product further purified by reverse phase flash column chromatography, 30 g Biotage® SNAP KP-C18-HS, eluting with 10% to 100% MeOH in $H_2O$+0.2% $NH_4OH$ to afford the title compound (102 mg, 16% yield) as a colourless gum. LCMS (method B) m/z 618 (ES+, M-Boc) at 1.84 min Step 2: N-(2-((2'-(2-(methylamino)ethoxy)-[1,1'-biphenyl]-3-yl)methyl)piperidin-3-yl)methanesulfonamide dihydrochloride_cis racemic

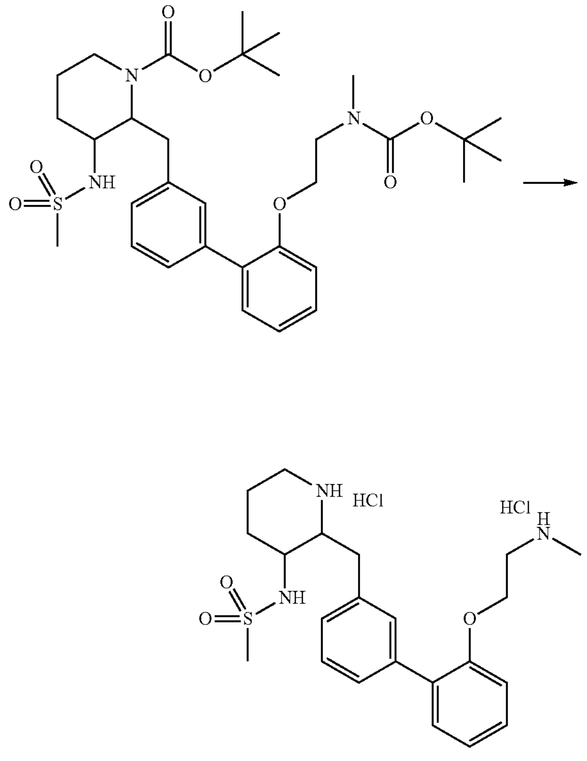

To a solution of tert-butyl 2-((2'-(2-((tert-butoxycarbonyl)(methyl)amino)ethoxy)-[1,1'-biphenyl]-3-yl)methyl)-3-(methylsulfonamido)piperidine-1-carboxylate_cis racemic (102 mg, 0.17 mmol) in 1,4-dioxane (3 mL) was added 4 M HCl in dioxane (10 eq) and the reaction stirred at room temperature for 18 h. The reaction was concentrated in vacuo to afford the title compound (81 mg, 100% yield) as a yellow foam. LCMS (method B) m/z 418 (ES+, M+H) at 1.32 min Step 3: N-(6-methyl-5-oxo-9-oxa-6-aza-4(2,1)-piperidina-1(1,2),2(1,3)-dibenzena-cyclo-nonaphane-$4^3$-yl)methanesulfonamide_cis racemic (Compound No. A1-2)

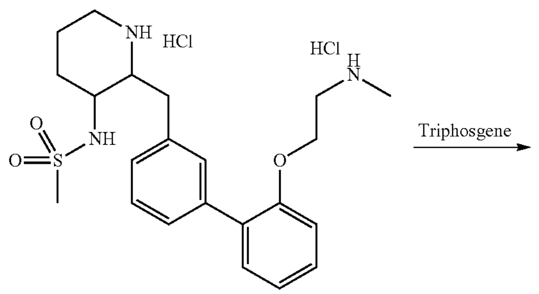

-continued

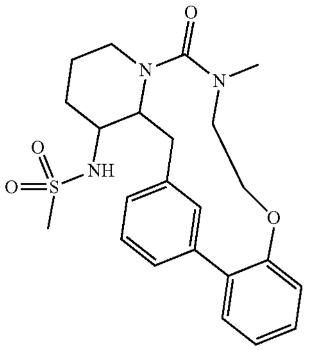

To a solution of N-(2-((2'-(2-(methylamino)ethoxy)-[1,1'-biphenyl]-3-yl)methyl)-piperidin-3-yl)methanesulfonamide dihydrochloride_cis racemic (81 mg, 0.17 mmol) and DIPEA (171 µL, 0.99 mmol) in dichloromethane (15 mL) was added triphosgene (17 mg, 0.06 mmol) as a solution in dichloromethane (5 mL) and the mixture was stirred at room temperature for 5 days. The reaction was washed with sat. $NaHCO_3$, the organic layer separated and concentrated in vacuo. The residue was purified by reverse phase HPLC (Phenomenex Gemini column, 100×30 mm, 5 µm, 30 mL/min, gradient of 30% to 60% (over 8.7 min) then 100% hold (1 min), solvents: Aqueous=Water with 0.2% of 28% Ammonia solution, Organic=Acetonitrile) to the title compound (2 mg, 3% yield) as a white solid. $^1H$ NMR (400 MHz, Methanol-$d_4$) δ 7.58-7.42 (m, 1H), 7.40 (s, 1H), 7.25-7.16 (m, 3H), 7.11-7.03 (m, 2H), 6.96 (t, 2H), 4.57-4.48 (m, 1H), 3.82 (d, 2H), 3.65 (q, 2H), 3.39-3.30 (m, 1H), 3.06-2.95 (m, 3H), 2.91 (d, 6H), 2.87 (d, J=5.2 Hz, 1H), 1.82-1.69 (m, 3H), 1.52 (dt, 1H). LCMS (method C): m/z 444 $(M+H)^+$ (ES+) at 3.52 min.

Example 31. Synthesis of Compound No. A1-27

Step 1: tert-butyl 2-((2'-(5-(1,3-dioxoisoindolin-2-yl)pent-1-yn-1-yl)-[1,1'-biphenyl]-3-yl)methyl)-3-(methylsulfonamido)piperidine-1-carboxylate_cis racemic

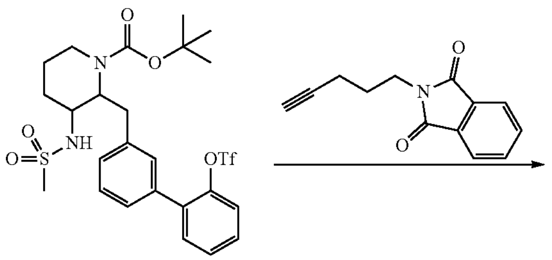

-continued

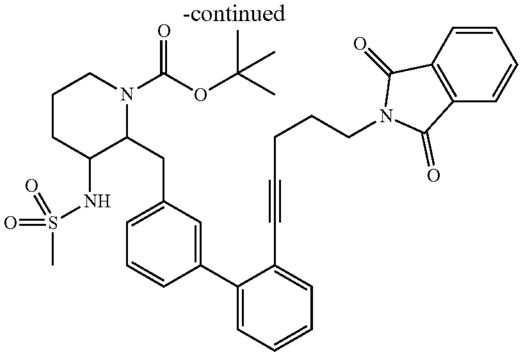

To a solution of bis(acetonitrile)dichloropalladium(II) (15 mg, 0.06 mmol), 2-Dicyclohexylphosphino-2',4',6'triisopropylbiphenyl (87 mg, 0.18 mmol), cesium carbonate (1.16 g, 3.54 mmol) and tert-butyl 3-(methylsulfonamido)-2-((2'-(((trifluoromethyl)sulfonyl)oxy)-[1,1'-biphenyl]-3-yl) methyl)piperidine-1-carboxylate_cis racemic, Intermediate 5 (700 mg, 1.18 mmol) in MeCN (24 mL) was added N-(4-pentynyl)phthalimide (519 mg, 2.36 mmol) and the reaction heated at 70 °C for 18 h. The reaction mixture was diluted with EtOAc (50 mL), washed with water (25 mL), sat. brine (25 mL), the organic layer separated, dried over $MgSO_4$, filtered and concentrated in vacuo. The residue was purified by flash column chromatography on Biotage Isolera 25 g silica cartridge eluting with 0%-80% ethyl acetate/isohexane to afford the title compound (261 mg, 34% yield) as a brown gum. LCMS (method B) m/z 556 (ES+, M-Boc) at 1.80 min Step 2: tert-butyl 2-((2'-(5-(1,3-dioxoisoindolin-2-yl)pentyl)-[1,1'-biphenyl]-3-yl)methyl)-3-(methylsulfonamido)piperidine-1-carboxylate_cis racemic

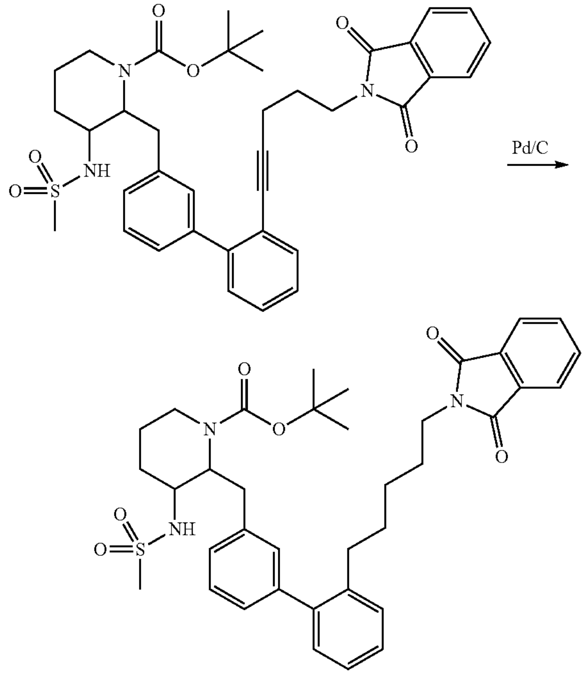

To a solution of tert-butyl 2-((2'-(5-(1,3-dioxoisoindolin-2-yl)pent-1-yn-1-yl)-[1,1'-biphenyl]-3-yl)methyl)-3-(methylsulfonamido)piperidine-1-carboxylate_cis racemic (490 mg, 0.75 mmol) in ethanol (30 mL) was added 10% Pd/C (DRY) (159 mg, 0.15 mmol) and the reaction stirred under 1 atm $H_2$ for 36 h. The reaction was filtered through a pad of celite, washing with EtOAc (2×25 mL). The solvent was removed in vacuo to afford the title compound (442 mg, 71% yield) as a yellow oil. LCMS (method B) m/z 560 (ES+, M-Boc) at 1.90 min Step 3: tert-butyl 2-((2'-(5-aminopentyl)-[1,1'-biphenyl]-3-yl)methyl)-3-(methyl-sulfonamido)piperidine-1-carboxylate_cis racemic

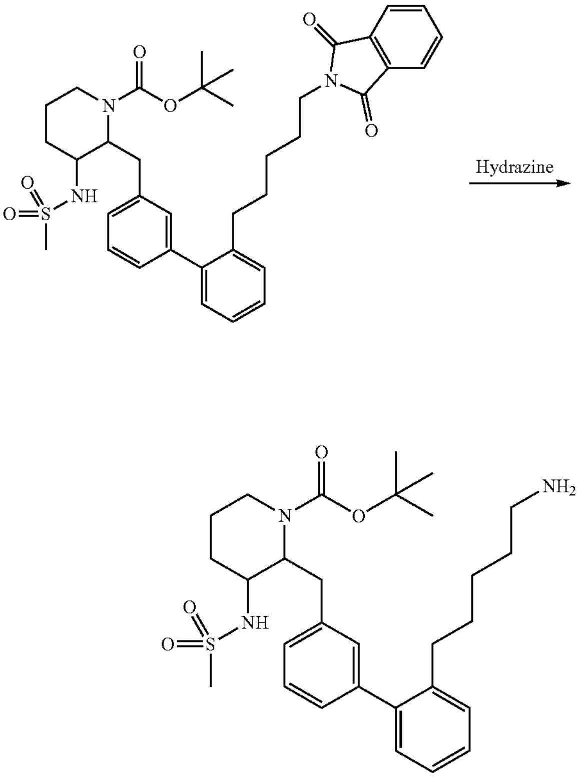

To a solution of tert-butyl 2-((2'-(5-(1,3-dioxoisoindolin-2-yl)pentyl)-[1,1'-biphenyl]-3-yl)methyl)-3-(methylsulfonamido)piperidine-1-carboxylate_cis racemic (442 mg, 0.53 mmol) in Ethanol (5 mL) and was added hydrazine hydrate (257 μL, 5.29 mmol) and the mixture stirred at room temperature for 18 h. The reaction was partitioned between EtOAc (25 mL) and sat. brine (25 mL), the organic layer separated, dried over $MgSO_4$, filtered and concentrated in vacuo to afford the title compound (280 mg, 99% yield) as a yellow gum. LCMS (method B) m/z 530 (ES+, M+H) at 2.09 min Step 4: N-(2-((2'-(5-aminopentyl)-[1,1'-biphenyl]-3-yl)methyl)piperidin-3-yl)-methanesulfonamide dihydrochloride_cis racemic

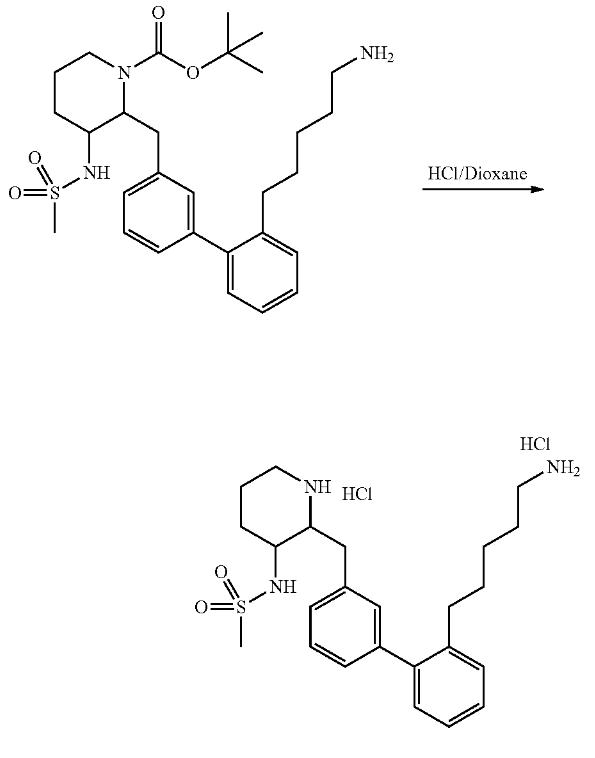

To a solution of tert-butyl 2-((2'-(5-aminopentyl)-[1,1'-biphenyl]-3-yl)methyl)-3-(methylsulfonamido)piperidine-1-carboxylate_cis racemic (28 mg, 0.53 mmol) in 1,4-dioxane (5 mL) was added 4 M HCl in dioxane (5.0 mL) and the reaction stirred at room temperature for 2 hrs. The reaction was concentrated in vacuo to afford the title compound (265 mg, 100% yield) as a yellow gum. LCMS (method B) m/z 430 (ES+, M+H) at 1.90 min Step 5: N-(5-oxo-6-aza-4(2,1)-piperidina-1(1,2),2(1,3)-dibenzenacyclo-undecaphane-4$^3$-yl)methanesulfonamide_cis racemic (Compound No. A1-27)

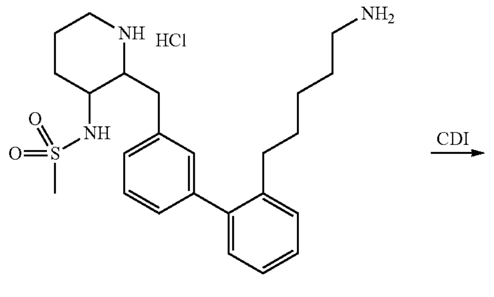

-continued

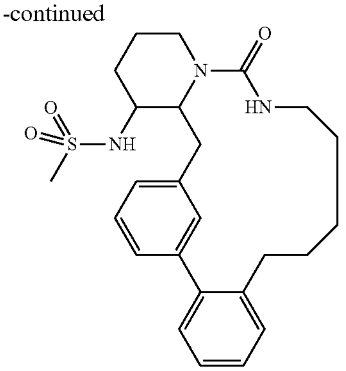

To a solution of N-(2-((2'-(5-aminopentyl)-[1,1'-biphenyl]-3-yl)methyl)piperidin-3-yl)methanesulfonamide dihydrochloride_cis racemic (265 mg, 0.53 mmol) in DMF (53 mL) and DIPEA (0.36 mL, 2.11 mmol) was added CDI (94 mg, 0.58 mmol) and the mixture was stirred at room temperature for 2 h and then heated at 70 °C for 1 h. The reaction was concentrated in vacuo, the product extracted with EtOAc (25 mL), washed with 10% citric acid (10 mL), sat. brine (10 mL), the organic layer separated and concentrated in vacuo. The resulting residue was purified by reverse phase flash column chromatography, 30 g Biotage® SNAP KP-C18-HS, eluting with 10% to 100% MeOH in $H_2O$+ 0.2% $NH_4OH$ to afford the title compound (54.5 mg, 23% yield) as a white solid. $^1H$ NMR (400 MHz, DMSO-$d_6$) δ 7.32-7.15 (m, 6H), 7.15-7.10 (m, 2H), 7.07 (dt, 1H), 5.85 (s, 1H), 4.82 (s, 1H), 3.62 (d, 1H), 3.15 (s, 1H), 2.98 (s, 3H), 2.96-2.79 (m, 3H), 2.72-2.55 (m, 3H), 1.79-1.57 (m, 4H), 1.31 (ddt, 3H), 1.09 (dt, 2H), 0.77 (t, 2H). LCMS (method C): m/z 456 $(M+H)^+$ (ES+) at 4.08 min.

Example 32. Synthesis of Compound No. A1-28

Step 1: tert-butyl 2-((2'-(7-methoxy-7-oxohept-1-yn-1-yl)-[1,1'-biphenyl]-3-yl)methyl)-3-(methylsulfonamido)piperidine-1-carboxylate_cis racemic

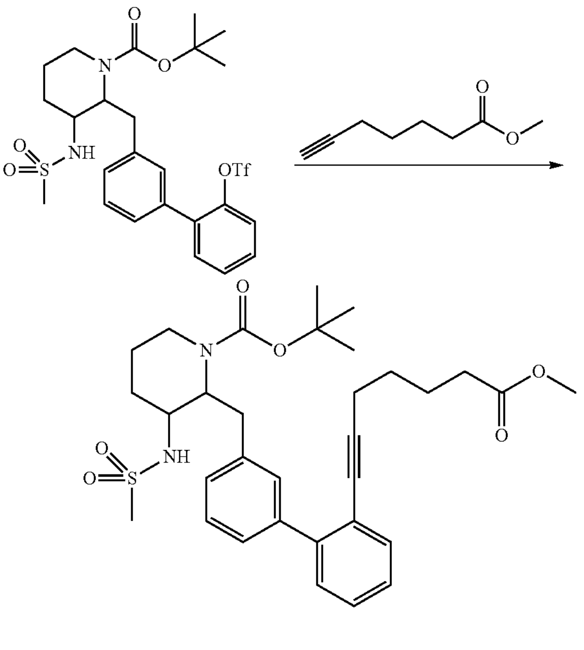

To a solution of bis(acetonitrile)dichloropalladium(II) (16 mg, 0.06 mmol), 2-Dicyclohexylphosphino-2',4',6'triisopropylbiphenyl (92 mg, 0.19 mmol), cesium carbonate (1.22 g, 3.75 mmol) and tert-butyl 3-(methylsulfonamido)-2-((2'-(((trifluoromethyl)sulfonyl)oxy)-[1,1'-biphenyl]-3-yl) methyl)piperidine-1-carboxylate_cis racemic, Intermediate 5 (740 mg, 1.25 mmol) in MeCN (25 mL) was added methyl hept-6-ynoate, Intermediate 11 (350 mg, 2.5 mmol) and the reaction heated at 70 °C for 18 h. The reaction mixture was diluted with EtOAc (50 mL), washed with water (25 mL), sat. brine (25 mL), the organic layer separated, dried over $MgSO_4$, filtered and concentrated in vacuo. The residue was purified by flash column chromatography on Biotage Isolera 25 g silica cartridge eluting with 0%-80% Ethyl acetate/isohexane. The fractions were combined and the solvent removed in vacuo to afford the title compound (557 mg, 57% yield) as a brown gum. LCMS (method D) m/z 483 (ES+, M-Boc) at 2.55 min Step 2: tert-butyl 2-((2'-(7-methoxy-7-oxoheptyl)-[1,1'-biphenyl]-3-yl)methyl)-3-(methylsulfonamido) piperidine-1-carboxylate_cis racemic

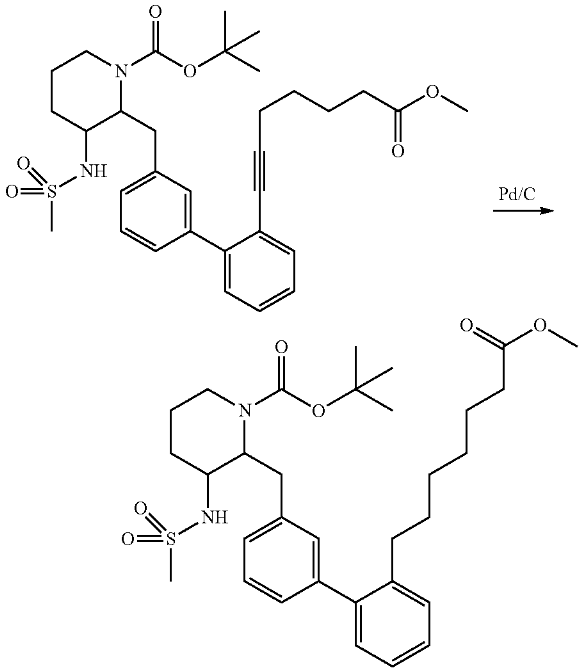

To a solution of tert-butyl 2-((2'-(7-methoxy-7-oxohept-1-yn-1-yl)-[1,1'-biphenyl]-3-yl)methyl)-3-(methylsulfonamido)piperidine-1-carboxylate_cis racemic (557 mg, 0.72 mmol) in ethanol (29 mL) was added 10% Pd/C (DRY) (153 mg, 0.14 mmol) and the reaction stirred under 1 atm $H_2$ for 18 h. The reaction was filtered through a pad of celite, washing with ethanol (2×25 mL). The solvent was removed in vacuo and the resulting oil purified by flash column chromatography, Biotage® Isolera SNAP KP-Sil 25 g silica cartridge eluting with 0%-100% EtOAc in iso-hexane. The product was further purified by reverse phase column chromatography, Biotage® 30 g SNAP KP-C18-HS, eluting with 10% to 100% MeOH in $H_2O$ afford the title compound (200 mg, 47% yield) as a colourless gum. LCMS (method B) m/z 487 (ES+, M-Boc) at 1.89 min Step 3: 7-(3'-((1-(tert-butoxycarbonyl)-3-(methylsulfonamido)piperidin-2-yl)-methyl)-[1,1'-biphenyl]-2-yl)heptanoic acid_cis racemic

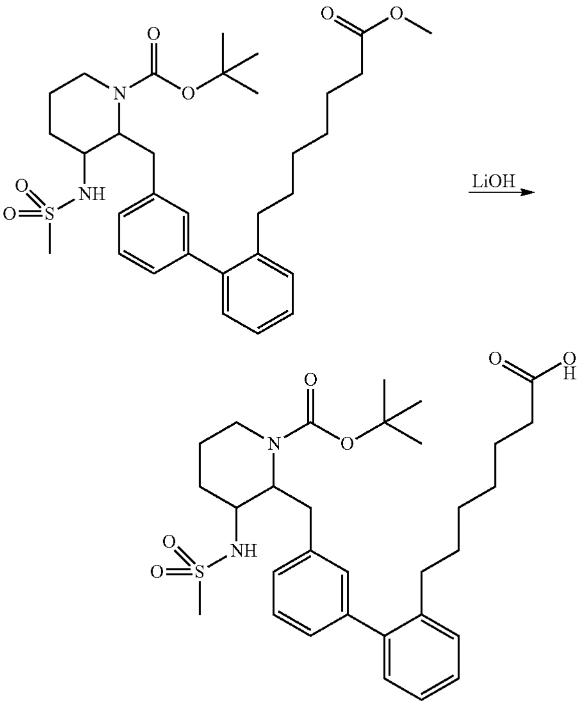

To a solution of tert-butyl 2-((2'-(7-methoxy-7-oxoheptyl)-[1,1'-biphenyl]-3-yl)methyl)-3-(methylsulfonamido)piperidine-1-carboxylate_cis racemic (200 mg, 0.34 mmol) in THF (9 mL) and water (3 mL) was added lithium hydroxide monohydrate (43 mg, 1.02 mmol) and the mixture was stirred at room temperature for 2 h. The reaction was acidified with 1 M HCl (10 mL), extracted into EtOAc (25 mL), the organic layer separated, dried over $MgSO_4$, filtered and the solvent removed in vacuo to afford the title compound (195 mg, 99% yield) as a colourless gum. LCMS (method B) m/z 473 (ES+, M-Boc) at 0.96 min Step 4: 7-(3'-((3-(methylsulfonamido)piperidin-2-yl) methyl)-[1,1'-biphenyl]-2-yl)heptanoic acid hydrochloride_cis racemic

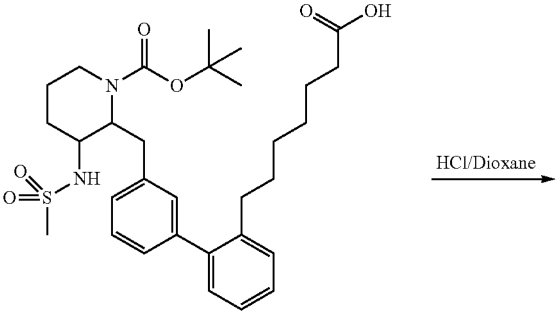

-continued

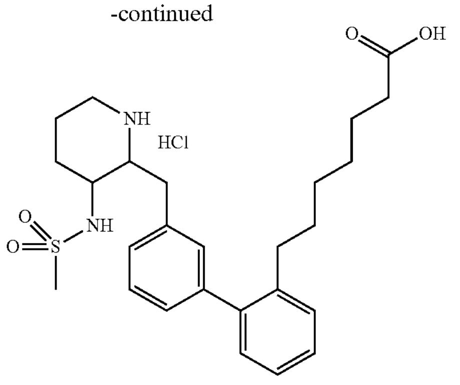

To a solution of 7-(3'-((1-(tert-butoxycarbonyl)-3-(methylsulfonamido)piperidin-2-yl)methyl)-[1,1'-biphenyl]-2-yl) heptanoic acid_cis racemic acid (195 mg, 0.34 mmol) in 1,4-dioxane (7 mL) and was added 4 M HCl in dioxane (0.85 mL, 3.4 mmol) and the mixture stirred at room temperature for 18 h. The reaction was concentrated in vacuo to afford the title compound (173 mg, 99% yield) as a colourless oil. LCMS (method B) m/z 473 (ES+, M+H) at 0.83 min Step 5: N-(5-oxo-4(2,1)-piperidina-1(1,2),2(1,3)-dibenzenacycloundecaphane-4$^3$-yl)methanesulfonamide_cis racemic (Compound No. A1-28)

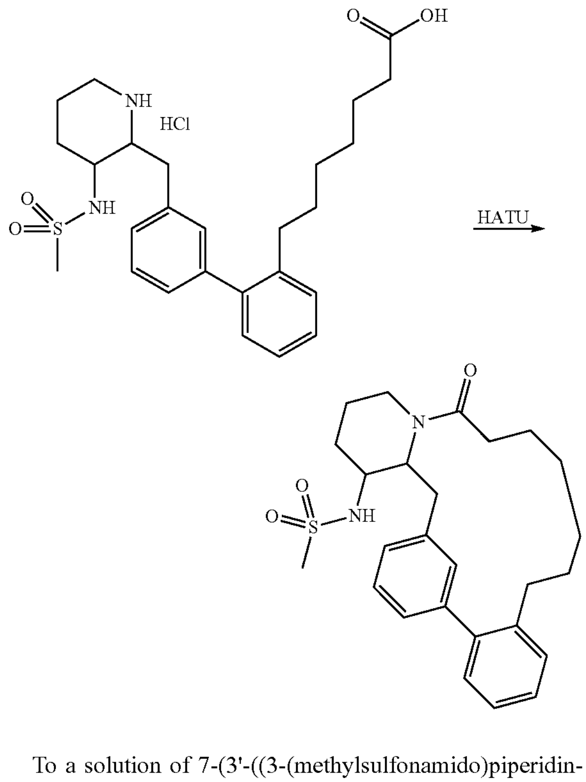

To a solution of 7-(3'-((3-(methylsulfonamido)piperidin-2-yl)methyl)-[1,1'-biphenyl]-2-yl)heptanoic acid hydrochloride_cis racemic (173 mg, 0.34 mmol) and DIPEA (0.24 mL, 1.36 mmol) in DMF (38 mL) was added HATU (194 mg, 0.51 mmol) and the mixture was stirred at room temperature for 2 h. The reaction was concentrated in vacuo, extracted into EtOAc (50 mL), washed with sat. brine (25 mL), the organic layer separated and concentrated in vacuo. The residue was purified by reverse phase flash column chromatography, 30 g Biotage® SNAP KP-C18-HS, eluting with 10% to 100% MeOH in $H_2O$+0.2% $NH_4OH$ to afford the title compound (104 mg, 67% yield) as a beige solid. $^1H$ NMR (400 MHz, DMSO-$d_6$) δ 7.51-6.95 (m, 9H), 4.36 (dd, 1H), 4.27-4.17 (m, 1H), 3.53 (s, 1H), 3.47-3.37 (m, 1H), 3.00 (d, 4H), 2.96 (d, 1H), 2.60 (t, 2H), 1.87-1.65 (m, 5H), 1.42 (s, 2H), 1.28 (s, 1H), 1.19-0.81 (m, 6H). LCMS (method C): m/z 455 $(M+H)^+$ (ES+) at 4.35 min.

Example 33. Synthesis of Compound No. A1-6

Step 1: tert-butyl 2-((2'-(4-methoxy-4-oxobutoxy)-[1,1'-biphenyl]-3-yl)methyl)-3-(methylsulfonamido) piperidine-1-carboxylate_cis racemic

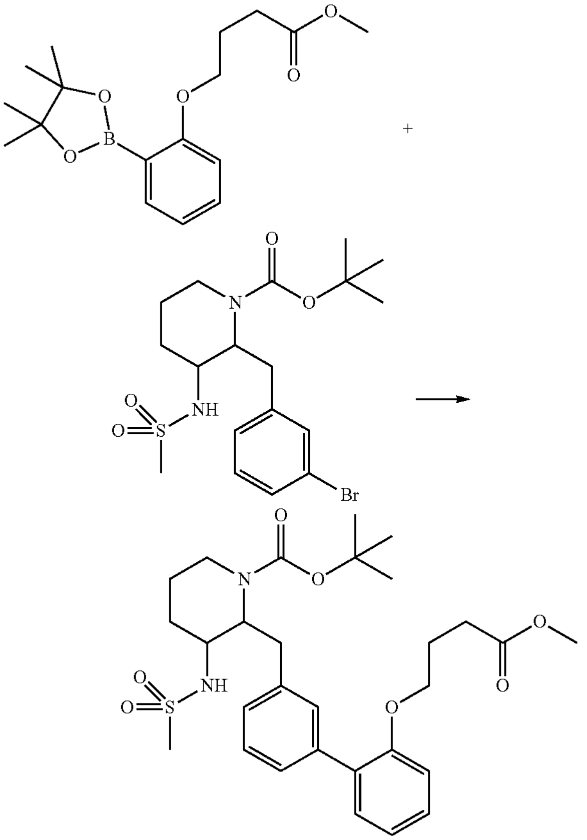

To a solution of tert-butyl 2-(3-bromobenzyl)-3-(methylsulfonamido)piperidine-1-carboxylate_cis racemic (Intermediate 3) (200 mg, 0.45 mmol) and methyl 4-[2-(4,4,5,5-tetramethyl-1,3,2-dioxaborolan-2-yl)phenoxy]butanoate, Intermediate 9 (143 mg, 0.45 mmol) in THF (9.0 mL) was added XPhos-Pd-G3 (19 mg, 0.02 mmol) and tripotassium phosphate 1M solution (1.79 mL, 1.79 mmol). The reaction was heated at 70 °C for 2 h. The reaction was extracted into EtOAc (50 mL), washed with water (25 mL), sat. brine (25 mL), the organic layer separated and concentrated in vacuo. The resulting residue was purified by flash column chromatography on Biotage Isolera 10 g silica cartridge eluting with 0%-100% EtOAc in iso-hexane to afford the title compound (271 mg, 98% yield) as a yellow gum. LCMS (method B) m/z 561 (ES+, M+H) at 1.63 min Step 2: 4-((3'-((1-(tert-butoxycarbonyl)-3-(methylsulfonamido)piperidin-2-yl)methyl)-[1,1'-biphenyl]-2-yl)oxy)butanoic acid_cis racemic

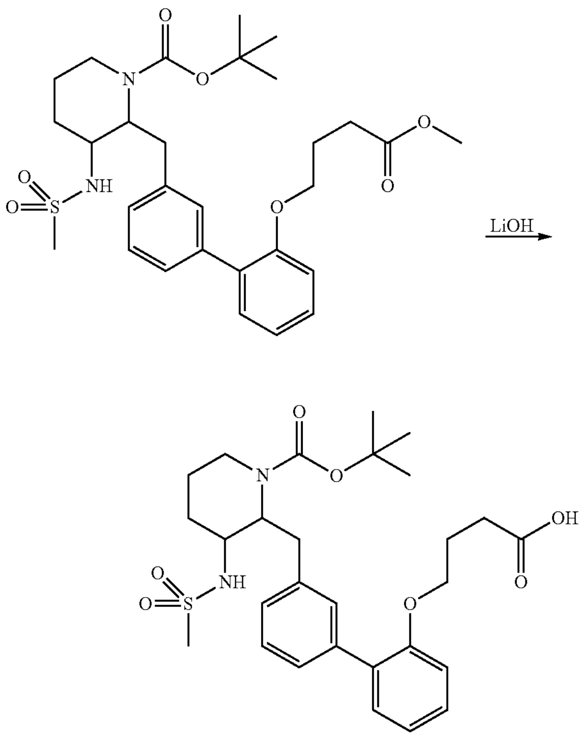

To a solution of tert-butyl 2-((2'-(4-methoxy-4-oxobutoxy)-[1,1'-biphenyl]-3-yl)methyl)-3-(methylsulfonamido)piperidine-1-carboxylate_cis racemic (271 mg, 0.44 mmol) in THF (9 mL) and water (3 mL) was added lithium hydroxide monohydrate (55 mg, 1.32 mmol) and the mixture was stirred at room temperature for 18 h. The reaction was neutralised with 1 M HCl, extracted into EtOAc (25 mL), washed with sat. $NaHCO_3$, the organic layer separated, dried over $MgSO_4$, filtered and the solvent removed in vacuo to afford the title compound (200 mg, 83% yield) as a yellow gum. LCMS (method B) m/z 447 (ES+, M-Boc) at 0.79 min.

Step 3: 4-((3'-((3-(methylsulfonamido)piperidin-2-yl)methyl)-[1,1'-biphenyl]-2-yl)oxy)butanoic acid hydrochloride_cis racemic

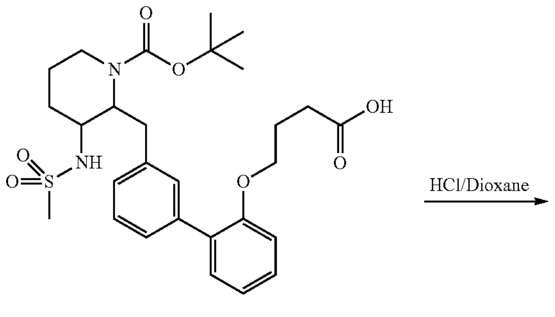

-continued

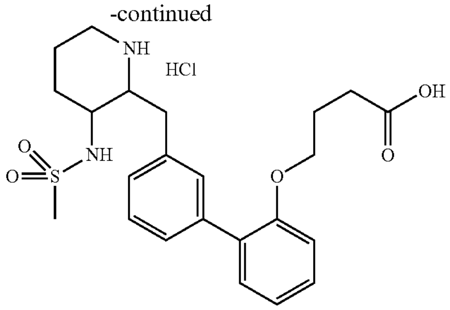

To a solution of 4-((3'-((1-(tert-butoxycarbonyl)-3-(methylsulfonamido)piperidin-2-yl)methyl)-[1,1'-biphenyl]-2-yl)oxy)butanoic acid_cis racemic (200 mg, 0.37 mmol) in 1,4-dioxane (4 mL) was added 4 M HCl in dioxane (5.0 mL) and the reaction stirred at room temperature for 18 h. The reaction was concentrated in vacuo to afford the title compound (177 mg, 100% yield) as a yellow foam. LCMS (method B) m/z 447 (ES+, M+H) at 0.68 min Step 4: N-(5-oxo-9-oxa-4(2,1)-piperidina-1(1,2),2(1,3)-dibenzenacyclononaphane-$4^3$-yl)methanesulfonamide_cis racemic (Compound No. A1-6)

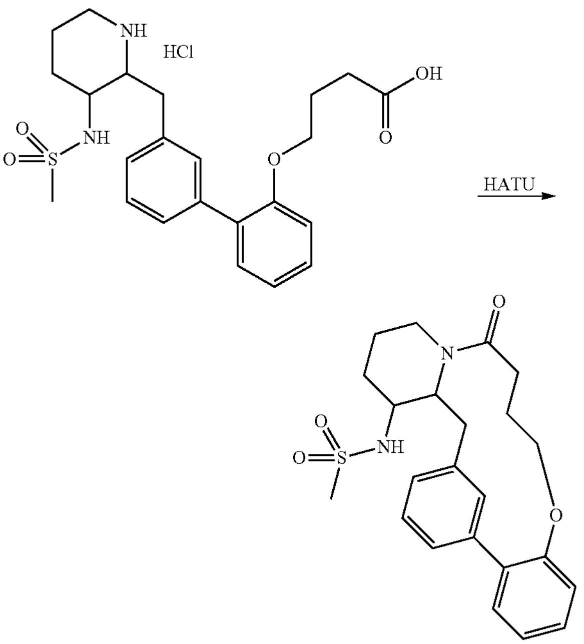

To a solution of 4-((3'-((3-(methylsulfonamido)piperidin-2-yl)methyl)-[1,1'-biphenyl]-2-yl)oxy)butanoic acid hydrochloride_cis racemic (177 mg, 0.37 mmol) and DIPEA (0.25 mL, 1.47 mmol) in DMF (37 mL) was added HATU (210 mg, 0.55 mmol) and the mixture was stirred at room temperature for 2 h. The reaction was concentrated in vacuo, extracted into EtOAc (50 mL), washed with sat. brine (25 mL), the organic layer separated and concentrated in vacuo. The residue was purified by reverse phase flash column chromatography, 30 g Biotage® SNAP KP-C18-HS, eluting with 10% to 100% MeOH in $H_2O$+0.2% $NH_4OH$ to the title compound (60 mg, 38% yield) as a beige solid. $^1H$ NMR (400 MHz, DMSO-$d_6$) δ 7.52-7.19 (m, 4H), 7.18-6.93 (m, 5H), 4.99 (ddd, 1H), 4.38 (d, 1H), 4.06 (ddd, 1H), 3.95-3.70 (m, 2H), 3.48-3.16 (m, 2H), 2.99 (d, 3H), 2.94-2.83 (m, 1H), 2.81-2.56 (m, 1H), 2.26 (ddd, 1H), 2.07-1.92 (m, 1H), 1.80-1.32 (m, 5H). LCMS (method C): m/z 429 $(M+H)^+$ (ES+) at 3.47 min Example 34. Synthesis of Compound No. A1-15

Step 1: tert-butyl (2-(2-(4,4,5,5-tetramethyl-1,3,2-dioxaborolan-2-yl)phenoxy)-ethyl)carbamate

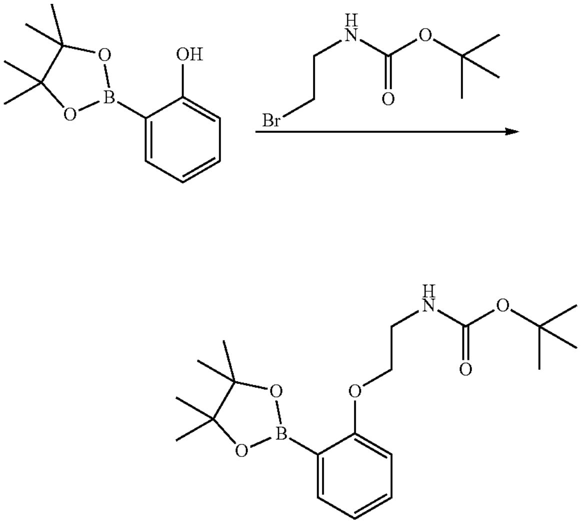

tert-butyl (2-bromoethyl)carbamate (3.05 g, 13.6 mmol) and 2-hydroxybenzeneboronic acid, pinacol ester (2.0 g, 9.09 mmol) were taken up in DMF (30 mL). To the solution was added potassium carbonate (2.51 g, 18.2 mmol) and the reaction heated at 60 °C for 18 h. The reaction was diluted with EtOAc (50 mL), washed with water (50 mL), sat. brine (25 mL), the organic layer separated and concentrated in vacuo. The residue was purified by flash column chromatography eluting with 0-50% EtOAc/isohexane to afford the title compound (795 mg, 19% yield) as a colourless oil. LCMS (method B) m/z 264 (ES+, M-Boc) at 1.72 min Step 2: tert-butyl 2-((2'-(2-((tert-butoxycarbonyl)amino)ethoxy)-[1,1'-biphenyl]-3-yl)methyl)-3-(methylsulfonamido)piperidine-1-carboxylate_cis racemic

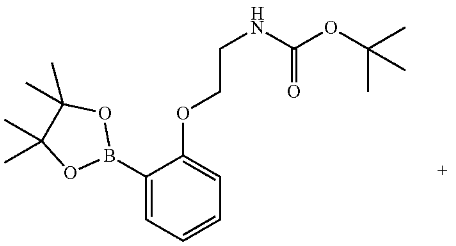

-continued

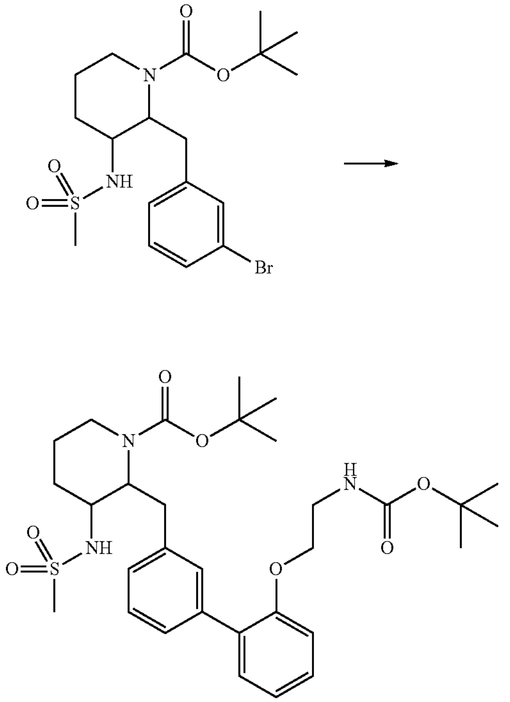

To a solution of tert-butyl 2-(3-bromobenzyl)-3-(methylsulfonamido)piperidine-1-carboxylate_cis racemic (Intermediate 3) (200 mg, 0.45 mmol) and tert-butyl (2-(2-(4,4,5,5-tetramethyl-1,3,2-dioxaborolan-2-yl)phenoxy)ethyl) carbamate (162 mg, 0.45 mmol) in THF (9 mL) was added XPhos-Pd-G3 (19 mg, 0.02 mmol) and tripotassium phosphate 1 M solution (1.79 mL, 1.79 mmol). The reaction was heated at 70 °C for 2 h. The reaction was extracted into EtOAc (50 mL), washed with water (25 mL), sat. brine (25 mL), the organic layer separated and concentrated in vacuo. The resulting residue was purified by flash column chromatography eluting with 0%-100% EtOAc in iso-hexane to afford the title compound (234 mg, 86% yield) as a brown gum. LCMS (method B) m/z 504 (ES+, M-Boc) at 1.71 min Step 3: N-(2-((2'-(2-aminoethoxy)-[1,1'-biphenyl]-3-yl)methyl)piperidin-3-yl)-methanesulfonamide dihydrochloride_cis racemic

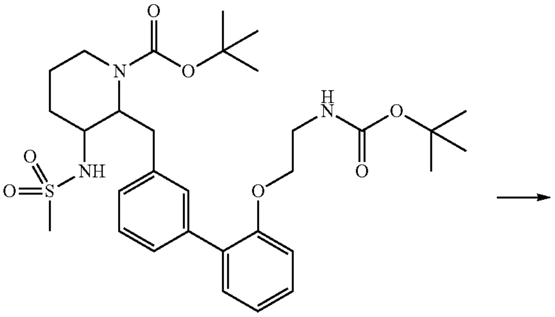

-continued

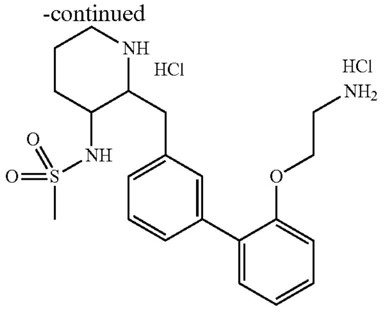

To a solution of tert-butyl 2-((2'-(2-((tert-butoxycarbonyl)amino)ethoxy)-[1,1'-biphenyl]-3-yl)methyl)-3-(methylsulfonamido)piperidine-1-carboxylate_cis racemic (234 mg, 0.39 mmol) in 1,4-dioxane (4 mL) was added 4 M HCl in dioxane (10 eq) and the reaction stirred at room temperature for 18 h and concentrated in vacuo to afford the title compound (185 mg, quantitative) as an off-white foam. LCMS (method B) m/z 404 (ES+, M+H) at 1.24 min Step 4: N-(5-oxo-9-oxa-6-aza-4(2,1)-piperidina-1(1,2),2(1,3)-dibenzenacyclo-nonaphane-4[3]-yl)methanesulfonamide_cis racemic (Compound No. A1-15)

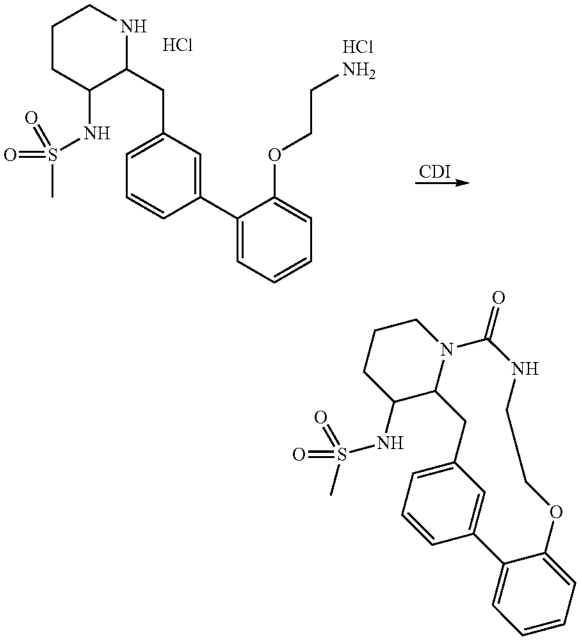

To a solution of N-(2-((2'-(2-aminoethoxy)-[1,1'-biphenyl]-3-yl)methyl)piperidin-3-yl)methanesulfonamide dihydrochloride_cis racemic (185 mg, 0.39 mmol) in DMF (4 mL) was added DIPEA (0.27 mL, 1.55 mmol) followed by CDI (76 mg, 0.47 mmol) and the mixture stirred at room temperature for 2 h and then heated at 70 °C for 1 h. The reaction was concentrated in vacuo, diluted with EtOAc (50 mL), washed with 10% citric acid (25 mL), sat. brine (25 mL), the organic layer separated and concentrated in vacuo. The residue was purified by flash column chromatography eluting with 0-100% EtOAc:MeOH(9:1)/isohexane. The fractions were combined and the solvent removed in vacuo. The resulting solid was triturated in MeOH (5.0 mL) and filtered to afford the title compound (39.3 mg, 23% yield) as a white solid. $^1$H NMR (400 MHz, DMSO-$d_6$) δ 7.42-7.25 (m, 3H), 7.21 (d, 1H), 7.06 (ddd, 4H), 6.25 (d, 1H), 4.62 (s, 1H), 3.89 (d, 1H), 3.81 (dt, 2H), 3.32 (s, 2H), 3.01 (s, 3H), 2.91 (dd, 2H), 2.79-2.64 (m, 2H), 1.70 (d, 3H), 1.44 (s, 1H). LCMS (method C): m/z 430 $(M+H)^+$ (ES+) at 2.98 min Examples 35 and 36. Synthesis of Compound Nos. A1-4 and A1-3

N-(5-oxo-9-oxa-6-aza-4(2,1)-piperidina-1(1,2),2(1,3)-dibenzenacyclononaphane-4[3]-yl)methanesulfonamide_cis racemic (Example 35) resolved on the Sepiatec SFC Prep100 system using a Lux A1 column and isocratic conditions of $CO_2$:(IPA+0.2% $NH_3$) 60:40.

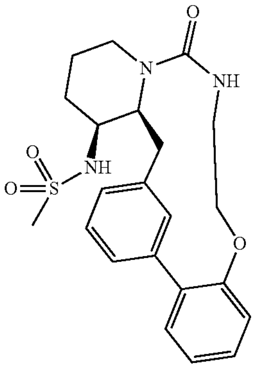 [SMILES: CS(=O)(=O)N[C@H]1CCCN2C(=O)NCCCOc3ccccc3-c3cccc(c3)C[C@@H]12]

N-((4[2]S,4[3]S)-5-oxo-9-oxa-6-aza-4(2,1)-piperidina-1(1,2),2(1,3)-dibenzenacyclo-nonaphane-4[3]-yl)methanesulfonamide (Example 35; Compound No. A1-4) Isomer 1: 99% ee retention time=2.28 min. $^1$H NMR (400 MHz, DMSO-$d_6$) δ 7.42-7.25 (m, 3H), 7.21 (d, 1H), 7.06 (ddd, 4H), 6.25 (d, 1H), 4.62 (s, 1H), 3.89 (d, 1H), 3.81 (dt, 2H), 3.32 (s, 2H), 3.01 (s, 3H), 2.91 (dd, 2H), 2.79-2.64 (m, 2H), 1.70 (d, 3H), 1.44 (s, 1H).

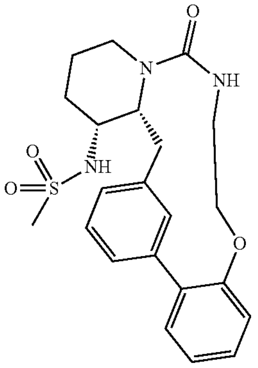 [SMILES: CS(=O)(=O)N[C@@H]1CCCN2C(=O)NCCCOc3ccccc3-c3cccc(c3)C[C@H]12]

N-((4[2]R,4[3]R)-5-oxo-9-oxa-6-aza-4(2,1)-piperidina-1(1,2),2(1,3)-dibenzenacyclo-nonaphane-4[3]-yl)methanesulfonamide (Example 36; Compound No. A1-3) Isomer 2: 99% ee retention time=2.44 min. $^1$H NMR (400 MHz, DMSO-$d_6$) δ 7.42-7.25 (m, 3H), 7.21 (d, 1H), 7.06 (ddd, 4H), 6.25 (d, 1H), 4.62 (s, 1H), 3.89 (d, 1H), 3.81 (dt, 2H), 3.32 (s, 2H), 3.01 (s, 3H), 2.91 (dd, 2H), 2.79-2.64 (m, 2H), 1.70 (d, 3H), 1.44 (s, 1H).

Example 37. Synthesis of Compound No. B1-1

Step 1: benzyl 2-(benzyloxy)-[1,1'-biphenyl]-3-carboxylate

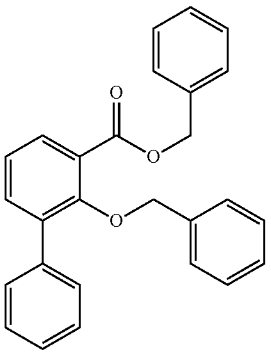 [SMILES: O=C(OCc1ccccc1)c1cccc(-c2ccccc2)c1OCc1ccccc1]

To a solution of 2-hydroxy-3-phenyl-benzoic acid (10 g, 46.7 mmol) in acetone (50 mL) was added potassium carbonate (14.2 g, 103 mmol) and benzyl bromide (17.6 g, 103 mmol). The mixture was stirred at 50 °C for 16 h. After this time, a heavy white precipitate had formed that was removed with filtration and further washed with acetone. The filtrate was evaporated to afford a pale yellow oil which was purified by flash column chromatography to afford the title compound (18.4 g, 100% yield) as a clear oil. LC-MS (method B) (ESI+): 395 [M+H]

Step 2: 2-(benzyloxy)-[1,1'-biphenyl]-3-carboxylic acid

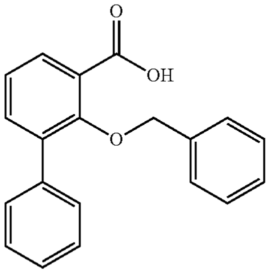 [SMILES: O=C(O)c1cccc(-c2ccccc2)c1OCc1ccccc1]

benzyl 2-(benzyloxy)-[1,1'-biphenyl]-3-carboxylate (13.3 g, 44 mmol) was solvated in THF (150 mL) and water (50 mL), to which lithium hydroxide (3.28 g, 137 mmol) was added. The mixture was stirred at 80 °C for 24 h and concentrated in vacuo to remove THF. The mixture was adjusted to pH 2 by the addition of 1N HCl and diluted with EtOAc. The layers were separated and the organics removed in vacuo. The product was purified by flash column chromatography to afford the title compound (13.3 g, 96% yield) as a white solid. LC-MS (method B) (ESI+): 305 [M+H]

Step 3: (2-(benzyloxy)-[1,1'-biphenyl]-3-yl)methanol

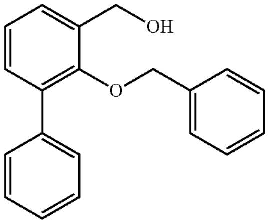 [SMILES: OCc1cccc(-c2ccccc2)c1OCc1ccccc1]

2-(benzyloxy)-[1,1'-biphenyl]-3-carboxylic acid (5.0 g, 16.4 mmol) was solvated in THF (80 mL) and cooled to 0 °C under a stream of nitrogen. To this solution, $LiAlH_4$ (21.4 mL, 21.4 mmol, 1 M in THF) was added and the mixture slowly warmed to room temperature and stirred for 24 h. The reaction mixture was cooled to 0 °C at which point 3 mL of water, 3 mL of 15% aqueous NaOH and 9 mL of water were subsequently added slowly. The mixture was then stirred at room temperature for 10 min after which time magnesium sulfate was added followed by dilution with EtOAc. The mixture was filtered and solvent removed in vacuo to afford the title compound (4.7 g, 98.5% yield) as a clear solid. LC-MS (method D) (ESI+): 313 [M+Na]

Step 4: 2-(benzyloxy)-3-(bromomethyl)-1,1'-biphenyl

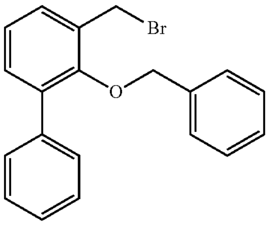 [SMILES: BrCc1cccc(-c2ccccc2)c1OCc1ccccc1]

(2-(benzyloxy)-[1,1'-biphenyl]-3-yl)methanol (4.77 g, 16.4 mmol) was solvated in dichloromethane (20 mL) to which a 1N solution of phosphorus tribromide (1.03 mL, 11 mmol, 1M in dichloromethane) was added. The reaction mixture was stirred at room temperature for 16 hours, cooled to 0 °C and quenched by the slow addition of saturated aqueous bicarbonate solution. The reaction mixture was passed through a phase separation cartridge and concentrated to afford the title compound (5.62 g, 97% yield) as a white solid. $^1H$ NMR (400 MHz, DMSO-d6) δ 7.63-7.57 (m, 2H), 7.55-7.46 (m, 3H), 7.46-7.37 (m, 2H), 7.36-7.30 (m, 3H), 7.27 (t, 1H), 7.18-7.13 (m, 2H), 4.74 (s, 2H), 4.49 (s, 2H).

Step 5: tert-butyl 2-((2-(benzyloxy)-[1,1'-biphenyl]-3-yl)methyl)-3-oxopyrrolidine-1-carboxylate

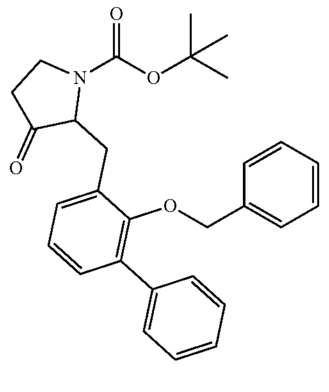 [SMILES: CC(C)(C)OC(=O)N1CCC(=O)C1Cc1cccc(-c2ccccc2)c1OCc1ccccc1]

To a mixture of 1-Boc-3-pyrrolidinone (2.95 g, 15.9 mmol) in toluene (20 mL) was added pyrrolidine (1.57 mL, 19. mmol) and the reaction heated at 145 °C for 24 h using a Dean-Stark trap. After this time, solvent was removed in vacuo to afford a brown gum that was taken up in MeCN (20 mL). To this, 2-benzyloxy-1-(bromomethyl)-3-phenyl-benzene (5.62 g, 15.9 mmol) and tetrabutylammonium iodide (1.18 g, 3.2 mmol) was added and the mixture heated to 80 °C for 24 hours. Solvent was removed in vacuo and the residue taken up in ethyl acetate. The mixture was washed with saturated brine, separated, dried with magnesium sulfate and concentrated. The residue was purified by flash column chromatography to afford the title compound (1.78 g, 24% yield). LC-MS (method D) (ESI+): 458 [M+H]

Step 6: tert-butyl 3-amino-2-((2-(benzyloxy)-[1,1'-biphenyl]-3-yl)methyl)-pyrrolidine-1-carboxylate-_cis racemic

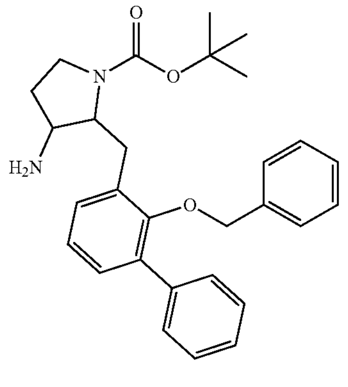 [SMILES: CC(C)(C)OC(=O)N1CCC(N)C1Cc1cccc(-c2ccccc2)c1OCc1ccccc1]

tert-butyl 2-((2-(benzyloxy)-[1,1'-biphenyl]-3-yl)methyl)-3-oxopyrrolidine-1-carboxylate (1.78 g, 3.89 mmol) and Ammonium formate (1.96 g, 31.1 mmol) were solvated in Methanol (35 mL) and degassed by sparging with nitrogen. To this, chloro[N-[4-(dimethylamino)phenyl]-2-pyridinecarboxamidato](pentamethylcyclopentadienyl)iridium(III) (117 mg, 0.19 mmol) was added and the mixture heated to 85 °C for 2 hours. Solvent was removed in vacuo, product taken up in dichloromethane and washed with saturated brine. The layers were separated, the organic phase passed through a phase sep cart. and solvent removed in vacuo to afford the title compound (1.78 g, 100% yield) as a bright orange oil. LC-MS (method D) (ESI+): 459 [M+H]

Step 7: tert-butyl 2-((2-(benzyloxy)-[1,1'-biphenyl]-3-yl)methyl)-3-(ethylsulfonamido)-pyrrolidine-1-carboxylate_cis racemic

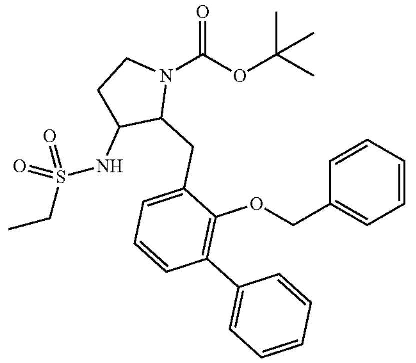 [SMILES: CCS(=O)(=O)NC1CCN(C(=O)OC(C)(C)C)C1Cc1cccc(-c2ccccc2)c1OCc1ccccc1]

tert-Butyl 3-amino-2-((2-(benzyloxy)-[1,1'-biphenyl]-3-yl)methyl)pyrrolidine-1-carboxylate cis racemic (1.92 g, 4.18 mmol) and $Et_3N$ (580 μL, 4.18 mmol) were dissolved in THF (25 mL) and cooled to 0 °C in an ice bath. Ethanesulfonyl chloride (0.44 mL, 4.6 mmol) was added slowly with stirring and allowed to warm to room temperature over 24 h. Solvent was removed in vacuo, the residue taken up in EtOAc and the mixture washed with sat. brine, separated, dried with magnesium sulfate and filtered. The organic fraction was concentrated and purified by flash column chromatography to afford the title compound (750 mg, 33% yield) as a beige foam. LC-MS (method D) (ESI+): 573 [M+Na]

Step 8: tert-butyl 2-((2-(benzyloxy)-[1,1'-biphenyl]-3-yl)methyl)-3-(N-(tert-butoxycarbonyl)ethylsulfonamido)pyrrolidine-1-carboxylate_cis racemic

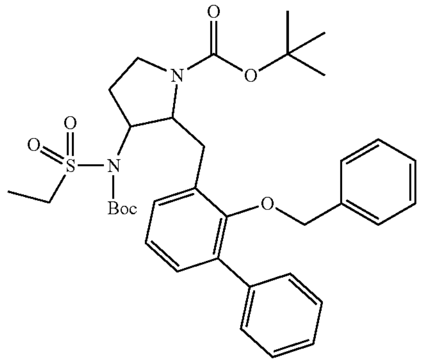 [SMILES: CCS(=O)(=O)N(C(=O)OC(C)(C)C)C1CCN(C(=O)OC(C)(C)C)C1Cc1cccc(-c2ccccc2)c1OCc1ccccc1]

To a solution of tert-butyl 2-((2-(benzyloxy)-[1,1'-biphenyl]-3-yl)methyl)-3-(ethylsulfonamido)pyrrolidine-1-carboxylate_cis racemic (690 mg, 1.25 mmol), DIPEA (0.54 mL, 3.13 mmol) and di-tert-butyl dicarbonate (301 mg, 1.38 mmol) in dichloromethane (10 mL) was added 4-dimethylaminopyridine (168 mg, 1.38 mmol) slowly. The mixture was stirred overnight at room temperature, diluted with dichloromethane, washed with saturated brine and the organic phase passed through a phase separation cartridge with further washing with dichloromethane and concentrated. The residue was purified by flash column chromatography to afford the title compound (700 mg, 86% yield) as a white powdery foam. LC-MS (method B) (ESI+): 651 [M+H]

Step 9: tert-butyl 3-(N-(tert-butoxycarbonyl)ethylsulfonamido)-2-((2-hydroxy-[1,1'-biphenyl]-3-yl) methyl)pyrrolidine-1-carboxylate_cis racemic

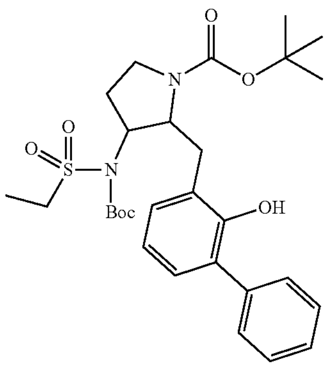 [SMILES: CCS(=O)(=O)N(C(=O)OC(C)(C)C)C1CCN(C(=O)OC(C)(C)C)C1Cc1cccc(-c2ccccc2)c1O]

Palladium on activated charcoal (26 mg, 0.22 mmol) was suspended in ethanol (10 mL) under an atmosphere of nitrogen. The mixture was degassed and back-filled with nitrogen three times and the procedure repeated with tert-butyl 2-((2-(benzyloxy)-[1,1'-biphenyl]-3-yl)methyl)-3-(N-(tert-butoxycarbonyl)ethylsulfonamido)pyrrolidine-1-carboxylate_cis racemic (700 mg, 1.08 mmol). The reaction mixture was left to stir under a balloon of hydrogen for 16 hours with vigorous stirring. A further portion of palladium on activated charcoal (26 mg, 0.22 mmol) was added and the mixture stirred for 4 days under a hydrogen balloon. The reaction mixture was diluted with methanol and filtered through a short plug of celite. Solvent was removed in vacuo to afford the title compound (600 mg, 99% yield) as a grey glassy foam. LC-MS (method D) (ESI+): 561 [M+H]

Step 10: N-(2-((2-hydroxy-[1,1'-biphenyl]-3-yl) methyl)pyrrolidin-3-yl)ethanesulfonamide hydrochloride_cis racemic

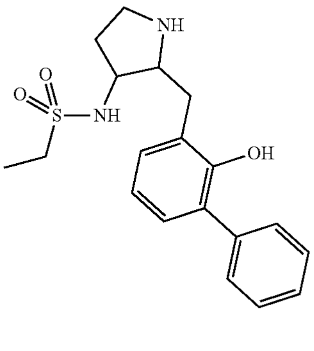 [SMILES: CCS(=O)(=O)NC1CCNC1Cc1cccc(-c2ccccc2)c1O]

tert-Butyl 3-(N-(tert-butoxycarbonyl)ethylsulfonamido)-2-((2-hydroxy-[1,1'-biphenyl]-3-yl) methyl)pyrrolidine-1-carboxylate_cis racemic (200 mg, 0.36 mmol) was stirred with 4 M HCl in dioxane (1.78 mL, 7.13 mmol) in 1,4-dioxane (3 mL) for 72 hours. Solvent was removed in vacuo to afford the title compound (128 mg, 99% yield) as a brown oil. LC-MS (method B) (ESI+): 361 [M+H]

Step 11: N-(1-(6-bromohexanoyl)-2-((2-hydroxy-[1,1'-biphenyl]-3-yl)methyl)pyrrolidin-3-yl)ethanesulfonamide_cis racemic

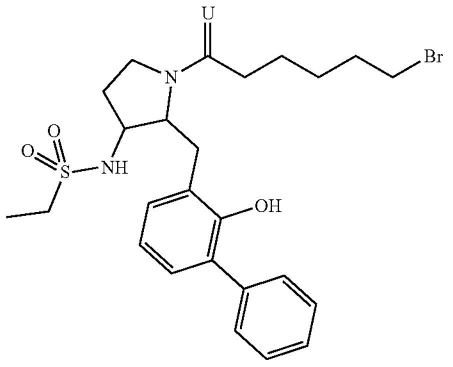

N-(2-((2-hydroxy-[1,1'-biphenyl]-3-yl)methyl)pyrrolidin-3-yl)ethanesulfonamide hydrochloride_cis racemic (128 mg, 0.32 mmol) and HOBt monohydrate (109 mg, 0.64 mmol) were stirred in THF (5 mL) to which 6-bromohexanoic acid (94 mg, 0.48 mmol) and 1-(3-dimethylaminopropyl)-3-ethylcarbodiimide hydrochloride (124 mg, 0.64 mmol) were added. DIPEA (0.17 mL, 0.97 mmol) was added and the mixture stirred for 24 hours at room temperature. After this time the solvent was removed in vacuo and the product purified by prep HPLC to afford the title compound. LC-MS (method B) (ESI+): 538 [M+H]

Step 12: N-(5-oxo-12-phenyl-2,3,5,6,7,8,9,10,16,16a-decahydro-1H-benzo[b]pyrrolo[2,1-e][1]oxa[6]azacyclododecin-1-yl)ethanesulfonamide_cis racemic (Compound No. B1-1)

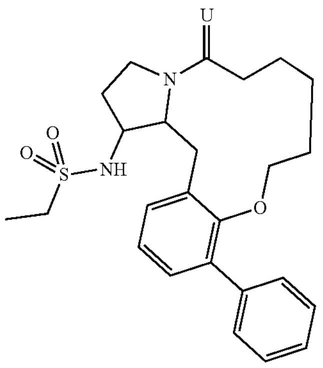

N-(1-(6-bromohexanoyl)-2-((2-hydroxy-[1,1'-biphenyl]-3-yl)methyl)pyrrolidin-3-yl) ethanesulfonamide_cis racemic (173 mg, 0.32 mmol) was dissolved in DMF (30 mL) to which potassium carbonate (445 mg, 3.22 mmol) was added. The mixture was then heated to 80 °C for 24 hours. The reaction mixture was concentrated in vacuo, the residue taken up in EtOAc and washed with saturated brine. The organic phase was dried with magnesium sulfate, filtered and concentrated to give a dark residue which was purified by prep HPLC to afford the title compound (15 mg, 10% yield) as a white solid.

$^1$H NMR (400 MHz, $CDCl_3$) δ 7.57-7.47 (m, 2H), 7.46-7.40 (m, 2H), 7.38-7.33 (m, 1H), 7.26 (s, 1H), 7.22 (dd, 1H), 7.12 (td, 1H), 4.80-4.60 (m, 1H), 4.38 (d, 1H), 4.06-3.89 (m, 1H), 3.79 (q, 1H), 3.58-3.50 (m, 1H), 3.44-3.30 (m, 2H), 3.29-3.05 (m, 3H), 2.74 (dd, 1H), 2.59-2.48 (m, 1H), 2.35-2.14 (m, 2H), 2.07 (d, 1H), 1.86 (d, 3H), 1.43 (t, 3H), 1.13 (s, 2H). LC-MS (method C) (ESI+): 457 [M+H] at 2.98 min Example 38. Synthesis of Compound No. A1-69

Step 1: tert-butyl 3-(methylsulfonamido)-2-(3-(4,4,5,5-tetramethyl-1,3,2-dioxaborolan-2-yl)benzyl) piperidine-1-carboxylate_cis racemic

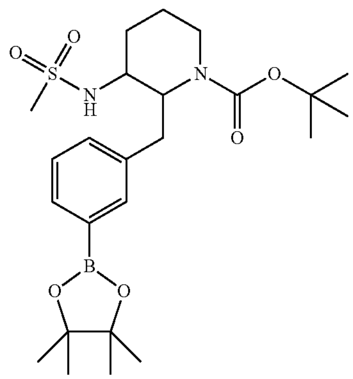 [SMILES: CC(C)(C)OC(=O)N1CCCC(NS(C)(=O)=O)C1Cc1cccc(B2OC(C)(C)C(C)(C)O2)c1]

To a 100 mL rb flask was added tert-butyl 2-(3-bromobenzyl)-3-(methylsulfonamido) piperidine-1-carboxylate_cis racemic, intermediate 3 (3.0 g, 6.71 mmol), potassium acetate (1.97 g, 20.1 mmol), dichloro[1,1'-bis(diphenylphosphino)ferrocene]palladium (II) dichloromethane adduct (491 mg, 0.67 mmol) and bis(pinacolato)diboron (5.11 g, 20.1 mmol) in 1,4-Dioxane (34 mL). The reaction was heated at 90 °C for 18 hours, filtered through celite, diluted with EtOAc, washed with brine, the organic layer separated, dried over $MgSO_4$, filtered and concentrated in vacuo to afford the title compound (3.31 g, 99.8% yield) which was taken on without further purification. LCMS (method B) m/z 395.4 (ES+, M-100) at 1.50 min Step 2: tert-butyl 2-((2'-(2-hydroxyethoxy)-[1,1'-biphenyl]-3-yl)methyl)-3-(methylsulfonamido)piperidine-1-carboxylate_cis racemic

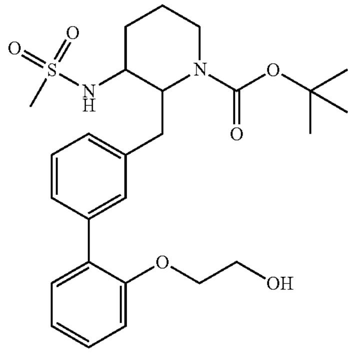 [SMILES: CC(C)(C)OC(=O)N1CCCC(NS(C)(=O)=O)C1Cc1cccc(-c2ccccc2OCCO)c1]

To a solution of tert-butyl 3-(methylsulfonamido)-2-(3-(4,4,5,5-tetramethyl-1,3,2-dioxaborolan-2-yl)benzyl)piperidine-1-carboxylate (3.3 g, 6.67 mmol), 2-(2-bromophenoxy) ethanol (1.74 g, 8.01 mmol) and XPhos-Pd-G3 (282 mg, 0.33 mmol) in THF (33 mL) was added tripotassium phosphate 1M solution (26.7 mL, 26.7 mmol) and the reaction heated at 70 °C for 2 hrs. The reaction was washed with sat. $NaHCO_3$, sat. brine, the organic layer separated, dried over $MgSO_4$, filtered and concentrated in vacuo. The resulting oil was purified by flash column chromatography on Biotage Isolera 25 g silica cartridge eluting with 0%-100% Ethyl acetate:MeOH (9:1)/isohexane. The fractions were combined and the solvent removed to afford the title compound (1.78 g, 52.8% yield) as a colourless gum. LCMS (method B) m/z 505.4 (ES+, M+H) at 1.39 min.

Step 3: N-(2-((2'-(2-hydroxyethoxy)-[1,1'-biphenyl]-3-yl)methyl)piperidin-3-yl)methanesulfonamide hydrochloride_cis racemic

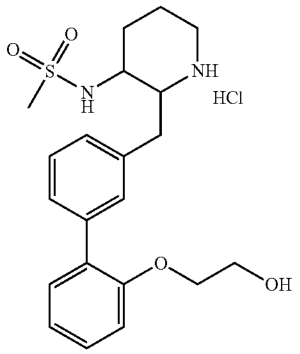 [SMILES: CS(=O)(=O)NC1CCCNC1Cc1cccc(-c2ccccc2OCCO)c1 ; Cl]

To a solution of tert-butyl 2-((2'-(2-hydroxyethoxy)-[1,1'-biphenyl]-3-yl)methyl)-3-(methylsulfonamido)piperidine-1-carboxylate (1.78 g, 3.53 mmol) in 1,4-dioxane (18 mL) was added 4 M HCl in dioxane (8.82 mL, 35.2 mmol) and the reaction stirred at RT for 18 hrs. The reaction was concentrated in vacuo to afford the title compound (1.55 g, 99% yield) as a yellow gum. LCMS (method B) m/z 405.4 (ES+, M+H) at 1.20 min.

Step 4: N-(($4^2S,4^3S$)-5-oxo-6,9-dioxa-4(2,1)-piperidina-1(1,2),2(1,3)-dibenzenacyclo-nonaphane-$4^3$-yl)methanesulfonamide

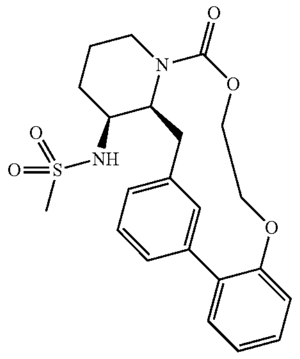 [SMILES: CS(=O)(=O)N[C@H]1CCCN2C(=O)OCCOc3ccccc3-c3cccc(c3)C[C@@H]12]

To a solution of triphosgene (355 mg, 1.2 mmol) in MeCN (351 mL) and DIPEA (2.43 mL, 14 mmol) was added N-(2-((2'-(2-hydroxyethoxy)-[1,1'-biphenyl]-3-yl)methyl)piperidin-3-yl)methanesulfonamide hydrochloride_cis racemic (1.55 g, 3.51 mmol) and the reaction heated at 70 °C for 18 hrs. The reaction was extracted into EtOAc, washed with sat. $NaHCO_3$, the organic layer separated and concentrated in vacuo. The resulting residue was purified by reverse phase flash column chromatography, 60 g Biotage® SNAP KP-C18-HS, eluting with 10% to 100% MeOH in $H_2O$+0.2% $NH_4OH$. The fractions were combined and the solvent removed in vacuo. The residue was taken up in MeOH (10 mL) and the resulting precipitate was removed under suction filtration to afford the crude racemic product which was resolved on a Sepiatec SFC Prep100 system using a Lux A1 column and isocratic conditions of $CO_2$:PA 0.2% $NH_3$ 60:40 to afford the title compound with the shorter retention time. $^1$H NMR (400 MHz, DMSO-$d_6$) δ 7.36-7.27 (m, 3H), 7.19 (ddt, 2H), 7.15-7.10 (m, 1H), 7.10-7.04 (m, 1H), 7.02-6.96 (m, 2H), 4.92 (td, 1H), 4.60-4.36 (m, 1H), 4.06-3.71 (m, 4H), 3.52-3.38 (m, 1H), 2.98 (d, 3H), 2.94-2.64 (m, 3H), 1.81-1.49 (m, 4H). LCMS (method C): m/z 431 $(M+H)^+$ (ES+) at 3.65 min Example 39. Synthesis of Compound No. A1-70

Step 1: methyl 4-(2-bromophenyl)butanoate

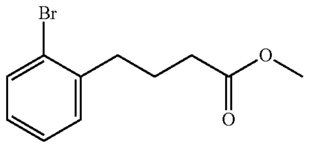

To a solution of AIBN (45 mg, 0.27 mmol) in 1,2-dichloroethane (12 mL), 1-bromo-2-vinyl-benzene (685 μL, 5.46 mmol), methyl 2-sulfanylacetate (733 μL, 8.19 mmol) and triethyl phosphite (1.12 mL, 6.56 mmol) were added. The tube was degassed with nitrogen for the whole time. The mixture was stirred at 80 °C overnight, diluted with water and extracted twice with dichloromethane. The combined organic extracts were washed with sat. NaCl, dried over $MgSO_4$, and evaporated. Crude was purified on Biotage purification system (40 g column, 15 μm, eluent: 0-50% of 6% EtOAC/cyclohexane) to afford 425 mg of the title compound. LC-MS (method A) (ESI+): 257.03[M+H]

Step 2: methyl 4-(2-(4,4,5,5-tetramethyl-1,3,2-dioxaborolan-2-yl)phenyl)butanoate

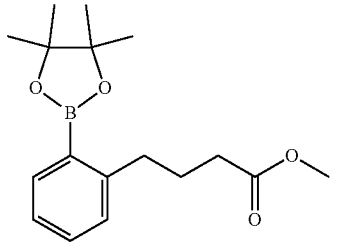

To a solution of methyl 4-(2-bromophenyl)butanoate (425 mg, 324 μL, 1.42 mmol), bis(pinacolato)diboron (1.08 g, 4.26 mmol) in 1,4-dioxane (15 mL), potassium acetate (837 mg, 8.53 mmol) was added. Reaction mixture was degassed with nitrogen for 10 min when Pd(dppf)$Cl_2$ (416 mg, 0.569 mmol) was added and the mixture was stirred at 80 °C overnight, cooled to room temperature before it was filtered through a pad of celite and evaporated. Residue was dissolved in EtOAC (50 mL) and washed twice with brine (2×50 mL) and water. Layers were separated, organic layer was dried over anhydrous $MgSO_4$ and evaporated. The crude product was dry loaded and purified on Biotage purification system (25 g column, 15 μm, eluant: 0-50%, 5% MeOH/dichloromethane) to afford 494 mg of the title compound. LC-MS (method A) (ESI+): 305.29[M+H]

Step 3: tert-butyl 2-((2'-(4-methoxy-4-oxobutyl)-[1,1'-biphenyl]-3-yl)methyl)-3-(methylsulfonamido)piperidine-1-carboxylate_cis racemic

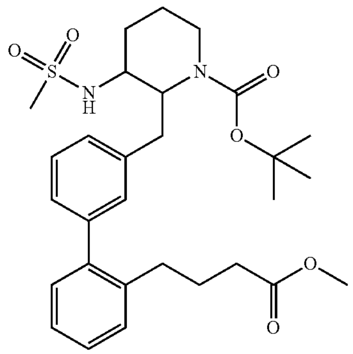 [SMILES: COC(=O)CCCc1ccccc1-c1cccc(CC2C(NS(C)(=O)=O)CCCN2C(=O)OC(C)(C)C)c1]

To a solution of tert-butyl 2-(3-bromobenzyl)-3-(methylsulfonamido)piperidine-1-carboxylate_cis racemic, intermediate 3 (630 mg, 1.41 mmol) in THF (15 mL), methyl 4-[2-(4,4,5,5-tetramethyl-1,3,2-dioxaborolan-2-yl)phenyl]butanoate (494 mg, 1.38 mmol), $K_3PO_4$ (879 mg, 4.14 mmol), dissolved in water (5 mL) and Pd XPhos G3 (234 mg, 0.276 mmol) were added. The reaction mixture was sealed and stirred at 70 °C overnight, cooled to room temperature and filtered off through a pad of celite. Filtrate was evaporated and then dissolved in EtOAc (50 mL) and extracted with water (2×30 mL). Layers were separated and organic layer was dried over $MgSO_4$ and evaporated. Crude was purified on Biotage purification system (25 g column, 15 μm, eluent: 0-100%, 5% MeOH in dichloromethane) to afford 806 mg of the title compound. LC-MS (method A) (ESI+): 545.25[M+H]

Step 4: methyl 4-(3'-((3-(methylsulfonamido)piperidin-2-yl)methyl)-[1,1'-biphenyl]-2-yl)butanoate_cis racemic

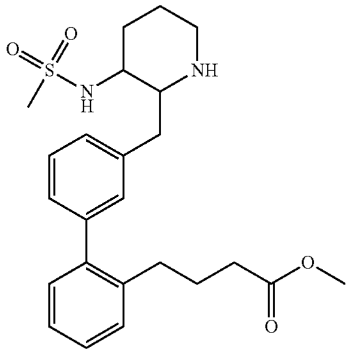 [SMILES: COC(=O)CCCc1ccccc1-c1cccc(CC2NCCCC2NS(C)(=O)=O)c1]

Tert-butyl2-((2'-(4-methoxy-4-oxobutyl)-[1,1'-biphenyl]-3-yl)methyl)-3-(methylsulfon-amido) piperidine-1-carboxylate (806 mg, 1.0 mmol) was dissolved in 4M HCl in 1,4-dioxane (5.2 mL) and the mixture was stirred at r.t for 1.5 h. Solvent was evaporated to afford 730 mg of the title compound. LC-MS (method A) (ESI+): 445.25[M+H]

Step 5: 4-(3'-((3-(methylsulfonamido)piperidin-2-yl)methyl)-[1,1'-biphenyl]-2-yl)butanoic acid_cis racemic

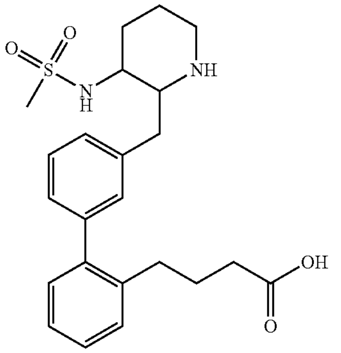 [SMILES: CS(=O)(=O)NC1CCCNC1Cc1cccc(-c2ccccc2CCCC(=O)O)c1]

Methyl 4-(3'-((3-(methylsulfonamido)piperidin-2-yl)methyl)-[1,1'-biphenyl]-2-yl)butanoate (730 mg, 1.6 mmol) was dissolved in tetrahydrofuran (5 mL). LiOH $H_2O$ (689 mg, 16 mmol) was dissolved in water (1 mL) and added to the reaction mixture which was left stirred at 40 °C for 5 h. Solvent was evaporated, residue was additionally diluted with water (15 mL) and neutralized with 2 M HCl to pH 7.5. Then it was extracted with EtOAc, layers were separated and organic layer was dried over anhydrous $MgSO_4$ and evaporated to dryness to afford 350 mg of the title compound. LC-MS (method A) (ESI+): 431.28[M+H]

Step 6: N-((4$^2$S,4$^3$S)-5-oxo-4(2,1)-piperidina-1(1,2),2(1,3)-dibenzenacyclooctaphane-4$^3$-yl)methanesulfonamide

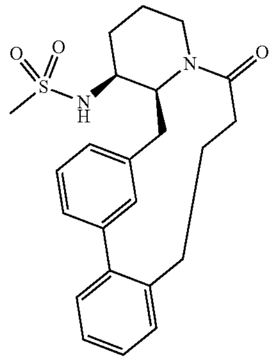 [SMILES: CS(=O)(=O)N[C@H]1CCCN2C(=O)CCCc3ccccc3-c3cccc(c3)C[C@@H]12]

To a solution of N,N-diisopropylethylamine (230 μL, 1.3 mmol) and HATU (371 mg, 1.0 mmol) in DMF (60 mL), a solution of N,N-diisopropylethylamine (110 μL, 0.65 mmol) and 4-(3'-((3-(methylsulfonamido)piperidin-2-yl)methyl)-[1,1'-biphenyl]-2-yl)butanoic acid (350 mg, 0.65 mmol) in DMF (40 mL) was added dropwise over 30 min and stirred at r.t. for 1 h. Solvent was evaporated. The residue was dissolved in EtOAc and washed with $NaHCO_3$, brine and a 5% solution of LiCl. Layers were separated and organic layer was dried over $MgSO_4$ and evaporated. Crude was dry loaded and purified on Biotage purification system (4 g column, 15 μm, eluent: 0-30% of 20% acetonitrile/dichloromethane) and then triturated with diethyl ether to afford 48.5 mg crude racemic material which was resolved on a Sepiatec SFC Prep100 system using a Lux C1 column and isocratic conditions of $CO_2$:MeOH 70:30 to afford the title compound (16 mg, 6% yield) with the shorter retention time. $^1$H NMR (500 MHz, chloroform-d): δ 7.35-7.39 (m, 1H), 7.28-7.34 (m, 3H), 7.25 (s, 1H), 7.20-7.24 (m, 1H), 7.10 (d, 1H), 6.81 (s, 1H), 5.01-5.08 (m, 1H), 4.38 (d, 1H), 3.71 (br d, 1H), 3.57-3.65 (m, 1H), 3.35-3.43 (m, 1H), 3.09 (s, 3H), 2.86-2.95 (m, 1H), 2.76 (dd, 1H), 2.68 (br dd, 1H), 2.39-2.50 (m, 1H), 2.26-2.34 (m, 1H), 2.16-2.23 (m, 1H), 2.04 (br d, 1H), 1.88 (br d, 1H), 1.62-1.77 (m, 3H), 1.27 (dd, 1H). LCMS (method C): m/z 413 $(M+H)^+$ (ES+) at 3.56 min Example 40. Synthesis of A1-74

Step 1: tert-butyl 2-(3-bromobenzyl)-3-(ethylsulfonamido)piperidine-1-carboxylate_cis racemic

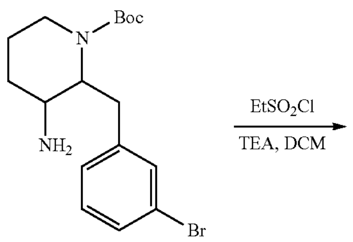

-continued

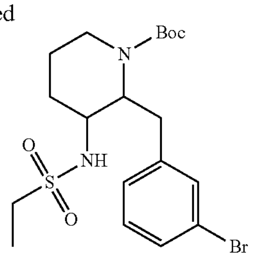

To a mixture of tert-butyl 3-amino-2-(3-bromobenzyl) piperidine-1-carboxylate_cis racemic (4.8 g, 13.0 mmol, 1 eq) and triethylamine (5.43 mL, 39.0 mmol, 3 eq) in dichloromethane (50 mL) was added ethanesulfonyl chloride (2.46 mL, 26.0 mmol, 2 eq) in one portion at 25 °C under nitrogen. The reaction mixture was stirred at 25 °C for 12 h, poured into water (150 mL) and stirred for 3 min. The aqueous phase was extracted with ethyl acetate (3×100 mL). The combined organic phase was washed with brine (3×100 mL), dried with anhydrous sodium sulfate, filtered and concentrated under reduce pressure to afford a residue. The residue was purified by column chromatography on silica gel eluting with PE:EA=(1:0 to 1:1) to afford the title compound (5.2 g, 86.7% yield) as a yellow solid. LCMS (method I) (ESI+): m/z 361.2 (M-100)+, RT: 0.804 min.

Step 2: tert-butyl 3-(ethylsulfonamido)-2-((2'-hydroxy-[1,1'-biphenyl]-3-yl)methyl)piperidine-1-carboxylate_cis racemic

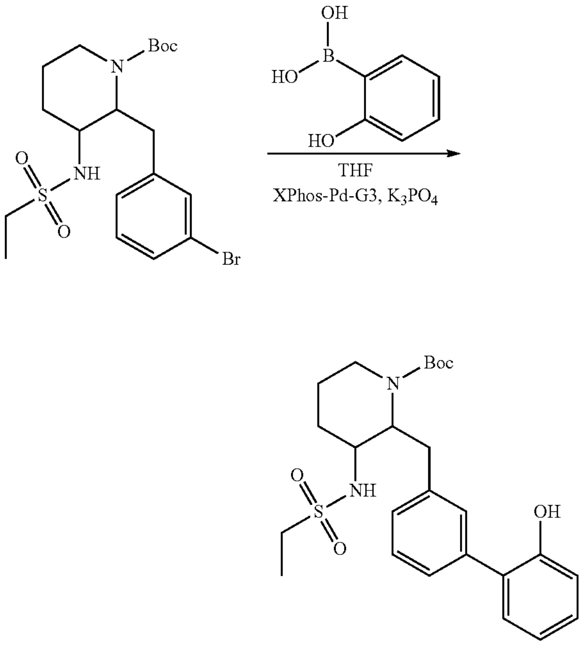

To a mixture of (2-hydroxyphenyl)boronic acid (2.03 g, 14.6 mmol, 1.5 eq) and tert-butyl 2-(3-bromobenzyl)-3-(ethylsulfonamido)piperidine-1-carboxylate_cis racemic (4.52 g, 9.80 mmol, 1 eq) in tetrahyfrofuran (50 mL) was added potassium phosphate (6.24 g, 29.3 mmol, 3 eq) and XPhose-Pd-G3 (415 mg, 490 μmol, 0.05 eq) in one portion at 25 °C under nitrogen. The mixture was stirred at 70 °C for 12 h. The mixture was cooled to 25 °C and concentrated under reduced pressure to afford a residue. The residue was poured into water (100 mL) and the aqueous phase was extracted with ethyl acetate (3×10 mL). The combined organic phase was washed with brine (3×10 mL), dried with anhydrous sodium sulfate, filtered and concentrated under reduced pressure to afford a residue. The residue was purified by silica gel chromatography with petroleum ether:ethyl acetate (1:0 to 1:1) to afford the title compound (3.2 g, 6.74 mmol, 68.8% yield) as a yellow solid. $^1$H NMR (400 MHz, chloroform-d) δ ppm 1.14 (s, 6H), 1.20 (s, 3H), 1.39-1.43 (m, 3H), 1.57-1.66 (m, 2H), 1.67-1.74 (m, 1H), 1.79 (br d, 1H), 1.88-1.99 (m, 1H), 2.76-2.84 (m, 1H), 2.85-2.93 (m, 2H), 2.95-3.02 (m, 1H), 3.08-3.13 (m, 2H), 3.54-3.62 (m, 1H), 4.38 (br d, 1H), 4.71-4.88 (m, 1H), 6.93-6.99 (m, 1H), 7.02 (d, 1H), 7.09-7.13 (m, 1H), 7.13-7.19 (m, 1H), 7.20-7.23 (m, 1H), 7.23-7.26 (m, 1H), 7.33-7.44 (m, 2H).

Step 3: tert-butyl (E/Z)-2-((2'-((3-(tert-butoxy)-3-oxoprop-1-en-1-yl)oxy)-[1,1'-biphenyl]-3-yl) methyl)-3-(ethylsulfonamido)piperidine-1-carboxylate_cis racemic

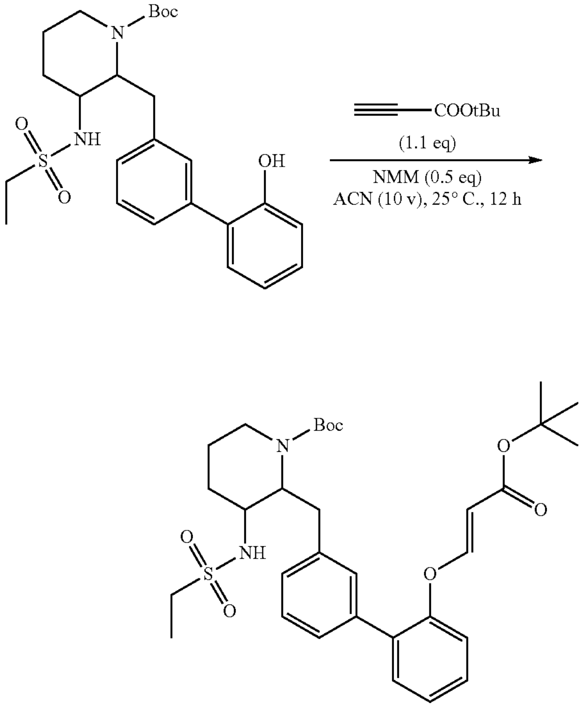

To a mixture of tert-butyl prop-2-ynoate (954 μL, 6.95 mmol, 1.1 eq) and 5 (3 g, 6.32 mmol, 1 eq) in acetonitrile (30 mL) was added n-methyl morpholine (347 μL, 3.16 mmol, 0.5 eq) in one portion at 25 °C under nitrogen. The mixture was stirred at 25 °C for 12 h. The residue was poured into water (30 mL) and stirred for 3 min. The aqueous phase was extracted with ethyl acetate (3×10 mL). The combined organic phase was washed with brine (3×10 mL), dried over anhydrous sodium sulfate, filtered and concentrated under reduced pressure to afford a residue. The residue was purified by silica gel chromatography eluted with PE:EA=(1:0 to 1:1) to afford the title compound (2 g, 52.6% yield) as a yellow solid. LCMS (method I) (ESI+): m/z 623.5 (M+Na)+, RT: 1.121 min.

Step 4: tert-butyl 2-((2'-(3-(tert-butoxy)-3-oxo-propoxy)-[1,1'-biphenyl]-3-yl)methyl)-3-(ethylsulfo-namido)piperidine-1-carboxylate_cis racemic

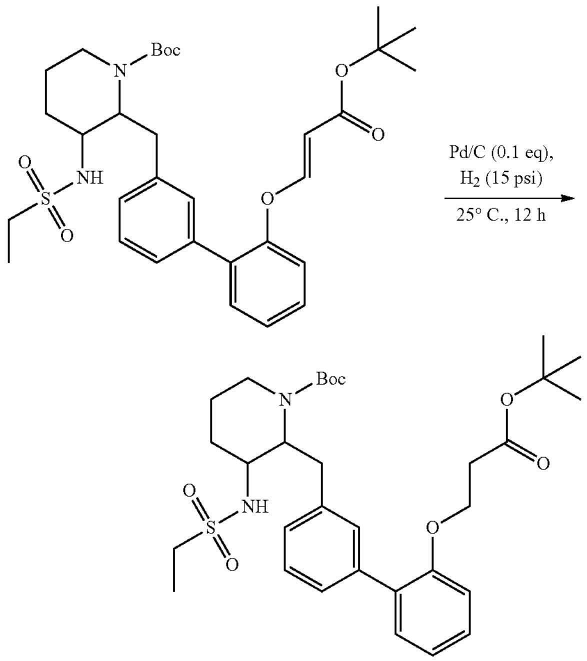

To a mixture of Pd/C (50 mg, 3.16 mmol, 10%, 1 eq) in methanol (20 mL) was added tert-butyl (E)-2-((2'-((3-(tert-butoxy)-3-oxoprop-1-en-1-yl)oxy)-[1,1'-biphenyl]-3-yl)methyl)-3-(ethylsulfonamido)piperidine-1-carboxylate_cis racemic (1.9 g, 3.16 mmol, 1 eq) in one portion. The mixture was stirred at 25 °C for 12 h under a hydrogen atmosphere. The reaction mixture was filtered via celite, washed with methanol (3×10 mL) and the filtrate was concentrated under reduce pressure to afford a residue. The residue was purified by silica gel chromatography eluted with PE:EA=(1:0 to 1:1) to afford the title compound (1.3 g, 68.2% yield) as colourless oil. LCMS (method I) (ESI+): m/z 624.4 (M+18)+, RT: 0.887 min.

Step 5: 3-((3'-((3-(ethylsulfonamido)piperidin-2-yl)methyl)-[1,1'-biphenyl]-2-yl)oxy)-propanoic acid-_cis racemic

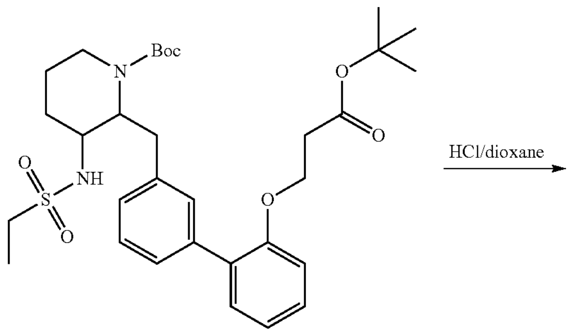

-continued

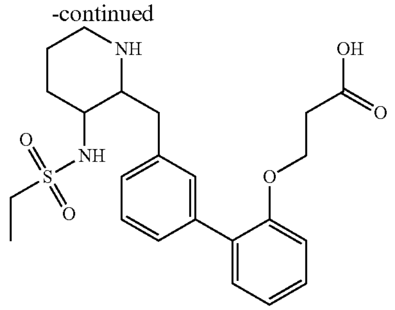

To a mixture of tert-butyl 2-((2'-(3-(tert-butoxy)-3-oxo-propoxy)-[1,1'-biphenyl]-3-yl)methyl)-3-(ethylsulfona-mido)piperidine-1-carboxylate_cis racemic (1.2 g, 1.99 mmol, 1 eq) in hydrochloric acid/dioxane (25 mL) in one portion at 25 °C under nitrogen. The mixture was stirred at 25 °C for 3 min, then heated to 25 °C and stirred for 2 h. The crude product was concentrated to afford the title compound (988 mg, 99.1% yield) as a white solid, which was used in the next step without further purification. LCMS (method I) (ESI+): m/z 447.3 (M+H)+, RT: 0.625 min.

Step 6: N-(($4^2$S,$4^3$S)-5-oxo-8-oxa-4(2,1)-piperidina-1(1,2),2(1,3)-dibenzenacyclo-octaphane-$4^3$-yl)eth-anesulfonamide

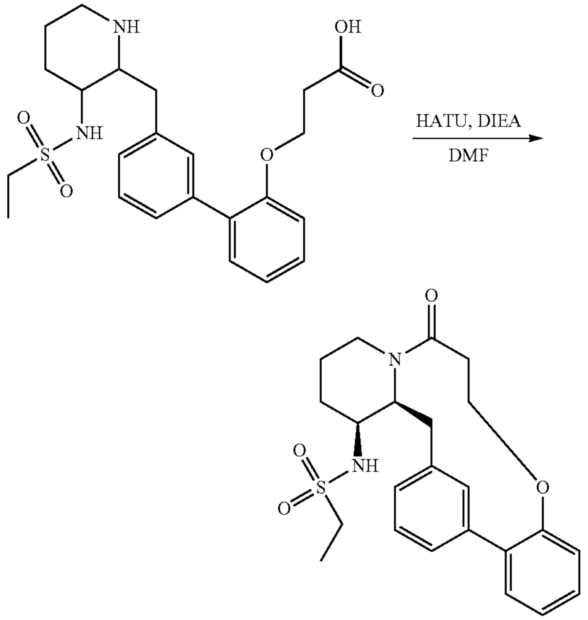

To a mixture of 3-((3'-((3-(ethylsulfonamido)piperidin-2-yl)methyl)-[1,1'-biphenyl]-2-yl)oxy)propanoic acid_cis racemic (200 mg, 448 μmol, 1 eq) in dimethyl formamide (200 mL) was added diisopropylethylamine (234 μL, 1.34 mmol, 3 eq) and HATU (221 mg, 582 mol, 1.3 eq) in one portion at 25 °C under nitrogen. The reaction mixture was stirred at 25 °C for 12 h. The mixture was concentrated under reduced pressure, poured into water (1000 mL) and stirred for 3 min. The aqueous phase was extracted with ethyl acetate (3×400 mL). The combined organic phase was washed with brine (3×500 mL), dried with anhydrous sodium sulfate, filtered and concentrated under reduced pressure. The resulting residue was purified by prep-HPLC (trifluoroacetic acid condition) to afford a white solid, which was further separated by SFC (column: DAICEL CHIRALPAK AD (250 mm×30 mm, 10 μm); mobile phase: [0.1% $NH_3 \cdot H_2O$ methanol]; B %: 50%-50%, 7 min.) to afford the title compound (57 mg, 29.4% yield) with the longer retention time as a white solid. 1H NMR (400 MHz, DMSO-$d_6$) δ ppm 7.42 (d, 1H), 7.37-7.34 (m, 1H), 7.34-7.28 (m, 2H), 7.16-7.06 (m, 5H), 5.08-5.00 (m, 1H), 4.19-4.12 (m, 1H), 4.06-3.98 (m, 1H), 3.83-3.75 (m, 1H), 3.42-3.35 (m, 1H), 3.19-2.88 (m, 6H), 2.20-2.13 (m, 1H), 1.84-1.69 (m, 3H), 1.57-1.42 (m, 1H), 1.31-1.03 (m, 3H). LCMS (method G): m/z 429 $(M+H)^+$ (ES+) at 2.28 min Example 41. Synthesis of Compound No. A1-76

Step 1: tert-butyl 2-((2'-hydroxy-[1,1'-biphenyl]-3-yl)methyl)-3-oxopiperidine-1-carboxylate

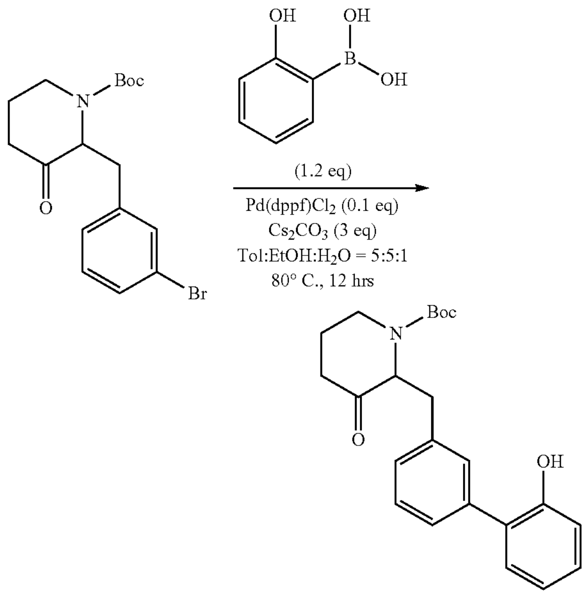

A mixture of tert-butyl 2-(3-bromobenzyl)-3-oxopiperidine-1-carboxylate (10 g, 27.2 mmol, 1 eq), (2-hydroxyphenyl)boronic acid (4.49 g, 32.59 mmol, 1.2 eq), Pd(dppf)$Cl_2$ (1.99 g, 2.72 mmol, 0.1 eq), cesium carbonate (26.5 g, 81.5 mmol, 3 eq) in toluene/ethanol/$H_2O$ (5:5:1, 110 mL) was degassed and purged with $N_2$ for 3 times. The reaction mixture was stirred at 80 °C for 12 h. The reaction mixture was diluted with water (100 mL) and extracted with ethyl acetate (200 mL×2). The combined organic layers were washed with aqueous sodium chloride (100 mL×2), dried over sodium sulfate, filtered and concentrated under reduced pressure to afford a residue. The residue was purified by column chromatography (PE:EA=3/1) to afford the title compound (6 g, 57.9% yield) as yellow solid.

$^1H$ NMR (400 MHz, methanol-$d_4$) 1.04-1.42 (m, 9H), 1.93 (br s, 2H), 2.03 (s, 1H), 2.39-2.66 (m, 2H), 2.92-3.17 (m, 2H), 3.78-4.16 (m, 1H), 4.45-4.79 (m, 1H), 6.84-6.92 (m, 2H), 7.06-7.18 (m, 2H), 7.23 (br d, 1H), 7.27-7.49 (m, 3H).

Step 2: tert-butyl 3-amino-2-((2'-hydroxy-[1,1'-biphenyl]-3-yl)methyl)piperidine-1-carboxylate_cis racemic

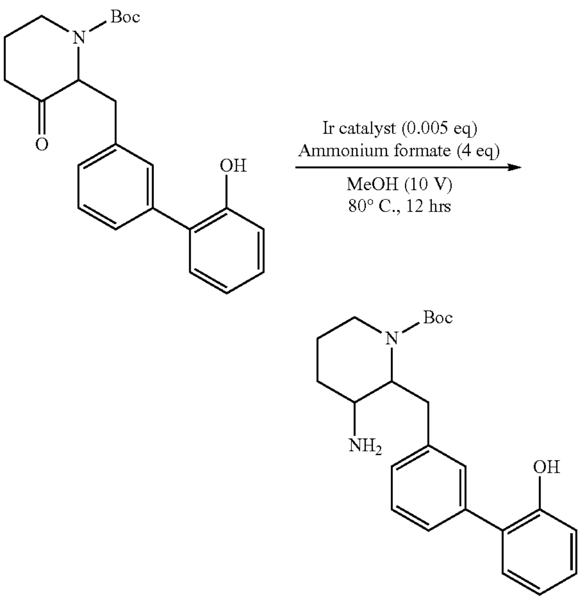

A mixture of tert-butyl 2-((2'-hydroxy-[1,1'-biphenyl]-3-yl)methyl)-3-oxopiperidine-1-carboxylate (3.00 g, 7.86 mmol, 1 eq), ammonium formate (1.98 g, 31.5 mmol, 4 eq), bis[2-(2-pyridyl)phenyl]iridium(1+);2-(2-pyridyl)pyridine; hexafluorophosphate (32 mg, 39.3 μmol, 0.005 eq) in methanol (30 mL) was degassed and purged with $N_2$ for 3 times, and then the mixture was stirred at 80 °C for 12 hours under $N_2$ atmosphere. The reaction mixture was diluted with water (15 mL) and extracted with ethyl acetate (20 mL×2). The combined organic layers were washed with aqueous sodium chloride (20 mL×2), dried over sodium sulfate, filtered and concentrated under reduced pressure to afford a residue. The residue was purified by column chromatography ($SiO_2$, petroleum ether/ethyl acetate=0/1) to afford the title compound (1.8 g, 53.9% yield) as white solid. LCMS (method I) (ESI+): m/z 383 (M+H)+, RT: 0.634 min.

Step 3: tert-butyl 3-((N,N-dimethylsulfamoyl)amino)-2-((2'-hydroxy-[1,1'-biphenyl]-3-yl)methyl)piperidine-1-carboxylate_cis racemic

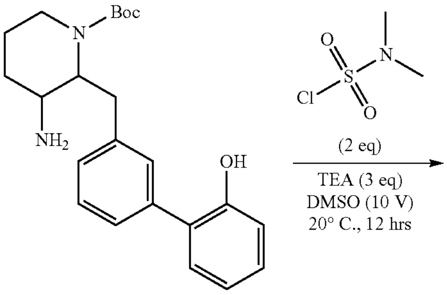

-continued

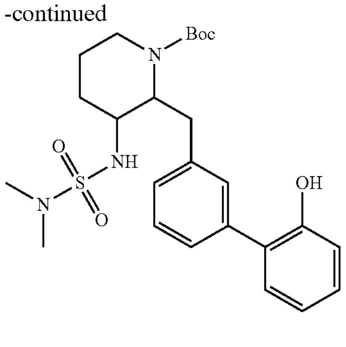

A mixture of tert-butyl 3-amino-2-((2'-hydroxy-[1,1'-biphenyl]-3-yl)methyl)piperidine-1-carboxylate_cis racemic (640 mg, 1.67 mmol, 1 eq), N, N-dimethylsulfamoyl chloride (359 µL, 3.35 mmol, 2 eq) and trimethylamine (699 µL, 5.02 mmol, 3 eq) in DMSO (6 mL) was degassed and purged with $N_2$ for 3 times, and then the mixture was stirred at 20 °C for 12 hrs under $N_2$ atmosphere. The reaction mixture was quenched by addition water (10 mL), and then extracted with ethyl acetate (20 mL) twice. The combined organic layers were washed with aqueous sodium chloride (10 mL) for twice, dried over sodium sulfate, filtered and concentrated under reduced pressure to afford a residue. The residue was purified by column chromatography ($SiO_2$, petroleum ether/ethyl acetate=100/0 to 5/1) to afford the title compound (400 mg, 48.8%) as white solid. $^1H$ NMR (400 MHz, DMSO-$d_6$) δ ppm 0.88-1.17 (m, 9H), 1.69 (br s, 3H), 2.68-2.79 (m, 6H), 2.85-2.93 (m, 2H), 3.17-3.28 (m, 1H), 3.74-3.91 (m, 1H), 4.44-4.62 (m, 1H), 6.80-6.97 (m, 2H), 7.04-7.23 (m, 3H), 7.23-7.39 (m, 3H), 7.51 (br d, 1H), 9.42 (s, 1H).

Step 4: tert-butyl (E/Z)-2-((2'-((3-(tert-butoxy)-3-oxoprop-1-en-1-yl)oxy)-[1,1'-biphenyl]-3-yl)methyl)-3-((N,N-dimethylsulfamoyl)amino)piperidine-1-carboxylate_cis racemic

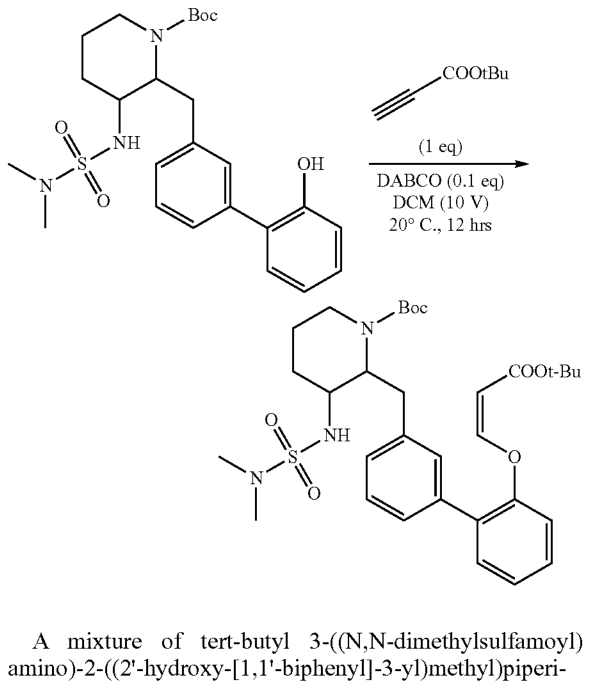

A mixture of tert-butyl 3-((N,N-dimethylsulfamoyl)amino)-2-((2'-hydroxy-[1,1'-biphenyl]-3-yl)methyl)piperidine-1-carboxylate_cis racemic (100 mg, 204 µmol, 1 eq), tert-butyl prop-2-ynoate (28.0 uL, 204.24 µmol, 1 eq), 1, 4-diazabicyclo[2.2.2]octane (2.25 µL, 20.4 µmol, 0.1 eq) in dichloromethane (1 mL) was degassed and purged with $N_2$ three times. The mixture was stirred at 20 °C for 12 hours under $N_2$ atmosphere. The reaction mixture was diluted with water (1 mL) and extracted with ethyl acetate (1 mL×2). The combined organic layers were washed with aqueous sodium chloride (1 mL×2), dried over sodium sulfate, filtered and concentrated under reduced pressure to afford a residue. The residue was purified by prep-TLC ($SiO_2$, petroleum ether/ethyl acetate=3:1) to afford the title compound (100 mg, 55.7% yield) as a white solid.

$^1H$ NMR (400 MHz, chloroform-d) 1.05-1.18 (m, 8H), 1.27 (t, 4H), 1.53-1.72 (m, 3H), 1.79 (br d, 1H), 1.88-2.00 (m, 1H), 2.05 (s, 3H), 2.82-2.87 (m, 6H), 2.88-3.03 (m, 3H), 3.50 (br d, 1H) 4.06-4.17 (m, 4H), 4.77 (br s, 1H), 5.36 (d, 1H), 6.57 (d, 1H), 7.10-7.25 (m, 3H), 7.30-7.54 (m, 4H).

Step 5: tert-butyl 2-((2'-(3-(tert-butoxy)-3-oxopropoxy)-[1,1'-biphenyl]-3-yl)methyl)-3-((N,N-dimethylsulfamoyl)amino)piperidine-1-carboxylate_cis racemic

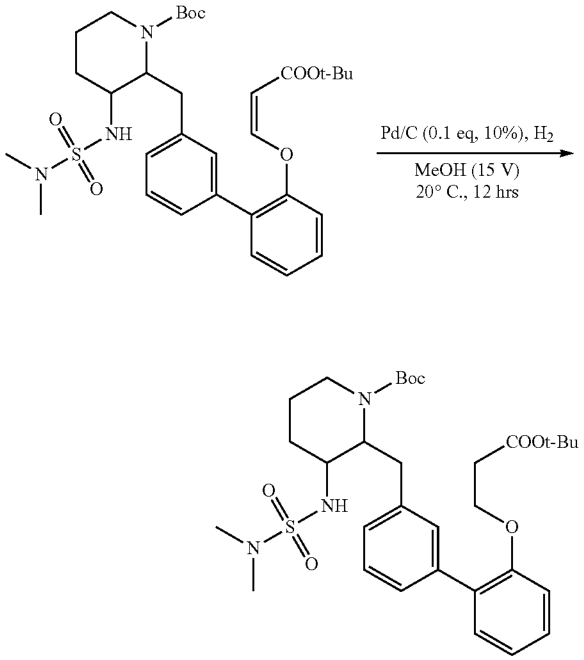

A mixture of tert-butyl (Z)-2-((2'-((3-(tert-butoxy)-3-oxoprop-1-en-1-yl)oxy)-[1,1'-biphenyl]-3-yl)methyl)-3-((N,N-dimethylsulfamoyl)amino)piperidine-1-carboxylate_cis racemic (100 mg, 162 µmol, 1 eq) and Pd/C (17 mg, 10% purity, 0.1 eq) in methanol (1.5 mL) was degassed and purged with $N_2$ three times The mixture was stirred at 20 °C for 12 hours under $H_2$ atmosphere. The reaction mixture was filtered and concentrated under reduced pressure to afford the title compound (80 mg, 79.7% yield) as colourless oil. The residue was used for the next step without further purification. LCMS (method I) (ESI+): m/z 462 (M-156)+, RT: 0.911 min.

Step 6: 3-((3'-((3-((N,N-dimethylsulfamoyl)amino)piperidin-2-yl)methyl)-[1,1'-biphenyl]-2-yl)oxy)propanoic acid_cis racemic

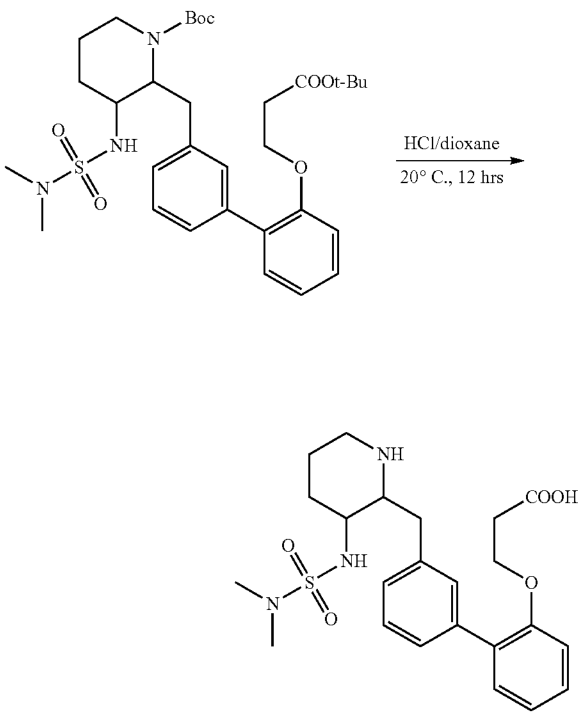

A mixture of tert-butyl 2-((2'-(3-(tert-butoxy)-3-oxopropoxy)-[1,1'-biphenyl]-3-yl)methyl)-3-((N,N-dimethylsulfamoyl)amino)piperidine-1-carboxylate_cis racemic (80 mg, 129 μmol, 1 eq) in HCl/dioxane (1 mL, 4 M) and then the mixture was stirred at 20 °C for 12 hours under $N_2$ atmosphere. The reaction was dried by vacuum to afford the title compound (60 mg, 85.6% yield) as white solid. LCMS (method I) (ESI+): m/z 462 (M+H)+, RT: 0.631 min.

Step 7: N-(($4^2$S,$4^3$S)-5-oxo-8-oxa-4(2,1)-piperidina-1(1,2),2(1,3)-dibenzena cyclooctaphane-$4^3$-yl)-N,N-dimethylsulfuric diamide

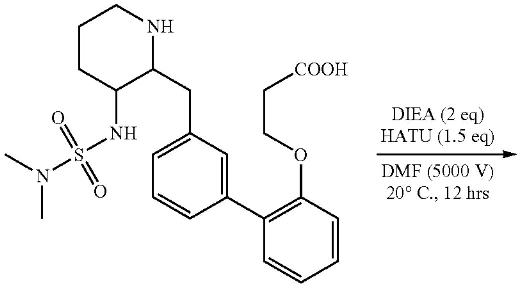

-continued

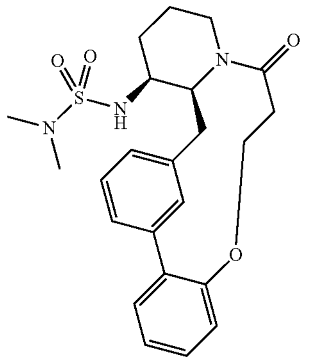

To a solution of 3-((3'-((3-((N,N-dimethylsulfamoyl)amino)piperidin-2-yl)methyl)-[1,1'-biphenyl]-2-yl)oxy)propanoic acid (60 mg, 120 μmol, 1 eq) in N,N-dimethylformamide (300 mL) was added N,N-diisopropylethylamine (42 μL, 241 μmol, 2 eq) and HATU (69 mg, 181 mol, 1.5 eq). The mixture was stirred at 20 °C for 12 hours. The reaction was dried by vacuum and the residue was purified by prep-HPLC to afford a white solid, which was further separated by SFC (column: DAICEL CHIRALCEL OJ (250 mm×30 mm, 10 μm); mobile phase: [0.1% $NH_3$·$H_2O$ ethanol]; B %: 30%-70%, 15 min.) to afford the title compound (16 mg, 29.9% yield) with the longer retention time as a white solid. 1H NMR (400 MHz, acetonitrile-d3) δ ppm 7.39 (dd, 1H), 7.35-7.29 (m, 2H), 7.18 (dd, 3H), 7.14-7.08 (m, 2H), 5.48-5.34 (m, 1H), 5.24-5.12 (m, 1H), 4.19-4.12 (m, 1H), 4.09-3.99 (m, 1H), 3.80 (br dd, 1H), 3.48-3.36 (m, 1H), 3.20-3.03 (m, 2H), 3.03-2.92 (m, 1H), 2.77 (s, 6H), 2.25-2.16 (m, 1H), 1.89-1.74 (m, 3H), 1.67-1.52 (m, 1H). Exchangeable proton not observed. LCMS (method H): m/z 444 $(M+H)^+$ (ES+) at 2.80 min Example 42. Synthesis of Compound No. A1-78

Step 1: tert-butyl (Z)-2-((2'-((3-(tert-butoxy)-3-oxoprop-1-en-1-yl)oxy)-[1,1'-biphenyl]-3-yl)methyl)-3-(methylsulfonamido)piperidine-1-carboxylate_cis racemic

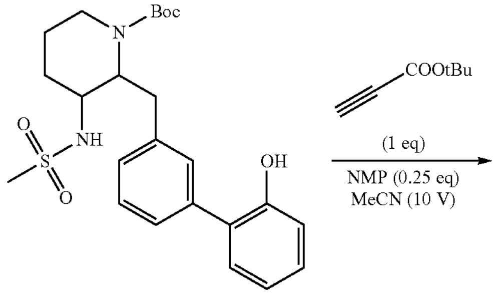

-continued

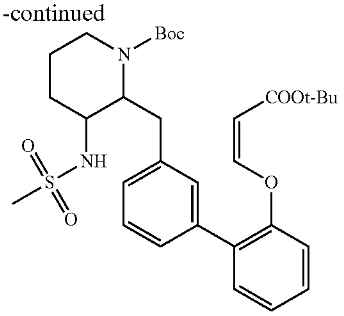

To a mixture of tert-butyl prop-2-ynoate (964 mg, 7.64 mmol, 1.05 mL, 1.1 eq) and tert-butyl 2-((2'-hydroxy-[1,1'-biphenyl]-3-yl)methyl)-3-(methylsulfonamido)piperidine-1-carboxylate_cis racemic, intermediate 4 (3.2 g, 6.95 mmol, 1 eq) in acetonitrile (32 mL) was added N-methyl morpholine (382 µL, 3.47 mmol, 0.5 eq) in one portion at 25 °C under nitrogen. The reaction mixture was stirred at 25 °C for 12 h. The residue was poured into water (100 mL) and stirred for 3 min. The aqueous phase was extracted with ethyl acetate (3×45 mL). The combined organic phase was washed with brine (30 mL), dried with anhydrous sodium sulfate, filtered and concentrated under reduced pressure. The residue was purified by column chromatography on silica gel eluted with petroleum ether:ethyl acetate(1:0 to 1:1) to afford the title compound (5.31 g, 73% yield) as yellow oil. LCMS (method I) (ESI+): m/z 587.27 (M+H)+, RT: 1.102 min.

Step 2: tert-butyl 2-((2'-(3-(tert-butoxy)-3-oxopropoxy)-[1,1'-biphenyl]-3-yl)methyl)-3-(methylsulfonamido)piperidine-1-carboxylate_cis racemic

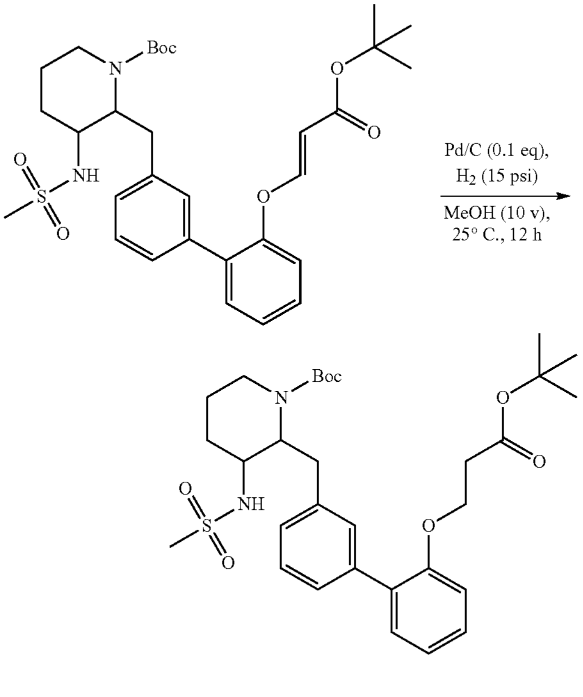

To a mixture of tert-butyl (Z)-2-((2'-((3-(tert-butoxy)-3-oxoprop-1-en-1-yl)oxy)-[1,1'-biphenyl]-3-yl)methyl)-3-(methylsulfonamido)piperidine-1-carboxylate_cis racemic (5.31 g, 9.05 mmol, 1 eq) in methanol (50 mL) was added Pd/C (5 g, 8.18 mmol, 10% purity, 1 eq) in one portion at 25 °C under hydrogen atmosphere. The mixture was stirred at 25 °C for 12 h. The reaction mixture was filtered with celite and the filtrate was concentrated under reduced pressure to afford a residue. The crude product was purified by silica gel chromatography eluted with petroleum ether:ethyl acetate (1:0 to 0:1) to afford the title compound (3.9 g, 97% yield) as a yellow solid. LCMS (method I) (ESI+): m/z 489.3 (M−100)+, RT: 0.878 min.

Step 3: 3-((3'-((3-(methylsulfonamido)piperidin-2-yl)methyl)-[1,1'-biphenyl]-2-yl)oxy)propanoic acid-_cis racemic

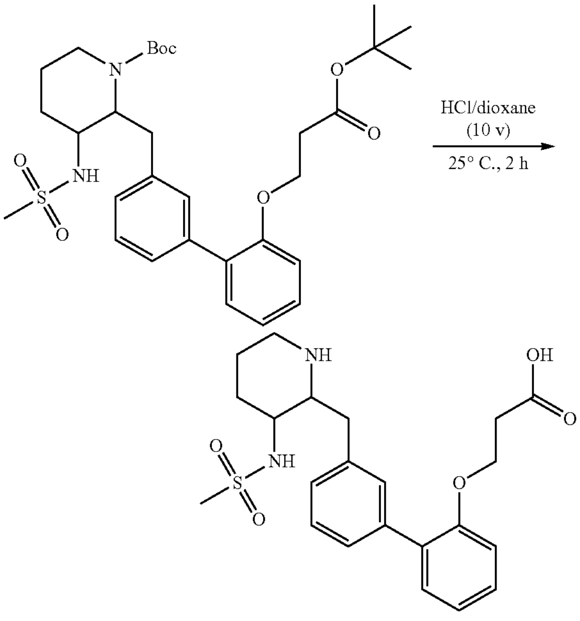

To a mixture of tert-butyl 2-((2'-(3-(tert-butoxy)-3-oxopropoxy)-[1,1'-biphenyl]-3-yl)methyl)-3-(methylsulfonamido)piperidine-1-carboxylate_cis racemic (1.5 g, 2.55 mmol, 1 eq) in hydrochloric acid/dioxane (25 mL, 10% purity) in one portion at 25 °C under nitrogen. The mixture was stirred at 25 °C for 2 h. The mixture was concentrated under reduced pressure to afford the title compound (1 g, 83.7% yield) as a white solid. LCMS (method I) (ESI+): m/z 433.1 (M+H)+, RT: 0.665 min.

Step 4: N-(($4^2$S,$4^3$S)-5-oxo-8-oxa-4(2,1)-piperidina-1(1,2),2(1,3)-dibenzenacyclo-octaphane-$4^3$-yl)methanesulfonamide

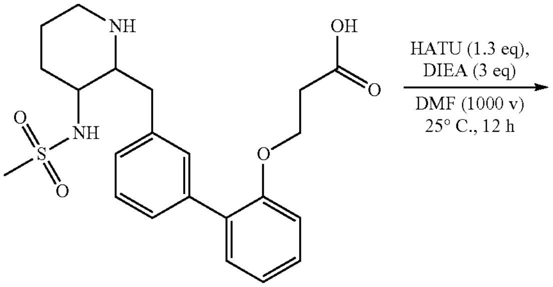

-continued

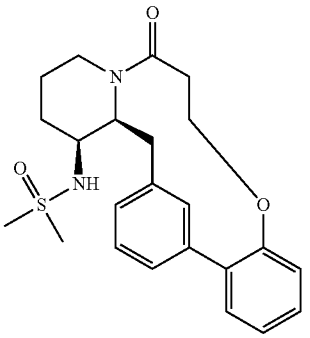

To a mixture of 3-((3'-((3-(methylsulfonamido)piperidin-2-yl)methyl)-[1,1'-biphenyl]-2-yl)oxy)propanoic acid_cis racemic (450 mg, 1.04 mmol, 1 eq) in dimethyl formamide (450 mL) was added diisopropylethylamine (403 mg, 3.12 mmol, 544 μL, 3 eq) and HATU (514 mg, 1.35 mmol, 1.3 eq) at 25 °C for 12 h. The reaction mixture was concentrated under reduced pressure and purified by prep-HPLC (base condition) to afford a white solid, which was further separated by SFC (column: REGIS(S,S)WHELK-O1(250 mm×25 mm, 10 μm); mobile phase: [0.1% $NH_3 \cdot H_2O$ ethanol]; B %: 60%-60%, 8 min) to afford the title compound (101 mg, 23.4% yield) with the longer retention time as a white solid. 1H NMR (400 MHz, chloroform-d) δ ppm 7.42-7.38 (m, 1H), 7.37-7.33 (m, 1H), 7.32-7.27 (m, 2H), 7.16-7.07 (m, 4H), 5.11-5.03 (m, 1H), 4.18-4.12 (m, 1H), 4.06-3.98 (m, 1H), 3.84-3.76 (m, 1H), 3.45-3.37 (m, 1H), 3.17-3.00 (m, 2H), 2.99-2.96 (m, 3H), 2.96-2.87 (m, 1H), 2.20-2.12 (m, 1H), 2.09-2.06 (m, 1H), 1.84-1.64 (m, 3H), 1.60-1.43 (m, 1H). Exchangeable proton not observed. LCMS (method G): m/z 415 $(M+H)^+$ (ES+) at 2.32 min

Example 43. Synthesis of Compound No. A1-82

Step 1: Tert-butyl 2-(3-bromo-2-fluorobenzyl)-3-oxopiperidine-1-carboxylate

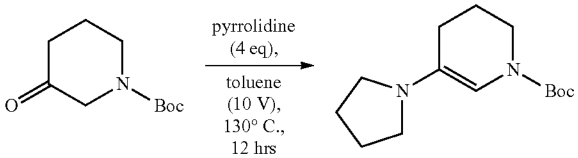 [SMILES: CC(C)(C)OC(=O)N1CCCC(=O)C1 ; CC(C)(C)OC(=O)N1C=C(N2CCCC2)CCC1]

To a solution of tert-butyl 3-oxopiperidine-1-carboxylate (250 g, 1.25 mol, 1 eq) in toluene (1.5 L) was added pyrrolidine (419 mL, 5.02 mol, 4 eq). The mixture was stirred at 130 °C for 12 hrs by Dean-Stark trap. After cooling to 25 °C, 22.5 mL of water was collected in Dean-Stark trap. Additional batch was set up as described above. Both batches were combined and concentrated under reduced pressure to afford a crude yellow oil.

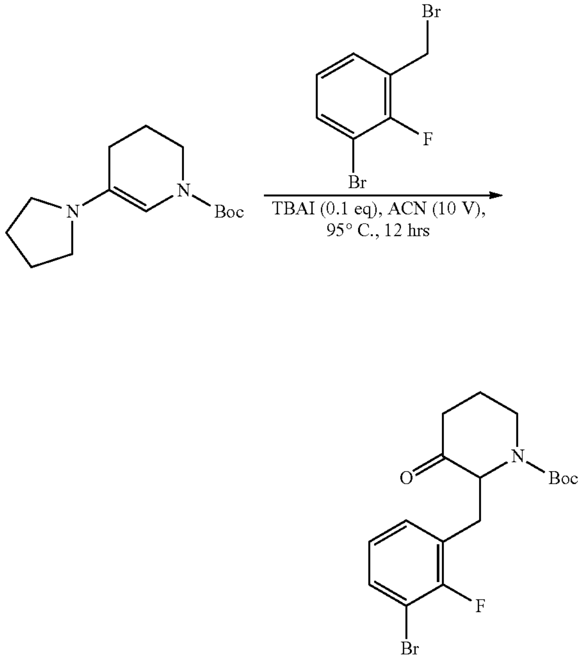

To a solution of tert-butyl 5-(pyrrolidin-1-yl)-3,4-dihydropyridine-1(2H)-carboxylate (266 g, 895 mmol, 1 eq) in acetonitrile (2.66 L) were added 1-bromo-3-(bromomethyl)-2-fluoro-benzene (288 g, 1.07 mol, 1.2 eq) and TBAI (33.1 g, 89.5 mmol, 0.1 eq). The mixture was stirred at 95 °C for 12 hrs. Two additional batches were set up as described above. After cooling to 20 °C, all three reactions were combined and concentrated. The residue was poured into water (1 L), extracted with ethyl acetate (3×300 mL). The organic layer was washed with brine (500 mL), dried over $Na_2SO_4$ (500 g), filtered and concentrated under reduce pressure to afford a residue. The residue was purified by column chromatography on silica gel (eluted with petroleum ether/ethyl acetate=40/1 to 20/1, 20 L) to afford the title compound (270 g, 664 mmol, 74.2% yield) as white solid. $^1H$ NMR (400 MHz, chloroform-d) δ 1.10-1.43 (m, 9H), 1.80-2.11 (m, 2H), 2.53 (br s, 2H), 2.88-3.26 (m, 3H), 4.19 (br d, 1H), 4.68-4.92 (m, 1H), 6.91-7.01 (m, 1H), 7.03-7.25 (m, 1H), 7.45 (br s, 1H).

Step 2: tert-butyl 3-amino-2-(3-bromo-2-fluorobenzyl)piperidine-1-carboxylate_cis racemic

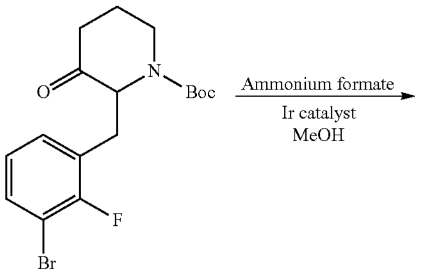

-continued

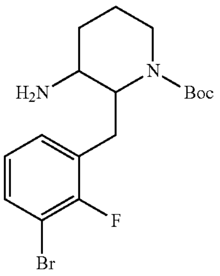

To a solution of tert-butyl 2-(3-bromo-2-fluorobenzyl)-3-oxopiperidine-1-carboxylate (10 g, 25.9 mmol, 1 eq) in methanol (100 mL) was added ammonium formate (4.90 g, 77.7 mmol, 3 eq) and Ir catalyst (245 mg, 388 μmol, 0.015 eq) in one portion at 25 °C under $N_2$. The mixture was stirred at 25 °C for 3 min, then heated to 80 °C and stirred for 12 hrs. The reaction mixture was poured into water (200 mL) and extracted with dichloromethane (3×100 mL). The combined organic layer was washed with brine (100 mL), dried over sodium sulfate, filtered and concentrated under reduced pressure to afford a residue. The residue was purified by column chromatography ($SiO_2$, petroleum ether/ethyl acetate=100/1 to 0/1) to afford the title compound (7.5 g, 74.8% yield) as white solid. $^1$H NMR (400 MHz, chloroform-d) δ ppm 1.01-1.15 (m, 9H), 1.32 (br s, 2H), 1.41-1.50 (m, 2H), 1.60-1.72 (m, 2H), 2.64-2.85 (m, 2H), 2.97-3.10 (m, 2H), 3.92-4.05 (m, 1H), 4.40 (br s, 1H), 6.80-6.89 (m, 1H), 7.02 (br s, 1H), 7.32 (br t, 1H).

Step 3: tert-butyl 2-(3-bromo-2-fluorobenzyl)-3-(methylsulfonamido)piperidine-1-carboxylate_cis racemic

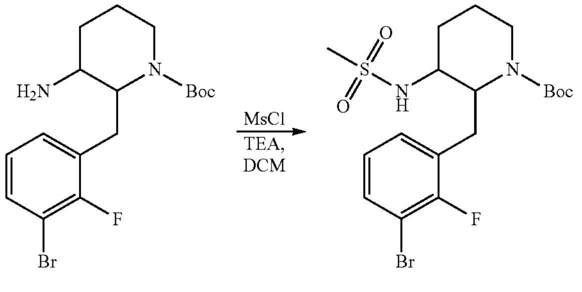 [SMILES: "MsCl" ; CC(C)(C)OC(=O)N1CCCC(N)C1Cc1cccc(Br)c1F ; "TEA,DCM" ; CC(C)(C)OC(=O)N1CCCC(NS(C)(=O)=O)C1Cc1cccc(Br)c1F]

To a solution of tert-butyl 3-amino-2-(3-bromo-2-fluorobenzyl)piperidine-1-carboxylate_cis racemic (7.5 g, 19.4 mmol, 1 eq) in dichloromethane (100 mL) was added triethylamine (8.09 mL, 58.1 mmol, 3 eq) and methanesulfonyl chloride (3.47 mL, 44.9 mmol, 2.32 eq) at 0 °C. The mixture was stirred at 25 °C for 2 hrs. The reaction mixture was poured into water (200 mL) and extracted with dichloromethane (3×100 mL). The combined organic layer was washed with brine (100 mL), dried over sodium sulfate, filtered and concentrated under reduced pressure to afford a residue. The residue was purified by column chromatography ($SiO_2$, petroleum ether/ethyl acetate=100/1 to 1/1) to afford the title compound (7.0 g, 77.7% yield) as yellow solid. $^1$H NMR (400 MHz, dimethyl sulfoxide-$d_6$) δ 0.80-1.14 (m, 9H), 1.39-1.54 (m, 1H), 1.60-1.72 (m, 3H), 2.80-2.93 (m, 2H), 2.99 (s, 3H), 3.31-3.33 (m, 1H), 3.40 (br d, 1H), 3.67-3.91 (m, 1H), 4.47-4.64 (m, 1H), 7.06 (br t, 1H), 7.19-7.26 (m, 1H), 7.44 (br d, 1H), 7.47-7.59 (m, 1H).

Step 4: tert-butyl 2-((2-fluoro-2'-hydroxy-[1,1'-biphenyl]-3-yl)methyl)-3-(methylsulfonamido)piperidine-1-carboxylate_cis racemic

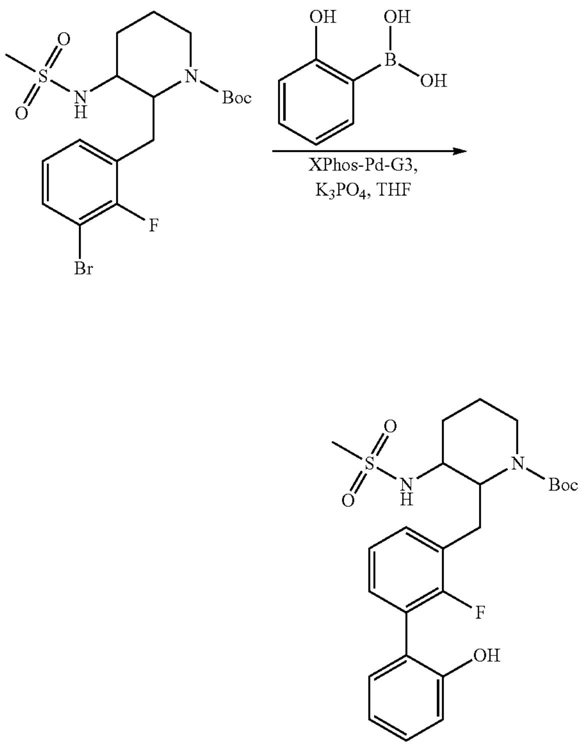

To a solution of (2-hydroxyphenyl) boronic acid (2.28 g, 16.6 mmol, 1.1 eq) in tetrahydrofuran (100 mL) was added tert-butyl 2-(3-bromo-2-fluorobenzyl)-3-(methylsulfonamido)piperidine-1-carboxylate_cis racemic (7 g, 15.0 mmol, 1 eq), XPhos-Pd-G3 (637 mg, 752 μmol, 0.05 eq) and potassium phosphate (9.58 g, 45.1 mmol, 3 eq) at 25 °C. The mixture was stirred at 70 °C for 12 hrs. The reaction mixture was poured into water (200 mL) and extracted with dichloromethane (3×100 mL). The combined organic layer was washed with brine (100 mL), dried over sodium sulfate, filtered and concentrated under reduced pressure to afford a residue. The residue was purified by column chromatography ($SiO_2$, Petroleum ether/Ethyl acetate=100/1 to 1/1) to afford the title compound (7.0 g, 97.2% yield) as yellow solid. $^1$H NMR (400 MHz, chloroform-d) δ 1.07 (s, 9H), 1.37-1.63 (m, 3H), 1.70 (br d, 1H), 1.80-1.93 (m, 1H), 2.63-2.92 (m, 2H), 2.99 (br s, 3H), 3.02-3.12 (m, 1H), 3.52-3.71 (m, 1H), 3.81 (br s, 1H), 4.56-5.06 (m, 2H), 6.78-6.93 (m, 2H), 6.96-7.16 (m, 4H), 7.33 (br t, 1H).

Step 5: tert-butyl (E/Z)-2-((2'-((3-(tert-butoxy)-3-oxoprop-1-en-1-yl)oxy)-2-fluoro-[1,1'-biphenyl]-3-yl)methyl)-3-(methylsulfonamido)piperidine-1-carboxylate_cis racemic Step 6: tert-butyl 2-((2'-(3-(tert-butoxy)-3-oxopropoxy)-2-fluoro-[1,1'-biphenyl]-3-yl)methyl)-3-(methylsulfonamido)piperidine-1-carboxylate_cis racemic

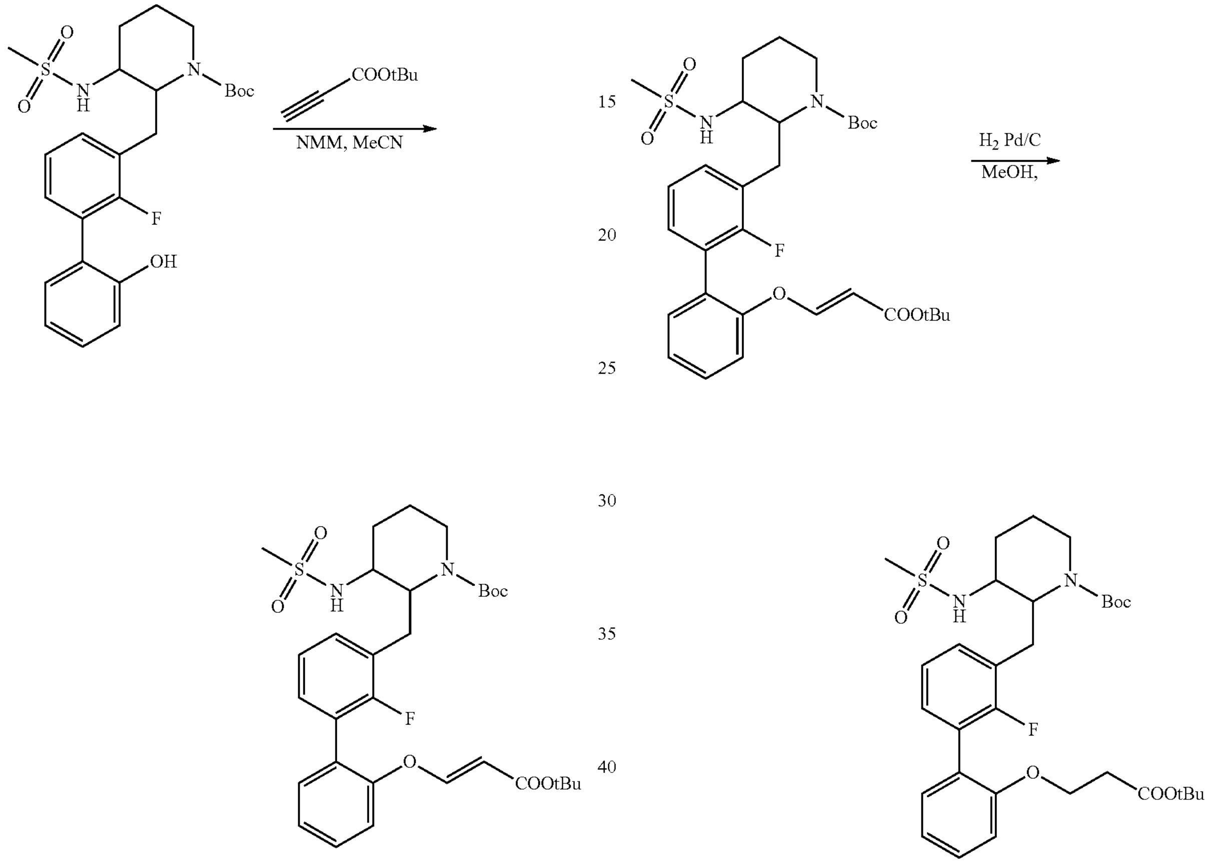

To a solution of tert-butyl 2-((2-fluoro-2'-hydroxy-[1,1'-biphenyl]-3-yl)methyl)-3-(methylsulfonamido)piperidine-1-carboxylate_cis racemic (6 g, 12.5 mmol, 1 eq) in acetonitrile (60 mL) was added N-methylmorpholine (634 mg, 6.27 mmol, 689.21 μL, 0.5 eq) and tert-butyl prop-2-ynoate (1.74 g, 13.79 mmol, 1.89 mL, 1.1 eq) at 25 °C. The mixture was stirred at 25 °C for 12 hrs. The reaction mixture was poured into water (200 mL) and extracted with ethyl acetate (3×100 mL). The combined organic layer was washed with brine (100 mL), dried over sodium sulfate, filtered and concentrated under reduced pressure to afford a residue. The residue was purified by column chromatography ($SiO_2$, Petroleum ether/Ethyl acetate=100/1 to 1/100) to afford the title compound (3.6 g, 5.95 mmol, 47.5% yield) as yellow solid. $^1H$ NMR (400 MHz, chloroform-d) δ 1.09 (br s, 9H), 1.36-1.44 (m, 9H), 1.49-1.67 (m, 3H), 1.71 (br d, 1H), 1.84 (br d, 1H), 2.82-2.89 (m, 2H), 2.92 (s, 3H), 3.55-3.64 (m, 1H), 3.98 (br s, 1H), 4.40 (d, 1H), 4.68 (br s, 1H), 5.30 (d, 1H), 7.01-7.19 (m, 4H), 7.20-7.37 (m, 2H), 7.52 (d, 1H).

To a solution of tert-butyl (E)-2-((2'-((3-(tert-butoxy)-3-oxoprop-1-en-1-yl)oxy)-2-fluoro-[1,1'-biphenyl]-3-yl)methyl)-3-(methylsulfonamido)piperidine-1-carboxylate_cis racemic (3.6 g, 5.95 mmol, 1 eq) in methanol (60 mL) was added Pd/C (0.2 g, 1.89 mmol, 10% purity) under $N_2$ atmosphere. The suspension was degassed and purged with $H_2$ 3 times at 25 °C. The mixture was stirred under $H_2$ (15 Psi) at 25 °C for 12 hrs. The reaction mixture was filtered over Celite and the filtrate was concentrated under reduced pressure to afford the title compound (3 g, 83.1% yield) as white solid. $^1H$ NMR (400 MHz, chloroform-d) δ ppm 1.03-1.16 (m, 9H), 1.32 (s, 9H), 1.50-1.63 (m, 2H), 1.75-1.89 (m, 2H), 2.53 (t, 2H), 2.74-2.80 (m, 1H), 2.84-2.90 (m, 3H), 2.94-3.01 (m, 1H), 3.53-3.62 (m, 1H), 3.68 (br t, 1H), 3.97 (br s, 1H), 4.07-4.25 (m, 2H), 4.49 (br d, 1H), 4.68 (br s, 1H), 6.85-7.02 (m, 3H), 7.06-7.18 (m, 3H), 7.22-7.30 (m, 1H).

Step 7: 3-((2'-fluoro-3'-((3-(methylsulfonamido) piperidin-2-yl)methyl)-[1,1'-biphenyl]-2-yl)oxy) propanoic acid_cis racemic hydrochloride

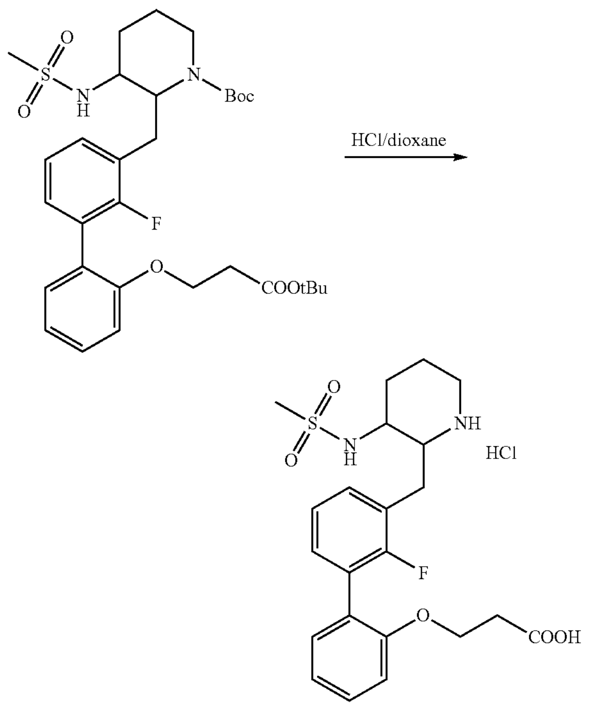

A solution of tert-butyl 2-((2'-(3-(tert-butoxy)-3-oxopropoxy)-2-fluoro-[1,1'-biphenyl]-3-yl)methyl)-3-(methylsulfonamido)piperidine-1-carboxylate_cis racemic (1.0 g, 1.65 mmol, 1 eq) in HCl/dioxane (4M, 30 mL) was stirred at 25 °C for 12 hrs. The reaction was concentrated under reduced pressure to afford the title compound (0.6 g, 80.8% yield) as yellow solid. $^1$H NMR (400 MHz, chloroform-d) δ ppm 1.71-1.87 (m, 2H), 2.12 (br d, 1H), 2.31 (br d, 1H), 2.41-2.71 (m, 2H), 3.08 (s, 3H), 3.21 (br dd, 2H), 3.42 (br dd, 1H), 3.57-3.71 (m, 2H), 4.07 (br d, 1H), 4.20-4.36 (m, 2H), 7.02 (d, 1H), 7.08 (t, 1H), 7.12-7.18 (m, 1H), 7.20-7.27 (m, 1H), 7.30-7.48 (m, 3H), 8.42 (br s, 1H), 9.10 (br s, 1H).

Step 8: N-(($4^2$S,$4^3$S)-22-fluoro-5-oxo-8-oxa-4(2,1)-piperidina-1(1,2),2(1,3)-dibenzenacyclooctaphane-$4^3$-yl)methanesulfonamide

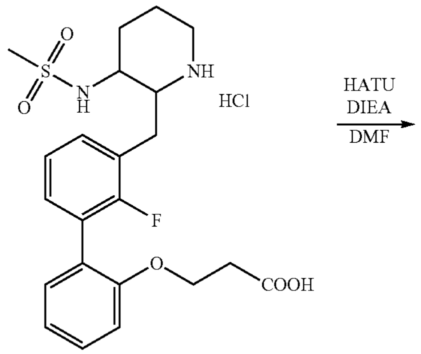

-continued

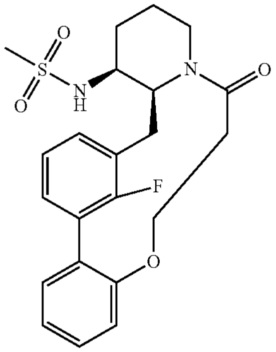

To a solution of 3-((2'-fluoro-3'-((3-(methylsulfonamido) piperidin-2-yl)methyl)-[1,1'-biphenyl]-2-yl)oxy)propanoic acid_cis racemic hydrochloride (0.6 g, 1.33 mmol, 1 eq) in N,N-dimethylformamide (600 mL) were added o-(7-azabenzotriazol-1-yl)-N,N,N',N'-tetramethyluronium hexafluorophosphate (658. mg, 1.73 mmol, 1.3 eq) and N,N-diisopropylethylamine (1.16 mL, 6.66 mmol, 5 eq) at 25 °C. The mixture was stirred at 25 °C for 12 hrs. The reaction mixture was poured into water (500 mL) and extracted with ethyl acetate (3×500 mL). The combined organic layer was washed with brine (1 L), dried over sodium sulfate, filtered and concentrated under reduced pressure to afford a residue which was separated by SFC (column: CHIRALPAK IC-3 (50 mm×6.4 mm, 3 μm); mobile phase: [0.1% IPA:methanol]; B %: 50%-50%, 8 min) to afford the title compound (59.7 mg, 10.4% yield) with the longer retention time as white solid. $^1$H NMR (400 MHz, chloroform-d) δ ppm 7.41-7.34 (m, 2H), 7.34-7.27 (m, 1H), 7.21-7.11 (m, 4H), 5.16 (br dd, 1H), 4.61 (br d, 1H), 4.07 (br t, 2H), 3.79 (br d, 1H), 3.57 (td, 2H), 3.22 (t, 1H), 3.08 (s, 3H), 3.03 (dt, 1H), 2.74 (br d, 1H), 2.53-2.44 (m, 1H), 2.07-1.99 (m, 1H), 1.86 (br d, 1H), 1.78-1.68 (m, 1H). Exchangeable proton not observed. LCMS (method G): m/z 433 $(M+H)^+$ (ES+) at 2.28 min Example 44. Synthesis of Compound No. A1-84

Step 1: tert-butyl 2-(3-bromobenzyl)-3-(cyclopropanesulfonamido)piperidine-1-carboxylate_cis racemic

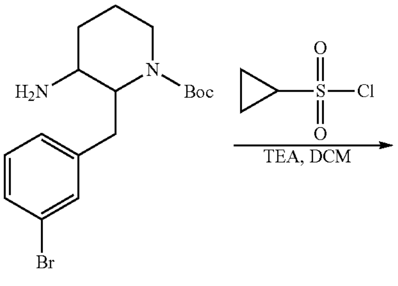

-continued

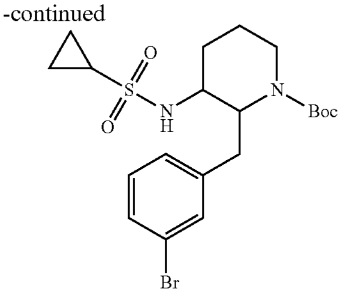

To a mixture of tert-butyl 3-amino-2-(3-bromobenzyl) piperidine-1-carboxylate_cis racemic (4 g, 13.5 mmol, 1 eq) in dichloromethane (50 mL) was added triethylamine (5.48 g, 54.1 mmol, 7.54 mL, 4 eq) and cyclopropanesulfonyl chloride (4.76 g, 33.9 mmol, 2.5 eq) at 0 °C under $N_2$. The mixture was stirred at 25 °C for 12 hrs, poured into saturated aqueous $NH_4Cl$ solution (30 mL) and extracted with dichloromethane (3×20 mL). The organic layer was washed with brine (15 mL) and dried over $Na_2SO_4$, concentrated under reduced pressure to give a residue which was purified by column chromatography ($SiO_2$, Petroleum ether/Ethyl acetate=100/1 to 1/1) to afford the title compound (3.4 g, 66% yield) as a yellow solid. $^1H$ NMR (400 MHz, chloroform-d) δ 1.00-1.13 (m, 2H), 1.20 (s, 9H), 1.23-1.33 (m, 2H), 1.59-1.73 (m, 2H), 1.79 (br d, 1H), 1.88-1.96 (m, 1H), 2.41-2.50 (m, 1H), 2.74-2.88 (m, 2H), 2.90-2.97 (m, 1H), 3.57-3.67 (m, 1H), 3.99-4.15 (m, 1H), 4.48-4.65 (m, 1H), 4.75 (br s, 1H), 7.07-7.16 (m, 2H), 7.31-7.36 (m, 2H).

Step 2: tert-butyl 3-(cyclopropanesulfonamido)-2-((2'-hydroxy-[1,1'-biphenyl]-3-yl)methyl)piperidine-1-carboxylate_cis racemic

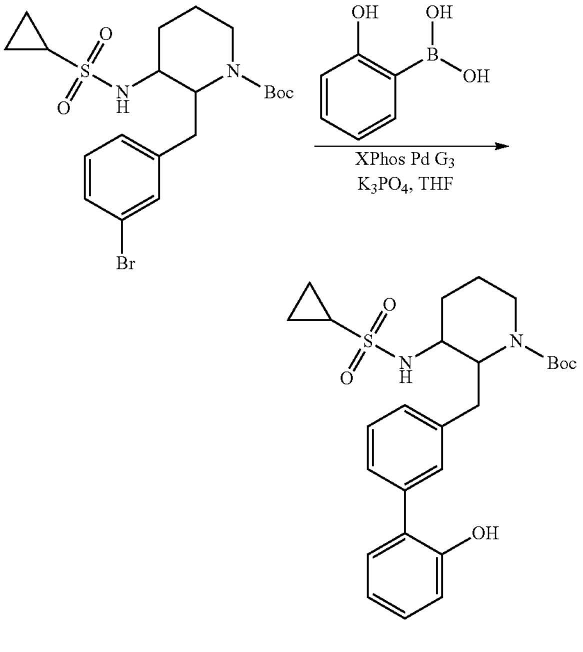

To a mixture of tert-butyl 2-(3-bromobenzyl)-3-(cyclopropanesulfonamido)piperidine-1-carboxylate_cis racemic (3.4 g, 7.18 mmol, 1 eq) in tetrahydrofuran (50 mL) was added (2-hydroxyphenyl) boronic acid (1.49 g, 10.77 mmol, 1.5 eq), XPhos-Pd-G3 (318 mg, 0.36 mol, 0.05 eq) and $K_3PO_4$ (4.57 g, 21.55 mmol, 3 eq) in one portion at 25 °C under $N_2$. The mixture was stirred at 80 °C for 12 hrs. After cooling down to 25 °C, water (40 mL) was added to the above reaction mixture. And the aqueous phase was extracted with ethyl acetate (3×20 mL). The organic layer was washed with brine (10 mL) and dried over $Na_2SO_4$, concentrated under reduced pressure to give the residue. The residue was purified by column chromatography ($SiO_2$, Petroleum ether/Ethyl acetate=100/1 to 3/1) to afford the title compound (2.4 g, 68.7% yield) as a yellow solid. $^1H$ NMR (400 MHz, chloroform-d) δ 0.96-1.11 (m, 2H), 1.13 (s, 9H), 1.25 (s, 2H), 1.56-1.72 (m, 2H), 1.74-1.86 (m, 1H), 1.96 (br d, 1H), 2.45-2.55 (m, 1H), 2.81-2.96 (m, 2H), 3.02 (dd, 1H), 3.60-3.71 (m, 1H), 3.95 (br s, 1H), 4.40 (d, 1H), 4.95 (br s, 1H), 6.93-6.98 (m, 1H), 7.02 (d, 1H), 7.17 (br d, 1H), 7.27 (s, 3H), 7.37 (br t, 2H).

Step 3: tert-butyl (E)-2-((2'-((3-(tert-butoxy)-3-oxoprop-1-en-1-yl)oxy)-[1,1'-biphenyl]-3-yl)methyl)-3-(cyclopropanesulfonamido)piperidine-1-carboxylate_cis racemic

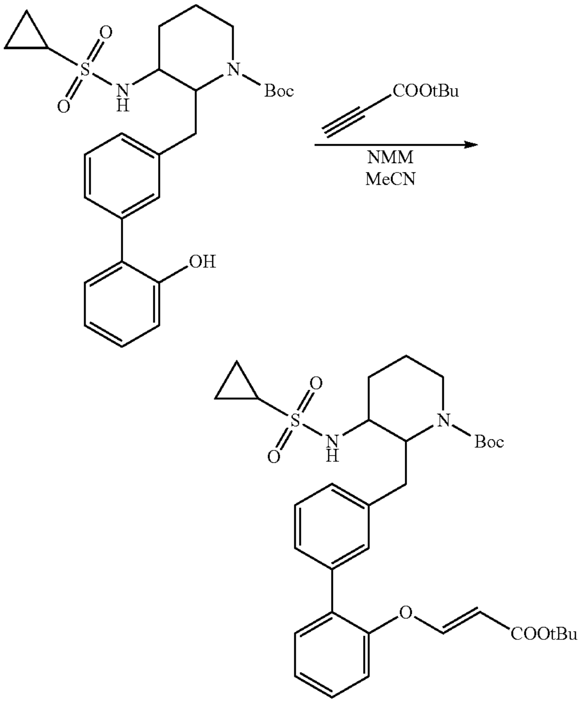

To a mixture of tert-butyl 3-(cyclopropanesulfonamido)-2-((2'-hydroxy-[1,1'-biphenyl]-3-yl)methyl)piperidine-1-carboxylate_cis racemic (2.4 g, 5.55 mmol, 1 eq) in $CH_3CN$ (20 mL) was added 4-methylmorpholine (281 mg, 2.77 mmol, 305 μL, 0.5 eq) and tert-butyl prop-2-ynoate (770 mg, 6.10 mmol, 838 μL, 1.1 eq) at 0 °C. The mixture was stirred at 25 °C for 12 hrs. Then water (40 mL) was added to the above reaction mixture and the aqueous phase was extracted with ethyl acetate (3×50 mL). The organic layer was washed with brine (50 mL), and dried over $Na_2SO_4$, concentrated under reduced pressure to give a residue. The residue was purified by column chromatography ($SiO_2$, petroleum ether/ethyl acetate=100/1 to 1/1) to afford the title compound (1.5 g, 49.6% yield) as a yellow solid. $^1H$ NMR (400 MHz, chloroform-d) δ 1.03 (br dd, 3H), 1.14 (br s, 9H), 1.18-1.25 (m, 2H), 1.47-1.50 (m, 9H), 1.56-1.78 (m, 3H), 1.90-1.99 (m, 1H), 2.40-2.50 (m, 1H), 2.85-3.00 (m, 3H), 3.66 (td, 1H), 4.44-4.56 (m, 1H), 4.80 (br s, 1H), 5.36 (d, 1H), 7.13 (d, 1H), 7.18-7.26 (m, 3H), 7.31-7.34 (m, 2H), 7.50-7.56 (m, 1H), 7.63 (d, 1H).

Step 4: tert-butyl 2-((2'-(3-(tert-butoxy)-3-oxo-propoxy)-[1,1'-biphenyl]-3-yl)methyl)-3-(cyclopropanesulfonamido)piperidine-1-carboxylate_cis racemic

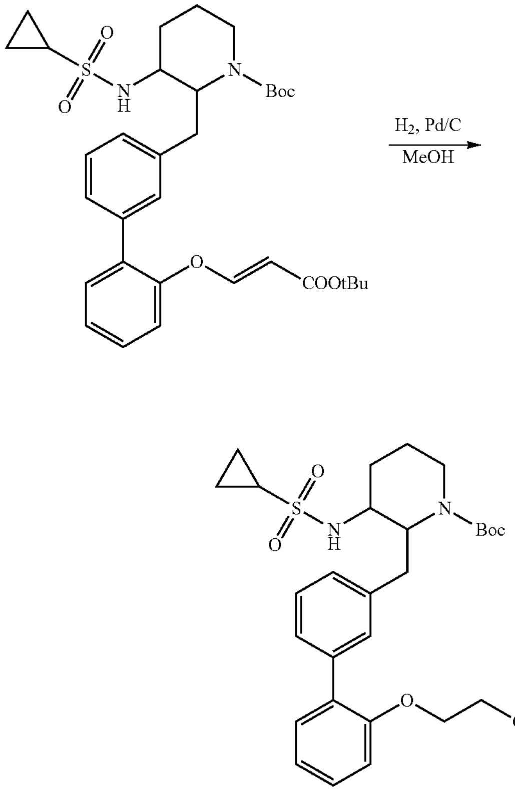

To a mixture of tert-butyl (E)-2-((2'-((3-(tert-butoxy)-3-oxoprop-1-en-1-yl)oxy)-[1,1'-biphenyl]-3-yl)methyl)-3-(cyclopropanesulfonamido)piperidine-1-carboxylate_cis racemic (1.5 g, 4.23 mmol, 1 eq) in $CH_3OH$ (15 mL) was added Pd/C (0.1 g) in one portion at 25 °C. The mixture was stirred at 25 °C for 2 hrs under $H_2$ (15 psi) atmosphere. The mixture was filtered and the filtrate was concentrated in vacuum to afford the title compound (1 g, 66.5% yield) as yellow oil, which was used in the next step without further purification. $^1$H NMR (400 MHz, chloroform-d) δ 0.94-1.05 (m, 2H), 1.18 (br s, 9H), 1.39-1.49 (m, 9H), 1.58-1.84 (m, 4H), 1.94 (br d, 1H), 2.30-2.48 (m, 1H), 2.65 (t, 2H), 2.83-3.04 (m, 3H), 3.60-3.69 (m, 1H), 4.10 (br s, 1H), 4.17-4.28 (m, 2H), 4.56 (br d, 1H), 4.80 (br s, 1H), 6.94-7.07 (m, 2H), 7.10-7.26 (m, 2H), 7.29-7.37 (m, 3H), 7.38-7.44 (m, 1H).

Step 5: 3-((3'-((3-(cyclopropanesulfonamido)piperidin-2-yl)methyl)-[1,1'-biphenyl]-2-yl)oxy)propanoic acid_cis racemic hydrochloride

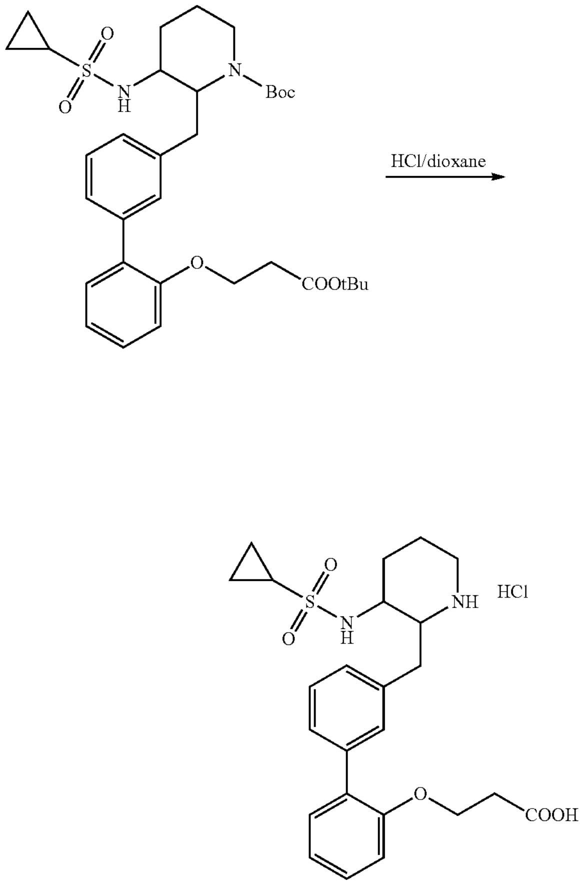

To a mixture of tert-butyl 2-((2'-(3-(tert-butoxy)-3-oxo-propoxy)-[1,1'-biphenyl]-3-yl)methyl)-3-(cyclopropanesulfonamido)piperidine-1-carboxylate_cis racemic (1 g, 1.63 mmol, 1 eq) in dioxane (5 mL) was added HCl/dioxane (20 mL) in one portion at 0 °C under $N_2$. The mixture was stirred at 25 °C for 2 hrs, concentrated in vacuo to afford the title compound (500 mg, 41.3% yield) as a white solid, which was used in next step without further purification. $^1$H NMR (400 MHz, chloroform-d) δ 0.80-0.94 (m, 2H), 1.08-1.25 (m, 2H), 1.55-1.73 (m, 2H), 2.01-2.15 (m, 1H), 2.24 (br d, 1H), 2.43 (br s, 1H), 2.51 (ddd, 1H), 2.61-2.70 (m, 1H), 3.14 (br dd, 1H), 3.18-3.27 (m, 1H), 3.43-3.60 (m, 3H), 3.95 (br s, 1H), 4.13-4.29 (m, 2H), 6.87-7.50 (m, 8H), 8.33 (br s, 1H), 9.06 (br s, 1H).

Step 6: N-((4²S,4³S)-5-oxo-8-oxa-4(2,1)-piperidina-1(1,2),2(1,3)-dibenzenacyclo-octaphane-4³-yl)cyclopropanesulfonamide

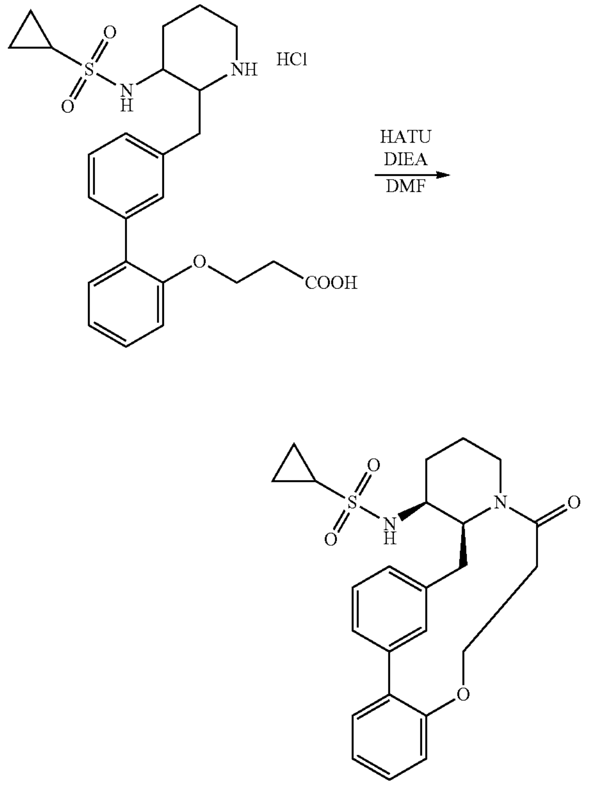

To a mixture of 3-((3'-((3-(cyclopropanesulfonamido)piperidin-2-yl)methyl)-[1,1'-biphenyl]-2-yl)oxy)propanoic acid_cis racemic hydrochloride (0.5 g, 1.09 mmol, 1 eq) in N,N-dimethylformamide (500 mL) was added o-(7-azabenzotriazol-1-yl)-N,N,N',N'-tetramethyluronium hexafluorophosphate (539 mg, 1.42 mmol, 1.3 eq) and N,N-diisopropylethylamine (570 μL, 3 eq) in one portion at 25 °C under $N_2$. The mixture was stirred at 25 °C for 12 hrs. The reaction mixture was concentrated under reduced pressure. Water (500 mL) was added, the aqueous phase extracted with ethyl acetate (3×200 mL), the organic layer washed with brine (100 mL), dried over $Na_2SO_4$ and concentrated under reduced pressure to give a residue. The residue was purified by prep-HPLC (neutral condition: column: Waters Xbridge C18 150*50 mm*10 μm; mobile phase: [water(10 mM $NH_4HCO_3$)—$CH_3CN$]; B %: 35%-55%,10 min) to afford racemic product (0.085 g, 10.4% yield) which was separated by SFC (column: DAICEL CHIRALPAK AD (250 mm*30 mm, 10 μm); mobile phase: [Neu-MeOH]; B %: 50%-50%,9 min) to afford the title compound (28.5 g, 34.9% yield) as white solid with the longer retention time. $^1$H NMR (400 MHz, DMSO-$d_6$) δ 7.45 (d, 1H), 7.37-7.25 (m, 3H), 7.17-7.04 (m, 5H), 5.19-5.09 (m, 1H), 4.16 (dt, 1H), 4.04 (td, 1H), 3.79 (br d, 1H), 3.46-3.36 (m, 1H), 3.18-2.93 (m, 4H), 2.64-2.56 (m, 1H), 2.18 (dt, 1H), 1.87-1.69 (m, 3H), 1.58-1.39 (m, 1H), 1.02-0.90 (m, 4H). LCMS (method G): m/z 441 $(M+H)^+$ (ES+) at 2.42 min Example 45. Synthesis of Compound No. A1-87

Step 1: tert-butyl 2-(3-bromo-4-fluorobenzyl)-3-oxopiperidine-1-carboxylate

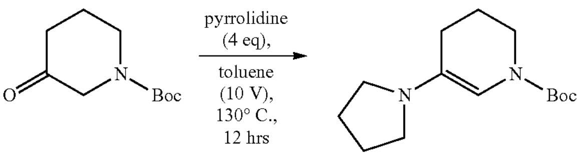 [SMILES: CC(C)(C)OC(=O)N1CCCC(=O)C1 ; CC(C)(C)OC(=O)N1C=C(N2CCCC2)CCC1]

To a solution of tert-butyl 3-oxopiperidine-1-carboxylate (12.4 g, 62.23 mmol, 1 eq) in toluene (124 mL) was added pyrrolidine (17.70 g, 248.94 mmol, 20.78 mL, 4 eq). The mixture was stirred at 130 °C for 12 hrs by Dean-Stark trap. The mixture was concentrated under reduced pressure to afford a crude brown oil (25.8 g, 82.1% yield) which was used in next step without further purification.

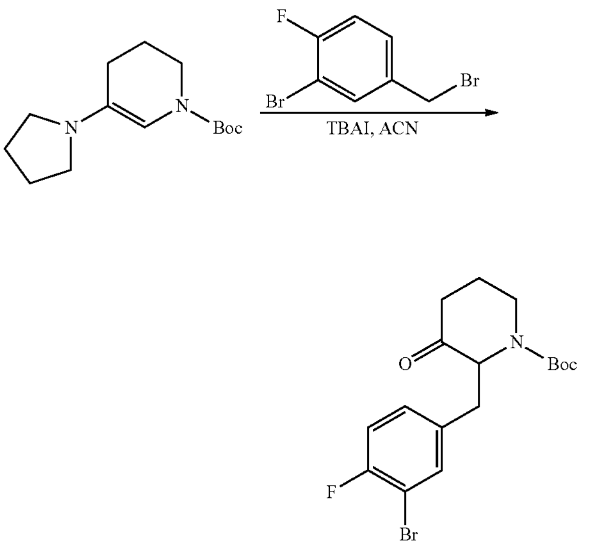

To a solution of tert-butyl 5-(pyrrolidin-1-yl)-3,4-dihydropyridine-1(2H)-carboxylate (12.9 g, 25.6 mmol, 1 eq) in acetonitrile (130 mL) were added 2-bromo-4-(bromomethyl)-1-fluorobenzene (10.3 g, 38.3 mmol, 1.5 eq) and TBAI (944 mg, 2.56 mmol, 0.1 eq) at 25 °C. The mixture was stirred at 95 °C for 12 hrs. Another reaction was set up as described above and the two batches were combined. The mixture was treated with 300 mL of water and extracted with ethyl acetate (3×200 mL). The organic layers were combined and dried over $Na_2SO_4$, filtered. The filtrate was concentrated under reduced pressure to afford the crude product, which was purified by column chromatography on silica gel (eluted with petroleum ether/ethyl acetate=50/1 to 5/1) to afford the title compound (12.2 g, 52.5% yield) as a yellow oil. $^1$H NMR (400 MHz, methanol-$d_4$) δ ppm 1.14-1.25 (m, 6H), 1.28-1.44 (m, 3H), 1.96 (br s, 2H), 2.41-2.64 (m, 2H), 2.87-3.09 (m, 2H), 3.22-3.29 (m, 1H), 3.89-4.09 (m, 1H), 4.55-4.72 (m, 1H), 7.07-7.22 (m, 2H), 7.46 (br d, 1H).

Step 2: tert-butyl 2-((6-fluoro-2'-hydroxy-[1,1'-biphenyl]-3-yl)methyl)-3-oxopiperidine-1-carboxylate

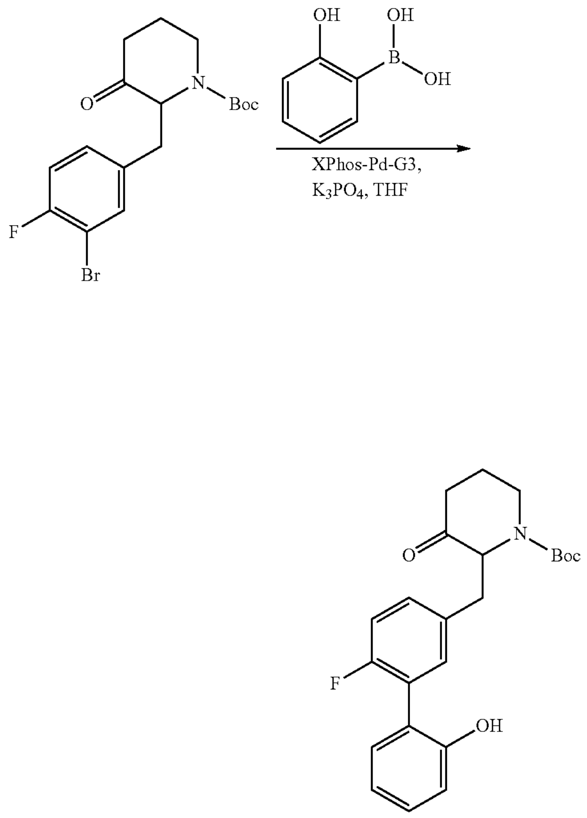

To a solution of tert-butyl 2-(3-bromo-4-fluorobenzyl)-3-oxopiperidine-1-carboxylate (4.4 g, 11.39 mmol, 1 eq) in tetrahydrofuran (44 mL) were added (2-hydroxyphenyl) boronic acid (5.50 g, 39.9 mmol, 3.5 eq), $K_3PO_4$ (4.84 g, 22.8 mmol, 2 eq) and Xphos G3 Pd (482 mg, 570 μmol, 0.05 eq) at 20 °C. The mixture was stirred at 70 °C for 12 hrs under $N_2$ atmosphere. Another reaction was set up as described above and the two batches were combined. The mixture was poured into water (100 mL) and extracted with ethyl acetate (3×100 mL). The organic layers were combined and dried over $Na_2SO_4$, filtered and the filtrate was concentrated under reduced pressure. The crude product was purified by column chromatography on silica gel (eluted with petroleum ether/ethyl acetate=50/1 to 5/1) to afford the title compound (9.5 g, 59.2% yield) as a yellow oil. $^1H$ NMR (400 MHz, chloroform-d) δ ppm 1.21-1.27 (m, 9H), 1.87-2.05 (m, 2H), 2.43-2.59 (m, 2H), 2.79-3.23 (m, 3H), 3.94-4.16 (br d, 1H), 4.55-5.04 (m, 1H), 6.94-7.42 (m, 7H).

Step 3: tert-butyl (E)-2-((2'-((3-(tert-butoxy)-3-oxoprop-1-en-1-yl)oxy)-6-fluoro-[1,1'-biphenyl]-3-yl)methyl)-3-oxopiperidine-1-carboxylate

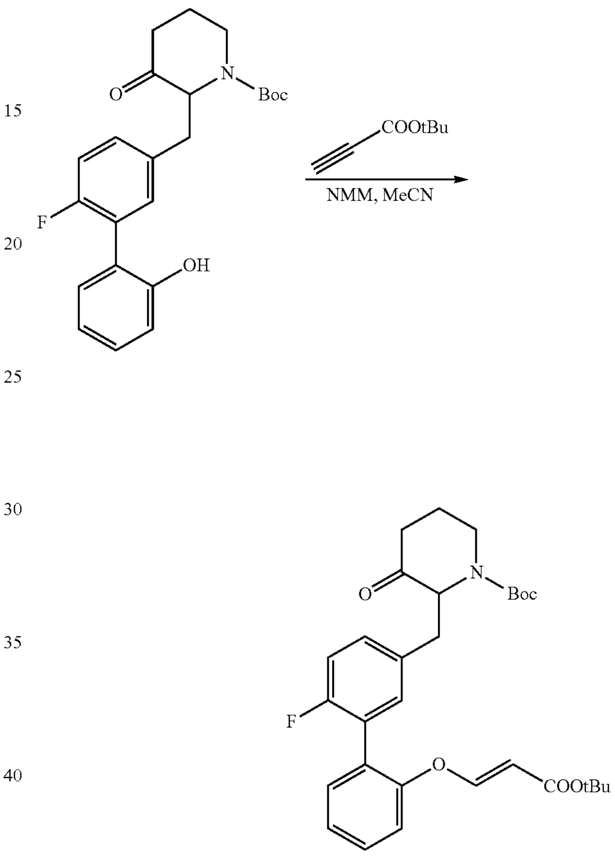

To a solution of tert-butyl 2-((6-fluoro-2'-hydroxy-[1,1'-biphenyl]-3-yl)methyl)-3-oxopiperidine-1-carboxylate (3.3 g, 8.26 mmol, 1 eq) in acetonitrile (33 mL) was added tert-butyl prop-2-ynoate (2.27 mL, 16.5 mmol, 2 eq) and NMM (636 μL, 5.78 mmol, 0.7 eq) at 25 °C. The mixture was stirred at 25 °C for 12 hrs. Another reaction was set up as described above and the two batches were combined. The mixture was poured into $H_2O$ (100 mL), then extracted with ethyl acetate (3×30 mL). The organic layer was dried over $Na_2SO_4$, filtered and concentrated under reduced pressure. The crude product was purified by column chromatography on silica gel (eluted with petroleum ether/ethyl acetate=50/1 to 5/1) to afford the title compound (6.2 g, 60.7% yield) as a yellow oil. $^1H$ NMR (400 MHz, chloroform-d) δ 1.24 (br d, 6H), 1.38 (s, 3H), 1.42-1.50 (m, 9H), 1.80-2.03 (m, 2H), 2.49 (br s, 2H), 2.97-3.15 (m, 3H), 4.15 (s, 1H), 4.63-4.91 (m, 1H), 5.36 (d, 1H), 7.02-7.10 (m, 2H), 7.12-7.16 (m, 2H), 7.22-7.26 (m, 1H), 7.33-7.38 (m, 1H), 7.39-7.45 (m, 1H), 7.60 (d, 1H).

Step 4: tert-butyl 2-((2'-(3-(tert-butoxy)-3-oxo-propoxy)-6-fluoro-[1,1'-biphenyl]-3-yl)methyl)-3-oxopiperidine-1-carboxylate

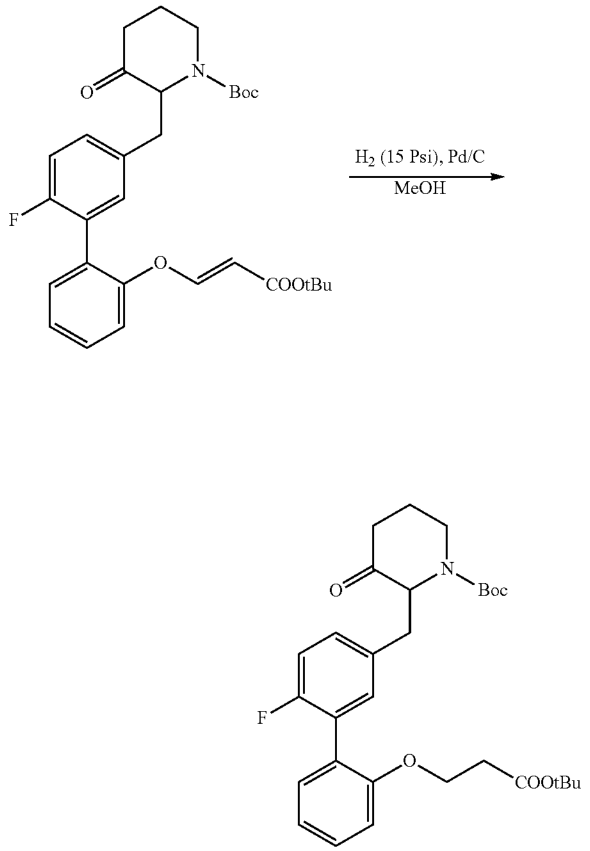

To a solution of tert-butyl (E)-2-((2'-((3-(tert-butoxy)-3-oxoprop-1-en-1-yl)oxy)-6-fluoro-[1,1'-biphenyl]-3-yl) methyl)-3-oxopiperidine-1-carboxylate (2.65 g, 5.04 mmol, 1 eq) in methanol (50 mL) was added Pd/C (2.6 g, 10%) at 25 °C. The suspension was degassed under vacuum and purged with $H_2$ several times. The mixture was stirred under $H_2$ balloon (15 psi) at 25 °C for 12 hrs. Another reaction was set up as described above and the two batches were combined. The mixture was filtered and the filtrate was concentrated under reduced pressure. The residue was purified by column chromatography on silica gel (eluted with petroleum ether/ethyl acetate=50/1 to 5/1) to afford the title compound (3.9 g, 66.0% yield) as a yellow oil. $^1$H NMR (400 MHz, chloroform-d) δ ppm 1.16-1.26 (m, 6H), 1.39 (s, 12H), 1.75-2.04 (m, 2H), 2.49 (br s, 2H), 2.60 (t, 2H), 2.93-3.21 (m, 3H), 4.13-4.31 (m, 3H), 4.61-4.91 (m, 1H), 6.97-7.06 (m, 3H), 7.06-7.12 (m, 2H), 7.23 (dd, 1H), 7.31-7.38 (m, 1H).

Step 5: 3-((2'-fluoro-5'-((3-oxopiperidin-2-yl) methyl)-[1,1'-biphenyl]-2-yl)oxy)-propanoic acid hydrochloride

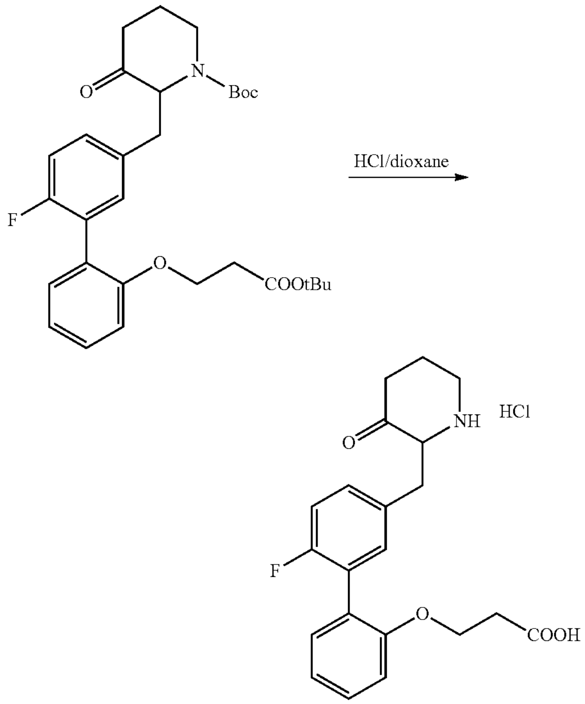

To a solution of tert-butyl 2-((2'-(3-(tert-butoxy)-3-oxo-propoxy)-6-fluoro-[1,1'-biphenyl]-3-yl)methyl)-3-oxopiperidine-1-carboxylate (3.9 g, 7.39 mmol, 1 eq) in dioxane (40 mL) was added a solution of HCl/dioxane (5.2 M, 80 mL) at 0 °C. The mixture stirred at 25 °C for 12 hrs. The reaction mixture was concentrated under reduced pressure to afford the title compound (3.1 g, 98.2% yield) as a yellow solid. $^1$H NMR (400 MHz, methanol-$d_4$) δ 1.62-1.97 (m, 3H), 2.22-2.38 (m, 1H), 2.63 (t, 2H), 2.75-2.88 (m, 1H), 2.90-3.02 (m, 1H), 3.24 (ddd, 1H), 3.39-3.50 (m, 2H), 4.20-4.30 (m, 2H), 7.04 (td, 1H), 7.09-7.16 (m, 2H), 7.24-7.31 (m, 3H), 7.34-7.40 (m, 1H).

Step 6: $2^6$-fluoro-8-oxa-4(2,1)-piperidina-1(1,2),2(1,3)-dibenzenacyclooctaphane-$4^3$,5-dione

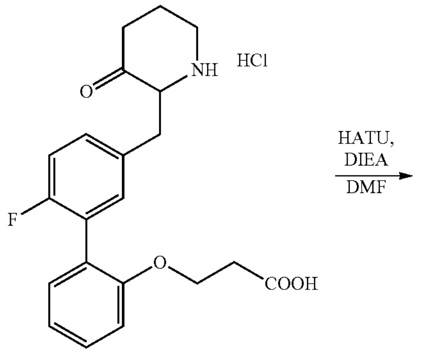

-continued

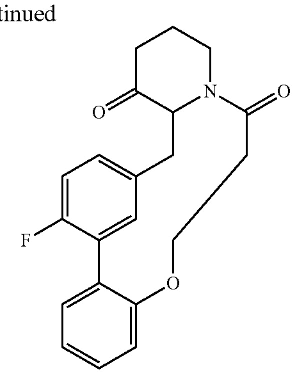

To a solution of 3-((2'-fluoro-5'-((3-oxopiperidin-2-yl) methyl)-[1,1'-biphenyl]-2-yl)oxy)-propanoic acid hydrochloride (0.2 g, 539 μmol, 1 eq) in DMF (1 L) was added HATU (266 mg, 700 μmol, 1.3 eq) and diisopropylethylamine (469 uL, 2.69 mmol, 5 eq) at 25 °C. The mixture was stirred at 25 °C for 12 hrs. Seven additional reactions were set up as detailed above and all eight reaction mixtures were combined. The mixture was concentrated in high vacuum to remove DMF. The residue was poured into water (50 mL) and extracted with ethyl acetate (3×50 mL). The organic layers were combined and washed with brine (3×50 mL), dried over $Na_2SO_4$, filtered and the filtrate was concentrated under reduced pressure. The crude product was purified by column chromatography on silica gel (eluted with petroleum ether/ethyl acetate=50/1 to 1/80) to afford the title compound (0.48 g, 28.4% yield) as a white solid. $^1H$ NMR (400 MHz, methanol-$d_4$) δ ppm 1.84-1.92 (m, 1H), 1.94-2.11 (m, 1H), 2.21-2.33 (m, 1H), 2.55 (td, 1H), 2.94-3.04 (m, 2H), 3.05-3.23 (m, 2H), 3.24-3.36 (m, 1H), 3.96-4.08 (m, 2H), 4.12-4.38 (m, 1H), 4.91-5.07 (m, 1H), 7.03-7.13 (m, 3H), 7.14-7.24 (m, 2H), 7.30-7.38 (m, 1H), 7.42 (ddt, 1H).

Step 7: $4^3$-amino-$2^6$-fluoro-8-oxa-4(2,1)-piperidina-1(1,2),2(1,3)-dibenzenacyclooctaphan-5-one_cis racemic

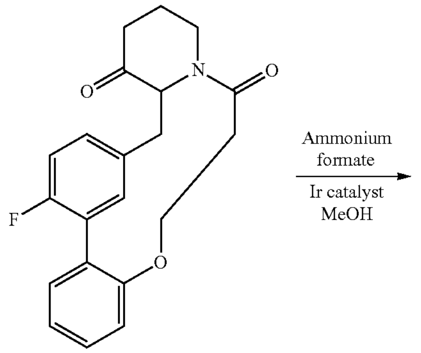

-continued

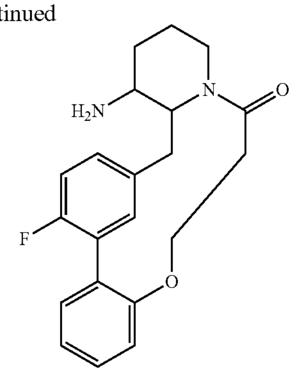

To a solution of $2^6$-fluoro-8-oxa-4(2,1)-piperidina-1(1,2),2(1,3)-dibenzenacyclo-octaphane-$4^3$,5-dione (0.48 g, 1.36 mmol, 1 eq) in methanol (4.8 mL) were added bis[2-(2-pyridyl)phenyl]iridium(1+);2-(2-pyridyl)pyridine;hexafluorophosphate (Ir catalyst) (16 mg, 20 μmol, 0.015 eq) and ammonium formate (257 mg, 4.07 mmol, 3 eq) at 25 °C. The mixture was stirred at 80 °C for 12 hrs under $N_2$. The mixture was poured into water (10 mL) and extracted with ethyl acetate (3×10 mL). The organic layer was washed with brine (3×10 mL), dried over $Na_2SO_4$, filtered and the filtrate was concentrated under reduced pressure to afford the title compound (0.31 g, 44.9% yield) as a yellow solid, which was used directly for the next step without further purification. LCMS (method I) (ESI+): m/z 355.2 (M+H)+, RT: 0.664 min Step 8: 1-fluoro-N-(($4^2$S,$4^3$S)-26-fluoro-5-oxo-8-oxa-4(2,1)-piperidina-1(1,2),2(1,3)-dibenzenacyclooctaphane-$4^3$-yl)methanesulfonamide

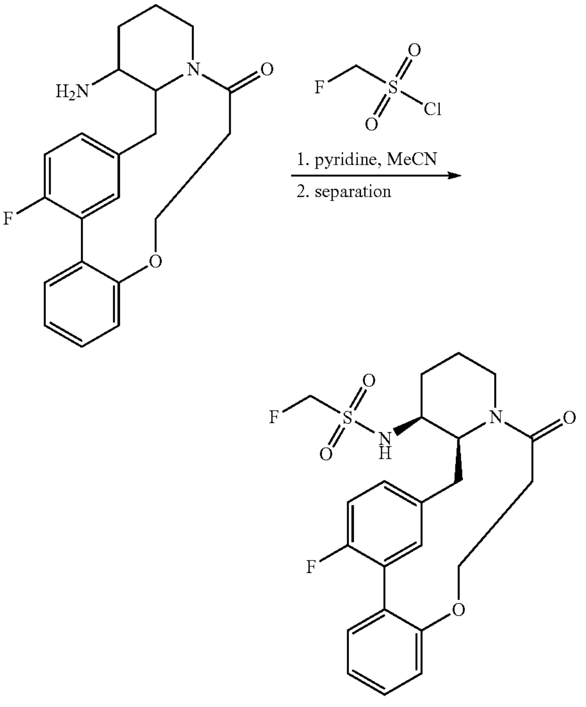

To a solution of $4^3$-amino-$2^6$-fluoro-8-oxa-4(2,1)-piperidina-1(1,2),2(1,3)-dibenzenacyclooctaphan-5-one_cis racemic (0.29 g, 818 μmol, 1 eq) in acetonitrile (6 mL) were added fluoromethanesulfonyl chloride (163 mg, 1.23 mmol, 1.5 eq) and pyridine (330 μL, 4.09 mmol, 5 eq) at 0 °C. The mixture stirred at 20 °C for 12 hrs. The reaction mixture was filtered and the filtrate was concentrated under reduced pressure. The residue was purified by prep-HPLC (neutral condition: Column: Phenomenex C18 80*40 mm*3 μm; mobile phase: [water ($NH_4HCO_3$)-acetonitrile]; B %: 30%-50%, 8 min) to afford racemic product, which was separated by SFC (column: REGIS(S,S)WHELK-O1(50 mm×4.6 mm, 3.5 μm); mobile phase: [0.1% IPA ethanol]; B %: 50%-50%, 8 min) to afford the title compound (19.1 mg, 5.1% yield) with the longer retention time as a white solid. $^1$H NMR (400 MHz, DMSO-$d_6$) δ ppm 8.12 (s, 1H), 7.39-7.32 (m, 2H), 7.21-7.05 (m, 4H), 6.95 (br d, 1H), 5.53-5.26 (m, 2H), 5.07-4.98 (m, 1H), 4.15 (br t, 2H), 3.71 (br d, 1H), 3.49-3.39 (m, 1H), 3.08-2.86 (m, 4H), 2.20 (dt, 1H), 1.90-1.77 (m, 1H), 1.71 (br d, 2H), 1.56-1.38 (m, 1H). LCMS (method G): m/z 451 $(M+H)^+$ (ES+) at 2.43 min Example 46. Synthesis of Compound No. A1-89

Step 1: tert-butyl 2-(3-bromobenzyl)-3-oxopiperidine-1-carboxylate

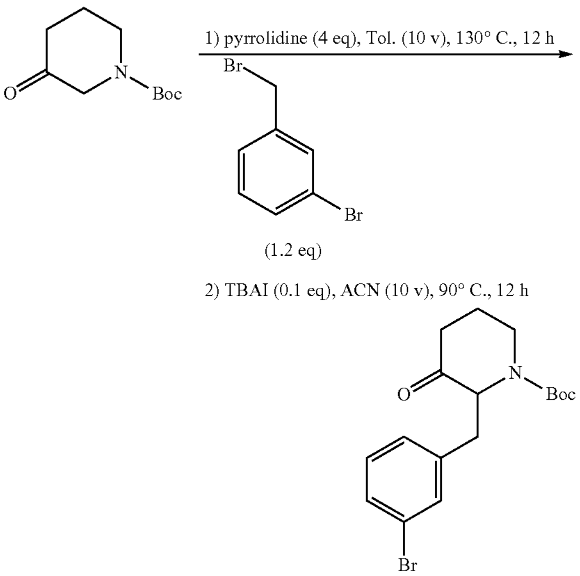

To a solution of tert-butyl 3-oxopiperidine-1-carboxylate (100 g, 502 mmol, 1 eq) in toluene (1000 mL) was added pyrrolidine (168 mL, 2.01 mol, 4 eq). The mixture was stirred at 130 °C for 12 h. The mixture was concentrated under reduce pressure to remove toluene. To the residue in acetonitrile (1000 mL) was added tetrabutylammoniumiodide (18.5 g, 50.2 mmol, 0.1 eq) and 1-bromo-3-(bromomethyl)benzene (150.5 g, 602 mmol, 1.2 eq) was stirring at 90 °C for 12 h. The reaction mixture was concentrated and acidified with 1N hydrogen chloride to pH=4~5, extracted with ethyl acetate (1 Lx 3), the combined organic layer was dried with anhydrous sodium sulfate and concentrated under reduced pressure to afford crude product. The residue was purified by column chromatography ($SiO_2$, Petroleum ether/Ethyl acetate=100/1 to 3/1) to afford the title compound (69 g, 37.3% yield) as brown oil. $^1$H NMR (400 MHz, methanol-$d_4$) δ ppm 1.10-1.44 (m, 9H), 1.85-2.01 (m, 2H), 2.41-2.68 (m, 2H), 2.86-3.10 (m, 2H), 3.27 (br d, 1H), 3.86-4.14 (m, 1H), 4.63 (br s, 1H), 7.12-7.25 (m, 2H), 7.32-7.44 (m, 2H).

Step 2: tert-butyl 3-oxo-2-(3-(4,4,5,5-tetramethyl-1,3,2-dioxaborolan-2-yl)benzyl)-piperidine-1-carboxylate

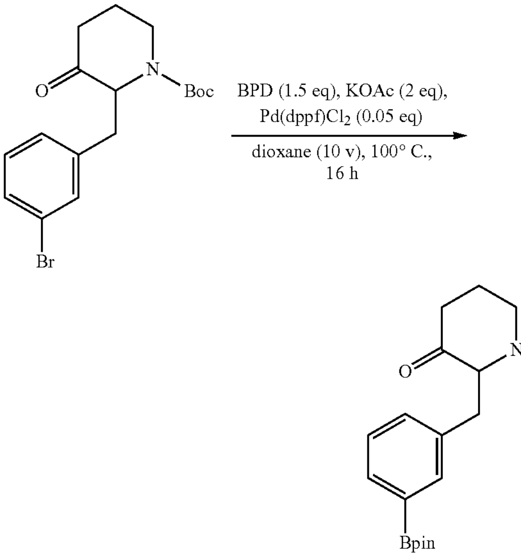

A mixture of tert-butyl 2-(3-bromobenzyl)-3-oxopiperidine-1-carboxylate (50 g, 136 mmol, 1 eq), Bis(pinacolato) diboron (51.7 g, 204 mmol, 1.5 eq), $Pd(dppf)Cl_2$ (4.97 g, 6.79 mmol, 0.05 eq), potassium acetate (26.7 g, 272 mmol, 2 eq) in dioxane (500 mL) was degassed and purged with nitrogen for 3 times, and then the mixture was stirred at 100 °C for 16 h under nitrogen atmosphere. The reaction mixture was quenched by addition water (300 mL) at 25 °C, and then extracted with Ethyl acetate (400 mL×3). The combined organic layers were dried over anhydrous sodium sulfate, filtered and concentrated under reduced pressure to afford a residue. The residue was purified by column chromatography ($SiO_2$, Petroleum ether/Ethyl acetate=1/0 to 3/1) to afford the title compound (50 g, 88.7% yield) as brown oil. $^1$H NMR (400 MHz, methanol-$d_4$) δ ppm 1.02-1.34 (m, 22H), 1.94-2.04 (m, 2H), 2.37-2.69 (m, 1H), 2.80-3.12 (m, 2H), 3.81-4.15 (m, 2H), 4.42-4.72 (m, 1H), 7.15-7.33 (m, 2H), 7.51-7.68 (m, 2H).

Step 3: tert-butyl (E)-3-(2-bromo-3-fluorophenoxy)acrylate

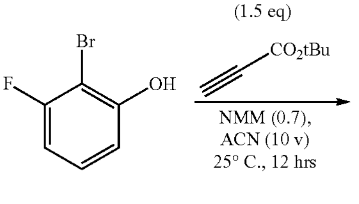

-continued

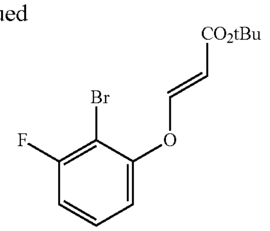

To a solution of 2-bromo-3-fluorophenol (5 g, 26.1 mmol, 1 eq) and tert-butyl prop-2-ynoate (5.39 mL, 39.3 mmol, 1.5 eq) in acetonitrile (50 mL) was added n-methyl morpholine (2.01 mL, 18.3 mmol, 0.7 eq) at 25 °C. The whole reaction mixture was stirred at 25 °C for 12 h. The reaction mixture was poured into saturated ammonium chloride solution (180 mL) and the mixture was extracted with ethyl acetate (100 mL). The aqueous phase was extracted with ethyl acetate (3×80 mL). The combined organic phase was dried with anhydrous sodium sulfate, filtered and concentrated under reduced pressure to give a residue. The residue was purified by column chromatography on silica gel eluted with petroleum ether:ethyl acetate (10:1 to 3:1) to afford the title compound (6.5 g, 78.2% yield) as yellow liquid. $^1$H NMR (400 MHz, chloroform-d) δ ppm 1.49 (s, 9H), 5.47 (d, 1H), 6.93 (td, 1H), 7.00 (dt, 1H), 7.31 (dt, 1H), 7.61 (d, 1H).

Step 4: tert-butyl (E)-2-((2'-((3-(tert-butoxy)-3-oxoprop-1-en-1-yl)oxy)-6'-fluoro-[1,1'-biphenyl]-3-yl)methyl)-3-oxopiperidine-1-carboxylate

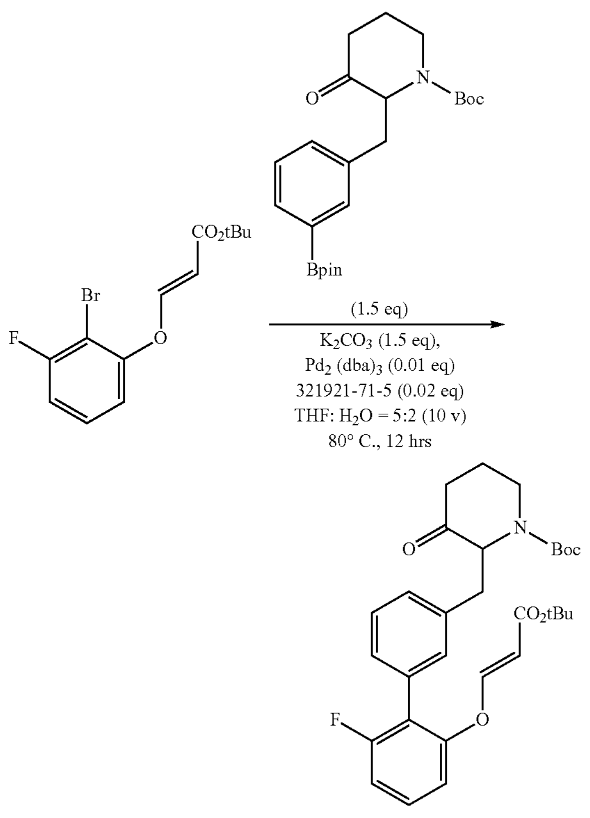

To a solution of tert-butyl (E)-3-(2-bromo-3-fluorophenoxy)acrylate (3.89 g, 12.3 mmol, 1 eq) and tert-butyl 3-oxo-2-(3-(4,4,5,5-tetramethyl-1,3,2-dioxaborolan-2-yl)benzyl)piperidine-1-carboxylate (5.36 g, 18.6 mmol, 1.5 eq) in tetrahyfrofuran (55 mL) and water (22 mL) was added potassium carbonate (2.57 g, 18.6 mmol, 1.5 eq), (1E,4E)-1,5-diphenylpenta-1,4-dien-3-one;palladium (113 mg, 124 μmol, 0.01 eq) and bis(1-adamantyl)-butyl-phosphane (89 mg, 248 μmol, 0.02 eq) at 25 °C. Nitrogen was bubbled into the reaction mixture for 2 min. Then the reaction mixture was stirred at 80 °C for 12 h. The reaction mixture was poured into saturated ammonium chloride solution (100 mL) and the mixture was extracted with ethyl acetate (50 mL). The aqueous phase was extracted with ethyl acetate (3×50 mL). The combined organic phase was dried with anhydrous sodium sulfate, filtered and concentrated under reduced pressure to afford a residue. The residue was purified by column chromatography on silica gel eluted with petroleum ether:ethyl acetate (10:1 to 1:1) to afford the title compound (6 g, 92.2% yield) as light brown oil. $^1$H NMR (400 MHz, DMSO-d$_6$) δ ppm 1.11 (br s, 6H), 1.21-1.33 (m, 3H), 1.40 (s, 9H), 1.82 (br d, 2H), 2.37 (dt, 1H), 2.55-2.69 (m, 1H), 2.89-3.27 (m, 3H), 3.67-3.99 (m, 1H), 4.43-4.67 (m, 1H), 5.25 (d, 1H), 7.14 (br s, 1H), 7.17-7.26 (m, 4H), 7.39 (br s, 1H), 7.44-7.52 (m, 1H), 7.60 (d, 1H).

Step 5: tert-butyl 2-((2'-(3-(tert-butoxy)-3-oxopropoxy)-6'-fluoro-[1,1'-biphenyl]-3-yl)methyl)-3-oxopiperidine-1-carboxylate

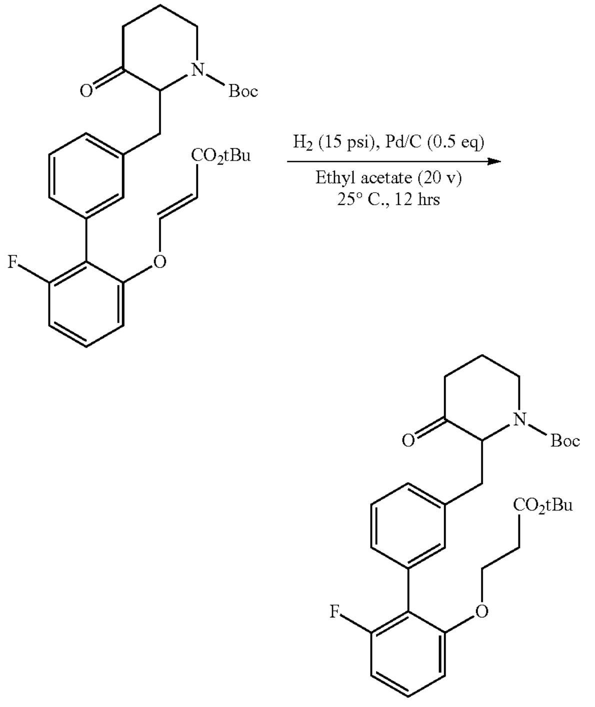

To a mixture of tert-butyl (E)-2-((2'-((3-(tert-butoxy)-3-oxoprop-1-en-1-yl)oxy)-6'-fluoro-[1,1'-biphenyl]-3-yl)methyl)-3-oxopiperidine-1-carboxylate (5 g, 9.51 mmol, 1 eq) in methanol (50 mL) was added Pd/C (2.5 g, 4.75 mmol, 10% purity, 0.5 eq) in one portion at 25 °C under hydrogen (15 psi) for 12 h. The reaction mixture was filtered via celite and the filtrate was concentrated under reduce pressure to afford a residue. The residue was purified by column chromatography on silica gel eluted with petroleum ether:ethyl acetate (10:1 to 3:1) to afford the title compound (3.7 g, 73.8 yield) as yellow oil. $^1$H NMR (400 MHz, chloroform-d) δ 1.13-1.27 (m, 7H), 1.31-1.51 (m, 12H), 1.71-2.02 (m, 2H), 2.27-2.62 (m, 4H), 2.79-3.32 (m, 3H), 4.15-4.21 (m, 2H), 4.61-4.97 (m, 1H), 6.75-6.82 (m, 2H), 7.08-7.14 (m, 1H), 7.15-7.26 (m, 2H), 7.30 (br d, 2H).

Step 6: 3-((6-fluoro-3'-((3-oxopiperidin-2-yl)methyl)-[1,1'-biphenyl]-2-yl)oxy)propanoic acid hydrochloride

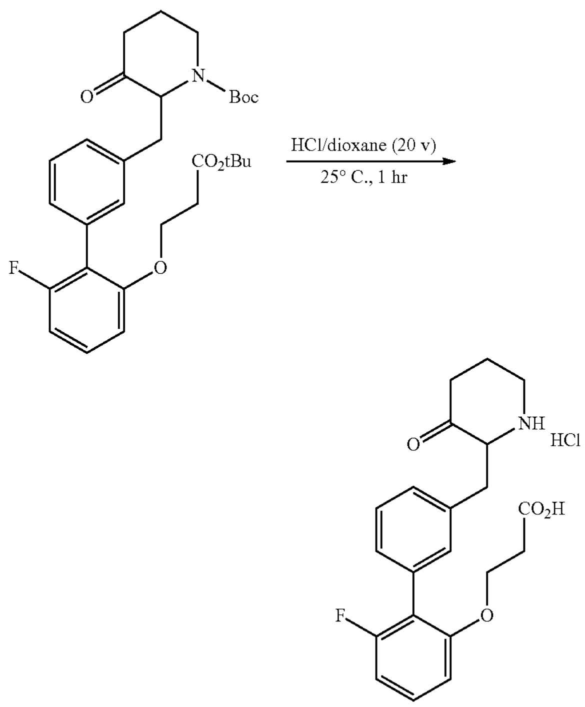

A mixture of tert-butyl 2-((2'-(3-(tert-butoxy)-3-oxopropoxy)-6'-fluoro-[1,1'-biphenyl]-3-yl)methyl)-3-oxopiperidine-1-carboxylate (3.7 g, 7.01 mmol, 1 eq) in HCl/dioxane (80 mL) was stirred at 25 °C for 2 h under nitrogen atmosphere. The mixture was concentrated under reduced pressure to afford the title compound (3 g, 100% yield) as yellow solid. LCMS (method I) (ESI+): m/z 389.1 (M+18)+, RT: 0.580 min.

Step 7: $1^6$-fluoro-8-oxa-4(2,1)-piperidina-1(1,2),2(1,3)-dibenzenacyclooctaphane-$4^3$,5-dione -continued

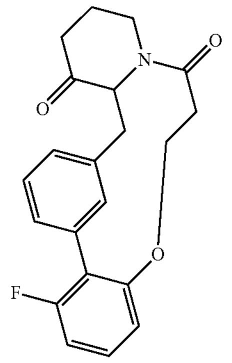

A solution of 3-((6-fluoro-3'-((3-oxopiperidin-2-yl)methyl)-[1,1'-biphenyl]-2-yl)oxy) propanoic acid hydrochloride (200 mg, 490 μmol, 1 eq) and N,N-diisopropylethylamine (256 μL, 1.47 mmol, 3 eq) in dimethyl formamide (1 L) was added HATU (223 mg, 588 mol, 1.2 eq). Then the reaction mixture was stirred at 25 °C for 12 h. The reaction mixture was concentrated to 200 mL and poured into brine (600 mL) and the mixture was extracted with ethyl acetate (300 mL). The aqueous phase was extracted with ethyl acetate (3×150 mL). The combined organic phase was extracted with brine (4×200 mL). The organic phase was dried with anhydrous sodium sulfate, filtered and concentrated to afford a residue. Five batches were set up as described above and all six residues were combined together. The crude product was triturated with ethyl acetate (5 mL) at 25 °C for 10 min to give the title compound (480 mg, 27.7% yield) as a white solid. LCMS (method I) (ESI+): m/z 354.0 (M+H)+, RT: 0.742 min.

Step 8: ($4^2$S,$4^3$S)-$4^3$-amino-$1^6$-fluoro-8-oxa-4(2,1)-piperidina-1(1,2),2(1,3)-dibenzen-acyclooctaphan-5-one

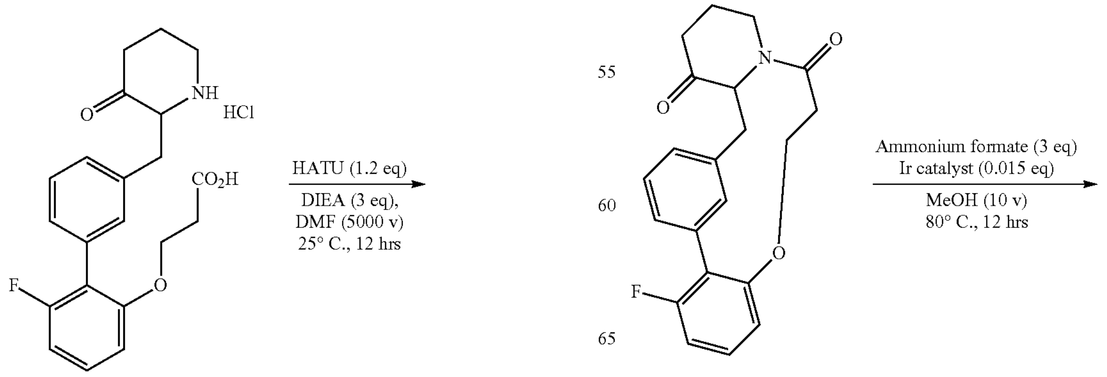

-continued

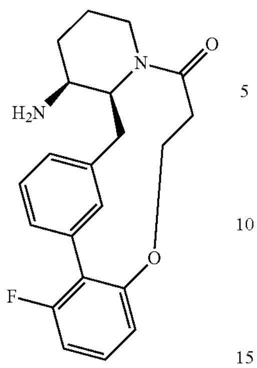

A solution of $1^6$-fluoro-8-oxa-4(2,1)-piperidina-1(1,2),2(1,3)-dibenzenacyclooctaphane-$4^3$,5-dione (200 mg, 490 μmol, 1 eq) and ammonia formate (102 mg, 1.61 mmol, 3 eq) in methanol (2 mL) was added bis[2-(2-pyridyl)phenyl]iridium(1+);2-(2-pyridyl)pyridine; hexafluorophosphate (6.0 mg, 7.11 μmol, 0.015 eq). Nitrogen was bubbled into the reaction mixture for 2 min. The reaction mixture was stirred at 80 °C for 12 h. The reaction mixture was concentrated under reduced pressure to afford a residue. One additional batch was set up as described above and the residues were combined together. The combined residue was dissolved with methanol (3 mL), filtered and the filtrate was purified by prep-HPLC (acid conditions; column: Phenomenex luna C18 80×40 mm×3 μm; mobile phase: [water (hydrochloric acid)-acetonitrile]; B %: 18%-25%,7 min) to afford racemic product as a white solid, which was further separated by SFC (column: REGIS(S,S)WHELK-O1 (250 mm×25 mm, 10 μm); mobile phase: [0.1% $NH_3$—$H_2O$ methanol]; B %: 45%-45%, 15 min) to afford the title compound (97 mg, 25.5% yield) with the longer retention time as a white solid. $^1H$ NMR (400 MHz, methanol-$d_4$) δ ppm 1.46-1.64 (m, 1H), 1.64-1.77 (m, 1H), 1.82 (br d, 2H), 2.23 (dt, 1H), 2.89-3.07 (m, 3H), 3.07-3.22 (m, 2H), 3.83 (br d, 1H), 4.06-4.32 (m, 2H), 5.11 (dt, 1H), 6.83-6.91 (m, 1H), 6.94 (d, 1H), 7.08 (s, 1H), 7.16 (br d, 1H), 7.21-7.33 (m, 3H).

Step 9: 1-fluoro-N-(($4^2$S,$4^3$S)-16-fluoro-5-oxo-8-oxa-4(2,1)-piperidina-1(1,2),2(1,3)-dibenzenacyclooctaphane-$4^3$-yl)methanesulfonamide

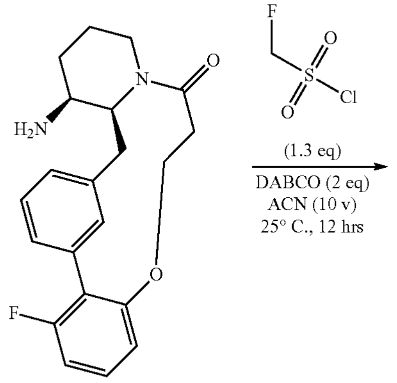

-continued

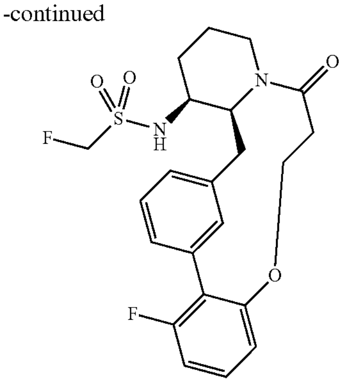

To a solution of ($4^2$S,$4^3$S)-$4^3$-amino-$1^6$-fluoro-8-oxa-4(2,1)-piperidina-1(1,2),2(1,3)-dibenzenacyclooctaphan-5-one (92.00 mg, 260 μmol, 1 eq) in acetonitrile (0.1 mL) was added 1,4-diazabicyclo[2.2.2]octane (57.1 μL, 519.16 μmol, 2 eq) and fluoromethanesulfonyl chloride (45 mg, 337 μmol, 1.3 eq). The mixture was stirred at 25 °C for 12 h. The reaction mixture was concentrated to afford a residue. The residue was dissolved in a mixture of dimethyl formamide (0.8 mL) and methanol (0.5 mL) and filtered. The filtrate was purified by prep-HPLC (Waters Xbridge Prep OBD C18 150×40 mm×10 μm; mobile phase: [water (ammonium bicarbonate)-acetonitrile]; B %: 30%-60%, 8 min) to afford the title compound (80 mg, 68.4% yield) as a white solid. $^1H$ NMR (400 MHz, DMSO-$d_6$) δ ppm 8.17-8.08 (m, 1H), 7.38-7.26 (m, 2H), 7.20-7.08 (m, 2H), 7.03-6.87 (m, 3H), 5.55-5.23 (m, 2H), 5.17-5.06 (m, 1H), 4.23-4.13 (m, 2H), 3.73-3.62 (m, 1H), 3.50-3.39 (m, 1H), 3.07-2.83 (m, 4H), 2.24-2.15 (m, 1H), 1.93-1.79 (m, 1H), 1.77-1.66 (m, 2H), 1.54-1.38 (m, 1H). LCMS (method H): m/z 451 $(M+H)^+$ (ES+) at 2.97 min

Example 47. Synthesis of Compound No. A1-90 (1-fluoro-N-(($4^2$S,$4^3$S)-13-fluoro-5-oxo-8-oxa-4(2,1)-piperidina-1(1,2),2(1,3)-dibenzenacyclooctaphane-$4^3$-yl)methanesulfonamide)

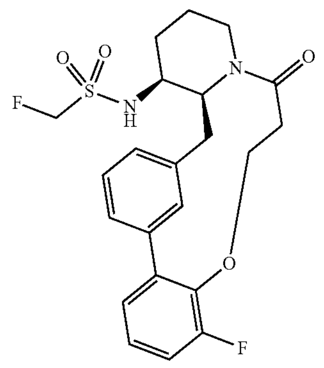 [SMILES: O=C1CCOc2c(F)cccc2-c2cccc(c2)C[C@H]2[C@@H](NS(=O)(=O)CF)CCCN12]

The compound was made analogous to example 46.

Example 48. Synthesis of Compound No. A1-91 (1-fluoro-N-(($4^2$S,$4^3$S)-15-fluoro-5-oxo-8-oxa-4(2,1)-piperidina-1(1,2),2(1,3)-dibenzenacyclooctaphane-$4^3$-yl)methanesulfonamide)

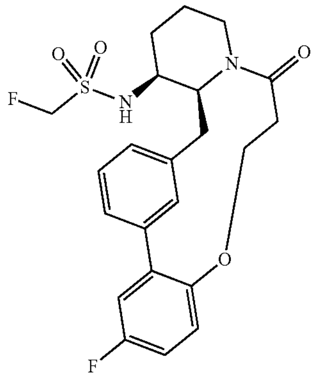 [SMILES: O=C1CCOc2ccc(F)cc2-c2cccc(c2)C[C@H]2[C@@H](NS(=O)(=O)CF)CCCN12]

The compound was made analogous to example 46.

Procedure for the Preparation of Intermediate 11

Step 1: benzyl 3-amino-2-(3-chloro-2-fluorobenzyl)-4-fluoropyrrolidine-1-carboxylate_cis racemic

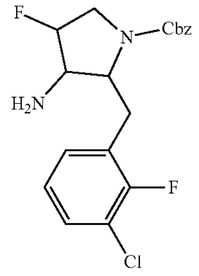 [SMILES: NC1C(F)CN(C(=O)OCc2ccccc2)C1Cc1cccc(Cl)c1F]

Compound was synthesised according to the procedure reported in WO2020/158958 A1.

Step 2: benzyl 2-(3-chloro-2-fluorobenzyl)-4-fluoro-3-(2,2,2-trifluoroacetamido)-pyrrolidine-1-carboxylate_cis racemic

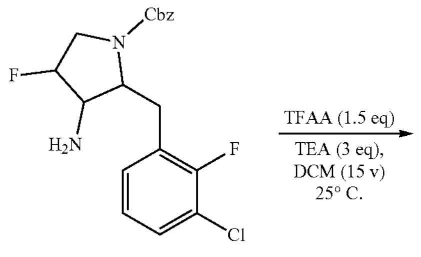

-continued

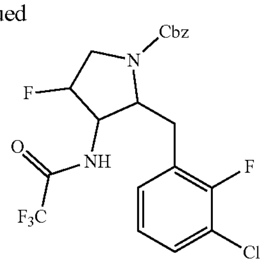

To a solution of benzyl 3-amino-2-(3-chloro-2-fluorobenzyl)-4-fluoropyrrolidine-1-carboxylate_cis racemic (9 g, 23.6 mmol, 1 eq) in DCM (135 mL) was added TEA (7.17 g, 70.9 mmol, 3 eq). The reaction mixture was cooled to 0 °C and TFAA (7.45 g, 35.5 mmol, 1.5 eq) was added. The mixture was stirred at 25 °C for 2 hrs. The reaction mixture was diluted with water (200 mL), extracted with ethyl acetate (3×200 mL), the combined organic phase was washed with brine (100 mL), dried over anhydrous sodium sulfate, filtered and the filtrate was concentrated under reduce pressure to afford a residue. The residue was purified by column chromatography on silica gel (eluted with petroleum ether:ethyl acetate=20:1 to 1:1) to afford the title compound (8 g, 70% yield) as colourless oil. LCMS (method I) (ESI+): m/z 477.1 $(M+H)^+$, R.T=0.698.

Step 3: N-(2-(3-chloro-2-fluorobenzyl)-4-fluoropyrrolidin-3-yl)-2,2,2-trifluoroacetamide_cis racemic

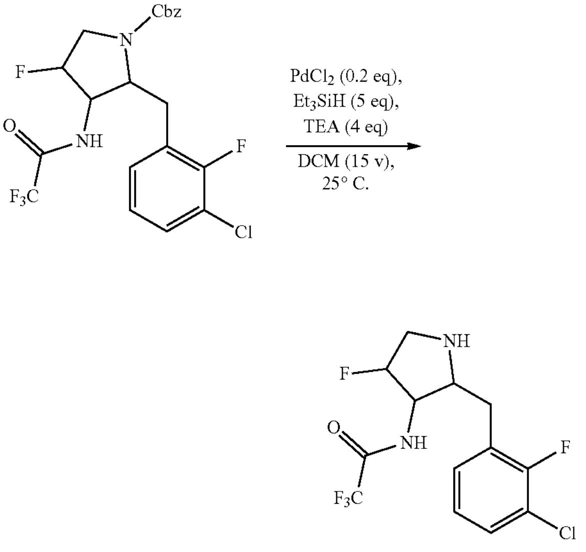

To a solution of benzyl 2-(3-chloro-2-fluorobenzyl)-4-fluoro-3-(2,2,2-trifluoroacetamido)pyrrolidine-1-carboxylate_cis racemic (7.5 g, 15.7 mmol, 1 eq) in DCM (123 mL) was added $Et_3SiH$ (12.6 mL, 78.7 mmol, 5 eq), TEA (8.76 mL, 62.9 mmol, 4 eq) and $PdCl_2$ (0.56 g, 3.14 mmol, 0.2 eq). The mixture was stirred at 25 °C for 2 hrs. The reaction mixture was filtered and the filtrate was concentrated under reduce pressure to afford the title compound (5 g, 92% yield) as yellow oil, which was used in the next step without further purification. LCMS (method I) (ESI+): m/z 343.0 $(M+H)^+$, R.T=0.583.

Step 4: tert-butyl 2-(3-chloro-2-fluorobenzyl)-4-fluoro-3-(2,2,2-trifluoroacetamido) pyrrolidine-1-carboxylate_cis racemic

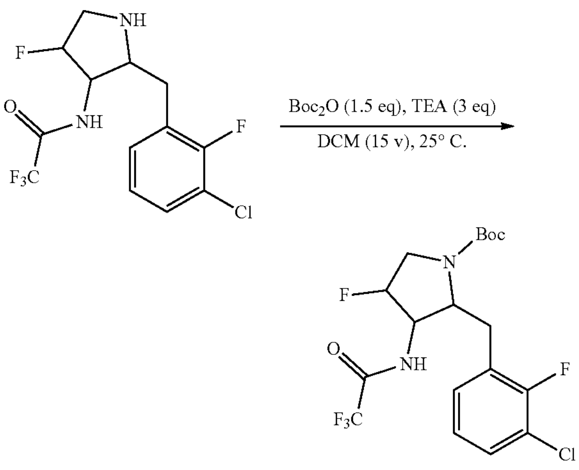

To a solution of N-(2-(3-chloro-2-fluorobenzyl)-4-fluoropyrrolidin-3-yl)-2,2,2-trifluoroacetamide_cis racemic (5 g, 14.6 mmol, 1 eq) in dichloromethane (75 mL) was added $Boc_2O$ (4.7 g, 21.9 mmol, 1.5 eq) and TEA (4.4 g, 43.8 mmol, 3 eq). The mixture was stirred at 25 °C for 12 hrs. The reaction mixture was diluted with water (80 mL), extracted with ethyl acetate (3×80 mL). The combined organic phases were washed with brine (100 mL), dried over anhydrous sodium sulfate, filtered and the filtrate was concentrated under reduce pressure to afford a residue. The residue was purified by column chromatography on silica gel (eluted with petroleum ether:ethyl acetate=20:1 to 1:1) to afford the title compound (3.5 g, 54% yield) as yellow oil. LCMS (method I) (ESI+): m/z 387.0 $(M+H-56)^+$, R.T=0.690.

Step 5: tert-butyl 3-amino-2-(3-chloro-2-fluorobenzyl)-4-fluoropyrrolidine-1-carboxylate_cis racemic (intermediate 11)

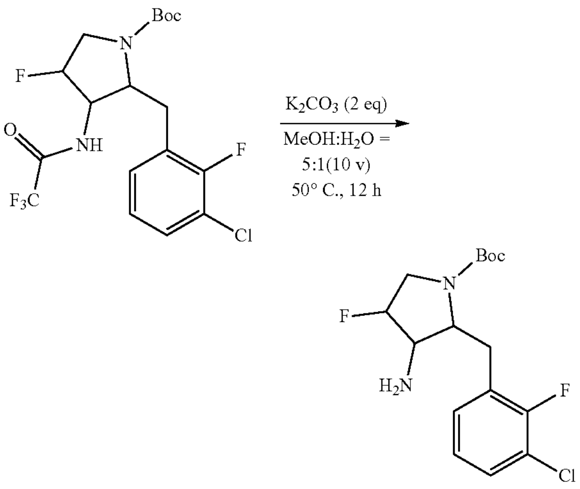

To a solution of tert-butyl 2-(3-chloro-2-fluorobenzyl)-4-fluoro-3-(2,2,2-trifluoroacetamido)pyrrolidine-1-carboxylate_cis racemic (3.5 g, 7.9 mmol, 1 eq) in MeOH (70 mL) and water (15 mL) was added $K_2CO_3$ (2.18 g, 15.8 mmol, 2 eq). The mixture was stirred at 50 °C for 12 hrs. The reaction mixture was filtered and the filtrate was concentrated under reduce pressure to afford a residue. The residue was purified by column chromatography on silica gel (eluted with petroleum ether:ethyl acetate=20:1 to 1:1) to afford the title compound (2 g, 72% yield) as yellow oil. LCMS (method I) (ESI+): m/z 291.0 $(M+H-56)^+$, R.T=0.639.

Procedure for the Preparation of Intermediate 12

Step 1: 2-((tert-butoxycarbonyl)amino)ethyl 4-methylbenzenesulfonate

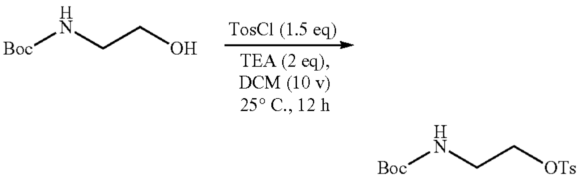

To a mixture of tert-butyl (2-hydroxyethyl)carbamate (100 g, 620 mmol, 96.2 mL, 1 eq) and triethylamine (173 mL, 1.24 mol, 2 eq) in dichloromethane (1 L) was added 4-methylbenzenesulfonyl chloride (177 g, 930 mmol, 1.5 eq) in one portion at 25 °C under nitrogen. The mixture was stirred at 25 °C for 12 hr. The residue was poured into water (1 L) and stirred for 3 min. The aqueous phase was extracted with ethyl acetate (500 mL×3). The combined organic phase was dried with anhydrous sodium sulfate, filtered and concentrated in vacuum. The residue was purified by column chromatography (silica, petroleum ether/ethyl acetate=1/0 to 8/1) to afford the title compound (120 g, 61.3% yield) as a white solid. $^1H$ NMR (400 MHz, $CDCl_3$-d) δ ppm 1.39 (s, 9H) 2.43 (s, 3H) 3.36 (br d, 2H) 4.05 (t, 2H) 4.92 (br s, 1H) 7.33 (d, 2H) 7.77 (d, 2H).

Step 2: tert-butyl (2-(2-bromophenoxy)ethyl)carbamate

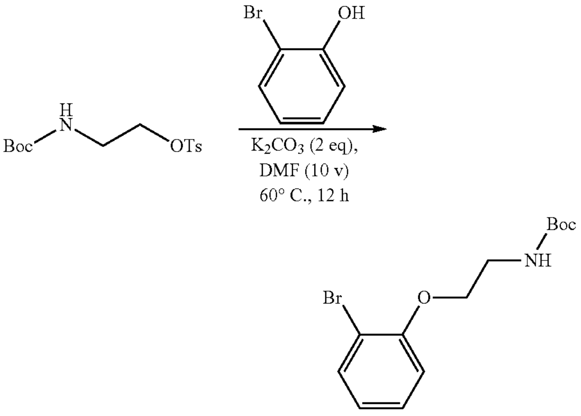

To a mixture of 2-bromophenol (30.2 mL, 260 mmol, 1 eq) and 2-((tert-butoxycarbonyl) amino)ethyl 4-methylbenzenesulfonate (82 g, 260 mmol, 1 eq) in N,N-dimethylformamide (500 mL) was added potassium carbonate (71.8 g, 520 mmol, 2 eq) in one portion at 25 °C under nitrogen. The mixture was stirred at 60 °C for 12 hr. The mixture was cooled to 25 °C. The residue was poured into ice-water (w/w=1/1) (1000 mL) and stirred for 3 min. The aqueous phase was extracted with ethyl acetate (500 mL×3). The combined organic phase was dried with anhydrous sodium sulfate, filtered and concentrated in vacuum. The residue was purified by column chromatography (silica, petroleum ether/ethyl acetate=1/0 to 3/1) to afford the title compound (70.1 g, 80.1% yield) as yellow oil. $^1$H NMR (400 MHz, $CDCl_3$-d) δ ppm 1.49 (s, 9H) 3.62 (q, 2H) 4.11 (t, 2H) 5.15 (br s, 1H) 6.86-6.96 (m, 2H) 7.27-7.32 (m, 1H) 7.57 (dd, 1H).

Step 3: tert-butyl (2-(2-bromophenoxy)ethyl)(methyl)carbamate

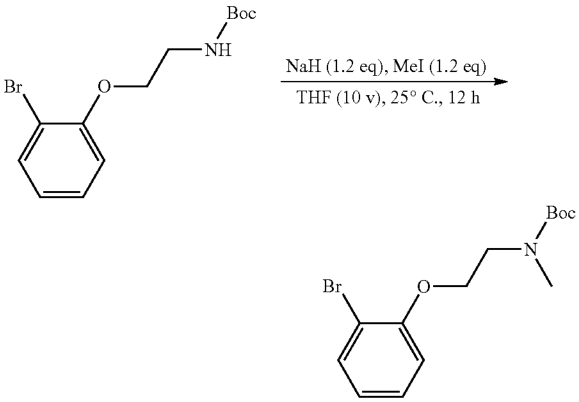

A solution of tert-butyl (2-(2-bromophenoxy)ethyl)carbamate (40 g, 126 mmol, 1 eq) in tetrahyfrofuran (400 mL) was added sodium hydride (6.07 g, 152 mmol, 60% purity, 1.2 eq) in one portion at 0 °C for 1 h, then the mixture was added methyl iodide (9.45 mL, 152 mmol, 1.2 eq). The mixture was stirred at 25 °C for 12 hours. The mixture was poured into ice water (w/w=1/1) (2000 mL) and stirred for 3 min. The aqueous phase was extracted with ethyl acetate (3×1000 mL). The combined organic phase was dried with anhydrous sodium sulfate, filtered and concentrated under reduced pressure. The residue was purified by column chromatography (silica, Petroleum ether/Ethyl acetate=1/0 to 10/1) to afford the title compound (41 g, 93.2% yield) as a yellow solid. LCMS (method I) (ESI+): m/z 274 (M-56+H)+, RT: 0.841 min

Step 4: tert-butyl methyl(2-(2-(4,4,5,5-tetramethyl-1,3,2-dioxaborolan-2-yl)phenoxy)ethyl)carbamate (intermediate 12)

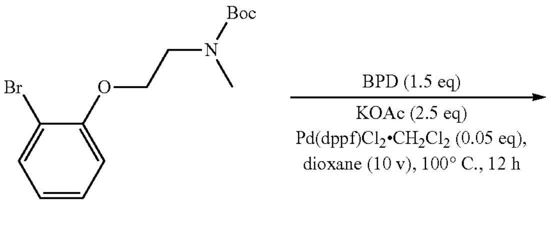

-continued

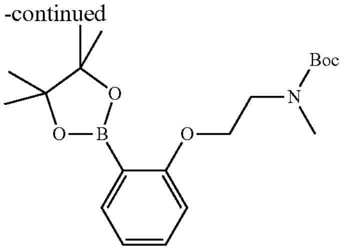

To a solution of tert-butyl (2-(2-bromophenoxy)ethyl)(methyl)carbamate (41 g, 124 mmol, 1 eq) in dioxane (400 mL) was added potassium acetate (30.5 g, 310 mmol, 2.5 eq) and bis(pinacol)diborane (47.3 g, 186 mmol, 1.5 eq) in one portion. Then to the mixture was added [1,1'-bis(diphenylphosphino)-ferrocene]palladium(II) chloride-dichloromethane complex (5.07 g, 6.21 mmol, 0.05 eq). The mixture was stirred at 100 °C for 12 hours. The mixture was concentrated under reduced pressure. The residue was purified by column chromatography ($SiO_2$, Petroleum ether/Ethyl acetate=1/0 to 10/1) to afford the title compound (30 g, 58.9% yield) as an orange solid. $^1$H NMR (400 MHz, chloroform-d) δ ppm 1.33 (s, 12H), 1.46 (s, 9H), 3.12 (s, 3H), 3.63 (br d, 2H), 4.03-4.17 (m, 2H), 6.83 (d, 1H), 6.95 (br s, 1H), 7.34-7.44 (m, 1H), 7.71 (br d, 1H).

Procedure for the Preparation of Intermediate 13 tert-butyl 3-amino-2-((2'-(2-((tert-butoxycarbonyl)(methyl)amino)ethoxy)-2-fluoro-[1,1'-biphenyl]-3-yl)methyl)-4-fluoropyrrolidine-1-carboxylate_cis racemic (intermediate 13)

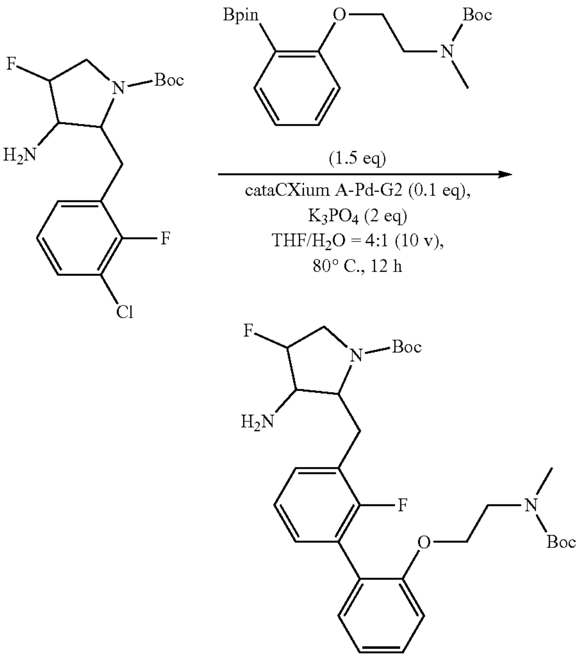

To a solution of tert-butyl 3-amino-2-(3-chloro-2-fluorobenzyl)-4-fluoropyrrolidine-1-carboxylate_cis racemic, intermediate 11 (5 g, 14.4 mmol, 1 eq) in tetrahydrofuran (80 mL) and water (20 mL) was added potassium phosphate (6.12 g, 28.9 mmol, 2 eq) and tert-butyl N-methyl-N-[2-[2-

(4,4,5,5-tetramethyl-1,3,2-dioxaborolan-2-yl)phenoxy] ethyl]carbamate, intermediate 12 (8.16 g, 21.6 mmol, 1.5 eq), then was added [2-(2-aminophenyl)phenyl]-chloro-palladium;bis(1-adamantyl)-butyl-phosphane (964 mg, 1.44 mmol, 0.1 eq). The mixture was stirred at 80 °C for 12 h. The residue was poured into ice-water (w/w=1/1, 500 mL) and stirred for 3 min. The aqueous phase was extracted with ethyl acetate (3×250 mL). The combined organic phase was dried with anhydrous sodium sulfate, filtered and concentrated in vacuum. The residue was purified by column chromatography (silica, petroleum ether/ethyl acetate=1/1 to 0/1) to afford the title compound (7.4 g, 90.5% yield) as black oil. LCMS (method I) (ESI+): m/z 562.2 (M+H)+, RT: 0.722 min.

Example 49. Synthesis of Compound No. A1-92

Step 1: tert-butyl 2-((2'-(2-((tert-butoxycarbonyl)(methyl)amino)ethoxy)-2-fluoro-[1,1'-biphenyl]-3-yl)methyl)-4-fluoro-3-((fluoromethyl)sulfonamido)pyrrolidine-1-carboxylate_cis racemic

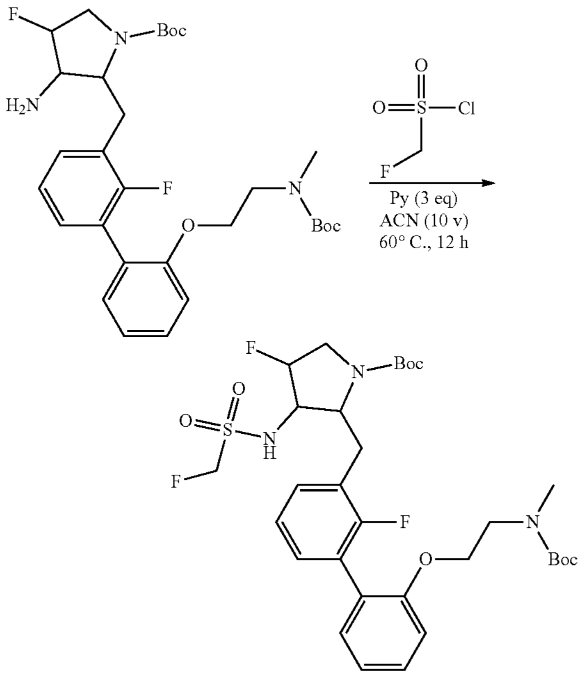

To a mixture of tert-butyl 3-amino-2-((2'-(2-((tert-butoxycarbonyl)-(methyl)amino)ethoxy)-2-fluoro-[1,1'-biphenyl]-3-yl)methyl)-4-fluoropyrrolidine-1-carboxylate_cis racemic, intermediate 13 (1.00 g, 1.78 mmol, 1 eq) in acetonitrile (10 mL) was added fluoromethanesulfonyl chloride (354 mg, 2.67 mmol, 1.5 eq) and pyridine (413 µL, 5.34 mmol, 3 eq) in one portion at 60 °C under nitrogen. The mixture was stirred at 60 °C for 12 h. The residue was poured into ice-water (w/w=1/1, 50 mL) and stirred for 3 min. The aqueous phase was extracted with ethyl acetate (3×25 mL). The combined organic phase was washed, dried with anhydrous sodium sulfate, filtered and concentrated in vacuum. The residue was purified by column chromatography (silica, petroleum ether/ethyl acetate=1/0 to 5/1) to afford the title compound (1 g, 83.7% yield) as a brown solid. LCMS (method I) (ESI+): m/z 558.1 (M-100+H)+, RT: 0.868 min.

Step 2: 1-fluoro-N-(4-fluoro-2-((2-fluoro-2'-(2-(methylamino)ethoxy)-[1,1'-biphenyl]-3-yl)methyl)pyrrolidin-3-yl)methanesulfonamide_cis racemic dihydrochloride

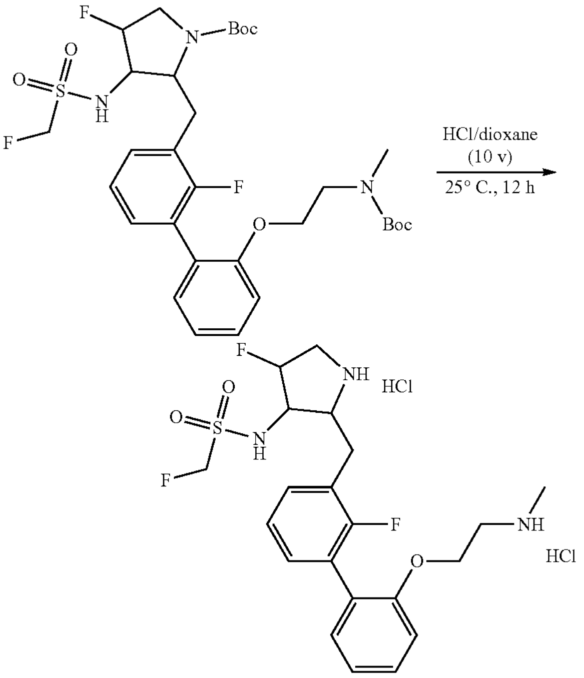

A solution of tert-butyl 2-((2'-(2-((tert-butoxycarbonyl)(methyl)amino)ethoxy)-2-fluoro-[1,1'-biphenyl]-3-yl)methyl)-4-fluoro-3-((fluoromethyl)sulfonamido)pyrrolidine-1-carboxylate_cis racemic (800 mg, 1.22 mmol, 1 eq) in hydrochloric acid/dioxane (8 mL) was stirred at 25 °C for 2 hr under nitrogen atmosphere. The mixture was concentrated in vacuum to afford the title compound (556 mg, 1.19 mmol, 97.9% yield) as a white solid, which was used in the next step without further purification. LCMS (method I) (ESI+): m/z 458.0 (M+H)+, RT: 0.508 min.

Step 3: N-(($4^2S,4^3R,4^4S$)-$2^2,4^4$-difluoro-6-methyl-5-oxo-9-oxa-6-aza-4(2,1)-pyrrolidina-1(1,2),2(1,3)-dibenzenacyclononaphane-$4^3$-yl)-1-fluoromethanesulfonamide

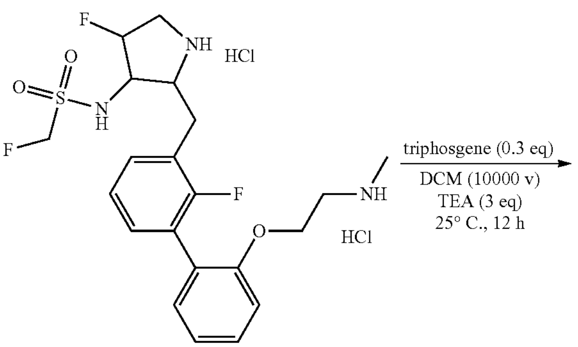

-continued

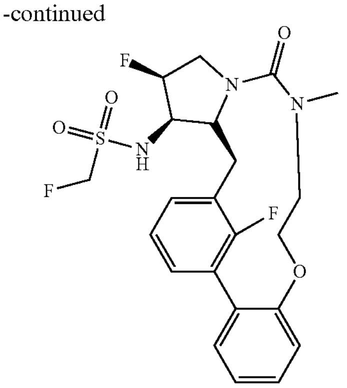

To a mixture of 1-fluoro-N-(4-fluoro-2-((2-fluoro-2'-(2-(methylamino)ethoxy)-[1,1'-biphenyl]-3-yl)methyl)pyrrolidin-3-yl)methanesulfonamide_cis racemic dihydrochloride (200 mg, 437 μmol, 1 eq) in dichloromethane (2 L) was added triethylamine (183 μL, 1.31 mmol, 3 eq) in one portion at 25 °C under nitrogen and stirred for 2 min. Then the mixture was added bis(trichloromethyl) carbonate (48.00 mg, 162 μmol, 0.37 eq) and stirred at 25 °C for 12 h. The residue was filtered and concentrated in vacuum. Two additional batches were set up as described above. All three reaction mixtures were combined. The combined crude product was purified by prep-HPLC (column: Phenomenex C18 75x30 mmx3 um;mobile phase: [water(sodium bicarbonate)-acetonitrile];B %: 30%-55%,12 min) to afford cis racemic product (100 mg) as a white solid, which was further separated by SFC (column: DAICEL CHIRALCEL OD(250 mm*30 mm, 10 μm);mobile phase: [0.1% $NH_3H_2O$ IPA]; B %: 60%-60%,10 min) to afford the title compound (50.3 mg, 23.6% yield) with the shorter retention time as a white solid. $^1$H NMR (400 MHz, acetonitrile-$d_3$) δ ppm 7.43-7.34 (m, 1H), 7.31 (dd, 1H), 7.23 (td, 1H), 7.16-7.01 (m, 3H), 6.97 (d, 1H), 6.44 (br s, 1H), 5.42-5.11 (t, 3H), 4.60 (ddd, 1H), 4.40-4.29 (m, 1H), 4.12-3.98 (m, 2H), 3.98-3.93 (m, 1H), 3.93-3.81 (m, 1H), 3.78-3.63 (m, 1H), 3.27 (br d, 1H), 3.00 (td, 1H), 2.71 (br d, 1H), 2.60 (s, 3H). LCMS (method H): m/z 484 $(M+H)^+$ (ES+) at 2.80 min Example 50. Synthesis of Compound No. A1-94

Step 1: tert-butyl 2-((2'-(2-((tert-butoxycarbonyl)(methyl)amino)ethoxy)-2-fluoro-[1,1'-biphenyl]-3-yl)methyl)-3-((difluoromethyl)sulfonamido)-4-fluoropyrrolidine-1-carboxylate_cis racemic

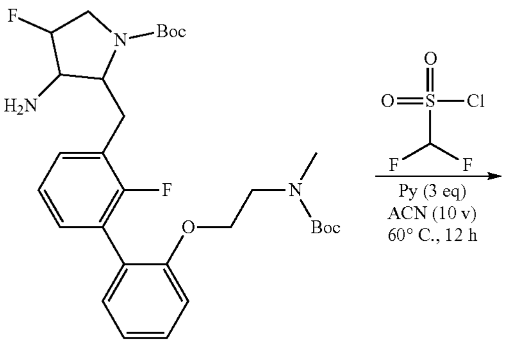

-continued

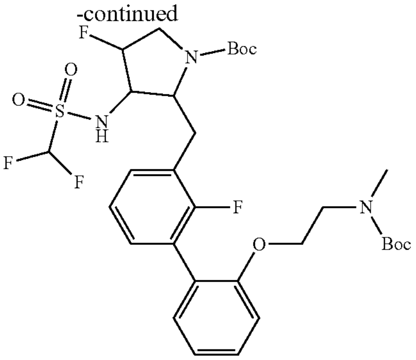

To a mixture of tert-butyl 3-amino-2-((2'-(2-((tert-butoxycarbonyl)(methyl)-amino)ethoxy)-2-fluoro-[1,1'-biphenyl]-3-yl)methyl)-4-fluoropyrrolidine-1-carboxylate_cis racemic, intermediate 13 (1.00 g, 1.78 mmol, 1 eq) in acetonitrile (10 mL) was added difluoromethanesulfonyl chloride (402 mg, 2.67 mmol, 1.5 eq) and pyridine (431 μL, 5.34 mmol, 3 eq) in one portion at 60 °C under nitrogen. The mixture was stirred at 60 °C for 12 hr. The residue was poured into ice-water (w/w=1/1, 50 mL) and stirred for 3 min. The aqueous phase was extracted with ethyl acetate (25 mLx3). The combined organic phase was washed, dried with anhydrous sodium sulfate, filtered and concentrated in vacuum. The residue was purified by column chromatography (silica, petroleum ether/ethyl acetate=1/0 to 5/1) to afford the title compound (1.0 g, 82.3% yield) as a brown solid. LCMS (method I) (ESI+): m/z 576.1 (M-100+H)+, RT: 0.885 min Step 2: 1,1-difluoro-N-(4-fluoro-2-((2-fluoro-2'-(2-(methylamino)ethoxy)-[1,1'-biphenyl]-3-yl)methyl)pyrrolidin-3-yl)methanesulfonamide_cis racemic dihydrochloride

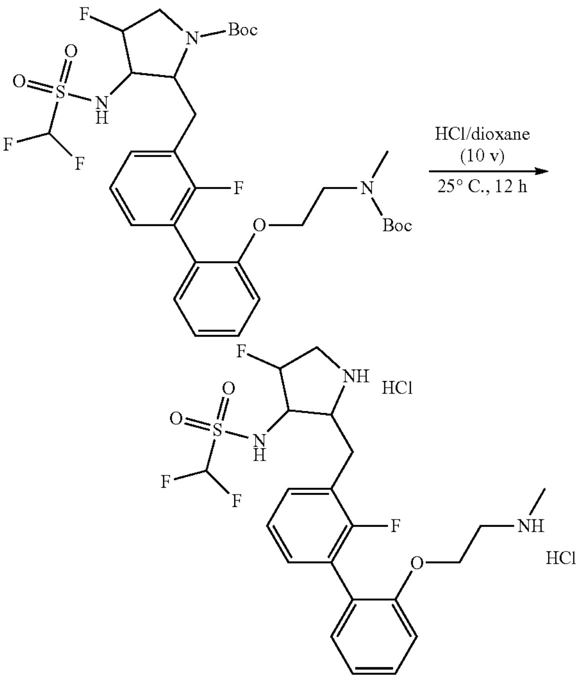

A solution of tert-butyl 2-((2'-(2-((tert-butoxycarbonyl)(methyl)amino)ethoxy)-2-fluoro-[1,1'-biphenyl]-3-yl)methyl)-3-((difluoromethyl)sulfonamido)-4-fluoropyrrolidine-1-carboxylate cis racemic (800 mg, 1.18 mmol, 1 eq) in hydrochloric acid/dioxane (8 mL) was stirred at 25 °C for 12 hr. The mixture was concentrated in vacuum to afford the title compound (560 mg, 1.15 mmol, 97.5% yield) as a white solid, which was used in the next step without further purification. LCMS (method I) (ESI+): m/z 476.0 (M+H)+, RT: 0.526 min.

Step 3: N-(($4^2$S,$4^3$R,$4^4$S)-$2^2$,$4^4$-difluoro-6-methyl-5-oxo-9-oxa-6-aza-4(2,1)-pyrrolidina-1(1,2),2(1,3)-dibenzenacyclononaphane-$4^3$-yl)-1,1-difluoromethanesulfonamide

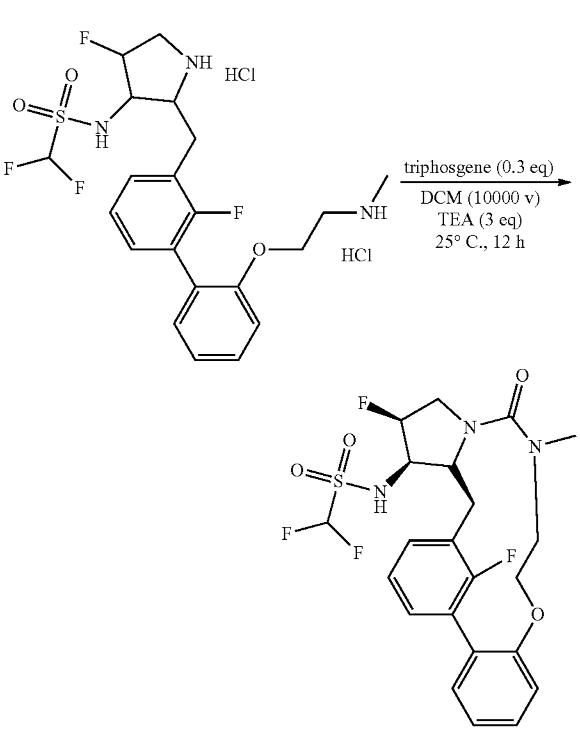

To a mixture of 1,1-difluoro-N-(4-fluoro-2-((2-fluoro-2'-(2-(methylamino)ethoxy)-[1,1'-biphenyl]-3-yl)methyl)pyrrolidin-3-yl)methanesulfonamide_cis racemic dihydrochloride (200 mg, 421 μmol, 1 eq) in dichloromethane (2 L) was added triethylamine (176 μL, 1.26 mmol, 3 eq) in one portion at 25 °C under nitrogen and stirred for 2 min. Then to the mixture was added bis(trichloromethyl) carbonate (46 mg, 156 μmol, 0.37 eq) and stirred at 25 °C for 12 h. The residue was filtered and concentrated in vacuum. Two additional batches were set up as described above. All three reaction mixtures were combined. The combined crude product was purified by prep-HPLC (column: Phenomenex C18 75×30 mm×3 μm; mobile phase: [water(ammonium bicarbonate)-acetonitrile];B %: 30%-55%,12 min) to afford cis racemic product (100 mg), which was further separated by SFC (column: DAICEL CHIRALCEL OD (250 mm*30 mm, 10 μm); mobile phase: [0.1% $NH_3H_2O$ EtOH];B %: 55%-55%, 10 min) to afford the title compound (28.2 mg, yield 13.37%) with the shorter retention time as a white solid. 1H NMR (400 MHz, acetonitrile-d3) δ ppm 7.41-7.34 (m, 1H), 7.31 (dd, 1H), 7.23 (td, 1H), 7.17-7.00 (m, 3H), 6.97 (d, 1H), 6.59 (t, 1H), 5.17 (dt, 1H), 4.65-4.56 (m, 1H), 4.39-4.30 (m, 1H), 4.65-3.99 (m, 2H), 3.98-3.93 (m, 1H), 3.93-3.81 (m, 1H), 3.79-3.64 (m, 1H), 3.27 (br d, 1H), 3.02 (td, 1H), 2.69 (br d, 1H), 2.60 (s, 3H). LCMS (method H): m/z 502 $(M+H)^+$ (ES+) at 2.78 min Procedure for the Preparation of Intermediate 14

Step-1: tert-butyl 6-(3-bromobenzyl)-7-oxo-5-azaspiro[2.4]heptane-5-carboxylate

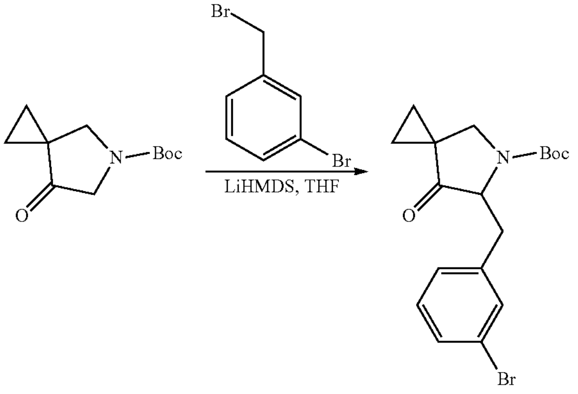

To a solution of tert-butyl 7-oxo-5-azaspiro[2.4]heptane-5-carboxylate (0.9 g, 4.26 mmol, 1 eq) in tetrahydrofuran (1.0 mL) was added a solution of bis(trimethylsily)amine lithium in tetrahydrofuran (1 M, 4.26 mL, 1 eq) drop-wise at −70 °C over a period of 5 mins under nitrogen, during which the temperature was maintained below −70 °C. The reaction mixture was warmed to 25 °C over a period of 5 min and stirred at 25 °C for 0.5 hour. Then 1-bromo-3-(bromomethyl)benzene (1.12 g, 4.47 mmol, 1.05 eq) in tetrahydrofuran (1 mL) was added at −70 °C over 5 min. The reaction mixture was stirred at 25 °C for another 2 h. The reaction mixture was quenched by MeOH and concentrated under reduced pressure to give a residue. The residue was purified by column chromatography ($SiO_2$, Petroleum ether/Ethyl acetate=100/0 to 95/5) to afford the title compound (0.42 g, 23% yield) as a colorless oil. LCMS (method J) (ESI+): m/z 324.0 (M+H-56)+, RT: 0.876 min Step-2: tert-butyl 7-amino-6-(3-bromobenzyl)spiro[2.4]heptane-5-carboxylate_cis racemic

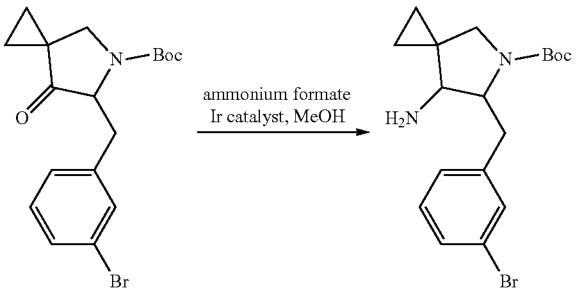 [SMILES: CC(C)(C)OC(=O)N1CC2(CC2)C(=O)C1Cc1cccc(Br)c1 ; CC(C)(C)OC(=O)N1CC2(CC2)C(N)C1Cc1cccc(Br)c1]

A mixture of tert-butyl 6-(3-bromobenzyl)-7-oxo-5-azaspiro[2.4]heptane-5-carboxylate (0.42 g, 1.10 mmol, 1 eq), ammonia formate (244 mg, 3.87 mmol, 3.5 eq) in methanol (1.0 mL) was degassed and purged with nitrogen 3 times, then bis[2-(2-pyridyl)phenyl]iridium(1+);2-(2-pyridyl)pyridine; hexafluorophosphate (18 mg, 22.1 μmol, 0.02 eq) was added. The mixture was stirred at 80 °C for 3 h under nitrogen atmosphere. The reaction mixture was quenched by water (5.0 mL), and then extracted with ethyl acetate (5.0 mL×3). The combined organic layers were washed with brine, dried over anhydrous sodium sulfate, filtered and concentrated under reduced pressure to afford the title compound (420 mg, crude) which was used for next step directly. LCMS (method J) (ESI+): m/z 325.2 (M+H-56)+, RT: 0.670 min Step 3: tert-butyl (6S,7S)-7-amino-6-(3-bromobenzyl)-5-azaspiro[2.4]heptane-5-carboxylate

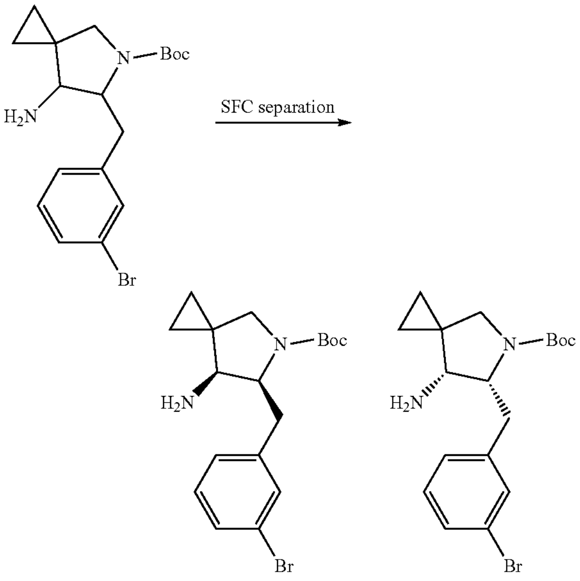

Tert-butyl 7-amino-6-(3-bromobenzyl)-5-azaspiro[2.4]heptane-5-carboxylate_cis racemic (20 g, 40.2 mmol, 1 eq) was separated by SFC (Column: Chiralcel OJ-3, 50×4.6 mm I.D., 3 μm; Mobile phase: A: $CO_2$ B: EtOH (0.1% IPA m, v/v); Gradient: B %: 5%-50%, 3 min) to afford the title compound (6.95 g, 31.9% yield) as colourless oil with the shorter retention time.

Step 4: tert-butyl (6S,7S)-7-amino-6-((2'-(2-((tert-butoxycarbonyl)(methyl)-amino)ethoxy)-[1,1'-biphenyl]-3-yl)methyl)-5-azaspiro[2.4]heptane-5-carboxylate (intermediate 14)

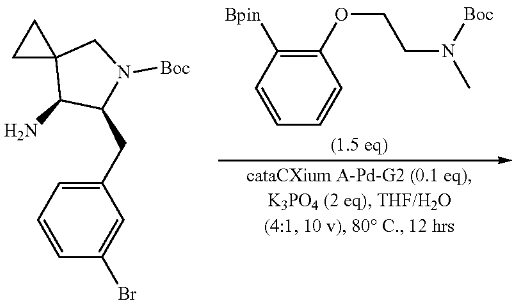

-continued

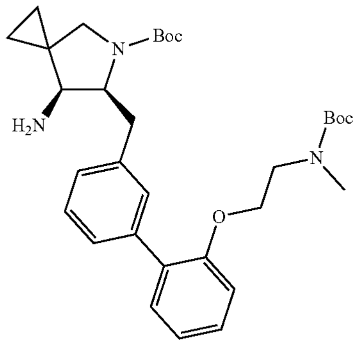

To a solution of tert-butyl (6S,7S)-7-amino-6-(3-bromobenzyl)-5-azaspiro[2.4]heptane-5-carboxylate (820 mg, 2.15 mmol, 1 eq) in tetrahydrofuran (12.8 mL) and water (3.2 mL) was added potassium phosphate (913 mg, 4.30 mmol, 2 eq) and tert-butyl (2-(2-(4,4,5,5-tetramethyl-1,3,2-dioxaborolan-2-yl)phenoxy)ethyl)carbamate, intermediate 12 (1.22 g, 3.23 mmol, 1.5 eq). Then [2-(2-aminophenyl)phenyl]-chloro-palladium; bis (1-adamantyl)-butyl-phosphane (144 mg, 215 μmol, 0.1 eq) was added into the mixture. Nitrogen was bubbled into the reaction mixture for 2 min. The mixture was stirred at 80 °C for 12 h. The reaction mixture was poured into brine (30 mL) and the mixture was extracted with ethyl acetate (30 mL). The aqueous phase was extracted with ethyl acetate (3×30 mL). The combined organic phase was dried with anhydrous sodium sulfate, filtered and concentrated to afford a residue. The residue was purified by column chromatography on silica gel eluted with petroleum ether:ethyl acetate (10:1-1:1) to afford the title compound (1.1 g, 92.7% yield) as yellow oil. LCMS (method I) (ESI+): m/z 552.2 (M+H)+, RT: 0.718 min.

Example 51. Synthesis of Compound No. A1-93

Step 1: tert-butyl (6S,7S)-6-((2'-(2-((tert-butoxycarbonyl)(methyl)amino)ethoxy)-[1,1'-biphenyl]-3-yl)methyl)-7-((fluoromethyl)sulfonamido)-5-azaspiro[2.4]heptane-5-carboxylate

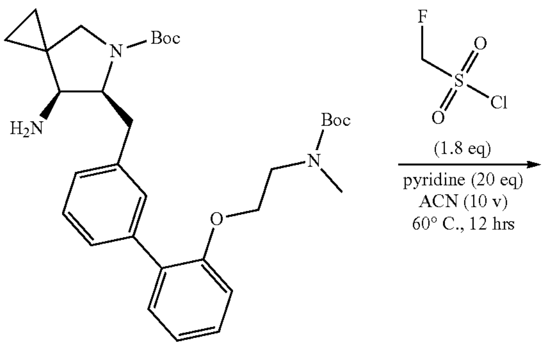

-continued

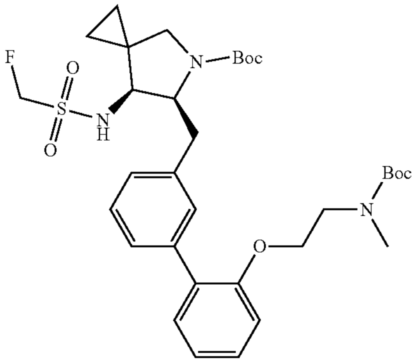

To a solution of tert-butyl (6S,7S)-7-amino-6-((2'-(2-((tert-butoxycarbonyl) (methyl)amino)ethoxy)-[1,1'-biphenyl]-3-yl)methyl)-5-azaspiro[2.4]heptane-5-carboxylate, intermediate 14 (458 mg, 830 μmol, 1 eq) in acetonitrile (4 mL) was added pyridine (1.34 mL, 16.6 mmol, 20 eq) and fluoromethanesulfonyl chloride (198 mg, 1.49 mmol, 1.8 eq). Then the reaction mixture was stirred at 60 °C for 12 h. The reaction mixture was poured into saturated sodium bicarbonate solution (25 mL) and the mixture was extracted with ethyl acetate (25 mL). The aqueous phase was extracted with ethyl acetate (3×15 mL). The combined organic phase was dried with anhydrous sodium sulfate, filtered and concentrated to afford a residue. The residue was purified by column chromatography on silica gel eluted with petroleum ether:ethyl acetate (10:1-3:1) to afford the title compound (425 mg, yield 79.0%) as yellow oil. LCMS (method I) (ESI+): m/z 548.1 (M−100)+, RT: 0.897 min.

Step 2: 1-fluoro-N-((6S,7S)-6-((2'-(2-(methylamino) ethoxy)-[1,1'-biphenyl]-3-yl)methyl)-5-azaspiro[2.4] heptan-7-yl)methanesulfonamide dihydrochloride

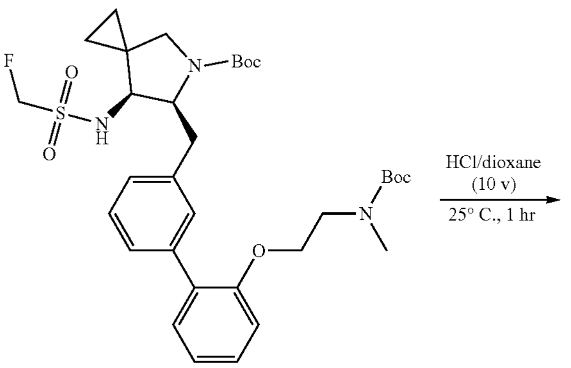

-continued

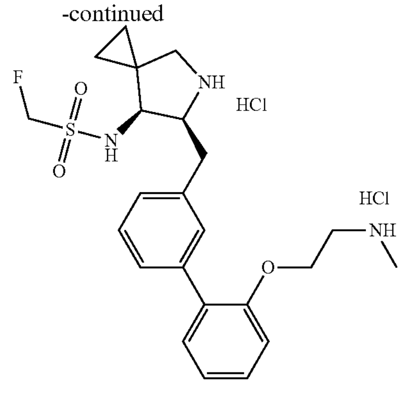

A solution of tert-butyl (6S,7S)-6-((2'-(2-((tert-butoxycarbonyl)(methyl)amino)ethoxy)-[1,1'-biphenyl]-3-yl)methyl)-7-((fluoromethyl)sulfonamido)-5-azaspiro[2.4]heptane-5-carboxylate (425 mg, 1 eq) in hydrochloric acid/dioxane (5 mL) was stirred at 25 °C for 1 h. The mixture was concentrated to afford the title compound (280 mg, 95.4% yield) as yellow oil. LCMS (method I) (ESI+): m/z 448.1 (M+H)+, RT: 0.540 min.

Step 3: 1-fluoro-N-((2'S,3'S)-6'-methyl-5'-oxospiro [cyclopropane-1,4'-9-oxa-6-aza-4(2,1)-pyrrolidina-1 (1,2),2(1,3)-dibenzenacyclononaphan]-3'-yl)methanesulfonamide

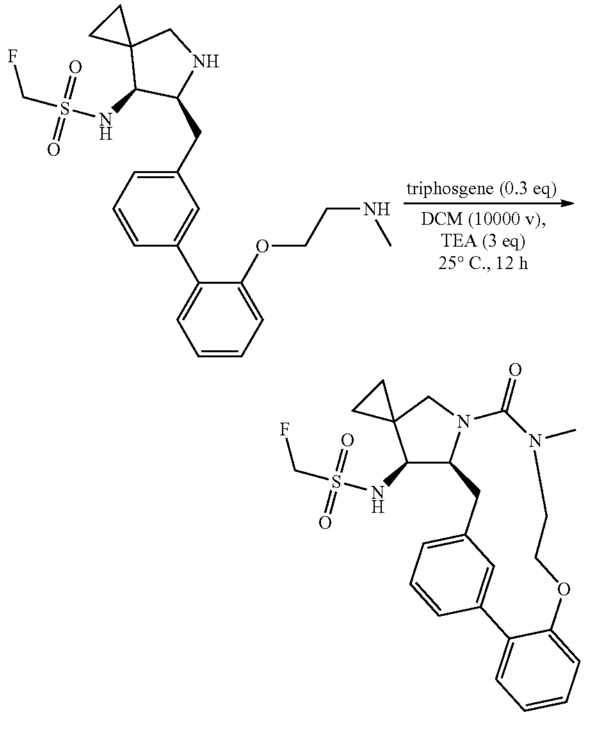

To a solution of 1-fluoro-N-((6S,7S)-6-((2'-(2-(methylamino)ethoxy)-[1,1'-biphenyl]-3-yl)methyl)-5-azaspiro[2.4] heptan-7-yl)methanesulfonamide dihydrochloride (353 mg, 789 μmol, 1 eq) in dichloromethane (3.6 L) was added triethylamine (329 μL, 2.37 mmol, 3 eq). Then triphosgene (70 mg, 237 μmol, 0.3 eq) in dichloromethane (2 mL) was added dropwise into the reaction mixture. The solution was stirred at 25 °C for 12 h. The reaction mixture was concentrated to afford a residue. The residue was purified by prep-HPLC (base conditions. column: Waters Xbridge Prep OBD C18 150×40 mm×10 μm; mobile phase: [water (ammonium bicarbonate)-acetonitrile]; B %: 35%-65%, 8 min) to afford the title compound (48 mg, 9.89% yield) as a white solid. 1H NMR (400 MHz, acetonitrile-d3) δ ppm 7.71 (s, 1H), 7.43-7.38 (m, 1H), 7.35-7.27 (m, 2H), 7.20 (dt, 1H), 7.15-7.11 (m, 1H), 7.05-6.94 (m, 2H), 5.33-5.25 (m, 1H), 5.21-5.14 (m, 1H), 4.63-4.54 (m, 1H), 4.25-4.16 (m, 1H), 4.12-4.00 (m, 1H), 3.98-3.91 (m, 1H), 3.87 (d, 1H), 3.74-3.65 (m, 1H), 3.38-3.25 (m, 2H), 2.88-2.81 (m, 1H), 2.68-2.57 (m, 4H), 0.93-0.85 (m, 1H), 0.68-0.53 (m, 3H). LCMS (method H): m/z 474 $(M+H)^+$ (ES+) at 2.89 min Example 52. Synthesis of Compound No. A1-95

Step 1: tert-butyl (6S,7S)-6-((2'-(2-((tert-butoxycarbonyl)(methyl)amino)ethoxy)-[1,1'-biphenyl]-3-yl) methyl)-7-((difluoromethyl)sulfonamido)-5-azaspiro [2.4]heptane-5-carboxylate

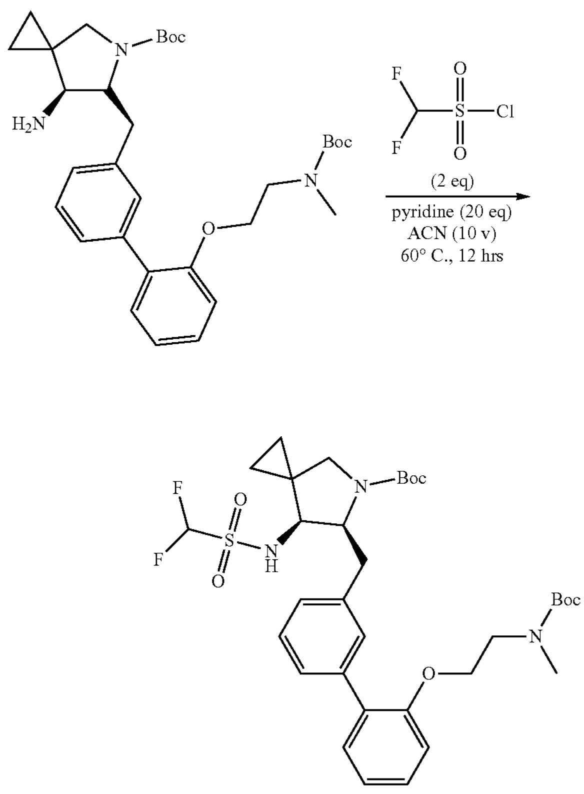

A solution of tert-butyl (6S,7S)-7-amino-6-((2'-(2-((tert-butoxycarbonyl)(methyl)amino)ethoxy)-[1,1'-biphenyl]-3-yl)methyl)-5-azaspiro[2.4]heptane-5-carboxylate, intermediate 14 (458 mg, 830 μmol, 1 eq) in acetonitrile (4 mL) was added pyridine (1.34 mL, 16.6 mmol, 20 eq) and difluoromethanesulfonyl chloride (250 mg, 1.66 mmol, 2 eq). The reaction mixture was stirred at 60 °C for 12 h. The reaction mixture was poured into saturated ammonium bicarbonate solution (20 mL) and the mixture was extracted with ethyl acetate (25 mL). The aqueous phase was extracted with ethyl acetate (3×20 mL). The combined organic phase was dried with anhydrous sodium sulfate, filtered and concentrated under reduced pressure to afford a residue. The residue was purified by column chromatography on silica gel eluted with petroleum ether:ethyl acetate (10:1 to 3:1) to afford the title compound (156 mg, 28.2% yield) as yellow oil. LCMS (method I) (ESI+): m/z 566.2 (M−100)+, RT: 0.921 min.

Step 2: 1,1-difluoro-N-((6S,7S)-6-((2'-(2-(methylamino)ethoxy)-[1,1'-biphenyl]-3-yl)methyl)-5-azaspiro[2.4]heptan-7-yl)methanesulfonamide dihydrochloride

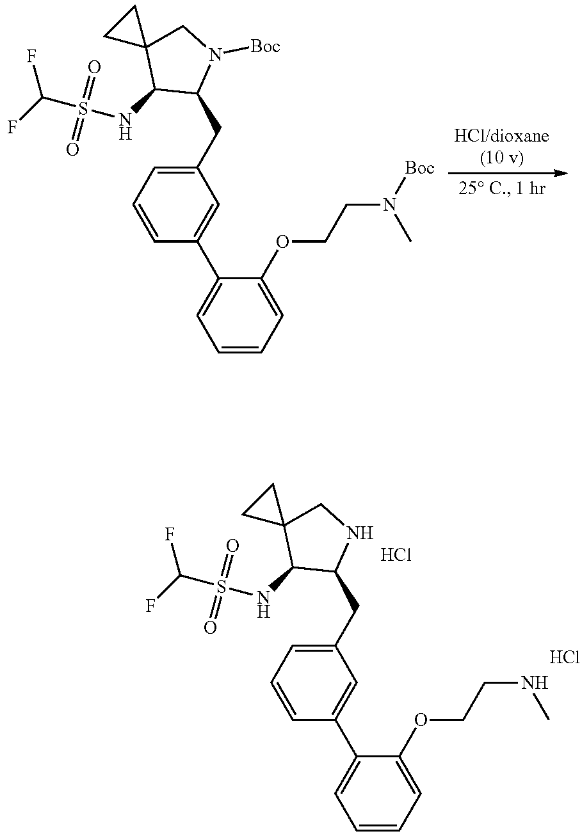

A solution of tert-butyl (6S,7S)-6-((2'-(2-((tert-butoxycarbonyl)(methyl)amino)ethoxy)-[1,1'-biphenyl]-3-yl)methyl)-7-((difluoromethyl)sulfonamido)-5-azaspiro[2.4]heptane-5-carboxylate (216 mg, 324 μmol, 1 eq) in HCl/dioxane (2 mL) was stirred at 25 °C for 1 h. The reaction was concentrated in vacuo to afford the title compound (130 mg, 86.0% yield) as a light yellow solid. LCMS (method I) (ESI+): m/z 466.1 (M+H)+, RT: 0.564 min.

Step 3: 1,1-difluoro-N-((2'S,3'S)-6'-methyl-5'-oxospiro[cyclopropane-1,4'-9-oxa-6-aza-4(2,1)-pyrrolidina-1(1,2),2(1,3)-dibenzenacyclononaphan]-3'-yl)methanesulfonamide

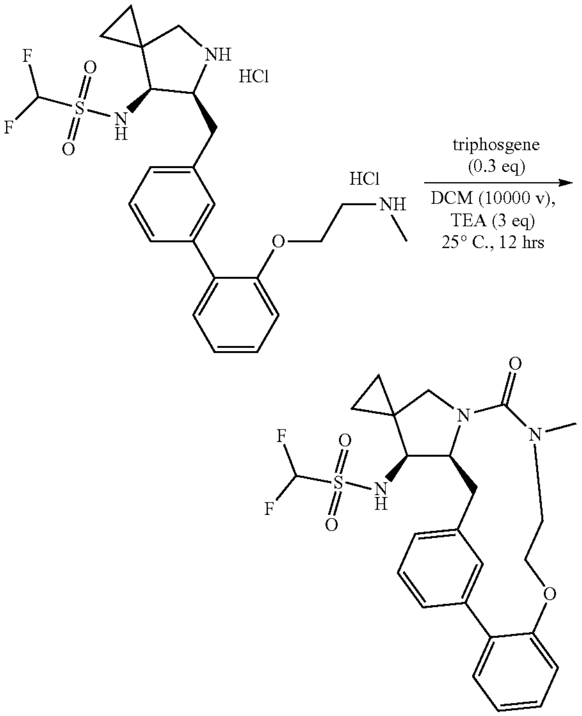

To a solution of 1,1-difluoro-N-((6S,7S)-6-((2'-(2-(methylamino)ethoxy)-[1,1'-biphenyl]-3-yl)methyl)-5-azaspiro[2.4]heptan-7-yl)methanesulfonamide dihydrochloride (92 mg, 198 μmol, 1 eq) in dichloromethane (1000 mL) was added triethylamine (83 μL, 592 mol, 3 eq). Triphosgene (18 mg, 59.3 μmol, 0.3 eq) in dichloromethane (2 mL) was added dropwise into the reaction mixture. The solution was stirred at 25 °C for 12 h. The reaction mixture was concentrated to afford a residue. The residue was purified by prep-HPLC (base conditions column: Phenomenex C18 75x30 mmx3 μm; mobile phase: [water ($NH_3 \cdot H_2O$+ammonium bicarbonate)-acetonitrile]; B %: 30%-60%,8 min) to afford the title compound (22 mg, 22.6% yield) as a white solid. 1H NMR (400 MHz, acetonitrile-d3) δ ppm 7.75-7.67 (m, 1H), 7.43-7.38 (m, 1H), 7.36-7.26 (m, 2H), 7.23-7.16 (m, 1H), 7.14-7.09 (m, 1H), 7.06-6.94 (m, 2H), 6.51 (t, 1H), 4.66-4.53 (m, 1H), 4.25-4.14 (m, 1H), 4.10-3.86 (m, 2H), 3.71 (br d, 1H), 3.41-3.30 (m, 1H), 3.26 (d, 1H), 2.83 (dd, 1H), 2.73-2.42 (m, 5H), 0.94-0.85 (m, 1H), 0.70-0.55 (m, 3H). LCMS (method H): m/z 492 $(M+H)^+$ (ES+) at 2.97 min Example 53. Orexin Type 2 Receptor Agonist Activity of Exemplary Compounds Stable cell line generation. Obtainment of cells stably expressing either human orexin type 2 or human orexin type 1 receptor: to obtain a stable cell line the Orexin receptor cDNA was inserted into pcDNA3.1(+) plasmid vector and clones identified by G418 drug resistance selection. Clones demonstrating functional activity in response to Orexin A were selected and taken into continuous culture. A single clone for OX2R-CHO and OX1R-CHO were grown in bulk and frozen to generate a cell bank for routine screening.

Measurement of orexin type 2 receptor agonist activity. Chinese hamster ovary (CHO) cells expressing human orexin type 2 receptor (hOX2R) or human orexin type 1 receptor (hOX1R) were seeded in each well of 384 well black clear bottom plates (BD Flacon) at 10,000 cells per well and cultured for 24 hr in an Ham's F12 (Gibco) medium containing 10% fetal calf serum (Sigma Aldrich) under the conditions of 37 °C, 5% $CO_2$. After removal of the medium, 50 μl of assay buffer 1 (0.1% bovine serum albumin (Sigma Aldrich), 20 mM HEPES (Molecular Dimensions), 250 mM probenecid (Sigma Aldrich), 1× Calcium 5 dye (Molecular Devices) in Hank's balanced salt solution (Invitrogen)) was added, and the cells were incubated for 60 min under the conditions of 37 °C, 5% $CO_2$. A test compound was dissolved in dimethyl sulfoxide (Sigma Aldrich) to 10 mM, and then diluted with assay buffer 2 (20 mM HEPES, Hank's balanced salt solution, 0.1% bovine serum albumin). For the reaction, a test compound solution (10 μl) was added using Fluorescent Imaging Plate Reader TETRA (FLIPR TETRA: manufactured by Molecular Devices), a fluorescence value (excitation wavelength 488 nm, measurement wavelength 570 nm) of each well was measured every one second for 2 min, and the agonist activity was determined using the area of the fluorescence value as an indicator of intracellular $Ca^{2+}$ concentration. The agonist activity of the test compound was calculated assuming that the fluorescence value of the well added with only the dilution buffer was 0% and the fluorescence value of the well added with 10 nM human orexin A (Tocris) buffer was 100%. The agonist activity values $EC_{50}$ and $E_{max}$ of each compound are shown in Table 1 below. As used herein, $E_{max}$ indicates the value at 10 μM concentration when orexin A is converted to a full agonist (maximum value of agonist activity: 100%).

Values of hOx2 $pEC_{50}$ in Table 1 are presented in ranges, in which 6.0≤"+"<7.0, 7.0≤"++"<8.0, 8.0≤"+++"<9.0, and 9.0≤"++++"<10.0.

Values of hOx2 $E_{max}$ in Table 1 are presented in ranges, in which 40≤"F"<50, 50≤"E"<60, 60≤"D"<70, 70≤"C"<80, 80≤"B"<90, 90≤"A"<100, and 100<"A+".

TABLE 1

| Compound No. | hOx2 $pEC_{50}$ | hOx2 $E_{max}$ |
|---|---|---|
| A1-1 | + | C |
| A1-2 | + | D |
| A1-3 | +++ | A |
| A1-4 | + | B |
| A1-6 | ++ | A |
| A1-7 | ++ | A |
| A1-10 | ++++ | A |
| A1-13 | ++ | A |
| A1-14 | ++ | A |
| A1-15 | +++ | A |
| A1-16 | ++ | A |
| A1-18 | +++ | A |
| A1-19 | + | B |
| A1-20 | + | A |
| A1-22 | ++ | C |
| A1-22 | ++ | C |
| A1-23 | + | C |
| A1-26 | + | F |
| A1-27 | +++ | A |
| A1-28 | ++ | A |
| A1-29 | + | A |
| A1-30 | ++ | A |
| A1-31 | + | B |
| A1-36 | + | B |

TABLE 1-continued

| Compound No. | hOx2 $pEC_{50}$ | hOx2 $E_{max}$ |
|---|---|---|
| A1-39 | +++ | A |
| A1-41 | ++ | B |
| A1-42 | ++++ | A |
| A1-43 | + | B |
| A1-48 | ++ | A |
| A1-49 | ++ | A |
| A1-50 | +++ | A |
| A1-51 | ++ | A |
| A1-52 | +++ | A |
| A1-53 | ++ | A |
| A1-54 | ++ | A |
| A1-56 | + | B |
| A1-59 | ++ | A |
| A1-60 | ++ | B |
| A1-61 | ++ | B |
| A1-63 | ++ | B |
| A1-64 | ++ | A |
| A1-65 | ++ | A |
| A1-66 | ++ | A |
| A1-67 | ++ | A |
| A1-68 | ++ | A |
| A1-69 | ++ | B |
| A1-70 | ++ | A |
| A1-71 | ++ | B |
| A1-72 | +++ | A+ |
| A1-73 | +++ | A+ |
| A1-74 | ++ | A |
| A1-75 | ++ | C |
| A1-76 | +++ | A+ |
| A1-77 | ++ | A |
| A1-78 | +++ | A |
| A1-79 | +++ | A+ |
| A1-80 | +++ | A+ |
| A1-81 | +++ | A |
| A1-82 | +++ | A+ |
| A1-83 | +++ | B |
| A1-84 | ++++ | A+ |
| A1-85 | ++ | A |
| A1-86 | +++ | C |
| A1-87 | +++ | A |
| A1-88 | ++ | F |
| A1-89 | ++ | A |
| A1-90 | ++++ | A |
| A1-91 | +++ | A |
| A1-92 | +++ | A |
| A1-93 | +++ | A |
| A1-94 | +++ | A |
| A1-95 | +++ | A |
| A1-96 | ++ | B |
| A1-97 | ++ | C |
| A1-98 | ++++ | A+ |
| A1-99 | ++ | B |
| A1-100 | +++ | A |
| A1-101 | +++ | A+ |
| A1-102 | ++ | B |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (IIB):

(IIB)

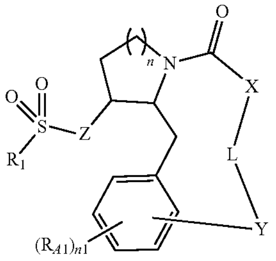

or a pharmaceutically acceptable salt or stereoisomer thereof, wherein:

$R_1$ is $C_1$-$C_6$ alkyl, $C_1$-$C_6$ haloalkyl, $C_2$-$C_6$ alkenyl, $C_2$-$C_6$ alkynyl, $NH_2$, $NHC_1$-$C_6$ alkyl, $N(C_1$-$C_6$ alkyl$)_2$, $NHC_3$-$C_{10}$ cycloalkyl, NH(3- to 7-membered heterocycloalkyl), $NHC_6$-$C_{10}$ aryl, NH(5- to 10-membered heteroaryl), OH, $OC_1$-$C_6$ alkyl, $OC_3$-$C_{10}$ cycloalkyl, O(3- to 7-membered heterocycloalkyl), $OC_6$-$C_{10}$ aryl, O(5- to 10-membered heteroaryl), SH, $SC_1$-$C_6$ alkyl, $SC_6$-$C_{10}$ aryl, $C_3$-$C_2$ cycloalkyl, 3- to 7-membered heterocycloalkyl, $C_6$-$C_{10}$ aryl, or 5- to 10-membered heteroaryl;

wherein the $C_1$-$C_6$ alkyl, $C_2$-$C_6$ alkenyl, $C_2$-$C_6$ alkynyl, $NHC_1$-$C_6$ alkyl, $N(C_1$-$C_6$ alkyl$)_2$, $OC_1$-$C_6$ alkyl, or $SC_1$-$C_6$ alkyl is optionally substituted with one or more substituents independently selected from the group consisting of halogen, CN, $NH_2$, $NHC_1$-$C_6$ alkyl, $N(C_1$-$C_6$ alkyl$)_2$, OH, $OC_1$-$C_6$ alkyl, $SC_1$-$C_6$ alkyl, $S(O)_2C_1$-$C_6$ alkyl, $C_3$-$C_2$ cycloalkyl, and 3- to 7-membered heterocycloalkyl;

wherein the $C_1$-$C_6$ haloalkyl is optionally substituted with one or more substituents independently selected from the group consisting of CN, $NH_2$, $NHC_1$-$C_6$ alkyl, $N(C_1$-$C_6$ alkyl$)_2$, OH, $OC_1$-$C_6$ alkyl, $SC_1$-$C_6$ alkyl, $S(O)_2C_1$-$C_6$ alkyl, $C_3$-$C_2$ cycloalkyl, and 3- to 7-membered heterocycloalkyl;

wherein the $NHC_3$-$C_{10}$ cycloalkyl, NH(3- to 7-membered heterocycloalkyl), $OC_3$-$C_{10}$ cycloalkyl, O(3- to 7-membered heterocycloalkyl), $C_3$-$C_2$ cycloalkyl, or 3- to 7-membered heterocycloalkyl is optionally substituted with one or more independently selected $R_{1S}$ substituents; and wherein the $NHC_6$-$C_{10}$ aryl, NH(5- to 10-membered heteroaryl), $OC_6$-$C_{10}$ aryl, O(5- to 10-membered heteroaryl), $SC_6$-$C_{10}$ aryl, $C_6$-$C_{10}$ aryl, or 5- to 10-membered heteroaryl is optionally substituted with one or more substituents independently selected from the group consisting of halogen, CN, $C_1$-$C_6$ alkyl, $C_2$-$C_6$ alkenyl, $C_2$-$C_6$ alkynyl, $NH_2$, $NHC_1$-$C_6$ alkyl, $N(C_1$-$C_6$ alkyl$)_2$, OH, $OC_1$-$C_6$ alkyl, $SC_1$-$C_6$ alkyl, $S(O)_2C_1$-$C_6$ alkyl, $C_3$-$C_2$ cycloalkyl, and 3- to 7-membered heterocycloalkyl;

each $R_{1S}$ is independently halogen, CN, $C_1$-$C_6$ alkyl, $C_2$-$C_6$ alkenyl, $C_2$-$C_6$ alkynyl, $NH_2$, $NHC_1$-$C_6$ alkyl, $N(C_1$-$C_6$ alkyl$)_2$, OH, $OC_1$-$C_6$ alkyl, =O, $SC_1$-$C_6$ alkyl, $S(O)_2C_1$-$C_6$ alkyl, $C_3$-$C_2$ cycloalkyl, or 3- to 7-membered heterocycloalkyl;

Z is —$NR_Z$— or —O—;

$R_Z$ is H or $C_1$-$C_6$ alkyl;

n is 1 or 2;

X is $C_1$-$C_4$ alkylene, —NH—, —N($C_1$-$C_6$ alkyl)-, or —O—, wherein the $C_1$-$C_4$ alkylene or —N($C_1$-$C_6$ alkyl)- is optionally substituted with one or more substituents independently selected from the group consisting of halogen, CN, $NH_2$, $NHC_1$-$C_6$ alkyl, N($C_1$-$C_6$ alkyl)$_2$, OH, and $OC_1$-$C_6$ alkyl;

L is absent, $C_1$-$C_2$ alkylene, or $C_2$-$C_6$ alkenylene, wherein the $C_1$-$C_2$ alkylene or $C_2$-$C_6$ alkenylene is optionally substituted with one or more substituents independently selected from the group consisting of halogen, CN, $NH_2$, $NHC_1$-$C_6$ alkyl, N($C_1$-$C_6$ alkyl)$_2$, and OH;

Y is $C_1$-$C_4$ alkylene or —O—, wherein the $C_1$-$C_4$ alkylene is optionally substituted with one or more substituents independently selected from the group consisting of halogen, CN, $NH_2$, $NHC_1$-$C_6$ alkyl, N($C_1$-$C_6$ alkyl)$_2$, OH, and $OC_1$-$C_6$ alkyl;

each $R_{A1}$ is independently halogen, CN, $C_1$-$C_6$ alkyl, $C_1$-$C_6$ haloalkyl, $C_2$-$C_6$ alkenyl, $C_2$-$C_6$ alkynyl, $NH_2$, $NHC_1$-$C_6$ alkyl, N($C_1$-$C_6$ alkyl)$_2$, OH, $OC_1$-$C_6$ alkyl, $OC_1$-$C_6$ haloalkyl, or $Ar_2$;

nl is 0, 1, 2, 3, or 4;

each $Ar_2$ is independently $C_6$-$C_{10}$ aryl or 5- to 10-membered heteroaryl, wherein each $C_6$-$C_{10}$ aryl and 5- to 10-membered heteroaryl is optionally and independently substituted with one or more independently selected $R_A2$ substituents; and each $R_{A2}$ is independently halogen, CN, $C_1$-$C_6$ alkyl, $C_1$-$C_6$ haloalkyl, $C_2$-$C_6$ alkenyl, $C_2$-$C_6$ alkynyl, $NH_2$, $NHC_1$-$C_6$ alkyl, N($C_1$-$C_6$ alkyl)$_2$, OH, $OC_1$-$C_6$ alkyl, or $OC_1$-$C_6$ haloalkyl.

2. The compound of claim 1, or a pharmaceutically acceptable salt or stereoisomer thereof, wherein $R_1$ is $C_1$-$C_6$ alkyl, wherein the $C_1$-$C_6$ alkyl is optionally substituted with one or more substituents independently selected from the group consisting of halogen, CN, $NH_2$, $NHC_1$-$C_6$ alkyl, N($C_1$-$C_6$ alkyl)$_2$, OH, $OC_1$-$C_6$ alkyl, $SC_1$-$C_6$ alkyl, $S(O)_2C_1$-$C_6$ alkyl, $C_3$-$C_2$ cycloalkyl, and 3- to 7-membered heterocycloalkyl, and further wherein at least one optional substituent is halogen.

3. The compound of claim 1, or a pharmaceutically acceptable salt or stereoisomer thereof, wherein $R_1$ is $CH_3$ or $CH_2CH_3$.

4. The compound of claim 1, or a pharmaceutically acceptable salt or stereoisomer thereof, wherein:

Z is —$NR_Z$—; and $R_Z$ is H.

5. The compound of claim 1, or a pharmaceutically acceptable salt or stereoisomer thereof, wherein n is 1.

6. The compound of claim 1, or a pharmaceutically acceptable salt or stereoisomer thereof, wherein n is 2.

7. The compound of claim 1, or a pharmaceutically acceptable salt or stereoisomer thereof, wherein X is $C_1$-$C_4$ alkylene, wherein the $C_1$-$C_4$ alkylene is optionally substituted with one or more substituents independently selected from the group consisting of halogen, CN, $NH_2$, NH $C_1$-$C_6$ alkyl, N($C_1$-$C_6$ alkyl)$_2$, OH, and $OC_1$-$C_6$ alkyl.

8. The compound of claim 1, or a pharmaceutically acceptable salt or stereoisomer thereof, wherein X is —NH—, —N($C_1$-$C_6$ alkyl)-, or —O—, wherein the —N($C_1$-$C_6$ alkyl)- is optionally substituted with one or more substituents independently selected from the group consisting of halogen, CN, $NH_2$, $NHC_1$-$C_6$ alkyl, N($C_1$-$C_6$ alkyl)$_2$, OH, and $OC_1$-$C_6$ alkyl.

9. The compound of claim 1, or a pharmaceutically acceptable salt or stereoisomer thereof, wherein L is absent.

10. The compound of claim 1, or a pharmaceutically acceptable salt or stereoisomer thereof, wherein L is $C_1$-$C_2$ alkylene or $C_2$-$C_6$ alkenylene, wherein the $C_1$-$C_2$ alkylene or $C_2$-$C_6$ alkenylene is optionally substituted with one or more substituents independently selected from the group consisting of halogen, CN, $NH_2$, $NHC_1$-$C_6$ alkyl, N($C_1$-$C_6$ alkyl)$_2$, and OH.

11. The compound of claim 1, or a pharmaceutically acceptable salt or stereoisomer thereof, wherein Y is $C_1$-$C_4$ alkylene, wherein the $C_1$-$C_4$ alkylene is optionally substituted with one or more substituents independently selected from the group consisting of halogen, CN, $NH_2$, NH $C_1$-$C_6$ alkyl, N($C_1$-$C_6$ alkyl)$_2$, OH, and $OC_1$-$C_6$ alkyl.

12. The compound of claim 1, or a pharmaceutically acceptable salt or stereoisomer thereof, wherein Y is —O—.

13. The compound of claim 1, or a pharmaceutically acceptable salt or stereoisomer thereof, wherein at least one $R_{A1}$ is $Ar_2$.

14. The compound of claim 1, or a pharmaceutically acceptable salt or stereoisomer thereof, wherein at least one $Ar_2$ is $C_6$-$C_{10}$ aryl, wherein each $C_6$-$C_{10}$ aryl is optionally and independently substituted with one or more independently selected $R_{A2}$ substituents.

15. The compound of claim 1, or a stereoisomer thereof, wherein the compound, or stereoisomer thereof, is selected from the group consisting of:

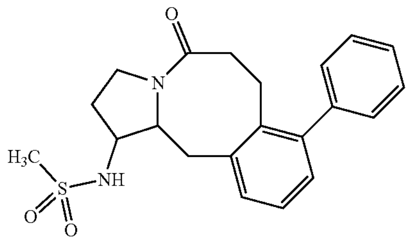

,

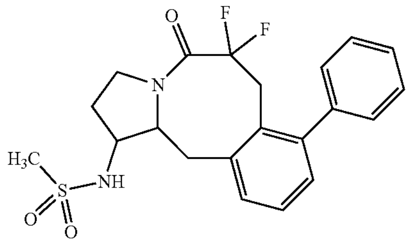

,

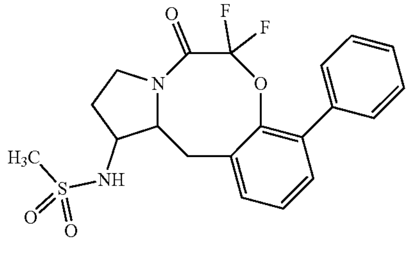

,

-continued
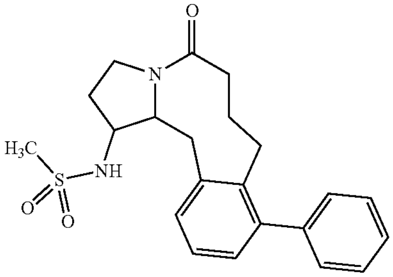
,
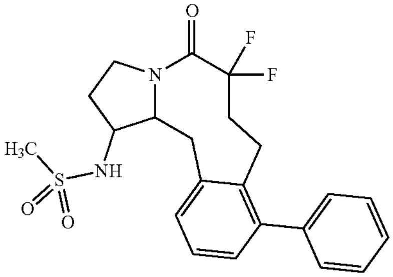
,
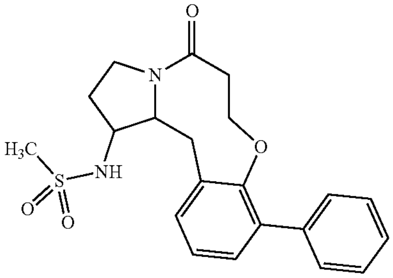
,
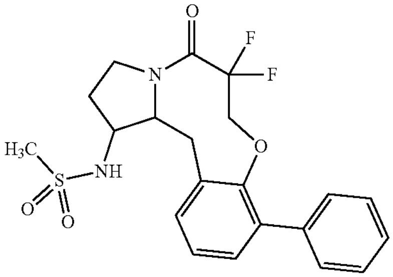
,
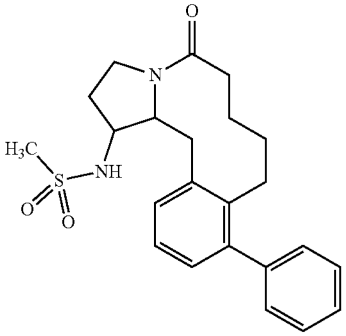
,
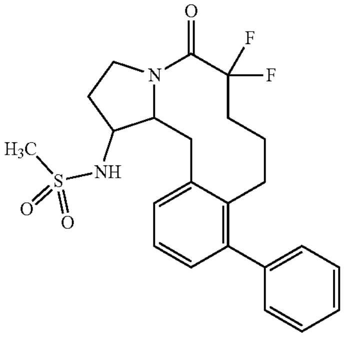
,
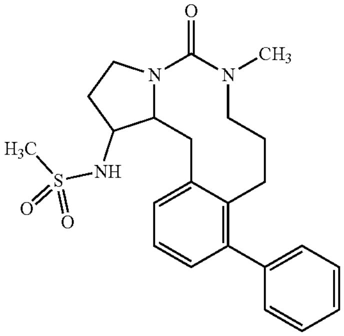
,
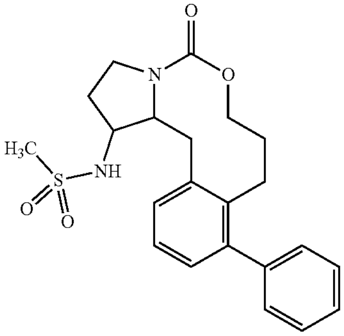
,
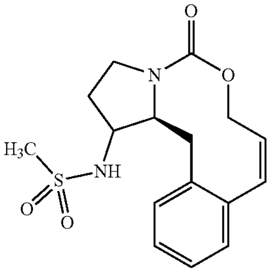
,
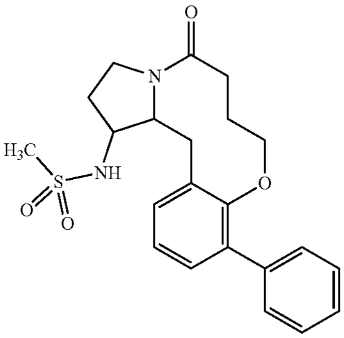
, -continued
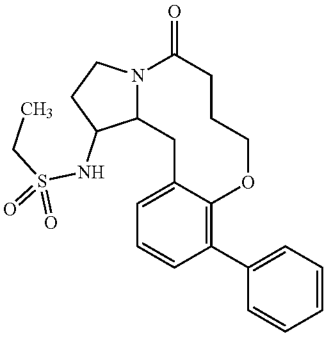
,
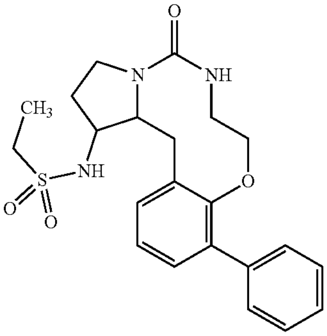
,
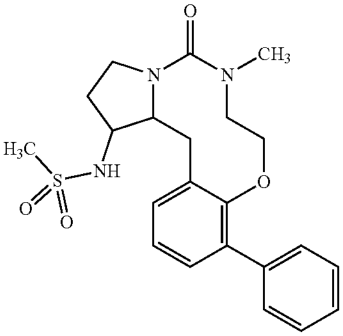
,
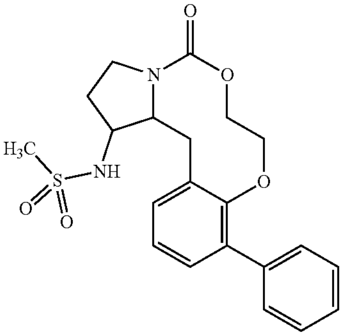
,
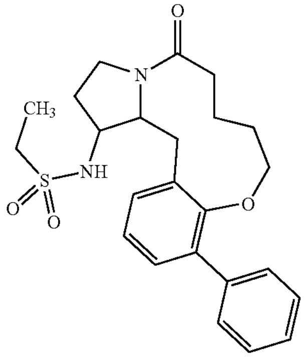
,
-continued
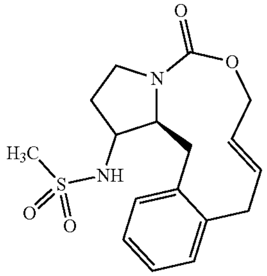
,
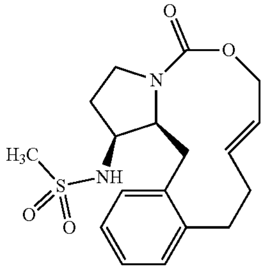
,
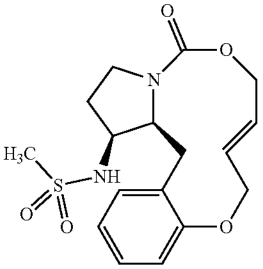
,
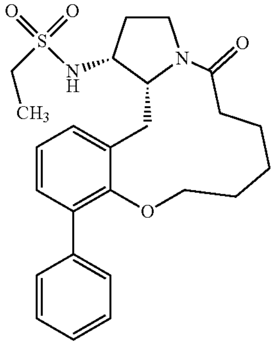
,
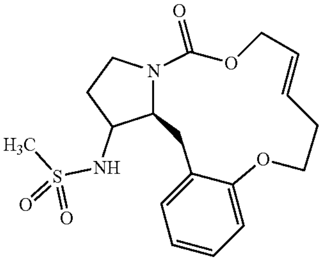
,
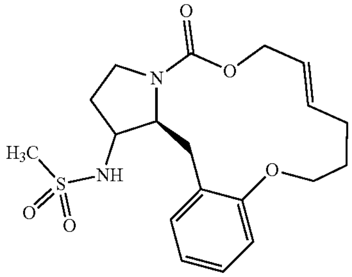
,
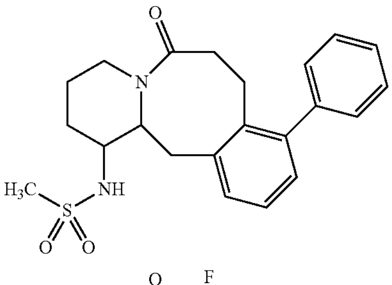
,
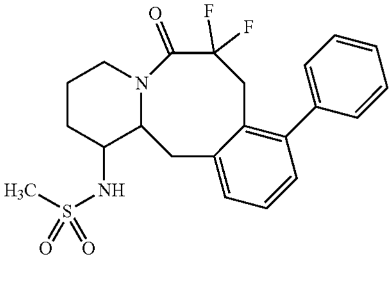
, -continued
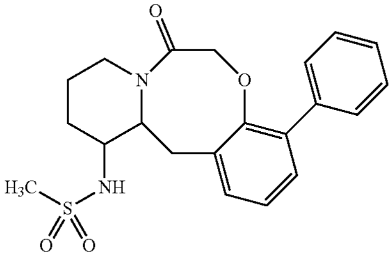,
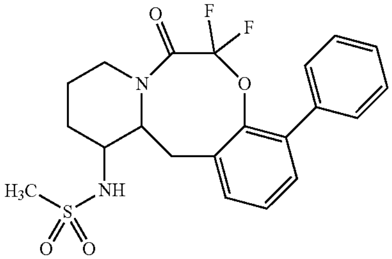,
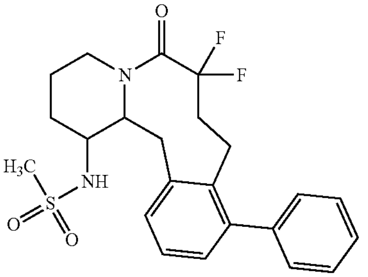,
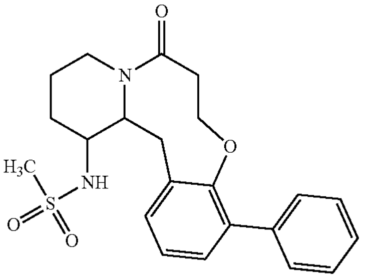,
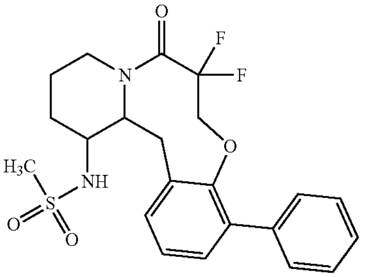,
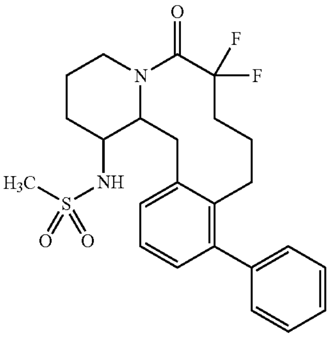,
-continued
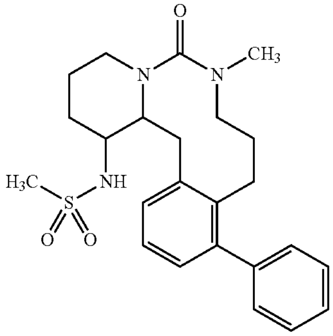,
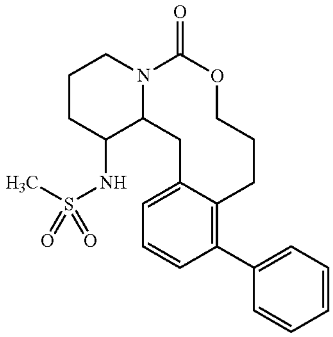,
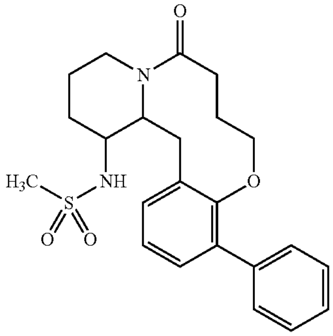,
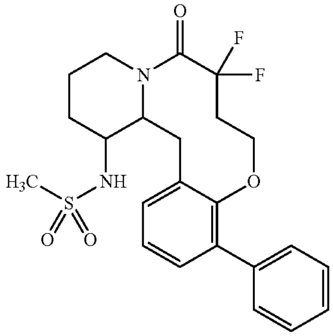,
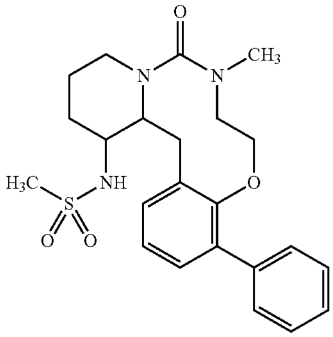, and -continued

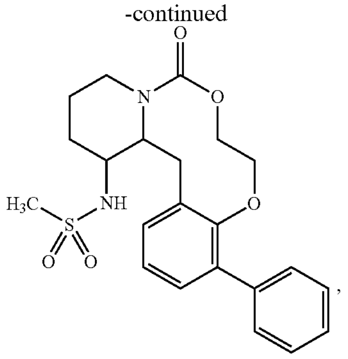

or a pharmaceutically acceptable salt thereof.

16. A pharmaceutical composition comprising a pharmaceutically acceptable diluent or carrier and the compound of claim 1, or a pharmaceutically acceptable salt or stereoisomer thereof.

17. A method for modulating orexin-2 receptor activity in a cell, wherein the method comprises contacting the cell with an effective amount of the compound of claim 1, or a pharmaceutically acceptable salt or stereoisomer thereof.

18. A method for modulating orexin-2 receptor activity in a subject in need thereof, wherein the method comprises administering to the subject a therapeutically effective amount of the compound of claim 1, or a pharmaceutically acceptable salt or stereoisomer thereof.

19. The method of claim 18, wherein the subject has a disease or disorder selected from the group consisting of cardiac failure, a circadian rhythm disorder, a coma, a complication in emergence from anesthesia, a hypersomnia disorder, a mental health disorder, a metabolic syndrome, narcolepsy, a neurodegenerative disorder, a neurological disorder, osteoporosis, a psychiatric disorder, and a symptom of a rare genetic disorder.

20. The method of claim 18, wherein the subject has a disease or disorder selected from the group consisting of idiopathic hypersomnia, insomnia, narcolepsy, and sleep apnea.

* * * * *